US010093887B2

(12) United States Patent
Aehle et al.

(10) Patent No.: US 10,093,887 B2
(45) Date of Patent: Oct. 9, 2018

(54) COMPOSITIONS AND METHODS COMPRISING SERINE PROTEASE VARIANTS

(71) Applicant: Danisco US Inc., Palo Alto, CA (US)

(72) Inventors: Wolfgang Aehle, Zwingenberg (DE); Luis G. Cascao-Pereira, Redwood City, CA (US); David A. Estell, San Francisco, CA (US); Frits Goedegebuur, Vlaardingen (NL); James T. Kellis, Jr., San Carlos, CA (US); Ayrookaran J. Poulose, Belmont, CA (US); Brian F. Schmidt, Half Moon Bay, CA (US)

(73) Assignee: DANISCO US INC., Palo Alto, CA (US)

( * ) Notice: Subject to any disclaimer, the term of this patent is extended or adjusted under 35 U.S.C. 154(b) by 77 days.

(21) Appl. No.: 14/337,024

(22) Filed: Jul. 21, 2014

(65) Prior Publication Data

US 2015/0031589 A1    Jan. 29, 2015

Related U.S. Application Data

(63) Continuation of application No. 12/616,097, filed on Nov. 10, 2009, now abandoned.

(60) Provisional application No. 61/113,545, filed on Nov. 11, 2008, provisional application No. 61/113,552, filed on Nov. 11, 2008, provisional application No. 61/113,548, filed on Nov. 11, 2008, provisional application No. 61/218,802, filed on Jun. 19, 2009.

(51) Int. Cl.
| | |
|---|---|
| *C12Q 1/37* | (2006.01) |
| *C12N 15/00* | (2006.01) |
| *C12N 9/54* | (2006.01) |
| *C11D 3/386* | (2006.01) |
| *C12N 9/50* | (2006.01) |
| *A61K 38/00* | (2006.01) |

(52) U.S. Cl.
CPC .......... *C11D 3/386* (2013.01); *C11D 3/38609* (2013.01); *C11D 3/38618* (2013.01); *C11D 3/38636* (2013.01); *C11D 3/38645* (2013.01); *C11D 3/38654* (2013.01); *C12N 9/50* (2013.01); *C12N 9/54* (2013.01); *C12Y 304/21062* (2013.01)

(58) Field of Classification Search
None
See application file for complete search history.

(56) References Cited

U.S. PATENT DOCUMENTS

| | | | |
|---|---|---|---|
| 4,246,612 A | 2/1981 | Berry et al. | |
| 4,430,243 A | 2/1984 | Bragg | |
| 4,435,307 A | 3/1984 | Barbesgaard et al. | |
| 4,683,195 A | 7/1987 | Mullis et al. | |
| 4,683,202 A | 7/1987 | Mullis | |
| 4,810,410 A | 3/1989 | Diakun et al. | |
| 4,965,188 A | 10/1990 | Mullis et al. | |
| 4,977,252 A | 12/1990 | Chiu | |
| 5,024,943 A | 6/1991 | Van Ee | |
| 5,227,084 A | 7/1993 | Martens et al. | |
| RE34,606 E | 5/1994 | Estell et al. | |
| 5,340,735 A | 8/1994 | Christianson et al. | |
| 5,354,559 A | 10/1994 | Morehouse | |
| 5,486,303 A | 1/1996 | Capeci et al. | |
| 5,489,392 A | 2/1996 | Capeci et al. | |
| 5,500,364 A | 3/1996 | Christianson et al. | |
| 5,516,448 A | 5/1996 | Capeci et al. | |
| 5,565,422 A | 10/1996 | Del Greco et al. | |
| 5,569,645 A | 10/1996 | Dinniwell et al. | |
| 5,576,282 A | 11/1996 | Miracle et al. | |
| 5,574,005 A | 12/1996 | Welch et al. | |
| 5,595,967 A | 1/1997 | Miracle et al. | |
| 5,597,936 A | 1/1997 | Perkins et al. | |
| 5,646,101 A | 7/1997 | MacBeath | |
| 5,686,014 A | 11/1997 | Baillely et al. | |
| 5,691,297 A | 11/1997 | Nassano et al. | |
| 5,695,679 A | 12/1997 | Christie et al. | |
| 5,698,504 A | 12/1997 | Christie et al. | |
| 5,700,676 A | 12/1997 | Bott et al. | |
| 5,705,464 A | 1/1998 | Scheper et al. | |
| 5,710,115 A | 1/1998 | Patel et al. | |
| 5,801,039 A | 9/1998 | Maurer et al. | |
| 5,855,625 A | 1/1999 | Maurer et al. | |
| 5,874,276 A | 2/1999 | Fowler et al. | |

(Continued)

FOREIGN PATENT DOCUMENTS

| | | |
|---|---|---|
| EP | 0 200 362 | 12/1986 |
| EP | 0 201 184 | 12/1986 |

(Continued)

OTHER PUBLICATIONS

U.S. Appl. No. 11/583,334, filed Oct. 19, 2006, Aehle, et al.
Altschul et al., "Basic Local Alignment Search Tool." *J. Molecular Biology*, 215: 403-410 (1990).
Altschul, et al., "Local alignment statistics." *Methods Enzymol.* 266:460-80 (1996).
Bolivar, et al., "Construction and Characterization of New Cloning Vehicles." *Gene* 2: 95-113 (1977).
Bryan, P.N., "Protein engineering of subtilisin." *Biochimica et Biophysica Acta* 1543(2): 203-222 (2000).

(Continued)

*Primary Examiner* — Manjunath N Rao
*Assistant Examiner* — Samuel W Liu

(57) ABSTRACT

The present invention provides methods for protein engineering and serine protease variants produced there from. Specifically, the present invention provides serine protease variants having one or more substitutions as compared to a reference serine protease. In addition, the present invention provides compositions comprising these serine protease variants. In some embodiments, the present invention provides cleaning compositions comprising at least one of these serine protease variants.

11 Claims, 5 Drawing Sheets

Specification includes a Sequence Listing.

(56) References Cited

U.S. PATENT DOCUMENTS

| | | | |
|---|---|---|---|
| 5,879,584 A | 3/1999 | Bianchetti et al. | |
| 5,935,826 A | 8/1999 | Blue et al. | |
| 5,955,340 A | 9/1999 | Bott et al. | |
| 6,225,464 B1 | 5/2001 | Hiler, II et al. | |
| 6,271,012 B1* | 8/2001 | Van Eekelen et al. | 435/221 |
| 6,287,841 B1* | 9/2001 | Mulleners et al. | 435/221 |
| 6,306,812 B1 | 10/2001 | Perkins et al. | |
| 6,312,936 B1* | 11/2001 | Poulose et al. | 435/219 |
| 6,326,348 B1 | 12/2001 | Vinson et al. | |
| 6,376,450 B1 | 4/2002 | Ghosh et al. | |
| 6,440,991 B1 | 8/2002 | Zhu et al. | |
| 6,472,184 B1 | 10/2002 | Hegemann | |
| 6,482,628 B1 | 12/2002 | Poulose et al. | |
| 6,566,114 B1 | 5/2003 | Kauppinen et al. | |
| 6,582,914 B1 | 6/2003 | Caldwell et al. | |
| 6,586,223 B1* | 7/2003 | Sikorski et al. | 435/220 |
| 6,599,730 B1* | 7/2003 | Brode et al. | 435/221 |
| 6,602,842 B2 | 8/2003 | Cuperus | |
| 6,605,458 B1 | 8/2003 | Hansen | |
| 6,610,642 B2 | 8/2003 | Ghosh | |
| 6,773,907 B2 | 8/2004 | Hansen et al. | |
| 6,946,128 B1 | 9/2005 | Rubingh et al. | |
| 8,008,241 B2* | 8/2011 | Souter | 510/226 |
| 8,753,861 B2* | 6/2014 | Cascao-Pereira et al. | 435/222 |
| 8,785,171 B2* | 7/2014 | Souter et al. | 435/212 |
| 2004/0147008 A1* | 7/2004 | Draborg | C11D 3/386 435/226 |
| 2005/0221461 A1 | 10/2005 | Poulose et al. | |
| 2008/0090747 A1* | 4/2008 | Augustinus | C11D 3/386 510/392 |
| 2010/0192985 A1* | 8/2010 | Aehle et al. | 134/26 |
| 2011/0281327 A1* | 11/2011 | Bott et al. | 435/212 |
| 2012/0067373 A1* | 3/2012 | Souter et al. | 134/18 |
| 2014/0302590 A1* | 10/2014 | Augustinus et al. | 435/222 |
| 2015/0087572 A1* | 3/2015 | Souter et al. | 510/226 |
| 2015/0132825 A1* | 5/2015 | Aehle et al. | 435/212 |
| 2016/0068788 A1* | 3/2016 | Nielsen | C11D 3/38663 510/222 |

FOREIGN PATENT DOCUMENTS

| | | |
|---|---|---|
| EP | 214 761 | 3/1987 |
| EP | 218 272 | 4/1987 |
| EP | 238 023 | 9/1987 |
| EP | 258 068 | 3/1988 |
| EP | 305 216 | 3/1989 |
| EP | 331 376 | 9/1989 |
| EP | 0 342 177 | 11/1989 |
| EP | 0 495 257 | 7/1992 |
| EP | 0 922 499 | 10/1994 |
| EP | 2 100 949 | 9/2008 |
| GB | 1296839 | 11/1972 |
| GB | 1372034 | 10/1974 |
| JP | 64/744992 | 3/1989 |
| WO | WO 88/09367 | 12/1988 |
| WO | WO 89/06270 | 7/1989 |
| WO | WO 90/09446 | 8/1990 |
| WO | WO 91/16422 | 10/1991 |
| WO | WO 92/21760 | 12/1992 |
| WO | WO 94/12621 | 6/1994 |
| WO | WO 94/26859 | 11/1994 |
| WO | WO 94/26860 | 11/1994 |
| WO | WO 95/01426 | 1/1995 |
| WO | WO 95/23221 | 8/1995 |
| WO | WO 96/34935 | 11/1996 |
| WO | WO 97/07770 | 3/1997 |
| WO | WO 97/11151 | 3/1997 |
| WO | WO 99/06521 | 2/1999 |
| WO | WO 99/34011 | 7/1999 |
| WO | WO 00/32601 | 6/2000 |
| WO | WO 02/014490 | 2/2002 |
| WO | WO 02/40997 | 5/2002 |
| WO | WO 04/059556 | 7/2004 |
| WO | WO 05/056782 | 6/2005 |
| WO | WO 07/044993 | 4/2007 |
| WO | WO 07/145964 | 12/2007 |
| WO | WO 09/149200 | 12/2009 |

OTHER PUBLICATIONS

Dartois, et al., "Cloning, nucleotide sequence and expression in *Escherichia coli* of a lipase gene from Bacillus subtilis 168." *Biochem. Biophys. Acta* 1131: 253-260 (1992).

Del Mar, et al. "A sensitive new substrate for chymotrypsin." *Analytical Biochemistry* 99(2): 316-320 (1979).

Devereux, et al. "A comprehensive set of sequence analysis programs for the VAX." *Nucl. Acids Res.* 12: 387-395 (1984).

Dynan, et al. "Control of eukaryotic messenger RNA synthesis by sequence-specific DNA-binding proteins." *Nature* 316(6031): 774-778 (1985).

Estell, et al., "Site-directed mutagenesis of the active site of Subtilisin BPN." In *World Biotech Report*, USA, Online Publications, London, vol. 2, pp. 181-187 (1984).

Feng, et al. "Progressive sequence alignment as a prerequisite to correct phylogenetic trees." *J. Mol. Evol.* 25(4): 351-360 (1987).

Ferrari, et al. "Genetics." In *Bacillus*, No. 2, Ed. C.R. Harwood, New York: Plenum Press, pp. 57-72 (1989).

Haas, et al., "Cloning, expression and characterization of a cDNA encoding a lipase from Rhizopus delema (Fungi; lipase; recombinant DNA; expression; signal sequence; nucleotide sequence)." *Gene* 109: 107-113 (1991).

Heinz, et al., "Changing the Inhibitory Specificity and Function of the Proteinase Inhibitor Eglin c by Site-Directed Mutagenesis: Functional and Structural Investigation." *Biochemistry* 31: 8755-8766 (1992).

Higgins, et al. "Fast and sensitive multiple alignment sequence on a microcomputer." *CABIOS* 5: 151-153 (1989).

Horinouchi, et al., "Nucleotide Sequence and Functional Map of pC194, a Plasmid that Specifies Inducible Chloramphenicol Resistance.", *J Bacteriol.* 150(2): 815-825 (1982).

Kalisz, H.M. "Microbial proteinases." *Advances in Biochemical Engineering/Biotechnology* 36: 1-65 (1988).

Karlin, et al. "Applications and statistics for multiple high-scoring segments in molecular sequences." *Proc. Natl. Acad. Sci. USA* 90(12): 5873-5877 (1993).

Kato, et al., "Novel Strategy for Protein Exploration: High-throughput Screening Assisted with Fuzzy Neural Network." *J. Mol. Biol.*, 351: 683-692 (2005).

Kugimiya, et al., "Cloning and Sequence Analysis of cDNA encoding Rhizopus niveus Lipase." *Biosci. Biotech. Biochem.* 56: 716-719 (1992).

McKenzie, et al., "The Nucleotide Sequence of pUB110: Some Salient Features in Relation to Replication and Its Regulation." *Plasmid* 15: 93-103 (1986).

Needleman, et al. "A general method applicable to the search for similarities in the amino acid sequence of two proteins." *J. Mol. Biol.* 48(3): 443-453 (1970).

Neidhardt, et al. "Culture Medium for Enterobacteria." *J. Bacteriol.* 119(3): 736-747 (1974).

Pearson, et al. "Improved Tools for Biological Sequence Comparison." *Proc. Natl. Acad. Sci. USA* 85(8): 2444-2448 (1988).

Pierce et al., "Protein Design is NP-hard." *Protein Engineer.* 15: 779-782 (2002).

Rawlings et al., "MEROPS: the peptidase database." *Nucl. Acids Res.*, 34 Database issue, D270-D272 (2006).

Rawlings, et al., "Evolutionary families of peptidases." *Biochem. J.* 290: 205-218 (1993).

Reetz et al., "Expanding the Range of Substrate Acceptance of Enzymes: Combinatorial Active-Site Saturation Test." *Angew. Chem. Int. Ed.* 44: 4192-4196 (2005).

Sandberg, et al., "Engineering multiple properties of a protein by combinatorial mutagenesis." *Proc. Natl. Acad. Sci. USA* 90: 8367-8371 (1993).

Schimada, et al., "cDNA Molecular Cloning of *Geotrichum candidum* Lipase." *J. Biochem.* 106: 383-388 (1989).

(56) References Cited

OTHER PUBLICATIONS

Smith, et al. "Comparison of Biosequences." *Adv. Appl. Math.* 2: 482-489 (1981).

Wells et al., "Cassette mutagenesis: an efficient method for generation of multiple mutations at defined sites." *Gene* 34: 315-323 (1985).

Wells et al., "Cloning sequencing, and secretion of *Bacillus amyloliquefaciens* Subtilisin in *Bacillus subtilis*." *Nucleic Acids Res.* 11(22): 7911-7925 (1983).

Yamaguchi et al., "Cloning and structure of the mono- and diacylglycerol lipase-encoding gene from *Penicillium camembertii* U-150." *Gene* 103:61-67 (1991).

International Search Report and the Written Opinion of the International Searching Authority for International Patent Application No. PCT/US2009/063808 dated Aug. 23, 2010.

International Search Report and the Written Opinion of the International Searching Authority for International Patent Application No. PCT/US2009/063837 dated Jul. 27, 2010.

* cited by examiner

FIG. 1

|          | 1         | 10        | 20         | 30         | 40         | 50 |
|----------|-----------|-----------|------------|------------|------------|----|
| BPN'     | AQSVPYGVSQIKAPALHSQGYTGSNVKVAVIDSGIDSSHPDLKVAGGASM |
| GCI-P036 | AQSVPWGISRVQAPAAHNRGLTGSGVKVAVLDTGIS:THPDLNIRGGASF |
| GCI-P037 | AQSVPWGISRVQAPAAHNRGLTGSGVKVAVLDTGIS:THPDLNIRGGASF |
| GCI-P038 | AQSVPWGISRVQAPAAHNRGLTGSGVKVAVLDTGIS:THPDLNIRGGASF |

|          | 51        | 60        | 70         | 80         | 90         | 100 |
|----------|-----------|-----------|------------|------------|------------|-----|
| BPN'     | VPSETNPFQDNNSHGTHVAGTVAALNNSIGVLGVAPSASLYAVKVLGADG |
| GCI-P036 | VPGEPST:QDGNGHGTHVAGTIAALNNSIGVLGVAPSAELYAVKVLGASG |
| GCI-P037 | VPGEPST:QDGNGHGTHVAGTIAALNNSIGVLGVAPNAELYAVKVLGASG |
| GCI-P038 | VPGEPST:QDGNGHGTHVAGTIAALNNSIGVLGVAPNAELYAVKVLGASG |

|          | 101       | 110       | 120        | 130        | 140        | 150 |
|----------|-----------|-----------|------------|------------|------------|-----|
| BPN'     | SGQYSWIINGIEWAIANNMDVINMSLGGPSGSAALKAAVDKAVASGVVVV |
| GCI-P036 | SGSVSSIAQGLEWAGNNGMHVANLSLGSPSPSATLEQAVNSATSRGVLVV |
| GCI-P037 | SGSVSSIAQGLEWAGNNGMHVANLSLGSPSPSATLEQAVNSATSRGVLVV |
| GCI-P038 | SGSVSSIAQGLEWAGNNVMHVANLSLGLQAPSATLEQAVNSATSRGVLVV |

|          | 151       | 160       | 170        | 180        | 190        | 200 |
|----------|-----------|-----------|------------|------------|------------|-----|
| BPN'     | AAAGNEGTSGSSSTVGYPGKYPSVIAVGAVDSSNQRASFSQYGPELDVMA |
| GCI-P036 | AASGNSGA::::GSISYPARYANAMAVGATDQNNNRASFSQYGAGLDIVA |
| GCI-P037 | AASGNSGA::::GSISYPARYANAMAVGATDQNNNRASFSQYGAGLDIVA |
| GCI-P038 | AASGNSGA::::GSISYPARYANAMAVGATDQNNNRASFSQYGAGLDIVA |

|          | 201       | 210       | 220        | 230        | 240        | 250 |
|----------|-----------|-----------|------------|------------|------------|-----|
| BPN'     | PGVSIQSTLPGNKYGAYNGTSMASPHVAGAAALILSKHPNWTNTQVRSSL |
| GCI-P036 | PGVNVQSTYPGSTYASLNGTSMATPHVAGAAALVKQKNPSWSNVQIRNHL |
| GCI-P037 | PGVNVQSTYPGSTYASLNGTSMATPHVAGAAALVKQKNPSWSNVQIRNHL |
| GCI-P038 | PGVNVQSTYPGSTYASLNGTSMATPHVAGAAALVKQKNPSWSNVQIRNHL |

|          | 251       | 260       | 270        |
|----------|-----------|-----------|------------|
| BPN'     | ENTTTKLGDSFYYGKGLINVQAAAQ |
| GCI-P036 | KNTATSLGSTNLYGSGLVNAEAATR |
| GCI-P037 | KNTATSLGSTNLYGSGLVNAEAATR |
| GCI-P038 | KNTATSLGSTNLYGSGLVNAEAATR |

SEQUENCE LISTING

<160> NUMBER OF SEQ ID NOS: 106

<210> SEQ ID NO 1
<211> LENGTH: 275
<212> TYPE: PRT
<213> ORGANISM: B. amyloliquefaciens

<400> SEQUENCE: 1

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala

```
            35                  40                  45
Ser Met Val Pro Ser Glu Thr Asn Pro Phe Gln Asp Asn Asn Ser His
 50                  55                  60

Gly Thr His Val Ala Gly Thr Val Ala Ala Leu Asn Asn Ser Ile Gly
 65                  70                  75                  80

Val Leu Gly Val Ala Pro Ser Ala Ser Leu Tyr Ala Val Lys Val Leu
                 85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Gln Tyr
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 2
<211> LENGTH: 269
<212> TYPE: PRT
<213> ORGANISM: Artificial Sequence
<220> FEATURE:
<223> OTHER INFORMATION: Chemically synthesized mature GCI-P036 protease

<400> SEQUENCE: 2

Ala Gln Ser Val Pro Trp Gly Ile Ser Arg Val Gln Ala Pro Ala Ala
  1               5                  10                  15

His Asn Arg Gly Leu Thr Gly Ser Gly Val Lys Val Ala Val Leu Asp
                 20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
```

```
            115                 120                 125
Pro Ser Ala Thr Leu Glu Gln Ala Val Asn Ser Ala Thr Ser Arg Gly
        130                 135                 140
Val Leu Val Val Ala Ala Ser Gly Asn Ser Gly Ala Gly Ser Ile Ser
145                 150                 155                 160
Tyr Pro Ala Arg Tyr Ala Asn Ala Met Ala Val Gly Ala Thr Asp Gln
                165                 170                 175
Asn Asn Asn Arg Ala Ser Phe Ser Gln Tyr Gly Ala Gly Leu Asp Ile
            180                 185                 190
Val Ala Pro Gly Val Asn Val Gln Ser Thr Tyr Pro Gly Ser Thr Tyr
        195                 200                 205
Ala Ser Leu Asn Gly Thr Ser Met Ala Thr Pro His Val Ala Gly Ala
    210                 215                 220
Ala Ala Leu Val Lys Gln Lys Asn Pro Ser Trp Ser Asn Val Gln Ile
225                 230                 235                 240
Arg Asn His Leu Lys Asn Thr Ala Thr Ser Leu Gly Ser Thr Asn Leu
                245                 250                 255
Tyr Gly Ser Gly Leu Val Asn Ala Glu Ala Ala Thr Arg
            260                 265

<210> SEQ ID NO 3
<211> LENGTH: 269
<212> TYPE: PRT
<213> ORGANISM: Artificial Sequence
<220> FEATURE:
<223> OTHER INFORMATION: Chemically synthesized GCI-P037 protease

<400> SEQUENCE: 3

Ala Gln Ser Val Pro Trp Gly Ile Ser Arg Val Gln Ala Pro Ala Ala
1               5                   10                  15
His Asn Arg Gly Leu Thr Gly Ser Gly Val Lys Val Ala Val Leu Asp
            20                  25                  30
Thr Gly Ile Ser Thr His Pro Asp Leu Asn Ile Arg Gly Gly Ala Ser
        35                  40                  45
Phe Val Pro Gly Glu Pro Ser Thr Gln Asp Gly Asn Gly His Gly Thr
    50                  55                  60
His Val Ala Gly Thr Ile Ala Ala Leu Asn Asn Ser Ile Gly Val Leu
65                  70                  75                  80
Gly Val Ala Pro Asn Ala Glu Leu Tyr Ala Val Lys Val Leu Gly Ala
                85                  90                  95
Ser Gly Ser Gly Ser Val Ser Ser Ile Ala Gln Gly Leu Glu Trp Ala
            100                 105                 110
Gly Asn Asn Gly Met His Val Ala Asn Leu Ser Leu Gly Ser Pro Ser
        115                 120                 125
Pro Ser Ala Thr Leu Glu Gln Ala Val Asn Ser Ala Thr Ser Arg Gly
    130                 135                 140
Val Leu Val Val Ala Ala Ser Gly Asn Ser Gly Ala Gly Ser Ile Ser
145                 150                 155                 160
Tyr Pro Ala Arg Tyr Ala Asn Ala Met Ala Val Gly Ala Thr Asp Gln
                165                 170                 175
Asn Asn Asn Arg Ala Ser Phe Ser Gln Tyr Gly Ala Gly Leu Asp Ile
            180                 185                 190
Val Ala Pro Gly Val Asn Val Gln Ser Thr Tyr Pro Gly Ser Thr Tyr
        195                 200                 205
Ala Ser Leu Asn Gly Thr Ser Met Ala Thr Pro His Val Ala Gly Ala
```

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265

<210> SEQ ID NO 4
<211> LENGTH: 269
<212> TYPE: PRT
<213> ORGANISM: Artificial Sequence
<220> FEATURE:
<223> OTHER INFORMATION: Chemically synthesized GCI-P038 protease

<400> SEQUENCE: 4

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Asn Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Val Met His Val Ala Asn Leu Ser Leu Gly Leu Gln Ala
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 5
<211> LENGTH: 1303
<212> TYPE: DNA
<213> ORGANISM: Artificial Sequence
<220> FEATURE:
<223> OTHER INFORMATION: Chemically synthesized oligonucleotide used in GCI-P036 Protease Production

<400> SEQUENCE: 5

```
atctcaaaaa aatgggtcta ctaaaatatt actccatcta ttataataaa ttcacagaat      60
agtcttttaa gtaagtctac tctgaatttt tttaaaagga gagggtaaag agtgagaagc     120
aaaaaattgt ggatcgtcgc gtcgaccgca ttgctgattt ctgttgcttt tagctcatcc     180
atcgcatccg ctgctgaaga agcaaaagaa aaatatttaa ttggctttaa tgagcaggaa     240
gctgtcagtg agtttgtaga acaagttgag gcaaatgacg aggtagccat tctctctgag     300
gaagaggaag tcgaaattga attgcttcat gaatttgaaa cgattcctgt tctgtccgtt     360
gagttaagcc cagaagatgt ggacgcgtta gagctcgatc cagctatttc ttatattgaa     420
gaggatgcag aagtaactac aatggcgcaa tcggtaccat ggggaattag cagagtacaa     480
gccccagctg cacataaccg tggattgaca ggttctggtg taaaagttgc tgtccttgat     540
accggtattt ccactcatcc agacttaaat attcgtggtg gagctagctt tgtaccaggg     600
gaaccatcca ctcaagatgg caatggacat ggcactcatg ttgccggcac aatcgcggct     660
cttaacaatt caattggtgt tcttggcgta gcgccaagcg cagaactata cgctgttaaa     720
gtattaggag caagcggttc aggctctgtc agctctattg cccaaggatt ggaatgggca     780
gggaacaatg gcatgcacgt tgctaatctt agtttaggat ctccttcgcc aagtgccaca     840
cttgagcaag ctgttaatag cgcgacttct agaggcgttc ttgttgtagc ggcctctgga     900
aattcaggtg caggctcaat cagctatccg gcccgttatg cgaacgctat ggcagtcgga     960
gctactgacc aaaacaacaa ccgcgccagc ttttcacagt atggcgcagg gcttgacatt    1020
gtcgcaccag gtgtaaacgt gcagagcact tacccaggtt caacatatgc cagcttaaac    1080
ggtacatcaa tggctactcc tcatgttgca ggtgcggctg cacttgttaa acaaaagaac    1140
ccatcttggt ccaatgtaca aatccgcaat catcttaaga atacggcaac tagcttagga    1200
agcacaaact tgtatggaag cggacttgtc aatgcagaag ctgcaactcg ttaaaagctt    1260
aactcgagat aaaaaaccgg ccttggcccc gccggttttt tat                      1303
```

<210> SEQ ID NO 6
<211> LENGTH: 380
<212> TYPE: PRT
<213> ORGANISM: ARTIFICIAL SEQUENCE
<220> FEATURE:
<223> OTHER INFORMATION: GCI-P036 precursor protein

<400> SEQUENCE: 6

```
Met Arg Ser Lys Lys Leu Trp Ile Val Ala Ser Thr Ala Leu Leu Ile
1               5                   10                  15

Ser Val Ala Phe Ser Ser Ser Ile Ala Ser Ala Glu Glu Ala Lys
            20                  25                  30

Glu Lys Tyr Leu Ile Gly Phe Asn Glu Gln Glu Ala Val Ser Glu Phe
        35                  40                  45

Val Glu Gln Val Glu Ala Asn Asp Glu Val Ala Ile Leu Ser Glu Glu
    50                  55                  60

Glu Glu Val Glu Ile Glu Leu Leu His Glu Phe Glu Thr Ile Pro Val
65                  70                  75                  80

Leu Ser Val Glu Leu Ser Pro Glu Asp Val Asp Ala Leu Glu Leu Asp
                85                  90                  95

Pro Ala Ile Ser Tyr Ile Glu Glu Asp Ala Glu Val Thr Thr Met Ala
            100                 105                 110
```

```
Gln Ser Val Pro Trp Gly Ile Ser Arg Val Gln Ala Pro Ala Ala His
            115                 120                 125
Asn Arg Gly Leu Thr Gly Ser Gly Val Lys Val Ala Val Leu Asp Thr
130                 135                 140
Gly Ile Ser Thr His Pro Asp Leu Asn Ile Arg Gly Gly Ala Ser Phe
145                 150                 155                 160
Val Pro Gly Glu Pro Ser Thr Gln Asp Gly Asn Gly His Gly Thr His
                165                 170                 175
Val Ala Gly Thr Ile Ala Ala Leu Asn Ser Ile Gly Val Leu Gly
            180                 185                 190
Val Ala Pro Ser Ala Glu Leu Tyr Ala Val Lys Val Leu Gly Ala Ser
            195                 200                 205
Gly Ser Gly Ser Val Ser Ser Ile Ala Gln Gly Leu Glu Trp Ala Gly
210                 215                 220
Asn Asn Gly Met His Val Ala Asn Leu Ser Leu Gly Ser Pro Ser Pro
225                 230                 235                 240
Ser Ala Thr Leu Glu Gln Ala Val Asn Ser Ala Thr Ser Arg Gly Val
                245                 250                 255
Leu Val Val Ala Ala Ser Gly Asn Ser Gly Ala Gly Ser Ile Ser Tyr
            260                 265                 270
Pro Ala Arg Tyr Ala Asn Ala Met Ala Val Gly Ala Thr Asp Gln Asn
            275                 280                 285
Asn Asn Arg Ala Ser Phe Ser Gln Tyr Gly Ala Gly Leu Asp Ile Val
290                 295                 300
Ala Pro Gly Val Asn Val Gln Ser Thr Tyr Pro Gly Ser Thr Tyr Ala
305                 310                 315                 320
Ser Leu Asn Gly Thr Ser Met Ala Thr Pro His Val Ala Gly Ala Ala
                325                 330                 335
Ala Leu Val Lys Gln Lys Asn Pro Ser Trp Ser Asn Val Gln Ile Arg
            340                 345                 350
Asn His Leu Lys Asn Thr Ala Thr Ser Leu Gly Ser Thr Asn Leu Tyr
            355                 360                 365
Gly Ser Gly Leu Val Asn Ala Glu Ala Ala Thr Arg
370                 375                 380
```

<210> SEQ ID NO 7
<211> LENGTH: 1148
<212> TYPE: DNA
<213> ORGANISM: ARTIFICIAL SEQUENCE
<220> FEATURE:
<223> OTHER INFORMATION: Chemically synthesized oligonucleotide used in
      GCI-P036 Protease Production

<400> SEQUENCE: 7

```
gtgagaagca aaaaattgtg gatcgtcgcg tcgaccgcac tactcatttc tgttgctttc      60
agttcatcga tcgcatcggc tgctgaagaa gcaaaagaaa atatttaat tggctttaat     120 gagcaggaag ctgtcagtga gtttgtagaa caagtagagg caaatgacga ggtcgccatt    180
ctctctgagg aagaggaagt cgaaattgaa ttgcttcatg aatttgaaac gattcctgtt    240
ttatccgttg agttaagccc agaagatgtg acgcgcttg agctcgatcc agcgatttct     300
tatattgaag aggatgcaga agtaacgaca atggcgcaat cagtgccatg gggaattagc    360
cgtgtgcaag ccccagctgc ccataaccgt ggattgacag ttctggtgt aaaagttgct    420 gtcctcgata caggtatttc cactcatcca gacttaaata ttcgtggtgg cgctagcttt   480
gtaccagggg aaccatccac tcaagatggg aatgggcatg gcacgcatgt ggccgggacg   540
```

| | |
|---|---|
| attgctgctt taaacaattc gattggcgtt cttggcgtag cgccgagcgc ggaactatac | 600 |
| gctgttaaag tattaggggc gagcggttca ggttcggtca gctcgattgc ccaaggattg | 660 |
| gaatgggcag ggaacaatgg catgcacgtt gctaatttga gtttaggaag cccttcgcca | 720 |
| agtgccacac ttgagcaagc tgttaatagc gcgacttcta gaggcgttct tgttgtagcg | 780 |
| gcatctggaa attcaggtgc aggctcaatc agctatccgg cccgttatgc gaacgcaatg | 840 |
| gcagtcggag ctactgacca aaacaacaac cgcgccagct tttcacagta tggcgcaggg | 900 |
| cttgacattg tcgcaccagg tgtaaacgtg cagagcacat acccaggttc aacgtatgcc | 960 |
| agcttaaacg gtacatcgat ggctactcct catgttgcag gtgcagcagc ccttgttaaa | 1020 |
| caaaagaacc catcttggtc caatgtacaa atccgcaatc atctaaagaa tacggcaacg | 1080 |
| agcttaggaa gcacgaactt gtatggaagc ggacttgtca atgcagaagc tgcaactcgt | 1140 |
| taaagctt | 1148 |

<210> SEQ ID NO 8
<211> LENGTH: 1797
<212> TYPE: DNA
<213> ORGANISM: Artificial Sequence
<220> FEATURE:
<223> OTHER INFORMATION: Chemically synthesized GCI-P036ci sequence of p2JH-GCI-P036ci

<400> SEQUENCE: 8

| | |
|---|---|
| aattctccat tttcttctgc tatcaaaata acagactcgt gattttccaa acgagctttc | 60 |
| aaaaaagcct ctgccccttg caaatcggat gcctgtctat aaaattcccg atattggtta | 120 |
| aacagcggcg caatggcggc cgcatctgat gtctttgctt ggcgaatgtt catcttattt | 180 |
| cttcctccct ctcaataatt ttttcattct atcccttttc tgtaaagttt atttttcaga | 240 |
| atacttttat catcatgctt tgaaaaaata tcacgataat atccattgtt ctcacggaag | 300 |
| cacacgcagg tcatttgaac gaattttttc gacaggaatt tgccgggact caggagcatt | 360 |
| taacctaaaa aagcatgaca tttcagcata atgaacattt actcatgtct attttcgttc | 420 |
| ttttctgtat gaaaatagtt atttcgagtc tctacgaaaa tagcgagaga tgatatacct | 480 |
| aaatagagat aaaatcatct caaaaaaatg ggtctactaa aatattattc catctattac | 540 |
| aataaattca cagaatagtc ttttaagtaa gtctactctg aattttttta aaaggagagg | 600 |
| gtaaagagtg agaagcaaaa aattgtggat cgtcgcgtcg accgcattgc tgatttctgt | 660 |
| tgcttttagc tcatccatcg catccgctgc tgaagaagca aaagaaaaat atttaattgg | 720 |
| ctttaatgag caggaagctg tcagtgagtt tgtagaacaa gttgaggcaa atgacgaggt | 780 |
| agccattctc tctgaggaag aggaagtcga aattgaattg cttcatgaat ttgaaacgat | 840 |
| tcctgttctg tccgttgagt taagcccaga agatgtggac gcgttagagc tcgatccagc | 900 |
| tatttcttat attgaagagg atgcagaagt aactacaatg gcgcaatcgg taccatgggg | 960 |
| aattagcaga gtacaagccc cagctgcaca taaccgtgga ttgacaggtt ctggtgtaaa | 1020 |
| agttgctgtc cttgataccg gtatttccac tcatccagac ttaaatattc gtggtggagc | 1080 |
| tagctttgta ccaggggaac catccactca agatggcaat ggacatggca tcatgttgc | 1140 |
| cggcacaatc gcggctctta caattcaat tggtgttctt ggcgtagcgc aagcgcaga | 1200 |
| actatacgct gttaaagtat taggagcaag cggttcaggc tctgtcagct ctattgccca | 1260 |
| aggattggaa tgggcaggga acaatggcat gcacgttgct aatcttagtt taggatctcc | 1320 |
| ttcgccaagt gccacacttg agcaagctgt taatagcgcg acttctagag gcgttcttgt | 1380 |

```
tgtagcggcc tctggaaatt caggtgcagg ctcaatcagc tatccggccc gttatgcgaa    1440
cgctatggca gtcggagcta ctgaccaaaa caacaaccgc gccagctttt cacagtatgg    1500
cgcagggctt gacattgtcg caccaggtgt aaacgtgcag agcacttacc caggttcaac    1560
atatgccagc ttaaacggta catcaatggc tactcctcat gttgcaggtg cggctgcact    1620
tgttaaacaa agaacccat cttggtccaa tgtacaaatc cgcaatcatc ttaagaatac     1680
ggcaactagc ttaggaagca caaacttgta tggaagcgga cttgtcaatg cagaagctgc    1740
aactcgttaa aagcttaact cgagataaaa accggcctt ggccccgccg gttttt         1797
```

<210> SEQ ID NO 9
<211> LENGTH: 35
<212> TYPE: DNA
<213> ORGANISM: Artificial Sequence
<220> FEATURE:
<223> OTHER INFORMATION: Synthetic primer: S126A-F

<400> SEQUENCE: 9

```
ctaatcttag tttaggagct ccttcgccaa gtgcc                                35
```

<210> SEQ ID NO 10
<211> LENGTH: 35
<212> TYPE: DNA
<213> ORGANISM: Artificial Sequence
<220> FEATURE:
<223> OTHER INFORMATION: Synthetic primer: S126A-R

<400> SEQUENCE: 10

```
ggcacttggc gaaggagctc ctaaactaag attag                                35
```

<210> SEQ ID NO 11
<211> LENGTH: 41
<212> TYPE: DNA
<213> ORGANISM: Artificial Sequence
<220> FEATURE:
<223> OTHER INFORMATION: Synthetic primer: S126C-F

<400> SEQUENCE: 11

```
cacgttgcta atcttagttt aggatgccct tcgccaagtg c                         41
```

<210> SEQ ID NO 12
<211> LENGTH: 41
<212> TYPE: DNA
<213> ORGANISM: Artificial Sequence
<220> FEATURE:
<223> OTHER INFORMATION: Synthetic primer: S126C-R

<400> SEQUENCE: 12

```
gcacttggcg aagggcatcc taaactaaga ttagcaacgt g                         41
```

<210> SEQ ID NO 13
<211> LENGTH: 41
<212> TYPE: DNA
<213> ORGANISM: Artificial Sequence
<220> FEATURE:
<223> OTHER INFORMATION: Synthetic primer: S126D-F

<400> SEQUENCE: 13

```
gcacgttgct aatcttagtt taggagatcc ttcgccaagt g                         41
```

<210> SEQ ID NO 14
<211> LENGTH: 41
<212> TYPE: DNA

```
<213> ORGANISM: Artificial Sequence
<220> FEATURE:
<223> OTHER INFORMATION: Synthetic primer: S126D-R

<400> SEQUENCE: 14
cacttggcga aggatctcct aaactaagat tagcaacgtg c                    41

<210> SEQ ID NO 15
<211> LENGTH: 46
<212> TYPE: DNA
<213> ORGANISM: Artificial Sequence
<220> FEATURE:
<223> OTHER INFORMATION: Synthetic primer: S126E-F

<400> SEQUENCE: 15
catgcacgtt gctaatctta gtttaggaga accttcgcca agtgcc               46

<210> SEQ ID NO 16
<211> LENGTH: 46
<212> TYPE: DNA
<213> ORGANISM: Artificial Sequence
<220> FEATURE:
<223> OTHER INFORMATION: Synthetic primer: S126E-R

<400> SEQUENCE: 16
ggcacttggc gaaggttctc ctaaactaag attagcaacg tgcatg               46

<210> SEQ ID NO 17
<211> LENGTH: 41
<212> TYPE: DNA
<213> ORGANISM: Artificial Sequence
<220> FEATURE:
<223> OTHER INFORMATION: Synthetic primer: S126F-F

<400> SEQUENCE: 17
cacgttgcta atcttagttt aggattccct tcgccaagtg c                    41

<210> SEQ ID NO 18
<211> LENGTH: 41
<212> TYPE: DNA
<213> ORGANISM: Artificial Sequence
<220> FEATURE:
<223> OTHER INFORMATION: Synthetic primer: S126F-R

<400> SEQUENCE: 18
gcacttggcg aagggaatcc taaactaaga ttagcaacgt g                    41

<210> SEQ ID NO 19
<211> LENGTH: 46
<212> TYPE: DNA
<213> ORGANISM: Artificial Sequence
<220> FEATURE:
<223> OTHER INFORMATION: Synthetic primer: S126G-F

<400> SEQUENCE: 19
catgcacgtt gctaatctta gtttaggagg cccttcgcca agtgcc               46

<210> SEQ ID NO 20
<211> LENGTH: 46
<212> TYPE: DNA
<213> ORGANISM: Artificial Sequence
<220> FEATURE:
<223> OTHER INFORMATION: Synthetic primer: S126G-R

<400> SEQUENCE: 20
ggcacttggc gaagggcctc ctaaactaag attagcaacg tgcatg               46
```

<210> SEQ ID NO 21
<211> LENGTH: 46
<212> TYPE: DNA
<213> ORGANISM: Artificial Sequence
<220> FEATURE:
<223> OTHER INFORMATION: Synthetic primer: S126H-F

<400> SEQUENCE: 21
catgcacgtt gctaatctta gtttaggaca cccttcgcca agtgcc        46

<210> SEQ ID NO 22
<211> LENGTH: 46
<212> TYPE: DNA
<213> ORGANISM: Artificial Sequence
<220> FEATURE:
<223> OTHER INFORMATION: Synthetic primer: S126H-R

<400> SEQUENCE: 22
ggcacttggc gaagggtgtc ctaaactaag attagcaacg tgcatg        46

<210> SEQ ID NO 23
<211> LENGTH: 46
<212> TYPE: DNA
<213> ORGANISM: Artificial Sequence
<220> FEATURE:
<223> OTHER INFORMATION: Synthetic primer: S126I-F

<400> SEQUENCE: 23
catgcacgtt gctaatctta gtttaggaat cccttcgcca agtgcc        46

<210> SEQ ID NO 24
<211> LENGTH: 46
<212> TYPE: DNA
<213> ORGANISM: Artificial Sequence
<220> FEATURE:
<223> OTHER INFORMATION: Synthetic primer: S126I-R

<400> SEQUENCE: 24
ggcacttggc gaagggattc ctaaactaag attagcaacg tgcatg        46

<210> SEQ ID NO 25
<211> LENGTH: 46
<212> TYPE: DNA
<213> ORGANISM: Artificial Sequence
<220> FEATURE:
<223> OTHER INFORMATION: Synthetic primer: S126K-F

<400> SEQUENCE: 25
catgcacgtt gctaatctta gtttaggaaa accttcgcca agtgcc        46

<210> SEQ ID NO 26
<211> LENGTH: 46
<212> TYPE: DNA
<213> ORGANISM: Artificial Sequence
<220> FEATURE:
<223> OTHER INFORMATION: Synthetic primer: S126K-R

<400> SEQUENCE: 26
ggcacttggc gaaggttttc ctaaactaag attagcaacg tgcatg        46

<210> SEQ ID NO 27
<211> LENGTH: 41
<212> TYPE: DNA
<213> ORGANISM: Artificial Sequence
<220> FEATURE:

<223> OTHER INFORMATION: Synthetic primer: S126L-F

<400> SEQUENCE: 27
gcacgttgct aatcttagtt taggacttcc ttcgccaagt g                41

<210> SEQ ID NO 28
<211> LENGTH: 41
<212> TYPE: DNA
<213> ORGANISM: Artificial Sequence
<220> FEATURE:
<223> OTHER INFORMATION: Synthetic primer: S126L-R

<400> SEQUENCE: 28
cacttggcga aggaagtcct aaactaagat tagcaacgtg c                41

<210> SEQ ID NO 29
<211> LENGTH: 46
<212> TYPE: DNA
<213> ORGANISM: Artificial Sequence
<220> FEATURE:
<223> OTHER INFORMATION: Synthetic primer: S126M-F

<400> SEQUENCE: 29
catgcacgtt gctaatctta gtttaggaat gccttcgcca agtgcc            46

<210> SEQ ID NO 30
<211> LENGTH: 46
<212> TYPE: DNA
<213> ORGANISM: Artificial Sequence
<220> FEATURE:
<223> OTHER INFORMATION: Synthetic primer: S126M-R

<400> SEQUENCE: 30
ggcacttggc gaaggcattc ctaaactaag attagcaacg tgcatg            46

<210> SEQ ID NO 31
<211> LENGTH: 46
<212> TYPE: DNA
<213> ORGANISM: Artificial Sequence
<220> FEATURE:
<223> OTHER INFORMATION: Synthetic primer: S126N-F

<400> SEQUENCE: 31
catgcacgtt gctaatctta gtttaggaaa cccttcgcca agtgcc            46

<210> SEQ ID NO 32
<211> LENGTH: 46
<212> TYPE: DNA
<213> ORGANISM: Artificial Sequence
<220> FEATURE:
<223> OTHER INFORMATION: Synthetic primer: S126N-R

<400> SEQUENCE: 32
ggcacttggc gaagggtttc ctaaactaag attagcaacg tgcatg            46

<210> SEQ ID NO 33
<211> LENGTH: 35
<212> TYPE: DNA
<213> ORGANISM: Artificial Sequence
<220> FEATURE:
<223> OTHER INFORMATION: Synthetic primer: S126P-F

<400> SEQUENCE: 33
ctaatcttag tttaggacct ccttcgccaa gtgcc                       35

```
<210> SEQ ID NO 34
<211> LENGTH: 35
<212> TYPE: DNA
<213> ORGANISM: Artificial Sequence
<220> FEATURE:
<223> OTHER INFORMATION: Synthetic primer: S126P-R

<400> SEQUENCE: 34
ggcacttggc gaaggaggtc ctaaactaag attag                             35

<210> SEQ ID NO 35
<211> LENGTH: 46
<212> TYPE: DNA
<213> ORGANISM: Artificial Sequence
<220> FEATURE:
<223> OTHER INFORMATION: Synthetic primer: S126Q-F

<400> SEQUENCE: 35
catgcacgtt gctaatctta gtttaggaca accttcgcca agtgcc                 46

<210> SEQ ID NO 36
<211> LENGTH: 46
<212> TYPE: DNA
<213> ORGANISM: Artificial Sequence
<220> FEATURE:
<223> OTHER INFORMATION: Synthetic primer: S126Q-R

<400> SEQUENCE: 36
ggcacttggc gaaggttgtc ctaaactaag attagcaacg tgcatg                 46

<210> SEQ ID NO 37
<211> LENGTH: 46
<212> TYPE: DNA
<213> ORGANISM: Artificial Sequence
<220> FEATURE:
<223> OTHER INFORMATION: Synthetic primer: S126R-F

<400> SEQUENCE: 37
catgcacgtt gctaatctta gtttaggaag accttcgcca agtgcc                 46

<210> SEQ ID NO 38
<211> LENGTH: 46
<212> TYPE: DNA
<213> ORGANISM: Artificial Sequence
<220> FEATURE:
<223> OTHER INFORMATION: Synthetic primer: S126R-R

<400> SEQUENCE: 38
ggcacttggc gaaggtcttc ctaaactaag attagcaacg tgcatg                 46

<210> SEQ ID NO 39
<211> LENGTH: 40
<212> TYPE: DNA
<213> ORGANISM: Artificial Sequence
<220> FEATURE:
<223> OTHER INFORMATION: Synthetic primer: S126T-F

<400> SEQUENCE: 39
cacgttgcta atcttagttt aggaacacct tcgccaagtg                        40

<210> SEQ ID NO 40
<211> LENGTH: 40
<212> TYPE: DNA
<213> ORGANISM: Artificial Sequence
<220> FEATURE:
<223> OTHER INFORMATION: Synthetic primer: S126T-R
```

```
<400> SEQUENCE: 40
cacttggcga aggtgttcct aaactaagat tagcaacgtg                               40

<210> SEQ ID NO 41
<211> LENGTH: 41
<212> TYPE: DNA
<213> ORGANISM: Artificial Sequence
<220> FEATURE:
<223> OTHER INFORMATION: Synthetic primer: S126V-F

<400> SEQUENCE: 41
gcacgttgct aatcttagtt taggagttcc ttcgccaagt g                            41

<210> SEQ ID NO 42
<211> LENGTH: 41
<212> TYPE: DNA
<213> ORGANISM: Artificial Sequence
<220> FEATURE:
<223> OTHER INFORMATION: Synthetic primer: S126V-R

<400> SEQUENCE: 42
cacttggcga aggaactcct aaactaagat tagcaacgtg c                            41

<210> SEQ ID NO 43
<211> LENGTH: 41
<212> TYPE: DNA
<213> ORGANISM: Artificial Sequence
<220> FEATURE:
<223> OTHER INFORMATION: Synthetic primer: S126W-F

<400> SEQUENCE: 43
cacgttgcta atcttagttt aggatggcct tcgccaagtg c                            41

<210> SEQ ID NO 44
<211> LENGTH: 41
<212> TYPE: DNA
<213> ORGANISM: Artificial Sequence
<220> FEATURE:
<223> OTHER INFORMATION: Synthetic primer: S126W-R

<400> SEQUENCE: 44
gcacttggcg aaggccatcc taaactaaga ttagcaacgt g                            41

<210> SEQ ID NO 45
<211> LENGTH: 41
<212> TYPE: DNA
<213> ORGANISM: Artificial Sequence
<220> FEATURE:
<223> OTHER INFORMATION: Synthetic primer: S126Y-F

<400> SEQUENCE: 45
cacgttgcta atcttagttt aggatacc ct tcgccaagtg c                           41

<210> SEQ ID NO 46
<211> LENGTH: 41
<212> TYPE: DNA
<213> ORGANISM: Artificial Sequence
<220> FEATURE:
<223> OTHER INFORMATION: Synthetic primer: S126Y-R

<400> SEQUENCE: 46
gcacttggcg aagggtatcc taaactaaga ttagcaacgt g                            41

<210> SEQ ID NO 47
<211> LENGTH: 42
```

-continued

<210> SEQ ID NO 47
<211> LENGTH: 42
<212> TYPE: DNA
<213> ORGANISM: Artificial Sequence
<220> FEATURE:
<223> OTHER INFORMATION: Synthetic primer: S9L-F

<400> SEQUENCE: 47
gcaatcggta ccatggggaa ttcttagagt acaagcccca gc                              42

<210> SEQ ID NO 48
<211> LENGTH: 42
<212> TYPE: DNA
<213> ORGANISM: Artificial Sequence
<220> FEATURE:
<223> OTHER INFORMATION: Synthetic primer: S9L-R

<400> SEQUENCE: 48
gctggggctt gtactctaag aattccccat ggtaccgatt gc                              42

<210> SEQ ID NO 49
<211> LENGTH: 34
<212> TYPE: DNA
<213> ORGANISM: Artificial Sequence
<220> FEATURE:
<223> OTHER INFORMATION: Synthetic primer: S9G-F

<400> SEQUENCE: 49
aatcggtacc atggggaatt ggcagagtac aagc                                      34

<210> SEQ ID NO 50
<211> LENGTH: 34
<212> TYPE: DNA
<213> ORGANISM: Artificial Sequence
<220> FEATURE:
<223> OTHER INFORMATION: Synthetic primer: S9G-R

<400> SEQUENCE: 50
gcttgtactc tgccaattcc ccatggtacc gatt                                      34

<210> SEQ ID NO 51
<211> LENGTH: 39
<212> TYPE: DNA
<213> ORGANISM: Artificial Sequence
<220> FEATURE:
<223> OTHER INFORMATION: Synthetic primer: A106C-F

<400> SEQUENCE: 51
caggctctgt cagctctatt tgccaaggat tggaatggg                                 39

<210> SEQ ID NO 52
<211> LENGTH: 39
<212> TYPE: DNA
<213> ORGANISM: Artificial Sequence
<220> FEATURE:
<223> OTHER INFORMATION: Synthetic primer: A106C-R

<400> SEQUENCE: 52
cccattccaa tccttggcaa atagagctga cagagcctg                                 39

<210> SEQ ID NO 53
<211> LENGTH: 37
<212> TYPE: DNA
<213> ORGANISM: Artificial Sequence
<220> FEATURE:
<223> OTHER INFORMATION: Synthetic primer: A106I-F

<400> SEQUENCE: 53

```
ggaacaatgg catgcacgct gctaatctta gtttagg                                    37
```

<210> SEQ ID NO 54
<211> LENGTH: 37
<212> TYPE: DNA
<213> ORGANISM: Artificial Sequence
<220> FEATURE:
<223> OTHER INFORMATION: Synthetic primer: A106I-R

<400> SEQUENCE: 54

```
cctaaactaa gattagcagc gtgcatgcca ttgttcc                                    37
```

<210> SEQ ID NO 55
<211> LENGTH: 43
<212> TYPE: DNA
<213> ORGANISM: Artificial Sequence
<220> FEATURE:
<223> OTHER INFORMATION: Synthetic primer: A106M-F

<400> SEQUENCE: 55

```
tcaggctctg tcagctctat tatgcaagga ttggaatggg cag                             43
```

<210> SEQ ID NO 56
<211> LENGTH: 43
<212> TYPE: DNA
<213> ORGANISM: Artificial Sequence
<220> FEATURE:
<223> OTHER INFORMATION: Synthetic primer: A106M-R

<400> SEQUENCE: 56

```
ctgcccattc caatccttgc ataatagagc tgacagagcc tga                             43
```

<210> SEQ ID NO 57
<211> LENGTH: 39
<212> TYPE: DNA
<213> ORGANISM: Artificial Sequence
<220> FEATURE:
<223> OTHER INFORMATION: Synthetic primer: V119A-F

<400> SEQUENCE: 57

```
caggctctgt cagctctatt atccaaggat tggaatggg                                  39
```

<210> SEQ ID NO 58
<211> LENGTH: 39
<212> TYPE: DNA
<213> ORGANISM: Artificial Sequence
<220> FEATURE:
<223> OTHER INFORMATION: Synthetic primer: V119A-R

<400> SEQUENCE: 58

```
cccattccaa tccttggata atagagctga cagagcctg                                  39
```

<210> SEQ ID NO 59
<211> LENGTH: 39
<212> TYPE: DNA
<213> ORGANISM: Artificial Sequence
<220> FEATURE:
<223> OTHER INFORMATION: Synthetic primer: L124F-F

<400> SEQUENCE: 59

```
gcatgcacgt tgctaatctt agtttcggat ctccttcgc                                  39
```

<210> SEQ ID NO 60
<211> LENGTH: 39
<212> TYPE: DNA
<213> ORGANISM: Artificial Sequence

```
<220> FEATURE:
<223> OTHER INFORMATION: Synthetic primer: L124F-R

<400> SEQUENCE: 60
gcgaaggaga tccgaaacta agattagcaa cgtgcatgc                              39

<210> SEQ ID NO 61
<211> LENGTH: 47
<212> TYPE: DNA
<213> ORGANISM: Artificial Sequence
<220> FEATURE:
<223> OTHER INFORMATION: Synthetic primer: L124N-F

<400> SEQUENCE: 61
acaatggcat gcacgttgct aatcttagta acggatctcc ttcgcca                    47

<210> SEQ ID NO 62
<211> LENGTH: 47
<212> TYPE: DNA
<213> ORGANISM: Artificial Sequence
<220> FEATURE:
<223> OTHER INFORMATION: Synthetic primer: L124N-R

<400> SEQUENCE: 62
tggcgaagga gatccgttac taagattagc aacgtgcatg ccattgt                    47

<210> SEQ ID NO 63
<211> LENGTH: 47
<212> TYPE: DNA
<213> ORGANISM: Artificial Sequence
<220> FEATURE:
<223> OTHER INFORMATION: Synthetic primer: G125S-F

<400> SEQUENCE: 63
atggcatgca cgttgctaat cttagtttat cttctccttc gccaagt                    47

<210> SEQ ID NO 64
<211> LENGTH: 47
<212> TYPE: DNA
<213> ORGANISM: Artificial Sequence
<220> FEATURE:
<223> OTHER INFORMATION: Synthetic primer: G125S-R

<400> SEQUENCE: 64
acttggcgaa ggagaagata aactaagatt agcaacgtgc atgccat                    47

<210> SEQ ID NO 65
<211> LENGTH: 29
<212> TYPE: DNA
<213> ORGANISM: Artificial Sequence
<220> FEATURE:
<223> OTHER INFORMATION: Synthetic primer: N167H-F

<400> SEQUENCE: 65
cggcccgtta tgcgcacgct atggcagtc                                        29

<210> SEQ ID NO 66
<211> LENGTH: 29
<212> TYPE: DNA
<213> ORGANISM: Artificial Sequence
<220> FEATURE:
<223> OTHER INFORMATION: Synthetic primer: N167H-R

<400> SEQUENCE: 66
gactgccata gcgtgcgcat aacgggccg                                        29
```

<210> SEQ ID NO 67
<211> LENGTH: 44
<212> TYPE: DNA
<213> ORGANISM: Artificial Sequence
<220> FEATURE:
<223> OTHER INFORMATION: Synthetic primer: V28A-F

<400> SEQUENCE: 67
gttctggtgt aaaagctgct gtccttgata ccggtatttc cact                    44

<210> SEQ ID NO 68
<211> LENGTH: 44
<212> TYPE: DNA
<213> ORGANISM: Artificial Sequence
<220> FEATURE:
<223> OTHER INFORMATION: Synthetic primer: V28A-R

<400> SEQUENCE: 68
caagaccaca ttttcgacga caggaactat ggccataaag gtga                    44

<210> SEQ ID NO 69
<211> LENGTH: 44
<212> TYPE: DNA
<213> ORGANISM: Artificial Sequence
<220> FEATURE:
<223> OTHER INFORMATION: Synthetic primer: V30A-F

<400> SEQUENCE: 69
gttctggtgt aaaagttgct gctcttgata ccggtatttc cact                    44

<210> SEQ ID NO 70
<211> LENGTH: 44
<212> TYPE: DNA
<213> ORGANISM: Artificial Sequence
<220> FEATURE:
<223> OTHER INFORMATION: Synthetic primer: V30A-R

<400> SEQUENCE: 70
agtggaaata ccggtatcaa gagcagcaac ttttacacca gaac                    44

<210> SEQ ID NO 71
<211> LENGTH: 38
<212> TYPE: DNA
<213> ORGANISM: Artificial Sequence
<220> FEATURE:
<223> OTHER INFORMATION: Synthetic primer: N60S-F

<400> SEQUENCE: 71
ccatccactc aagatggctc tggacatggc actcatgt                           38

<210> SEQ ID NO 72
<211> LENGTH: 38
<212> TYPE: DNA
<213> ORGANISM: Artificial Sequence
<220> FEATURE:
<223> OTHER INFORMATION: Synthetic primer: N60S-R

<400> SEQUENCE: 72
acatgagtgc catgtccaga gccatcttga gtggatgg                           38

<210> SEQ ID NO 73
<211> LENGTH: 45
<212> TYPE: DNA
<213> ORGANISM: Artificial Sequence
<220> FEATURE:
<223> OTHER INFORMATION: Synthetic primer: V91T-F

<400> SEQUENCE: 73
ccaagcgcag aactatacgc tacaaaagta ttaggagcaa gcggt    45

<210> SEQ ID NO 74
<211> LENGTH: 45
<212> TYPE: DNA
<213> ORGANISM: Artificial Sequence
<220> FEATURE:
<223> OTHER INFORMATION: Synthetic primer: V91T-R

<400> SEQUENCE: 74
accgcttgct cctaatactt ttgtagcgta tagttctgcg cttgg    45

<210> SEQ ID NO 75
<211> LENGTH: 46
<212> TYPE: DNA
<213> ORGANISM: Artificial Sequence
<220> FEATURE:
<223> OTHER INFORMATION: Synthetic primer: L94A-F

<400> SEQUENCE: 75
aagcgcagaa ctatacgctg ttaaagtagc tggagcaagc ggttca    46

<210> SEQ ID NO 76
<211> LENGTH: 46
<212> TYPE: DNA
<213> ORGANISM: Artificial Sequence
<220> FEATURE:
<223> OTHER INFORMATION: Synthetic primer: L94A-R

<400> SEQUENCE: 76
tgaaccgctt gctccagcta ctttaacagc gtatagttct gcgctt    46

<210> SEQ ID NO 77
<211> LENGTH: 47
<212> TYPE: DNA
<213> ORGANISM: Artificial Sequence
<220> FEATURE:
<223> OTHER INFORMATION: Synthetic primer: G95P-F

<400> SEQUENCE: 77
gcgcagaact atacgctgtt aaagtattac ctgcaagcgg ttcaggc    47

<210> SEQ ID NO 78
<211> LENGTH: 47
<212> TYPE: DNA
<213> ORGANISM: Artificial Sequence
<220> FEATURE:
<223> OTHER INFORMATION: Synthetic primer: G95P-R

<400> SEQUENCE: 78
gcctgaaccg cttgcaggta atactttaac agcgtatagt tctgcgc    47

<210> SEQ ID NO 79
<211> LENGTH: 38
<212> TYPE: DNA
<213> ORGANISM: Artificial Sequence
<220> FEATURE:
<223> OTHER INFORMATION: Synthetic primer: I105F-F

<400> SEQUENCE: 79
gttcaggctc tgtcagctct ttcgcccaag gattggaa    38

<210> SEQ ID NO 80

-continued

```
<211> LENGTH: 38
<212> TYPE: DNA
<213> ORGANISM: Artificial Sequence
<220> FEATURE:
<223> OTHER INFORMATION: Synthetic primer: I105F-R

<400> SEQUENCE: 80
ttccaatcct tgggcgaaag agctgacaga gcctgaac                                38

<210> SEQ ID NO 81
<211> LENGTH: 43
<212> TYPE: DNA
<213> ORGANISM: Artificial Sequence
<220> FEATURE:
<223> OTHER INFORMATION: Synthetic primer: G113M-F

<400> SEQUENCE: 81
tcaggctctg tcagctctat tatgcaagga ttggaatggg cag                          43

<210> SEQ ID NO 82
<211> LENGTH: 43
<212> TYPE: DNA
<213> ORGANISM: Artificial Sequence
<220> FEATURE:
<223> OTHER INFORMATION: Synthetic primer: G113M-R

<400> SEQUENCE: 82
ctgcccattc caatccttgc ataatagagc tgacagagcc tga                          43

<210> SEQ ID NO 83
<211> LENGTH: 40
<212> TYPE: DNA
<213> ORGANISM: Artificial Sequence
<220> FEATURE:
<223> OTHER INFORMATION: Synthetic primer: S123A-F

<400> SEQUENCE: 83
catgcacgtt gctaatcttg ctttaggatc tccttcgcca                              40

<210> SEQ ID NO 84
<211> LENGTH: 24
<212> TYPE: DNA
<213> ORGANISM: Artificial Sequence
<220> FEATURE:
<223> OTHER INFORMATION: Synthetic primer: S123A-R

<400> SEQUENCE: 84
tggcgaagga gatcctaaag caag                                               24

<210> SEQ ID NO 85
<211> LENGTH: 39
<212> TYPE: DNA
<213> ORGANISM: Artificial Sequence
<220> FEATURE:
<223> OTHER INFORMATION: Synthetic primer: S130N-F

<400> SEQUENCE: 85
tttaggatct ccttcgccaa acgccacact tgagcaagc                               39

<210> SEQ ID NO 86
<211> LENGTH: 39
<212> TYPE: DNA
<213> ORGANISM: Artificial Sequence
<220> FEATURE:
<223> OTHER INFORMATION: Synthetic primer: S130N-R

<400> SEQUENCE: 86
```
gcttgctcaa gtgtggcgtt tggcgaagga gatcctaaa    39

<210> SEQ ID NO 87
<211> LENGTH: 35
<212> TYPE: DNA
<213> ORGANISM: Artificial Sequence
<220> FEATURE:
<223> OTHER INFORMATION: Synthetic primer: V145I-F

<400> SEQUENCE: 87
cgcgacttct agaggcatcc ttgttgtagc ggcct    35

<210> SEQ ID NO 88
<211> LENGTH: 35
<212> TYPE: DNA
<213> ORGANISM: Artificial Sequence
<220> FEATURE:
<223> OTHER INFORMATION: Synthetic primer: V145I-R

<400> SEQUENCE: 88
aggccgctac aacaaggatg cctctagaag tcgcg    35

<210> SEQ ID NO 89
<211> LENGTH: 37
<212> TYPE: DNA
<213> ORGANISM: Artificial Sequence
<220> FEATURE:
<223> OTHER INFORMATION: Synthetic primer: F183G-F

<400> SEQUENCE: 89
acaacaaccg cgccagcggc tcacagtatg gcgcagg    37

<210> SEQ ID NO 90
<211> LENGTH: 37
<212> TYPE: DNA
<213> ORGANISM: Artificial Sequence
<220> FEATURE:
<223> OTHER INFORMATION: Synthetic primer: F183G-R

<400> SEQUENCE: 90
cctgcgccat actgtgagcc gctggcgcgg ttgttgt    37

<210> SEQ ID NO 91
<211> LENGTH: 27
<212> TYPE: DNA
<213> ORGANISM: Artificial Sequence
<220> FEATURE:
<223> OTHER INFORMATION: Synthetic primer: I192L-F

<400> SEQUENCE: 91
cgcagggctt gaccttgtcg caccagg    27

<210> SEQ ID NO 92
<211> LENGTH: 27
<212> TYPE: DNA
<213> ORGANISM: Artificial Sequence
<220> FEATURE:
<223> OTHER INFORMATION: Synthetic primer: I192L-R

<400> SEQUENCE: 92
cctggtgcga caaggtcaag ccctgcg    27

<210> SEQ ID NO 93
<211> LENGTH: 40
<212> TYPE: DNA

```
<213> ORGANISM: Artificial Sequence
<220> FEATURE:
<223> OTHER INFORMATION: Synthetic primer: T218N-F

<400> SEQUENCE: 93
aaacggtaca tcaatggcta accctcatgt tgcaggtgcg                           40

<210> SEQ ID NO 94
<211> LENGTH: 40
<212> TYPE: DNA
<213> ORGANISM: Artificial Sequence
<220> FEATURE:
<223> OTHER INFORMATION: Synthetic primer: T218N-R

<400> SEQUENCE: 94
cgcacctgca acatgagggt tagccattga tgtaccgttt                           40

<210> SEQ ID NO 95
<211> LENGTH: 33
<212> TYPE: DNA
<213> ORGANISM: Artificial Sequence
<220> FEATURE:
<223> OTHER INFORMATION: Synthetic primer: A222G-F

<400> SEQUENCE: 95
gctactcctc atgttggcgg tgcggctgca ctt                                  33

<210> SEQ ID NO 96
<211> LENGTH: 33
<212> TYPE: DNA
<213> ORGANISM: Artificial Sequence
<220> FEATURE:
<223> OTHER INFORMATION: Synthetic primer: A222G-R

<400> SEQUENCE: 96
aagtgcagcc gcaccgccaa catgaggagt agc                                  33

<210> SEQ ID NO 97
<211> LENGTH: 20
<212> TYPE: DNA
<213> ORGANISM: Artificial Sequence
<220> FEATURE:
<223> OTHER INFORMATION: Synthetic primer: ISH-PCR-GCI-P036-5832F

<400> SEQUENCE: 97
acaaataggg gttccgcgca                                                 20

<210> SEQ ID NO 98
<211> LENGTH: 20
<212> TYPE: DNA
<213> ORGANISM: Artificial Sequence
<220> FEATURE:
<223> OTHER INFORMATION: Synthetic primer: ISH-PCR-GCI-P036-1902R

<400> SEQUENCE: 98
cgcaagaatt gattggctcc                                                 20

<210> SEQ ID NO 99
<211> LENGTH: 27
<212> TYPE: DNA
<213> ORGANISM: Artificial Sequence
<220> FEATURE:
<223> OTHER INFORMATION: Synthetic primer: SacI-Fw

<400> SEQUENCE: 99
cgcgcttgag ctcgatccag cgatttc                                         27
```

<210> SEQ ID NO 100
<211> LENGTH: 25
<212> TYPE: DNA
<213> ORGANISM: Artificial Sequence
<220> FEATURE:
<223> OTHER INFORMATION: Synthetic primer: HindIII-Rv

<400> SEQUENCE: 100
gtctccaagc tttaacgagt tgcag                                         25

<210> SEQ ID NO 101
<211> LENGTH: 30
<212> TYPE: DNA
<213> ORGANISM: Artificial Sequence
<220> FEATURE:
<223> OTHER INFORMATION: Synthetic primer: pHPLT-BglII-Fw

<400> SEQUENCE: 101
gcaattcaga tcttccttca ggttatgacc                                    30

<210> SEQ ID NO 102
<211> LENGTH: 30
<212> TYPE: DNA
<213> ORGANISM: Artificial Sequence
<220> FEATURE:
<223> OTHER INFORMATION: Synthetic primer: pHPLT-BglII-Rv

<400> SEQUENCE: 102
gcatcgaaga tctgattgct taactgcttc                                    30

<210> SEQ ID NO 103
<211> LENGTH: 4
<212> TYPE: PRT
<213> ORGANISM: Artificial Sequence
<220> FEATURE:
<223> OTHER INFORMATION: Synthetic peptide motif

<400> SEQUENCE: 103

His Gly Thr His
1

<210> SEQ ID NO 104
<211> LENGTH: 7
<212> TYPE: PRT
<213> ORGANISM: Artificial Sequence
<220> FEATURE:
<223> OTHER INFORMATION: Synthetic peptide motif
<220> FEATURE:
<221> NAME/KEY: misc_feature
<222> LOCATION: (6)..(6)
<223> OTHER INFORMATION: Xaa can be any naturally occurring amino acid

<400> SEQUENCE: 104

Gly Thr Ser Met Ala Xaa Pro
1               5

<210> SEQ ID NO 105
<211> LENGTH: 4
<212> TYPE: PRT
<213> ORGANISM: Artificial Sequence
<220> FEATURE:
<223> OTHER INFORMATION: Synthetic peptide motif

<400> SEQUENCE: 105

His Gly Thr Arg
1

```
<210> SEQ ID NO 106
<211> LENGTH: 6
<212> TYPE: PRT
<213> ORGANISM: Artificial Sequence
<220> FEATURE:
<223> OTHER INFORMATION: Synthetic peptide motif
<220> FEATURE:
<221> NAME/KEY: misc_feature
<222> LOCATION: (4)..(4)
<223> OTHER INFORMATION: Xaa is Ala or Val
<220> FEATURE:
<221> NAME/KEY: misc_feature
<222> LOCATION: (5)..(5)
<223> OTHER INFORMATION: Xaa is Ala or Ser

<400> SEQUENCE: 106

Gly Thr Ser Xaa Xaa Pro
1               5
```

COMPOSITIONS AND METHODS COMPRISING SERINE PROTEASE VARIANTS

The present application is a continuation of U.S. patent application Ser. No. 12/616,097, filed Nov. 10, 2009, which claims priority to U.S. Provisional Patent Application Ser. Nos. 61/113,545, 61/113,552, and 61/113,548, all of which were filed on Nov. 11, 2008, and 61/218,802, which was filed on Jun. 19, 2009, and all of which are herein incorporated by reference.

FIELD OF THE INVENTION

The present invention provides methods for protein engineering and serine protease variants produced therefrom. Specifically, the present invention provides serine protease variants having one or more substitutions as compared to a reference serine protease. In addition, the present invention provides compositions comprising these serine protease variants. In some embodiments, the present invention provides cleaning compositions comprising at least one of these serine protease variants.

BACKGROUND OF THE INVENTION

Various protein engineering methods are known to those in the art. In general, proteins are modified in order to obtain desired protein properties. In most methods, the nucleotide sequence of a cloned gene encoding a protein is mutated and the modified gene is expressed to produce mutants, which are screened for activities of interest. Often, the mutant properties are compared with the properties of wild-type protein.

Historically, the protein design process has been approached as equivalent to the problem of finding in all of protein space the one best sequence for the desired application. This problem is extremely difficult and is "NP hard." In complexity theory, problems defined as being in class P, are considered easy and efficient, polynomial-time algorithms exist for their solution. NP-hard problems are problems for which efficient polynomial-time algorithms are not currently known, and if any NP-hard problem could be solved, all NP-hard problems could be solved (See e.g., Pierce and Winfree, Protein Engineer., 15:779-782, 2002). Current strategies for building and screening libraries generally involve generating protein sequence diversity randomly across the whole sequence or in controlled random fashion at defined positions within the protein. These libraries generally have a large number of members that are "negative" with respect to the primary property of interest, and require large numbers be screened in order to find the relatively small numbers of positive mutations. Generally, negative mutations are ignored, and sequence information is only obtained for the positive members.

Saturation mutagenesis (Estell et al., in World Biotech Report 1984, vol. 2, USA, Online Publications, London, pp. 181-187, 1984; and Wells et al., Gene, 34:315-323, 1985) is one technique that can be used to search protein space for mutations that optimize several properties in a protein. Several groups have developed strategies for identifying sites to be changed by saturation mutagenesis (Reetz et al., Angew. Chem. Int Edn, 44:4192-4196, 2005; Kato et al., J Mol Biol, 351:683-692, 2005; and Sandberg et al., Proc Natl Acad Sci USA, 90:8367-8371, 1993), but no general system for site identification has been proposed.

In addition, because most protein engineering methods produce a great number of amino acid mutation options, screening of a large number of variants generally is required to produce a desired protein property. Generally, screening is repeated multiple times to produce a beneficial variant. Thus, most methods are laborious and time-consuming. There is a continuing need in the art for protein engineering methods that are efficient and produce the desired results.

SUMMARY OF THE INVENTION

The present invention provides methods for protein engineering. Specifically, the invention provides methods utilizing site evaluation libraries. In particular, the present invention provides means to use information obtained about a number of desired properties, in order to rationally and efficiently design libraries that will optimize those properties. In some embodiments, the present invention provides means to design libraries that are improved for at least two desired properties. The present invention also provides serine protease variants having one or more substitutions as compared to a reference serine protease, produced using the protein engineering methods described herein.

The present invention provides means to identify positions within an amino acid sequence of a protein that are relevant in improving desired properties of the protein. In some particularly preferred embodiments, the present invention provides means to determine which mutations are desirable in order to produce proteins with these desired properties, as well as improved properties. In some additional particularly preferred embodiments, the present invention provides means to identify amino acid positions and mutations that have improvements of a particular percentage better than the wild-type protein (e.g., better than about 110% of the wild-type for one property). In still further preferred embodiments, the present invention provides means to identify mutations that provide at least one much improved property and at least one additional property that is not significantly worse than the wild-type protein (e.g., better than 110% of wild-type for one property, yet not worse than 90% of wild-type for another property). In yet further preferred embodiments, libraries are constructed based on this information. In some embodiments, the libraries are constructed using all of the identified mutations, while in some other embodiments the libraries are constructed using a subset of the identified mutations. Indeed, it is not intended that the libraries be constrained to any particular number and/or type of mutations.

The present invention provides methods for protein engineering comprising the steps of: providing a library of protein variants; testing the library of protein variants for at least one property of interest in a test of interest; identifying a range of values for at least one property of interest; identifying a minimum within the range of values that is associated with a favorable outcome in the test of interest; and providing a plurality of protein variants having at least one mutation above the minimum in the range of the at least one property of interest, thereby providing a library of protein variants comprising at least one mutation, and wherein the library is enriched in members having a favorable outcome in the test of interest. In some embodiments, the favorable outcome corresponds to a value of greater than about 50%, about 60%, about 70%, about 80%, about 90%, or about 95% of a maximal value observed in the test set forth in the first step above. In some alternative embodiments, more than one test of interest is used in the methods of the present invention. In some preferred embodiments, the protein is an enzyme. In some particularly preferred embodiments, the enzyme is selected from proteases, transferases, metalloproteases, esterases, amylases, cellulases, oxidases, cutinases, and lipases.

The present invention also provides methods for protein engineering comprising the steps of: providing a library of protein variants; testing the library of protein variants for at least two properties of interest in a test of interest; identifying a range of values for the at least two properties of interest; identifying a minimum within the range of values that is associated with a favorable outcome in the test of interest; and providing a plurality of protein variants above the minimum of the range of the at least two properties of interest, thereby providing a library of protein variants enriched in members having the favorable outcome in the test of interest. In some preferred embodiments, the favorable outcome corresponds to a value of greater than about 50%, about 60%, about 70%, about 80%, about 90%, or about 95% of a maximal value observed in the test set forth in the first step above. In some preferred embodiments, the protein is an enzyme. In some particularly preferred embodiments, the enzyme is selected from proteases, transferases, metalloproteases, esterases, amylases, cellulases, oxidases, cutinases, and lipases.

The present invention also provides methods for protein engineering comprising the steps of: providing a wild-type protein and a library of protein variants of the wild-type protein; testing the library of protein variants and the wild-type protein for at least one property of interest in a test of interest; identifying a range of values for the at least one property of interest; identifying a minimum within the range of values that is associated with a favorable outcome in the test of interest; identifying the protein variants having a favorable outcome as compared to the results obtained for the wild-type, wherein the favorable outcome is an improved property of interest; and providing a plurality of protein variants above the minimum of the range of the at least one property of interest, thereby providing a library of improved protein variants enriched in members having the favorable outcome in the test of interest. In some preferred embodiments, the methods further comprise the step of determining the performance index, wherein the performance index is determined by dividing the value obtained for each of the improved protein variants and the value obtained for the wild-type protein. In some particularly preferred embodiments, the methods further comprise the step of identifying the improved protein variants, wherein the improved protein variants achieve performance index values greater than about 1.1 in the test of interest. In some additional embodiments, the protein is an enzyme. In some particularly preferred embodiments, the enzyme is selected from proteases, transferases, metalloproteases, esterases, amylases, cellulases, oxidases, cutinases, and lipases. In some alternative embodiments, the protein is selected from antibodies and growth factors. In still additional preferred embodiments, the wild-type protein is a mature form of an enzyme selected from proteases, transferases, metalloproteases, esterases, amylases, cellulases, oxidases, cutinases, and lipases. In some preferred embodiments, the property of interest is selected from charge, wash performance, hard surface cleaning performance, thermal stability, storage stability, detergent stability, substrate binding, enzyme inhibition, expression level, reaction rate, and substrate degradation. In some embodiments, the wild-type protein and the protein variant are components of at least one detergent composition. In some preferred embodiments, wash performance is tested in a detergent composition formulated into a powdered or liquid detergent having a pH of between about 5 and about 12.0.

The present invention also provides methods for producing an improved variant of a reference protein within a protein fold, comprising: assaying multiple variants of a test protein within the protein fold spanning a range of a property of interest in an assay of interest; identifying a minimum within the range of the property of interest that is associated with a favorable outcome in the assay of interest; assaying a reference protein of the protein fold in the assay of interest; and producing an improved variant of the reference protein by introducing an amino acid substitution is the reference protein such that the improved variant is above the minimum of the range of the property of interest. In some preferred embodiments, the reference protein and the test protein are different. In some embodiments, the methods further comprise the step of determining the performance index, wherein the performance index is determined by dividing the value obtained for the improved protein variant and the value obtained for the reference protein. In some embodiments, the test proteins and the reference proteins are enzymes. In some particularly preferred embodiments, the enzymes are selected from proteases, transferases, metalloproteases, esterases, amylases, cellulases, oxidases, cutinases, and lipases. In some alternative embodiments, the test and reference proteins are selected from antibodies and growth factors. In still additional preferred embodiments, the reference protein is a mature form an enzyme selected from proteases, transferases, metalloproteases, esterases, amylases, cellulases, oxidases, cutinases, and lipases. In some preferred embodiments, the property of interest is selected from charge, wash performance, hard surface cleaning performance, thermal stability, storage stability, detergent stability, substrate binding, enzyme inhibition, expression level, reaction rate, and substrate degradation. In some embodiments, the test and reference proteins are components of at least one detergent composition. In some alternative embodiment, the improved protein variant is a component of a detergent composition. In some preferred embodiments, wash performance is tested in a detergent composition formulated into a powdered or liquid detergent having a pH of between about 5 and about 12.0.

In some embodiments, the present invention provides cleaning compositions comprising at least one serine protease variant described herein. In some preferred embodiments, the cleaning composition is a laundry detergent. In a subset of these embodiments, the laundry detergent is a cold water detergent, a low pH detergent, or a compact detergent. In other embodiments, the cleaning composition is a dishwashing detergent. In some embodiments, the dishwashing detergent is a phosphate-free detergent, while in other embodiments the dishwashing detergent is a phosphate-containing detergent. In some preferred embodiments, the cleaning compositions further comprise at least one additional enzyme, which in particularly preferred embodiments is selected from a neutral metalloprotease, a lipase, a cutinase, an amylase, a carbohydrase, a cellulase, a pectinase, a mannanase, an arabinase, a galactanase, a xylanase, an oxidase, and a peroxidase. Also provided by the present invention are isolated nucleic acids encoding the serine protease variant, expression vectors comprising the nucleic acid, and host cells comprising the expression vector.

In addition, the present invention provides methods for producing a serine protease variant of a *Bacillus* serine protease, comprising: transforming a host cell with an expression vector comprising a nucleic acid encoding the serine protease variant; and cultivating the transformed host cell under conditions suitable for the production of the serine protease variant. In some embodiments, the methods further comprise the step of harvesting the produced serine protease variant. In some embodiments, the host cell is a *Bacillus* species, and in a subset of these embodiments, the *Bacillus* species is *B. subtilis*. Furthermore, the present invention provides methods of cleaning, comprising the step of contacting a surface and/or an article comprising a fabric with a cleaning composition comprising an isolated serine protease variant. In some alternative methods, the present invention provides methods of cleaning, comprising the step of contacting a surface and/or an article comprising dishware with a cleaning composition comprising an isolated serine protease variant.

Additionally the present invention provides methods for protease engineering comprising the steps of: a) providing a plurality of site evaluation libraries (SELs) each comprising a plurality of protease variants having distinct substitutions at an identical amino acid position of the protease; b) testing the protease variants of the SELs and a standard protease in a test of a property of interest; c) determining a performance index (PI) for each of the protease variants for the test; d) identifying two or more of the amino acid positions as non-restrictive positions, wherein at least one of the plurality of protease variants in each of two of the SELs has a PI greater than about 0.5; and f) providing a multiple mutation library comprising a plurality of multiply-substituted protease variants each comprising substitutions in the two or more non-restrictive positions. In some embodiments, the test comprises two or more different assays selected from stain removal assays (microswatch), LAS stability assays, detergent stability assays, and specific activity assays. In some further embodiments, additional and/or alternative assay methods find use.

In some further embodiments, the present invention provides methods for producing a multiply substituted serine protease variant of a *Bacillus* serine protease, comprising: testing a plurality of singly-substituted serine protease variants in a first test of a first property and a second test of a second property, wherein the property of a reference serine protease is given a value of 1.0 in each test, a favorable first or second property has a value greater than 1.0, and an unduly unfavorable first or second property has a value less than about 0.80 or in some preferred embodiments, less than about 0.60; identifying a substitution in at least one of the singly-substituted serine protease variants that is associated with a favorable first property and which is not associated with an unduly unfavorable second property; identifying a substitution in at least one of the singly-substituted serine protease variants that is associated with a favorable second property and which is not associated with an unduly unfavorable first property; and introducing the substitution from the previous steps into a serine protease to yield a multiply-substituted serine protease variant. In some embodiments, the methods further comprise testing the multiply-substituted serine protease variant in the first test and the second test, wherein an improved serine protease variant achieves a value of greater than about 1.0 in both of the first and second tests, or a value of greater than 1.0 in the first test and a value of about 0.80 to about 1.0 in the second test. In some embodiments, the methods further comprise producing the improved serine protease variant(s). In some embodiments, the first and second properties are negatively correlated. In some embodiments, a favorable first or second property has a value greater than about 1.2. In some embodiments, an unduly unfavorable first or second property has a value less than about 0.40. In some embodiments, the first property is stability, and the second property is wash performance. In a subset of these the stability comprises stability in detergent and wash performance comprises blood milk ink (BMI) wash performance in detergent. In some embodiments, the reference bacterial serine protease is a wild type mature form of a *B. amyloliquefaciens* serine protease BPN' having an amino acid sequence set forth as SEQ ID NO:1. In other embodiments, the reference bacterial serine protease is a wild type of GG36 serine protease having an amino acid sequence set forth as SEQ ID NO:2 (i.e., the reference bacterial serine protease used to produce "GG36 variants"). In some embodiments of the present invention, wash performance is tested in a powder or liquid detergent composition having a pH of between about 5 and about 12.0. It is not intended that the steps be limited to the exact order listed above, as any suitable order finds use in the present invention. However in some preferred embodiments, the substitutions are in positions in a reference serine protease having a solvent accessible surface (SAS) of greater than about 50% or greater than about 65%.

In addition the present invention provides subtilisin variants, wherein the variants are mature forms having proteolytic activity and comprising a substitution at one or more (preferably 1, 2, 3, 4, 5, 6, 7, 8, 9, 10, 11, 12, or more) positions selected from: 1, 2, 3, 4, 5, 6, 7, 8, 9, 10, 11, 12, 13, 14, 15, 16, 17, 18, 19, 20, 21, 22, 24, 25, 26, 27, 28, 29, 30, 31, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 66, 67, 68, 69, 71, 72, 73, 74, 75, 76, 77, 78, 79, 80, 81, 82, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 203, 204, 205, 206, 207, 208, 209, 210, 211, 212, 213, 214, 215, 216, 217, 218, 219, 220, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274 and 275 and wherein the positions are numbered by correspondence with the amino acid sequence of *B. amyloliquefaciens* subtilisin BPN' set forth as SEQ ID NO:1.

In some preferred embodiments, the substitution comprises one or more of: X001A, X001C, X001E, X001F, X001G, X001H, X001I, X001K, X001L, X001N, X001P, X001Q, X001R, X001S, X001T, X001V, X001Y, X002A, X002C, X002E, X002G, X002K, X002L, X002M, X002N, X002P, X002Q, X002R, X002S, X002T, X002V, X002W, X002Y, X003D, X003E, X003F, X003G, X003H, X003I, X003L, X003M, X003N, X003P, X003R, X003S, X003T, X003V, X003W, X003Y, X004A, X004C, X004D, X004E, X004F, X004G, X004H, X004K, X004L, X004N, X004P, X004R, X004S, X004T, X004V, X004W, X005A, X005C, X005D, X005E, X005G, X005I, X005M, X005P, X005Q, X005S, X005T, X005W, X005Y, X006A, X006D, X006E, X006M, X006W, X007A, X007C, X007D, X007G, X007H, X007N, X007P, X007Q, X007S, X007T, X008A, X008F, X008G, X008I, X008L, X008M, X008Q, X008T, X008V, X008W, X008Y, X009A, X009C, X009D, X009E, X009F, X009G, X009H, X009L, X009N, X009P, X009Q, X009R, X009S, X009T, X009V, X009W, X009Y, X010A, X010C, X010F, X010G, X010H, X010I, X010K, X010L, X010M, X010N, X010Q, X010R, X010S, X010T, X010V, X010W, X010Y, X011A, X011C, X011D, X011G, X011I, X011M, X011R, X011S, X011T, X011V, X011Y, X012D, X012F, X012G, X012H, X012I, X012K, X012L, X012M, X012N, X012P, X012Q, X012R, X012S, X012T, X012V, X012W, X012Y, X013A, X013G, X013I, X013M, X013Q, X013T, X013V, X014A, X014C, X014D, X014E, X014F, X014G, X014H, X014I, X014K, X014L, X014P, X014Q, X014S, X014T, X014V, X014Y, X015A, X015D, X015F, X015G, X015I, X015K, X015L, X015M, X015P, X015Q, X015R, X015S, X015V, X015W, X016A, X016D, X016E, X016G, X016L, X016N, X016P, X016Q, X016R, X016S, X016T, X016V, X017A, X017D, X017E, X017F, X017G, X017H, X017I, X017K, X017M, X017N, X017R, X017S, X017T, X017V, X017W, X017Y, X018A, X018C, X018D, X018E, X018F, X018G, X018H, X018I, X018K, X018L, X018M, X018N, X018P, X018Q, X018R, X018S, X018T, X018V, X018W, X018Y, X019A, X019C, X019D, X019E, X019F, X019G, X019H, X019K, X019L, X019M, X019N, X019P, X019R, X019S, X019T, X019V, X019W, X019Y, X020A, X020C, X020D, X020F, X020G, X020I, X020K, X020L, X020M, X020P, X020Q, X020R, X020S, X020T, X020V, X020W, X020Y, X021A, X021C, X021D, X021E, X021G, X021H, X021I, X021K, X021L, X021M, X021N, X021P, X021Q, X021R, X021S, X021T, X021V, X021W, X022A, X022C, X022G, X022I, X022K, X022L, X022M, X022N, X022P, X022Q, X022R, X022S, X022T, X022V, X022W, X022Y, X023A, X023G, X023S, X024A, X024C, X024D, X024F, X024G, X024H, X024L, X024M, X024N, X024P, X024Q, X024R, X024S, X024T, X024V, X024W, X025C, X025D, X025E, X025F, X025G, X025H, X025K, X025L, X025M, X025N, X025Q, X025R, X025S, X025T, X025V, X025W, X026C, X026F, X026G, X026I, X026L, X026M, X026N, X026P, X026R, X026S, X026T, X026V, X027A, X027C, X027D, X027F, X027G, X027I, X027K, X027L, X027M, X027N, X027P, X027R, X027S, X027T, X027V, X027W, X027Y, X028A, X028E, X028G, X028H, X028I, X028L, X028M, X028N, X028P, X028S, X028V, X028Y, X029A, X029C, X029G, X029I, X029K, X029S, X029T, X029V, X030A, X030C, X030D, X030E, X030F, X030G, X030L, X030M, X030Q, X030S, X030T, X030V, X030Y, X031A, X031F, X031I, X031L, X031M, X031S, X031T, X031V, X032A, X032C, X032D, X032E, X032G, X032V, X032W, X033A, X033C, X033D, X033E, X033G, X033H, X033I, X033L, X033M, X033N, X033Q, X033R, X033S, X033T, X033V, X033Y, X034E, X034G, X034H, X034L, X034Q, X034S, X035A, X035F, X035H, X035I, X035K, X035L, X035M, X035P, X035Q, X035R, X035S, X035A, X035C, X035E, X035F, X035G, X035H, X035I, X035L, X035M, X035N, X035P, X035Q, X035R, X035T, X035V, X035W, X035Y, X038C, X038F, X038G, X038H, X038I, X038K, X038L, X038M, X038N, X038Q, X038R, X038T, X038V, X038W, X038Y, X039A, X039E, X039G, X039H, X039L, X039M, X039N, X039Q, X039S, X039T, X039V, X039Y, X040A, X040C, X040D, X040E, X040G, X040H, X040I, X040K, X040L, X040M, X040N, X040P, X040R, X040S, X040T, X040V, X040W, X040Y, X041C, X041D, X041E, X041N, X041P, X041Q, X041S, X042A, X042C, X042F, X042G, X042H, X042I, X042L, X042M, X042N, X042Q, X042S, X042T, X042V, X042Y, X043A, X043C, X043D, X043E, X043F, X043G, X043I, X043L, X043M, X043N, X043P, X043R, X043T, X043V, X043W, X043Y, X044A, X044C, X044D, X044F, X044G, X044I, X044K, X044L, X044M, X044N, X044P, X044Q, X044R, X044S, X044T, X044V, X044W, X044Y, X045A, X045D, X045F, X045G, X045H, X045I, X045K, X045L, X045M, X045N, X045P, X045Q, X045R, X045S, X045T, X045V, X045W, X045Y, X046C, X046D, X046E, X046F, X046G, X046H, X046I, X046K, X046L, X046M, X046N, X046P, X046Q, X046R, X046S, X046T, X046V, X046W, X047A, X047C, X047E, X047F, X047G, X047H, X047K, X047L, X047M, X047N, X047P, X047Q, X047R, X047S, X047T, X047W, X048A, X048C, X048E, X048F, X048G, X048H, X048I, X048K, X048L, X048M, X048N, X048P, X048Q, X048R, X048S, X048T, X048V, X048Y, X049A, X049E, X049F, X049G, X049H, X049K, X049L, X049M, X049P, X049Q, X049R, X049S, X049T, X050C, X050F, X050G, X050H, X050I, X050L, X050N, X050T, X050V, X050Y, X051F, X051G, X051H, X051K, X051L, X051N, X051P, X051R, X051S, X051T, X051V, X051W, X052A, X052C, X052E, X052F, X052G, X052H, X052I, X052L, X052M, X052N, X052P, X052Q, X052R, X052T, X052V, X052W, X052Y, X053A, X053C, X053D, X053E, X053G, X053H, X053I, X053K, X053L, X053M, X053P, X053Q, X053R, X053S, X053T, X053V, X053W, X053Y, X054A, X054C, X054D, X054E, X054F, X054G, X054H, X054I, X054K, X054L, X054M, X054N, X054P, X054Q, X054R, X054S, X054V, X054W, X054Y, X055A, X055C, X055E, X055F, X055G, X055H, X055I, X055K, X055L, X055M, X055N, X055P, X055Q, X055R, X055S, X055T, X055W, X055Y, X056A, X056C, X056D, X056E, X056H, X056L, X056M, X056N, X056P, X056Q, X056R, X056S, X056T, X056V, X057A, X057C, X057E, X057F, X057G, X057H, X057I, X057K, X057L, X057M, X057N, X057P, X057Q, X057R, X057S, X057T, X057V, X057W, X057Y, X059A, X059C, X059D, X059E, X059F, X059G, X059I, X059K, X059L, X059M, X059N, X059P, X059Q, X059R, X059S, X059T, X059V, X059W, X059Y, X060A, X060C, X060D, X060F, X060G, X060K, X060L, X060M, X060N, X060P, X060Q, X060S, X060T, X060V, X060W, X060Y, X061A, X061C, X061D, X061F, X061G, X061H, X061I, X061L, X061M, X061N, X061P, X061R, X061S, X061T, X061V, X061Y, X062C, X062E, X062F, X062G, X062H, X062I, X062K, X062L, X062M, X062N, X062P, X062Q, X062R, X062S, X062T, X062V, X062Y, X063A, X063C, X063D, X063E, X063F, X063G, X063H, X063I, X063K, X063M, X063P, X063Q, X063R, X063S, X063T, X063V, X063W, X064H, X064S, X065G, X066A, X066C, X066D, X066E, X066I, X066K, X066L, X066N, X066Q, X066S, X067A, X067C, X067F, X067H, X067L, X067M, X067N, X067P, X067Q, X067R, X067S, X067T, X067V, X068A, X068C, X068D, X068E, X068G, X068H, X068I, X068L, X068M, X068N, X068Q, X068S, X068T, X068V, X069A, X069C, X069E, X069F, X069G, X069I, X069L, X069M, X069N, X069P, X069R, X069S, X069T, X069V, X069W, X070G, X071A, X071C, X071D, X071E, X071G, X071I, X071L, X071M, X071N, X071P, X071S, X071T, X071V, X071W, X072C, X072D, X072F, X072H, X072I, X072K, X072L, X072M, X072N, X072Q, X072S, X072T, X072V, X072W, X073A, X073C, X073D, X073E, X073H, X073K, X073L, X073N, X073R, X073S, X073T, X073V, X074A, X074C, X074S, X074T, X075A, X075C, X075D, X075E, X075F, X075G, X075H, X075I, X075L, X075M, X075N, X075P, X075Q, X075R, X075S, X075T, X075V, X075W, X076C, X076D, X076E, X076F, X076G, X076H, X076I, X076K, X076L, X076M, X076N, X076Q, X076R, X076S, X076T, X076W, X076Y, X077A, X077C, X077D, X077E, X077F, X077G, X077H, X077K, X077L, X077M, X077N, X077Q, X077R, X077S, X077V, X077Y, X078A, X078C, X078E, X078G, X078H, X078I, X078K, X078L, X078M, X078N, X078P, X078Q, X078R, X078S, X078T, X078V, X078W, X078Y, X079C, X079D, X079E, X079F, X079G, X079I, X079K, X079L, X079M, X079N, X079P, X079Q, X079R, X079S, X079T, X079V, X079W, X079Y, X080A, X080D, X080E, X080G, X080K, X080L, X080M, X080R, X080T, X080V, X080W, X080Y, X081A, X081C, X081D, X081E, X081F, X081G, X081H, X081I, X081K, X081L, X081M, X081P, X081Q, X081R, X081S, X081T, X081V, X081W, X081Y, X082A, X082E, X082F, X082G, X082K, X082L, X082M, X082N, X082Q, X082R, X082S, X082T, X082V, X082W, X082Y, X083G, X083S, X084C, X084E, X084F, X084G, X084H, X084I, X084L, X084M, X084N, X084Q, X084S, X084T, X084V, X085A, X085C, X085I, X085L, X085N, X086A, X086C, X086D, X086E, X086G, X086I, X086L, X086P, X086R, X086S, X086V, X086W, X086Y, X087A, X087C, X087D, X087E, X087F, X087G, X087I, X087K, X087L, X087N, X087P, X087T, X087V, X087Y, X088A, X088C, X088D, X088E, X088G, X088H, X088K, X088M, X088Q, X088R, X088S, X088V, X088W, X089A, X089C, X089D, X089E, X089F, X089G, X089H, X089I, X089L, X089N, X089P, X089Q, X089R, X089S, X089T, X089V, X089W, X090A, X090C, X090E, X090F, X090G, X090I, X090K, X090L, X090M, X090P, X090Q, X090T, X090V, X090W, X090Y, X091C, X091D, X091F, X091I, X091K, X091L, X091M, X091N, X091Q, X091R, X091S, X091T, X091V, X091W, X091Y, X092A, X092C, X092D, X092E, X092F, X092G, X092H, X092I, X092K, X092L, X092N, X092P, X092Q, X092R, X092T, X092V, X092W, X092Y, X093A, X093C, X093D, X093F, X093G, X093L, X093M, X093N, X093P, X093S, X093T, X093V, X093W, X093Y, X094A, X094D, X094E, X094G, X094H, X094I, X094K, X094L, X094M, X094N, X094Q, X094R, X094V, X095A, X095C, X095E, X095G, X095I, X095K, X095L, X095M, X095R, X095S, X095T, X095V, X095W, X096A, X096E, X096F, X096G, X096H, X096I, X096L, X096M, X096Q, X096R, X096S, X096T, X096W, X096Y, X097A, X097D, X097E, X097F, X097G, X097H, X097I, X097K, X097L, X097M, X097N, X097P, X097Q, X097R, X097S, X097T, X097V, X097W, X097Y, X098A, X098C, X098D, X098E, X098F, X098G, X098K, X098L, X098N, X098P, X098Q, X098R, X098S, X098T, X098V, X098Y, X099A, X099C, X099F, X099G, X099K, X099M, X099P, X099Q, X099R, X099S, X099T, X099V, X099Y, X100D, X100E, X100F, X100G, X100I, X100K, X100L, X100M, X100N, X100P, X100Q, X100R, X100S, X100T, X100V, X100W, X100Y, X101A, X101C, X101D, X101E, X101F, X101G, X101H, X101I, X101K, X101N, X101P, X101Q, X101R, X101S, X101T, X101V, X101Y, X102A, X102C, X102D, X102E, X102F, X102G, X102H, X102M, X102N, X102T, X103A, X103C, X103D, X103E, X103F, X103G, X103I, X103L, X103N, X103P, X103Q, X103R, X103S, X103T, X103V, X103W, X103Y, X104A, X104C, X104D, X104E, X104F, X104G, X104H, X104I, X104L, X104P, X104R, X104S, X104T, X104V, X104W, X104Y, X105A, X105C, X105D, X105E, X105F, X105G, X105H, X105I, X105K, X105L, X105M, X105N, X105Q, X105R, X105S, X105T, X105V, X105W, X105Y, X106A, X106D, X106E, X106F, X106G, X106I, X106L, X106M, X106P, X106R, X106S, X106T, X106V, X106W, X107A, X107C, X107E, X107F, X107H, X107I, X107L, X107M, X107Q, X107S, X107T, X107V, X107W, X107Y, X108A, X108C, X108F, X108G, X108I, X108L, X108M, X108Q, X108S, X108T, X108V, X109A, X109C, X109E, X109F, X109G, X109H, X109I, X109K, X109L, X109M, X109N, X109P, X109Q, X109R, X109S, X109T, X109V, X109Y, X110A, X110G, X110S, X111C, X111E, X111F, X111I, X111L, X111M, X111P, X111T, X111V, X111Y, X112A, X112C, X112D, X112E, X112F, X112G, X112I, X112L, X112M, X112N, X112Q, X112S, X112T, X112V, X112W, X112Y, X113A, X113C, X113D, X113E, X113L, X113M, X113N, X113S, X113V, X113W, X114A, X114C, X114G, X114T, X115C, X115E, X115F, X115G, X115H, X115I, X115K, X115L, X115M, X115N, X115P, X115Q, X115R, X115S, X115T, X115V, X115W, X115Y, X116A, X116C, X116D, X116F, X116G, X116I, X116K, X116L, X116M, X116N, X116Q, X116S, X116T, X116V, X116W, X117A, X117C, X117D, X117F, X117G, X117I, X117N, X117Q, X117R, X117T, X117Y, X118A, X118C, X118D, X118E, X118F, X118G, X118I, X118K, X118L, X118M, X118N, X118P, X118R, X118S, X118T, X118V, X118W, X119A, X119C, X119E, X119F, X119G, X119H, X119K, X119M, X119N, X119P, X119Q, X119T, X119W, X120A, X120C, X120E, X120F, X120G, X120H, X120I, X120L, X120M, X120N, X120R, X120S, X120T, X120W, X121A, X121C, X121E, X121F, X121G, X121I, X121K, X121L, X121M, X121Q, X121S, X121T, X121V, X121Y, X122A, X122C, X122G, X122I, X122L, X122S, X122T, X122V, X123E, X123G, X123I, X123L, X123M, X123N, X123P, X123S, X123V, X124G, X124H, X124L, X124N, X124Q, X124S, X124T, X124Y, X125A, X125C, X125G, X125P, X125S, X125T, X126A, X126C, X126E, X126F, X126G, X126H, X126I, X126K, X126L, X126M, X126N, X126Q, X126S, X126T, X126V, X126W, X126Y, X127D, X127F, X127G, X127I, X127L, X127Q, X127R, X127S, X127T, X127V, X128A, X128C, X128D, X128F, X128G, X128H, X128I, X128K, X128L, X128M, X128N, X128P, X128Q, X128R, X128S, X128T, X128W, X128Y, X129A, X129E, X129F, X129G, X129I, X129L, X129M, X129N, X129P, X129R, X129S, X129T, X129V, X129W, X129Y, X130C, X130K, X130L, X130N, X130P, X130Q, X130R, X130S, X130V, X130W, X130Y, X131A, X131D, X131E, X131F, X131G, X131I, X131K, X131L, X131M, X131P, X131Q, X131R, X131V, X132A, X132E, X132F, X132H, X132I, X132L, X132M, X132N, X132Q, X132R, X132S, X132T, X132W, X133A, X133F, X133K, X133L, X133N, X133P, X133Q, X133S, X133T, X133V, X133Y, X134A, X134F, X134I, X134L, X134M, X134P, X134S, X134T, X134V, X135A, X135C, X135E, X135F, X135L, X135M, X135Q, X135T, X135W, X136A, X136D, X136E, X136F, X136G, X136K, X136M, X136N, X136Q, X136R, X136S, X136V, X136W, X136Y, X137A, X137C, X137E, X137G, X137H, X137K, X137L, X137M, X137Q, X137R, X137S, X137V, X137W, X138A, X138C, X138E, X138G, X138H, X138L, X138M, X138Q, X138R, X138V, X139A, X139C, X139E, X139F, X139G, X139I, X139M, X139Q, X139S, X139T, X139V, X139Y, X140A, X140C, X140D, X140E, X140F, X140G, X140I, X140K, X140L, X140M, X140N, X140Q, X140R, X140S, X140T, X140V, X140Y, X141D, X141E, X141G, X141H, X141I, X141K, X141L, X141N, X141Q, X141R, X141S, X141V, X141Y, X142A, X142C, X142E, X142G, X142I, X142L, X142M, X142N, X142Q, X142S, X142T, X142V, X142Y, X143C, X143D, X143F, X143G, X143H, X143I, X143K, X143L, X143M, X143N, X143R, X143S, X143T, X143V, X143W, X143Y, X144A, X144C, X144D, X144G, X144H, X144I, X144L, X144M, X144N, X144Q, X144R, X144S, X144T, X144V, X144W, X144Y, X145A, X145C, X145D, X145E, X145F, X145G, X145K, X145L, X145M, X145N, X145Q, X145R, X145S, X145T, X145W, X145Y, X146A, X146C, X146D, X146E, X146F, X146G, X146I, X146K, X146L, X146M, X146Q, X146R, X146S, X146T, X146W, X146Y, X147F, X147G, X147I, X147L, X147M, X147P, X147Q, X147T, X147V, X148A, X148C, X148E, X148F, X148G, X148H, X148I, X148L, X148M, X148N, X148S, X148T, X148V, X148W, X148Y, X149A, X149C, X149F, X149G, X149H, X149I, X149L, X149M, X149P, X149Q, X149S, X149T, X149V, X150A, X150E, X150F, X150G, X150H, X150L, X150P, X150Q, X150S, X150T, X150V, X151A, X151G, X151M, X151S, X151T, X151V, X152A, X152C, X152P, X152R, X152S, X152T, X152V, X153A, X153E, X153F, X153G, X153I, X153M, X153N, X153Q, X153S, X153V, X153Y, X154A, X154C, X154G, X154N, X154Q, X154S, X155A, X155D, X155E, X155F, X155I, X155L, X155N, X155P, X155Q, X155R, X155S, X155T, X155V, X155Y, X156A, X156C, X156D, X156E, X156F, X156G, X156I, X156K, X156L, X156M, X156N, X156P, X156Q, X156R, X156S, X156T, X156V, X156Y, X157A, X157C, X157D, X157G, X157K, X157L, X157Q, X157R, X157S, X157V, X158A, X158C, X158E, X158F, X158H, X158K, X158L, X158M, X158P, X158Q, X158R, X158S, X158T, X158V, X158W, X159A, X159C, X159E, X159G, X159H, X159L, X159M, X159P, X159Q, X159R, X159S, X159V, X159W, X159Y, X160A, X160C, X160D, X160F, X160G, X160I, X160L, X160M, X160N, X160Q, X160R, X160S, X160T, X160V, X160Y, X165A, X165C, X165D, X165E, X165F, X165G, X165H, X165I, X165K, X165L, X165M, X165P, X165R, X165S, X165T, X165V, X165W, X165Y, X166A, X166C, X166D, X166E, X166F, X166H, X166I, X166L, X166M, X166N, X166P, X166R, X166S, X166T, X166V, X166W, X166Y, X167A, X167C, X167D, X167E, X167F, X167G, X167H, X167I, X167K, X167L, X167M, X167N, X167P, X167Q, X167R, X167S, X167T, X167V, X167W, X167Y, X168A, X168C, X168F, X168I, X168M, X168N, X168P, X168S, X168T, X168V, X169A, X169C, X169G, X169I, X169L, X169S, X170A, X170D, X170E, X170G, X170H, X170K, X170L, X170N, X170P, X170Q, X170R, X170S, X170V, X170W, X170Y, X171A, X171C, X171D, X171E, X171F, X171G, X171H, X171I, X171L, X171M, X171N, X171Q, X171S, X171T, X171V, X171W, X171Y, X172A, X172C, X172D, X172F, X172G, X172I, X172K, X172L, X172M, X172P, X172Q, X172R, X172S, X172T, X172V, X172W, X172Y, X173A, X173C, X173D, X173E, X173F, X173G, X173H, X173I, X173K, X173L, X173M, X173N, X173P, X173Q, X173R, X173T, X173V, X173W, X173Y, X174A, X174G, X174I, X174N, X174P, X174S, X174T, X174V, X175A, X175C, X175E, X175G, X175H, X175I, X175K, X175L, X175M, X175Q, X175S, X175T, X175V, X175W, X175Y, X176A, X176C, X176E, X176G, X176I, X176K, X176P, X176S, X176T, X176V, X177A, X177C, X177I, X177T, X177V, X178A, X178G, X178S, X178T, X179A, X179C, X179G, X179H, X179I, X180C, X180G, X180H, X180I, X180L, X180N, X180Q, X180S, X180T, X180V, X181A, X181D, X181E, X181G, X181H, X181L, X181M, X181N, X182A, X182D, X182E, X182F, X182G, X182H, X182I, X182K, X182L, X182M, X182N, X182P, X182Q, X182R, X182S, X182T, X182V, X182W, X182Y, X183A, X183D, X183F, X183G, X183H, X183I, X183K, X183L, X183M, X183N, X183P, X183Q, X183R, X183S, X183T, X183V, X183W, X183Y, X184A, X184C, X184D, X184E, X184F, X184G, X184H, X184L, X184M, X184N, X184S, X184T, X184W, X184Y, X185A, X185C, X185E, X185F, X185G, X185H, X185I, X185K, X185L, X185M, X185N, X185Q, X185R, X185S, X185T, X185V, X185Y, X186A, X186C, X186G, X186H, X186I, X186K, X186L, X186M, X186N, X186P, X186Q, X186R, X186S, X186T, X186W, X187A, X187C, X187D, X187E, X187F, X187G, X187H, X187I, X187L, X187M, X187N, X187P, X187Q, X187S, X187T, X187V, X187W, X187Y, X188A, X188D, X188E, X188F, X188G, X188H, X188I, X188K, X188L, X188P, X188Q, X188R, X188S, X188T, X188W, X188Y, X189A, X189C, X189E, X189F, X189G, X189H, X189K, X189L, X189M, X189N, X189P, X189Q, X189R, X189S, X189T, X189V, X189Y, X190A, X190D, X190E, X190F, X190G, X190H, X190I, X190K, X190L, X190M, X190N, X190P, X190Q, X190R, X190S, X190V, X190W, X190Y, X191A, X191D, X191E, X191F, X191H, X191I, X191K, X191L, X191P, X191Q, X191R, X191S, X191T, X191V, X191W, X191Y, X192C, X192D, X192E, X192G, X192H, X192I, X192K, X192L, X192M, X192N, X192P, X192Q, X192R, X192S, X192T, X192V, X192W, X192Y, X193A, X193D, X193E, X193F, X193G, X193H, X193I, X193K, X193L, X193R, X193S, X193T, X193V, X193W, X193Y, X194A, X194C, X194D, X194E, X194F, X194G, X194H, X194I, X194L, X194M, X194P, X194Q, X194R, X194S, X194T, X194V, X194W, X194Y, X195A, X195C, X195D, X195E, X195F, X195G, X195I, X195K, X195L, X195Q, X195R, X195S, X195T, X195V, X195W, X195Y, X196A, X196D, X196E, X196F, X196I, X196L, X196M, X196P, X196Q, X196T, X196V, X196Y, X197A, X197C, X197D, X197E, X197F, X197G, X197H, X197I, X197L, X197M, X197N, X197Q, X197R, X197S, X197T, X197V, X197W, X197Y, X198A, X198D, X198E, X198F, X198G, X198H, X198I, X198L, X198M, X198N, X198Q, X198R, X198S, X198T, X198W, X198Y, X199A, X199C, X199D, X199E, X199F, X199G, X199H, X199I, X199L, X199M, X199Q, X199S, X199T, X199V, X199W, X200A, X200C, X200G, X200H, X200I, X200S, X201C, X201G, X201P, X201S, X201T, X201V, X202F, X202G, X203A, X203C, X203E, X203F, X203G, X203H, X203I, X203K, X203L, X203N, X203R, X203S, X203T, X203V, X203W, X203Y, X204A, X204C, X204E, X204F, X204G, X204I, X204K, X204L, X204N, X204P, X204R, X204S, X204T, X204W, X204Y, X205A, X205F, X205G, X205I, X205L, X205M, X205Q, X205T, X205V, X206A, X206C, X206D, X206E, X206F, X206G, X206H, X206I, X206K, X206L, X206N, X206P, X206Q, X206R, X206S, X206T, X206V, X206W, X206Y, X207A, X207G, X207H, X207S, X208A, X208C, X208L, X208N, X208P, X208S, X208T, X208V, X209A, X209C, X209D, X209E, X209F, X209G, X209H, X209I, X209K, X209L, X209M, X209N, X209R, X209S, X209T, X209V, X209W, X209Y, X210A, X210C, X210D, X210E, X210F, X210G, X210H, X210I, X210L, X210M, X210N, X210P, X210Q, X210R, X210S, X210V, X210W, X210Y, X211A, X211C, X211E, X211F, X211G, X211H, X211I, X211L, X211M, X211P, X211Q, X211R, X211T, X211V, X211W, X211Y, X212C, X212F, X212G, X212H, X212I, X212M, X212N, X212P, X212R, X212S, X212T, X212V, X212Y, X213A, X213C, X213D, X213E, X213F, X213G, X213I, X213K, X213L, X213M, X213N, X213P, X213Q, X213R, X213S, X213T, X213V, X213W, X213Y, X214A, X214C, X214E, X214F, X214G, X214H, X214I, X214K, X214L, X214M, X214N, X214P, X214Q, X214R, X214S, X214T, X214V, X214W, X214Y, X215A, X215C, X215D, X215E, X215F, X215G, X215H, X215I, X215K, X215M, X215N, X215P, X215R, X215S, X215T, X215V, X215W, X215Y, X216A, X216C, X216D, X216E, X216F, X216G, X216H, X216I, X216K, X216L, X216M, X216N, X216P, X216Q, X216R, X216S, X216V, X216W, X216Y, X217A, X217C, X217D, X217E, X217F, X217G, X217I, X217K, X217L, X217M, X217N, X217Q, X217S, X217T, X217V, X217Y, X218C, X218D, X218E, X218F, X218G, X218H, X218I, X218L, X218M, X218N, X218P, X218Q, X218R, X218S, X218T, X218V, X218W, X218Y, X219A, X219G, X219S, X220A, X220C, X220G, X220H, X220N, X220S, X220T, X220V, X221G, X221S, X221T, X222A, X222C, X222E, X222F, X222G, X222I, X222K, X222L, X222M, X222N, X222P, X222Q, X222R, X222S, X222T, X222V, X222W, X223A, X223C, X223G, X223M, X223S, X223T, X224A, X224D, X224E, X224G, X224I, X224L, X224M, X224N, X224P, X224S, X224T, X225A, X225C, X225G, X225I, X225N, X225P, X225S, X225T, X225V, X226C, X226F, X226G, X226H, X226I, X226L, X226M, X226N, X226R, X226S, X226T, X226V, X226Y, X227A, X227C, X227F, X227G, X227I, X227L, X227M, X227P, X227Q, X227S, X227T, X227V, X227Y, X228A, X228C, X228G, X228I, X228L, X228M, X228P, X228S, X228V, X229A, X229G, X229P, X229S, X230A, X230D, X230E, X230F, X230G, X230H, X230I, X230L, X230N, X230P, X230Q, X230S, X230T, X230V, X230W, X230Y, X231A, X231C, X231F, X231G, X231H, X231I, X231L, X231S, X231T, X231W, X231Y, X232A, X232G, X232H, X232K, X232L, X232M, X232P, X232S, X232V, X233A, X233C, X233E, X233F, X233G, X233I, X233L, X233M, X233N, X233P, X233Q, X233R, X233S, X233T, X233V, X233Y, X234D, X234F, X234G, X234H, X234L, X234M, X234N, X234P, X234Q, X234S, X234T, X234V, X234Y, X235C, X235D, X235E, X235F, X235G, X235H, X235I, X235K, X235L, X235M, X235N, X235Q, X235R, X235S, X235V, X235W, X235Y, X236A, X236C, X236E, X236F, X236G, X236H, X236K, X236L, X236N, X236P, X236Q, X236R, X236S, X236T, X236V, X236W, X236Y, X237A, X237C, X237F, X237G, X237H, X237I, X237K, X237L, X237M, X237P, X237Q, X237R, X237S, X237T, X237V, X237W, X237Y, X238C, X238D, X238E, X238F, X238G, X238H, X238I, X238K, X238L, X238M, X238N, X238Q, X238R, X238S, X238T, X238V, X238Y, X239C, X239D, X239F, X239G, X239H, X239I, X239K, X239L, X239M, X239N, X239P, X239Q, X239R, X239S, X239T, X239V, X239W, X239Y, X240A, X240C, X240E, X240F, X240I, X240K, X240L, X240M, X240N, X240Q, X240R, X240S, X240T, X240W, X240Y, X241A, X241C, X241D, X241E, X241F, X241G, X241H, X241I, X241K, X241L, X241M, X241N, X241P, X241Q, X241R, X241S, X241T, X241V, X241W, X241Y, X242A, X242C, X242D, X242F, X242G, X242H, X242I, X242L, X242M, X242P, X242Q, X242R, X242S, X242T, X242V, X242W, X243C, X243D, X243E, X243F, X243G, X243H, X243I, X243K, X243L, X243M, X243N, X243P, X243Q, X243R, X243S, X243T, X243V, X243W, X244A, X244D, X244E, X244F, X244H, X244I, X244L, X244M, X244N, X244P, X244Q, X244R, X244S, X244T, X244V, X244W, X244Y, X245A, X245C, X245E, X245G, X245H, X245K, X245L, X245P, X245Q, X245R, X245S, X245V, X245W, X245Y, X246A, X246C, X246E, X246F, X246G, X246H, X246I, X246L, X246M, X246N, X246P, X246Q, X246R, X246S, X246T, X246V, X246W, X246Y, X247A, X247C, X247D, X247E, X247F, X247G, X247H, X247I, X247K, X247L, X247M, X247N, X247P, X247Q, X247R, X247S, X247T, X247V, X247W, X247Y, X248C, X248D, X248E, X248G, X248H, X248I, X248K, X248L, X248M, X248N, X248P, X248R, X248S, X248T, X248V, X248W, X248Y, X249A, X249D, X249E, X249F, X249G, X249H, X249I, X249K, X249L, X249M, X249N, X249Q, X249R, X249S, X249T, X249V, X249W, X249Y, X250A, X250C, X250E, X250F, X250G, X250H, X250I, X250L, X250M, X250N, X250Q, X250S, X250V, X250Y, X251A, X251D, X251E, X251F, X251G, X251K, X251L, X251M, X251P, X251Q, X251R, X251S, X251T, X251V, X251Y, X252A, X252C, X252D, X252F, X252G, X252H, X252I, X252K, X252L, X252M, X252N, X252P, X252R, X252S, X252V, X252W, X252Y, X253A, X253D, X253E, X253F, X253G, X253H, X253I, X253K, X253M, X253R, X253S, X253T, X253V, X253W, X254A, X254C, X254D, X254E, X254G, X254N, X254P, X254S, X254T, X254V, X255A, X255C, X255D, X255E, X255F, X255H, X255I, X255L, X255N, X255P, X255Q, X255R, X255S, X255T, X255V, X255W, X255Y, X256C, X256D, X256E, X256G, X256H, X256I, X256K, X256L, X256M, X256N, X256P, X256R, X256S, X256T, X256V, X256W, X256Y, X257A, X257C, X257E, X257F, X257G, X257H, X257I, X257K, X257L, X257M, X257P, X257S, X257T, X257V, X257W, X257Y, X258A, X258C, X258D, X258E, X258F, X258G, X258H, X258I, X258L, X258M, X258P, X258Q, X258R, X258S, X258T, X258V, X258W, X258Y, X259A, X259C, X259E, X259G, X259I, X259L, X259M, X259P, X259Q, X259R, X259S, X259T, X259V, X260A, X260D, X260E, X260F, X260H, X260I, X260L, X260M, X260N, X260P, X260R, X260S, X260T, X260V, X260Y, X261A, X261C, X261E, X261F, X261G, X261I, X261K, X261L, X261N, X261P, X261Q, X261R, X261S, X261T, X261V, X261W, X261Y, X262A, X262C, X262D, X262F, X262G, X262H, X262I, X262K, X262L, X262M, X262P, X262Q, X262R, X262S, X262T, X262V, X262W, X262Y, X263A, X263C, X263D, X263F, X263G, X263H, X263I, X263K, X263L, X263M, X263N, X263P, X263Q, X263R, X263W, X263Y, X264A, X264C, X264E, X264F, X264G, X264H, X264I, X264L, X264P, X264Q, X264S, X264T, X264V, X264Y, X265A, X265C, X265D, X265F, X265G, X265H, X265I, X265K, X265L, X265M, X265N, X265P, X265Q, X265R, X265S, X265T, X265V, X265W, X265Y, X266G, X266W, X266Y, X267A, X267C, X267D, X267E, X267F, X267G, X267H, X267I, X267K, X267L, X267M, X267N, X267S, X267T, X267V, X267Y, X268A, X268D, X268E, X268G, X268H, X268K, X268L, X268M, X268N, X268P, X268Q, X268R, X268S, X268V, X268W, X268Y, X269C, X269D, X269F, X269G, X269H, X269I, X269L, X269M, X269N, X269Q, X269R, X269S, X269T, X269V, X270A, X270C, X270D, X270E, X270F, X270G, X270H, X270I, X270L, X270M, X270N, X270P, X270Q, X270S, X270T, X270V, X271A, X271C, X271E, X271F, X271G, X271H, X271I, X271K, X271L, X271M, X271N, X271P, X271T, X271V, X271Y, X272A, X272C, X272D, X272E, X272F, X272G, X272H, X272K, X272L, X272M, X272N, X272P, X272R, X272S, X272T, X272W, X272Y, X273A, X273C, X273D, X273E, X273F, X273G, X273H, X273I, X273K, X273L, X273R, X273S, X273T, X273V, X273W, X273Y, X274A, X274C, X274D, X274E, X274G, X274H, X274K, X274L, X274M, X274N, X274P, X274Q, X274R, X274S, X274T, X274W, X275A, X275C, X275D, X275E, X275F, X275G, X275H, X275K, X275L, X275M, X275P, X275Q, X275R, X275V, and X275W.

The present invention also provides dishwashing compositions comprising the subtilisin variant, and fabric cleaning compositions comprising the subtilisin variant. In some preferred embodiments, the dishwashing and fabric cleaning compositions further comprise at least one additional enzyme. In some preferred embodiments, the additional enzyme is selected from: a protease (e.g., a neutral metalloprotease, a wild type serine protease, or a second variant serine protease) a lipase, a cutinase, an amylase, a carbohydrase, a cellulase, a pectinase, a mannanase, an arabinase, a galactanase, a xylanase, an oxidase, and a peroxidase. Moreover, the present invention provides dishwashing methods, comprising the steps of: providing i) the dishwashing composition comprising the subtilisin variant, and ii) dishware in need of cleaning; and contacting the dishware with the dishwashing composition under conditions effective to provide cleaning of the dishware. Similarly, the present invention provides fabric cleaning methods, comprising the steps of: providing i) the fabric cleaning composition comprising the subtilisin variant, and ii) laundry in need of cleaning; and contacting the laundry with the fabric cleaning composition under conditions effective to provide cleaning of the laundry. In still further embodiments, the present invention provides an isolated nucleic acid encoding the variant, an expression vector comprising the isolated nucleic acid in operable combination with a promoter, and/or host cells comprising the expression vector are provided.

The present invention also provides isolated subtilisin variants of a *Bacillus* subtilisin, wherein the subtilisin variant is a mature form having proteolytic activity and comprising substitutions at three or more positions selected from: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, and 275, wherein the positions are numbered by correspondence with the amino acid sequence of *B. amyloliquefaciens* subtilisin BPN' set forth as SEQ ID NO:1. In some embodiments, the subtilisin variant comprises four, five, six, seven, eight, nine, ten, eleven, twelve or more of the positions recited above.

In some embodiments, the subtilisin variant is a mature form having proteolytic activity and comprising substitutions at three or more positions selected from: 1, 3, 4, 8, 9, 10, 11, 12, 13, 15, 16, 17, 18, 19, 20, 21, 22, 23, 24, 25, 26, 27, 28, 29, 30, 31, 33, 35, 36, 38, 40, 43, 44, 45, 46, 47, 48, 49, 50, 51, 52, 53, 54, 55, 56, 57, 59, 61, 62, 68, 69, 72, 73, 76, 78, 84, 86, 87, 88, 89, 90, 91, 92, 93, 94, 95, 96, 97, 98, 99, 100, 101, 102, 103, 104, 105, 106, 107, 108, 109, 110, 111, 112, 114, 115, 116, 117, 118, 119, 120, 121, 122, 124, 126, 128, 129, 130, 131, 132, 133, 134, 135, 136, 137, 139, 140, 141, 142, 143, 144, 145, 146, 147, 148, 149, 150, 151, 152, 156, 158, 159, 160, 165, 166, 167, 170, 171, 172, 173, 174, 175, 176, 177, 180, 182, 183, 184, 185, 186, 187, 188, 191, 194, 195, 198, 199, 203, 204, 206, 209, 210, 211, 212, 213, 215, 216, 217, 218, 222, 223, 224, 227, 228, 230, 231, 232, 233, 234, 235, 236, 237, 238, 239, 240, 241, 242, 243, 244, 245, 246, 247, 248, 249, 250, 251, 252, 253, 255, 256, 258, 259, 260, 261, 262, 265, 267, 268, 269, 270, 271, 272, 273, 274, and 275, wherein the positions are numbered by correspondence with the amino acid sequence of *B. amyloliquefaciens* subtilisin BPN' set forth as SEQ ID NO:1. In some embodiments, the subtilisin variant comprises four, five, six, seven, eight, nine, ten, eleven, twelve or more of the positions recited above.

The present invention also provides isolated subtilisin variants, wherein the subtilisin variants are mature forms having proteolytic activity and comprising substitutions at three or more positions selected from: 1, 2, 3, 4, 5, 7, 8, 9, 10, 11, 12, 13, 14, 15, 16, 17, 18, 19, 20, 21, 22, 23, 24, 25, 26, 27, 28, 29, 30, 31, 33, 35, 36, 38, 39, 40, 41, 42, 43, 44, 45, 46, 47, 48, 49, 50, 51, 52, 53, 54, 55, 56, 57, 59, 60, 61, 62, 63, 66, 68, 69, 71, 72, 73, 74, 75, 76, 77, 78, 79, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 156, 158, 159, 160, 165, 166, 167, 169, 170, 171, 172, 173, 174, 175, 176, 177, 178, 179, 180, 181, 182, 183, 184, 185, 186, 187, 188, 191, 192, 194, 195, 196, 197, 198, 199, 200, 203, 204, 205, 206, 207, 208, 209, 210, 211, 212, 213, 214, 215, 216, 217, 218, 220, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 267, 268, 269, 270, 271, 272, 273, 274, and 275, wherein the positions are numbered by correspondence with the amino acid sequence of *B. amyloliquefaciens* subtilisin BPN' set forth as SEQ ID NO:1. In some embodiments, the subtilisin variant comprises four, five, six, seven, eight, nine, ten, eleven, twelve or more of the positions recited above.

The present invention further comprises isolated subtilisin variants comprising substitutions at three or more positions selected from: X001A, X001C, X001E, X001F, X001G, X001H, X001I, X001K, X001L, X001N, X001P, X001Q, X001R, X001S, X001T, X001V, X001Y, X002A, X002C, X002E, X002G, X002K, X002L, X002M, X002N, X002P, X002Q, X002R, X002S, X002T, X002V, X002W, X002Y, X003D, X003E, X003F, X003G, X003H, X003I, X003L, X003M, X003N, X003P, X003R, X003S, X003T, X003V, X003W, X003Y, X004A, X004C, X004D, X004E, X004F, X004G, X004H, X004K, X004L, X004N, X004P, X004R, X004S, X004T, X004V, X004W, X005A, X005C, X005D, X005E, X005G, X005I, X005M, X005P, X005Q, X005S, X005T, X005W, X005Y, X006A, X006D, X006E, X006M, X006W, X007A, X007C, X007D, X007G, X007H, X007N, X007P, X007Q, X007S, X007T, X008A, X008F, X008G, X008I, X008L, X008M, X008Q, X008T, X008V, X008W, X008Y, X009A, X009C, X009D, X009E, X009F, X009G, X009H, X009L, X009N, X009P, X009Q, X009R, X009S, X009T, X009V, X009W, X009Y, X010A, X010C, X010F, X010G, X010H, X010I, X010K, X010L, X010M, X010N, X010Q, X010R, X010S, X010T, X010V, X010W, X010Y, X011A, X011C, X011D, X011G, X011I, X011M, X011R, X011S, X011T, X011V, X011Y, X012D, X012F, X012G, X012H, X012I, X012K, X012L, X012M, X012N, X012P, X012Q, X012R, X012S, X012T, X012V, X012W, X012Y, X013A, X013G, X013I, X013M, X013Q, X013T, X013V, X014A, X014C, X014D, X014E, X014F, X014G, X014H, X014I, X014K, X014L, X014P, X014Q, X014S, X014T, X014V, X014Y, X015A, X015D, X015F, X015G, X015I, X015K, X015L, X015M, X015P, X015Q, X015R, X015S, X015V, X015W, X016A, X016D, X016E, X016G, X016L, X016N, X016P, X016Q, X016R, X016S, X016T, X016V, X017A, X017D, X017E, X017F, X017G, X017H, X017I, X017K, X017M, X017N, X017R, X017S, X017T, X017V, X017W, X017Y, X018A, X018C, X018D, X018E, X018F, X018G, X018H, X018I, X018K, X018L, X018M, X018N, X018P, X018Q, X018R, X018S, X018T, X018V, X018W, X018Y, X019A, X019C, X019D, X019E, X019F, X019G, X019H, X019K, X019L, X019M, X019N, X019P, X019R, X019S, X019T, X019V, X019W, X019Y, X020A, X020C, X020D, X020F, X020G, X020I, X020K, X020L, X020M, X020P, X020Q, X020R, X020S, X020T, X020V, X020W, X020Y, X021A, X021C, X021D, X021E, X021G, X021H, X021I, X021K, X021L, X021M, X021N, X021P, X021Q, X021R, X021S, X021T, X021V, X021W, X022A, X022C, X022G, X022I, X022K, X022L, X022M, X022N, X022P, X022Q, X022R, X022S, X022T, X022V, X022W, X022Y, X023A, X023G, X023S, X024A, X024C, X024D, X024F, X024G, X024H, X024L, X024M, X024N, X024P, X024Q, X024R, X024S, X024T, X024V, X024W, X025C, X025D, X025E, X025F, X025G, X025H, X025K, X025L, X025M, X025N, X025Q, X025R, X025S, X025T, X025V, X025W, X026C, X026F, X026G, X026I, X026L, X026M, X026N, X026P, X026R, X026S, X026T, X026V, X027A, X027C, X027D, X027F, X027G, X027I, X027K, X027L, X027M, X027N, X027P, X027R, X027S, X027T, X027V, X027W, X027Y, X028A, X028E, X028G, X028H, X028I, X028L, X028M, X028N, X028P, X028S, X028V, X028Y, X029A, X029C, X029G, X029I, X029K, X029S, X029T, X029V, X030A, X030C, X030D, X030E, X030F, X030G, X030L, X030M, X030Q, X030S, X030T, X030V, X031A, X031F, X031I, X031L, X031M, X031S, X031T, X031V, X032A, X032C, X032D, X032E, X032G, X032V, X032W, X033A, X033C, X033D, X033E, X033G, X033H, X033I, X033L, X033M, X033N, X033Q, X033R, X033S, X033T, X033V, X033Y, X034E, X034G, X034H, X034L, X034Q, X034S, X035A, X035F, X035H, X035I, X035K, X035L, X035M, X035P, X035Q, X035R, X035S, X035A, X035C, X035E, X035F, X035G, X035H, X035I, X035L, X035M, X035N, X035P, X035Q, X035R, X035T, X035V, X035W, X035Y, X038C, X038F, X038G, X038H, X038I, X038K, X038L, X038M, X038N, X038Q, X038R, X038T, X038V, X038W, X038Y, X039A, X039E, X039G, X039H, X039L, X039M, X039N, X039Q, X039S, X039T, X039V, X039Y, X040A, X040C, X040D, X040E, X040G, X040H, X040I, X040K, X040L, X040M, X040N, X040P, X040R, X040S, X040T, X040V, X040W, X040Y, X041C, X041D, X041E, X041N, X041P, X041Q, X041S, X042A, X042C, X042F, X042G, X042H, X042I, X042L, X042M, X042N, X042Q, X042S, X042T, X042V, X042Y, X043A, X043C, X043D, X043E, X043F, X043G, X043I, X043L, X043M, X043N, X043P, X043R, X043S, X043T, X043V, X043W, X043Y, X044A, X044C, X044D, X044F, X044G, X044I, X044K, X044L, X044M, X044N, X044P, X044Q, X044R, X044S, X044T, X044V, X044W, X044Y, X045A, X045D, X045F, X045G, X045H, X045I, X045K, X045L, X045M, X045N, X045P, X045Q, X045R, X045S, X045T, X045V, X045W, X045Y, X046C, X046D, X046E, X046F, X046G, X046H, X046I, X046K, X046L, X046M, X046N, X046P, X046Q, X046R, X046S, X046T, X046V, X046W, X047A, X047C, X047E, X047F, X047G, X047H, X047K, X047L, X047M, X047N, X047P, X047Q, X047R, X047S, X047T, X047W, X048A, X048C, X048E, X048F, X048G, X048H, X048I, X048K, X048L, X048M, X048N, X048P, X048Q, X048R, X048S, X048T, X048V, X048Y, X049A, X049E, X049F, X049G, X049H, X049K, X049L, X049M, X049P, X049Q, X049R, X049S, X049T, X050C, X050F, X050G, X050H, X050I, X050L, X050N, X050T, X050V, X050Y, X051F, X051G, X051H, X051K, X051L, X051N, X051P, X051R, X051S, X051T, X051V, X051W, X052A, X052C, X052E, X052F, X052G, X052H, X052I, X052L, X052M, X052N, X052P, X052Q, X052R, X052T, X052V, X052W, X052Y, X053A, X053C, X053D, X053E, X053G, X053H, X053I, X053K, X053L, X053M, X053P, X053Q, X053R, X053S, X053T, X053V, X053W, X053Y, X054A, X054C, X054D, X054E, X054F, X054G, X054H, X054I, X054K, X054L, X054M, X054N, X054P, X054Q, X054R, X054S, X054V, X054W, X054Y, X055A, X055C, X055E, X055F, X055G, X055H, X055I, X055K, X055L, X055M, X055N, X055P, X055Q, X055R, X055S, X055T, X055W, X055Y, X056A, X056C, X056D, X056E, X056H, X056I, X056L, X056M, X056N, X056P, X056Q, X056R, X056S, X056T, X056V, X056W, X057C, X057E, X057F, X057G, X057H, X057I, X057K, X057L, X057M, X057N, X057P, X057Q, X057R, X057S, X057T, X057V, X057W, X057Y, X059A, X059C, X059D, X059E, X059F, X059G, X059I, X059K, X059L, X059M, X059N, X059P, X059Q, X059R, X059S, X059T, X059V, X059W, X059Y, X060A, X060C, X060D, X060F, X060G, X060K, X060L, X060M, X060N, X060P, X060Q, X060S, X060T, X060V, X060W, X060Y, X061A, X061C, X061D, X061F, X061G, X061H, X061I, X061L, X061M, X061N, X061P, X061R, X061S, X061T, X061V, X061Y, X062C, X062E, X062F, X062G, X062H, X062I, X062K, X062L, X062M, X062N, X062P, X062Q, X062R, X062S, X062T, X062V, X062Y, X063A, X063C, X063D, X063E, X063F, X063G, X063H, X063I, X063K, X063M, X063P, X063Q, X063R, X063S, X063T, X063V, X063W, X064H, X064S, X065G, X066A, X066C, X066D, X066E, X066I, X066K, X066L, X066N, X066Q, X066S, X066T, X067A, X067C, X067F, X067H, X067L, X067M, X067N, X067P, X067Q, X067R, X067S, X067T, X067V, X068A, X068C, X068D, X068E, X068G, X068H, X068I, X068L, X068M, X068N, X068Q, X068S, X068T, X068V, X069A, X069C, X069E, X069F, X069G, X069I, X069L, X069M, X069N, X069P, X069R, X069S, X069T, X069V, X069W, X070G, X071A, X071C, X071D, X071E, X071G, X071I, X071L, X071M, X071N, X071P, X071S, X071T, X071V, X071W, X072C, X072D, X072F, X072H, X072I, X072K, X072L, X072M, X072N, X072Q, X072S, X072T, X072V, X072W, X073A, X073C, X073D, X073E, X073H, X073K, X073L, X073N, X073R, X073S, X073T, X073V, X074A, X074C, X074S, X074T, X075A, X075C, X075D, X075E, X075F, X075G, X075H, X075I, X075L, X075M, X075N, X075P, X075Q, X075R, X075S, X075T, X075V, X075W, X076C, X076D, X076E, X076F, X076G, X076H, X076I, X076K, X076L, X076M, X076N, X076Q, X076R, X076S, X076T, X076W, X076Y, X077A, X077C, X077D, X077E, X077F, X077G, X077H, X077K, X077L, X077M, X077N, X077Q, X077R, X077S, X077V, X077Y, X078A, X078C, X078E, X078F, X078G, X078H, X078I, X078K, X078L, X078M, X078N, X078P, X078Q, X078R, X078S, X078T, X078V, X078W, X078Y, X079C, X079D, X079E, X079F, X079G, X079I, X079K, X079L, X079M, X079N, X079P, X079Q, X079R, X079S, X079T, X079V, X079W, X079Y, X080A, X080D, X080E, X080G, X080K, X080L, X080M, X080R, X080T, X080V, X080W, X080Y, X081A, X081C, X081D, X081E, X081F, X081G, X081H, X081I, X081K, X081L, X081M, X081P, X081Q, X081R, X081S, X081T, X081V, X081W, X081Y, X082A, X082E, X082F, X082G, X082K, X082L, X082M, X082N, X082Q, X082R, X082S, X082T, X082V, X082W, X082Y, X083G, X083S, X084C, X084E, X084F, X084G, X084H, X084I, X084L, X084M, X084N, X084Q, X084S, X084T, X084V, X085A, X085C, X085I, X085L, X085N, X086A, X086C, X086D, X086E, X086G, X086I, X086L, X086P, X086R, X086S, X086V, X086W, X086Y, X087A, X087C, X087D, X087E, X087F, X087G, X087I, X087K, X087L, X087N, X087P, X087T, X087V, X087Y, X088A, X088C, X088D, X088E, X088G, X088H, X088K, X088M, X088Q, X088R, X088S, X088V, X088W, X089A, X089C, X089D, X089E, X089F, X089G, X089H, X089I, X089L, X089N, X089P, X089Q, X089R, X089S, X089T, X089V, X089W, X090A, X090C, X090E, X090F, X090G, X090I, X090K, X090L, X090M, X090P, X090Q, X090T, X090V, X090W, X090Y, X091C, X091D, X091F, X091I, X091K, X091L, X091M, X091N, X091Q, X091R, X091S, X091T, X091V, X091W, X091Y, X092A, X092C, X092D, X092E, X092F, X092G, X092H, X092I, X092K, X092L, X092N, X092P, X092Q, X092R, X092T, X092V, X092W, X092Y, X093A, X093C, X093D, X093F, X093G, X093L, X093M, X093N, X093P, X093S, X093T, X093V, X093W, X093Y, X094A, X094D, X094E, X094G, X094H, X094I, X094K, X094L, X094M, X094N, X094Q, X094R, X094V, X095A, X095C, X095E, X095G, X095I, X095K, X095L, X095M, X095R, X095S, X095T, X095V, X095W, X096A, X096E, X096F, X096G, X096H, X096I, X096L, X096M, X096Q, X096R, X096S, X096T, X096W, X096Y, X097A, X097D, X097E, X097F, X097G, X097H, X097I, X097K, X097L, X097M, X097N, X097P, X097Q, X097R, X097S, X097T, X097V, X097W, X097Y, X098A, X098C, X098D, X098E, X098F, X098G, X098K, X098L, X098N, X098P, X098Q, X098R, X098S, X098T, X098V, X098Y, X099A, X099C, X099F, X099G, X099K, X099M, X099P, X099Q, X099R, X099S, X099T, X099V, X099Y, X100D, X100E, X100F, X100G, X100I, X100K, X100L, X100M, X100N, X100P, X100Q, X100R, X100S, X100T, X100V, X100W, X100Y, X101A, X101C, X101D, X101E, X101F, X101G, X101H, X101I, X101K, X101N, X101P, X101Q, X101R, X101S, X101T, X101V, X101Y, X102A, X102C, X102D, X102E, X102F, X102G, X102H, X102M, X102N, X102T, X103A, X103C, X103D, X103E, X103F, X103G, X103I, X103L, X103N, X103P, X103Q, X103R, X103S, X103T, X103V, X103W, X103Y, X104A, X104C, X104D, X104E, X104F, X104G, X104H, X104I, X104L, X104P, X104R, X104S, X104T, X104V, X104W, X104Y, X105A, X105C, X105D, X105E, X105F, X105G, X105H, X105I, X105K, X105L, X105M, X105N, X105Q, X105R, X105S, X105T, X105V, X105W, X105Y, X106A, X106D, X106E, X106F, X106G, X106I, X106L, X106M, X106P, X106R, X106S, X106T, X106V, X106W, X107A, X107C, X107E, X107F, X107H, X107I, X107L, X107M, X107Q, X107S, X107T, X107V, X107W, X107Y, X108A, X108C, X108F, X108G, X108I, X108L, X108M, X108Q, X108S, X108T, X108V, X109A, X109C, X109E, X109F, X109G, X109H, X109I, X109K, X109L, X109M, X109N, X109P, X109Q, X109R, X109S, X109T, X109W, X109Y, X110A, X110G, X110S, X111A, X111C, X111E, X111F, X111I, X111L, X111M, X111P, X111T, X111V, X111Y, X112A, X112C, X112D, X112E, X112F, X112G, X112I, X112L, X112M, X112N, X112Q, X112S, X112T, X112V, X112W, X112Y, X113A, X113C, X113D, X113E, X113L, X113M, X113N, X113S, X113V, X113W, X114A, X114C, X114G, X114T, X115C, X115E, X115F, X115G, X115H, X115I, X115K, X115L, X115M, X115N, X115P, X115Q, X115R, X115S, X115T, X115V, X115W, X115Y, X116A, X116C, X116D, X116F, X116G, X116I, X116K, X116L, X116M, X116N, X116Q, X116S, X116T, X116V, X116W, X117A, X117C, X117D, X117F, X117G, X117I, X117N, X117Q, X117R, X117T, X117Y, X118A, X118C, X118D, X118E, X118F, X118G, X118I, X118K, X118L, X118M, X118N, X118P, X118R, X118S, X118T, X118V, X118W, X119A, X119C, X119E, X119F, X119G, X119H, X119K, X119M, X119N, X119P, X119Q, X119T, X119W, X120A, X120C, X120E, X120F, X120G, X120H, X120I, X120L, X120M, X120N, X120R, X120S, X120T, X120W, X121A, X121C, X121E, X121F, X121G, X121I, X121K, X121L, X121M, X121Q, X121S, X121T, X121V, X121Y, X122A, X122C, X122G, X122I, X122L, X122S, X122T, X122V, X123E, X123G, X123I, X123L, X123M, X123N, X123P, X123S, X123V, X124G, X124H, X124L, X124N, X124Q, X124S, X124T, X124Y, X125A, X125C, X125G, X125P, X125S, X125T, X126A, X126C, X126E, X126F, X126G, X126H, X126I, X126K, X126L, X126M, X126N, X126Q, X126S, X126T, X126V, X126W, X126Y, X127D, X127F, X127G, X127I, X127L, X127Q, X127R, X127S, X127T, X127V, X128A, X128C, X128D, X128F, X128G, X128H, X128I, X128K, X128L, X128M, X128N, X128P, X128Q, X128R, X128S, X128T, X128W, X128Y, X129A, X129E, X129F, X129G, X129I, X129L, X129M, X129N, X129P, X129R, X129S, X129T, X129V, X129W, X129Y, X130C, X130K, X130L, X130N, X130P, X130Q, X130R, X130S, X130V, X130W, X130Y, X131A, X131D, X131E, X131F, X131G, X131I, X131K, X131L, X131M, X131P, X131Q, X131R, X131V, X132A, X132E, X132F, X132H, X132I, X132L, X132M, X132N, X132Q, X132R, X132S, X132T, X132W, X133A, X133F, X133K, X133L, X133N, X133P, X133Q, X133S, X133T, X133V, X133Y, X134A, X134F, X134I, X134L, X134M, X134P, X134S, X134T, X134V, X135A, X135C, X135E, X135F, X135L, X135M, X135Q, X135T, X135W, X136A, X136D, X136E, X136F, X136G, X136K, X136M, X136N, X136Q, X136R, X136S, X136V, X136W, X136Y, X137A, X137C, X137E, X137G, X137H, X137K, X137L, X137M, X137Q, X137R, X137S, X137V, X137W, X138A, X138C, X138E, X138G, X138H, X138L, X138M, X138Q, X138R, X138V, X139A, X139C, X139E, X139F, X139G, X139I, X139M, X139Q, X139S, X139T, X139V, X139Y, X140A, X140C, X140D, X140E, X140F, X140G, X140I, X140K, X140L, X140M, X140N, X140Q, X140R, X140S, X140T, X140V, X140Y, X141D, X141E, X141G, X141H, X141I, X141K, X141L, X141N, X141Q, X141R, X141S, X141V, X141Y, X142A, X142C, X142E, X142G, X142I, X142L, X142M, X142N, X142Q, X142S, X142T, X142V, X142Y, X143C, X143D, X143F, X143G, X143H, X143I, X143K, X143L, X143M, X143N, X143R, X143S, X143T, X143V, X143W, X143Y, X144A, X144C, X144D, X144G, X144H, X144I, X144L, X144M, X144N, X144Q, X144R, X144S, X144T, X144V, X144W, X144Y, X145A, X145C, X145D, X145E, X145F, X145G, X145K, X145L, X145M, X145N, X145Q, X145R, X145S, X145T, X145W, X145Y, X146A, X146C, X146D, X146E, X146F, X146G, X146I, X146K, X146L, X146M, X146Q, X146R, X146S, X146T, X146W, X146Y, X147F, X147G, X147I, X147L, X147M, X147P, X147Q, X147T, X147V, X148A, X148C, X148E, X148F, X148G, X148H, X148I, X148L, X148M, X148N, X148S, X148T, X148V, X148W, X148Y, X149A, X149C, X149F, X149G, X149H, X149I, X149L, X149M, X149P, X149Q, X149S, X149T, X149V, X150A, X150E, X150F, X150G, X150H, X150L, X150P, X150Q, X150S, X150T, X150V, X151A, X151G, X151M, X151S, X151T, X151V, X152A, X152C, X152P, X152R, X152S, X152T, X152V, X153A, X153E, X153F, X153G, X153I, X153M, X153N, X153Q, X153S, X153V, X153Y, X154A, X154C, X154G, X154N, X154Q, X154S, X155A, X155D, X155E, X155F, X155I, X155L, X155N, X155P, X155Q, X155R, X155S, X155T, X155V, X155Y, X156A, X156C, X156D, X156E, X156F, X156G, X156I, X156K, X156L, X156M, X156N, X156P, X156Q, X156R, X156S, X156T, X156V, X156Y, X157A, X157C, X157D, X157G, X157K, X157L, X157Q, X157R, X157S, X157V, X158A, X158C, X158E, X158F, X158H, X158K, X158L, X158M, X158P, X158Q, X158R, X158S, X158T, X158V, X158W, X159A, X159C, X159E, X159G, X159H, X159L, X159M, X159P, X159Q, X159R, X159S, X159V, X159W, X159Y, X160A, X160C, X160D, X160F, X160G, X160I, X160L, X160M, X160N, X160Q, X160R, X160S, X160T, X160V, X160Y, X165A, X165C, X165D, X165E, X165F, X165G, X165H, X165I, X165K, X165L, X165M, X165P, X165R, X165S, X165T, X165V, X165W, X165Y, X166A, X166C, X166D, X166E, X166F, X166H, X166I, X166L, X166M, X166N, X166P, X166R, X166S, X166T, X166V, X166W, X166Y, X167A, X167C, X167D, X167E, X167F, X167G, X167H, X167I, X167K, X167L, X167M, X167N, X167P, X167Q, X167R, X167S, X167T, X167V, X167W, X167Y, X168A, X168C, X168F, X168I, X168M, X168N, X168P, X168S, X168T, X168V, X169A, X169C, X169G, X169I, X169L, X169S, X170A, X170D, X170E, X170G, X170H, X170K, X170L, X170N, X170P, X170Q, X170R, X170S, X170V, X170W, X170Y, X171A, X171C, X171D, X171E, X171F, X171G, X171H, X171I, X171L, X171M, X171N, X171Q, X171S, X171T, X171V, X171W, X171Y, X172A, X172C, X172D, X172F, X172G, X172I, X172K, X172L, X172M, X172P, X172Q, X172R, X172S, X172T, X172V, X172W, X172Y, X173A, X173C, X173D, X173E, X173F, X173G, X173H, X173I, X173K, X173L, X173M, X173N, X173P, X173Q, X173R, X173T, X173V, X173W, X173Y, X174A, X174G, X174I, X174N, X174P, X174S, X174T, X174V, X175A, X175C, X175E, X175G, X175H, X175I, X175K, X175L, X175M, X175Q, X175S, X175T, X175V, X175W, X175Y, X176A, X176C, X176E, X176G, X176I, X176K, X176P, X176S, X176T, X176V, X177A, X177C, X177I, X177T, X177V, X178A, X178G, X178S, X178T, X179A, X179C, X179G, X179H, X179I, X180C, X180G, X180H, X180I, X180L, X180N, X180Q, X180S, X180T, X180V, X181A, X181D, X181E, X181G, X181H, X181L, X181M, X181N, X182A, X182D, X182E, X182F, X182G, X182H, X182I, X182K, X182L, X182M, X182N, X182P, X182Q, X182R, X182S, X182T, X182V, X182W, X182Y, X183A, X183D, X183F, X183G, X183H, X183I, X183K, X183L, X183M, X183N, X183P, X183Q, X183R, X183S, X183T, X183V, X183W, X183Y, X184A, X184C, X184D, X184E, X184F, X184G, X184H, X184L, X184M, X184N, X184S, X184T, X184W, X184Y, X185A, X185C, X185E, X185F, X185G, X185H, X185I, X185K, X185L, X185M, X185N, X185Q, X185R, X185S, X185T, X185V, X185Y, X186A, X186C, X186G, X186H, X186I, X186K, X186L, X186M, X186N, X186P, X186Q, X186R, X186S, X186T, X186W, X187A, X187C, X187D, X187E, X187F, X187G, X187H, X187I, X187L, X187M, X187N, X187P, X187Q, X187S, X187T, X187V, X187W, X187Y, X188A, X188D, X188E, X188F, X188G, X188H, X188I, X188K, X188L, X188P, X188Q, X188R, X188S, X188T, X188V, X188W, X188Y, X189A, X189C, X189E, X189F, X189G, X189H, X189K, X189L, X189M, X189N, X189P, X189Q, X189R, X189S, X189T, X189V, X189Y, X190A, X190D, X190E, X190F, X190G, X190H, X190I, X190K, X190L, X190M, X190N, X190P, X190Q, X190R, X190S, X190V, X190W, X190Y, X191A, X191D, X191E, X191F, X191H, X191I, X191K, X191L, X191P, X191Q, X191R, X191S, X191T, X191V, X191W, X191Y, X192C, X192D, X192E, X192G, X192H, X192I, X192K, X192L, X192M, X192N, X192P, X192Q, X192R, X192S, X192T, X192V, X192W, X192Y, X193A, X193D, X193E, X193F, X193G, X193H, X193I, X193K, X193L, X193R, X193S, X193T, X193V, X193W, X193Y, X194A, X194C, X194D, X194E, X194F, X194G, X194H, X194I, X194L, X194M, X194P, X194Q, X194R, X194S, X194T, X194V, X194W, X194Y, X195A, X195C, X195D, X195E, X195F, X195G, X195I, X195K, X195L, X195Q, X195R, X195S, X195T, X195V, X195W, X195Y, X196A, X196D, X196E, X196F, X196I, X196L, X196M, X196P, X196Q, X196T, X196V, X196Y, X197A, X197C, X197D, X197E, X197F, X197G, X197H, X197I, X197L, X197M, X197N, X197Q, X197R, X197S, X197T, X197V, X197W, X197Y, X198A, X198D, X198E, X198F, X198G, X198H, X198I, X198L, X198M, X198N, X198Q, X198R, X198S, X198T, X198W, X198Y, X199A, X199C, X199D, X199E, X199F, X199G, X199H, X199I, X199L, X199M, X199Q, X199S, X199T, X199V, X199W, X200A, X200C, X200G, X200H, X200I, X200S, X201C, X201G, X201P, X201S, X201T, X201V, X202F, X202G, X203A, X203C, X203E, X203F, X203G, X203H, X203I, X203K, X203L, X203N, X203R, X203S, X203T, X203V, X203W, X203Y, X204A, X204C, X204E, X204F, X204G, X204I, X204K, X204L, X204N, X204P, X204R, X204S, X204T, X204W, X204Y, X205A, X205F, X205G, X205I, X205L, X205M, X205Q, X205T, X205V, X206A, X206C, X206D, X206E, X206F, X206G, X206H, X206I, X206K, X206L, X206N, X206P, X206Q, X206R, X206S, X206T, X206V, X206W, X206Y, X207A, X207G, X207H, X207S, X208A, X208C, X208L, X208N, X208P, X208S, X208T, X208V, X209A, X209C, X209D, X209E, X209F, X209G, X209H, X209I, X209K, X209L, X209M, X209N, X209R, X209S, X209T, X209V, X209W, X209Y, X210A, X210C, X210D, X210E, X210F, X210G, X210H, X210I, X210L, X210M, X210N, X210P, X210Q, X210R, X210S, X210V, X210W, X210Y, X211A, X211C, X211E, X211F, X211G, X211H, X211I, X211L, X211M, X211P, X211Q, X211R, X211T, X211V, X211W, X211Y, X212C, X212F, X212G, X212H, X212I, X212M, X212N, X212P, X212R, X212S, X212T, X212V, X212Y, X213A, X213C, X213D, X213E, X213F, X213G, X213I, X213K, X213L, X213M, X213N, X213P, X213Q, X213R, X213S, X213T, X213V, X213W, X213Y, X214A, X214C, X214E, X214F, X214G, X214H, X214I, X214K, X214L, X214M, X214N, X214P, X214Q, X214R, X214S, X214T, X214V, X214W, X214Y, X215A, X215C, X215D, X215E, X215F, X215G, X215H, X215I, X215K, X215M, X215N, X215P, X215R, X215S, X215T, X215V, X215W, X215Y, X216A, X216C, X216D, X216E, X216F, X216G, X216H, X216I, X216K, X216L, X216M, X216N, X216P, X216Q, X216R, X216S, X216V, X216W, X216Y, X217A, X217C, X217D, X217E, X217F, X217G, X217I, X217K, X217L, X217M, X217N, X217Q, X217S, X217T, X217V, X217Y, X218C, X218D, X218E, X218F, X218G, X218H, X218I, X218L, X218M, X218N, X218P, X218Q, X218R, X218S, X218T, X218V, X218W, X218Y, X219A, X219G, X219S, X220A, X220C, X220G, X220H, X220N, X220S, X220T, X220V, X221G, X221S, X221T, X222A, X222C, X222E, X222F, X222G, X222I, X222K, X222L, X222M, X222N, X222P, X222Q, X222R, X222S, X222T, X222V, X222W, X223A, X223C, X223G, X223M, X223S, X223T, X224A, X224D, X224E, X224G, X224I, X224L, X224M, X224N, X224P, X224S, X224T, X225A, X225C, X225G, X225I, X225N, X225P, X225S, X225T, X225V, X226C, X226F, X226G, X226H, X226I, X226L, X226M, X226N, X226R, X226S, X226T, X226V, X226Y, X227A, X227C, X227F, X227G, X227I, X227L, X227M, X227P, X227Q, X227S, X227T, X227V, X227Y, X228A, X228C, X228G, X228I, X228L, X228M, X228P, X228S, X228W, X229A, X229G, X229P, X229S, X230A, X230D, X230E, X230F, X230G, X230I, X230L, X230N, X230P, X230Q, X230S, X230T, X230V, X230W, X230Y, X231A, X231C, X231F, X231G, X231H, X231I, X231L, X231S, X231T, X231W, X231Y, X232A, X232G, X232H, X232K, X232L, X232M, X232P, X232S, X232V, X233A, X233C, X233E, X233F, X233G, X233I, X233L, X233M, X233N, X233P, X233Q, X233R, X233S, X233T, X233V, X233Y, X234D, X234F, X234G, X234H, X234L, X234M, X234N, X234P, X234Q, X234S, X234T, X234V, X234Y, X235C, X235D, X235E, X235F, X235G, X235H, X235I, X235K, X235L, X235M, X235N, X235Q, X235R, X235S, X235V, X235W, X235Y, X236A, X236C, X236E, X236F, X236G, X236H, X236K, X236L, X236N, X236P, X236Q, X236R, X236S, X236T, X236V, X236W, X236Y, X237A, X237C, X237F, X237G, X237H, X237I, X237K, X237L, X237M, X237P, X237Q, X237R, X237S, X237T, X237V, X237W, X237Y, X238C, X238D, X238E, X238F, X238G, X238H, X238I, X238K, X238L, X238M, X238N, X238Q, X238R, X238S, X238T, X238V, X238Y, X239C, X239D, X239F, X239G, X239H, X239I, X239K, X239L, X239M, X239N, X239P, X239Q, X239R, X239S, X239T, X239V, X239W, X239Y, X240A, X240C, X240E, X240F, X240I, X240K, X240L, X240M, X240N, X240Q, X240R, X240S, X240T, X240W, X240Y, X241A, X241C, X241D, X241E, X241F, X241G, X241H, X241I, X241K, X241L, X241M, X241N, X241P, X241Q, X241R, X241S, X241T, X241V, X241W, X241Y, X242A, X242C, X242D, X242F, X242G, X242H, X242I, X242L, X242M, X242P, X242Q, X242R, X242S, X242T, X242V, X242W, X243C, X243D, X243E, X243F, X243G, X243H, X243I, X243K, X243L, X243M, X243N, X243P, X243Q, X243R, X243S, X243T, X243V, X243W, X244A, X244D, X244E, X244F, X244H, X244I, X244L, X244M, X244N, X244P, X244Q, X244R, X244S, X244T, X244V, X244W, X244Y, X245A, X245C, X245E, X245G, X245H, X245K, X245L, X245P, X245Q, X245R, X245S, X245V, X245W, X245Y, X246A, X246C, X246E, X246F, X246G, X246H, X246I, X246L, X246M, X246N, X246P, X246Q, X246R, X246S, X246T, X246V, X246W, X246Y, X247A, X247C, X247D, X247E, X247F, X247G, X247H, X247I, X247K, X247L, X247M, X247N, X247P, X247Q, X247R, X247S, X247T, X247V, X247W, X247Y, X248C, X248D, X248E, X248G, X248H, X248I, X248K, X248L, X248M, X248N, X248P, X248R, X248S, X248T, X248V, X248W, X248Y, X249A, X249D, X249E, X249F, X249G, X249H, X249I, X249K, X249L, X249M, X249N, X249Q, X249R, X249S, X249T, X249V, X249W, X249Y, X250A, X250C, X250E, X250F, X250G, X250H, X250I, X250L, X250M, X250N, X250Q, X250S, X250V, X250Y, X251A, X251D, X251E, X251F, X251G, X251K, X251L, X251M, X251P, X251Q, X251R, X251S, X251T, X251V, X251Y, X252A, X252C, X252D, X252F, X252G, X252H, X252I, X252K, X252L, X252M, X252N, X252P, X252R, X252S, X252V, X252W, X252Y, X253A, X253D, X253E, X253F, X253G, X253H, X253I, X253K, X253M, X253R, X253S, X253T, X253V, X253W, X254A, X254C, X254D, X254E, X254G, X254N, X254P, X254S, X254T, X254V, X255A, X255C, X255D, X255E, X255F, X255H, X255I, X255L, X255N, X255P, X255Q, X255R, X255S, X255T, X255V, X255W, X255Y, X256A, X256C, X256D, X256E, X256G, X256H, X256I, X256K, X256L, X256M, X256N, X256P, X256R, X256S, X256T, X256V, X256W, X256Y, X257A, X257C, X257E, X257F, X257G, X257H, X257I, X257K, X257L, X257M, X257P, X257S, X257T, X257V, X257W, X257Y, X258A, X258C, X258D, X258E, X258F, X258G, X258H, X258I, X258L, X258M, X258P, X258Q, X258R, X258S, X258T, X258V, X258W, X258Y, X259A, X259C, X259E, X259G, X259I, X259L, X259M, X259P, X259Q, X259R, X259S, X259T, X259V, X260A, X260D, X260E, X260F, X260H, X260I, X260L, X260M, X260N, X260P, X260R, X260S, X260T, X260V, X260Y, X261A, X261C, X261E, X261F, X261G, X261I, X261K, X261L, X261N, X261P, X261Q, X261R, X261S, X261T, X261V, X261W, X261Y, X262A, X262C, X262D, X262F, X262G, X262H, X262I, X262K, X262L, X262M, X262P, X262Q, X262R, X262S, X262T, X262V, X262W, X262Y, X263A, X263C, X263D, X263F, X263G, X263H, X263I, X263K, X263L, X263M, X263N, X263P, X263Q, X263R, X263W, X263Y, X264A, X264C, X264E, X264F, X264G, X264H, X264I, X264L, X264P, X264Q, X264S, X264T, X264V, X264Y, X265A, X265C, X265D, X265F, X265G, X265H, X265I, X265K, X265L, X265M, X265N, X265P, X265Q, X265R, X265S, X265T, X265V, X265W, X265Y, X266G, X266W, X266Y, X267A, X267C, X267D, X267E, X267F, X267G, X267H, X267I, X267K, X267L, X267M, X267N, X267S, X267T, X267V, X267Y, X268A, X268D, X268E, X268G, X268H, X268K, X268L, X268M, X268N, X268P, X268Q, X268R, X268S, X268V, X268W, X268Y, X269C, X269D, X269F, X269G, X269H, X269I, X269L, X269M, X269N, X269Q, X269R, X269S, X269T, X269V, X270A, X270C, X270D, X270E, X270F, X270G, X270H, X270I, X270L, X270M, X270N, X270P, X270Q, X270S, X270T, X270V, X271A, X271C, X271E, X271F, X271G, X271H, X271I, X271K, X271L, X271M, X271N, X271P, X271T, X271V, X271Y, X272A, X272C, X272D, X272E, X272F, X272G, X272H, X272K, X272L, X272M, X272N, X272P, X272R, X272S, X272T, X272W, X272Y, X273A, X273C, X273D, X273E, X273F, X273G, X273H, X273I, X273K, X273L, X273R, X273S, X273T, X273V, X273W, X273Y, X274A, X274C, X274D, X274E, X274G, X274H, X274K, X274L, X274M, X274N, X274P, X274Q, X274R, X274S, X274T, X274W, X275A, X275C, X275D, X275E, X275F, X275G, X275H, X275K, X275L, X275M, X275P, X275Q, X275R, X275V, and X275W, wherein the positions are numbered by correspondence with the amino acid sequence of *B. amyloliquefaciens* subtilisin BPN' set forth as SEQ ID NO:1. In some embodiments, the subtilisin variant comprises four, five, six, seven, eight, nine, ten, eleven, twelve or more of the positions recited above.

In some preferred embodiments, the present invention provides isolated subtilisin variants having a performance index greater than 1 in at least one assay selected from a BMI assay, an egg yolk microswatch assay, and/or an AAPF activity assay, and a performance index of greater than 0.8 for LAS stability or in a TCA assay, wherein the variants comprise at least one substitution at one or more positions selected from: 1, 2, 3, 4, 5, 7, 8, 9, 10, 11, 12, 13, 14, 15, 16, 17, 18, 19, 20, 21, 22, 23, 24, 25, 26, 27, 28, 29, 30, 31, 33, 35, 36, 38, 39, 40, 41, 42, 43, 44, 45, 46, 47, 48, 49, 50, 51, 52, 53, 54, 55, 56, 57, 59, 60, 61, 62, 63, 66, 68, 69, 71, 72, 73, 74, 75, 76, 77, 78, 79, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 156, 158, 159, 160, 165, 166, 167, 169, 170, 171, 172, 173, 174, 175, 176, 177, 178, 179, 180, 181, 182, 183, 184, 185, 186, 187, 188, 191, 192, 194, 195, 196, 197, 198, 199, 200, 203, 204, 205, 206, 207, 208, 209, 210, 211, 212, 213, 214, 215, 216, 217, 218, 220, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 267, 268, 269, 270, 271, 272, 273, 274, and 275, wherein the positions are numbered by correspondence with the amino acid sequence of *B. amyloliquefaciens* subtilisin BPN' set forth as SEQ ID NO:1. In some embodiments, the subtilisin variant comprises two, three, four, five, six, seven, eight, nine, ten, eleven, twelve or more of the positions recited above.

In some preferred embodiments, the present invention provides isolated subtilisin variants having a performance index greater than 1 in at least one assay selected from a BMI assay, an egg yolk microswatch assay, and/or an AAPF activity assay, and a performance index of greater than 0.8 for LAS stability and/or in a TCA assay, wherein the variants comprise at least one substitution at one or more positions selected from: 1, 2, 3, 4, 5, 7, 8, 9, 10, 11, 12, 13, 14, 15, 16, 17, 18, 19, 20, 21, 22, 23, 24, 25, 26, 27, 28, 29, 30, 31, 33, 35, 36, 38, 39, 40, 41, 42, 43, 44, 45, 46, 47, 48, 49, 50, 51, 52, 53, 54, 55, 56, 57, 59, 60, 61, 62, 63, 66, 68, 69, 71, 72, 73, 74, 75, 76, 77, 78, 79, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 156, 158, 159, 160, 165, 166, 167, 169, 170, 171, 172, 173, 174, 175, 176, 177, 178, 179, 180, 181, 182, 183, 184, 185, 186, 187, 188, 191, 192, 194, 195, 196, 197, 198, 199, 200, 203, 204, 205, 206, 207, 208, 209, 210, 211, 212, 213, 214, 215, 216, 217, 218, 220, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 267, 268, 269, 270, 271, 272, 273, 274, and 275, wherein the positions are numbered by correspondence with the amino acid sequence of *B. amyloliquefaciens* subtilisin BPN' set forth as SEQ ID NO:1. In some embodiments, the subtilisin variant comprises two, three, four, five, six, seven, eight, nine, ten, eleven, twelve or more of the positions recited above.

In some further embodiments, the present invention provides isolated subtilisin variants having a performance index greater than 0.8 in at least one assay selected from a BMI assay, egg yolk microswatch assay, and/or an AAPF activity assay, and a performance index of greater than 0.8 for LAS stability and in a TCA assay, wherein the variants comprise at least one substitution at one or more positions selected from: 1, 3, 4, 8, 9, 10, 11, 12, 13, 15, 16, 17, 18, 19, 20, 21, 22, 23, 24, 25, 26, 27, 28, 29, 30, 31, 33, 35, 36, 38, 40, 43, 44, 45, 46, 47, 48, 49, 50, 51, 52, 53, 54, 55, 56, 57, 59, 61, 62, 68, 69, 72, 73, 76, 78, 84, 86, 87, 88, 89, 90, 91, 92, 93, 94, 95, 96, 97, 98, 99, 100, 101, 102, 103, 104, 105, 106, 107, 108, 109, 110, 111, 112, 114, 115, 116, 117, 118, 119, 120, 121, 122, 124, 126, 128, 129, 130, 131, 132, 133, 134, 135, 136, 137, 139, 140, 141, 142, 143, 144, 145, 146, 147, 148, 149, 150, 151, 152, 156, 158, 159, 160, 165, 166, 167, 170, 171, 172, 173, 174, 175, 176, 177, 180, 182, 183, 184, 185, 186, 187, 188, 191, 194, 195, 198, 199, 203, 204, 206, 209, 210, 211, 212, 213, 215, 216, 217, 218, 222, 223, 224, 227, 228, 230, 231, 232, 233, 234, 235, 236, 237, 238, 239, 240, 241, 242, 243, 244, 245, 246, 247, 248, 249, 250, 251, 252, 253, 255, 256, 258, 259, 260, 261, 262, 265, 267, 268, 269, 270, 271, 272, 273, 274, and 275, wherein the positions are numbered by correspondence with the amino acid sequence of *B. amyloliquefaciens* subtilisin BPN' set forth as SEQ ID NO:1. In some embodiments, the subtilisin variant comprises two, three, four, five, six, seven, eight, nine, ten, eleven, twelve or more of the positions recited above.

In some further embodiments, the present invention provides isolated subtilisin variants having a performance index greater than 1 in at least one assay selected from a BMI assay, egg yolk microswatch assay, and/or AAPF activity assay, and a performance index of greater than 0.8 for LAS/EDTA stability or in a TCA assay, wherein the variants comprise at least three substitutions selected from: X001A, X001C, X001E, X001F, X001G, X001H, X001I, X001K, X001L, X001N, X001Q, X001R, X001S, X001T, X001V, X001Y, X002A, X002C, X002E, X002G, X002K, X002L, X002M, X002N, X002P, X002Q, X002R, X002S, X002T, X002V, X002W, X002Y, X003D, X003E, X003F, X003G, X003H, X003I, X003L, X003M, X003N, X003P, X003R, X003S, X003T, X003V, X003W, X003Y, X004A, X004C, X004D, X004E, X004F, X004H, X004K, X004L, X004N, X004P, X004R, X004S, X004T, X004V, X004W, X005A, X005C, X005D, X005E, X005G, X005P, X005Q, X005S, X005T, X007A, X007C, X007D, X007G, X007H, X007N, X007S, X007T, X008A, X008F, X008I, X008L, X008M, X008T, X008V, X009D, X009E, X009F, X009G, X009H, X009L, X009N, X009P, X009Q, X009R, X009S, X009T, X009V, X009W, X009Y, X010A, X010C, X010G, X010H, X010K, X010M, X010N, X010Q, X010R, X010S, X010T, X010W, X011A, X011I, X011M, X011S, X011V, X012D, X012F, X012G, X012H, X012I, X012K, X012L, X012M, X012N, X012Q, X012R, X012S, X012T, X012V, X012W, X013A, X013G, X013I, X013T, X013V, X014A, X014D, X014E, X014F, X014H, X014I, X014K, X014L, X014P, X014Q, X014S, X014T, X014V, X014Y, X015A, X015D, X015F, X015G, X015I, X015K, X015L, X015M, X015P, X015Q, X015R, X015S, X015V, X015W, X016A, X016G, X016L, X016N, X016P, X016Q, X016S, X016T, X016V, X017A, X017F, X017H, X017I, X017K, X017M, X017N, X017R, X017S, X017V, X017W, X017Y, X018A, X018C, X018D, X018E, X018F, X018G, X018H, X018K, X018L, X018M, X018N, X018P, X018Q, X018R, X018S, X018T, X018V, X018W, X018Y, X019A, X019C, X019D, X019E, X019F, X019G, X019H, X019K, X019L, X019M, X019N, X019R, X019S, X019T, X019V, X019W, X019Y, X020A, X020C, X020D, X020F, X020G, X020I, X020K, X020L, X020M, X020P, X020Q, X020R, X020S, X020T, X020V, X020W, X020Y, X021A, X021C, X021D, X021E, X021G, X021H, X021I, X021K, X021L, X021M, X021N, X021P, X021Q, X021R, X021S, X021T, X021V, X021W, X022A, X022C, X022G, X022I, X022K, X022L, X022M, X022N, X022P, X022Q, X022R, X022S, X022T, X022V, X022W, X022Y, X023A, X023G, X023S, X024A, X024C, X024D, X024F, X024G, X024H, X024L, X024M, X024N, X024P, X024Q, X024R, X024S, X024T, X024V, X024W, X025C, X025D, X025E, X025F, X025G, X025H, X025K, X025L, X025M, X025N, X025Q, X025R, X025S, X025T, X025V, X025W, X026C, X026F, X026G, X026I, X026L, X026M, X026N, X026P, X026R, X026S, X026T, X026V, X027A, X027C, X027D, X027F, X027G, X027I, X027K, X027L, X027M, X027N, X027P, X027R, X027S, X027T, X027V, X027W, X027Y, X028A, X028E, X028H, X028I, X028L, X028M, X028N, X028S, X028V, X029A, X029C, X029G, X029S, X029V, X030C, X030E, X030L, X030S, X030T, X030V, X031A, X031F, X031I, X031L, X031M, X031S, X031T, X031V, X033A, X033D, X033E, X033G, X033H, X033M, X033N, X033Q, X033S, X033T, X033Y, X035A, X035F, X035I, X035L, X035M, X035P, X036A, X036C, X036E, X036F, X036G, X036H, X036I, X036L, X036M, X036N, X036Q, X036R, X036S, X036T, X036V, X038C, X038F, X038G, X038H, X038I, X038K, X038L, X038M, X038N, X038Q, X038R, X038T, X038V, X038W, X038Y, X039H, X039V, X040A, X040C, X040D, X040E, X040G, X040H, X040I, X040K, X040L, X040M, X040N, X040P, X040R, X040S, X040T, X040V, X040W, X040Y, X041D, X041E, X042C, X042H, X042I, X042L, X042M, X042N, X042T, X042V, X043A, X043C, X043D, X043E, X043F, X043G, X043I, X043L, X043M, X043N, X043P, X043R, X043S, X043T, X043V, X043W, X043Y, X044A, X044C, X044D, X044G, X044I, X044K, X044L, X044M, X044N, X044P, X044Q, X044R, X044S, X044T, X044V, X044W, X044Y, X045A, X045D, X045F, X045G, X045H, X045I, X045K, X045L, X045M, X045N, X045P, X045Q, X045R, X045S, X045T, X045V, X045W, X045Y, X046C, X046D, X046E, X046F, X046G, X046H, X046I, X046K, X046L, X046M, X046N, X046P, X046Q, X046R, X046S, X046T, X046V, X046W, X047A, X047F, X047G, X047N, X047R, X047S, X047T, X047W, X048A, X048C, X048E, X048F, X048G, X048H, X048I, X048K, X048L, X048M, X048N, X048P, X048Q, X048R, X048S, X048T, X048V, X048Y, X049A, X049F, X049G, X049L, X049M, X049P, X049S, X049T, X050C, X050F, X050H, X050I, X050L, X050N, X050T, X050V, X050Y, X051F, X051G, X051H, X051K, X051L, X051N, X051P, X051R, X051S, X051T, X051V, X051W, X052A, X052C, X052E, X052F, X052G, X052H, X052I, X052L, X052M, X052N, X052P, X052Q, X052R, X052T, X052V, X052W, X052Y, X053A, X053C, X053D, X053E, X053G, X053H, X053K, X053L, X053M, X053P, X053Q, X053R, X053S, X053T, X053V, X053W, X053Y, X054A, X054C, X054D, X054E, X054F, X054I, X054M, X054N, X054Q, X054S, X054V, X055A, X055C, X055E, X055F, X055G, X055H, X055I, X055K, X055L, X055M, X055N, X055P, X055Q, X055S, X055T, X055W, X055Y, X056A, X056C, X056D, X056E, X056H, X056L, X056M, X056N, X056P, X056Q, X056S, X056T, X057A, X057C, X057E, X057F, X057G, X057H, X057I, X057K, X057L, X057M, X057N, X057P, X057Q, X057R, X057S, X057T, X057V, X057W, X057Y, X059A, X059C, X059D, X059E, X059F, X059G, X059I, X059L, X059M, X059N, X059P, X059Q, X059R, X059S, X059T, X059V, X059W, X059Y, X060D, X060S, X060V, X061A, X061C, X061D, X061F, X061G, X061H, X061I, X061L, X061M, X061N, X061P, X061R, X061S, X061T, X061V, X061Y, X062C, X062E, X062F, X062G, X062H, X062I, X062K, X062L, X062M, X062N, X062P, X062Q, X062R, X062S, X062T, X062V, X062Y, X063A, X063C, X063D, X063E, X063F, X063G, X063H, X063K, X063M, X063Q, X063R, X063S, X063W, X066K, X066S, X066T, X068I, X068T, X068V, X069A, X069E, X069G, X069N, X069S, X069T, X071A, X071I, X071N, X071T, X071V, X072C, X072F, X072I, X072L, X072M, X072T, X072V, X073A, X073C, X073D, X073E, X073H, X073K, X073L, X073N, X073S, X073T, X073V, X074A, X074C, X074S, X075A, X075H, X075I, X075L, X075M, X075N, X075P, X075Q, X075R, X075S, X075V, X076D, X076E, X076F, X076G, X076H, X076K, X076M, X076N, X076Q, X076R, X076S, X076T, X076W, X076Y, X077D, X077N, X078A, X078C, X078E, X078F, X078G, X078H, X078I, X078K, X078L, X078M, X078N, X078P, X078Q, X078R, X078S, X078T, X078V, X078Y, X079C, X079D, X079E, X079F, X079G, X079I, X079K, X079L, X079N, X079Q, X079R, X079S, X079T, X079V, X079W, X079Y, X081C, X081G, X081H, X081I, X081L, X081M, X081Q, X081S, X081T, X081V, X082A, X082E, X082F, X082K, X082L, X082M, X082Q, X082R, X082T, X082V, X082Y, X083G, X083S, X084C, X084E, X084G, X084I, X084L, X084M, X084N, X084T, X084V, X085A, X085C, X085I, X086A, X086C, X086D, X086E, X086G, X086P, X086S, X086W, X086Y, X087A, X087C, X087D, X087E, X087F, X087G, X087I, X087K, X087L, X087N, X087S, X087T, X087V, X087Y, X088A, X088C, X088D, X088G, X088Q, X088S, X088W, X089A, X089C, X089D, X089E, X089F, X089G, X089H, X089I, X089L, X089N, X089Q, X089S, X089T, X089V, X089W, X090A, X090C, X090F, X090G, X090I, X090K, X090L, X090M, X090Q, X090T, X090V, X091C, X091D, X091F, X091I, X091K, X091L, X091M, X091N, X091Q, X091R, X091S, X091T, X091V, X091W, X091Y, X092A, X092D, X092G, X092N, X092P, X092R, X092T, X092V, X093A, X093C, X093G, X093L, X093M, X093S, X093T, X093V, X093Y, X094K, X094N, X094Q, X094R, X095A, X095C, X095G, X095I, X095K, X095R, X095S, X095T, X095V, X095W, X096E, X096I, X096L, X096M, X096T, X097A, X097D, X097E, X097G, X097H, X097I, X097K, X097L, X097M, X097N, X097P, X097Q, X097R, X097S, X097T, X097V, X097Y, X098A, X098C, X098D, X098E, X098F, X098G, X098K, X098L, X098N, X098P, X098Q, X098R, X098S, X098T, X098V, X098Y, X099A, X099C, X099F, X099G, X099K, X099M, X099P, X099Q, X099R, X099S, X099T, X099V, X099Y, X100D, X100E, X100G, X100I, X100P, X100S, X100V, X100Y, X101A, X101D, X101E, X101F, X101G, X101H, X101I, X101K, X101N, X101P, X101Q, X101R, X101S, X101T, X101V, X101Y, X102A, X102C, X102D, X102G, X102N, X102T, X103A, X103D, X103E, X103F, X103G, X103I, X103L, X103N, X103P, X103Q, X103R, X103S, X103T, X103V, X103Y, X104A, X104C, X104D, X104E, X104F, X104H, X104I, X104L, X104P, X104R, X104S, X104T, X104V, X104W, X104Y, X105A, X105C, X105D, X105E, X105F, X105G, X105H, X105I, X105K, X105L, X105N, X105Q, X105R, X105S, X105T, X105V, X105W, X105Y, X106A, X106E, X106F, X106G, X106I, X106L, X106M, X106P, X106R, X106S, X106V, X106W, X107A, X107F, X107I, X107L, X107M, X107Q, X107S, X107T, X107V, X108A, X108G, X108I, X108L, X108S, X108T, X108V, X109A, X109C, X109E, X109F, X109G, X109H, X109I, X109K, X109L, X109M, X109N, X109Q, X109R, X109S, X109T, X109W, X109Y, X110A, X110G, X110S, X111C, X111E, X111F, X111I, X111L, X111M, X111V, X111Y, X112A, X112C, X112D, X112E, X112F, X112G, X112I, X112L, X112N, X112Q, X112S, X112T, X112V, X112W, X112Y, X114A, X114C, X114G, X114T, X115C, X115E, X115F, X115G, X115H, X115I, X115K, X115L, X115M, X115N, X115P, X115Q, X115R, X115S, X115T, X115V, X115W, X115Y, X116A, X116C, X116D, X116F, X116G, X116I, X116K, X116L, X116M, X116N, X116Q, X116S, X116T, X116V, X116W, X117A, X117C, X117D, X117F, X117G, X117I, X117N, X117Q, X117R, X117T, X117Y, X118A, X118C, X118D, X118E, X118F, X118G, X118I, X118K, X118L, X118M, X118N, X118P, X118R, X118S, X118T, X118V, X118W, X119A, X119C, X119F, X119H, X119M, X119N, X119Q, X119T, X119W, X120A, X120C, X120E, X120F, X120G, X120H, X120I, X120L, X120M, X120N, X120R, X120S, X120T, X120W, X121A, X121C, X121E, X121F, X121G, X121I, X121L, X121M, X121Q, X121S, X121T, X121V, X121Y, X122A, X122C, X122G, X122I, X122L, X122S, X122T, X122V, X123G, X123N, X123S, X124G, X124L, X124S, X124T, X125A, X125S, X126A, X126F, X126L, X127F, X127G, X127I, X127R, X127S, X127T, X128A, X128F, X128G, X128I, X128K, X128L, X128M, X128N, X128Q, X128R, X128S, X128T, X128W, X129A, X129E, X129F, X129G, X129I, X129L, X129M, X129N, X129P, X129R, X129S, X129T, X129V, X129W, X129Y, X130C, X130K, X130L, X130N, X130Q, X130R, X130S, X130V, X130W, X130Y, X131A, X131D, X131E, X131F, X131G, X131I, X131K, X131L, X131P, X131Q, X131R, X131V, X132A, X132E, X132F, X132H, X132I, X132L, X132M, X132N, X132Q, X132S, X132T, X132W, X133A, X133F, X133K, X133L, X133N, X133P, X133Q, X133S, X133T, X133V, X133Y, X134A, X134F, X134I, X134L, X134M, X134P, X134S, X134T, X134V, X135C, X135E, X135L, X135M, X135W, X136A, X136E, X136F, X136K, X136Q, X136R, X136S, X136V, X136W, X136Y, X137A, X137C, X137E, X137G, X137H, X137K, X137L, X137M, X137Q, X137R, X137S, X137V, X137W, X138A, X138G, X138M, X138R, X138V, X139A, X139C, X139I, X139M, X139T, X139V, X140A, X140C, X140D, X140E, X140F, X140G, X140I, X140L, X140M, X140N, X140Q, X140R, X140S, X140T, X140V, X140Y, X141D, X141E, X141G, X141H, X141I, X141K, X141L, X141N, X141Q, X141R, X141S, X141V, X141Y, X142A, X142C, X142L, X142T, X142V, X142Y, X143C, X143D, X143F, X143G, X143H, X143I, X143K, X143L, X143M, X143N, X143S, X143T, X143V, X143W, X143Y, X144A, X144C, X144D, X144G, X144H, X144I, X144L, X144M, X144N, X144Q, X144R, X144S, X144T, X144V, X144W, X144Y, X145A, X145C, X145D, X145E, X145F, X145G, X145K, X145L, X145M, X145N, X145Q, X145R, X145S, X145T, X145W, X145Y, X146A, X146C, X146D, X146E, X146G, X146K, X146Q, X147I, X147L, X147M, X147T, X147V, X148A, X148C, X148E, X148F, X148H, X148I, X148L, X148M, X148N, X148S, X148T, X148V, X148Y, X149A, X149C, X149I, X149L, X149M, X149P, X149S, X149T, X149V, X150A, X150F, X150L, X150T, X150V, X151A, X151G, X151S, X152A, X152S, X153A, X153G, X153S, X153V, X156A, X156C, X156D, X156E, X156F, X156L, X156M, X156N, X156S, X156T, X158A, X158C, X158E, X158F, X158H, X158K, X158L, X158M, X158Q, X158R, X158S, X158T, X158V, X158W, X159A, X159C, X159E, X159G, X159H, X159M, X159P, X159Q, X159R, X159S, X159W, X160A, X160C, X160D, X160F, X160G, X160I, X160L, X160M, X160N, X160Q, X160R, X160S, X160T, X160V, X160Y, X165I, X165L, X165T, X165V, X166A, X166C, X166D, X166E, X166H, X166M, X166N, X166S, X167C, X167D, X167E, X167F, X167P, X167V, X167W, X167Y, X169A, X169G, X169S, X170A, X170D, X170E, X170G, X170H, X170K, X170L, X170P, X170Q, X170R, X170S, X170V, X170W, X170Y, X171C, X171F, X171L, X171N, X171Y, X172A, X172C, X172D, X172F, X172G, X172I, X172K, X172L, X172M, X172P, X172Q, X172R, X172S, X172T, X172V, X172Y, X173A, X173C, X173D, X173E, X173F, X173G, X173H, X173K, X173L, X173M, X173N, X173Q, X173R, X173T, X173V, X173W, X174A, X174G, X174S, X174T, X174V, X175A, X175C, X175I, X175L, X175M, X175Q, X175T, X175V, X175Y, X176A, X176G, X176S, X177A, X177C, X177I, X177T, X177V, X178A, X178G, X179A, X179G, X180C, X180I, X180L, X180S, X180T, X180V, X181D, X181N, X182A, X182D, X182E, X182F, X182G, X182H, X182I, X182K, X182L, X182M, X182N, X182P, X182Q, X182R, X182S, X182T, X182V, X182W, X182Y, X183A, X183D, X183F, X183G, X183H, X183I, X183K, X183L, X183M, X183N, X183Q, X183R, X183S, X183T, X183V, X183W, X183Y, X184D, X184N, X185A, X185C, X185E, X185F, X185G, X185H, X185I, X185K, X185L, X185M, X185N, X185Q, X185R, X185S, X185T, X185V, X185Y, X186H, X186I, X186K, X186L, X186R, X187A, X187P, X187W, X188A, X188D, X188E, X188F, X188G, X188H, X188I, X188K, X188L, X188P, X188Q, X188R, X188S, X188T, X188V, X188W, X188Y, X191D, X191Q, X192W, X192Y, X194A, X194C, X194D, X194E, X194F, X194G, X194H, X194I, X194L, X194M, X194P, X194Q, X194R, X194S, X194T, X194V, X194W, X194Y, X195A, X195C, X195D, X195E, X195G, X195Q, X195Y, X196L, X196M, X197A, X197C, X197D, X197E, X197G, X197N, X197Q, X197S, X197T, X198A, X198F, X198G, X198H, X198I, X198L, X198M, X198N, X198R, X198S, X198T, X198Y, X199A, X199C, X199I, X199M, X199S, X199T, X199V, X200A, X200C, X200G, X200S, X203A, X203C, X203E, X203I, X203L, X203S, X203T, X203V, X204A, X204C, X204E, X204F, X204G, X204I, X204K, X204L, X204N, X204R, X204S, X204T, X204W, X204Y, X205I, X205T, X205V, X206A, X206C, X206D, X206E, X206G, X206H, X206I, X206K, X206L, X206N, X206P, X206Q, X206R, X206S, X206T, X206V, X206W, X206Y, X207A, X207S, X208C, X208L, X208S, X208T, X208V, X209A, X209C, X209F, X209G, X209H, X209I, X209K, X209L, X209M, X209N, X209R, X209S, X209V, X209W, X209Y, X210A, X210C, X210E, X210G, X210H, X210I, X210L, X210M, X210N, X210P, X210R, X210S, X210V, X210Y, X211A, X211C, X211E, X211F, X211G, X211H, X211I, X211L, X211M, X211P, X211Q, X211R, X211T, X211V, X211W, X211Y, X212C, X212F, X212G, X212H, X212I, X212M, X212N, X212P, X212R, X212S, X212T, X212V, X212Y, X213A, X213C, X213D, X213E, X213F, X213G, X213I, X213K, X213L, X213M, X213N, X213Q, X213R, X213S, X213T, X213V, X213W, X213Y, X214F, X214L, X214W, X214Y, X215A, X215C, X215D, X215E, X215F, X215G, X215H, X215I, X215K, X215M, X215N, X215P, X215R, X215S, X215T, X215V, X215W, X215Y, X216A, X216C, X216D, X216E, X216F, X216G, X216H, X216I, X216K, X216L, X216M, X216N, X216P, X216Q, X216R, X216S, X216V, X216W, X216Y, X217A, X217C, X217E, X217F, X217G, X217I, X217K, X217L, X217M, X217Q, X218C, X218D, X218E, X218F, X218G, X218H, X218I, X218M, X218N, X218Q, X218R, X218S, X218T, X218V, X218Y, X220S, X220T, X222A, X222M, X222Q, X223A, X223G, X223S, X224A, X224G, X224L, X224N, X224S, X224T, X225C, X225P, X226C, X226F, X226H, X226M, X226V, X227A, X227C, X227G, X227I, X227L, X227M, X227S, X227T, X227V, X228A, X228C, X228G, X228I, X228S, X228V, X229A, X229G, X229P, X229S, X230A, X230D, X230E, X230G, X230H, X230I, X230L, X230N, X230Q, X230S, X230T, X230V, X231A, X231C, X231F, X231G, X231H, X231I, X231L, X231S, X231T, X231Y, X232A, X232G, X232H, X232L, X232M, X232S, X232V, X233A, X233C, X233E, X233F, X233G, X233I, X233L, X233M, X233N, X233P, X233Q, X233S, X233T, X233V, X233Y, X234D, X234F, X234G, X234H, X234L, X234M, X234N, X234Q, X234S, X234T, X234V, X234Y, X235C, X235D, X235E, X235F, X235G, X235H, X235I, X235K, X235L, X235M, X235N, X235Q, X235R, X235S, X235V, X235W, X235Y, X236A, X236C, X236E, X236F, X236H, X236K, X236N, X236P, X236Q, X236R, X236S, X236T, X236V, X236W, X236Y, X237A, X237C, X237F, X237G, X237H, X237I, X237K, X237L, X237M, X237P, X237Q, X237R, X237S, X237T, X237V, X237W, X237Y, X238C, X238D, X238E, X238F, X238G, X238H, X238I, X238K, X238L, X238M, X238N, X238Q, X238R, X238S, X238T, X238V, X238Y, X239C, X239D, X239F, X239G, X239H, X239I, X239K, X239L, X239M, X239N, X239P, X239Q, X239R, X239S, X239T, X239V, X239W, X239Y, X240A, X240C, X240E, X240F, X240I, X240K, X240L, X240M, X240N, X240Q, X240R, X240S, X240T, X240W, X240Y, X241A, X241C, X241D, X241E, X241F, X241G, X241H, X241I, X241K, X241L, X241M, X241N, X241P, X241Q, X241R, X241S, X241T, X241V, X241W, X241Y, X242A, X242C, X242D, X242F, X242G, X242H, X242I, X242L, X242M, X242P, X242Q, X242R, X242S, X242T, X242V, X242W, X243C, X243D, X243E, X243F, X243G, X243H, X243I, X243K, X243L, X243M, X243N, X243P, X243Q, X243R, X243S, X243T, X243V, X243W, X244A, X244D, X244E, X244F, X244H, X244I, X244L, X244M, X244N, X244P, X244Q, X244R, X244S, X244T, X244V, X244W, X244Y, X245A, X245C, X245E, X245G, X245H, X245K, X245L, X245P, X245Q, X245R, X245S, X245V, X245W, X245Y, X246A, X246C, X246E, X246F, X246G, X246H, X246I, X246L, X246M, X246N, X246Q, X246S, X246T, X246V, X246W, X246Y, X247A, X247C, X247D, X247E, X247F, X247G, X247H, X247I, X247K, X247L, X247M, X247N, X247P, X247Q, X247R, X247S, X247T, X247V, X247W, X247Y, X248C, X248D, X248E, X248G, X248H, X248I, X248K, X248L, X248N, X248P, X248R, X248S, X248T, X248V, X248W, X248Y, X249A, X249D, X249E, X249F, X249G, X249H, X249I, X249K, X249L, X249M, X249N, X249Q, X249R, X249S, X249T, X249V, X249W, X249Y, X250A, X250C, X250F, X250I, X250L, X250M, X250Q, X250S, X250V, X251A, X251D, X251E, X251F, X251G, X251K, X251L, X251M, X251Q, X251R, X251T, X251V, X251Y, X252A, X252C, X252D, X252F, X252G, X252H, X252I, X252K, X252L, X252M, X252N, X252R, X252S, X252V, X252W, X252Y, X253A, X253D, X253E, X253F, X253G, X253H, X253I, X253K, X253M, X253R, X253S, X253T, X253V, X253W, X254A, X254C, X254G, X254S, X254T, X255A, X255C, X255E, X255F, X255H, X255I, X255L, X255N, X255P, X255Q, X255S, X255T, X255V, X255W, X255Y, X256A, X256C, X256D, X256E, X256G, X256H, X256I, X256K, X256L, X256M, X256N, X256P, X256R, X256S, X256T, X256V, X256W, X256Y, X257C, X257F, X257I, X257K, X257L, X257M, X257V, X258A, X258C, X258D, X258E, X258F, X258G, X258H, X258I, X258L, X258M, X258P, X258Q, X258R, X258S, X258T, X258V, X258W, X258Y, X259A, X259C, X259E, X259G, X259I, X259L, X259M, X259P, X259Q, X259R, X259S, X259T, X259V, X260A, X260D, X260E, X260F, X260H, X260I, X260L, X260M, X260N, X260P, X260R, X260S, X260T, X260V, X260Y, X261A, X261C, X261E, X261F, X261G, X261I, X261K, X261L, X261N, X261P, X261Q, X261R, X261S, X261T, X261V, X261W, X261Y, X262A, X262C, X262D, X262F, X262G, X262H, X262I, X262K, X262L, X262M, X262Q, X262R, X262S, X262T, X262V, X262W, X262Y, X263C, X263F, X263L, X263Y, X264A, X264G, X265A, X265C, X265D, X265F, X265G, X265H, X265K, X265M, X265Q, X265R, X265S, X265T, X265W, X265Y, X267G, X267I, X267L, X267M, X267N, X267V, X268A, X268G, X268H, X268L, X268M, X268N, X268P, X268Q, X268S, X268V, X269C, X269D, X269F, X269G, X269H, X269I, X269L, X269M, X269N, X269Q, X269R, X269S, X269T, X269V, X270A, X270C, X270D, X270G, X270I, X270L, X270M, X270N, X270S, X270T, X270V, X271A, X271C, X271E, X271F, X271G, X271H, X271I, X271K, X271L, X271M, X271N, X271P, X271T, X271V, X271Y, X272A, X272C, X272D, X272E, X272F, X272G, X272H, X272K, X272L, X272M, X272N, X272P, X272R, X272S, X272T, X272W, X272Y, X273A, X273C, X273D, X273E, X273F, X273G, X273H, X273I, X273L, X273S, X273T, X273V, X274A, X274C, X274D, X274E, X274G, X274H, X274L, X274M, X274N, X274P, X274Q, X274R, X274S, X274T, X274W, X275A, X275C, X275D, X275E, X275F, X275G, X275H, X275K, X275L, X275M, X275P, X275Q, X275R, X275V, and X275W, wherein the positions are numbered by correspondence with the amino acid sequence of *B. amyloliquefaciens* subtilisin BPN' set forth as SEQ ID NO:1. In some embodiments, the subtilisin variant comprises two, three, four, five, six, seven, eight, nine, ten, eleven, twelve or more of the positions recited above.

In some embodiments, the present invention provides isolated subtilisin variants having a performance index greater than 1 in at least one assay selected from a BMI assay, an egg yolk microswatch assay, and/or an AAPF activity assay, and a performance index of greater than 0.8 for LAS stability and in a TCA assay, wherein the variant comprises at least three substitutions selected from: X001A, X001E, X001G, X001H, X001Q, X001V, X003E, X003H, X003I, X003M, X003S, X003T, X003V, X004T, X004V, X008I, X008V, X009E, X009H, X009N, X009Q, X009S, X009T, X010A, X010C, X010G, X010H, X010K, X010M, X010N, X010R, X010S, X010T, X011I, X011V, X012G, X012I, X012N, X012Q, X012S, X012T, X012V, X013A, X013G, X015A, X015D, X015F, X015G, X015I, X015L, X015M, X015P, X015Q, X015S, X015V, X015W, X016A, X016G, X016N, X016P, X016S, X016T, X016V, X017H, X017I, X017M, X017N, X018A, X018C, X018D, X018E, X018G, X018H, X018L, X018M, X018N, X018P, X018Q, X018S, X018T, X018V, X018Y, X019A, X019C, X019D, X019E, X019F, X019G, X019H, X019K, X019L, X019M, X019N, X019R, X019S, X019V, X019W, X019Y, X020A, X020C, X020D, X020F, X020G, X020I, X020K, X020L, X020M, X020P, X020Q, X020R, X020S, X020T, X020V, X020W, X020Y, X021A, X021C, X021E, X021G, X021H, X021I, X021K, X021L, X021M, X021N, X021P, X021Q, X021S, X021V, X021W, X022A, X022C, X022G, X022I, X022L, X022M, X022N, X022P, X022Q, X022T, X022V, X022W, X023A, X023G, X023S, X024A, X024C, X024D, X024F, X024G, X024H, X024L, X024M, X024N, X024P, X024Q, X024R, X024S, X024T, X024V, X024W, X025C, X025D, X025E, X025F, X025G, X025K, X025L, X025M, X025Q, X025R, X025S, X025T, X025V, X025W, X026C, X026F, X026G, X026M, X026N, X026R, X026S, X026T, X026V, X027A, X027C, X027D, X027F, X027G, X027K, X027L, X027M, X027N, X027P, X027R, X027S, X027T, X027W, X028A, X028I, X028L, X028M, X028V, X029A, X029C, X029G, X029S, X029V, X030A, X030C, X030L, X030M, X030T, X030V, X031A, X031F, X031I, X031L, X031M, X031S, X031V, X033C, X033M, X033S, X033T, X035I, X035L, X035M, X035P, X036A, X036E, X036S, X036T, X036V, X038C, X038F, X038H, X038I, X038K, X038L, X038M, X038N, X038Q, X038R, X038T, X038V, X038Y, X040A, X040D, X040E, X040I, X040L, X040P, X040V, X043A, X043C, X043D, X043E, X043F, X043G, X043I, X043L, X043M, X043N, X043R, X043S, X043T, X043W, X043Y, X044A, X044C, X044D, X044F, X044G, X044I, X044K, X044L, X044M, X044N, X044Q, X044R, X044S, X044T, X044V, X044Y, X045A, X045D, X045F, X045G, X045H, X045I, X045K, X045L, X045M, X045N, X045P, X045Q, X045R, X045S, X045T, X045V, X045W, X045Y, X046C, X046D, X046E, X046G, X046H, X046I, X046K, X046L, X046M, X046N, X046P, X046Q, X046R, X046S, X046T, X046V, X047G, X047R, X048A, X048C, X048E, X048F, X048H, X048I, X048K, X048L, X048M, X048N, X048P, X048Q, X048R, X048S, X048T, X048V, X048Y, X049A, X049G, X049H, X049S, X049T, X050F, X050H, X050I, X050L, X050T, X050V, X050Y, X051F, X051H, X051K, X051L, X051R, X051S, X051T, X051V, X051W, X052A, X052C, X052E, X052F, X052G, X052H, X052I, X052L, X052M, X052N, X052P, X052Q, X052R, X052T, X052V, X052W, X052Y, X053A, X053C, X053D, X053E, X053G, X053H, X053K, X053L, X053M, X053Q, X053R, X053S, X053T, X053W, X053Y, X054A, X054C, X054D, X054E, X054F, X054H, X054M, X054N, X054Q, X054S, X055C, X055E, X055G, X055H, X055K, X055L, X055P, X055Q, X055S, X055T, X055W, X056A, X056C, X056D, X056E, X056H, X056L, X056M, X056N, X056P, X056Q, X056S, X056T, X057C, X057E, X057F, X057G, X057H, X057I, X057L, X057M, X057N, X057P, X057Q, X057R, X057S, X057T, X057V, X057W, X057Y, X059A, X059D, X059G, X059I, X059L, X059M, X059N, X059Q, X059R, X059S, X059T, X059V, X061A, X061C, X061D, X061F, X061G, X061H, X061I, X061L, X061M, X061N, X061P, X061R, X061S, X061T, X061V, X061Y, X062C, X062E, X062F, X062H, X062I, X062K, X062L, X062M, X062N, X062Q, X062R, X062S, X062T, X062V, X068I, X068L, X068V, X069A, X069G, X069S, X069T, X072I, X072L, X072T, X072V, X073A, X073C, X073S, X076D, X076N, X078A, X078C, X078E, X078H, X078L, X078M, X078N, X078Q, X078S, X078T, X084C, X084G, X084I, X084M, X084V, X086C, X086P, X087A, X087C, X087D, X087E, X087G, X087K, X087L, X087N, X087S, X087V, X088A, X088C, X088G, X088S, X089A, X089D, X089E, X089G, X089H, X089I, X089N, X089Q, X089R, X089S, X089T, X089W, X090C, X090I, X090L, X090M, X090Q, X090T, X090V, X091D, X091F, X091I, X091N, X091S, X091V, X091W, X091Y, X092A, X092G, X092P, X092R, X092V, X093A, X093C, X093G, X093L, X093M, X093T, X093V, X094K, X094R, X095A, X095C, X095I, X095S, X095V, X096F, X096I, X096L, X096M, X097A, X097D, X097E, X097F, X097G, X097H, X097K, X097L, X097M, X097N, X097P, X097Q, X097R, X097S, X097T, X097V, X097W, X097Y, X098A, X098C, X098D, X098E, X098F, X098G, X098K, X098L, X098N, X098P, X098Q, X098R, X098S, X098T, X098V, X098Y, X099A, X099C, X099F, X099G, X099K, X099M, X099P, X099Q, X099R, X099S, X099T, X099V, X099Y, X100D, X100E, X100G, X100I, X100K, X100N, X100R, X100S, X100T, X100V, X100Y, X101A, X101C, X101D, X101E, X101F, X101G, X101H, X101I, X101K, X101N, X101P, X101Q, X101R, X101S, X101T, X101V, X101Y, X102A, X102G, X102T, X103A, X103C, X103D, X103F, X103G, X103I, X103L, X103N, X103P, X103Q, X103R, X103S, X103T, X103V, X103W, X104C, X104F, X104H, X104I, X104L, X104R, X104S, X104T, X104V, X104W, X104Y, X105A, X105C, X105D, X105E, X105F, X105G, X105K, X105L, X105N, X105Q, X105R, X105S, X105T, X105V, X106A, X106D, X106E, X106G, X106I, X106L, X106R, X106S, X106T, X106V, X106W, X107A, X107C, X107F, X107I, X107L, X107M, X107Q, X107S, X107T, X107V, X108A, X108C, X108I, X108S, X108T, X108V, X109A, X109E, X109F, X109G, X109H, X109I, X109K, X109L, X109M, X109N, X109Q, X109R, X109S, X109T, X109W, X109Y, X110A, X110G, X111F, X111I, X111L, X111M, X112D, X112E, X112I, X112Q, X112V, X114A, X114C, X115C, X115E, X115G, X115L, X115M, X115P, X115Q, X115S, X115T, X115W, X115Y, X116A, X116C, X116D, X116F, X116G, X116I, X116K, X116L, X116M, X116N, X116Q, X116S, X116T, X116V, X116W, X117A, X117C, X117N, X117Q, X117R, X117T, X117Y, X118A, X118C, X118D, X118E, X118F, X118G, X118K, X118M, X118N, X118R, X118S, X118V, X118W, X119A, X119F, X119M, X119T, X120A, X120C, X120E, X120F, X120G, X120H, X120I, X120L, X120M, X120N, X120R, X120S, X120T, X120W, X121A, X121C, X121F, X121I, X121L, X121M, X121S, X121T, X121V, X122A, X122G, X122S, X122V, X124G, X124L, X124T, X126A, X126F, X126I, X126L, X126M, X126V, X128A, X128F, X128G, X128I, X128K, X128L, X128M, X128N, X128Q, X128R, X128S, X128T, X128W, X129A, X129E, X129F, X129G, X129M, X129N, X129P, X129R, X129S, X129Y, X130C, X130K, X130L, X130N, X130Q, X130R, X130S, X130V, X130W, X130Y, X131A, X131D, X131E, X131F, X131G, X131K, X131P, X131Q, X132A, X132H, X132I, X132N, X132Q, X132R, X132S, X132T, X133A, X133F, X133K, X133N, X133P, X133S, X133T, X133V, X133Y, X134A, X134S, X134T, X134V, X135L, X135M, X135W, X136E, X136Q, X137A, X137C, X137E, X137H, X137K, X137L, X137M, X137Q, X137R, X137S, X137W, X139C, X139I, X139V, X140D, X140E, X140N, X141D, X141E, X141G, X141H, X141I, X141K, X141L, X141N, X141Q, X141R, X141S, X141V, X141Y, X142A, X142C, X142V, X143C, X143D, X143F, X143H, X143N, X143T, X144A, X144C, X144D, X144G, X144H, X144I, X144L, X144M, X144N, X144R, X144S, X144T, X144V, X144Y, X145A, X145C, X145D, X145F, X145K, X145L, X145N, X145Q, X145R, X146D, X146G, X147I, X147L, X147T, X147V, X148C, X148I, X148L, X148M, X148N, X148V, X149C, X149I, X149L, X149V, X150A, X150L, X150T, X150V, X151A, X151S, X152A, X152S, X156D, X156E, X156L, X156N, X156S, X156T, X158A, X158C, X158E, X158F, X158H, X158K, X158L, X158M, X158Q, X158R, X158S, X158T, X158V, X159A, X159C, X159E, X159G, X159H, X159M, X159P, X159S, X160A, X160C, X160D, X160F, X160I, X160L, X160M, X160N, X160Q, X160S, X160T, X160V, X160Y, X165I, X165L, X165V, X166A, X166C, X166D, X166E, X166H, X166M, X166S, X166T, X167F, X167Y, X170A, X170D, X170E, X170G, X170H, X170K, X170Q, X170R, X170S, X170V, X170Y, X171C, X171Y, X172A, X172C, X172D, X172G, X172I, X172K, X172L, X172M, X172P, X172Q, X172R, X172S, X172V, X172Y, X173A, X173C, X173D, X173H, X173M, X173N, X173Q, X173T, X174A, X174S, X174T, X174V, X175L, X175M, X175V, X176A, X176S, X177C, X177V, X180T, X180V, X182A, X182D, X182E, X182Q, X183A, X183D, X183N, X183Q, X183S, X184D, X184N, X185A, X185C, X185E, X185H, X185K, X185M, X185N, X185Q, X185T, X185V, X186I, X186K, X186L, X186R, X187A, X187C, X188A, X188D, X188E, X188F, X188H, X188I, X188K, X188L, X188P, X188Q, X188S, X188T, X191A, X191D, X191Q, X191S, X194A, X194C, X194D, X194E, X194F, X194H, X194I, X194L, X194M, X194P, X194Q, X194R, X194S, X194T, X194W, X194Y, X195C, X195D, X195E, X195G, X195Q, X198I, X198L, X199C, X199M, X199S, X199V, X203C, X203E, X203T, X203V, X204A, X204C, X204E, X204G, X204N, X204S, X206D, X206E, X206H, X206L, X206N, X206Q, X206S, X209F, X209M, X209W, X209Y, X210A, X210C, X210I, X210L, X210M, X210N, X210P, X211A, X211C, X211E, X211G, X211H, X211I, X211M, X211P, X211Q, X211T, X211V, X212C, X212F, X212G, X212H, X212M, X212N, X212R, X212S, X212Y, X213A, X213D, X213E, X213N, X213Q, X213S, X213T, X215A, X215C, X215D, X215E, X215H, X215I, X215K, X215M, X215N, X215S, X215T, X215V, X215Y, X216A, X216C, X216D, X216E, X216F, X216H, X216I, X216L, X216M, X216N, X216Q, X216S, X216V, X216W, X216Y, X217A, X217C, X217D, X217E, X217F, X217K, X217L, X217M, X217Q, X218C, X218D, X218E, X218N, X218Q, X222C, X222M, X222S, X223A, X223S, X224A, X224N, X224S, X224T, X227A, X227C, X227V, X228A, X228G, X228S, X228V, X230A, X230G, X230N, X230S, X230T, X230V, X231A, X231C, X231F, X231G, X231S, X232A, X232L, X232M, X233A, X233C, X233E, X233G, X233I, X233L, X233N, X233Q, X233S, X233T, X233V, X234L, X234M, X234N, X234Q, X234S, X234T, X234V, X235C, X235F, X235G, X235H, X235I, X235K, X235L, X235M, X235N, X235Q, X235R, X235S, X235V, X235W, X235Y, X236A, X236C, X236E, X236F, X236H, X236N, X236Q, X236S, X236T, X236Y, X237A, X237C, X237F, X237G, X237H, X237I, X237K, X237L, X237M, X237Q, X237R, X237S, X237T, X237V, X237W, X237Y, X238C, X238D, X238E, X238F, X238G, X238H, X238I, X238K, X238L, X238M, X238N, X238Q, X238R, X238S, X238T, X238V, X238Y, X239C, X239D, X239F, X239G, X239H, X239K, X239L, X239M, X239N, X239P, X239Q, X239R, X239S, X239T, X239V, X239W, X239Y, X240A, X240C, X240E, X240F, X240I, X240K, X240M, X240N, X240Q, X240R, X240S, X240T, X240W, X240Y, X241A, X241C, X241D, X241E, X241F, X241G, X241H, X241I, X241K, X241L, X241M, X241N, X241Q, X241R, X241S, X241T, X241V, X241W, X241Y, X242A, X242C, X242D, X242G, X242H, X242I, X242L, X242M, X242P, X242Q, X242S, X242T, X242V, X243C, X243D, X243E, X243F, X243G, X243H, X243I, X243L, X243M, X243N, X243P, X243Q, X243S, X243T, X243V, X243W, X244D, X244E, X244F, X244H, X244I, X244L, X244M, X244N, X244Q, X244S, X244T, X244V, X244W, X245A, X245C, X245E, X245G, X245H, X245K, X245L, X245P, X245Q, X245S, X245V, X245W, X245Y, X246A, X246C, X246I, X246L, X246M, X246T, X246V, X247A, X247C, X247F, X247G, X247H, X247K, X247L, X247M, X247N, X247R, X247S, X247T, X247V, X247W, X247Y, X248C, X248D, X248E, X248G, X248H, X248I, X248L, X248N, X248P, X248R, X248S, X248T, X248V, X248Y, X249A, X249D, X249E, X249F, X249G, X249H, X249I, X249K, X249L, X249M, X249N, X249Q, X249S, X249T, X249W, X249Y, X250C, X250I, X250L, X250M, X250V, X251A, X251C, X251D, X251E, X251F, X251G, X251H, X251K, X251L, X251M, X251Q, X251R, X251T, X251V, X251Y, X252A, X252C, X252D, X252F, X252G, X252H, X252I, X252K, X252L, X252M, X252N, X252R, X252S, X252V, X252W, X253A, X253E, X253H, X253M, X253S, X253T, X253W, X255A, X255C, X255D, X255E, X255I, X255L, X255N, X255Q, X255T, X255V, X255Y, X256A, X256C, X256D, X256E, X256G, X256H, X256I, X256K, X256L, X256M, X256N, X256P, X256S, X256V, X256W, X256Y, X258D, X258G, X259A, X259C, X259E, X259P, X259Q, X259S, X260A, X260D, X260E, X260H, X260I, X260N, X260P, X260S, X260T, X260V, X261A, X261C, X261E, X261F, X261I, X261K, X261L, X261N, X261P, X261Q, X261S, X261T, X261V, X261W, X261Y, X262A, X262C, X262D, X262F, X262H, X262I, X262L, X262M, X262Q, X262T, X262V, X262Y, X265A, X265D, X265S, X267I, X267L, X268A, X268L, X268V, X269D, X269H, X269N, X269Q, X269S, X270A, X270C, X270G, X270I, X270L, X270N, X270S, X270T, X270V, X271C, X271E, X272A, X272C, X272D, X272E, X272F, X272G, X272H, X272L, X272M, X272N, X272P, X272S, X272T, X272W, X272Y, X273A, X273C, X273G, X273S, X274A, X274C, X274G, X274L, X274M, X274N, X274S, X274T, X275D, X275E, X275F, X275H, X275K, X275L, X275M, X275P, X275Q, and X275R, wherein the positions are numbered by correspondence with the amino acid sequence of *B. amyloliquefaciens* subtilisin BPN' set forth as SEQ ID NO:1. In some embodiments, the subtilisin variant comprises two, three, four, five, six, seven, eight, nine, ten, eleven, twelve or more of the positions recited above.

In some embodiments, the present invention provides isolated subtilisin variants having a performance index greater than 1 in at least one assay selected from a BMI assay, an egg yolk microswatch assay, and/or an AAPF activity assay, and a performance index of greater than 0.8 for LAS stability or in a TCA assay, wherein the variant comprises at least three substitutions selected from: X001A, X001E, X001G, X001H, X001Q, X001V, X003E, X003H, X003I, X003M, X003S, X003T, X003V, X004T, X004V, X008I, X008V, X009E, X009H, X009N, X009Q, X009S, X009T, X010A, X010C, X010G, X010H, X010K, X010M, X010N, X010R, X010S, X010T, X011I, X011V, X012G, X012I, X012N, X012Q, X012S, X012T, X012V, X013A, X013G, X015A, X015D, X015F, X015G, X015I, X015L, X015M, X015P, X015Q, X015S, X015V, X015W, X016A, X016G, X016N, X016P, X016S, X016T, X016V, X017H, X017I, X017M, X017N, X018A, X018C, X018D, X018E, X018G, X018H, X018L, X018M, X018N, X018P, X018Q, X018S, X018T, X018V, X018Y, X019A, X019C, X019D, X019E, X019F, X019G, X019H, X019K, X019L, X019M, X019N, X019R, X019S, X019V, X019W, X019Y, X020A, X020C, X020D, X020F, X020G, X020I, X020K, X020L, X020M, X020P, X020Q, X020R, X020S, X020T, X020V, X020W, X020Y, X021A, X021C, X021E, X021G, X021H, X021I, X021K, X021L, X021M, X021N, X021P, X021Q, X021S, X021T, X021V, X021W, X022A, X022C, X022G, X022I, X022L, X022M, X022N, X022P, X022Q, X022T, X022V, X022W, X023A, X023G, X023S, X024A, X024C, X024D, X024F, X024G, X024H, X024L, X024M, X024N, X024P, X024Q, X024R, X024S, X024T, X024V, X024W, X025C, X025D, X025E, X025F, X025G, X025K, X025L, X025M, X025Q, X025R, X025S, X025T, X025V, X025W, X026C, X026F, X026G, X026M, X026N, X026R, X026S, X026T, X026V, X027A, X027C, X027D, X027F, X027G, X027K, X027L, X027M, X027N, X027P, X027R, X027S, X027T, X027W, X028A, X028I, X028L, X028M, X028V, X029A, X029C, X029G, X029S, X029V, X030A, X030C, X030L, X030M, X030T, X030V, X031A, X031F, X031I, X031L, X031M, X031S, X031V, X033C, X033M, X033S, X033T, X035I, X035L, X035M, X035P, X036A, X036E, X036S, X036T, X036V, X038C, X038F, X038H, X038I, X038K, X038L, X038M, X038N, X038Q, X038R, X038T, X038V, X038Y, X040A, X040D, X040E, X040I, X040L, X040P, X040V, X043A, X043C, X043D, X043E, X043F, X043G, X043I, X043L, X043M, X043N, X043R, X043S, X043T, X043W, X043Y, X044A, X044C, X044D, X044F, X044G, X044I, X044K, X044L, X044M, X044N, X044Q, X044R, X044S, X044T, X044V, X044Y, X045A, X045D, X045F, X045G, X045H, X045I, X045K, X045L, X045M, X045N, X045P, X045Q, X045R, X045S, X045T, X045V, X045W, X045Y, X046C, X046D, X046E, X046G, X046H, X046I, X046K, X046L, X046M, X046N, X046P, X046Q, X046R, X046S, X046T, X046V, X047G, X047R, X048A, X048C, X048E, X048F, X048H, X048I, X048K, X048L, X048M, X048N, X048P, X048Q, X048R, X048S, X048T, X048V, X048Y, X049A, X049G, X049H, X049S, X049T, X050F, X050H, X050I, X050L, X050T, X050V, X050Y, X051F, X051H, X051K, X051L, X051R, X051S, X051T, X051V, X051W, X052A, X052C, X052E, X052F, X052G, X052H, X052I, X052L, X052M, X052N, X052P, X052Q, X052R, X052T, X052V, X052W, X052Y, X053A, X053C, X053D, X053E, X053G, X053H, X053K, X053L, X053M, X053Q, X053R, X053S, X053T, X053W, X053Y, X054A, X054C, X054D, X054E, X054F, X054H, X054M, X054N, X054Q, X054S, X055C, X055E, X055G, X055H, X055K, X054Q, X054S, X055C, X055E, X055G, X055H, X055K, X055L, X055P, X055Q, X055S, X055T, X055W, X056A, X056C, X056D, X056E, X056H, X056L, X056M, X056N, X056P, X056Q, X056S, X056T, X057C, X057E, X057F, X057G, X057H, X057I, X057L, X057M, X057N, X057P, X057Q, X057R, X057S, X057T, X057V, X057W, X057Y, X059A, X059D, X059G, X059I, X059L, X059M, X059N, X059Q, X059R, X059S, X059T, X059V, X059W, X061A, X061C, X061D, X061F, X061G, X061H, X061I, X061L, X061M, X061N, X061P, X061R, X061S, X061T, X061V, X061Y, X062C, X062E, X062F, X062H, X062I, X062K, X062L, X062M, X062N, X062Q, X062R, X062S, X062T, X062V, X068I, X068L, X068V, X069A, X069G, X069S, X069T, X072I, X072L, X072T, X072V, X073A, X073C, X073S, X076D, X076N, X078A, X078C, X078E, X078H, X078L, X078M, X078N, X078Q, X078S, X078T, X084C, X084G, X084I, X084M, X084V, X086C, X086P, X087A, X087C, X087D, X087E, X087G, X087K, X087L, X087N, X087S, X087V, X088A, X088C, X088G, X088S, X089A, X089D, X089E, X089G, X089H, X089I, X089N, X089Q, X089R, X089S, X089T, X090C, X090I, X090L, X090M, X090Q, X090T, X090V, X091D, X091F, X091I, X091N, X091S, X091V, X091W, X091Y, X092A, X092G, X092P, X092R, X092V, X093A, X093C, X093G, X093L, X093M, X093T, X093V, X094K, X094R, X095A, X095C, X095I, X095S, X095V, X096F, X096I, X096L, X096M, X097A, X097D, X097E, X097F, X097G, X097H, X097K, X097L, X097M, X097N, X097P, X097Q, X097R, X097S, X097T, X097V, X097W, X097Y, X098A, X098C, X098D, X098E, X098F, X098G, X098K, X098L, X098N, X098P, X098Q, X098R, X098S, X098T, X098V, X098Y, X099A, X099C, X099F, X099G, X099K, X099M, X099P, X099Q, X099R, X099S, X099T, X099V, X099Y, X100D, X100E, X100G, X100I, X100K, X100N, X100R, X100S, X100T, X100V, X100Y, X101A, X101C, X101D, X101E, X101F, X101G, X101H, X101I, X101K, X101N, X101P, X101Q, X101R, X101S, X101T, X101V, X101Y, X102A, X102G, X102T, X103A, X103C, X103D, X103F, X103G, X103I, X103L, X103N, X103P, X103Q, X103R, X103S, X103T, X103V, X103W, X104C, X104F, X104H, X104I, X104L, X104R, X104S, X104T, X104V, X104W, X104Y, X105A, X105C, X105D, X105E, X105F, X105G, X105K, X105L, X105N, X105Q, X105R, X105S, X105T, X105V, X106A, X106D, X106E, X106G, X106I, X106L, X106R, X106S, X106T, X106V, X106W, X107A, X107C, X107F, X107I, X107L, X107M, X107Q, X107S, X107T, X107V, X108A, X108C, X108I, X108S, X108T, X108V, X109A, X109E, X109F, X109G, X109H, X109I, X109K, X109L, X109M, X109N, X109Q, X109R, X109S, X109T, X109W, X109Y, X110A, X110G, X111F, X111I, X111L, X111M, X112D, X112E, X112I, X112Q, X112V, X114A, X114C, X115C, X115E, X115G, X115L, X115M, X115P, X115Q, X115S, X115T, X115W, X115Y, X116A, X116C, X116D, X116F, X116G, X116I, X116K, X116L, X116M, X116N, X116Q, X116S, X116T, X116V, X116W, X117A, X117C, X117N, X117Q, X117R, X117T, X117Y, X118A, X118C, X118D, X118E, X118F, X118G, X118K, X118M, X118N, X118R, X118S, X118V, X118W, X119A, X119F, X119M, X119T, X120A, X120C, X120E, X120F, X120G, X120H, X120I, X120L, X120M, X120N, X120R, X120S, X120T, X120W, X121A, X121C, X121F, X121I, X121L, X121M, X121S, X121T, X121V, X122A, X122G, X122S, X122V, X124G, X124L, X124T, X126A, X126F, X126I, X126L, X126M, X126V, X128A, X128F, X128G, X128I, X128K, X128L, X128M, X128N, X128Q, X128R, X128S, X128T, X128W, X129A, X129E, X129F, X129G, X129M, X129N, X129P, X129R, X129S, X129Y, X130C, X130K, X130L, X130N, X130Q, X130R, X130S, X130V, X130W, X130Y, X131A, X131D, X131E, X131F, X131G, X131K, X131P, X131Q, X132A, X132H, X132I, X132N, X132Q, X132R, X132S, X132T, X133A, X133F, X133K, X133N, X133P, X133S, X133T, X133V, X133Y, X134A, X134S, X134T, X134V, X135L, X135M, X135W, X136E, X136Q, X137A, X137C, X137E, X137H, X137K, X137L, X137M, X137Q, X137R, X137S, X137W, X139C, X139I, X139V, X140D, X140E, X140N, X141D, X141E, X141G, X141H, X141I, X141K, X141L, X141N, X141Q, X141R, X141S, X141V, X141Y, X142A, X142C, X142V, X143C, X143D, X143F, X143H, X143N, X143T, X144A, X144C, X144D, X144G, X144H, X144I, X144L, X144M, X144N, X144R, X144S, X144T, X144V, X144Y, X145A, X145C, X145D, X145F, X145K, X145L, X145N, X145Q, X145R, X146D, X146G, X147I, X147L, X147T, X147V, X148C, X148I, X148L, X148M, X148N, X148V, X149C, X149I, X149L, X149V, X150A, X150L, X150T, X150V, X151A, X151S, X152A, X152S, X156D, X156E, X156L, X156N, X156S, X156T, X158A, X158C, X158E, X158F, X158H, X158K, X158L, X158M, X158Q, X158R, X158S, X158T, X158V, X159A, X159C, X159E, X159G, X159H, X159M, X159P, X159S, X160A, X160C, X160D, X160F, X160I, X160L, X160M, X160N, X160Q, X160S, X160T, X160V, X160Y, X165I, X165L, X165V, X166A, X166C, X166D, X166E, X166H, X166M, X166S, X166T, X167F, X167Y, X170A, X170D, X170E, X170G, X170H, X170K, X170Q, X170R, X170S, X170V, X170Y, X171C, X171Y, X172A, X172C, X172D, X172G, X172I, X172K, X172L, X172M, X172P, X172Q, X172R, X172S, X172V, X172Y, X173A, X173C, X173D, X173H, X173M, X173N, X173Q, X173T, X174A, X174S, X174T, X174V, X175L, X175M, X175V, X176A, X176S, X177C, X177V, X180T, X180V, X182A, X182D, X182E, X182Q, X183A, X183D, X183N, X183Q, X183S, X184D, X184N, X185A, X185C, X185E, X185H, X185K, X185M, X185N, X185Q, X185T, X185V, X186I, X186K, X186L, X186R, X187A, X187C, X188A, X188D, X188E, X188F, X188H, X188I, X188K, X188L, X188P, X188Q, X188S, X188T, X191A, X191D, X191Q, X191S, X194A, X194C, X194D, X194E, X194F, X194H, X194I, X194L, X194M, X194P, X194Q, X194R, X194S, X194T, X194W, X194Y, X195C, X195D, X195E, X195G, X195Q, X198I, X198L, X199C, X199M, X199S, X199V, X203C, X203E, X203T, X203V, X204A, X204C, X204E, X204G, X204N, X204S, X206D, X206E, X206H, X206L, X206N, X206Q, X206S, X209F, X209M, X209W, X209Y, X210A, X210C, X210I, X210L, X210M, X210N, X210P, X211A, X211C, X211E, X211G, X211H, X211I, X211M, X211P, X211Q, X211T, X211V, X212C, X212F, X212G, X212H, X212M, X212N, X212R, X212S, X212Y, X213A, X213D, X213E, X213N, X213Q, X213S, X213T, X215A, X215C, X215D, X215E, X215H, X215I, X215K, X215M, X215N, X215S, X215T, X215V, X215Y, X216A, X216C, X216D, X216E, X216F, X216H, X216I, X216L, X216M, X216N, X216Q, X216S, X216V, X216W, X216Y, X217A, X217C, X217D, X217E, X217F, X217K, X217L, X217M, X217Q, X218C, X218D, X218E, X218N, X218Q, X222C, X222M, X222S, X223A, X223S, X224A, X224N, X224S, X224T, X227A, X227C, X227V, X228A, X228G, X228S, X228V, X230A, X230G, X230N, X230S, X230T, X230V, X231A, X231C, X231F, X231G, X231S, X232A, X232L, X232M, X233A, X233C, X233E, X233G, X233I, X233L, X233N, X233Q, X233S, X233T, X233V, X234L, X234M, X234N, X234Q, X234S, X234T, X234V, X235C, X235F, X235G, X235H, X235I, X235K, X235L, X235M, X235N, X235Q, X235R, X235S, X235V, X235W, X235Y, X236A, X236C, X236E, X236F, X236H, X236N, X236Q, X236S, X236T, X237A, X237C, X237F, X237G, X237H, X237I, X237K, X237L, X237M, X237R, X237S, X237T, X237V, X237W, X237Y, X238C, X238D, X238E, X238F, X238G, X238H, X238I, X238K, X238L, X238M, X238N, X238Q, X238R, X238S, X238T, X238V, X238Y, X239C, X239D, X239F, X239G, X239H, X239K, X239L, X239M, X239N, X239P, X239Q, X239R, X239S, X239T, X239V, X239W, X239Y, X240A, X240C, X240E, X240F, X240I, X240K, X240M, X240N, X240Q, X240R, X240S, X240T, X240W, X240Y, X241A, X241C, X241D, X241E, X241F, X241G, X241H, X241I, X241K, X241L, X241M, X241N, X241Q, X241R, X241S, X241T, X241V, X241W, X241Y, X242A, X242C, X242D, X242G, X242H, X242I, X242L, X242M, X242P, X242Q, X242S, X242T, X242V, X243C, X243D, X243E, X243F, X243G, X243H, X243I, X243L, X243M, X243N, X243P, X243Q, X243S, X243T, X243V, X243W, X244D, X244E, X244F, X244H, X244I, X244L, X244M, X244N, X244Q, X244S, X244T, X244V, X244W, X245A, X245C, X245E, X245G, X245H, X245K, X245L, X245P, X245Q, X245S, X245V, X245W, X245Y, X246A, X246C, X246I, X246L, X246M, X246T, X246V, X247A, X247C, X247F, X247G, X247H, X247K, X247L, X247M, X247N, X247R, X247S, X247T, X247V, X247W, X247Y, X248C, X248D, X248E, X248G, X248H, X248I, X248L, X248N, X248P, X248R, X248S, X248T, X248V, X248Y, X249A, X249D, X249E, X249F, X249G, X249H, X249I, X249K, X249L, X249M, X249N, X249Q, X249S, X249T, X249W, X249Y, X250C, X250I, X250L, X250M, X250V, X251A, X251D, X251E, X251F, X251G, X251K, X251L, X251M, X251Q, X251R, X251T, X251V, X251Y, X252A, X252C, X252D, X252F, X252G, X252H, X252I, X252K, X252L, X252M, X252N, X252R, X252S, X252V, X252W, X253A, X253E, X253H, X253M, X253S, X253T, X253W, X255A, X255C, X255D, X255E, X255I, X255L, X255N, X255Q, X255T, X255V, X255Y, X256A, X256C, X256D, X256E, X256G, X256H, X256I, X256K, X256L, X256M, X256N, X256P, X256S, X256V, X256W, X256Y, X258D, X258G, X259A, X259C, X259E, X259P, X259Q, X259S, X260A, X260D, X260E, X260H, X260I, X260N, X260P, X260S, X260T, X260V, X261A, X261C, X261E, X261F, X261I, X261K, X261L, X261N, X261P, X261Q, X261S, X261T, X261V, X261W, X261Y, X262A, X262C, X262D, X262F, X262H, X262I, X262L, X262M, X262Q, X262T, X262V, X262Y, X265A, X265D, X265S, X267I, X267L, X268A, X268L, X268V, X269D, X269H, X269N, X269Q, X269S, X270A, X270C, X270G, X270I, X270L, X270N, X270S, X270T, X270V, X271C, X271E, X272A, X272C, X272D, X272E, X272F, X272G, X272H, X272L, X272M, X272N, X272P, X272S, X272T, X272W, X272Y, X273A, X273C, X273G, X273S, X274A, X274C, X274G, X274L, X274M, X274N, X274S, X274T, X275D, X275E, X275F, X275H, X275K, X275L, X275M, X275P, X275Q, and X275R, wherein the positions are numbered by correspondence with the amino acid sequence of *B. amyloliquefaciens* subtilisin BPN' set forth as SEQ ID NO:1. In some embodiments, the subtilisin variant comprises two, three, four, five, six, seven, eight, nine, ten, eleven, twelve or more of the positions recited above.

In some embodiments, the subtilisin variants comprise a further substitution at one or more positions selected from the group consisting of: 18, 52, 72, 117, 119, 127, 144, 185, 209 and 213, and wherein the positions are numbered by correspondence with the amino acid sequence of *B. amyloliquefaciens* subtilisin BPN' set forth as SEQ ID NO:1.

In some particularly preferred embodiments, the isolated subtilisin variants described above and herein are GG36 variants. In some preferred embodiments, the GG36 variants are variants of SEQ ID NO:2. In some alternative embodiments, the isolated subtilisin variants described above and herein are BPN' variants.

In some yet additional embodiments, the isolated subtilisin variants comprise a combination of substitutions selected from: S87N/Q109Q/G118D/S128L/P129Q/S130A/S188S/T213E/N248R, S87N/Q109R/G118V/S128L/P129Q/S130A/S188D/T213R/N248D, S87N/Q109Q/G118V/S128L/P129Q/S130A/S188S/T213T/N248N, S87N/Q109R/G118V/S128L/P129Q/S130A/S188D/T213E/N248N, S87N/Q109R/G118V/S128L/P129Q/S130A/S188D/T213E/N248R, S87N/Q109R/G118V/S128L/P129Q/S130A/S188D/T213T/N248R, S87N/Q109R/G118V/S128L/P129Q/S130A/S188S/T213T/N248R, S87R/Q109R/G118V/S128L/P129Q/S130A/S188D/T213E/N248R, S87R/Q109R/G118R/S128L/P129Q/S130A/S188D/T213T/N248R, S87R/Q109R/G118R/S128L/P129Q/S130A/S188D/T213T/N248R, S87N/Q109Q/G118R/S128L/P129Q/S130A/S188D/T213E/N248R, S87N/Q109R/G118V/S128L/P129Q/S130A/S188D/T213R/N248R, S87R/Q109Q/G118R/S128L/P129Q/S130A/S188S/T213E/N248R, S87N/Q109R/G118V/S128L/P129Q/S130A/S188D/T213T/N248N, S87R/Q109Q/G118R/S128L/P129Q/S130A/S188D/T213E/N248R, S87N/Q109R/G118V/S128L/P129Q/S130A/S188S/T213E/N248R, S87D/Q109D/G118D/S128L/P129Q/S130A/S188D/T213E/N248R, S87N/Q109R/G118V/S128L/P129Q/S130A/S188S/T213R/N248R, S87N/Q109R/G118V/S128L/P129Q/S130A/S188R/T213T/N248R, S87R/Q109R/G118R/S128L/P129Q/S130A/S188D/T213E/N248R, S87R/Q109Q/G118R/S128L/P129Q/S130A/S188D/T213E/N248N, S87N/Q109R/G118R/S128L/P129Q/S130A/S188D/T213E/N248R, S87N/Q109R/G118V/S128L/P129Q/S130A/S188R/T213E/N248N, S87N/Q109R/G118V/S128L/P129Q/S130A/S188R/T213E/N248R, S87N/Q109Q/G118V/S128L/P129Q/S130A/S188D/T213T/N248N, S87N/Q109R/G118V/S128L/P129Q/S130A/S188R/T213R/N248D, S87N/Q109Q/G118V/S128L/P129Q/S130A/S188S/T213T/N248R, S87N/Q109R/G118V/S128L/P129Q/S130A/S188R/T213R/N248R, S87N/Q109R/G118V/S128L/P129Q/S130A/S188S/T213R/N248N, S87N/Q109R/G118V/S128L/P129Q/S130A/S188D/T213T/N248D, S87N/Q109R/G118V/S128L/P129Q/S130A/S188D/T213R/N248N, S87N/Q109R/G118V/S128L/P129Q/
S130A/S188S/T213E/N248N, S87N/Q109R/G118V/S128L/P129Q/S130A/S188R/T213T/N248D, S87R/Q109D/G118D/S128L/P129Q/S130A/S188D/T213E/N248R, S87N/Q109Q/G118V/S128L/P129Q/S130A/S188D/T213R/N248R, S87N/Q109Q/G118V/S128L/P129Q/S130A/S188D/T213R/N248N, S87N/Q109R/G118V/S128L/P129Q/S130A/S188R/T213R/N248N, S87N/Q109Q/G118V/S128L/P129Q/S130A/S188R/T213E/N248N, S87N/Q109Q/G118V/S128L/P129Q/S130A/S188D/T213E/N248N, S87N/Q109Q/G118V/S128L/P129Q/S130A/S188R/T213R/N248R, S87N/Q109Q/G118V/S128L/P129Q/S130A/S188D/T213T/N248R, S87N/Q109R/G118V/S128L/P129Q/S130A/S188S/T213R/N248N, S87N/Q109R/G118V/S128L/P129Q/S130A/S188R/T213T/N248N, S87R/Q109Q/G118V/S128L/P129Q/S130A/S188D/T213E/N248R, S87N/Q109Q/G118V/S128L/P129Q/S130A/S188D/T213E/N248R, S87N/Q109D/G118V/S128L/P129Q/S130A/S188R/T213R/N248N, S87N/Q109R/G118V/S128L/P129Q/S130A/S188S/T213T/N248D, S87N/Q109R/G118V/S128L/P129Q/S130A/S188R/T213E/N248D, S87N/Q109Q/G118V/S128L/P129Q/S130A/S188D/T213R/N248D, S87N/Q109Q/G118V/S128L/P129Q/S130A/S188D/T213T/N248D, S87N/Q109R/G118V/S128L/P129Q/S130A/S188D/T213E/N248D, S87R/Q109D/G118R/S128L/P129Q/S130A/S188D/T213E/N248N, S87N/Q109R/G118V/S128L/P129Q/S130A/S188R/T213R/N248R, S87N/Q109Q/G118V/S128L/P129Q/S130A/S188R/T213T/N248R, S87N/Q109Q/G118V/S128L/P129Q/S130A/S188R/T213T/N248N, S87N/Q109R/G118V/S128L/P129Q/S130A/S188S/T213E/N248R, S87N/Q109R/G118V/S128L/P129Q/S130A/S188S/T213R/N248D, and S87N/Q109Q/G118V/S128LP129Q/S130A/S188R/T213E/N248R, wherein the positions are numbered by correspondence with the amino acid sequence of *B. amyloliquefaciens* subtilisin BPN' set forth as SEQ ID NO:1.

In some still further embodiments, the isolated subtilisin variants comprise a combination of substitutions selected from: S87N/Q109Q/G118V/S128L/P129Q/S130A/S188S/T213T/N248D, S87N/Q109Q/G118V/S128L/P129Q/S130A/S188S/T213R/N248N, S87N/Q109V/S128L/P129Q/S130A/S188R/T213R/N248D, S87N/Q109Q/G118V/S128L/P129Q/S130A/S188S/T213E/N248D, S87R/Q109D/G118R/S128L/P129Q/S130A/S188S/T213E/N248R, S87R/Q109D/G118R/S128L/P129Q/S130A/S188D/T213E/N248R, S87N/Q109D/G118V/S128L/P129Q/S130A/S188D/T213E/N248D, and S87N/Q109Q/G118V/S128L/P129Q/S130A/S188R/T213E/N248D, wherein the positions are numbered by correspondence with the amino acid sequence of *B. amyloliquefaciens* subtilisin BPN' set forth as SEQ ID NO:1.

In some yet further embodiments, the isolated subtilisin variants comprise a combination of substitutions selected from: S87D/Q109D/G118R/S128L/P129Q/S130A/S188R/T213E/N248D, S87N/Q109D/G118R/S128L/P129Q/S130A/S188D/T213E/N248R, S87D/Q109D/G118D/S128L/P129Q/S130A/S188S/T213E/N248D, S87N/Q109R/G118V/S128L/P129Q/S130A/S188S/T213E/N248D, S87N/Q109V/G118V/S128L/P129Q/S130A/S188D/T213E/N248D, S87N/Q109Q/G118V/S128L/P129Q/S130A/S188R/T213T/N248D, S87R/Q109D/G118V/S128L/P129Q/S130A/S188D/T213E/N248R, S87N/Q109Q/G118V/S128L/P129Q/S130A/S188S/T213R/N248D, and S87R/Q109D/G118R/S128L/P129Q/S130A/S188D/T213T/N248R, wherein the positions are numbered by correspondence with the amino acid sequence of *B. amyloliquefaciens* subtilisin BPN' set forth as SEQ ID NO:1.

In some additional embodiments, the present invention provides isolated subtilisin variants comprising a combination of substitutions selected from: A001C/S024V/I107L, A001I/R045T/I107R/A172T, A001K/A172L, A001K/A172W, A001K/I072C/L126F, A001K/I072C/L126F/S164Q, A001K/I072C/V104I/L126F, A001K/I072C/V104I/L126F/S164Q, A001K/I072V, A001K/I072V/L126F, A001K/I072V/L126F/S164F, A001K/I072V/V104I, A001K/I072V/V104I/L126F/S164I, A001K/I072V/V104I/S164F, A001K/I072V/V104I/S164Q, A001K/I107T/A172Q, A001K/I107V/G127Q, A001K/I107V/G127Q/A172Q, A001K/I107V/G127R/A172Q, A001K/L126F, A001K/L126F/S164F, A001K/L126F/S164I, A001K/L126F/S164Q, A001K/R045F/I072C, A001K/R045F/I072C/L126F, A001K/R045F/I072C/V104I/S164F, A001K/R045F/I072V/L126F/S164I, A001K/R045F/I072V/L126F/S164Q, A001K/R045F/I072V/S164F, A001K/R045F/I072V/V104G/S164T, A001K/R045F/I107L/A172N, A001K/R045F/I107T, A001K/R045F/I107V/G127Q, A001K/R045F/L126F/S164F, A001K/R045F/L126F/S164I, A001K/R045F/S164F, A001K/R045F/V104I/L126F/S164Q, A001K/R045K/I072C/L126F/S164Q, A001K/R045K/I072V/L126F, A001K/R045K/I072V/L126F/S164F, A001K/R045K/I072V/L126F/S164Q, A001K/R045K/I072V/S164F, A001K/R045K/I072V/S164Q, A001K/R045K/I072V/V104I/L126F/S164F, A001K/R045K/I072V/V104I/L126F/S164I, A001K/R045K/I072V/V104I/L126F/S164Q, A001K/R045K/I107A/A172T, A001K/R045K/I107R/G127A/A172N, A001K/R045K/I107T/G127R, A001K/R045K/I107T/G127R/A172Q, A001K/R045K/L126F, A001K/R045K/L126F/S164I, A001K/R045K/L126F/S164P, A001K/R045K/L126F/S164Q, A001K/R045K/S164F, A001K/R045K/V104I/S164Q, A001K/R045K/V104L/S164A, A001K/R045N/I107T/G127Q, A001K/R045S/V104C/L126Y/S164F, A001K/S024H/I107T/G127Q, A001K/S024H/I107T/G127R, A001K/S024H/I107V, A001K/S024H/R045N/I107T, A001K/S024H/R045N/I107T/G127Q/A172Q, A001K/S024L/R045A, A001K/S024N/I107V/G127T, A001K/S024N/R045K/A172Y, A001K/S024R/I107T, A001K/S024R/R045N/A172C, A001K/S024R/R045N/I107T, A001K/S024R/R045N/I107T/G127R, A001K/S024T/I107T/G127Q/A172Q, A001K/S024T/R045N/G127Q/A172Q, A001K/S024W/I107T/G127R, A001K/S024W/I107V/G127T/A172Q, A001K/S164Q, A001K/V104E, A001K/V104I/L126F, A001K/V104I/L126F/S164I, A001K/V104I/L126F/S164Q, A001L/I072C, A001L/R045Q/G127H/A172R, A001L/S024D/R045Y/I107Y, A001M/R045S/I107E/A172D, A001P/A172V, A001Q/R045K/I107T, A001R/A172G, A001R/A172Q, A001R/I107T, A001R/I107T/A172Q, A001R/I107T/G127Q/A172Q, A001R/I107V/A172Q, A001R/R045F, A001R/R045K/A172Q, A001R/R045K/G127R, A001R/R045K/I107T/G127Q, A001R/R045K/I107V/G127R, A001R/R045N/A172K, A001R/R045N/A172Q, A001R/R045N/I107T, A001R/R045N/I107T/G127Q, A001R/R045N/I107V/A172V, A001R/R045N/I107V/G127Q/A172Q, A001R/R045N/I107V/G127R, A001R/S024H/I107T, A001R/S024H/R045K/I107T, A001R/S024H/R045K/I107T/A172Q, A001R/S024H/R045N/I107T/A172Q, A001R/S024N, A001R/S024R, A001R/S024R/A172H, A001R/S024R/A172Q, A001R/S024R/I107V/A172L, A001R/S024R/I107V/G127R, A001R/S024R/R045F/I107T/G127Q, A001R/S024R/R045F/I107T/G127R, A001R/S024R/R045K/I107T/G127Q, A001R/S024T/I107T/A172Q, A001R/S024T/R045K/A172Q, A001R/S024T/R045K/I107L/G127P/A172P, A001R/S024T/R045N/I107T/A172Q, A001R/S024W/I107V/A172S, A001R/S024W/R045F/I107V/G127Q, A001R/S024W/R045F/I107V/G127R, A001R/S024W/R045K, A001R/S024W/R045K/I107T/A172Q, A001R/S024W/R045N/I107T, A001S/A172V, A001S/S024L/I107Y/A172S, A001T/S024H/I107L/A172Y, A001V/I107L/A172I, G097P/N185Q/A215I, G097P/Y209W/A215V/S256W, G118L/G127R/S132L, G118T/G127Q, I107A/G127K/A172G, I107C/A172S, I107P/A172S, I107Q/A172D, L126A/S164N, L126F/S164V, M119F/N185R, M119F/N185R/Y209W/S256T, M119F/N185V/Y209W, M119F/S144T/N185V/S256I, M119F/S144W/N185R/S256L, M119F/Y209W, M119F/Y209W/S256I, N018K/A215I, N018K/A215R, N018K/A215V, N018K/G097P/A215I/S256W, N018K/G097P/N185K/S256W, N018K/G097P/N185K/Y209W/A215I/S256W, N018K/G097P/N185Q/Y209W/A215V/S256W, N018K/G097P/N185R/A215R/S256W, N018K/G097P/N185R/A215V/S256W, N018K/G097P/N185R/S256W, N018K/G097P/N185R/Y209W, N018K/G097P/N185R/Y209W/S256W, N018K/G097P/Y209W/A215V/S256W, N018K/N185K, N018K/N185K/A215V/S256W, N018K/N185K/S256W, N018K/N185K/Y209W/A215R, N018K/N185Q/A215R/S256W, N018K/N185Q/A215V/S256W, N018K/N185Q/S256W, N018K/N185Q/Y209W/S256W, N018K/N185R/A215I/S256W, N018K/N185R/A215R/S256W, N018K/N185R/A215V, N018K/N185R/Y209W/A215V/S256W, N018K/S256W, N018Q/G097P/N185K/A215V, N018Q/G097P/N185K/Y209W, N018Q/N185K, N018Q/N185K/S256W, N018Q/N185K/Y209W/A215I/S256W, N018Q/N185K/Y209W/A215V, N018Q/N185K/Y209W/A215V/S256W, N018Q/N185Q/A215V, N018Q/N185Q/S256W, N018Q/N185Q/Y209W/S256W, N018Q/N185R/A215R, N018Q/N185Q/S256W, N018R/G097P/N185Q/A215I, N018R/G097P/Y209W/A215V, N018R/G097P/Y209W/S256W, N018R/N185K/A215V/S256W, N018R/N185K/S256W, N018R/N185Q/A215V/S256W, N018R/N185Q/Y209W/S256W, N018R/N185R/A215R, N018R/N185R/S256W, N018R/N185R/Y209W/S256W, N018R/Y209W/A215V/S256W, N018R/Y209W/S256W, N043E/S101E, N043E/S101E/N248K, N043E/S101F, N043E/S101N/N117Y, N043E/S101V, N043E/S101Y/N117I/N248K, N043E/S101Y/N117/N248K, N043F/N117I, N043F/S101E/N117I/N248K, N043F/S101R, N043I/N117Y, N043I/S101E/N248I, N043I/S101F/N117Y/N248K, N043I/S101N/N117Y/N248K, N043I/S101R/N248K, N043I/S101Y/N117I/N248I, N043I/S101Y/N117Y/N248K, N043S/N117Y/N248K, N043S/N248I, N043S/S101E, N043S/S101E/N117I/N248I, N043S/S101E/N117Y/N248K, N043S/S101E/N248K, N043S/S101F, N043S/S101F/N248K, N043S/S101N/N117I, N043S/S101R/N117I/N248K, N043S/S101V/N117I/N248I, N043S/S101Y, N043S/S101Y/N117I, N043S/S101Y/N117Y, N043S/S101Y/N248K, N043V/N117Y/N248I, N043V/N248I, N043V/N248K, N043V/S101E/N117I/N248K, N043V/S101E/N248I, N043V/S101F, N043V/S101F/N117I, N043V/S101F/N117Y, N043V/S101F/N248K, N043V/S101R/N117I/N248K, N043V/S101T/N248K, N043V/S101V/N117I, N043V/S101V/N248K, N043V/S101Y, N043V/S101Y/N117I, N043V/S101Y/N117I/N248K, N185K/A215V, N185K/Y209W/S256W, N185Q/A215R/S256W, N185Q/S256W, N185R/S256W, N185R/Y209W/A215I, N185R/Y209W/S256W, N185V/Y209W, P052I/M119F, P052I/M119F/S144T/N185R/Y209W, P052I/M119F/S144V/Y209W, P052I/M119F/S144Y/N185R, P052I/M119F/S144Y/N185R/Y209W/

S256I, P052I/M119F/Y209W/S256I, P052I/N185R/ Y209W/S256I, P052I/N185V/Y209W, P052I/N185V/ Y209W/S256I, P052I/S144T, P052I/S144T/N185R/ Y209W/S256T, P052I/S144T/N185V/Y209W/S256T, P052I/S144T/S256I, P052I/S144T/Y209W/S256I, P052I/ S144T/Y209W/S256T, P052I/S144V/Y209W, P052I/ S144Y/N185R/Y209W, P052I/S144Y/N185V, P052I/ S144Y/N185V/S256T, P052I/S144Y/S256T, P052I/S144Y/ Y209W/S256I, P052V/M119F/N185V/Y209W/S256I, P052V/M119F/S144T, P052V/M119F/S144T/N185R/ S256T, P052V/M119F/S144T/N185R/Y209W, P052V/ M119F/S144T/S256T, P052V/M119F/S144T/Y209W, P052V/M119F/S144V/N185V/S256I, P052V/N185V/ Y209W/S256I, P052V/S144T, P052V/S144T/N185V/ Y209W/S256I, P052V/S144T/N185V/Y209W/S256T, P052V/S144T/Y209W/S256I, P052V/S144V/N185R/ Y209W/S256T, P052V/S144V/N185V/Y209W, P052V/ S144V/Y209W/S256I, P052V/S144W/N185R, P052V/ S144W/N185V/Y209W, P052V/S144W/Y209W, P052V/ S144Y/S256T, P052V/S144Y/Y209W, P052V/S256T, Q109A/G118S, Q109D/G118V/G127H, Q109H/G118S/ S132P, Q109H/G127R, Q109I/G118R, Q109I/G118S, Q109I/G127C, Q109I/G127T/S132Y, Q109I/S132N, Q109K/G118F/G127Q/S132N, Q109L/G118L/G127Q/ S132N, Q109P/G118Q, Q109R/G118V, Q109S/G118R, Q109T/G118N, Q109V/G118F, Q109V/G127Q, Q109V/ G127R, Q109V/G127R/S132N, Q109V/G127R/S132Y, R045F/I072V/L126F/S164Q, R045F/I107T, R045K/I072C/ V104I/L126F/S164F, R045K/I107T, R045K/L126F/S164F, R045L/I072S/S164I, R045N/I107A/A172R, R045N/I107T/ A172Q, R045N/I107V/A172Q, R045S/I107L, R045V/ I107R/A172D, S024A/G118I, S024A/Q109Y/G118C, S024C/Q109K/G118I, S024G/G118F/G127R/S132N, S024H/G118K/G127I, S024H/G118L/G127T/S132Y, S024H/G127R, S024H/I107K, S024H/Q109L, S024H/ Q109T/G118R, S024H/Q109V/G127R/S132N, S024H/ Q109V/G127T, S024H/S099K/G118F/G127R, S024H/ S099K/G118R/G127R/S132H, S024H/S099K/S103P, S024H/S099K/S103P/G118F, S024H/S099K/S103R/ G118A/S132P, S024H/S099Q/G118R/G127Q/S132H, S024H/S099Q/G118R/S132H, S024H/S099Q/S103N/ G118R/G127T/S132N, S024H/S099Q/S103N/G118T/ S132H, S024H/S099Q/S103P, S024H/S099Q/S103P/ G118R/S132H, S024H/S099Q/S132H, S024H/ S099Q/S132H, S024H/S099Q/S132N, S024H/S099T/ G118R, S024H/S099T/S103N, S024H/S099T/S103N/ G127R/S132N, S024H/S099T/S103N/S132N, S024H/ S099T/S103P/G118R, S024H/S099T/S103P/G118R/ S132H, S024H/S099T/S103P/S132N, S024H/S103N/ S132H, S024H/S103P/G127R/S132R, S024H/S132N, S024H/S132R, S024I/I107R/G127I/A172R, S024L/G127R, S024L/Q109K/G127R/S132Y, S024L/Q109V/G118V/ G127Q/S132R, S024L/Q109V/G118R/G127Q, S024M/ G118V, S024N/G118R/G127L/S132Y, S024N/G127R, S024N/I107T, S024N/Q109T/G127R/S132N, S024N/ Q109T/G127T/S132R, S024N/Q109T/G127T/S132Y, S024N/Q109V/G118L/G127Q, S024N/Q109V/G118R/ G127T/S132Y, S024N/Q109V/G127R/S132N, S024N/ R045K/A172L, S024N/R045K/I107V/A172N, S024N/ S099T/G127T/S132H, S024N/S132R, S024P/S099Q/ S103P/G118R, S024Q/Q109R/S132R, S024R/G118H/ S132V, S024R/G118L/G127R/S132R, S024R/G118 S132N, S024R/Q109C/G127H, S024R/Q109I/G127T, S024R/Q109L/G118T/G127Q/S132N, S024R/Q109L/ G127Q, S024R/Q109R/G118T/G127R, S024R/Q109T/ G127R/S132N, S024R/Q109T/G127R/S132Y, S024R/ Q109T/G127T/S132Y, S024R/Q109T/S132Y, S024R/ Q109V, S024R/Q109V/G118C/S132A, S024R/Q109V/ G118R/G127T, S024R/Q109V/G127S, S024R/Q109V/ S132N, S024R/R045F/I107T/A172Q, S024R/S132Y, S024T/G118D, S024T/I107T, S024T/Q109I/G127T, S024T/ R045K/I107T/G127R/A172Q, S024T/R045K/I107V, S024V/Q109C/G118L, S024V/Q109L/G118V, S024V/ Q109R/G118F, S024V/R045I/A172V, S024W/A172Q, S024W/G118K, S024W/G118L/G127T/S132Y, S024W/ G127R, S024W/G127R/S132N, S024W/Q109I, S024W/ Q109I/G127T, S024W/Q109K/G118R, S024W/Q109L, S024W/Q109L/G127R/S132N, S024W/Q109R/G127T/ S132N, S024W/Q109T/G118L, S024W/Q109T/G118R/ G127Q/S132N, S024W/Q109T/G118T/G127T, S024W/ Q109T/G127R/S132R, S024W/Q109V/G118S/S132Y, S024W/Q109V/G127T, S024W/Q109V/G127T/S132Y, S024W/R045N/A172Q, S024W/S099K/S103P/G118R/ S132H, S024W/S099K/S103P/S132H, S024W/S099Q, S024W/S099Q/G118T, S024W/S099Q/S103N/G118R/ G127Q/S132N, S024W/S099Q/S103N/G118R/S132N, S024W/S099Q/S103N/G118T, S024W/S099Q/S103P, S024W/S099Q/S103P/G118R/S132H, S024W/S099Q/ S103P/G118T/S132N, S024W/S099Q/S103P/S132N, S024W/S099T, S024W/S099T/G118R, S024W/S099T/ G118R/G127Q, S024W/S099T/G118R/S132R, S024W/ S099T/G118T/S132H, S024W/S099T/S103N, S024W/ S099T/S103N/G118R, S024W/S099T/S103N/G127R/ S132H, S024W/S099T/S103N/S132H, S024W/S099T/ S103N/S132N, S024W/S099T/S103P, S024W/S099T/ S103P/G118R, S024W/S099T/S103P/G118R/S132H, S024W/S099T/S103P/G118T, S024W/S099T/S103P/ G118T/S132N, S024W/S099T/S103P/S132H, S024W/ S103K/S132R, S024W/S103P, S024W/S103P/G118F/ S132H, S024W/S132H, S024W/S132N, S024Y/G127R/ A172E, S024E/I107G, S087N/G118V/S128L/P129Q/S130A/A001C/ S087N/G118V/S128L/P129Q/S130A/ A001K/I072C, S087N/G118V/S128L/P129Q/S130A/ A001K/I072C/L126F, S087N/G118V/S128L/P129Q/ S130A/A001K/I072C/L126F/S164F, S087N/G118V/ S128L/P129Q/S130A/A001K/I072C/L126F/S164I, S087N/ G118V/S128L/P129Q/S130A/A001K/I072C/S164I, S087N/G118V/S128L/P129Q/S130A/A001K/I072C/ S164Q, S087N/G118V/S128L/P129Q/S130A/A001K/ I072C/V104I/L126F, S087N/G118V/S128L/P129Q/S130A/ A001K/I072C/V104I/S164I, S087N/G118V/S128L/P129Q/ S130A/A001K/I072V/S164F, S087N/G118V/S128L/ P129Q/S130A/A001K/I072V/S164I, S087N/G118V/ S128L/P129Q/S130A/A001K/I072V/S164Q, S087N/ G118V/S128L/P129Q/S130A/A001K/I072V/V104I/ L126F/S164F, S087N/G118V/S128L/P129Q/S130A/ A001K/I107T, S087N/G118V/S128L/P129Q/S130A/ A001K/I107T/A172Q, S087N/G118V/S128L/P129Q/ S130A/A001K/I107W/A172P, S087N/G118V/S128L/ P129Q/S130A/A001K/L126F/S164F, S087N/G118V/ S128L/P129Q/S130A/A001K/R045F, S087N/G118V/ S128L/P129Q/S130A/A001K/R045K/I105S, S087N/ G118V/S128L/P129Q/S130A/A001K/R045N/I107T/ A172Q, S087N/G118V/S128L/P129Q/S130A/A001K/ R045N/I107V, S087N/G118V/S128L/P129Q/S130A/ A001K/S024H/A172Q, S087N/G118V/S128L/P129Q/ S130A/A001K/S024H/I107V, S087N/G118V/S128L/ P129Q/S130A/A001K/S024T/I107V/A172W, S087N/ G118V/S128L/P129Q/S130A/A001K/S024W/R045N/ I107T, S087N/G118V/S128L/P129Q/S130A/A001K/ S164F, S087N/G118V/S128L/P129Q/S130A/A001K/ S164I, S087N/G118V/S128L/P129Q/S130A/A001K/ V104I/L126F/S164F, S087N/G118V/S128L/P129Q/ S130A/A001K/V104I/L126F/S164Q, S087N/G118V/

S128L/P129Q/S130A/A001K/V104I/S164F, S087N/G118V/S128L/P129Q/S130A/A001K/V104I/S164I, S087N/G118V/S128L/P129Q/S130A/A001N/R045N/I107T, S087N/G118V/S128L/P129Q/S130A/A001R, S087N/G118V/S128L/P129Q/S130A/A001R/A172I, S087N/G118V/S128L/P129Q/S130A/A001R/A172Q, S087N/G118V/S128L/P129Q/S130A/A001R/I107V/A172P, S087N/G118V/S128L/P129Q/S130A/A001R/I107V/A172Q, S087N/G118V/S128L/P129Q/S130A/A001R/I107V/A172W, S087N/G118V/S128L/P129Q/S130A/A001R/R045K, S087N/G118V/S128L/P129Q/S130A/A001R/R045K/I107T, S087N/G118V/S128L/P129Q/S130A/A001R/R045N/I107T/A172Q, S087N/G118V/S128L/P129Q/S130A/A001R/S024H/R045F/I107T, S087N/G118V/S128L/P129Q/S130A/A001R/S024H/R045K/A172N, S087N/G118V/S128L/P129Q/S130A/A001R/S024H/R045K/I107T/A172Q, S087N/G118V/S128L/P129Q/S130A/A001R/S024N/I107T, S087N/G118V/S128L/P129Q/S130A/A001R/S024R/R045K/I107G/A172L, S087N/G118V/S128L/P129Q/S130A/A001R/S024T/R045N/I107T, S087N/G118V/S128L/P129Q/S130A/A001R/S024W/A172W, S087N/G118V/S128L/P129Q/S130A/A001S/S024L/R045L/I107W/A172F, S087N/G118V/S128L/P129Q/S130A/A172N, S087N/G118V/S128L/P129Q/S130A/A215V, S087N/G118V/S128L/P129Q/S130A/A215V/S256W, S087N/G118V/S128L/P129Q/S130A/G097P/N185K/A215I, S087N/G118V/S128L/P129Q/S130A/G097P/N185Q/Y209W/A215V/S256W, S087N/G118V/S128L/P129Q/S130A/G097P/N185R/A215I/S256W, S087N/G118V/S128L/P129Q/S130A/G097S/N185R/S256I, S087N/G118V/S128L/P129Q/S130A/G097S/S144V/Y209W/S256I, S087N/G118V/S128L/P129Q/S130A/G097S/S144Y/S256I, S087N/G118V/S128L/P129Q/S130A/G097T/S144T/N185R/Y209W/S256I, S087N/G118V/S128L/P129Q/S130A/G097T/S144T/S256I, S087N/G118V/S128L/P129Q/S130A/G097T/S144W/N185R/Y209W/S256I, S087N/G118V/S128L/P129Q/S130A/G097T/S144W/Y209W/S256I, S087N/G118V/S128L/P129Q/S130A/G097T/Y209W, S087N/G118V/S128L/P129Q/S130A/G097T/Y209W/S256I, S087N/G118V/S128L/P129Q/S130A/G127Q, S087N/G118V/S128L/P129Q/S130A/G127T, S087N/G118V/S128L/P129Q/S130A/I072C, S087N/G118V/S128L/P129Q/S130A/I072C/L126F, S087N/G118V/S128L/P129Q/S130A/I072C/L126F/S164F, S087N/G118V/S128L/P129Q/S130A/I072C/S164I, S087N/G118V/S128L/P129Q/S130A/I072C/S164Q, S087N/G118V/S128L/P129Q/S130A/I072C/V104I/L126F/S164I, S087N/G118V/S128L/P129Q/S130A/I072P, S087N/G118V/S128L/P129Q/S130A/I072V/S164F, S087N/G118V/S128L/P129Q/S130A/L126F, S087N/G118V/S128L/P129Q/S130A/L126F/S164I, S087N/G118V/S128L/P129Q/S130A/N018K, S087N/G118V/S128L/P129Q/S130A/N018K/A215R/S256W, S087N/G118V/S128L/P129Q/S130A/N018K/G097P/N185Q/A215I/S256W, S087N/G118V/S128L/P129Q/S130A/N018K/G097P/N185R/A215R, S087N/G118V/S128L/P129Q/S130A/N018K/G097P/N185R/Y209W, S087N/G118V/S128L/P129Q/S130A/N018K/N185K, S087N/G118V/S128L/P129Q/S130A/N018K/N185K/S256W, S087N/G118V/S128L/P129Q/S130A/N018K/N185K/Y209W, S087N/G118V/S128L/P129Q/S130A/N018K/N185K/Y209W/A215I, S087N/G118V/S128L/P129Q/S130A/N018K/N185Q, S087N/G118V/S128L/P129Q/S130A/N018K/N185Q/A215R, S087N/G118V/S128L/P129Q/S130A/N018K/N185Q/A215V/S256W, S087N/G118V/S128L/P129Q/S130A/N018K/N185Q/

S256W, S087N/G118V/S128L/P129Q/S130A/N018K/N185R, S087N/G118V/S128L/P129Q/S130A/N018K/N185R/A215I/S256W, S087N/G118V/S128L/P129Q/S130A/N018K/N185R/A215V/S256W, S087N/G118V/S128L/P129Q/S130A/N018K/S256W, S087N/G118V/S128L/P129Q/S130A/N018K/Y209W, S087N/G118V/S128L/P129Q/S130A/N018K/Y209W/A215V, S087N/G118V/S128L/P129Q/S130A/N018Q/A215I/S256W, S087N/G118V/S128L/P129Q/S130A/N018Q/A215R/S256W, S087N/G118V/S128L/P129Q/S130A/N018Q/G097P/N185R, S087N/G118V/S128L/P129Q/S130A/N018Q/N185K/A215R, S087N/G118V/S128L/P129Q/S130A/N018Q/N185K/A215V, S087N/G118V/S128L/P129Q/S130A/N018Q/N185K/S256W, S087N/G118V/S128L/P129Q/S130A/N018Q/N185Q/S256W, S087N/G118V/S128L/P129Q/S130A/N018Q/N185Q/Y209W/S256W, S087N/G118V/S128L/P129Q/S130A/N018Q/N185R/A215R/S256P, S087N/G118V/S128L/P129Q/S130A/N018Q/Y209W/S256W, S087N/G118V/S128L/P129Q/S130A/N018R, S087N/G118V/S128L/P129Q/S130A/N018R/G097P/N185K/A215R, S087N/G118V/S128L/P129Q/S130A/N018R/G097P/N185K/Y209W/A215I/S256W, S087N/G118V/S128L/P129Q/S130A/N018R/N185K, S087N/G118V/S128L/P129Q/S130A/N018R/N185K/A215V/S256W, S087N/G118V/S128L/P129Q/S130A/N018R/N185K/Y209W, S087N/G118V/S128L/P129Q/S130A/N018R/N185K/Y209W/A215I/S256W, S087N/G118V/S128L/P129Q/S130A/N018R/N185Q/A215I/S256W, S087N/G118V/S128L/P129Q/S130A/N018R/N185R/A215R, S087N/G118V/S128L/P129Q/S130A/N018R/N185R/Y209W/S256W, S087N/G118V/S128L/P129Q/S130A/N018R/S256W, S087N/G118V/S128L/P129Q/S130A/N018R/Y209W/A215I/S256W, S087N/G118V/S128L/P129Q/S130A/N018R/Y209W/S256W, S087N/G118V/S128L/P129Q/S130A/N043E, S087N/G118V/S128L/P129Q/S130A/N043E/P052I/S101Y/N248K, S087N/G118V/S128L/P129Q/S130A/N043E/P052V/S101E/N248K, S087N/G118V/S128L/P129Q/S130A/N043E/S101E, S087N/G118V/S128L/P129Q/S130A/N043E/S101R, S087N/G118V/S128L/P129Q/S130A/N043E/S101Y, S087N/G118V/S128L/P129Q/S130A/N043F/P052V/S101T/N248K, S087N/G118V/S128L/P129Q/S130A/N043F/S101Y/N248K, S087N/G118V/S128L/P129Q/S130A/N043I/P052I/S101F/N248K, S087N/G118V/S128L/P129Q/S130A/N043I/P052V/S101F/N248K, S087N/G118V/S128L/P129Q/S130A/N043I/S101E/N248K, S087N/G118V/S128L/P129Q/S130A/N043I/S101N, S087N/G118V/S128L/P129Q/S130A/N043I/S101Y, S087N/G118V/S128L/P129Q/S130A/N043I/S101Y/N248K, S087N/G118V/S128L/P129Q/S130A/N043S, S087N/G118V/S128L/P129Q/S130A/N043S/N185R/Y209W/S256T, S087N/G118V/S128L/P129Q/S130A/N043S/N185V/S256T, S087N/G118V/S128L/P129Q/S130A/N043S/P052I, S087N/G118V/S128L/P129Q/S130A/N043S/P052I/N248K, S087N/G118V/S128L/P129Q/S130A/N043S/P052V, S087N/G118V/S128L/P129Q/S130A/N043S/P052V/N248K, S087N/G118V/S128L/P129Q/S130A/N043S/P052V/S101F, S087N/G118V/S128L/P129Q/S130A/N043S/P052V/S101R, S087N/G118V/S128L/P129Q/S130A/N043S/P052V/S101V/N248K, S087N/G118V/S128L/P129Q/S130A/N043S/P052V/S101Y/N248K, S087N/G118V/S128L/P129Q/S130A/N043S/S101E/N248K, S087N/G118V/S128L/P129Q/S130A/N043S/S101N/N248I, S087N/G118V/S128L/P129Q/S130A/N043S/S101T, S087N/G118V/S128L/P129Q/S130A/N043S/S144W, S087N/G118V/

S128L/P129Q/S130A/N043S/S144W/N185R/S256P, S087N/G118V/S128L/P129Q/S130A/N043S/S144W/N185V/S256T, S087N/G118V/S128L/P129Q/S130A/N043S/S256I, S087N/G118V/S128L/P129Q/S130A/N043T, S087N/G118V/S128L/P129Q/S130A/N043T/N248K, S087N/G118V/S128L/P129Q/S130A/N043T/P052I/S101Y, S087N/G118V/S128L/P129Q/S130A/N043T/P052V/S101Y/N248K, S087N/G118V/S128L/P129Q/S130A/N043T/S101E/N248I, S087N/G118V/S128L/P129Q/S130A/N043T/S144V/Y209W/S256T, S087N/G118V/S128L/P129Q/S130A/N043T/N185V/Y209W/S256I, S087N/G118V/S128L/P129Q/S130A/N043V/P052I, S087N/G118V/S128L/P129Q/S130A/N043V/P052I/S101T/N248K, S087N/G118V/S128L/P129Q/S130A/N043V/P052I/S101Y, S087N/G118V/S128L/P129Q/S130A/N043V/P052V/N248K, S087N/G118V/S128L/P129Q/S130A/N043V/P052V/S101F, S087N/G118V/S128L/P129Q/S130A/N043V/P052V/S101F/N248K, S087N/G118V/S128L/P129Q/S130A/N043V/P052V/S144V/N185R/Y209W/S256I, S087N/G118V/S128L/P129Q/S130A/N043V/P052V/S144W/S256T, S087N/G118V/S128L/P129Q/S130A/N043V/P052V/S144Y/N185R/Y209W/S256T, S087N/G118V/S128L/P129Q/S130A/N043V/S101E/N248I, S087N/G118V/S128L/P129Q/S130A/N043V/S101E/N248K, S087N/G118V/S128L/P129Q/S130A/N043V/S101F, S087N/G118V/S128L/P129Q/S130A/N043V/S101R, S087N/G118V/S128L/P129Q/S130A/N043V/S101R/N248I, S087N/G118V/S128L/P129Q/S130A/N043V/S101T, S087N/G118V/S128L/P129Q/S130A/N043V/S101T/N248K, S087N/G118V/S128L/P129Q/S130A/N043V/S101Y, S087N/G118V/S128L/P129Q/S130A/N043V/S101Y/N248I, S087N/G118V/S128L/P129Q/S130A/N043V/S144T/N185V/S256I, S087N/G118V/S128L/P129Q/S130A/N043V/S144W/N185V, S087N/G118V/S128L/P129Q/S130A/N043V/S144W/Y209W/S256I, S087N/G118V/S128L/P129Q/S130A/N043V/S144Y/N185R/Y209W, S087N/G118V/S128L/P129Q/S130A/N043V/S144Y/N185V/Y209W/S256I, S087N/G118V/S128L/P129Q/S130A/N043V/P052V/S101E/N248K, S087N/G118V/S128L/P129Q/S130A/N043W/P052V/S101Y, S087N/G118V/S128L/P129Q/S130A/N043W/P052V/S101Y/N248K, S087N/G118V/S128L/P129Q/S130A/N043W/S101E, S087N/G118V/S128L/P129Q/S130A/N043W/S101F/N248K, S087N/G118V/S128L/P129Q/S130A/N185K/A215V/S256W, S087N/G118V/S128L/P129Q/S130A/N185K/Y209W/A215V, S087N/G118V/S128L/P129Q/S130A/N185K/Y209W/A215V/S256W, S087N/G118V/S128L/P129Q/S130A/N185Q/Y209W/A215R, S087N/G118V/S128L/P129Q/S130A/N185Q/Y209W/A215V/S256W, S087N/G118V/S128L/P129Q/S130A/N185R/A215V/S256W, S087N/G118V/S128L/P129Q/S130A/N185R/S256T, S087N/G118V/S128L/P129Q/S130A/N185R/Y209W, S087N/G118V/S128L/P129Q/S130A/N185R/Y209W/A215V/S256R, S087N/G118V/S128L/P129Q/S130A/N185R/Y209W/S256L, S087N/G118V/S128L/P129Q/S130A/N185V/Y209W, S087N/G118V/S128L/P129Q/S130A/N248I, S087N/G118V/S128L/P129Q/S130A/N248K, S087N/G118V/S128L/P129Q/S130A/P052I/N248K, S087N/G118V/S128L/P129Q/S130A/P052I/S101E/N248K, S087N/G118V/S128L/P129Q/S130A/P052I/S101F/N248K, S087N/G118V/S128L/P129Q/S130A/P052I/S101V/N248K, S087N/G118V/S128L/P129Q/S130A/P052V, S087N/G118V/S128L/P129Q/S130A/P052V/G097T/N185R/Y209W/S256T, S087N/G118V/S128L/P129Q/S130A/P052V/S101E/N248I, S087N/G118V/S128L/P129Q/S130A/P052V/S101R, S087N/G118V/S128L/P129Q/S130A/P052V/S144T, S087N/G118V/S128L/P129Q/S130A/P052V/S144T/N185R/S256T, S087N/G118V/S128L/P129Q/S130A/P052V/S144T/N185R/Y209W, S087N/G118V/S128L/P129Q/S130A/P052V/S144T/Y209W/S256T, S087N/G118V/S128L/P129Q/S130A/P052V/S144V/N185R/S256I, S087N/G118V/S128L/P129Q/S130A/P052V/S144V/N185R/Y209W, S087N/G118V/S128L/P129Q/S130A/P052V/S144V/N185R/Y209W/S256T, S087N/G118V/S128L/P129Q/S130A/P052V/S144V/N185V/Y209W/S256I, S087N/G118V/S128L/P129Q/S130A/P052V/S144V/Y209W, S087N/G118V/S128L/P129Q/S130A/P052V/S144Y/N185R/Y209W/S256I, S087N/G118V/S128L/P129Q/S130A/P052V/S144Y/N185R/Y209W/S256T, S087N/G118V/S128L/P129Q/S130A/P052V/S144Y/N185V, S087N/G118V/S128L/P129Q/S130A/P052V/S144Y/N185V/Y209W/S256I, S087N/G118V/S128L/P129Q/S130A/P052V/Y209W, S087N/G118V/S128L/P129Q/S130A/P052V/Y209W/S256T, S087N/G118V/S128L/P129Q/S130A/Q109I, S087N/G118V/S128L/P129Q/S130A/Q109L/G127Q, S087N/G118V/S128L/P129Q/S130A/Q109T, S087N/G118V/S128L/P129Q/S130A/Q109T/G127Q, S087N/G118V/S128L/P129Q/S130A/Q109V, S087N/G118V/S128L/P129Q/S130A/R045F/I107T/A172Q, S087N/G118V/S128L/P129Q/S130A/R045K/I072C/L126F, S087N/G118V/S128L/P129Q/S130A/R045N/A172Q, S087N/G118V/S128L/P129Q/S130A/R045N/I107V/A172P, S087N/G118V/S128L/P129Q/S130A/R045S, S087N/G118V/S128L/P129Q/S130A/S024H, S087N/G118V/S128L/P129Q/S130A/S024H/I107V/A172S, S087N/G118V/S128L/P129Q/S130A/S024H/Q109V, S087N/G118V/S128L/P129Q/S130A/S024H/Q109V/G127Q, S087N/G118V/S128L/P129Q/S130A/S024H/R045N/I107T, S087N/G118V/S128L/P129Q/S130A/S024H/S099K/S103N, S087N/G118V/S128L/P129Q/S130A/S024H/S099K/S103N/S132N, S087N/G118V/S128L/P129Q/S130A/S024H/S099Q, S087N/G118V/S128L/P129Q/S130A/S024H/S099Q/S103P, S087N/G118V/S128L/P129Q/S130A/S024H/S099Q/S132N, S087N/G118V/S128L/P129Q/S130A/S024H/S099T/S103P, S087N/G118V/S128L/P129Q/S130A/S024H/S099T/S103P/S132H, S087N/G118V/S128L/P129Q/S130A/S024H/S099T/S103P/S132N, S087N/G118V/S128L/P129Q/S130A/S024H/S099T/S132N, S087N/G118V/S128L/P129Q/S130A/S024H/S103P/S132N, S087N/G118V/S128L/P129Q/S130A/S024L/S099K/S103P/S132N, S087N/G118V/S128L/P129Q/S130A/S024N/I107N, S087N/G118V/S128L/P129Q/S130A/S024N/I107T, S087N/G118V/S128L/P129Q/S130A/S024N/I107V, S087N/G118V/S128L/P129Q/S130A/S024N/Q109K, S087N/G118V/S128L/P129Q/S130A/S024N/Q109T/G127T, S087N/G118V/S128L/P129Q/S130A/S024R, S087N/G118V/S128L/P129Q/S130A/S024R/G127R, S087N/G118V/S128L/P129Q/S130A/S024R/I107T/A172Q, S087N/G118V/S128L/P129Q/S130A/S024R/I107V/A172S, S087N/G118V/S128L/P129Q/S130A/S024R/Q109K, S087N/G118V/S128L/P129Q/S130A/S024R/Q109L, S087N/G118V/S128L/P129Q/S130A/S024R/Q109L/G127Q, S087N/G118V/S128L/P129Q/S130A/S024R/Q109V, S087N/G118V/S128L/P129Q/S130A/S024R/R045F/I107T, S087N/G118V/S128L/P129Q/S130A/S024T, S087N/G118V/S128L/P129Q/S130A/S024T/G127T, S087N/G118V/S128L/P129Q/S130A/S024T/I107T/A172Q, S087N/G118V/S128L/P129Q/S130A/S024T/Q109V/G127T, S087N/G118V/

S128L/P129Q/S130A/S024T/R045N/I107V/A172S, S087N/G118V/S128L/P129Q/S130A/S024W, S087N/G118V/S128L/P129Q/S130A/S024W/G127T, S087N/G118V/S128L/P129Q/S130A/S024W/I107T, S087N/G118V/S128L/P129Q/S130A/S024W/Q109I, S087N/G118V/S128L/P129Q/S130A/S024W/Q109L, S087N/G118V/S128L/P129Q/S130A/S024W/Q109R/G127Q, S087N/G118V/S128L/P129Q/S130A/S024W/Q109T, S087N/G118V/S128L/P129Q/S130A/S024W/Q109V, S087N/G118V/S128L/P129Q/S130A/S024W/R045F/I107V/A172Q, S087N/G118V/S128L/P129Q/S130A/S024W/S099K, S087N/G118V/S128L/P129Q/S130A/S024W/S099K/S103P, S087N/G118V/S128L/P129Q/S130A/S024W/S099K/S132H, S087N/G118V/S128L/P129Q/S130A/S024W/S099Q, S087N/G118V/S128L/P129Q/S130A/S024W/S099Q/S103N/G127R/S132N, S087N/G118V/S128L/P129Q/S130A/S024W/S099Q/S103N/S132N, S087N/G118V/S128L/P129Q/S130A/S024W/S099Q/S103P, S087N/G118V/S128L/P129Q/S130A/S024W/S099Q/S132H, S087N/G118V/S128L/P129Q/S130A/S024W/S099Q/S132N, S087N/G118V/S128L/P129Q/S130A/S024W/S099T, S087N/G118V/S128L/P129Q/S130A/S024W/S099T/G127R/S132H, S087N/G118V/S128L/P129Q/S130A/S024W/S099T/S103N, S087N/G118V/S128L/P129Q/S130A/S024W/S099T/S103N/G127R/S132N, S087N/G118V/S128L/P129Q/S130A/S024W/S099T/S103N/S132N, S087N/G118V/S128L/P129Q/S130A/S024W/S099T/S103P/S132H, S087N/G118V/S128L/P129Q/S130A/S024W/S099T/S132N, S087N/G118V/S128L/P129Q/S130A/S099K, S087N/G118V/S128L/P129Q/S130A/S099K/S103N, S087N/G118V/S128L/P129Q/S130A/S099K/S103P, S087N/G118V/S128L/P129Q/S130A/S099K/S132H, S087N/G118V/S128L/P129Q/S130A/S099Q, S087N/G118V/S128L/P129Q/S130A/S099Q/S103N, S087N/G118V/S128L/P129Q/S130A/S099Q/S103P, S087N/G118V/S128L/P129Q/S130A/S099Q/S103P/S132H, S087N/G118V/S128L/P129Q/S130A/S099Q/S132H, S087N/G118V/S128L/P129Q/S130A/S099T/G127Q, S087N/G118V/S128L/P129Q/S130A/S099T/S103N, S087N/G118V/S128L/P129Q/S130A/S099T/S103N/S132H, S087N/G118V/S128L/P129Q/S130A/S099T/S103P, S087N/G118V/S128L/P129Q/S130A/S099T/S103P/S132H, S087N/G118V/S128L/P129Q/S130A/S099T/S132H, S087N/G118V/S128L/P129Q/S130A/S101E, S087N/G118V/S128L/P129Q/S130A/S101E/N248K, S087N/G118V/S128L/P129Q/S130A/S101F/N248K, S087N/G118V/S128L/P129Q/S130A/S101N/N248K, S087N/G118V/S128L/P129Q/S130A/S101R/N248K, S087N/G118V/S128L/P129Q/S130A/S101Y, S087N/G118V/S128L/P129Q/S130A/S103N/S132H, S087N/G118V/S128L/P129Q/S130A/S103P, S087N/G118V/S128L/P129Q/S130A/S144T/N185R, S087N/G118V/S128L/P129Q/S130A/S144T/N185R/S256I, S087N/G118V/S128L/P129Q/S130A/S144T/N185R/Y209W, S087N/G118V/S128L/P129Q/S130A/S144T/N185R/Y209W/S256I, S087N/G118V/S128L/P129Q/S130A/S144T/N185V/S256I, S087N/G118V/S128L/P129Q/S130A/S144T/N185V/Y209W, S087N/G118V/S128L/P129Q/S130A/S144T/S256I, S087N/G118V/S128L/P129Q/S130A/S144T/Y209W/S256I, S087N/G118V/S128L/P129Q/S130A/S144V, S087N/G118V/S128L/P129Q/S130A/S144V/N185R/S256I, S087N/G118V/S128L/P129Q/S130A/S144V/N185R/Y209W, S087N/G118V/S128L/P129Q/S130A/S144V/N185V, S087N/G118V/S128L/P129Q/S130A/S144V/N185V/S256I, S087N/G118V/S128L/P129Q/S130A/S144V/N185V/Y209W, S087N/G118V/S128L/P129Q/S130A/S144V/Y209W/S256I, S087N/G118V/S128L/P129Q/S130A/S144V/Y209W/S256T, S087N/G118V/S128L/P129Q/S130A/S144W/Y209W, S087N/G118V/S128L/P129Q/S130A/S144Y/N185R, S087N/G118V/S128L/P129Q/S130A/S144Y/N185R/Y209W/S256T, S087N/G118V/S128L/P129Q/S130A/S144Y/N185V/Y209W, S087N/G118V/S128L/P129Q/S130A/S164I, S087N/G118V/S128L/P129Q/S130A/S164Q, S087N/G118V/S128L/P129Q/S130A/V104I, S087N/G118V/S128L/P129Q/S130A/V104I/L126F/S164F, S087N/G118V/S128L/P129Q/S130A/V104I/L126F/S164I, S087N/G118V/S128L/P129Q/S130A/V104I/S164I, S087N/G118V/S128L/P129Q/S130A/V104I/S164Q, S087N/G118V/S128L/P129Q/S130A/Y209W, S087N/G118V/S128L/P129Q/S130A/Y209W/A215I/S256W, S087N/G118V/S128L/P129Q/S130A/Y209W/S256W, S099H/S103I/G118N, S099K/G118R, S099K/S103N/G118T, S099K/S103P/G118L/S132N, S099K/S103P/G127Q, S099K/S103P/S132H, S099K/S103R/G118A/S132P, S099N/S132R, S099Q/G118F/G127R, S099Q/G118T/G127Q, S099Q/S103N/G118R/S132N, S099Q/S103N/G118T, S099Q/S103N/G118T/S132H, S099Q/S103N/S132H, S099Q/S103P/G118R, S099Q/S103P/G118R/S132N, S099Q/S103P/S132H, S099Q/S132R, S099T/G118F, S099T/G118R/S132H, S099T/G118T/S132H, S099T/G118T/S132N, S099T/S103P, S099T/S103P/G118L/S132H, S101E/N117I, S101E/N117Y/N248K, S101F/N117I/N248I, S101F/N117Y/N248I, S101F/N117Y/N248K, S101F/N248K, S101R/N117I/N248K, S101R/N117Y, S101R/N248K, S101T/N117Y/N248K, S101T/N248I, S101V/N248K, S101Y/N117I/N248K, S101Y/N117Y, S101Y/N248K, S103G/G118I/G127E/S132E, S103L/S132E, S103R/S132P, S144T/N185R, S144T/N185R/Y209W/S256I, S144T/N185R/Y209W/S256T, S144T/N185V, S144V/N185R/S256I, S144V/N185R/Y209W, S144V/N185R/Y209W/S256T, S144V/S256I, S144V/Y209W, S144W/N185R/Y209W/S256T, S144W/N185V/Y209W/S256I, S144W/S256I, S144Y/Y209W/S256I, V104E/L126I/S164L, wherein the positions are numbered by correspondence with the amino acid sequence of *B. amyloliquefaciens* subtilisin BPN' set forth as SEQ ID NO: 1.

In some still further embodiments, the present invention provides isolated subtilisin variants comprising a combination of substitutions selected from: TS87N/G118V/S128L/P129Q/S130A/S24W/S101L/Q109K, S87N/G118V/S128L/P129Q/S130A/N18K/G97P/S101L/Q109R/N185R/A215R, S87N/G118V/S128L/P129Q/S130A/172V/Q109R/S164I, S87N/G118V/S128L/P129Q/S130A/S101Y/Q109R/S188D/N248R, S87N/G118V/S128L/P129Q/S130A/N18K/G97P/S101Y/Q109L/N185R/A215R, S87R/G118R/S128L/P129Q/S130A/S101K/S188D/N248R, S87N/G118V/S128L/P129Q/S130A/S24W/S101L/Q109L, S87N/G118V/S128L/P129Q/S130A/N18K/G97P/S101Y/Q109R/N185R/A215R, S87N/G118V/S128L/P129Q/S130A/172V/S101L/Q109R/S164I, S87N/G118V/S128L/P129Q/S130A/S101Y/Q109R/S188D/T213E/N248R, S87R/G118R/S128L/P129Q/S130A/172V/S164I/S188D/N248R, S87N/G118V/S128L/P129Q/S130A/N76D, S87N/G118V/S128L/P129Q/S130A/S24W/S101Y/Q109K, S87N/G118V/S128L/P129Q/S130A/N43S/P52V/S101R/Q109R, S87N/G118V/S128L/P129Q/S130A/172V/S101Y/Q109R/S164I, S87N/G118V/S128L/P129Q/S130A/S101L/Q109L/S188D/N248R, S87N/G118V/S128L/P129Q/S130A/172V/Q109R/S164I/S188D/N248R, S87N/G118V/S128L/P129Q/S130A/N76D/S101L, S87N/G118V/S128L/P129Q/S130A/S24W/

S101Y/Q109L, S87N/G118V/S128L/P129Q/S130A/N76D/ S164I, S87R/G118R/S128L/P129Q/S130A/N76D/S188D/ N248R, S87N/G118V/S128L/P129Q/S130A/S101Y/ Q109L/S188D/N248R, S87R/G118R/S128L/P129Q/ S130A/V118R/S188D/N248R, S87N/G118V/S128L/ P129Q/S130A/N76D/S101M, S87N/G118V/S128L/P129Q/ S130A/N18K/N76D/G97P/N185R/A215R, S87N/G118V/ S128L/P129Q/S130A/172V/S101L/S164I, S87R/G118R/ S128L/P129Q/S130A/S101L/S188D/N248R, S87N/ G118V/S128L/P129Q/S130A/S101Y/Q109L/S188D/ T213E/N248R, S87R/G118R/S128L/P129Q/S130A/ Q109L/S188D/N248R, S87N/G118V/S128L/P129Q/ S130A/N18K/G97P/S101L/N185R/A215R, S87N/G118V/ S128L/P129Q/S130A/172V/S101Y/S164I, S87N/G118V/ S128L/P129Q/S130A/S101Y/T213E/N248R, S87N/ G118V/S128L/P129Q/S130A/172V/S101L/Q109L/S164I, S87R/G118R/S128L/P129Q/S130A/S101V/S188D/N248R, S87N/G118V/S128L/P129Q/S130A/N18K/G97P/S101Y/ N185R/A215R, S87N/G118V/S128L/P129Q/S130A/172V/ S101V/S164I, S87N/G118V/S128L/P129Q/S130A/S101L/ T213E/N248R, S87N/G118V/S128L/P129Q/S130A/172V/ S101Y/Q109L/S164I, S87R/G118R/S128L/P129Q/S130A/ S101H/S188D/N248R, S87N/G118V/S128L/P129Q/ S130A/N18K/G97P/Q109R/N185R/A215R, S87N/G118V/ S128L/P129Q/S130A/172V/S101H/S164I, S87N/G118V/ S128L/P129Q/S130A/S101L/Q109R/S188D/N248R, S87N/G118V/S128L/P129Q/S130A/N18K/G97P/S101L/ Q109L/N185R/A215R, S87R/G118R/S128L/P129Q/ S130A/S101M/S188D/N248R, N76D/S87R/G118R/S128L/ P129Q/S130A/S188D, N76D/S87R/G118R/S128L/P129Q/ S130A/S188D/N248K, S87N/G118V/G127S/S128L/ P129Q/S130A, S87N/S101H/G118V/S128L/P129Q/ S130A, S87N/S101K/G118V/S128L/P129Q/S130A, S87N/ S101V/G118V/S128L/P129Q/S130A, S87N/S101Y/ G118V/S128L/P129Q/S130A, S87N/S101L/G118V/ S128L/P129Q/S130A, 172V/S87N/G118V/S128L/P129Q/ S130A/S164I, wherein the positions are numbered by correspondence with the amino acid sequence of *B. amyloliquefaciens* subtilisin BPN' set forth as SEQ ID NO:1.

The present invention also provides isolated nucleic acids encoding the subtilisin variants set forth above and herein. The present invention further provides expression vectors comprising the nucleic acids encoding these subtilisin variants provided above and herein. In addition, the present invention provides host cells comprising the expression vectors encoding the nucleic acids encoding these subtilisin variants provided above and herein.

The present invention also provides cleaning compositions comprising the subtilisin variants provided herein. In some embodiments, these cleaning compositions comprise more than one of the subtilisin variants provided herein. In some preferred embodiments, these cleaning compositions comprise a liquid, gel, tablet, powder and/or granule detergent. In some further embodiments, these cleaning compositions are selected from laundry detergents and dish detergents. In some preferred embodiments, these cleaning compositions comprise laundry detergents. In some particularly preferred embodiments, these cleaning compositions are heavy duty detergents. In some additional embodiments, these cleaning compositions comprise dish detergents selected from hand dishwashing and automatic dishwashing detergents. In some further preferred embodiments, these cleaning compositions provided herein further comprise at least one bleaching agent. In some further embodiments, these cleaning compositions further comprise one or more adjunct ingredients, in addition to the at least one subtilisin variant provided herein. In some additional embodiments, these cleaning compositions provided herein are phosphate-free, while in some alternative embodiments, these cleaning compositions provided herein are phosphate-containing detergents. In some still further embodiments, these cleaning compositions provided herein are cold water detergents. In yet some additional embodiments, these cleaning compositions provided herein further comprise at least one additional enzyme, in addition to the one or more subtilisin variants provided herein. In some embodiments, these cleaning compositions comprise at least one additional enzyme selected from hemicellulases, cellulases, peroxidases, proteases, metalloproteases, xylanases, lipases, phospholipases, esterases, perhydrolasess, cutinases, pectinases, pectate lyases, mannanases, keratinases, reductases, oxidases, phenoloxidases, lipoxygenases, ligninases, pullulanases, tannases, pentosanases, malanases, ß-glucanases, arabinosidases, hyaluronidase, chondroitinase, laccase, and amylases, or mixtures thereof.

The present invention also provides methods for cleaning, comprising providing an item to be cleaned and a composition comprising at least one cleaning composition provided herein, and contacting the item with the composition, under conditions effective to provide cleaning of the item. In some embodiments, the methods further comprise the step of rinsing the item after contacting the item with the cleaning composition. In some preferred embodiments, the item to be cleaned comprises dishware. In some alternative embodiments, the item to be cleaned comprises fabric.

BRIEF DESCRIPTION OF THE DRAWINGS

FIG. 1 provides an alignment of various reference proteases including: BPN' (SEQ ID NO:1), GC GCI-P036 (SEQ ID NO:2), GCI-P037 (SEQ ID NO:3), and GCI-P038 (SEQ ID NO:4). Unless otherwise specified, substitution positions are given in relationship to BPN'.

DESCRIPTION OF THE INVENTION

Figure 2:
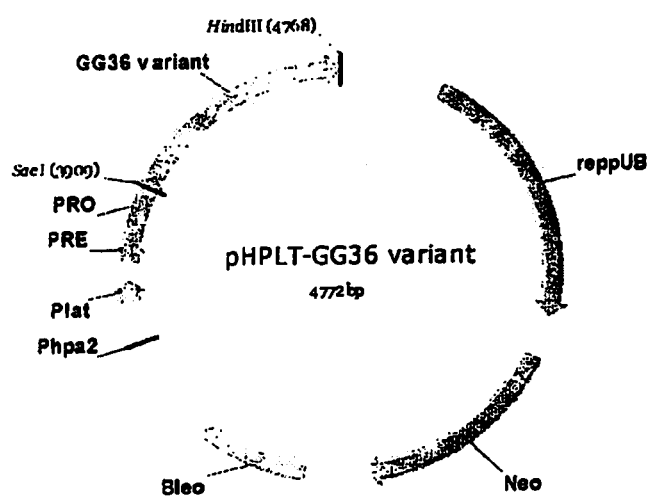
FIG. 2 provides a map of pHPLT-GG36.

The present invention provides methods for protein engineering and serine protease variants produced therefrom. Specifically, the present invention provides serine protease variants having one or more substitutions as compared to a reference serine protease. In addition, the present invention provides compositions comprising these serine protease variants. In some embodiments, the present invention provides cleaning compositions comprising at least one of these serine protease variants.

For practical purposes, it is not usually necessary to find the best sequence in a protein space in order to create a protein that is optimum for a particular application. For most applications, the problem to be solved is to identify at least one protein sequence that meets or exceeds the minimum value required for a number of properties. This requires knowledge of mutations that are good for a particular property, as well as knowledge of those mutations that are bad for any of the desired properties. The present invention provides means to meet the goal by identifying those positions in the protein that can be altered to improve the primary property and keep the values for other properties within desired limits.

The present invention provides means to evaluate all positions in a protein for all the properties of interest by building "site evaluation libraries" at each site. In preferred embodiments, these libraries contain 9-19 mutations at each position, and are used to evaluate each position for use in engineering the protein and constructing libraries. Each property is measured relative to the reference enzyme and an apparent free energy difference for each mutant vs. wild type is calculated. These delta delta G ("i.e., ΔΔG") apparent values are then used to determine additivity.

One ideal way to analyze variants would be through the difference in free energy for the variant versus the reference protein in the process of interest. The Gibbs Free Energy for a process represents the maximum amount of work that can be performed by a system. The change in Free energy relative to the reference enzyme (ΔΔ G) is given as follows;

$$\Delta\Delta G = -RT \ln(k_{variant}/k_{reference})$$

where $k_{variant}$ is the rate constant for the variant enzyme, and $k_{reference}$ is the rate constant for the reference enzyme, R is the Gas law constant and T is the absolute temperature. Most assays are not constructed to allow determination of true Free Energies, so we utilized a quantity $$\Delta\Delta G_{app} = -RT \ln(P_{variant}/P_{reference})$$

where $P_{variant}$ is the performance value for the variant and $P_{reference}$ the performance value for the reference enzyme under the same conditions. The ΔΔ $G_{app}$ values may be expected to behave in a similar fashion as to ΔΔ G for data distributions and additivity. However, since ΔΔ G is the maximum amount of work that can be carried out by the variant compared to the reference enzyme, the quantity ΔΔ $G_{app}$ will generally underestimate the ΔΔ G and lead to results that appear synergistic in that the properties of two additive positions may be greater than the value predicted by adding their ΔΔ $G_{app}$ values together.

In addition, the present invention provides subtilisin variants and compositions comprising these variants.

Definitions

Unless otherwise indicated, the practice of the present invention involves conventional techniques commonly used in molecular biology, protein engineering, microbiology, and recombinant DNA, which are within the skill of the art. Such techniques are known to those of skill in the art and are described in numerous texts and reference works well known to those of skill in the art. All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention pertains. Many technical dictionaries are known to those of skill in the art. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular "a", "an" and "the" includes the plural reference unless the context clearly indicates otherwise. Numeric ranges are inclusive of the numbers defining the range. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

The practice of the present invention employs, unless otherwise indicated, conventional techniques of protein purification, molecular biology, microbiology, recombinant DNA techniques and protein sequencing, all of which are within the skill of those in the art.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, a number of terms are defined below.

As used herein, the terms "protease," and "proteolytic activity" refer to a protein or peptide exhibiting the ability to hydrolyze peptides or substrates having peptide linkages. Many well known procedures exist for measuring proteolytic activity (Kalisz, "Microbial Proteinases," In: Fiechter (ed.), *Advances in Biochemical Engineering/Biotechnology*, [1988]). For example, proteolytic activity may be ascertained by comparative assays which analyze the respective protease's ability to hydrolyze a commercial substrate. Exemplary substrates useful in the analysis of protease or proteolytic activity, include, but are not limited to di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO 99/34011; and U.S. Pat. No. 6,376,450, both of which are incorporated herein by reference). The pNA assay (See e.g., Del Mar et al., Anal. Biochem., 99:316-320 [1979]) also finds use in determining the active enzyme concentration for fractions collected during gradient elution. This assay measures the rate at which p-nitroaniline is released as the enzyme hydrolyzes the soluble synthetic substrate, succinyl-alanine-alanine-proline-phenylalanine-p-nitroanilide (suc-AAPF-pNA). The rate of production of yellow color from the hydrolysis reaction is measured at 410 nm on a spectrophotometer and is proportional to the active enzyme concentration. In addition, absorbance measurements at 280 nm can be used to determine the total protein concentration. The active enzyme/total-protein ratio gives the enzyme purity.

As used herein, the term "subtilisin" refers any member of the S8 serine protease family as described in MEROPS—The Peptidase Data base (Rawlings et al., MEROPS: the peptidase database, Nucl Acids Res, 34 Database issue, D270-272, 2006). As described therein, the peptidase family S8 contains the serine endopeptidase subtilisin and its homologues (Biochem J, 290:205-218, 1993). Family S8, also known as the subtilase family, is the second largest family of serine peptidases, and can be divided into two subfamilies, with subtilisin (S08.001) the type-example for subfamily S8A and kexin (S08.070) the type-example for subfamily S8B. Tripeptidyl-peptidase II (TPP-II; 508.090) was formerly considered to be the type-example of a third subfamily, but has since been determined to be misclassified. Members of family S8 have a catalytic triad in the order Asp, His and Ser in the sequence, which is a different order to that of families S1, S9 and S10. In subfamily S8A, the active site residues frequently occurs in the motifs Asp-Thr/Ser-Gly (which is similar to the sequence motif in families of aspartic endopeptidases in clan AA), His-Gly-Thr-His and Gly-Thr-Ser-Met-Ala-Xaa-Pro. In subfamily S8B, the catalytic residues frequently occur in the motifs Asp-Asp-Gly, His-Gly- Thr-Arg and Gly-Thr-Ser-Ala/Val-Ala/Ser-Pro. Most members of the S8 family are endopeptidases, and are active at neutral-mildly alkali pH. Many peptidases in the family are thermostable. Casein is often used as a protein substrate and a typical synthetic substrate is suc-AAPF. Most members of the family are nonspecific peptidases with a preference to cleave after hydrophobic residues. However, members of subfamily S8B, such as kexin (S08.070) and furin (S08.071), cleave after dibasic amino acids. Most members of the S8 family are inhibited by general serine peptidase inhibitors such as DFP and PMSF. Because many members of the family bind calcium for stability, inhibition can be seen with EDTA and EGTA, which are often thought to be specific inhibitors of metallopeptidases. Protein inhibitors include turkey ovomucoid third domain (101.003), *Streptomyces* subtilisin inhibitor (116.003), and members of family 113 such as eglin C (113.001) and barley inhibitor CI-1A (113.005), many of which also inhibit chymotrypsin (S01.001). The subtilisin propeptide is itself inhibitory, and the homologous proteinase B inhibitor from *Saccharomyces* inhibits cerevisin (S08.052). The tertiary structures for several members of family S8 have now been determined. A typical S8 protein structure consists of three layers with a seven-stranded β sheet sandwiched between two layers of helices. Subtilisin (S08.001) is the type structure for clan SB (SB). Despite the different structure, the active sites of subtilisin and chymotrypsin (S01.001) can be superimposed, which suggests the similarity is the result of convergent rather than divergent evolution.

As used herein, the terms "protease variant" and "variant protease" are used in reference to proteases that are similar to a reference protease, particularly in their function, but have mutations in their amino acid sequence that make them different in sequence from the wild-type protease at from one to 20 positions. The amino acid sequences of the mature region of several exemplary reference proteases are shown in the alignment of FIG. 1. In some preferred embodiments, the present invention provides "GG36 variants," wherein the mutations are present in the mature GG36 sequence set forth in SEQ ID NO:2. In some embodiments, variant proteases herein are referred to as "GCI-P036 variants" or "variants of GCI-P036." In some embodiments, the variant proteases provided herein are also referred to as "*Bacillus* sp. subtilisin variants" and "subtilisin variants."

As used herein, "the genus *Bacillus*" includes all species within the genus "*Bacillus*," as known to those of skill in the art, including but not limited to *B. subtilis, B. licheniformis, B. lentils, B. brevis, B. stearothermophilus, B. alkalophilus, B. amyloliquefaciens, B. clausii, B. halodurans, B. megaterium, B. coagulans, B. circulans, B. lautus,* and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus,* and *Virgibacillus*.

The terms "polynucleotide" and "nucleic acid", used interchangeably herein, refer to a polymeric form of nucleotides of any length, either ribonucleotides or deoxyribonucleotides. These terms include, but are not limited to, a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The following are non-limiting examples of polynucleotides: genes, gene fragments, chromosomal fragments, ESTs, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. In some embodiments, polynucleotides comprise modified nucleotides, such as methylated nucleotides and nucleotide analogs, uracyl, other sugars and linking groups such as fluororibose and thioate, and nucleotide branches. In alternative embodiments, the sequence of nucleotides is interrupted by non-nucleotide components.

As used herein, the terms "DNA construct" and "transforming DNA" are used interchangeably to refer to DNA used to introduce sequences into a host cell or organism. The DNA may be generated in vitro by PCR or any other suitable technique(s) known to those in the art. In particularly preferred embodiments, the DNA construct comprises a sequence of interest (e.g., as an incoming sequence). In some embodiments, the sequence is operably linked to additional elements such as control elements (e.g., promoters, etc.). The DNA construct may further comprise a selectable marker. It may further comprise an incoming sequence flanked by homology boxes. In a further embodiment, the transforming DNA comprises other non-homologous sequences, added to the ends (e.g., stuffer sequences or flanks). In some embodiments, the ends of the incoming sequence are closed such that the transforming DNA forms a closed circle. The transforming sequences may be wild-type, mutant or modified. In some embodiments, the DNA construct comprises sequences homologous to the host cell chromosome. In other embodiments, the DNA construct comprises non-homologous sequences. Once the DNA construct is assembled in vitro it may be used to: 1) insert heterologous sequences into a desired target sequence of a host cell, and/or 2) mutagenize a region of the host cell chromosome (i.e., replace an endogenous sequence with a heterologous sequence), 3) delete target genes, and/or 4) introduce a replicating plasmid into the host.

As used herein, the terms "expression cassette" and "expression vector" refer to nucleic acid constructs generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In preferred embodiments, expression vectors have the ability to incorporate and express heterologous DNA fragments in a host cell. Many prokaryotic and eukaryotic expression vectors are commercially available. Selection of appropriate expression vectors is within the knowledge of those of skill in the art. The term "expression cassette" is used interchangeably herein with "DNA construct," and their grammatical equivalents. Selection of appropriate expression vectors is within the knowledge of those of skill in the art.

As used herein, the term "vector" refers to a polynucleotide construct designed to introduce nucleic acids into one or more cell types. Vectors include cloning vectors, expression vectors, shuttle vectors, plasmids, cassettes and the like. In some embodiments, the polynucleotide construct comprises a DNA sequence encoding the protease (e.g., precursor or mature protease) that is operably linked to a suitable prosequence (e.g., secretory, etc.) capable of effecting the expression of the DNA in a suitable host.

As used herein, the term "plasmid" refers to a circular double-stranded (ds) DNA construct used as a cloning vector, and which forms an extrachromosomal self-replicating genetic element in some eukaryotes or prokaryotes, or integrates into the host chromosome.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction (See e.g., Ferrari et al., "*Genetics*," in Hardwood et al, (eds.), *Bacillus*, Plenum Publishing Corp., pages 57-72, [1989]).

As used herein, the terms "transformed" and "stably transformed" refers to a cell that has a non-native (heterologous) polynucleotide sequence integrated into its genome or as an episomal plasmid that is maintained for at least two generations.

As used herein, a nucleic acid is "operably linked" when it is placed into a functional relationship with another nucleic acid sequence. For example, DNA encoding a secretory leader (i.e., a signal peptide), is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous Linking is accomplished by ligation at convenient restriction sites. If such sites do not exist, the synthetic oligonucleotide adaptors or linkers are used in accordance with conventional practice.

As used herein the term "gene" refers to a polynucleotide (e.g., a DNA segment), that encodes a polypeptide and includes regions preceding and following the coding regions as well as intervening sequences (introns) between individual coding segments (exons).

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, proteins are defined as having a common "fold" if they have the same major secondary structures in the same arrangement and with the same topological connections. Different proteins with the same fold often have peripheral elements of secondary structure and turn regions that differ in size and conformation. In some cases, these differing peripheral regions may comprise half the structure. Proteins placed together in the same fold category do not necessarily have a common evolutionary origin (e.g., structural similarities arising from the physics and chemistry of proteins favoring certain packing arrangements and chain topologies).

As used herein, "homology" refers to sequence similarity or identity, with identity being preferred. This homology is determined using standard techniques known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps.

Another example of a useful algorithm is the BLAST algorithm, described by Altschul et al., (Altschul et al., J. Mol. Biol., 215:403-410, [1990]; and Karlin et al., Proc. Natl. Acad. Sci. USA 90:5873-5787 [1993]). A particularly useful BLAST program is the WU-BLAST-2 program (See, Altschul et al., Meth. Enzymol., 266:460-480 [1996]). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Thus, "percent (%) nucleic acid sequence identity" is defined as the percentage of nucleotide residues in a candidate sequence that are identical with the nucleotide residues of the starting sequence (i.e., the sequence of interest). A preferred method utilizes the BLASTN module of WU-BLAST-2 set to the default parameters, with overlap span and overlap fraction set to 1 and 0.125, respectively.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. "Recombination," "recombining," and generating a "recombined" nucleic acid are generally the assembly of two or more nucleic acid fragments wherein the assembly gives rise to a chimeric gene.

In some preferred embodiments, mutant DNA sequences are generated with site saturation mutagenesis in at least one codon. In another preferred embodiment, site saturation mutagenesis is performed for two or more codons. In a further embodiment, mutant DNA sequences have more than about 50%, more than about 55%, more than about 60%, more than about 65%, more than about 70%, more than about 75%, more than about 80%, more than about 85%, more than about 90%, more than about 95%, or more than about 98% homology with the wild-type sequence. In alternative embodiments, mutant DNA is generated in vivo using any known mutagenic procedure such as, for example, radiation, nitrosoguanidine and the like. The desired DNA sequence is then isolated and used in the methods provided herein.

As used herein, the terms "amplification" and "gene amplification" refer to a process by which specific DNA sequences are disproportionately replicated such that the amplified gene becomes present in a higher copy number than was initially present in the genome. In some embodiments, selection of cells by growth in the presence of a drug (e.g., an inhibitor of an inhibitable enzyme) results in the amplification of either the endogenous gene encoding the gene product required for growth in the presence of the drug or by amplification of exogenous (i.e., input) sequences encoding this gene product, or both.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" (PCR) refers to the methods of U.S. Pat. Nos. 4,683,195 4,683,202, and 4,965,188, hereby incorporated by reference, which include methods for increasing the concentration of a segment of a target sequence in a mixture of genomic DNA without cloning or purification. This process for amplifying the target sequence is well known in the art.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

A "restriction site" refers to a nucleotide sequence recognized and cleaved by a given restriction endonuclease and is frequently the site for insertion of DNA fragments. In certain embodiments of the invention restriction sites are engineered into the selective marker and into 5' and 3' ends of the DNA construct.

"Homologous recombination" means the exchange of DNA fragments between two DNA molecules or paired chromosomes at the site of identical or nearly identical nucleotide sequences. In a preferred embodiment, chromosomal integration is homologous recombination.

As used herein "amino acid" refers to peptide or protein sequences or portions thereof. The terms "protein," "peptide," and "polypeptide" are used interchangeably.

As used herein, "protein of interest" and "polypeptide of interest" refer to a protein/polypeptide that is desired and/or being assessed. In some embodiments, the protein of interest is expressed intracellularly, while in other embodiments, it is a secreted polypeptide. In particularly preferred embodiments, these enzymes include the serine proteases of the present invention. In some embodiments, the protein of interest is a secreted polypeptide which is fused to a signal peptide (i.e., an amino-terminal extension on a protein to be secreted). Nearly all secreted proteins use an amino-terminal protein extension which plays a crucial role in the targeting to and translocation of precursor proteins across the membrane. This extension is proteolytically removed by a signal peptidase during or immediately following membrane transfer.

A polynucleotide is said to "encode" an RNA or a polypeptide if, in its native state or when manipulated by methods known to those of skill in the art, it can be transcribed and/or translated to produce the RNA, the polypeptide or a fragment thereof. The anti-sense strand of such a nucleic acid is also said to encode the sequences. As is known in the art, a DNA can be transcribed by an RNA polymerase to produce RNA, but an RNA can be reverse transcribed by reverse transcriptase to produce a DNA. Thus a DNA can encode a RNA and vice versa.

"Host strain" or "host cell" refers to a suitable host for an expression vector comprising DNA according to the present invention.

An enzyme is "overexpressed" in a host cell if the enzyme is expressed in the cell at a higher level that the level at which it is expressed in a corresponding wild-type cell.

The terms "protein" and "polypeptide" are used interchangeability herein. The 3-letter code for amino acids as defined in conformity with the IUPAC-IUB Joint Commission on Biochemical Nomenclature (JCBN) is used throughout this disclosure. It is also understood that a polypeptide may be coded for by more than one nucleotide sequence due to the degeneracy of the genetic code.

A "prosequence" is an amino acid sequence between the signal sequence and mature protease that is necessary for the secretion of the protease. Cleavage of the pro sequence results in a mature active protease.

The term "signal sequence" or "signal peptide" refers to any sequence of nucleotides and/or amino acids which may participate in the secretion of the mature or precursor forms of the protein. This definition of signal sequence is a functional one, meant to include all those amino acid sequences encoded by the N-terminal portion of the protein gene, which participate in the effectuation of the secretion of protein. They are often, but not universally, bound to the N-terminal portion of a protein or to the N-terminal portion of a precursor protein. The signal sequence may be endogenous or exogenous. The signal sequence may be that normally associated with the protein (e.g., protease), or may be from a gene encoding another secreted protein. One exemplary exogenous signal sequence comprises the first seven amino acid residues of the signal sequence from *Bacillus subtilis* subtilisin fused to the remainder of the signal sequence of the subtilisin from *Bacillus lentus* (ATCC 21536).

The term "hybrid signal sequence" refers to signal sequences in which part of sequence is obtained from the expression host fused to the signal sequence of the gene to be expressed. In some embodiments, synthetic sequences are utilized.

The term "mature" form of a protein or peptide refers to the final functional form of the protein or peptide.

The term "precursor" form of a protein or peptide refers to a mature form of the protein having a prosequence operably linked to the amino or carbonyl terminus of the protein. The precursor may also have a "signal" sequence operably linked, to the amino terminus of the prosequence. The precursor may also have additional polynucleotides that are involved in post-translational activity (e.g., polynucleotides cleaved therefrom to leave the mature form of a protein or peptide).

"Naturally occurring enzyme" refers to an enzyme having the unmodified amino acid sequence identical to that found in nature. Naturally occurring enzymes include native enzymes, those enzymes naturally expressed or found in the particular microorganism.

The terms "derived from" and "obtained from" refer to not only a protease produced or producible by a strain of the organism in question, but also a protease encoded by a DNA sequence isolated from such strain and produced in a host organism containing such DNA sequence. Additionally, the term refers to a protease which is encoded by a DNA sequence of synthetic and/or cDNA origin and which has the identifying characteristics of the protease in question. To exemplify, "proteases derived from *Bacillus*" refers to those enzymes having proteolytic activity which are naturally-produced by *Bacillus*, as well as to serine proteases like those produced by *Bacillus* sources but which through the use of genetic engineering techniques are produced by non-*Bacillus* organisms transformed with a nucleic acid encoding the serine proteases.

A "derivative" within the scope of this definition generally retains the characteristic proteolytic activity observed in the wild-type, native or reference form to the extent that the derivative is useful for similar purposes as the wild-type, native or reference form. Functional derivatives of serine protease encompass naturally occurring, synthetically or recombinantly produced peptides or peptide fragments which have the general characteristics of the serine protease of the present invention.

The term "functional derivative" refers to a derivative of a nucleic acid which has the functional characteristics of a nucleic acid which encodes serine protease. Functional derivatives of a nucleic acid which encode serine protease of the present invention encompass naturally occurring, synthetically or recombinantly produced nucleic acids or fragments and encode serine protease characteristic of the present invention. Wild type nucleic acid encoding serine proteases according to the invention include naturally occurring alleles and homologues based on the degeneracy of the genetic code known in the art.

The term "identical" in the context of two nucleic acids or polypeptide sequences refers to the residues in the two sequences that are the same when aligned for maximum correspondence, as measured using one of the following sequence comparison or analysis algorithms.

The term "optimal alignment" refers to the alignment giving the highest percent identity score.

"Percent sequence identity," "percent amino acid sequence identity," "percent gene sequence identity," and/or "percent nucleic acid/polynucloetide sequence identity," with respect to two amino acid, polynucleotide and/or gene sequences (as appropriate), refer to the percentage of residues that are identical in the two sequences when the sequences are optimally aligned. Thus, 80% amino acid sequence identity means that 80% of the amino acids in two optimally aligned polypeptide sequences are identical.

The phrase "substantially identical" in the context of two nucleic acids or polypeptides thus refers to a polynucleotide or polypeptide that comprising at least about 70% sequence identity, preferably at least about 75%, preferably at least about 80%, preferably at least about 85%, preferably at least about 90%, preferably at least about 95%, preferably at least about 97%, preferably at least about 98%, and preferably at least about 99% sequence identity as compared to a reference sequence using the programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

The phrase "equivalent," in this context, refers to serine proteases enzymes that are encoded by a polynucleotide capable of hybridizing to the polynucleotide having the sequence as shown in SEQ ID NO:1 or SEQ ID NO:5, under conditions of medium to maximum stringency. For example, being equivalent means that an equivalent mature serine protease comprises at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, and/or at least about 99% sequence identity to the mature BPN' or GG36 serine protease having the amino acid sequence of SEQ ID NO:1 or SEQ ID NO:2.

The term "isolated" or "purified" refers to a material that is removed from its original environment (e.g., the natural environment if it is naturally occurring). For example, the material is said to be "purified" when it is present in a particular composition in a higher or lower concentration than exists in a naturally occurring or wild type organism or in combination with components not normally present upon expression from a naturally occurring or wild type organism. For example, a naturally-occurring polynucleotide or polypeptide present in a living animal is not isolated, but the same polynucleotide or polypeptide, separated from some or all of the coexisting materials in the natural system, is isolated. In some embodiments, such polynucleotides are part of a vector, and/or such polynucleotides or polypeptides are part of a composition, and still be isolated in that such vector or composition is not part of its natural environment. In preferred embodiments, a nucleic acid or protein is said to be purified, for example, if it gives rise to essentially one band in an electrophoretic gel or blot.

The term "isolated", when used in reference to a DNA sequence, refers to a DNA sequence that has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (See e.g., Dynan and Tijan, Nature 316:774-78 [1985]). The term "an isolated DNA sequence" is alternatively referred to as "a cloned DNA sequence".

The term "isolated," when used in reference to a protein, refers to a protein that is found in a condition other than its native environment. In a preferred form, the isolated protein is substantially free of other proteins, particularly other homologous proteins. An isolated protein is more than about 10% pure, preferably more than about 20% pure, and even more preferably more than about 30% pure, as determined by SDS-PAGE. Further aspects of the invention encompass the protein in a highly purified form (i.e., more than about 40% pure, more than about 60% pure, more than about 70% pure, more than about 80% pure, more than about 90% pure, more than about 95% pure, more than about 97% pure, and even more than about 99% pure), as determined by SDS-PAGE.

As used herein, the term, "combinatorial mutagenesis" refers to methods in which libraries of variants of a starting sequence are generated. In these libraries, the variants contain one or several mutations chosen from a predefined set of mutations. In addition, the methods provide means to introduce random mutations which were not members of the predefined set of mutations. In some embodiments, the methods include those set forth in U.S. patent application Ser. No. 09/699,250, filed Oct. 26, 2000, hereby incorporated by reference. In alternative embodiments, combinatorial mutagenesis methods encompass commercially available kits (e.g., QUIKCHANGE® Multisite (Stratagene).

As used herein, the terms "library of mutants" and "library of variants" refer to a population of cells which are identical in most of their genome but include different homologues of one or more genes. Such libraries can be used, for example, to identify genes or operons with improved traits.

As used herein, the term "starting gene" refers to a gene of interest that encodes a protein of interest that is to be improved and/or changed using the present invention.

As used herein, the term "multiple sequence alignment" ("MSA") refers to the sequences of multiple homologs of a starting gene that are aligned using an algorithm (e.g., Clustal W).

As used herein, the terms "consensus sequence" and "canonical sequence" refer to an archetypical amino acid sequence against which all variants of a particular protein or sequence of interest are compared. The terms also refer to a sequence that sets forth the nucleotides that are most often present in a DNA sequence of interest. For each position of a gene, the consensus sequence gives the amino acid that is most abundant in that position in the MSA.

As used herein, the term "consensus mutation" refers to a difference in the sequence of a starting gene and a consensus sequence. Consensus mutations are identified by comparing the sequences of the starting gene and the consensus sequence resulting from an MSA. In some embodiments, consensus mutations are introduced into the starting gene such that it becomes more similar to the consensus sequence. Consensus mutations also include amino acid changes that change an amino acid in a starting gene to an amino acid that is more frequently found in an MSA at that position relative to the frequency of that amino acid in the starting gene. Thus, the term consensus mutation comprises all single amino acid changes that replace an amino acid of the starting gene with an amino acid that is more abundant than the amino acid in the MSA.

As used herein, the term "initial hit" refers to a variant that was identified by screening a combinatorial consensus mutagenesis library. In preferred embodiments, initial hits have improved performance characteristics, as compared to the starting gene.

As used herein, the term "improved hit" refers to a variant that was identified by screening an enhanced combinatorial consensus mutagenesis library.

As used herein, the terms "improving mutation" and "performance-enhancing mutation" refer to a mutation that leads to improved performance when it is introduced into the starting gene. In some preferred embodiments, these mutations are identified by sequencing hits that were identified during the screening step of the method. In most embodiments, mutations that are more frequently found in hits are likely to be improving mutations, as compared to an unscreened combinatorial consensus mutagenesis library.

As used herein, the term "enhanced combinatorial consensus mutagenesis library" refers to a CCM library that is designed and constructed based on screening and/or sequencing results from an earlier round of CCM mutagenesis and screening. In some embodiments, the enhanced CCM library is based on the sequence of an initial hit resulting from an earlier round of CCM. In additional embodiments, the enhanced CCM is designed such that mutations that were frequently observed in initial hits from earlier rounds of mutagenesis and screening are favored. In some preferred embodiments, this is accomplished by omitting primers that encode performance-reducing mutations or by increasing the concentration of primers that encode performance-enhancing mutations relative to other primers that were used in earlier CCM libraries.

As used herein, the term "performance-reducing mutations" refer to mutations in the combinatorial consensus mutagenesis library that are less frequently found in hits resulting from screening as compared to an unscreened combinatorial consensus mutagenesis library. In preferred embodiments, the screening process removes and/or reduces the abundance of variants that contain "performance-reducing mutations."

As used herein, the term "functional assay" refers to an assay that provides an indication of a protein's activity. In particularly preferred embodiments, the term refers to assay systems in which a protein is analyzed for its ability to function in its usual capacity. For example, in the case of enzymes, a functional assay involves determining the effectiveness of the enzyme in catalyzing a reaction.

As used herein, the term "target property" refers to the property of the starting gene that is to be altered. It is not intended that the present invention be limited to any particular target property. However, in some preferred embodiments, the target property is the stability of a gene product (e.g., resistance to denaturation, proteolysis or other degradative factors), while in other embodiments, the level of production in a production host is altered. Indeed, it is contemplated that any property of a starting gene will find use in the present invention.

The term "property" or grammatical equivalents thereof in the context of a nucleic acid, as used herein, refer to any characteristic or attribute of a nucleic acid that can be selected or detected. These properties include, but are not limited to, a property affecting binding to a polypeptide, a property conferred on a cell comprising a particular nucleic acid, a property affecting gene transcription (e.g., promoter strength, promoter recognition, promoter regulation, enhancer function), a property affecting RNA processing (e.g., RNA splicing, RNA stability, RNA conformation, and post-transcriptional modification), a property affecting translation (e.g., level, regulation, binding of mRNA to ribosomal proteins, post-translational modification). For example, a binding site for a transcription factor, polymerase, regulatory factor, etc., of a nucleic acid may be altered to produce desired characteristics or to identify undesirable characteristics.

The term "property" or grammatical equivalents thereof in the context of a polypeptide (including proteins), as used herein, refer to any characteristic or attribute of a polypeptide that can be selected or detected. These properties include, but are not limited to oxidative stability, substrate specificity, catalytic activity, thermal stability, alkaline stability, pH activity profile, resistance to proteolytic degradation, $K_M$, $k_{cat}$, $k_{cat}/k_M$ ratio, protein folding, inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, and/or ability to treat disease, etc.

As used herein, the term "screening" has its usual meaning in the art and is, in general a multi-step process. In the first step, a mutant nucleic acid or variant polypeptide therefrom is provided. In the second step, a property of the mutant nucleic acid or variant polypeptide is determined. In the third step, the determined property is compared to a property of the corresponding precursor nucleic acid, to the property of the corresponding naturally occurring polypeptide or to the property of the starting material (e.g., the initial sequence) for the generation of the mutant nucleic acid.

It will be apparent to the skilled artisan that the screening procedure for obtaining a nucleic acid or protein with an altered property depends upon the property of the starting material the modification of which the generation of the mutant nucleic acid is intended to facilitate. The skilled artisan will therefore appreciate that the invention is not limited to any specific property to be screened for and that the following description of properties lists illustrative examples only. Methods for screening for any particular property are generally described in the art. For example, one can measure binding, pH, specificity, etc., before and after mutation, wherein a change indicates an alteration. Preferably, the screens are performed in a high-throughput manner, including multiple samples being screened simultaneously, including, but not limited to assays utilizing chips, phage display, and multiple substrates and/or indicators.

As used herein, in some embodiments, screens encompass selection steps in which variants of interest are enriched from a population of variants. Examples of these embodiments include the selection of variants that confer a growth advantage to the host organism, as well as phage display or any other method of display, where variants can be captured from a population of variants based on their binding or catalytic properties. In a preferred embodiment, a library of variants is exposed to stress (heat, protease, denaturation) and subsequently variants that are still intact are identified in a screen or enriched by selection. It is intended that the term encompass any suitable means for selection. Indeed, it is not intended that the present invention be limited to any particular method of screening.

As used herein, the term "targeted randomization" refers to a process that produces a plurality of sequences where one or several positions have been randomized. In some embodiments, randomization is complete (i.e., all four nucleotides, A, T, G, and C can occur at a randomized position. In alternative embodiments, randomization of a nucleotide is limited to a subset of the four nucleotides. Targeted randomization can be applied to one or several codons of a sequence, coding for one or several proteins of interest. When expressed, the resulting libraries produce protein populations in which one or more amino acid positions can contain a mixture of all 20 amino acids or a subset of amino acids, as determined by the randomization scheme of the randomized codon. In some embodiments, the individual members of a population resulting from targeted randomization differ in the number of amino acids, due to targeted or random insertion or deletion of codons. In further embodiments, synthetic amino acids are included in the protein populations produced. In some preferred embodiments, the majority of members of a population resulting from targeted randomization show greater sequence homology to the consensus sequence than the starting gene. In some embodiments, the sequence encodes one or more proteins of interest. In alternative embodiments, the proteins have differing biological functions. In some preferred embodiments, the incoming sequence comprises at least one selectable marker. This sequence can code for one or more proteins of interest. It can have other biological function. In many cases the incoming sequence will include a selectable marker, such as a gene that confers resistance to an antibiotic.

The terms "modified sequence" and "modified genes" are used interchangeably herein to refer to a sequence that includes a deletion, insertion or interruption of naturally occurring nucleic acid sequence. In some preferred embodiments, the expression product of the modified sequence is a truncated protein (e.g., if the modification is a deletion or interruption of the sequence). In some particularly preferred embodiments, the truncated protein retains biological activity. In alternative embodiments, the expression product of the modified sequence is an elongated protein (e.g., modifications comprising an insertion into the nucleic acid sequence). In some embodiments, an insertion leads to a truncated protein (e.g., when the insertion results in the formation of a stop codon). Thus, an insertion may result in either a truncated protein or an elongated protein as an expression product.

As used herein, the terms "mutant sequence" and "mutant gene" are used interchangeably and refer to a sequence that has an alteration in at least one codon occurring in a host cell's wild-type sequence. The expression product of the mutant sequence is a protein with an altered amino acid sequence relative to the wild-type. The expression product may have an altered functional capacity (e.g., enhanced enzymatic activity).

The terms "mutagenic primer" or "mutagenic oligonucleotide" (used interchangeably herein) are intended to refer to oligonucleotide compositions which correspond to a portion of the template sequence and which are capable of hybridizing thereto. With respect to mutagenic primers, the primer will not precisely match the template nucleic acid, the mismatch or mismatches in the primer being used to introduce the desired mutation into the nucleic acid library. As used herein, "non-mutagenic primer" or "non-mutagenic oligonucleotide" refers to oligonucleotide compositions which will match precisely to the template nucleic acid. In one embodiment of the invention, only mutagenic primers are used. In another preferred embodiment of the invention, the primers are designed so that for at least one region at which a mutagenic primer has been included, there is also non-mutagenic primer included in the oligonucleotide mixture. By adding a mixture of mutagenic primers and non-mutagenic primers corresponding to at least one of the mutagenic primers, it is possible to produce a resulting nucleic acid library in which a variety of combinatorial mutational patterns are presented. For example, if it is desired that some of the members of the mutant nucleic acid library retain their precursor sequence at certain positions while other members are mutant at such sites, the non-mutagenic primers provide the ability to obtain a specific level of non-mutant members within the nucleic acid library for a given residue. The methods of the invention employ mutagenic and non-mutagenic oligonucleotides which are generally between about 10-50 bases in length, or more preferably, about 15-45 bases in length. However, it may be necessary to use primers that are either shorter than about 10 bases or longer than about 50 bases to obtain the mutagenesis result desired. With respect to corresponding mutagenic and non-mutagenic primers, it is not necessary that the corresponding oligonucleotides be of identical length, but only that there is overlap in the region corresponding to the mutation to be added. Primers may be added in a pre-defined ratio according to the present invention. For example, if it is desired that the resulting library have a significant level of a certain specific mutation and a lesser amount of a different mutation at the same or different site, by adjusting the amount of primer added, it is possible to produce the desired biased library. Alternatively, by adding lesser or greater amounts of non-mutagenic primers, it is possible to adjust the frequency with which the corresponding mutation(s) are produced in the mutant nucleic acid library.

As used herein, the phrase "contiguous mutations" refers to mutations which are presented within the same oligonucleotide primer. For example, contiguous mutations may be adjacent or nearby each other, however, they will be introduced into the resulting mutant template nucleic acids by the same primer.

As used herein, the phrase "discontiguous mutations" refers to mutations which are presented in separate oligonucleotide primers. For example, discontiguous mutations will be introduced into the resulting mutant template nucleic acids by separately prepared oligonucleotide primers.

The terms "wild-type sequence" or "wild-type gene" are used interchangeably herein, to refer to a sequence that is native or naturally occurring in a host cell. In some embodiments, the wild-type sequence refers to a sequence of interest that is the starting point of a protein engineering project. The wild-type sequence may encode either a homologous or heterologous protein. A homologous protein is one the host cell would produce without intervention. A heterologous protein is one that the host cell would not produce but for the intervention.

As used herein, the term "antibodies" refers to immunoglobulins. Antibodies include but are not limited to immunoglobulins obtained directly from any species from which it is desirable to produce antibodies. In addition, the present invention encompasses modified antibodies. The term also refers to antibody fragments that retain the ability to bind to the epitope that the intact antibody binds and include polyclonal antibodies, monoclonal antibodies, chimeric antibodies, anti-idiotype (anti-ID) antibodies. Antibody fragments include, but are not limited to the complementarity-determining regions (CDRs), single-chain fragment variable regions (scFv), heavy chain variable region (VH), light chain variable region (VL). Polyclonal and monoclonal antibodies are also encompassed by the present invention. Preferably, the antibodies are monoclonal antibodies.

As used herein, the phrase "alteration in substrate specificity" refers to changes in the substrate specificity of an enzyme. In some embodiments, a change in substrate specificity is defined as a change in $k_{cat}$ and/or $K_m$ for a particular substrate, resulting from mutations of the enzyme or alteration of reaction conditions. The substrate specificity of an enzyme is determined by comparing the catalytic efficiencies it exhibits with different substrates. These determinations find particular use in assessing the efficiency of mutant enzymes, as it is generally desired to produce variant enzymes that exhibit greater ratios of $k_{cat}/K_m$ for substrates of interest. However, it is not intended that the present invention be limited to any particular substrate composition or substrate specificity.

As used herein, "surface property" is used in reference to electrostatic charge, as well as properties such as the hydrophobicity and hydrophilicity exhibited by the surface of a protein.

As used herein, the phrase "is independently selected from the group consisting of . . . " means that moieties or elements that are selected from the referenced Markush group can be the same, can be different or any mixture of elements as indicated in the following example:

A molecule having 3 R groups wherein each R group is independently selected from the group consisting of A, B and C. Here the three R groups may be: AAA, BBB, CCC, AAB, AAC, BBA, BBC, CCA, CCB, or ABC.

In reference to chemical compositions, the term "substituted" as used herein, means that the organic composition or radical to which the term is applied is:

(a) made unsaturated by the elimination of at least one element or radical; or (b) at least one hydrogen in the compound or radical is replaced with a moiety containing one or more (i) carbon, (ii) oxygen, (iii) sulfur, (iv) nitrogen or (v) halogen atoms; or (c) both (a) and (b).

Moieties which may replace hydrogen as described in (b) immediately above, that contain only carbon and hydrogen atoms, are hydrocarbon moieties including, but not limited to, alkyl, alkenyl, alkynyl, alkyldienyl, cycloalkyl, phenyl, alkyl phenyl, naphthyl, anthryl, phenanthryl, fluoryl, steroid groups, and combinations of these groups with each other and with polyvalent hydrocarbon groups such as alkylene, alkylidene and alkylidyne groups. Moieties containing oxygen atoms that may replace hydrogen as described in (b) immediately above include, but are not limited to, hydroxy, acyl or keto, ether, epoxy, carboxy, and ester containing groups. Moieties containing sulfur atoms that may replace hydrogen as described in (b) immediately above include, but are not limited to, the sulfur-containing acids and acid ester groups, thioether groups, mercapto groups and thioketo groups. Moieties containing nitrogen atoms that may replace hydrogen as described in (b) immediately above include, but are not limited to, amino groups, the nitro group, azo groups, ammonium groups, amide groups, azido groups, isocyanate groups, cyano groups and nitrile groups. Moieties containing halogen atoms that may replace hydrogen as described in (b) immediately above include chloro, bromo, fluoro, iodo groups and any of the moieties previously described where a hydrogen or a pendant alkyl group is substituted by a halo group to form a stable substituted moiety.

It is understood that any of the above moieties (b)(i) through (b)(v) can be substituted into each other in either a monovalent substitution or by loss of hydrogen in a polyvalent substitution to form another monovalent moiety that can replace hydrogen in the organic compound or radical.

The term "oxidation stable" refers to proteases of the present invention that retain a specified amount of enzymatic activity over a given period of time under conditions prevailing during the proteolytic, hydrolyzing, cleaning or other process of the invention, for example while exposed to or contacted with bleaching agents or oxidizing agents. In some embodiments, the proteases retain at least about 50%, about 60%, about 70%, about 75%, about 80%, about 85%, about 90%, about 92%, about 95%, about 96%, about 97%, about 98%, or about 99% proteolytic activity after contact with a bleaching or oxidizing agent over a given time period, for example, at least about 1 minute, about 3 minutes, about 5 minutes, about 8 minutes, about 12 minutes, about 16 minutes, about 20 minutes, etc. In some embodiments, the stability is measured as described in the Examples.

The term "chelator stable" refers to proteases of the present invention that retain a specified amount of enzymatic activity over a given period of time under conditions prevailing during the proteolytic, hydrolyzing, cleaning or other process of the invention, for example while exposed to or contacted with chelating agents. In some embodiments, the proteases retain at least about 50%, about 60%, about 70%, about 75%, about 80%, about 85%, about 90%, about 92%, about 95%, about 96%, about 97%, about 98%, or about 99% proteolytic activity after contact with a chelating agent over a given time period, for example, at least about 10 minutes, about 20 minutes, about 40 minutes, about 60 minutes, about 100 minutes, etc. In some embodiments, the chelator stability is measured as described in the Examples.

The terms "thermally stable" and "thermostable" refer to proteases of the present invention that retain a specified amount of enzymatic activity after exposure to identified temperatures over a given period of time under conditions prevailing during the proteolytic, hydrolyzing, cleaning or other process of the invention, for example while exposed altered temperatures. Altered temperatures include increased or decreased temperatures. In some embodiments, the proteases retain at least about 50%, about 60%, about 70%, about 75%, about 80%, about 85%, about 90%, about 92%, about 95%, about 96%, about 97%, about 98%, or about 99% proteolytic activity after exposure to altered temperatures over a given time period, for example, at least about 60 minutes, about 120 minutes, about 180 minutes, about 240 minutes, about 300 minutes, etc. In some embodiments, the thermostability is determined as described in the Examples.

The term "enhanced stability" in the context of an oxidation, chelator, thermal and/or pH stable protease refers to a higher retained proteolytic activity over time as compared to other serine proteases (e.g., subtilisin proteases) and/or wild-type enzymes.

The term "diminished stability" in the context of an oxidation, chelator, thermal and/or pH stable protease refers to a lower retained proteolytic activity over time as compared to other serine proteases (e.g., subtilisin proteases) and/or wild-type enzymes.

The term "cleaning activity" refers to the cleaning performance achieved by the protease under conditions prevailing during the proteolytic, hydrolyzing, cleaning or other process of the invention. In some embodiments, cleaning performance is determined by the application of various cleaning assays concerning enzyme sensitive stains, for example grass, blood, milk, or egg protein as determined by various chromatographic, spectrophotometric or other quantitative methodologies after subjection of the stains to standard wash conditions. Exemplary assays include, but are not limited to those described in WO 99/34011, and U.S. Pat. No. 6,605,458 (both of which are herein incorporated by reference), as well as those methods included in the Examples.

The term "cleaning effective amount" of a protease refers to the quantity of protease described hereinbefore that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid or dry (e.g., granular, bar) composition is required, etc.

The term "cleaning adjunct materials," as used herein, means any liquid, solid or gaseous material selected for the particular type of cleaning composition desired and the form of the product (e.g., liquid, granule, powder, bar, paste, spray, tablet, gel; or foam composition), which materials are also preferably compatible with the protease enzyme used in the composition. In some embodiments, granular compositions are in "compact" form, while in other embodiments, the liquid compositions are in a "concentrated" form.

The term "enhanced performance" in the context of cleaning activity refers to an increased or greater cleaning activity of certain enzyme sensitive stains such as egg, milk, grass or blood, as determined by usual evaluation after a standard wash cycle and/or multiple wash cycles.

The term "diminished performance" in the context of cleaning activity refers to a decreased or lesser cleaning activity of certain enzyme sensitive stains such as egg, milk, grass or blood, as determined by usual evaluation after a standard wash cycle.

The term "comparative performance" in the context of cleaning activity refers to at least about 60%, at least about 70%, at least about 80%, at least about 90%, at least about 95% of the cleaning activity of a comparative or reference protease (e.g., commercially available proteases), including but not limited to OPTIMASE™ protease (Genencor), PURAFECT™ protease products (Genencor), SAVINASE™ protease (Novozymes), BPN'-variants (See e.g., U.S. Pat. No. Re 34,606), RELASE™, DURAZYME™, EVERLASE™, KANNASE™ protease (Novozymes), MAXACAL™, MAXAPEM™, PROPERASE™ proteases (Genencor; See also, U.S. Pat. No. Re 34,606, and U.S. Pat. Nos. 5,700,676; 5,955,340; 6,312,936; and 6,482,628), and *B. lentus* variant protease products (e.g., those described in WO 92/21760, WO 95/23221 and/or WO 97/07770). Cleaning performance can be determined by comparing the proteases of the present invention with those subtilisin proteases in various cleaning assays concerning enzyme sensitive stains such as grass, blood or milk as determined by usual spectrophotometric or analytical methodologies after standard wash cycle conditions.

As used herein, "cleaning compositions" and "cleaning formulations" refer to compositions that find use in the removal of undesired compounds from items to be cleaned, such as fabric, dishes, contact lenses, other solid substrates, hair (shampoos), skin (soaps and creams), teeth (mouthwashes, toothpastes) etc. The term encompasses any materials/compounds selected for the particular type of cleaning composition desired and the form of the product (e.g., liquid, gel, granule, or spray composition), as long as the composition is compatible with the protease and other enzyme(s) used in the composition. The specific selection of cleaning composition materials are readily made by considering the surface, item or fabric to be cleaned, and the desired form of the composition for the cleaning conditions during use.

The terms further refer to any composition that is suited for cleaning, bleaching, disinfecting, and/or sterilizing any object and/or surface. It is intended that the terms include, but are not limited to detergent compositions (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish detergents).

Indeed, the term "cleaning composition" as used herein, includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, car shampoos, carpet shampoos, bathroom cleaners; hair shampoos and/or hair-rinses for humans and other animals; shower gels and foam baths and metal cleaners; as well as cleaning auxiliaries such as bleach additives and "stain-stick" or pre-treat types.

As used herein, "fabric cleaning compositions" include hand and machine laundry detergent compositions including laundry additive compositions and compositions suitable for use in the soaking and/or pretreatment of stained fabrics (e.g., clothes, linens, and other textile materials).

As used herein, "non-fabric cleaning compositions" include non-textile (i.e., fabric) surface cleaning compositions, including but not limited to dishwashing detergent compositions, oral cleaning compositions, denture cleaning compositions, and personal cleansing compositions.

As used herein, the terms "detergent composition" and "detergent formulation" are used in reference to mixtures which are intended for use in a wash medium for the cleaning of soiled objects. In preferred embodiments, the term is used in reference to detergents used to clean dishes, cutlery, etc. (e.g., "dish detergents" or "dishwashing detergents"). It is not intended that the present invention be limited to any particular detergent formulation or composition. Indeed, it is intended that in addition to detergents that contain at least one protease of the present invention, the term encompasses detergents that contain surfactants, transferase(s), hydrolytic enzymes, oxido reductases, builders, bleaching agents, bleach activators, bluing agents and fluorescent dyes, caking inhibitors, masking agents, enzyme activators, antioxidants, and solubilizers.

As used herein, "dishwashing composition" refers to all forms of compositions for cleaning dishware, including cutlery, including but not limited to granular and liquid forms. In some embodiments, the dishwashing composition is an "automatic dishwashing" composition that finds use in automatic dish washing machines. It is not intended that the present invention be limited to any particular type or dishware composition. Indeed, the present invention finds use in cleaning dishware (e.g., dishes, including, but not limited to plates, cups, glasses, bowls, etc.) and cutlery (e.g., utensils, including but not limited to spoons, knives, forks, serving utensils, etc.) of any material, including but not limited to ceramics, plastics, metals, china, glass, acrylics, etc. The term "dishware" is used herein in reference to both dishes and cutlery.

As used herein, the term "bleaching" refers to the treatment of a material (e.g., fabric, laundry, pulp, etc.) or surface for a sufficient length of time and under appropriate pH and temperature conditions to effect a brightening (i.e., whitening) and/or cleaning of the material. Examples of chemicals suitable for bleaching include but are not limited to $ClO_2$, $H_2O_2$, peracids, $NO_2$, etc.

As used herein, "wash performance" of a variant protease refers to the contribution of a variant protease to washing that provides additional cleaning performance to the detergent without the addition of the variant protease to the composition. Wash performance is compared under relevant washing conditions.

The term "relevant washing conditions" is used herein to indicate the conditions, particularly washing temperature, time, washing mechanics, sud concentration, type of detergent and water hardness, actually used in households in a dish or laundry detergent market segment.

The term "improved wash performance" is used to indicate that a better end result is obtained in stain removal under relevant washing conditions, or that less variant protease, on weight basis, is needed to obtain the same end result relative to the corresponding wild-type or starting parent protease.

As used herein, the term "disinfecting" refers to the removal of contaminants from the surfaces, as well as the inhibition or killing of microbes on the surfaces of items. It is not intended that the present invention be limited to any particular surface, item, or contaminant(s) or microbes to be removed.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically about 17 to about 35% by weight of the total composition. In contrast, in compact compositions, the filler salt is present in amounts not exceeding about 15% of the total composition. In some embodiments, the filler salt is present in amounts that do not exceed about 10%, or more preferably, about 5%, by weight of the composition. In some embodiments, the inorganic filler salts are selected from the alkali and alkaline-earth-metal salts of sulfates and chlorides. In some embodiments, a preferred filler salt is sodium sulfate.

Cleaning Compositions

Unless otherwise noted, all component or composition levels provided herein are made in reference to the active level of that component or composition, and are exclusive of impurities, for example, residual solvents or by-products, which may be present in commercially available sources. Enzyme components weights are based on total active protein. All percentages and ratios are calculated by weight unless otherwise indicated. All percentages and ratios are calculated based on the total composition unless otherwise indicated. In the exemplified detergent compositions, the enzymes levels are expressed by pure enzyme by weight of the total composition and unless otherwise specified, the detergent ingredients are expressed by weight of the total compositions.

As indicated herein, in some embodiments, the cleaning compositions of the present invention further comprise adjunct materials including, but not limited to, surfactants, builders, bleaches, bleach activators, bleach catalysts, other enzymes, enzyme stabilizing systems, chelants, optical brighteners, soil release polymers, dye transfer agents, dispersants, suds suppressors, dyes, perfumes, colorants, filler salts, hydrotropes, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (See e.g., U.S. Pat. Nos. 6,610,642, 6,605,458, 5,705,464, 5,710,115, 5,698,504, 5,695,679, 5,686,014 and 5,646,101, all of which are incorporated herein by reference). Embodiments of specific cleaning composition materials are exemplified in detail below. In embodiments in which the cleaning adjunct materials are not compatible with the variant proteases of the present invention in the cleaning compositions, then suitable methods of keeping the cleaning adjunct materials and the protease(s) separated (i.e., not in contact with each other) until combination of the two components is appropriate are used. Such separation methods include any suitable method known in the art (e.g., gelcaps, encapsulation, tablets, physical separation, etc.).

The cleaning compositions of the present invention are advantageously employed for example, in laundry applications, hard surface cleaning, dishwashing applications, as well as cosmetic applications such as dentures, teeth, hair and skin. In addition, due to the unique advantages of increased effectiveness in lower temperature solutions, the enzymes of the present invention are ideally suited for laundry applications. Furthermore, the enzymes of the present invention find use in granular and liquid compositions.

The variant proteases of the present invention also find use cleaning additive products. In some embodiments, low temperature solution cleaning applications find use. In some embodiments, the present invention provides cleaning additive products including at least one enzyme of the present invention is ideally suited for inclusion in a wash process when additional bleaching effectiveness is desired. Such instances include, but are not limited to low temperature solution cleaning applications. In some embodiments, the additive product is in its simplest form, one or more proteases. In some embodiments, the additive is packaged in dosage form for addition to a cleaning process. In some embodiments, the additive is packaged in dosage form for addition to a cleaning process where a source of peroxygen is employed and increased bleaching effectiveness is desired. Any suitable single dosage unit form finds use with the present invention, including but not limited to pills, tablets, gelcaps, or other single dosage units such as pre-measured powders or liquids. In some embodiments, filler(s) or carrier material(s) are included to increase the volume of such compositions. Suitable filler or carrier materials include, but are not limited to, various salts of sulfate, carbonate and silicate as well as talc, clay and the like. Suitable filler or carrier materials for liquid compositions include, but are not limited to water or low molecular weight primary and secondary alcohols including polyols and diols. Examples of such alcohols include, but are not limited to, methanol, ethanol, propanol and isopropanol. In some embodiments, the compositions contain from about 5% to about 90% of such materials. Acidic fillers find use to reduce pH. Alternatively, in some embodiments, the cleaning additive includes adjunct ingredients, as more fully described below.

The present cleaning compositions and cleaning additives require an effective amount of at least one of the protease variants provided herein, alone or in combination with other proteases and/or additional enzymes. The required level of enzyme is achieved by the addition of one or more protease variants of the present invention. Typically the present cleaning compositions will comprise at least about 0.0001 weight percent, from about 0.0001 to about 10, from about 0.001 to about 1, or even from about 0.01 to about 0.1 weight percent of at least one of the variant proteases of the present invention.

The cleaning compositions herein are typically formulated such that, during use in aqueous cleaning operations, the wash water will have a pH of from about 5.0 to about 11.5 or even from about 7.5 to about 10.5. Liquid product formulations are typically formulated to have a neat pH from about 3.0 to about 9.0 or even from about 3 to about 5. Granular laundry products are typically formulated to have a pH from about 9 to about 11. Techniques for controlling pH at recommended usage levels include the use of buffers, alkalis, acids, etc., and are well known to those skilled in the art.

Suitable low pH cleaning compositions typically have a neat pH of from about 3 to about 5, and are typically free of surfactants that hydrolyze in such a pH environment. Such surfactants include sodium alkyl sulfate surfactants that comprise at least one ethylene oxide moiety or even from about 1 to about 16 moles of ethylene oxide. Such cleaning compositions typically comprise a sufficient amount of a pH modifier, such as sodium hydroxide, monoethanolamine or hydrochloric acid, to provide such cleaning composition with a neat pH of from about 3 to about 5. Such compositions typically comprise at least one acid stable enzyme. In some embodiments, the compositions are liquids, while in other embodiments, they are solids. The pH of such liquid compositions is typically measured as a neat pH. The pH of such solid compositions is measured as a 10% solids solution of said composition wherein the solvent is distilled water. In these embodiments, all pH measurements are taken at 20° C., unless otherwise indicated.

In some embodiments, when the variant protease(s) is/are employed in a granular composition or liquid, it is desirable for the variant protease to be in the form of an encapsulated particle to protect the variant protease from other components of the granular composition during storage. In addition, encapsulation is also a means of controlling the availability of the variant protease during the cleaning process. In some embodiments, encapsulation enhances the performance of the variant protease(s) and/or additional enzymes. In this regard, the variant proteases of the present invention are encapsulated with any suitable encapsulating material known in the art. In some embodiments, the encapsulating material typically encapsulates at least part of the catalyst for the variant protease(s) of the present invention. Typically, the encapsulating material is water-soluble and/or water-dispersible. In some embodiments, the encapsulating material has a glass transition temperature (Tg) of 0° C. or higher. Glass transition temperature is described in more detail in WO 97/11151. The encapsulating material is typically selected from consisting of carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. In some typical embodiments, the encapsulating material is a starch (See e.g., EP 0 922 499; U.S. Pat. No. 4,977,252; U.S. Pat. No. 5,354,559, and U.S. Pat. No. 5,935,826). In some embodiments, the encapsulating material is a microsphere made from plastic such as thermoplastics, acrylonitrile, methacrylonitrile, polyacrylonitrile, polymethacrylonitrile and mixtures thereof; commercially available microspheres that find use include, but are not limited to those supplied by EXPANCEL® (Stockviksverken, Sweden), and PM 6545, PM 6550, PM 7220, PM 7228, EXTENDOSPHERES®, LUXSIL®, Q-CEL®, and SPHERICEL® (PQ Corp., Valley Forge, Pa.).

As described herein, the variant proteases of the present invention find particular use in the cleaning industry, including, but not limited to laundry and dish detergents. These applications place enzymes under various environmental stresses. The variant proteases of the present invention provide advantages over many currently used enzymes, due to their stability under various conditions.

Indeed, there are a variety of wash conditions including varying detergent formulations, wash water volumes, wash water temperatures, and lengths of wash time, to which proteases involved in washing are exposed. In addition, detergent formulations used in different geographical areas have different concentrations of their relevant components present in the wash water. For example, European detergents typically have about 4500-5000 ppm of detergent components in the wash water, while Japanese detergents typically have approximately 667 ppm of detergent components in the wash water. In North America, particularly the United States, detergents typically have about 975 ppm of detergent components present in the wash water.

A low detergent concentration system includes detergents where less than about 800 ppm of the detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of the detergent components are present in the wash water. North American detergents are generally considered to be medium detergent concentration systems as they have approximately 975 ppm of detergent components present in the wash water. Brazil typically has approximately 1500 ppm of detergent components present in the wash water.

A high detergent concentration system includes detergents where greater than about 2000 ppm of the detergent components are present in the wash water. European detergents are generally considered to be high detergent concentration systems as they have approximately 4500-5000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. As mentioned above, Brazil typically has approximately 1500 ppm of detergent components present in the wash water. However, other high suds phosphate builder detergent geographies, not limited to other Latin American countries, may have high detergent concentration systems up to about 6000 ppm of detergent components present in the wash water.

In light of the foregoing, it is evident that concentrations of detergent compositions in typical wash solutions throughout the world varies from less than about 800 ppm of detergent composition ("low detergent concentration geographies"), for example about 667 ppm in Japan, to between about 800 ppm to about 2000 ppm ("medium detergent concentration geographies"), for example about 975 ppm in U.S. and about 1500 ppm in Brazil, to greater than about 2000 ppm ("high detergent concentration geographies"), for example about 4500 ppm to about 5000 ppm in Europe and about 6000 ppm in high suds phosphate builder geographies.

The concentrations of the typical wash solutions are determined empirically. For example, in the U.S., a typical washing machine holds a volume of about 64.4 L of wash solution. Accordingly, in order to obtain a concentration of about 975 ppm of detergent within the wash solution about 62.79 g of detergent composition must be added to the 64.4 L of wash solution. This amount is the typical amount measured into the wash water by the consumer using the measuring cup provided with the detergent.

As a further example, different geographies use different wash temperatures. The temperature of the wash water in Japan is typically less than that used in Europe. For example, the temperature of the wash water in North America and Japan is typically between about 10 and about 30° C. (e.g., about 20° C.), whereas the temperature of wash water in Europe is typically between about 30 and about 60° C. (e.g., about 40° C.). However, in the interest of saving energy, many consumers are switching to using cold water washing. In addition, in some further regions, cold water is typically used for laundry, as well as dish washing applications. In some embodiments, the "cold water washing" of the present invention utilizes washing at temperatures from about 10° C. to about 40° C., or from about 20° C. to about 30° C., or from about 15° C. to about 25° C., as well as all other combinations within the range of about 15° C. to about 35° C., and all ranges within 10° C. to 40° C.

As a further example, different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million (parts per million converted to grains per U.S. gallon is ppm # divided by 17.1 equals grains per gallon) of hardness minerals.

| Water | Grains per gallon | Parts per million |
| --- | --- | --- |
| Soft | less than 1.0 | less than 17 |
| Slightly hard | 1.0 to 3.5 | 17 to 60 |

| Water | Grains per gallon | Parts per million |
|---|---|---|
| Moderately hard | 3.5 to 7.0 | 60 to 120 |
| Hard | 7.0 to 10.5 | 120 to 180 |
| Very hard | greater than 10.5 | greater than 180 |

European water hardness is typically greater than about 10.5 (for example about 10.5 to about 20.0) grains per gallon mixed $Ca^{2+}/Mg^{2+}$ (e.g., about 15 grains per gallon mixed $Ca^{2+}/Mg^{2+}$). North American water hardness is typically greater than Japanese water hardness, but less than European water hardness. For example, North American water hardness can be between about 3 to about 10 grains, about 3 to about 8 grains or about 6 grains. Japanese water hardness is typically lower than North American water hardness, usually less than about 4, for example about 3 grains per gallon mixed $Ca^{2+}/Mg^{2+}$.

Accordingly, in some embodiments, the present invention provides variant proteases that show surprising wash performance in at least one set of wash conditions (e.g., water temperature, water hardness, and/or detergent concentration). In some embodiments, the variant proteases of the present invention are comparable in wash performance to other subtilisin proteases. In some embodiments, the variant proteases of the present invention exhibit enhanced wash performance as compared to subtilisin proteases currently commercially available. Thus, in some preferred embodiments of the present invention, the variant proteases provided herein exhibit enhanced oxidative stability, enhanced thermal stability, enhanced cleaning capabilities under various conditions, and/or enhanced chelator stability. In addition, the variant proteases of the present invention find use in cleaning compositions that do not include detergents, again either alone or in combination with builders and stabilizers.

In some embodiments of the present invention, the cleaning compositions comprise at least one variant protease of the present invention at a level from about 0.00001% to about 10% by weight of the composition and the balance (e.g., about 99.999% to about 90.0%) comprising cleaning adjunct materials by weight of composition. In other aspects of the present invention, the cleaning compositions of the present invention comprises at least one variant protease at a level of about 0.0001% to about 10%, about 0.001% to about 5%, about 0.001% to about 2%, about 0.005% to about 0.5% by weight of the composition and the balance of the cleaning composition (e.g., about 99.9999% to about 90.0%, about 99.999% to about 98%, about 99.995% to about 99.5% by weight) comprising cleaning adjunct materials.

In some embodiments, the cleaning compositions of the present invention comprise one or more additional detergent enzymes, which provide cleaning performance and/or fabric care and/or dishwashing benefits. Examples of suitable enzymes include, but are not limited to, hemicellulases, cellulases, peroxidases, proteases, xylanases, lipases, phospholipases, esterases, cutinases, pectinases, pectate lyases, mannanases, keratinases, reductases, oxidases, phenoloxidases, lipoxygenases, ligninases, pullulanases, tannases, pentosanases, malanases, ß-glucanases, arabinosidases, hyaluronidase, chondroitinase, laccase, and amylases, or mixtures thereof. In some embodiments, a combination of enzymes is used (i.e., a "cocktail") comprising conventional applicable enzymes like protease, lipase, cutinase and/or cellulase in conjunction with amylase is used.

In addition to the protease variants provided herein, any other suitable protease finds use in the compositions of the present invention. Suitable proteases include those of animal, vegetable or microbial origin. In some particularly preferred embodiments, microbial proteases are used. In some embodiments, chemically or genetically modified mutants are included. In some embodiments, the protease is a serine protease, preferably an alkaline microbial protease or a trypsin-like protease. Examples of alkaline proteases include subtilisins, especially those derived from *Bacillus* (e.g., subtilisin, *lentus, amyloliquefaciens*, subtilisin Carlsberg, subtilisin 309, subtilisin 147 and subtilisin 168). Additional examples include those mutant proteases (i.e., variant proteases) described in U.S. Pat. Nos. RE 34,606, 5,955,340, 5,700,676, 6,312,936, and 6,482,628, all of which are incorporated herein by reference. Additional protease examples include, but are not limited to trypsin (e.g., of porcine or bovine origin), and the *Fusarium* protease described in WO 89/06270. In some embodiments, commercially available protease enzymes that find use in the present invention include, but are not limited to MAXATASE®, MAXACAL™, MAXAPEM™, OPTICLEAN®, OPTIMASE®, PROPERASE®, PURAFECT®, PURAFECT® OXP, PURAMAX™, EXCELLASE™, and PURAFAST™ (Genencor); ALCALASE®, SAVINASE®, PRIMASE®, DURAZYM™, POLARZYME®, OVOZYME®, KANNASE®, LIQUANASE®, NEUTRASE®, RELASE® and ESPERASE® (Novozymes); and BLAP™ (Henkel Kommanditgesellschaft auf Aktien, Duesseldorf, Germany. Various proteases are described in WO95/23221, WO 92/21760, U.S. Pat. Publ. No. 2008/0090747, and U.S. Pat. Nos. 5,801,039, 5,340,735, 5,500,364, 5,855,625, U.S. RE 34,606, U.S. Pat. Nos. 5,955,340, 5,700,676, 6,312,936, and 6,482,628, and various other patents. In some further embodiments, metalloproteases find use in the present invention, including but not limited to the neutral metalloprotease described in WO 07/044,993.

In addition, any suitable lipase finds use in the present invention. Suitable lipases include, but are not limited to those of bacterial or fungal origin. Chemically or genetically modified mutants are encompassed by the present invention. Examples of useful lipases include *Humicola lanuginosa* lipase (See e.g., EP 258 068, and EP 305 216), *Rhizomucor miehei* lipase (See e.g., EP 238 023), *Candida* lipase, such as *C. antarctica* lipase (e.g., the *C. antarctica* lipase A or B; See e.g., EP 214 761), *Pseudomonas* lipases such as *P. alcaligenes* lipase and *P. pseudoalcaligenes* lipase (See e.g., EP 218 272), *P. cepacia* lipase (See e.g., EP 331 376), *P. stutzeri* lipase (See e.g., GB 1,372,034), *P. fluorescens* lipase, *Bacillus* lipase (e.g., *B. subtilis* lipase [Dartois et al., Biochem. Biophys. Acta 1131:253-260 [1993]); *B. stearothermophilus* lipase [See e.g., JP 64/744992]; and *B. pumilus* lipase [See e.g., WO 91/16422]).

Furthermore, a number of cloned lipases find use in some embodiments of the present invention, including but not limited to *Penicillium camembertii* lipase (See, Yamaguchi et al., Gene 103:61-67 [1991]), *Geotricum candidum* lipase (See, Schimada et al., J. Biochem., 106:383-388 [1989]), and various *Rhizopus* lipases such as *R. delemar* lipase (See, Hass et al., Gene 109:117-113 [1991]), a *R. niveus* lipase (Kugimiya et al., Biosci. Biotech. Biochem. 56:716-719 [1992]) and *R. oryzae* lipase.

Other types of lipolytic enzymes such as cutinases also find use in some embodiments of the present invention, including but not limited to the cutinase derived from

*Pseudomonas mendocina* (See, WO 88/09367), and the cutinase derived from *Fusarium solani pisi* (See, WO 90/09446).

Additional suitable lipases include commercially available lipases such as M1 LIPASE™, LUMA FAST™, and LIPOMAX™ (Genencor); LIPOLASE® and LIPOLASE® ULTRA (Novozymes); and LIPASE P™ "Amano" (Amano Pharmaceutical Co. Ltd., Japan).

In some embodiments of the present invention, the cleaning compositions of the present invention further comprise lipases at a level from about 0.00001% to about 10% of additional lipase by weight of the composition and the balance of cleaning adjunct materials by weight of composition. In other aspects of the present invention, the cleaning compositions of the present invention also comprise lipases at a level of about 0.0001% to about 10%, about 0.001% to about 5%, about 0.001% to about 2%, about 0.005% to about 0.5% lipase by weight of the composition.

In some embodiments of the present invention, any suitable amylase finds use in the present invention. In some embodiments, any amylase (e.g., alpha and/or beta) suitable for use in alkaline solutions also find use. Suitable amylases include, but are not limited to those of bacterial or fungal origin. Chemically or genetically modified mutants are included in some embodiments. Amylases that find use in the present invention, include, but are not limited to α-amylases obtained from *B. licheniformis* (See e.g., GB 1,296, 839). Commercially available amylases that find use in the present invention include, but are not limited to DURAMYL®, TERMAMYL®, FUNGAMYL®, STAINZYME®, STAINZYME PLUS®, STAINZYME ULTRA®, and BAN™ (Novozymes), as well as POWERASE™, RAPIDASE® and MAXAMYL® P (Genencor).

In some embodiments of the present invention, the cleaning compositions of the present invention further comprise amylases at a level from about 0.00001% to about 10% of additional amylase by weight of the composition and the balance of cleaning adjunct materials by weight of composition. In other aspects of the present invention, the cleaning compositions of the present invention also comprise amylases at a level of about 0.0001% to about 10%, about 0.001% to about 5%, about 0.001% to about 2%, about 0.005% to about 0.5% amylase by weight of the composition.

In some further embodiments, any suitable cellulase finds used in the cleaning compositions of the present invention. Suitable cellulases include, but are not limited to those of bacterial or fungal origin. Chemically or genetically modified mutants are included in some embodiments. Suitable cellulases include, but are not limited to *Humicola insolens* cellulases (See e.g., U.S. Pat. No. 4,435,307). Especially suitable cellulases are the cellulases having color care benefits (See e.g., EP 0 495 257). Commercially available cellulases that find use in the present include, but are not limited to CELLUZYME®, CAREZYME® (Novozymes), and KAC-500(B)™ (Kao Corporation). In some embodiments, cellulases are incorporated as portions or fragments of mature wild-type or variant cellulases, wherein a portion of the N-terminus is deleted (See e.g., U.S. Pat. No. 5,874, 276). In some embodiments, the cleaning compositions of the present invention further comprise cellulases at a level from about 0.00001% to about 10% of additional cellulase by weight of the composition and the balance of cleaning adjunct materials by weight of composition. In other aspects of the present invention, the cleaning compositions of the present invention also comprise cellulases at a level of about 0.0001% to about 10%, about 0.001% to about 5%, about 0.001% to about 2%, about 0.005% to about 0.5% cellulase by weight of the composition.

Any mannanase suitable for use in detergent compositions also finds use in the present invention. Suitable mannanases include, but are not limited to those of bacterial or fungal origin. Chemically or genetically modified mutants are included in some embodiments. Various mannanases are known which find use in the present invention (See e.g., U.S. Pat. No. 6,566,114, U.S. Pat. No. 6,602,842, and U.S. Pat. No. 6,440,991, all of which are incorporated herein by reference). In some embodiments, the cleaning compositions of the present invention further comprise mannanases at a level from about 0.00001% to about 10% of additional mannanase by weight of the composition and the balance of cleaning adjunct materials by weight of composition. In other aspects of the present invention, the cleaning compositions of the present invention also comprise mannanases at a level of about 0.0001% to about 10%, about 0.001% to about 5%, about 0.001% to about 2%, about 0.005% to about 0.5% mannanase by weight of the composition.

In some embodiments, peroxidases are used in combination with hydrogen peroxide or a source thereof (e.g., a percarbonate, perborate or persulfate) in the compositions of the present invention. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO 94/12621 and WO 95/01426). Suitable peroxidases/oxidases include, but are not limited to those of plant, bacterial or fungal origin. Chemically or genetically modified mutants are included in some embodiments. In some embodiments, the cleaning compositions of the present invention further comprise peroxidase and/or oxidase enzymes at a level from about 0.00001% to about 10% of additional peroxidase and/or oxidase by weight of the composition and the balance of cleaning adjunct materials by weight of composition. In other aspects of the present invention, the cleaning compositions of the present invention also comprise, peroxidase and/or oxidase enzymes at a level of about 0.0001% to about 10%, about 0.001% to about 5%, about 0.001% to about 2%, about 0.005% to about 0.5% peroxidase and/or oxidase enzymes by weight of the composition.

In some embodiments, additional enzymes find use, including but not limited to perhydrolases (See e.g., WO 05/056782). In addition, in some particularly preferred embodiments, mixtures of the above mentioned enzymes are encompassed herein, in particular one or more additional protease, amylase, lipase, mannanase, and/or at least one cellulase. Indeed, it is contemplated that various mixtures of these enzymes will find use in the present invention. It is also contemplated that the varying levels of the variant protease(s) and one or more additional enzymes may both independently range to about 10%, the balance of the cleaning composition being cleaning adjunct materials. The specific selection of cleaning adjunct materials are readily made by considering the surface, item, or fabric to be cleaned, and the desired form of the composition for the cleaning conditions during use (e.g., through the wash detergent use).

Examples of suitable cleaning adjunct materials include, but are not limited to, surfactants, builders, bleaches, bleach activators, bleach catalysts, other enzymes, enzyme stabilizing systems, chelants, optical brighteners, soil release polymers, dye transfer agents, dye transfer inhibiting agents, catalytic materials, hydrogen peroxide, sources of hydrogen peroxide, preformed peracis, polymeric dispersing agents, clay soil removal agents, structure elasticizing agents, dispersants, suds suppressors, dyes, perfumes, colorants, filler salts, hydrotropes, photoactivators, fluorescers, fabric conditioners, fabric softeners, carriers, hydrotropes, processing aids, solvents, pigments, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (See e.g., U.S. Pat. Nos. 6,610,642, 6,605,458, 5,705,464, 5,710,115, 5,698,504, 5,695,679, 5,686,014 and 5,646,101, all of which are incorporated herein by reference). Embodiments of specific cleaning composition materials are exemplified in detail below. In embodiments in which the cleaning adjunct materials are not compatible with the variant proteases of the present invention in the cleaning compositions, then suitable methods of keeping the cleaning adjunct materials and the protease(s) separated (i.e., not in contact with each other) until combination of the two components is appropriate are used. Such separation methods include any suitable method known in the art (e.g., gelcaps, encapsulation, tablets, physical separation, etc.).

In some preferred embodiments, an effective amount of one or more variant protease(s) provided herein are included in compositions useful for cleaning a variety of surfaces in need of proteinaceous stain removal. Such cleaning compositions include cleaning compositions for such applications as cleaning hard surfaces, fabrics, and dishes. Indeed, in some embodiments, the present invention provides fabric cleaning compositions, while in other embodiments, the present invention provides non-fabric cleaning compositions. Notably, the present invention also provides cleaning compositions suitable for personal care, including oral care (including dentrifices, toothpastes, mouthwashes, etc., as well as denture cleaning compositions), skin, and hair cleaning compositions. It is intended that the present invention encompass detergent compositions in any form (i.e., liquid, granular, bar, semi-solid, gels, emulsions, tablets, capsules, etc.).

By way of example, several cleaning compositions wherein the variant proteases of the present invention find use are described in greater detail below. In some embodiments in which the cleaning compositions of the present invention are formulated as compositions suitable for use in laundry machine washing method(s), the compositions of the present invention preferably contain at least one surfactant and at least one builder compound, as well as one or more cleaning adjunct materials preferably selected from organic polymeric compounds, bleaching agents, additional enzymes, suds suppressors, dispersants, lime-soap dispersants, soil suspension and anti-redeposition agents and corrosion inhibitors. In some embodiments, laundry compositions also contain softening agents (i.e., as additional cleaning adjunct materials). The compositions of the present invention also find use detergent additive products in solid or liquid form. Such additive products are intended to supplement and/or boost the performance of conventional detergent compositions and can be added at any stage of the cleaning process. In some embodiments, the density of the laundry detergent compositions herein ranges from about 400 to about 1200 g/liter, while in other embodiments, it ranges from about 500 to about 950 g/liter of composition measured at 20° C.

In embodiments formulated as compositions for use in manual dishwashing methods, the compositions of the invention preferably contain at least one surfactant and preferably at least one additional cleaning adjunct material selected from organic polymeric compounds, suds enhancing agents, group II metal ions, solvents, hydrotropes and additional enzymes.

In some embodiments, various cleaning compositions such as those provided in U.S. Pat. No. 6,605,458, find use with the variant proteases of the present invention. Thus, in some embodiments, the compositions comprising at least one variant protease of the present invention is a compact granular fabric cleaning composition, while in other embodiments, the composition is a granular fabric cleaning composition useful in the laundering of colored fabrics, in further embodiments, the composition is a granular fabric cleaning composition which provides softening through the wash capacity, in additional embodiments, the composition is a heavy duty liquid fabric cleaning composition. In some embodiments, the compositions comprising at least one variant protease of the present invention are fabric cleaning compositions such as those described in U.S. Pat. Nos. 6,610,642 and 6,376,450. In addition, the variant proteases of the present invention find use in granular laundry detergent compositions of particular utility under European or Japanese washing conditions (See e.g., U.S. Pat. No. 6,610,642).

In some alternative embodiments, the present invention provides hard surface cleaning compositions comprising at least one variant protease provided herein. Thus, in some embodiments, the compositions comprising at least one variant protease of the present invention is a hard surface cleaning composition such as those described in U.S. Pat. Nos. 6,610,642, 6,376,450, and 6,376,450.

In yet further embodiments, the present invention provides dishwashing compositions comprising at least one variant protease provided herein. Thus, in some embodiments, the compositions comprising at least one variant protease of the present invention is a hard surface cleaning composition such as those in U.S. Pat. Nos. 6,610,642 and 6,376,450. In some still further embodiments, the present invention provides dishwashing compositions comprising at least one variant protease provided herein. In some further embodiments, the compositions comprising at least one variant protease of the present invention comprise oral care compositions such as those in U.S. Pat. Nos. 6,376,450, and 6,376,450. The formulations and descriptions of the compounds and cleaning adjunct materials contained in the aforementioned U.S. Pat. Nos. 6,376,450, 6,605,458, 6,605,458, and 6,610,642, find use with the variant proteases provided herein.

The cleaning compositions of the present invention are formulated into any suitable form and prepared by any process chosen by the formulator, non-limiting examples of which are described in U.S. Pat. Nos. 5,879,584, 5,691,297, 5,574,005, 5,569,645, 5,565,422, 5,516,448, 5,489,392, and 5,486,303, all of which are incorporated herein by reference. When a low pH cleaning composition is desired, the pH of such composition is adjusted via the addition of a material such as monoethanolamine or an acidic material such as HCl.

While not essential for the purposes of the present invention, the non-limiting list of adjuncts illustrated hereinafter are suitable for use in the instant cleaning compositions. In some embodiments, these adjuncts are incorporated for example, to assist or enhance cleaning performance, for treatment of the substrate to be cleaned, or to modify the aesthetics of the cleaning composition as is the case with perfumes, colorants, dyes or the like. It is understood that such adjuncts are in addition to the variant proteases of the present invention. The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812, and 6,326,348, incorporated by reference. The aforementioned adjunct ingredients may constitute the balance of the cleaning compositions of the present invention.

In some embodiments, the cleaning compositions according to the present invention comprise at least one surfactant and/or a surfactant system wherein the surfactant is selected from nonionic surfactants, anionic surfactants, cationic surfactants, ampholytic surfactants, zwitterionic surfactants, semi-polar nonionic surfactants and mixtures thereof. In some low pH cleaning composition embodiments (e.g., compositions having a neat pH of from about 3 to about 5), the composition typically does not contain alkyl ethoxylated sulfate, as it is believed that such surfactant may be hydrolyzed by such compositions the acidic contents. In some embodiments, the surfactant is present at a level of from about 0.1% to about 60%, while in alternative embodiments the level is from about 1% to about 50%, while in still further embodiments the level is from about 5% to about 40%, by weight of the cleaning composition.

In some embodiments, the cleaning compositions of the present invention comprise one or more detergent builders or builder systems. In some embodiments incorporating at least one builder, the cleaning compositions comprise at least about 1%, from about 3% to about 60% or even from about 5% to about 40% builder by weight of the cleaning composition. Builders include, but are not limited to, the alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1, 3, 5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present invention.

In some embodiments, the builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present invention, including those known in the art (See e.g., EP 2 100 949).

In some embodiments, the cleaning compositions of the present invention contain at least one chelating agent. Suitable chelating agents include, but are not limited to copper, iron and/or manganese chelating agents and mixtures thereof. In embodiments in which at least one chelating agent is used, the cleaning compositions of the present invention comprise from about 0.1% to about 15% or even from about 3.0% to about 10% chelating agent by weight of the subject cleaning composition.

In some still further embodiments, the cleaning compositions provided herein contain at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

As indicated herein, in some embodiments, anti-redeposition agents find use in some embodiments of the present invention. In some preferred embodiments, non-ionic surfactants find use. For example, in automatic dishwashing embodiments, non-ionic surfactants find use for surface modification purposes, in particular for sheeting, to avoid filming and spotting and to improve shine. These non-ionic surfactants also find use in preventing the re-deposition of soils. In some preferred embodiments, the anti-redeposition agent is a non-ionic surfactant as known in the art (See e.g., EP 2 100 949).

In some embodiments, the cleaning compositions of the present invention include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. In embodiments in which at least one dye transfer inhibiting agent is used, the cleaning compositions of the present invention comprise from about 0.0001% to about 10%, from about 0.01% to about 5%, or even from about 0.1% to about 3% by weight of the cleaning composition.

In some embodiments, silicates are included within the compositions of the present invention. In some such embodiments, sodium silicates (e.g., sodium disilicate, sodium metasilicate, and crystalline phyllosilicates) find use. In some embodiments, silicates are present at a level of from about 1% to about 20%. In some preferred embodiments, silicates are present at a level of from about 5% to about 15% by weight of the composition.

In some still additional embodiments, the cleaning compositions of the present invention also contain dispersants. Suitable water-soluble organic materials include, but are not limited to the homo- or co-polymeric acids or their salts, in which the polycarboxylic acid comprises at least two carboxyl radicals separated from each other by not more than two carbon atoms.

In some further embodiments, the enzymes used in the cleaning compositions are stabilized any suitable technique. In some embodiments, the enzymes employed herein are stabilized by the presence of water-soluble sources of calcium and/or magnesium ions in the finished compositions that provide such ions to the enzymes. In some embodiments, the enzyme stabilizers include oligosaccharides, polysaccharides, and inorganic divalent metal salts, including alkaline earth metals, such as calcium salts. It is contemplated that various techniques for enzyme stabilization will find use in the present invention. For example, in some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), nickel (II), and oxovanadium (IV). Chlorides and sulfates also find use in some embodiments of the present invention. Examples of suitable oligosaccharides and polysaccharides (e.g., dextrins) are known in the art (See e.g., WO 07/145,964). In some embodiments, reversible protease inhibitors also find use, such as boron-containing compounds (e.g., borate, 4-formyl phenyl boronic acid) and/or a tripeptide aldehyde find use to further improve stability, as desired.

In some embodiments, bleaches, bleach activators and/or bleach catalysts are present in the compositions of the present invention. In some embodiments, the cleaning compositions of the present invention comprise inorganic and/or organic bleaching compound(s). Inorganic bleaches include, but are not limited to perhydrate salts (e.g., perborate, percarbonate, perphosphate, persulfate, and persilicate salts). In some embodiments, inorganic perhydrate salts are alkali metal salts. In some embodiments, inorganic perhydrate salts are included as the crystalline solid, without additional protection, although in some other embodiments, the salt is coated. Any suitable salt known in the art finds use in the present invention (See e.g., EP 2 100 949).

In some embodiments, bleach activators are used in the compositions of the present invention. Bleach activators are typically organic peracid precursors that enhance the bleaching action in the course of cleaning at temperatures of 60° C. and below. Bleach activators suitable for use herein include compounds which, under perhydrolysis conditions, give aliphaic peroxoycarboxylic acids having preferably from about 1 to about 10 carbon atoms, in particular from about 2 to about 4 carbon atoms, and/or optionally substituted perbenzoic acid. Additional bleach activators are known in the art and find use in the present invention (See e.g., EP 2 100 949).

In addition, in some embodiments and as further described herein, the cleaning compositions of the present invention further comprise at least one bleach catalyst. In some embodiments, the manganese triazacyclononane and related complexes find use, as well as cobalt, copper, manganese, and iron complexes. Additional bleach catalysts find use in the present invention (See e.g., U.S. Pat. Nos. 4,246,612, 5,227,084, 4,810,410, WO 99/06521, and EP 2 100 949).

In some embodiments, the cleaning compositions of the present invention contain one or more catalytic metal complexes. In some embodiments, a metal-containing bleach catalyst finds use. In some preferred embodiments, the metal bleach catalyst comprises a catalyst system comprising a transition metal cation of defined bleach catalytic activity, (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof are used (See e.g., U.S. Pat. No. 4,430,243). In some embodiments, the cleaning compositions of the present invention are catalyzed by means of a manganese compound. Such compounds and levels of use are well known in the art (See e.g., U.S. Pat. No. 5,576,282). In additional embodiments, cobalt bleach catalysts find use in the cleaning compositions of the present invention. Various cobalt bleach catalysts are known in the art (See e.g., U.S. Pat. Nos. 5,597,936 and 5,595,967) and are readily prepared by known procedures.

In some additional embodiments, the cleaning compositions of the present invention include a transition metal complex of a macropolycyclic rigid ligand (MRL). As a practical matter, and not by way of limitation, in some embodiments, the compositions and cleaning processes provided by the present invention are adjusted to provide on the order of at least one part per hundred million of the active MRL species in the aqueous washing medium, and in some preferred embodiments, provide from about 0.005 ppm to about 25 ppm, more preferably from about 0.05 ppm to about 10 ppm, and most preferably from about 0.1 ppm to about 5 ppm, of the MRL in the wash liquor.

In some embodiments, preferred transition-metals in the instant transition-metal bleach catalyst include, but are not limited to manganese, iron and chromium. Preferred MRLs also include, but are not limited to special ultra-rigid ligands that are cross-bridged (e.g., 5,12-diethyl-1,5,8,12-tetraazabicyclo[6.6.2]hexadecane). Suitable transition metal MRLs are readily prepared by known procedures (See e.g., WO 2000/32601, and U.S. Pat. No. 6,225,464).

In some embodiments, the cleaning compositions of the present invention comprise metal care agents. Metal care agents find use in preventing and/or reducing the tarnishing, corrosion, and/or oxidation of metals, including aluminum, stainless steel, and non-ferrous metals (e.g., silver and copper). Suitable metal care agents include those described in EP 2 100 949, WO 9426860 and WO 94/26859). In some embodiments, the metal care agent is a zinc salt. In some further embodiments, the cleaning compositions of the present invention comprise from about 0.1% to about 5% by weight of one or more metal care agent.

As indicated above, the cleaning compositions of the present invention are formulated into any suitable form and prepared by any process chosen by the formulator, non-limiting examples of which are described in U.S. Pat. Nos. 5,879,584, 5,691,297, 5,574,005, 5,569,645, 5,516,448, 5,489,392, and 5,486,303, all of which are incorporated herein by reference. In some embodiments in which a low pH cleaning composition is desired, the pH of such composition is adjusted via the addition of an acidic material such as HCl.

The cleaning compositions disclosed herein of find use in cleaning a situs (e.g., a surface, dishware, or fabric). Typically, at least a portion of the situs is contacted with an embodiment of the present cleaning composition, in neat form or diluted in a wash liquor, and then the situs is optionally washed and/or rinsed. For purposes of the present invention, "washing" includes but is not limited to, scrubbing, and mechanical agitation. In some embodiments, the cleaning compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric mass ratio is typically from about 1:1 to about 30:1.

EXPERIMENTAL

The present invention is described in further detail in the following examples which are not in any way intended to limit the scope of the invention as claimed.

In the experimental disclosure which follows, the following abbreviations apply: PI (proteinase inhibitor), ppm (parts per million); M (molar); mM (millimolar); µM (micromolar); nM (nanomolar); mol (moles); mmol (millimoles); μmol (micromoles); nmol (nanomoles); gm (grams); mg (milligrams); μg (micrograms); pg (picograms); L (liters); ml and mL (milliliters); μl and μL (microliters); cm (centimeters); mm (millimeters); μm (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); rpm (revolutions per minute); $H_2O$ (water); $dH_2O$ (deionized water); (HCl (hydrochloric acid); aa (amino acid); bp (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); $MgCl_2$ (magnesium chloride); NaCl (sodium chloride); w/v (weight to volume); v/v (volume to volume); g (gravity); OD (optical density); ppm (parts per million); Dulbecco's phosphate buffered solution (DPBS); SOC (2% Bacto-Tryptone, 0.5% Bacto Yeast Extract, 10 mM NaCl, 2.5 mM KCl); Terrific Broth (TB; 12 g/l Bacto-Tryptone, 24 g/l glycerol, 2.31 g/l $KH_2PO_4$, and 12.54 g/l $K_2HPO_4$); $OD_{280}$ (optical density at 280 nm); $OD_{600}$ (optical density at 600 nm); $A_{405}$ (absorbance at 405 nm); Vmax (the maximum initial velocity of an enzyme catalyzed reaction); PAGE (polyacrylamide gel electrophoresis); PBS (phosphate buffered saline [150 mM NaCl, 10 mM sodium phosphate buffer, pH 7.2]); PBST (PBS+0.25% TWEEN®-20); PEG (polyethylene glycol); PCR (polymerase chain reaction); RT-PCR (reverse transcription PCR); SDS (sodium dodecyl sulfate); Tris(tris (hydroxymethyl)aminomethane); HEPES (N-[2-Hydroxyethyl]piperazine-N-[2-ethanesulfonic acid]); HBS (HEPES buffered saline); Tris-HCl (tris[Hydroxymethyl]aminomethane-hydrochloride); Tricine (N-[tris-(hydroxymethyl)-methyl]-glycine); CHES (2-(N-cyclo-hexylamino) ethanesulfonic acid); TAPS (3-{[tris-(hydroxymethyl)-methyl]-amino}-propanesulfonic acid); CAPS (3-(cyclohexylamino)-propane-sulfonic acid; DMSO (dimethyl sulfoxide); DTT (1,4-dithio-DL-threitol); SA (sinapinic acid (s,5-dimethoxy-4-hydroxy cinnamic acid); TCA (trichloroacetic acid); Glut and GSH (reduced glutathione); GSSG (oxidized glutathione); TCEP (Tris[2-carboxyethyl]phosphine); Ci (Curies); mCi (milliCuries); μCi (microCuries); HPLC (high pressure liquid chromatography); RP-HPLC (reverse phase high pressure liquid chromatography); TLC (thin layer chromatography); MALDI-TOF (matrix-assisted laser desorption/ionization—time of flight); Ts (tosyl); Bn (benzyl); Ph (phenyl); Ms (mesyl); Et (ethyl), Me (methyl); Tag (*Thermus aquaticus* DNA polymerase); Klenow (DNA polymerase I large (Klenow) fragment); EGTA (ethylene glycol-bis(ß-aminoethyl ether) N,N, N',N'-tetraacetic acid); EDTA (ethylenediaminetetracetic acid); bla (β-lactamase or ampicillin-resistance gene); HDL (high density liquid); MJ Research (MJ Research, Reno, Nev.); Baseclear (Baseclear BV, Inc., Leiden, the Netherlands); PerSeptive (PerSeptive Biosystems, Framingham, Mass.); ThermoFinnigan (ThermoFinnigan, San Jose, Calif.); Argo (Argo BioAnalytica, Morris Plains, N.J.); Seitz EKS (SeitzSchenk Filtersystems GmbH, Bad Kreuznach, Germany); Pall (Pall Corp., East Hills, N.Y. and Bad Kreuznach, Germany); Spectrum (Spectrum Laboratories, Dominguez Rancho, Calif.); Molecular Structure (Molecular Structure Corp., Woodlands, Tex.); Accelrys (Accelrys, Inc., San Diego, Calif.); Chemical Computing (Chemical Computing Corp., Montreal, Canada); New Brunswick (New Brunswick Scientific, Co., Edison, N.J.); CFT (Center for Test Materials, Vlaardingen, the Netherlands); Procter & Gamble (Procter & Gamble, Inc., Cincinnati, Ohio); GE Healthcare (GE Healthcare, Chalfont St. Giles, United Kingdom); DNA2.0 (DNA2.0, Menlo Park, Calif.); OXOID (Oxoid, Basingstoke, Hampshire, UK); Megazyme (Megazyme International Ireland Ltd., Bray Business Park, Bray, Co., Wicklow, Ireland); Finnzymes (Finnzymes Oy, Espoo, Finland); Kelco (CP Kelco, Wilmington, Del.); Corning (Corning Life Sciences, Corning, N.Y.); (NEN (NEN Life Science Products, Boston, Mass.); Pharma AS (Pharma AS, Oslo, Norway); Dynal (Dynal, Oslo, Norway); Bio-Synthesis (Bio-Synthesis, Lewisville, Tex.); ATCC (American Type Culture Collection, Rockville, Md.); Gibco/BRL (Gibco/BRL, Grand Island, N.Y.); Sigma (Sigma Chemical Co., St. Louis, Mo.); Pharmacia (Pharmacia Biotech, Piscataway, N.J.); NCBI (National Center for Biotechnology Information); Applied Biosystems (Applied Biosystems, Foster City, Calif.); BD Biosciences and/or Clontech (BD Biosciences CLONTECH Laboratories, Palo Alto, Calif.); Operon Technologies (Operon Technologies, Inc., Alameda, Calif.); MWG Biotech (MWG Biotech, High Point, N.C.); Oligos Etc (Oligos Etc. Inc, Wilsonville, Oreg.); Bachem (Bachem Bioscience, Inc., King of Prussia, Pa.); Difco (Difco Laboratories, Detroit, Mich.); Mediatech (Mediatech, Herndon, Va.; Santa Cruz (Santa Cruz Biotechnology, Inc., Santa Cruz, Calif.); Oxoid (Oxoid Inc., Ogdensburg, N.Y.); Worthington (Worthington Biochemical Corp., Freehold, N.J.); GIBCO BRL or Gibco BRL (Life Technologies, Inc., Gaithersburg, Md.); Millipore (Millipore, Billerica, Mass.); Bio-Rad (Bio-Rad, Hercules, Calif.); Invitrogen (Invitrogen Corp., San Diego, Calif.); NEB (New England Biolabs, Beverly, Mass.); Sigma (Sigma Chemical Co., St. Louis, Mo.); Pierce (Pierce Biotechnology, Rockford, Ill.); Takara (Takara Bio Inc. Otsu, Japan); Roche (Hoffmann-La Roche, Basel, Switzerland); EM Science (EM Science, Gibbstown, N.J.); Qiagen (Qiagen, Inc., Valencia, Calif.); Biodesign (Biodesign Intl., Saco, Me.); Aptagen (Aptagen, Inc., Herndon, Va.); Sorvall (Sorvall brand, from Kendro Laboratory Products, Asheville, N.C.); Molecular Devices (Molecular Devices, Corp., Sunnyvale, Calif.); R&D Systems (R&D Systems, Minneapolis, Minn.); Stratagene (Stratagene Cloning Systems, La Jolla, Calif.); Marsh (Marsh Biosciences, Rochester, N.Y.); Geneart (Geneart GmbH, Regensburg, Germany); Bio-Tek (Bio-Tek Instruments, Winooski, Vt.); (Biacore (Biacore, Inc., Piscataway, N.J.); PeproTech (PeproTech, Rocky Hill, N.J.); SynPep (SynPep, Dublin, Calif.); New Objective (New Objective brand; Scientific Instrument Services, Inc., Ringoes, N.J.); Waters (Waters, Inc., Milford, Mass.); Matrix Science (Matrix Science, Boston, Mass.); Dionex (Dionex, Corp., Sunnyvale, Calif.); Monsanto (Monsanto Co., St. Louis, Mo.); Wintershall (Wintershall AG, Kassel, Germany); BASF (BASF Co., Florham Park, N.J.); Huntsman (Huntsman Petrochemical Corp., Salt Lake City, Utah); Enichem (Enichem Iberica, Barcelona, Spain); Fluka Chemie AG (Fluka Chemie AG, Buchs, Switzerland); Gist-Brocades (Gist-Brocades, Nev., Delft, the Netherlands); Dow Corning (Dow Corning Corp., Midland, Mich.); and Microsoft (Microsoft, Inc., Redmond, Wash.).

As used herein, in some lists, a leading "0" is indicated, in order to provide a three number designation for each site (e.g., "001" is the same as "1," so "A001C" is the same as "A1C"). In some lists, the leading "0" is not included. In addition, as used herein, "X" refers to any amino acid.

In the exemplified detergent compositions provided herein, the enzymes levels are expressed by pure enzyme by weight of the total composition and unless otherwise specified, the detergent ingredients are expressed by weight of the total compositions. The abbreviated component identifications therein have the following meanings:

Abbreviation Ingredient
LAS: Sodium linear $C_{11-13}$ alkyl benzene sulfonate.
NaC16-17HSAS: Sodium $C_{16-17}$ highly soluble alkyl sulfate
TAS: Sodium tallow alkyl sulphate.
CxyAS: Sodium $C_{1x}$-$C_{1y}$ alkyl sulfate.
CxyEz: $C_{1x}$-$C_{1y}$ predominantly linear primary alcohol condensed with an average of z moles of ethylene oxide.
CxyAEzS: $C_{1x}$-$C_{1y}$ sodium alkyl sulfate condensed with an average of z moles of ethylene oxide. Added molecule name in the examples.
Nonionic: Mixed ethoxylated/propoxylated fatty alcohol e.g. Plurafac LF404 being an alcohol with an average degree of ethoxylation of 3.8 and an average degree of propoxylation of 4.5.
QAS: $R_2.N+(CH_3)_2(C_2H_4OH)$ with $R_2=C_{12}$-$C_{14}$.
Silicate: Amorphous Sodium Silicate ($SiO_2$:$Na_2O$ ratio=1.6-3.2:1).
Metasilicate: Sodium metasilicate ($SiO_2$:$Na_2O$ ratio=1.0).
Zeolite A: Hydrated aluminosilicate of formula $Na_{12}(AlO_2SiO_2)_{12} \cdot 27H_2O$
SKS-6: Crystalline layered silicate of formula $\delta$-$Na_2Si_2O_5$.
Sulfate: Anhydrous sodium sulphate.
STPP: Sodium Tripolyphosphate.
MA/AA: Random copolymer of 4:1 acrylate/maleate, average molecular weight about 70,000-80,000.
AA: Sodium polyacrylate polymer of average molecular weight 4,500.
Polycarboxylate: Copolymer comprising mixture of carboxylated monomers such as acrylate, maleate and methyacrylate with a MW ranging between 2,000-80,000 such as Sokolan commercially available from BASF, being a copolymer of acrylic acid, MW4,500.
BB1: 3-(3,4-Dihydroisoquinolinium)propane sulfonate
BB2 1-(3,4-dihydroisoquinolinium)-decane-2-sulfate
PB1: Sodium perborate monohydrate.
PB4: Sodium perborate tetrahydrate of nominal formula $NaBO_3 \cdot 4H_2O$.
Percarbonate: Sodium percarbonate of nominal formula $2Na_2CO_3 \cdot 3H_2O_2$.
TAED: Tetraacetyl ethylene diamine.
NOBS: Nonanoyloxybenzene sulfonate in the form of the sodium salt.
DTPA: Diethylene triamine pentaacetic acid.
HEDP: 1,1-hydroxyethane diphosphonic acid.
DETPMP: Diethyltriamine penta(methylene) phosphonate, marketed by Monsanto under the Trade name Dequest 2060.
EDDS: Ethylenediamine-N,N'-disuccinic acid, (S,S) isomer in the form of its sodium salt
Diamine: Dimethyl aminopropyl amine; 1,6-hezane diamine; 1,3-propane diamine; 2-methyl-1,5-pentane diamine; 1,3-pentanediamine; 1-methyl-diaminopropane.
DETBCHD 5,12-diethyl-1,5,8,12-tetraazabicyclo [6,6,2] hexadecane, dichloride, Mn(II) SALT
PAAC: Pentaamine acetate cobalt(III) salt.
Paraffin: Paraffin oil sold under the tradename Winog 70 by Wintershall.
Paraffin Sulfonate: A Paraffin oil or wax in which some of the hydrogen atoms have been replaced by sulfonate groups.
Aldose oxidase: Oxidase enzyme sold under the tradename Aldose Oxidase by Novozymes A/S
Galactose oxidase: Galactose oxidase from Sigma
nprE: The recombinant form of neutral metalloprotease expressed in *Bacillus subtilis* (See e.g., WO 07/044,993)
PMN: Purified neutral metalloprotease from *Bacillus amyloliquefaciens*.
Amylase: A suitable amylolytic enzyme, such as those sold under the tradenames PURAFECT® Ox described in WO 94/18314, WO96/05295 sold by Genencor; NATALASE®, TERMAMYL®, FUNGAMYI® and DURAMYL™, all available from Novozymes A/S.
Lipase: A suitable lipolytic enzyme such as those sold under the tradenames LIPOLASE®, LIPOLASE® Ultra by Novozymes A/S and Lipomax™ by Gist-Brocades.
Cellulase: A suitable cellulytic enzyme such as those sold under the tradenames CAREZYME®, CELLUZYME®, and/or ENDOLASE® by Novozymes A/S.
Pectin Lyase: A suitable pectin lyase, such as those sold under the tradenames PECTAWAY® and PECTAWASH® available from Novozymes A/S.
PVP: Polyvinylpyrrolidone with an average molecular weight of 60,000
PVNO: Polyvinylpyridine-N-Oxide, with an average molecular weight of 50,000.
PVPVI: Copolymer of vinylimidazole and vinylpyrrolidone, with an average molecular weight of 20,000.
Brightener 1: Disodium 4,4'-bis(2-sulphostyryl)biphenyl.
Silicone antifoam: Polydimethylsiloxane foam controller with siloxane-oxyalkylene copolymer as dispersing agent with a ratio of said foam controller to said dispersing agent of 10:1 to 100:1.
Suds Suppressor: 12% Silicone/silica, 18% stearyl alcohol, 70% starch in granular form.
SRP 1: Anionically end capped poly esters.
PEG X: Polyethylene glycol, of a molecular weight of x.
PVP K60®: Vinylpyrrolidone homopolymer (average MW 160,000)
Jeffamine® ED-2001: Capped polyethylene glycol from Huntsman
Isachem® AS: A branched alcohol alkyl sulphate from Enichem
MME PEG (2000): Monomethyl ether polyethylene glycol (MW 2000) from Fluka Chemie AG.
DC3225C: Silicone suds suppresser, mixture of Silicone oil and Silica from Dow Corning.
TEPAE: Tetreaethylenepentaamine ethoxylate.
BTA: Benzotriazole.
Betaine: $(CH_3)_3N^+CH_2COO^-$
Sugar: Industry grade D-glucose or food grade sugar
CFAA: $C_{12}$-$C_{14}$ alkyl N-methyl glucamide
TPKFA: $C_{12}$-$C_{14}$ topped whole cut fatty acids.
Clay: A hydrated aluminumu silicate in a general formula $Al_2O_3SiO_2 \cdot xH_2O$. Types: Kaolinite, montmorillonite, atapulgite, illite, bentonite, halloysite.
pH: Measured as a 1% solution in distilled water at 20° C.

Example 1

Assays

In the following Example, various assays were used as set forth below for ease in reading. Any deviations from the protocols provided below are indicated.

A. TCA Assay for Protein Content Determination in 96-Well Microtiter Plates ("TCA Assay")

For BPN' (e.g., a reference protease) and variants thereof, this assay was started using filtered culture supernatant from microtiter plates grown 3-4 days at 33° C. with shaking at 230 rpm and humidified aeration. A fresh 96-well flat bottom microtiter plate (MTP) was used for the assay. First, 100 µL/well of 0.25 N HCl was placed in each well. Then, 50 µL of filtered culture broth was added. The light scattering/absorbance at 405 nm (use 5 sec mixing mode in the plate reader) was then determined, in order to provide the "blank" reading. For the test, 100 μL/well of 15% (w/v) trichloroacetic acid (TCA) was placed in the plates and incubated between 5 and 30 min at room temperature. The light scattering/absorbance at 405 nm (use 5 sec mixing mode in the plate reader) was then determined.

The TCA assay for protein content determination of GCI-P036 and variants thereof was performed using filtered culture supernatant from microtiter plates grown approximately 3 days at 37° C. with shaking at 300 rpm and humidified aeration. In this assay, 100 μL of a 0.25 M HCl solution was added to each well of a 96-well flat bottom microtiter plate. Subsequently, 25 μL aliquots of the filtered culture supernatants (containing the proteases) were added to wells. The light scattering/absorbance at 405 nm (using the 5 sec mixing mode in the plate reader) was then determined, in order to provide the "blank" reading. After this measurement, 100 μL of a 30% (w/v) TCA solution was added to each well and the microtiter plates were incubated between 5 and 15 minutes at room temperature. Finally, the resulting light scattering/absorbance at 405 nm (using the 5 sec mixing mode in the plate reader) was determined. The equipment used was a Biomek FX Robot (Beckman Coulter) and a SpectraMAX (type 340; Molecular Devices) MTP Reader; the MTP's were from Costar (type 9017).

The calculations were performed by subtracting the blank (no TCA) from the test reading with TCA to provide a relative measure of the protein content in the samples. If desired, a standard curve can be created by calibrating the TCA readings with AAPF assays of clones with known conversion factors. However, the TCA results are linear with respect to protein concentration from 50 to 500 micrograms protein per ml (ppm) and can thus be plotted directly against enzyme performance for the purpose of choosing good-performing variants. The turbidity/light scatter increase in the samples correlates to the total amount of precipitable protein in the culture supernatant.

B. AAPF Protease Assay in 96-Well Microtiter Plates ("AAPF Assay")

In order to determine the protease activity of the proteases and variants thereof of the present invention, the hydrolysis of N-succinyl-L-alanyl-L-alanyl-L-prolyl-L-phenyl-p-nitroanilide (suc-AAPF-pNA) was measured. The reagent solutions used were: 100 mM Tris/HCl, pH 8.6, containing 0.005% TWEEN®-80 (Tris dilution buffer); 100 mM Tris buffer, pH 8.6, containing 10 mM $CaCl_2$ and 0.005% TWEEN®-80 (Tris/Ca buffer); and 160 mM suc-AAPF-pNA in DMSO (suc-AAPF-pNA stock solution) (Sigma: S-7388). To prepare a suc-AAPF-pNA working solution, 1 ml suc-AAPF-pNA stock solution was added to 100 ml Tris/Ca buffer and mixed well for at least 10 seconds. The assay was performed by adding 10 μl of diluted protease solution to each well, immediately followed by the addition of 190 μl 1 mg/ml suc-AAPF-pNA working solution. The solutions were mixed for 5 sec., and the absorbance change in kinetic mode (20 readings in 5 minutes) was read at 410 nm in an MTP reader, at 25° C. The protease activity was expressed as AU (activity=$\Delta OD \cdot min^{-1} \cdot ml^{-1}$).

AAPF Hydrolysis Method

The thermostability of serine proteases was determined by assaying protease activity using the AAPF assay after incubation of protease variants at 68° C. for 1 hour. Under the conditions of the assay, the residual activity of the reference protease (e.g., wild type GG36=GCI-P036) was about 50%. The equipment used was: F-bottom MTPs (Costar No. 9017), Biomek FX and/or Biomek FXp Robot (Beckman Coulter), Spectramax Plus 384 MTP Reader (Molecular Devices), iEMS Incubator/Shaker (1 mm amplitude) (Thermo/Labsystems), Sealing tape (Nunc No. 236366), and ice bath. Glycine buffer was prepared by dissolving 3.75 g glycine (Merck No. 1.04201.1000) in 960 mL water. 1 ml of 5% Tween 80 (Sigma No. P-8074) and 10 ml of a stock solution of 1000 mM $CaCl_2$ (Merck No. 1.02382.1000) (29.4 g dissolved to 200 ml) was added to this solution. The pH was adjusted to 10.5 with 4N NaOH and the volume brought up to 1000 ml. Final concentrations of glycine, $CaCl_2$ and TWEEN®-80 were: 50 mM, 10 mM and 0.005% respectively. The incubators were set at 68° C. (for incubation) and at 25° C. (for the AAPF assay). 90 μl and 190 μl glycine buffer was added to the empty dilution and incubation plates respectively. 10 μl of supernatant was then added to the dilution plate, followed by addition of 100 from the dilution plate to the incubation plate. Then 10 μl of mixture from the incubation plate was added to a pre-warmed plate containing suc-AAPF-pNA substrate. The suc-AAPF-pNA plate was read in MTP Reader at 410 nm (t=0 measurement). The incubation plate was covered with tape and incubated for 1 hour at 68° C. and 400 rpm. At the end of the incubation, the plate was removed from the incubator and cooled down on ice for at least 5 minutes. 10 μl of mixture from the incubation plate was transferred to the plate containing suc-AAPF-pNA substrate and the plate read at 410 nm (t=60 measurement). Percent residual activity was calculated as:

$$\% \text{ residual activity: } (m\text{OD·min}-1 \text{ at } t=60)/(m\text{OD·min}-1 \text{ at } t=0) \times 100$$

C. LAS/EDTA Stability Assay ("LAS/EDTA Assay" or "LAS-EDTA Assay" or "LAS Assay")

LAS/EDTA stability was measured after incubation of the test protease in the presence of LAS/EDTA respectively, as a function of residual activity determined using the AAPF assay.

The stability of protease variants in the presence of a representative anionic surfactant (LAS=linear alkylbene sulfonate, sodium dodecylbenzenesulfonate-DOBS) and di-sodium EDTA was measured after incubation under defined conditions and the residual activity was determined using the AAPF assay. The reagents used were dodecyllbenzene sulfonate, sodium salt (DOBS, Sigma No. D-2525), TWEEN®-80 (Sigma No. P-8074), di-sodium EDTA (Siegfried Handel No. 164599-02), HEPES (Sigma No. H-7523), unstress buffer: 50 mM HEPES (11.9 g/l)+0.005% TWEEN®-80, pH 8.0, Stress buffer: 50 mM HEPES (11.9 g/l), 0.1% (w/v) DOBS (1 g/l), 10 mM EDTA (3.36 g/l), pH 8.0, reference protease and protease variant culture supernatants, containing 200-400 μg/ml protein. The equipment used was V- or U-bottom MTP as dilution plates (Greiner 651101 and 650161 respectively), F-bottom MTP (Corning 9017) for unstress and LAS/EDTA buffer as well as for suc-AAPF-pNA plates, Biomek FX (Beckman Coulter), Spectramax Plus 384 MTP Reader (Molecular Devices), iEMS Incubator/Shaker (1 mm amplitude) from Thermo Electron Corporation, sealing tape: Nunc (236366)

The iEMS incubator/shaker (Thermo/Labsystems) was set at 29° C. Culture supernatants were diluted into plates containing unstress buffer to a concentration of ~25 ppm (master dilution plate). 20 μl of sample from the master dilution plate was added to plates containing 180 μl unstress buffer to give a final incubation concentration of 2.5 ppm. The contents were mixed and kept at room temperature and a AAPF assay was performed on this plate. 20 μl of sample from the master dilution plate was also added to plates containing 180 µl stress buffer (50 mM HEPES (11.9 g/l), 0.1% (w/v) DOBS (1 g/l), 10 mM EDTA (3.36 g/l), pH 8.0). The solutions were mixed and immediately placed in 29° C. iEMS shaker for 30 min at 400 rpm. Following 30 minutes of incubation, a AAPF assay was performed on the stress plate. The stability of the samples was determined by calculating the ration of the residual and initial AAPF activity as follows: Residual Activity (%)=[mOD·min−1 stressed]*100/[mOD·min−1 unstressed].

D. Cleaning Performance Assays

The stain removal performance of the protease variants was determined in commercially available detergents. Heat inactivation of commercial detergent formulas serves to destroy the enzymatic activity of any protein components while retaining the properties of non-enzymatic components. Thus, this method was suitable for preparing commercially purchased detergents for use in testing the enzyme variants of the present invention.

Microswatches:

Microswatches of ¼" circular diameter were ordered and delivered by CFT (Vlaardingen, The Netherlands). Single microswatches or two microswatches were placed vertically in each well of a 96-well MTP to expose the whole surface area (i.e., not flat on the bottom of the well).

BMI Microswatch Assay

Microswatches containing blood milk and ink (BMI) of 0.25 inch circular diameter were obtained from CFT Vlaardingen. Before cutting of the swatches, the fabric (EMPA 116) was washed with water. One microswatch was vertically placed in each well of a 96-well microtiter plate in order to expose the whole surface area (i.e., not flat on the bottom of the well). The desired detergent solution was prepared as described herein. After equilibrating the Thermomixer at 25° C., 190 µl of detergent solution was added to each well of the MTP, containing microswatches. To this mixture, 10 µl of the diluted enzyme solution was added so that the final enzyme concentration was 1 µg/ml (determined from BCA assay). The MTP was sealed with tape and placed in the incubator for 30 minutes, with agitation at 1400 rpm. Following incubation under the appropriate conditions, 100 µl of the solution from each well was transferred into a fresh MTP. The new MTP containing 100 µl of solution/well was read at 405 nm using a MTP SpectraMax reader. Blank controls, as well as a control containing two microswatches and detergent but no enzyme were also included.

Baked Egg Microtiter Assay

For this assay, 96-well baked egg yolk substrate plates were prepared from chicken egg yolks. Chicken egg yolks were separated from the whites, released from the membrane sac, and diluted 20% (vol/weight) with Milli-Q water. The diluted yolk was stirred for 15 min at room temperature using a magnetic stirrer. Five µL was carefully pipetted into the center of each well of a 96-well V-bottom plate (Costar #3894) using an 8-channel pipette. The plates were baked at 90° C. for 1 hour and cooled at room temperature. The baked egg yolk substrate plates were stored at room temperature and used within one week of preparation. Automatic dish detergents were prepared as described herein and pre-heated to 50° C. A 190 µL aliquot of detergent was added to each well of the 96-well plate using an 8-channel pipette. Ten µL of diluted enzyme was added to each well using a 96-channel pipetting device. The plate was carefully sealed with an adhesive foil sealer and incubated at 50° C. with shaking for 30 min. 120 µL of the reaction mixture was transferred to a new 96-well flat-bottom plate, and the absorbance/light scattering was determined at 405 nm. The absorbance/light scattering at 405 nm is proportional to egg yolk removal.

Egg Yolk Microswatch Assay ("CS-38 Microswatch Assay"; or "EGG" or "Dish")

Automatic dish detergents were prepared as described herein. The equipment used included a New Brunswick Innova 4230 shaker/incubator and a SpectraMAX (type 340) MTP reader. The MTPs were obtained from Costar (type 9017). Aged egg yolk with pigment swatches (CS-38) were obtained from Center for Test Materials (Vlaardingen, Netherlands). Before cutting 0.25-inch circular microswatches, the fabric was washed with water. One microswatch was placed in each well of a 96-well microtiter plate. The test detergent was equilibrated at 50° C. 190 µl of detergent solution was added to each well of the MTP, containing microswatches. To this mixture, 10 µl of the diluted enzyme solution was added. The MTP was sealed with adhesive foil and placed in the incubator for 30 minutes, with agitation. Following incubation, 100 µl of the solution from each well was transferred into a fresh MTP. This MTP was read at 405 nm using a SpectraMax MTP reader. Blank controls, as well as controls containing microswatches and detergent but no enzyme were also included.

"Pre-Washed" Swatch

This type of microswatch was pre-washed in deionised water for 20 minutes at ambient temperature. After the pre-washing step, the swatches were put on top of paper towels to dry. The air-dried swatches were then punched using a ¼" circular die on an expulsion press. Finally two microswatches were put into each well of a 96-well MTP vertically to expose the whole surface area (i.e. not flat on the bottom of the well).

Detergents

For North American (NA) and Western European (WE) heavy duty liquid laundry (HDL) detergents, heat inactivation was performed by placing pre-weighed liquid detergent (in a glass bottle) in a water bath at 95° C. for 2 hours. All of the detergents used in the Examples were commercially-available detergents purchased from local supermarket stores. The enzymes present in these detergents were inactivated by heat treatment, as described herein. The incubation time for heat inactivation of North American (NA) and Japanese (JPN) heavy duty granular laundry (HDG) detergent was 8 hours and that for Western European (WE) HDG detergent was 5 hours. The incubation time for heat inactivation of NA and WE auto dish washing (ADW) detergents was 8 hours. Both un-heated and heated detergents were assayed within 5 minutes of dissolving the detergent to accurately determine percentage deactivated. Enzyme activity was tested by the AAPF assay.

For testing of enzyme activity in heat-inactivated detergents, working solutions of detergents were made from the heat inactivated stocks. Appropriate amounts of water hardness (6 gpg or 12 gpg) and buffer were added to the detergent solutions to match the desired conditions. The solutions were mixed by vortexing or inverting the bottles. Table 1-1 provides information regarding some of the commercially-available detergents and test conditions used herein. In some experiments, additional and/or other commercially available detergents were used as described in the following Examples.

TABLE 1-1

Laundry and Dish Washing Conditions

| Region | Form | Dose | Detergent* | Buffer | Gpg | pH | T (° C.) |
|---|---|---|---|---|---|---|---|
| Laundry (Heavy Duty Liquid and Granular) | | | | | | | |
| NA | HDL | 0.78 g/l | P&G TIDE ® 2X | 5 mM HEPES | 6 | 8.0 | 20 |
| WE | HDL | 5.0 g/L | Henkel PERSIL ™ | 5 mM HEPES | 12 | 8.2 | 40 |
| WE | HDG | 8.0 g/L | P&G ARIEL ® | 2 mM Na$_2$CO$_3$ | 12 | 10.5 | 40 |
| JPN | HDG | 0.7 g/L | P&G TIDE ® | 2 mM Na$_2$CO$_3$ | 6 | 10.0 | 20 |
| NA | HDG | 1.0 g/L | P&G TIDE ® | 2 mM Na$_2$CO$_3$ | 6 | 10.0 | 20 |
| Automatic Dish Washing | | | | | | | |
| WE | ADW | 3.0 g/L | RB CALGONIT ™ | 2 mM Na$_2$CO$_3$ | 21 | 10.0 | 40 |
| NA | ADW | 3.0 g/L | P&G CASCADE ® | 2 mM Na$_2$CO$_3$ | 9 | 10.0 | 40 |

*Abbreviations: Procter & Gamble (P&G); and Reckitt Benckiser (RB).

Enzymes and Equipment

Samples of GCI-P036 and variants thereof were obtained from filtered culture broth of cultures grown in MTP plates. The equipment used was a Biomek FX Robot (Beckman Coulter), a SpectraMAX MTP Reader (type 340; Molecular Devices), an iEMS incubator/shaker (Thermo/Labsystems); F-bottom MTPs (Costar type 9017 used for reading reaction plates after incubation); and V-bottom MTPs (Greiner 651101 used for pre-dilution of supernatant). In this assay, the proteases hydrolyze the substrate and liberate pigment and insoluble particles from the substrate. Thus the rate of turbidity is a measure of enzyme activity.

The stain removal performance of reference serine proteases and variants therefrom on microswatches was determined on a MTP scale in commercially available detergent (Calgonit 5 in 1). CS-38 microswatches (egg-yolk with pigment, aged by heating), obtained from CFT Vlaardingen were used as substrate. Two swatches were used per well. ADW tablets from Calgonit 5 in 1 were used to prepare the detergent solution. To inactivate the protease activity present in the tablets, a 21 g tablet was dissolved in Milli-Q water heated in a water bath to a temperature of 60° C. The solution was cooled to room temperature and the volume of water adjusted to 700 mL. The solution was further diluted with water to achieve a final concentration of 3 g/l. Water hardness was adjusted to 21° GH by adding 1.46 ml of the Ca/Mg-mixture (Ca/Mg mixture [(3:1), 1.92 M CaCl$_2$=282.3 g/L CaCl$_2$.2H$_2$O; 0.64 M MgCl$_2$=130.1 g/L MgCl$_2$.6H$_2$O), 15000 gpg]. The enzyme samples were pre-diluted in 10 mM NaCl, 0.1 mM CaCl$_2$, 0.005% TWEEN®-80 solution and tested at appropriate concentrations.

The incubator was set at the desired temperature of 50° C. 72 μl of dilution buffer was added to the empty V-bottom plate (i.e., a "dilution plate") followed by 8 μl supernatant. 9 μl from the dilution plate was added to plates containing the microswatches incubated in 171 μl detergent solution. 9 μl from the dilution plate was added to plates containing the microswatches to give a total dilution of supernatant of 200×. The microswatch plate (with detergent and enzyme) was covered with tape and placed in the incubator/shaker for 30 minutes at 1400 rpm. Following incubation, 75 μl of the reaction mixture was transferred to an empty F-bottom plate and the absorbance was read in a MTP Reader at 405 nm after de-bubbling with a hair dryer. Blank controls, containing one or two microswatches and detergent without the addition of reference protease containing samples were also included in the test.

The stain removal performance of reference serine proteases and variants therefrom on microswatches was also determined on a MTP scale in commercially available detergent (Calgonit 5 in 1). The reagents used were: 5 mM HEPES, pH 8.0 or 5 mM MOPS, pH 7 buffer, 3:1 Ca:Mg for medium water hardness. (CaCl$_2$: MgCl2.6H2O); 15000 grains per gallon (gpg) stock diluted to 6 gpg, 2 BMI (blood/milk/ink) swatches per plate: EMPA-116 BMI cotton swatches processed by CFT: pre-rinsed and punched 2 swatches per well, and heat inactivated TIDE® 2× Coldwater off-the-shelf detergent in which lack of protease activity was confirmed. In some experiments described herein, the following solutions were used, as indicated in the Examples.

TABLE 1-2

Working Detergent Solutions

| Detergent | Temp (C.) | Detergent g/L | pH | Buffer | gpg | Protease |
|---|---|---|---|---|---|---|
| TIDE ® 2X Cold | 16 | 0.98 | 8 | 5 mM HEPES | 6 | BPN' |
| TIDE ® 2X Cold | 32 | 0.98 | 8 | 5 mM HEPES | 6 | GG36, BPN' |
| TIDE ® 2X Cold | 16 | 0.98 | 7 | 5 mM MOPS | 6 | BPN' |

The incubator was set at the desired temperature (16° C. or 32° C.). For the test, 10 μL samples from the master dilution plate of ~10 ppm enzyme was added to BMI 2-swatch plates with 190 μL working detergent solutions listed above. The volume was adjusted to give final concentration of 0.5 ppm for variants in the assay plates. The plates were immediately transferred to iEMS incubators and incubated for 30 minutes with 1400 rpm shaking at given temperature. Following incubation, 100 μL of supernatant was transferred into a new 96-well plate and the absorbance was measured in MTP Reader at 405 nm and/or 600 nm. Control wells, containing 1 or 2 microswatches and detergent without the addition of protease samples were also included in the test. The measurement at 405 nm provides a higher value and tracks pigment removal, while the measurement at 600 nm tracks turbidity and cleaning.

Calculation of the Stain Removal Activity for all Microswatch Assay Methods:

The absorbance value obtained was corrected for the blank value (substrate without enzyme), providing a measure of hydrolytic activity. For each sample (variant) the performance index was calculated. The performance index compares the performance of the variant (actual value) and the standard enzyme (theoretical value) at the same protein concentration. In addition, the theoretical values can be calculated, using the parameters of the Langmuir equation of the standard enzyme.

E. Relative Specific Activity of Proteases and Variants Thereof

In order to discriminate the protease variants, the relative specific activity was calculated using suc-AAPF-pNA as a substrate, which enabled the comparison and ranking of the variants versus the wild-type or standard protease. The specific activity on the suc-AAPF-pNA substrate was determined by dividing the proteolytic activity by the measured TCA-values of each sample, using the assays described above. Using these values, the relative specific activity was calculated (specific activity of variant/specific activity of reference protease).

F. Eglin C Inhibition Assay

As described herein, serine protease concentration and specific activity was determined by titration with an inhibitor. Eglin c from the leech *Hirudo medicinalis* is a tight-binding protein inhibitor of subtilisins (Heinz et al., Biochemistry, 31: 8755-66, 1992), and can therefore be used to measure enzyme concentration, which in turn permits specific activity to be calculated. Briefly, one measures the amount of enzyme inhibition produced by several known concentrations of eglin c. From this information, the concentration of eglin c required for complete inhibition is calculated. This is equivalent to the enzyme concentration in the sample.

Protease activity was measured using the chromogenic AAPF assay described above. The gene for eglin c was synthesized and expressed in *E. coli* by standard methods. Its properties and inhibitory potency were the same as eglin c purchased from Sigma. The concentration of an eglin c stock solution was determined by measuring the inhibition of a sample of *Bacillus lentus* subtilisin of known specific activity. Then the calibrated eglin c sample was used to determine the concentration and specific activity of subtilisin variants. These values were used to create normalized 96-well enzyme stock plates, where all of the variants were diluted to a common concentration.

G. Performance Index

The performance index compares the performance of the variant (actual value) and the standard or reference protease (theoretical value) at the same protein concentration. In addition, the theoretical values can be calculated, using the parameters of the Langmuir equation of the standard protease. A performance index (PI) that is greater than 1 (PI>1) identifies a better variant as compared to the standard (e.g., wild-type), while a PI of 1 (PI=1) identifies a variant that performs the same as the standard, and a PI that is less than 1 (PI<1) identifies a variant that performs worse than the standard. Thus, the PI identifies winners, as well as variants that are less desirable for use under certain circumstances.

Example 2

Production of GCI-P036 Protease in *B. subtilis*

In this Example, experiments conducted to produce GCI-P036 protease in *B. subtilis* are described. Transformation of expression vector encoding GCI-P036 and variants thereof into *B. subtilis* cells (AaprE, AnprE, oppA, AspoIIE, degUHy32, ΔamyE::[xylR,pxylA-comK]) was performed as described previously (See e.g., WO 2002/014490).

GCI-P036 Protease Production—pAC-GCI-P036ci

Exemplary methods to produce GCI-P036 (also referred to herein as "*B. lentus* subtilisin" and "GG36") in *B. subtilis* are provided. The expression plasmid pAC-GG36ci was assembled using the GCI-P036 codon-improved gene fused at the eighth codon of the aprE signal sequence under the control of the consensus aprE promoter and the BPN' transcriptional terminator. In the sequence provided below, bold and italicized font indicates the consensus aprE promoter, standard font indicates the signal sequence, underlined font indicates the pro sequence, bold font indicates DNA that encodes the GCI-P036 mature protease, and underlined italicized font indicates the BPN' terminator. The coding region of the GCI-P036 mature protease is flanked by KpnI and XhoI restriction sites for cloning purposes:

(SEQ ID NO: 5)

*atctcaaaaaaatgggtctactaaaatattactccatctattataataaattcacagaatagtcttttaagtaagtctac*

*tctgaattttttaaaaggagagggtaaaga* gtgagaagcaaaaaattgtggatcgtcgcgtcgaccgcattgctgatttctgttgc ttttagctcatccatcgcatccgct<u>gctgaagaagcaaaagaaaaatatttaattggctttaatgagcaggaagctgtcagtgagtttgtagaa caagttgaggcaaatgacgaggtagccattctctctgaggaagaggaagtcgaaattgaattgcttcatgaatttgaaacgattcctgttctgt ccgttgagttaagcccagaagatgtggacgcgttagagctcgatccagctatttcttatattgaagaggatgcagaagtaactacaatg</u>gcgca atcggtaccatggggaattagcagagtacaagccccagctgcacataaccgtggattgacaggttctggtgtaaaagttgctgtccttgatacc ggtatttccactcatccagacttaaatattcgtggtggagctagctttgtaccaggggaaccatccactcaagatggcaatggacatggcactc atgttgccggcacaatcgcggctcttaacaattcaattggtgttcttggcgtagcgccaagcgcagaactatacgctgttaaagtattaggagc aagcggttcaggctctgtcagctctattgcccaaggattggaatgggcagggaacaatggcatgcacgttgctaatcttagtttaggatctcct tcgccaagtgccacacttgagcaagctgttaatagcgcgacttctagaggcgttcttgttgtagcggcctctggaaattcaggtgcaggctcaa tcagctatccggcccgttatgcgaacgctatggcagtcggagctactgaccaaaacaaccgcgccagcttttcacagtatggcgcagggct tgacattgtcgcaccaggtgtaaacgtgcagagcacttacccaggttcaacatatgccagcttaaacggtacatcaatggctactcctcatgtt gcaggtgcggctgcacttgttaaacaaaagaaaccatcttggtccaatgtacaaatccgcaatcatcttaagaatacggcaactagcttaggaa gcacaaacttgtatggaagcggacttgtcaatgcagaagctgcaactcgttaa<u>*aaaagcttaactcgagataaaaaaccggccttggccccgcc*</u>

<u>*ggttttttat*</u>.

The amino acid sequence of the GCI-P036 precursor protein is provided below. In this sequence, the signal peptide is shown in italics (beginning with an N-terminal formylmethionine), the pro-sequence is underlined, and the mature GCI-P036 protease sequence is shown in bold:

(SEQ ID NO: 6)

*MRSKKLWIVASTALLISVAFSSSIAS*<u>AEEAKEKYLIGFNEQEAVSEFVE</u>

<u>QVEANDEVAILSEEEEVEIELLHEFETIPVLSVELSPEDVDALELDPAIS</u>

-continued
YIEEDAEVTTMAQSVPWGISRVQAPAAHNRGLTGSGVKVAVLDTGISTHP
DLNIRGGASFVPGEPSTQDGNGHGTHVAGTIAALNNSIGVLGVAPSAELY
AVKVLGASGSGSVSSIAQGLEWAGNNGMHVANLSLGSPSPSATLEQAVNS
ATSRGVLVVAASGNSGAGSISYPARYANAMAVGATDQNNNRASFSQYGAG
LDIVAPGVNVQSTYPGSTYASLNGTSMATPHVAGAAALVKQKNPSWSNVQ
IRNHLKNTATSLGSTNLYGSGLVNAEAATR.

The amino acid sequence of the mature GCI-P036 protease:

(SEQ ID NO: 2)
AQSVPWGISRVQAPAAHNRGLTGSGVKVAVLDTGISTHPDLNIRGGASFV
PGEPSTQDGNGHGTHVAGTIAALNNSIGVLGVAPSAELYAVKVLGASGSG
SVSSIAQGLEWAGNNGMHVANLSLGSPSPSATLEQAVNSATSRGVLVVAA
SGNSGAGSISYPARYANAMAVGATDQNNNRASFSQYGAGLDIVAPGVNVQ
STYPGSTYASLNGTSMATPHVAGAAALVKQKNPSWSNVQIRNHLKNTATS
LGSTNLYGSGLVNAEAATR.

Elements of plasmid pAC-GG36ci include: pUB110=DNA fragment from plasmid pUB110 (McKenzie et al., Plasmid 15:93-103, 1986), pBR322=DNA fragment from plasmid pBR322 (Bolivar et al., Gene 2:95-113, 1977), pC194=DNA fragment from plasmid pC194 (Horinouchi et al., J Bacteriol, 150:815-825, 1982). The plasmid features as follows: On for *B. subtilis*=origin of replication from pUB110, CAT=chloramphenicol resistance gene from pC194, pMB1 origin=origin of replication from pBR322, bla=beta-lactamase from pBR322, Short aprE promoter=consensus transcriptional promoter, Signal Peptide=signal peptide, Pro Peptide=GCI-P036 pro region, GG36ci Mature Peptide=mature GCI-P036 (replaced by the coding regions for each variant expressed in this work), BPN' Terminator=transcriptional terminator from subtilisin BPN'.

GCI-P036 Protease Production—pHPLT-GCI-P036

Additional methods to produce the GCI-P036 reference protease in *B. subtilis* are described. The synthetic gene encoding GCI-P036 protease precursor was assembled from synthetic oligonucleotides and PCR products. The fragment was cloned into plasmid backbone pHPLT (U.S. Pat. No. 5,024,943) using BsmBI and HindIII restriction sites. The amino acid sequence of the mature GCI-P036 protease (SEQ ID NO:2) of pHPLT-GCI-P036 is identical to that of pAC-GG36ci. The pHPLT *B. subtilis* expression vector contains the *B. licheniformis* LAT promoter (Plat), and additional elements from pUB110 (McKenzie et al., Plasmid, 15:93-103, 1986) including a replicase gene (reppUB), a neomycin/kanamycin resistance gene (neo) and a bleomycin resistance marker (bleo). The plasmid DNA was purified from transformed bacteria using Pure Yield™ Plasmid Midiprep kit (Promega), and DNA concentration was determined by UV spectroscopy as known in the art. The final vector construct was verified by DNA sequencing of the GCI-P036 gene and showed 100% sequence congruence to the expected sequence. The DNA sequence of the GCI-P036 protease gene of pHPLT-GCI-P036 is shown below with the cloning sites SacI and HindIII underlined:

(SEQ ID NO: 7)
GTGAGAAGCAAAAAATTGTGGATCGTCGCGTCGACCGCACTACTCATTTC

TGTTGCTTTCAGTTCATCGATCGCATCGGCTGCTGAAGAAGCAAAAGAAA

AATATTTAATTGGCTTTAATGAGCAGGAAGCTGTCAGTGAGTTTGTAGAA

CAAGTAGAGGCAAATGACGAGGTCGCCATTCTCTCTGAGGAAGAGGAAGT

CGAAATTGAATTGCTTCATGAATTTGAAACGATTCCTGTTTTATCCGTTG

AGTTAAGCCCAGAAGATGTGGACGCGCTT<u>GAGCTC</u>GATCCAGCGATTTCT

TATATTGAAGAGGATGCAGAAGTAACGACAATGGCGCAATCAGTGCCATG

GGGAATTAGCCGTGTGCAAGCCCCAGCTGCCCATAACCGTGGATTGACAG

GTTCTGGTGTAAAAGTTGCTGTCCTCGATACAGGTATTTCCACTCATCCA

GACTTAAATATTCGTGGTGGCGCTAGCTTTGTACCAGGGGAACCATCCAC

TCAAGATGGGAATGGGCATGGCACGCATGTGGCCGGGACGATTGCTGCTT

TAAACAATTCGATTGGCGTTCTTGGCGTAGCGCCGAGCGCGGAACTATAC

GCTGTTAAAGTATTAGGGGCGAGCGGTTCAGGTTCGGTCAGCTCGATTGC

CCAAGGATTGGAATGGGCAGGGAACAATGGCATGCACGTTGCTAATTTGA

GTTTAGGAAGCCCTTCGCCAAGTGCCACACTTGAGCAAGCTGTTAATAGC

GCGACTTCTAGAGGCGTTCTTGTTGTAGCGGCATCTGGAAATTCAGGTGC

AGGCTCAATCAGCTATCCGGCCCGTTATGCGAACGCAATGGCAGTCGGAG

CTACTGACCAAAACAACAACCGCGCCAGCTTTTCACAGTATGGCGCAGGG

CTTGACATTGTCGCACCAGGTGTAAACGTGCAGAGCACATACCCAGGTTC

AACGTATGCCAGCTTAAACGGTACATCGATGGCTACTCCTCATGTTGCAG

GTGCAGCAGCCCTTGTTAAACAAAAGAACCCATCTTGGTCCAATGTACAA

ATCCGCAATCATCTAAAGAATACGGCAACGAGCTTAGGAAGCACGAACTT

GTATGGAAGCGGACTTGTCAATGCAGAAGCTGCAACTCGTTA<u>AAGCTT</u>.

Recombinant Proteases—2 ml Scale

*B. subtilis* clones containing protease expression vectors were replicated with a steel 96-well replicator from glycerol stocks into 96-well culture plates (BD, 353075) containing 200 μl of LB media+25 μg/ml chloramphenicol, grown overnight at 37° C., 220 rpm in a humidified enclosure. A 200 μl aliquot from the overnight culture was used to inoculate 2000 μl defined media+25 μg/ml chloramphenicol in 5 ml plastic culture tubes. The cultivation media was an enriched semi-defined media based on MOPS buffer, with urea as major nitrogen source, glucose as the main carbon source, and supplemented with 1% soytone for robust cell growth. Culture tubes were incubated at 37° C., 220 rpm, for 60 hours. Following this incubation, the culture broths were centrifuged at greater than 8000×RCF. The supernatant solution was decanted into 15 ml polypropylene conical tubes for storage. No further purification or concentration was performed. Supernatant stocks were formulated to 40% propylene glycol final concentration for long-term stability and stored at 4° C.

Recombinant Proteases—Microtiter Plate (MTP) Scale

Alternatively, the variant proteases were produced by growing the *B. subtilis* transformants in 96 well microtiter plates (MTP) in 200 μL of a MOPS-based defined medium ("MBD"). MBD medium was made essentially as known in the art (See, Neidhardt et al., J Bacteriol, 119: 736-747, 1974), except that $NH_4Cl_2$, $FeSO_4$, and $CaCl_2$ were left out of the base medium, 3 mM $K_2HPO_4$ was used, and the base medium was supplemented with 60 mM urea, 75 g/L glucose, and 1% soytone. Also the micronutrients were made up as a 100× stock containing in one liter, 400 mg $FeSO_4.7H_2O$, 100 mg $MnSO_4.H_2O$, 100 mg $ZnSO_4.7H_2O$, 50 mg $CuCl_2.2H_2O$, 100 mg $CoCl_2.6H_2O$, 100 mg $NaMoO_4.2H_2O$, 100 mg $Na_2B_4O_7.10H_2O$, 10 ml of 1M $CaCl_2$, and 10 ml of 0.5 M sodium citrate. The plates were incubated at 37° C. for 68 hours, cells were separated by centrifugation, and proteins of interest were obtained from the culture medium.

Example 3

Generation of GCI-P036 Variants

In this Example, methods used to produce the protease variants are described.
Generation of GCI-P036 Site Evaluation Libraries (SELs)

SEL production was performed by GENEART using a proprietary process (WO 20041059556A3). Methods and devices for optimizing a nucleotide sequence for the purpose of expression of a protein by PCR, and the manufacture of DNA molecules utilized technology owned by or licensed to GENEART (European Patent Nos. 0 200 362 and 0 201 184; and U.S. Pat. Nos. 4,683,195, 4,683,202 and 6,472,184). The construction of GCI-P036 SEL described in this example was performed by GENEART using their methods and technology platform for gene optimization, gene synthesis and library generation and analysis.

GCI-P036 SELs were produced by GENEART at positions pre-selected by the inventors. The pHPLT-GCI-P036 plasmid DNA (See, FIG. 2) was digested with SacI and HindIII restriction enzymes, releasing a 3.9 kb fragment that was subsequently purified from an agarose gel using a Qiagen gel purification kit. Each amino acid of the mature sequence was mutated into at least 16 different amino acids. To construct GCI-P036 SELs, three PCR reactions were performed: two mutagenesis reactions to introduce the mutated codon of interest in the mature GCI-P036 DNA sequence, and a third reaction to fuse the two mutagenesis PCR products together to construct the pHPLT-GCI-P036 expression vector having the desired mutated codons in the mature GCI-P036 sequence.

The method of mutagenesis was based on the codon-specific mutation approach in which the creation of all possible mutations at once in a specific DNA triplet was performed using a forward and reverse oligonucleotide primer with a length of 25 up to 45 nucleotides using a specifically designed triple DNA sequence NNS ((A, C, T or G), (A, C, T or G), (C or G)) that corresponded with the sequence of the codon to be mutated and guarantee random incorporation of nucleotides at the specific codon of interest. Two additional primers that are used to construct a site evaluation library include an upstream primer containing a SacI site, and a downstream primer containing a HindIII site. Construction of each SEL begins with two primary PCR amplifications using the forward SacI primer and a specific GCI-P036 reverse mutagenesis primer, and for the second PCR reaction the reverse HindIII primer and a specific GCI-P036 forward mutagenesis primer (equal GCI-P036 mature codon positions for the forward and reverse mutagenesis primers).

The introduction of the mutations in the mature GCI-P036 sequence was performed using Phusion High-Fidelity DNA Polymerase (Finnzymes catalog no. F-530L). All PCR reactions were executed according to manufacturer's protocols that were supplied with the polymerase. The PCR conditions were as follows:

for primary PCR 1:
FW SacI primer and a specific GCI-P036 reverse mutagenesis primer—both 1 µL (10 µM); and for primary PCR 2: RV HindIII primer and a specific GCI-P036 forward mutagenesis primer—both 1 µL (10 µM).

The primer sequences used in this Example are provided below:

| | |
|---|---|
| CGCGCTTGAGCTCGATCCAGCGATTTC (SEQ ID NO: 99) | SacI-Fw |
| GTCTCCAAGCTTTAACGAGTTGCAG (SEQ ID NO: 100) | HindIII-Rv |
| GCAATTCAGATCTTCCTTCAGGTTATGACC (SEQ ID NO: 101) | pHPLT-BgIII-Fw |
| GCATCGAAGATCTGATTGCTTAACTGCTTC (SEQ ID NO: 102) | pHPLT-BgIII-Rv |

Each reaction included: 10 µL of 5× Phusion HF buffer, 1 µL of 10 mM dNTP mixture, 0.75 µL of Phusion DNA polymerase (2 units/µL), 1 µL neat DMSO, 1 µL of pHPLT-GCI-P036 template DNA (0.1-1 ng/µL), and dH2O to 50 µL total volume.

PCR was completed using a MJ Research PTC-200 Peltier thermal cycler with the following program: 30 seconds 98° C., 30× (10 seconds 98° C., 20 seconds 55° C., 1 minute 72° C.) and 5 min 72° C. The reactions yielded two fragments of approximately 2 to 3 kb having approximately 30 nucleotide overlap surrounding the GCI-P036 mature codon of interest.

Fragments were fused in a third reaction using the two aforementioned fragments and the forward and reverse SacI-Fw and HindIII-Rv primers. The fusion PCR reaction was carried out in a solution containing: 1 µL each of SacI-Fw and HindIII-Rv primers (10 µM), 10 µL of 5× Phusion HF buffer, 1 µL of 10 mM dNTP mixture, 0.75 µL of Phusion™ DNA polymerase (2 units/µL), 1 µL of neat DMSO, 1 µL of primary PCR 1 reaction mix, 1 µL of primary PCR 2 reaction mix, and dH2O to adjust final volume to 50 µL. The PCR fusion program was as follows: 30 seconds 98° C., 30× (10 seconds 98° C., 20 seconds 55° C., 40 seconds 72° C.) and 5 min 72° C., using a MJ Research PTC-200 Peltier thermal cycler. The amplified linear 859 bp fragment encoding the GCI-P036 gene was purified (using QIAGEN® Qiaquick PCR purification kit, catalog no. 28106) and digested with SacI and HindIIII restriction enzyme to create cohesive ends on both sides of the fusion fragment. About 50 ng of plasmid pHPLT-GCI-P036 was digested with SacI and HindII11 restriction enzymes. The 3.9 kb vector backbone fragment was isolated and ligated with 50 ng of the digested 859 bp fragment encoding the variant enzyme, using T4 DNA ligase (Invitrogen) following the manufacturer's protocol for cloning of cohesive ends. Subsequently, the ligation mixture was used to transform B. subtilis cells (ΔaprE, ΔnprE, oppA, ΔspoIIE, degUHy32, ΔamyE::[xylR,pxylA-comK]) as described (WO 2002/014490).

For each library, 96 single colonies were picked and grown in TSB (tryptone and soy based broth) liquid media under neomycin selection for subsequent DNA isolation and gene sequence analysis. The library numbers ranged from 1 up to 269, with each number representing the codon of the mature GCI-P036 sequence that was mutated. Each library contained a maximum of 19 GCI-P036 variants.
Generation of GCI-P036 Multiple Mutation Libraries (MML)

Each synthetic GCI-P036 multiple mutation library contains a mix of GCI-P036 genes in which two or more selected codons are replaced by specific DNA sequences.

Cloning of the combinatorial GCI-P036 genes was performed by Sloning BioTechnology GmbH using the Slonomax Technology. Tables 3-1 and 3-2 below list the substitutions present in members of the MML numbered according to the GCI-P036 reference sequence and the BPN' reference sequence respectively.

TABLE 3-1

GCI-P036 Multiple Mutation Libraries (GCI-P036 Numbering)

| Library Position (Amino Acids) | Nos. |
|---|---|
| Library 1<br>001 (A, K) 044 (R, F, K) 070 (I, C, V) 102 (V, I) 124 (L, F) 158 (S, F, I, Q) | 288 |
| Library 2<br>001 (A, K) 044 (R, F, K) 070 (I, C, V) 102 (V, I) 125 (G, Q, R, T) 157 (G, P) | 288 |
| Library 3<br>024 (S, H, L, N, R, T, W) 107 (Q, I, K, L, R, T, V) 116 (G, F, K, L, R, T, V) 128 (S, N, R, Y) | 1372 |
| Library 4<br>024 (S, H, L, N, R, T, W) 107 (Q, I, K, L, R, T, V) 116 (G, F, K, L, R, T, V) 125 (G, Q, R, T) 128 (S, N, R, Y) | 5488 |
| Library 5<br>001 (A, K, R) 024 (S, H, L, N, R, T, W) 044 (R, F, K, N) 105 (I, V, T) 166 (A, Q) | 504 |
| Library 6<br>001 (A, K, R) 024 (S, H, L, N, R, T, W) 044 (R, F, K, N) 105 (I, V, T) 125 (G, Q, R, T) 166 (A, Q) | 2016 |
| Library 7<br>024 (S, H, L, W) 097 (S, K, Q, T) 101 (S, N, P) 116 (G, F, R, T) 130 (S, H, N) | 576 |
| Library 8<br>024 (S, H, L, W) 097 (S, K, Q, T) 101 (S, N, P) 116 (G, F, R, T) 125 (G, Q, R, T) 130 (S, H, N) | 2304 |
| Library 9<br>001 (A, K) 044 (R, F, K) 070 (I, C, V) 102 (V, I) 124 (L, F) 158 (S, F, I, Q)<br>with 85N, 116V, 126L, 127Q and 128A | 288 |
| Library 10<br>024 (S, H, L, N, R, T, W) 107 (Q, I, K, L, R, T, V) 125 (G, Q, R, T)<br>with 85N, 116V, 126L, 127Q and 128A | 196 |
| Library 11<br>001 (A, K, R) 024 (S, H, L, N, R, T, W) 044 (R, F, K, N) 105 (I, V, T) 166 (A, Q)<br>with 85N, 116V, 126L, 127Q and 128A | 504 |
| Library 12<br>024 (S, H, L, W) 097 (S, K, Q, T) 101 (S, N, P) 125 (G, Q, R, T) 130 (S, H, N)<br>with 85N, 116V, 126L, 127Q and 128A | 576 |
| Library 13<br>018 (N, K, Q, R) 095 (G, P) 179 (N, K, Q, R) 203 (Y, W) 209 (A, I, R, V) 250 (S, P, W) | 768 |
| Library 14<br>042 (N, E, F, I, S, T, V, W), 096 (A, E, L, N, T, V) 099 (S, E, F, N, R, T, V, Y) 115 (N, I, Y) 242 (N, I, K) | 3456 |
| Library 15<br>051 (P, I, V) 117 (M, F) 142 (S, T, V, W, Y) 179 (N, R, V) 203 (Y, W) 250 (S, I, P, T) | 1200 |
| Library 16<br>018 (N, K, Q, R) 095 (G, P) 179 (N, K, Q, R) 203 (Y, W) 209 (A, I, R, V) 250 (S, P, W) with 85N, 116V, 126L, 127Q and 128<sup>a</sup> | 768 |
| Library 17<br>042 (N, E, F, I, S, T, V, W), 051 (P, I, V) 096 (A, E, L, N, T, V)<br>099 (S, E, F, N, R, T, V, Y) 242 (N, I, K) with 85N, 116V, 126L, 127Q and 128A | 2880 |
| Library 18<br>024 (S, H, L, W) 097 (S, K, Q, T) 101 (S, N, P) 125 (G, Q, R, T) 130 (S, H, N)<br>with 85N, 116V, 126L, 127Q and 128A | 2880 |

TABLE 3-2

GCI-P036 Multiple Mutation Libraries (BPN' Numbering)

| Library Position (Amino Acids) | Nos. |
|---|---|
| Library 1<br>001 (A, K) 045 (R, F, K) 072 (I, C, V) 104 (V, I) 126 (L, F) 164 (S, F, I, Q) | 288 |
| Library 2<br>001 (A, K) 045 (R, F, K) 072 (I, C, V) 104 (V, I) 127 (G, Q, R, T) 163 (G, P) | 288 |
| Library 3<br>024 (S, H, L, N, R, T, W) 109 (Q, I, K, L, R, T, V) 118 (G, F, K, L, R, T, V) 130 (S, N, R, Y) | 1372 |
| Library 4<br>024 (S, H, L, N, R, T, W) 109 (Q, I, K, L, R, T, V) 118 (G, F, K, L, R, T, V) 127 (G, Q, R, T) 130 (S, N, R, Y) | 5488 |
| Library 5<br>001 (A, K, R) 024 (S, H, L, N, R, T, W) 045 (R, F, K, N) 107 (I, V, T) 172 (A, Q) | 504 |

TABLE 3-2-continued

GCI-P036 Multiple Mutation Libraries (BPN' Numbering)

| Library<br>Position (Amino Acids) | Nos. |
|---|---|
| Library 6<br>001 (A, K, R) 024 (S, H, L, N, R, T, W) 045 (R, F, K, N) 107 (I, V, T) 127 (G, Q, R, T) 172 (A, Q) | 2016 |
| Library 7<br>024 (S, H, L, W) 099 (S, K, Q, T) 103 (S, N, P) 118 (G, F, R, T) 132 (S, H, N) | 576 |
| Library 8<br>024 (S, H, L, W) 099 (S, K, Q, T) 103 (S, N, P) 118 (G, F, R, T) 127 (G, Q, R, T) 132 (S, H, N) | 2304 |
| Library 9<br>001 (A, K) 045 (R, F, K) 072 (I, C, V) 104 (V, I) 126 (L, F) 164 (S, F, I, Q)<br>with 87N, 118V, 128L, 129Q and 130A | 288 |
| Library 10<br>024 (S, H, L, N, R, T, W) 109 (Q, I, K, L, R, T, V) 127 (G, Q, R, T)<br>with 87N, 118V, 128L, 129Q and 130A | 196 |
| Library 11<br>001 (A, K, R) 024 (S, H, L, N, R, T, W) 045 (R, F, K, N) 107 (I, V, T) 172 (A, Q)<br>with 87N, 118V, 128L, 129Q and 130A | 504 |
| Library 12<br>024 (S, H, L, W) 099 (S, K, Q, T) 103 (S, N, P) 127 (G, Q, R, T) 132 (S, H, N)<br>with 87N, 118V, 128L, 129Q and 130A | 576 |
| Library 13<br>018 (N, K, Q, R) 097 (G, P) 185 (N, K, Q, R) 209 (Y, W) 215 (A, I, R, V) 256 (S, P, W) | 768 |
| Library 14<br>043 (N, E, F, I, S, T, V, W), 098 (A, E, L, N, T, V) 101 (S, E, F, N, R, T, V, Y)<br>117 (N, I, Y) 248 (N, I, K) | 3456 |
| Library 15<br>052 (P, I, V) 119 (M, F) 144 (S, T, V, W, Y) 185 (N, R, V) 209 (Y, W) 256 (S, I, P, T) | 1200 |
| Library 16<br>018 (N, K, Q, R) 097 (G, P) 185 (N, K, Q, R) 209 (Y, W) 215 (A, I, R, V) 256 (S, P, W) with<br>87N, 118V, 128L, 129Q and 130$^a$ | 768 |
| Library 17<br>043 (N, E, F, I, S, T, V, W), 052 (P, I, V) 098 (A, E, L, N, T, V)<br>101 (S, E, F, N, R, T, V, Y) 248 (N, I, K) with 87N, 118V, 128L, 129Q and 130A | 2880 |
| Library 18<br>024 (S, H, L, W) 099 (S, K, Q, T) 103 (S, N, P) 127 (G, Q, R, T) 132 (S, H, N)<br>with 87N, 118V, 128L, 129Q and 130A | 2880 |

Example 4

Performance of GCI-P036 Variants

Experiments conducted to determine the stain removal performance of various single substitution GCI-P036 variants in a BMI assay (TIDE 2X® Cold; 32° C., pH8) and CS-38 microswatch assay (CALGONIT®; WE ADW) are described. Performance indices for LAS/EDTA stability, AAPF activity and protein content were also determined. All assays were performed using the methods of Example 1.

Table 4-1 shows performance index values for 4,210 variants of subtilisin GCI-P036 at 269 positions. The performance of the variant GCI-P036 was compared to the wild-type GCI-P036 enzyme. Those variants with a performance index greater than 1 (PI>1) have improved performance. Performance indices less than or equal to 0.05 were fixed to 0.05 and indicated in bold italics in the table. For the stability measure, if the performance index of activity in the stability assays was less than or equal to 0.05, the associated stability performance index was assigned the value ND, for not determined. Also, variants for which the values were not determined are listed as ND.

Performance index (PI) is the ratio of performance of the variant to the parent or reference protease. Various terms set forth below are used to describe the mutation: up mutations have a PI>1; neutral mutations have a PI>0.5, non-deleterious mutations have a PI>0.05; deleterious mutations have a PI=0.05; combinable mutations are those mutations for which the variant has Performance index values=0.5 for at least one property, and >0.05 for all properties. Combinable mutations are mutations that can be combined to deliver proteins with appropriate performance indices for one or more desired properties. Positions at which mutations occur are classified as follows: Non-restrictive positions have ≥20% neutral mutations for at least one property; and Restrictive positions have <20% neutral mutations for activity and stability.

These data find use in engineering any subtilisin/subtilase. Even if the subtilase to be engineered has an amino acid different from that of subtilisin GCI-P036 at a particular position, these data find use in finding a substitution that will alter the desired properties by identifying the best choice for substitution(s), including substitution(s) to the GCI-P036 wild type amino acid.

TABLE 4-1

Performance Index (PI) Values for Variants of GCI-P036 for Various Tested Properties.

| POSI-<br>TION<br>(BPN'<br>Number-<br>ing) | GG36<br>Variant<br>(BPN'<br>Number-<br>ing) | TCA<br>Assay<br>PI | CS-38<br>Micro-<br>swatch<br>Assay<br>PI | PI<br>BMI<br>pH 8<br>32° C. | LAS-<br>EDTA<br>PI | AAPF<br>Assay<br>PI |
|---|---|---|---|---|---|---|
| 1 | A001C | 0.93 | 0.87 | 1.14 | 0.62 | 1.11 |
| 1 | A001E | 1.25 | 0.94 | 1.00 | 1.08 | 1.34 |
| 1 | A001F | 1.15 | 1.18 | 1.01 | 0.53 | 1.24 |
| 1 | A001G | 1.19 | 1.37 | 1.01 | 0.92 | 1.47 |
| 1 | A001H | 1.33 | 0.97 | 0.93 | 0.83 | 1.43 |
| 1 | A001I | 1.40 | 0.92 | 0.97 | 0.63 | 1.74 |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 1 | A001K | 1.24 | 1.13 | 0.76 | 0.63 | 1.30 |
| 1 | A001L | 1.31 | 1.05 | 0.98 | 0.72 | 1.33 |
| 1 | A001N | 1.38 | 0.96 | 1.02 | 0.68 | 1.55 |
| 1 | A001P | 0.44 | *0.05* | 1.20 | 0.37 | 0.47 |
| 1 | A001Q | 1.30 | 1.23 | 1.07 | 0.98 | 1.58 |
| 1 | A001R | 1.28 | 0.97 | 0.74 | 0.39 | 1.41 |
| 1 | A001S | 1.39 | 1.10 | 0.98 | 0.74 | 1.43 |
| 1 | A001T | 1.54 | 0.82 | 1.01 | 0.76 | 1.59 |
| 1 | A001V | 1.48 | 0.89 | 0.94 | 0.89 | 1.53 |
| 1 | A001Y | 1.42 | 0.86 | 0.79 | 0.70 | 1.34 |
| 2 | Q002A | 1.55 | 1.29 | 1.06 | *0.05* | 1.73 |
| 2 | Q002C | 1.19 | 0.68 | 0.95 | *0.05* | 1.44 |
| 2 | Q002E | 1.80 | 0.94 | 1.03 | *0.05* | 1.79 |
| 2 | Q002G | 1.67 | 1.22 | 0.92 | *0.05* | 1.70 |
| 2 | Q002K | 1.32 | 1.16 | 0.73 | *0.05* | 1.40 |
| 2 | Q002L | 1.27 | 1.00 | 1.09 | *0.05* | 1.31 |
| 2 | Q002M | 1.35 | 1.08 | 0.94 | *0.05* | 1.37 |
| 2 | Q002N | 1.57 | 1.11 | 0.91 | *0.05* | 1.67 |
| 2 | Q002P | 1.81 | 1.04 | 0.89 | *0.05* | 1.90 |
| 2 | Q002R | 1.31 | 1.08 | 0.67 | *0.05* | 1.38 |
| 2 | Q002S | 1.79 | 1.20 | 0.95 | *0.05* | 1.86 |
| 2 | Q002T | 1.55 | 1.04 | 0.89 | *0.05* | 1.33 |
| 2 | Q002V | 1.60 | 0.97 | 0.91 | *0.05* | 1.64 |
| 2 | Q002W | 1.60 | 1.10 | 0.87 | *0.05* | 1.67 |
| 2 | Q002Y | 1.52 | 0.95 | 0.95 | *0.05* | 1.48 |
| 3 | S003D | 1.36 | 1.01 | 1.09 | 0.43 | 1.55 |
| 3 | S003E | 1.25 | 0.99 | 1.17 | 1.03 | 1.33 |
| 3 | S003F | 1.07 | 0.98 | 0.90 | 0.23 | 1.10 |
| 3 | S003G | 1.48 | 1.00 | 0.79 | *0.05* | 1.47 |
| 3 | S003H | 1.40 | 0.90 | 0.91 | 0.87 | 1.42 |
| 3 | S003I | 1.41 | 0.91 | 0.93 | 1.02 | 1.37 |
| 3 | S003L | 1.24 | 1.00 | 0.86 | 0.57 | 1.27 |
| 3 | S003M | 1.45 | 0.89 | 0.89 | 0.90 | 1.45 |
| 3 | S003N | 1.42 | 0.97 | 0.94 | 0.71 | 1.45 |
| 3 | S003P | 1.41 | 0.94 | 0.90 | *0.05* | 1.54 |
| 3 | S003R | 1.27 | 1.09 | 0.75 | *0.05* | 1.44 |
| 3 | S003T | 1.46 | 0.95 | 0.90 | 1.14 | 1.66 |
| 3 | S003V | 1.37 | 0.99 | 0.81 | 0.95 | 1.39 |
| 3 | S003W | 1.42 | 0.88 | 0.81 | 0.30 | 1.33 |
| 3 | S003Y | 1.38 | 0.95 | 0.86 | 0.29 | 1.35 |
| 4 | V004A | 1.23 | 1.13 | 0.92 | *0.05* | 1.47 |
| 4 | V004C | 1.16 | 1.00 | 0.90 | 0.34 | 1.40 |
| 4 | V004D | 1.15 | 0.99 | 1.16 | *0.05* | 1.47 |
| 4 | V004E | 1.34 | 0.95 | 1.05 | 0.19 | 1.54 |
| 4 | V004F | 1.30 | 0.92 | 1.05 | *0.05* | 1.34 |
| 4 | V004G | 0.73 | 1.90 | 1.09 | *0.05* | 0.90 |
| 4 | V004H | 1.27 | 0.97 | 0.91 | *0.05* | 1.47 |
| 4 | V004K | 1.36 | 0.93 | 0.75 | *0.05* | 1.51 |
| 4 | V004L | 1.33 | 0.96 | 0.86 | 0.22 | 1.34 |
| 4 | V004N | 1.46 | 0.86 | 0.86 | *0.05* | 1.50 |
| 4 | V004P | 1.27 | 1.02 | 0.87 | *0.05* | 1.40 |
| 4 | V004R | 1.20 | 1.03 | 0.76 | *0.05* | 1.37 |
| 4 | V004S | 1.12 | 1.33 | 0.99 | *0.05* | 1.35 |
| 4 | V004T | 1.32 | 1.02 | 0.80 | 0.93 | 1.55 |
| 4 | V004W | 1.24 | 1.01 | 1.00 | *0.05* | 1.35 |
| 5 | P005A | 1.60 | 1.71 | 1.02 | *0.05* | 1.03 |
| 5 | P005C | 0.95 | 1.22 | 1.22 | 0.11 | 0.92 |
| 5 | P005D | 1.35 | 1.48 | 1.22 | *0.05* | 1.52 |
| 5 | P005E | 1.30 | 1.97 | 1.19 | *0.05* | 1.31 |
| 5 | P005F | *0.05* | *0.05* | *0.05* | ND | *0.05* |
| 5 | P005G | 1.63 | 1.77 | 0.91 | 0.39 | 2.04 |
| 5 | P005I | 0.26 | *0.05* | 1.77 | *0.05* | 0.56 |
| 5 | P005K | *0.05* | *0.05* | *0.05* | ND | *0.05* |
| 5 | P005L | *0.05* | *0.05* | *0.05* | ND | *0.05* |
| 5 | P005M | 0.69 | 2.30 | 1.15 | *0.05* | 0.45 |
| 5 | P005Q | 1.46 | 1.56 | 0.83 | *0.05* | 0.47 |
| 5 | P005R | *0.05* | *0.05* | *0.05* | ND | *0.05* |
| 5 | P005S | 1.91 | 1.34 | 0.99 | 0.07 | 1.12 |
| 5 | P005T | 1.40 | 1.85 | 1.00 | *0.05* | 1.88 |
| 5 | P005W | 0.10 | *0.05* | 3.05 | *0.05* | 0.28 |
| 5 | P005Y | 0.07 | *0.05* | 5.25 | *0.05* | 0.25 |
| 6 | W006A | 0.12 | *0.05* | 2.59 | *0.05* | 0.21 |
| 6 | W006D | 0.13 | *0.05* | 4.70 | 0.42 | 0.30 |
| 6 | W006E | 0.12 | *0.05* | 4.66 | 0.41 | 0.23 |
| 6 | W006G | *0.05* | *0.05* | *0.05* | ND | *0.05* |
| 6 | W006I | *0.05* | *0.05* | *0.05* | ND | *0.05* |
| 6 | W006K | *0.05* | *0.05* | *0.05* | ND | *0.05* |
| 6 | W006M | 0.07 | *0.05* | 5.94 | *0.05* | 0.23 |
| 6 | W006P | *0.05* | *0.05* | *0.05* | ND | *0.05* |
| 6 | W006Q | *0.05* | *0.05* | *0.05* | ND | *0.05* |
| 6 | W006R | *0.05* | *0.05* | *0.05* | ND | *0.05* |
| 6 | W006S | *0.05* | *0.05* | *0.05* | ND | *0.05* |
| 6 | W006T | *0.05* | *0.05* | *0.05* | ND | *0.05* |
| 6 | W006V | *0.05* | *0.05* | *0.05* | ND | *0.05* |
| 7 | G007A | 1.97 | 1.10 | 1.02 | *0.05* | 1.88 |
| 7 | G007C | 1.77 | 1.12 | 0.92 | 0.08 | 1.76 |
| 7 | G007D | 1.51 | 0.69 | 1.03 | *0.05* | 1.24 |
| 7 | G007E | 0.24 | *0.05* | *0.05* | ND | *0.05* |
| 7 | G007F | 0.06 | *0.05* | *0.05* | ND | *0.05* |
| 7 | G007H | 1.93 | 1.08 | 0.96 | *0.05* | 1.68 |
| 7 | G007I | 0.23 | *0.05* | *0.05* | ND | *0.05* |
| 7 | G007K | 0.58 | *0.05* | *0.05* | ND | *0.05* |
| 7 | G007L | 0.42 | *0.05* | *0.05* | ND | *0.05* |
| 7 | G007M | 0.17 | *0.05* | 0.62 | 0.11 | 0.09 |
| 7 | G007N | 2.08 | 0.95 | 0.97 | 0.29 | 1.52 |
| 7 | G007P | 0.12 | *0.05* | 2.42 | *0.05* | 0.35 |
| 7 | G007Q | 0.37 | *0.05* | 1.23 | *0.05* | 0.36 |
| 7 | G007R | 0.38 | *0.05* | *0.05* | ND | *0.05* |
| 7 | G007S | 2.29 | 1.04 | 0.97 | 0.17 | 1.67 |
| 7 | G007T | 1.64 | 1.05 | 0.97 | *0.05* | 1.24 |
| 7 | G007V | *0.05* | *0.05* | *0.05* | ND | *0.05* |
| 7 | G007W | *0.05* | *0.05* | *0.05* | ND | *0.05* |
| 8 | I008A | 1.90 | 1.12 | 0.88 | *0.05* | 1.92 |
| 8 | I008E | 0.06 | *0.05* | *0.05* | ND | *0.05* |
| 8 | I008F | 1.68 | 1.02 | 0.93 | *0.05* | 1.81 |
| 8 | I008G | 0.22 | *0.05* | 1.82 | *0.05* | 0.42 |
| 8 | I008K | 0.19 | *0.05* | *0.05* | ND | *0.05* |
| 8 | I008L | 2.13 | 0.91 | 0.96 | 0.08 | 2.08 |
| 8 | I008M | 2.08 | 1.01 | 0.82 | *0.05* | 2.01 |
| 8 | I008P | *0.05* | *0.05* | *0.05* | ND | *0.05* |
| 8 | I008Q | 0.80 | 1.03 | 1.03 | *0.05* | 0.98 |
| 8 | I008R | 0.08 | *0.05* | *0.05* | ND | *0.05* |
| 8 | I008T | 1.79 | 1.35 | 0.98 | 0.46 | 2.15 |
| 8 | I008V | 2.16 | 0.92 | 0.94 | 1.09 | 2.00 |
| 8 | I008W | 0.14 | *0.05* | 2.66 | *0.05* | 0.50 |
| 8 | I008Y | 0.22 | *0.05* | 2.27 | *0.05* | 0.61 |
| 9 | S009A | 0.78 | 3.26 | 1.15 | 0.75 | 1.02 |
| 9 | S009C | 0.73 | 2.26 | 1.39 | 0.72 | 0.90 |
| 9 | S009D | 0.77 | 2.59 | 1.49 | 1.17 | 0.91 |
| 9 | S009E | 0.94 | 1.28 | 1.28 | 1.14 | 1.12 |
| 9 | S009F | 1.06 | 1.13 | 1.02 | 0.15 | 1.21 |
| 9 | S009G | 0.88 | 1.97 | 1.27 | 0.70 | 1.12 |
| 9 | S009H | 1.23 | 1.05 | 1.19 | 1.02 | 1.33 |
| 9 | S009L | 1.25 | 0.75 | 1.01 | 0.30 | 1.31 |
| 9 | S009N | 1.29 | 0.89 | 1.03 | 0.91 | 1.58 |
| 9 | S009P | 1.03 | 1.31 | 1.19 | *0.05* | 1.28 |
| 9 | S009Q | 1.38 | 0.86 | 0.90 | 0.89 | 1.69 |
| 9 | S009R | 1.27 | 0.99 | 0.77 | 0.09 | 1.49 |
| 9 | S009T | 0.97 | 1.54 | 1.09 | 0.92 | 1.11 |
| 9 | S009V | 1.18 | 1.05 | 0.98 | 0.57 | 1.22 |
| 9 | S009W | 1.29 | 0.89 | 0.99 | 0.16 | 1.52 |
| 9 | S009Y | 1.16 | 0.84 | 1.03 | 0.34 | 1.36 |
| 10 | R010A | 1.05 | 1.05 | 1.16 | 0.98 | 1.09 |
| 10 | R010C | 0.90 | 1.04 | 1.15 | 0.90 | 0.92 |
| 10 | R010F | 0.64 | 1.71 | 1.46 | 0.57 | 0.61 |
| 10 | R010G | 0.92 | 1.07 | 1.22 | 0.83 | 1.14 |
| 10 | R010H | 1.06 | 0.83 | 1.24 | 1.19 | 1.01 |
| 10 | R010I | 0.69 | 1.18 | 1.28 | 0.45 | 0.71 |
| 10 | R010K | 1.20 | 1.08 | 1.09 | 0.99 | 1.23 |
| 10 | R010L | 0.61 | 1.60 | 1.38 | 0.18 | 0.53 |
| 10 | R010M | 1.26 | 0.79 | 1.11 | 1.02 | 1.32 |
| 10 | R010N | 0.86 | 0.75 | 1.16 | 1.15 | 0.87 |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 10 | R010P | 0.22 | *0.05* | *0.05* | ND | *0.05* |
| 10 | R010Q | 0.24 | *0.05* | 2.44 | 1.25 | 0.27 |
| 10 | R010S | 1.00 | 0.94 | 1.29 | 0.99 | 1.04 |
| 10 | R010T | 1.21 | 0.98 | 0.99 | 1.08 | 1.27 |
| 10 | R010V | 0.78 | 0.74 | 1.19 | 0.74 | 0.77 |
| 10 | R010W | 0.85 | 0.74 | 1.24 | 0.66 | 0.74 |
| 10 | R010Y | 0.62 | 1.73 | 1.40 | 0.55 | 0.54 |
| 11 | V011A | 1.42 | 1.16 | 1.10 | 0.59 | 2.07 |
| 11 | V011C | 0.64 | 1.38 | 1.48 | 0.62 | 0.89 |
| 11 | V011D | 0.20 | *0.05* | 1.40 | 0.62 | 0.13 |
| 11 | V011F | 0.20 | *0.05* | *0.05* | ND | *0.05* |
| 11 | V011G | 0.38 | *0.05* | 2.03 | *0.05* | 0.53 |
| 11 | V011I | 1.13 | 1.30 | 1.25 | 0.98 | 1.34 |
| 11 | V011K | 0.23 | *0.05* | *0.05* | ND | *0.05* |
| 11 | V011M | 1.13 | 1.14 | 1.20 | 0.19 | 1.44 |
| 11 | V011N | 0.19 | *0.05* | *0.05* | ND | *0.05* |
| 11 | V011P | 0.22 | *0.05* | *0.05* | ND | *0.05* |
| 11 | V011R | 0.17 | *0.05* | *0.05* | ND | *0.05* |
| 11 | V011S | 1.26 | 1.30 | 1.15 | 0.47 | 1.78 |
| 11 | V011T | 0.28 | *0.05* | 2.38 | 0.47 | 0.40 |
| 11 | V011W | 0.21 | *0.05* | *0.05* | ND | *0.05* |
| 11 | V011Y | 0.17 | *0.05* | *0.05* | ND | *0.05* |
| 12 | Q012D | 0.85 | 0.46 | 1.28 | 0.79 | 0.93 |
| 12 | Q012F | 1.24 | 1.21 | 1.10 | 0.63 | 1.59 |
| 12 | Q012G | 1.30 | 0.83 | 1.10 | 1.18 | 1.60 |
| 12 | Q012H | 1.21 | 1.23 | 1.00 | 0.60 | 1.46 |
| 12 | Q012I | 1.39 | 1.06 | 1.13 | 0.80 | 1.58 |
| 12 | Q012K | 1.16 | 1.34 | 0.88 | 0.15 | 1.50 |
| 12 | Q012L | 0.21 | *0.05* | 2.38 | 0.97 | 0.30 |
| 12 | Q012M | 0.57 | 1.67 | 1.40 | 0.98 | 0.76 |
| 12 | Q012N | 1.17 | 1.27 | 1.14 | 1.14 | 1.46 |
| 12 | Q012P | 0.16 | *0.05* | 0.88 | 1.02 | 0.09 |
| 12 | Q012R | 1.17 | 1.19 | 1.09 | 0.23 | 1.49 |
| 12 | Q012S | 1.59 | 1.10 | 1.01 | 0.96 | 1.74 |
| 12 | Q012T | 1.26 | 0.96 | 1.07 | 1.00 | 1.32 |
| 12 | Q012V | 1.33 | 1.00 | 1.12 | 0.84 | 1.57 |
| 12 | Q012W | 1.37 | 1.05 | 0.89 | 0.49 | 1.58 |
| 12 | Q012Y | 0.21 | *0.05* | 0.83 | 0.92 | 0.10 |
| 13 | A013E | 0.21 | *0.05* | *0.05* | ND | *0.05* |
| 13 | A013G | 1.37 | 1.04 | 1.00 | 1.00 | 1.62 |
| 13 | A013I | 0.92 | 0.91 | 1.09 | *0.05* | 1.01 |
| 13 | A013K | 0.25 | *0.05* | *0.05* | ND | *0.05* |
| 13 | A013L | 0.23 | *0.05* | 0.46 | 0.77 | 0.08 |
| 13 | A013M | 0.40 | *0.05* | 1.26 | 0.09 | 0.44 |
| 13 | A013N | 0.20 | *0.05* | *0.05* | ND | *0.05* |
| 13 | A013P | 0.18 | *0.05* | *0.05* | 0.56 | 0.08 |
| 13 | A013Q | 0.62 | 4.03 | 1.33 | 0.09 | 0.72 |
| 13 | A013R | 0.31 | *0.05* | *0.05* | ND | *0.05* |
| 13 | A013T | 1.14 | 1.24 | 1.00 | 0.24 | 1.29 |
| 13 | A013V | 1.13 | 1.02 | 0.93 | 0.08 | 1.20 |
| 13 | A013Y | 0.12 | *0.05* | *0.05* | ND | *0.05* |
| 14 | P014A | 1.06 | 1.25 | *0.05* | 0.27 | 1.32 |
| 14 | P014C | 0.57 | 35.83 | 1.39 | 0.56 | 0.81 |
| 14 | P014D | 0.73 | 2.04 | 1.43 | 0.93 | 0.97 |
| 14 | P014E | 0.68 | 2.26 | 1.49 | 1.06 | 0.90 |
| 14 | P014F | 0.81 | 1.68 | 1.00 | *0.05* | 1.02 |
| 14 | P014G | 0.62 | 26.84 | 1.26 | 0.49 | 0.78 |
| 14 | P014H | 0.89 | 1.45 | 1.14 | 0.28 | 1.11 |
| 14 | P014I | 1.06 | 1.23 | 1.08 | 0.66 | 1.14 |
| 14 | P014K | 1.16 | 1.15 | 0.84 | *0.05* | 1.32 |
| 14 | P014L | 1.29 | 1.12 | 1.13 | 0.77 | 1.40 |
| 14 | P014Q | 1.20 | 1.07 | 0.91 | 0.62 | 1.32 |
| 14 | P014S | 0.84 | 1.60 | 1.27 | 0.37 | 1.07 |
| 14 | P014T | 1.06 | 1.25 | 1.13 | 0.80 | 1.18 |
| 14 | P014V | 1.08 | 1.29 | 1.06 | 0.63 | 1.32 |
| 14 | P014Y | 1.09 | 1.20 | 1.09 | 0.13 | 1.24 |
| 15 | A015D | 1.02 | 0.87 | 1.10 | 1.13 | 1.16 |
| 15 | A015F | 1.23 | 1.04 | 1.08 | 0.84 | 1.56 |
| 15 | A015G | 1.14 | 1.17 | 1.04 | 1.00 | 1.25 |
| 15 | A015I | 1.47 | 0.89 | 0.95 | 1.03 | 1.47 |
| 15 | A015K | 1.25 | 1.06 | 0.82 | 0.30 | 1.23 |
| 15 | A015L | 1.38 | 0.94 | 0.90 | 1.09 | 1.45 |
| 15 | A015M | 1.43 | 0.89 | 0.98 | 0.99 | 1.53 |
| 15 | A015P | 1.53 | 0.79 | 0.97 | 0.99 | 1.57 |
| 15 | A015Q | 1.40 | 0.92 | 1.00 | 1.08 | 1.42 |
| 15 | A015R | 1.14 | 1.00 | 0.89 | 0.08 | 1.32 |
| 15 | A015S | 1.35 | 1.07 | 0.84 | 1.14 | 1.33 |
| 15 | A015V | 1.36 | 0.90 | 0.95 | 1.02 | 1.50 |
| 15 | A015W | 1.44 | 0.80 | 0.87 | 0.87 | 1.41 |
| 16 | A016D | 0.16 | *0.05* | 1.24 | *0.05* | 0.13 |
| 16 | A016E | 0.20 | *0.05* | 1.39 | 0.09 | 0.19 |
| 16 | A016F | 0.27 | *0.05* | *0.05* | ND | *0.05* |
| 16 | A016G | 1.28 | 1.13 | 1.02 | 1.00 | 1.51 |
| 16 | A016K | 0.13 | *0.05* | *0.05* | *0.05* | 0.10 |
| 16 | A016L | 1.19 | 0.90 | 1.10 | 0.53 | 1.50 |
| 16 | A016N | 1.15 | 1.05 | 1.05 | 0.89 | 1.40 |
| 16 | A016P | 1.41 | 0.92 | 0.98 | 0.87 | 1.55 |
| 16 | A016Q | 0.59 | 3.00 | 1.13 | 0.84 | 0.72 |
| 16 | A016R | 0.40 | *0.05* | 1.02 | *0.05* | 0.49 |
| 16 | A016S | 1.30 | 0.98 | 0.93 | 1.01 | 1.25 |
| 16 | A016T | 1.16 | 1.01 | 1.12 | 0.86 | 1.27 |
| 16 | A016V | 1.46 | 1.00 | 1.01 | 0.89 | 1.45 |
| 16 | A016W | 0.13 | *0.05* | *0.05* | ND | *0.05* |
| 16 | A016Y | 0.12 | *0.05* | *0.05* | ND | *0.05* |
| 17 | H017A | 0.88 | 1.01 | 1.02 | 0.70 | 1.07 |
| 17 | H017D | 0.31 | *0.05* | 1.81 | 0.57 | 0.39 |
| 17 | H017E | 0.70 | 1.87 | 1.29 | 0.75 | 0.93 |
| 17 | H017F | 1.40 | 0.91 | 0.93 | 0.69 | 1.60 |
| 17 | H017G | 0.69 | 2.24 | 1.09 | 0.73 | 0.91 |
| 17 | H017I | 1.28 | 0.91 | 0.91 | 1.01 | 1.37 |
| 17 | H017K | 0.90 | 1.25 | 0.81 | *0.05* | 1.05 |
| 17 | H017M | 0.92 | 1.26 | 1.00 | 1.04 | 1.05 |
| 17 | H017N | 1.10 | 0.99 | 1.03 | 0.84 | 1.30 |
| 17 | H017P | 0.13 | *0.05* | *0.05* | ND | *0.05* |
| 17 | H017R | 0.94 | 1.35 | 0.98 | *0.05* | 1.11 |
| 17 | H017S | 0.97 | 1.32 | 1.01 | 0.60 | 1.16 |
| 17 | H017T | 0.78 | 1.73 | 1.10 | 0.54 | 0.91 |
| 17 | H017V | 0.81 | 1.38 | 1.13 | 0.52 | 0.88 |
| 17 | H017W | 1.16 | 0.98 | 1.01 | 0.13 | 1.41 |
| 17 | H017Y | 1.20 | 0.94 | 0.94 | 0.56 | 1.26 |
| 18 | N018A | 1.21 | 0.88 | 0.91 | 0.96 | 1.28 |
| 18 | N018C | 1.13 | 1.01 | 1.03 | 0.86 | 1.34 |
| 18 | N018D | 1.26 | 1.12 | 1.11 | 1.15 | 1.41 |
| 18 | N018E | 1.46 | 0.92 | 1.02 | 1.20 | 1.47 |
| 18 | N018F | 1.14 | 1.07 | 1.05 | 0.66 | 1.32 |
| 18 | N018G | 1.10 | 1.10 | 1.05 | 1.01 | 1.17 |
| 18 | N018H | 1.26 | 1.08 | 1.01 | 1.02 | 1.37 |
| 18 | N018I | 0.94 | 0.21 | *0.05* | ND | *0.05* |
| 18 | N018K | 1.39 | 0.95 | 0.74 | 0.43 | 1.43 |
| 18 | N018L | 1.35 | 0.91 | 0.97 | 0.92 | 1.26 |
| 18 | N018M | 0.88 | 1.57 | 0.97 | 0.87 | 1.06 |
| 18 | N018P | 1.26 | 1.09 | 1.00 | 0.92 | 1.37 |
| 18 | N018Q | 1.32 | 1.01 | 0.92 | 1.02 | 1.44 |
| 18 | N018R | 1.20 | 1.02 | 0.82 | 0.12 | 1.36 |
| 18 | N018S | 1.02 | 1.19 | 1.07 | 1.03 | 1.08 |
| 18 | N018T | 1.21 | 1.03 | 0.90 | 0.97 | 1.41 |
| 18 | N018V | 1.32 | 0.92 | 1.09 | 0.86 | 1.36 |
| 18 | N018W | 1.39 | 0.90 | 0.89 | 0.54 | 1.38 |
| 18 | N018Y | 1.36 | 0.83 | 1.04 | 0.90 | 1.31 |
| 19 | R019A | 1.31 | 1.04 | 1.07 | 1.06 | 1.38 |
| 19 | R019C | 1.23 | 0.79 | 1.03 | 1.31 | 1.26 |
| 19 | R019D | 1.09 | 1.07 | 1.15 | 1.08 | 1.33 |
| 19 | R019E | 1.36 | 0.74 | 1.00 | 1.21 | 1.58 |
| 19 | R019F | 1.35 | 0.90 | 1.07 | 1.16 | 1.46 |
| 19 | R019G | 1.06 | 1.05 | 1.11 | 1.10 | 1.15 |
| 19 | R019H | 0.99 | 0.90 | 1.05 | 1.04 | 1.22 |
| 19 | R019K | 1.38 | 0.88 | 0.92 | 1.08 | 1.57 |
| 19 | R019L | 1.24 | 1.01 | 1.16 | 1.23 | 1.27 |
| 19 | R019M | 1.30 | 1.03 | 1.12 | 1.14 | 1.34 |
| 19 | R019N | 1.18 | 0.98 | 1.15 | 1.18 | 1.21 |
| 19 | R019P | 0.27 | *0.05* | 1.89 | 0.58 | 0.27 |
| 19 | R019Q | 0.36 | *0.05* | *0.05* | ND | *0.05* |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 19 | R019S | 0.95 | 1.28 | 1.26 | 1.05 | 1.04 |
| 19 | R019T | 0.71 | 2.30 | 1.34 | 1.06 | 0.86 |
| 19 | R019V | 1.00 | 1.26 | 1.12 | 1.05 | 1.18 |
| 19 | R019W | 1.22 | 0.94 | 1.11 | 1.17 | 1.13 |
| 19 | R019Y | 1.50 | 0.84 | 1.04 | 1.03 | 1.36 |
| 20 | G020A | 1.76 | 0.87 | 0.82 | 0.90 | 2.04 |
| 20 | G020C | 1.25 | 0.83 | 1.00 | 0.99 | 1.55 |
| 20 | G020D | 1.20 | 0.77 | 1.07 | 1.14 | 1.59 |
| 20 | G020F | 1.43 | 0.90 | 0.85 | 1.04 | 1.58 |
| 20 | G020I | 1.66 | 0.92 | 0.86 | 1.11 | 1.71 |
| 20 | G020K | 1.89 | 1.07 | 0.69 | 0.92 | 1.98 |
| 20 | G020L | 1.77 | 0.96 | 0.83 | 1.03 | 2.11 |
| 20 | G020M | 0.99 | 0.89 | 1.15 | 1.04 | 1.22 |
| 20 | G020P | 1.47 | 0.98 | 0.92 | 0.91 | 1.59 |
| 20 | G020Q | 1.95 | 0.96 | 0.76 | 1.02 | 2.27 |
| 20 | G020R | 1.75 | 0.95 | 0.70 | 0.81 | 1.94 |
| 20 | G020S | 1.25 | 1.32 | 0.95 | 0.92 | 1.66 |
| 20 | G020T | 1.39 | 0.94 | 0.92 | 1.03 | 1.54 |
| 20 | G020V | 1.68 | 0.95 | 0.86 | 1.04 | 1.77 |
| 20 | G020W | 1.31 | 0.91 | 0.93 | 0.91 | 1.39 |
| 20 | G020Y | 1.94 | 0.88 | 0.80 | 0.92 | 2.22 |
| 21 | L021A | 1.43 | 0.88 | 0.81 | 0.87 | 1.82 |
| 21 | L021C | 0.99 | 1.06 | 1.10 | 0.92 | 1.22 |
| 21 | L021D | 0.63 | *0.05* | 1.64 | 0.86 | 0.92 |
| 21 | L021E | 1.08 | 1.00 | 1.22 | 1.08 | 1.24 |
| 21 | L021G | 0.96 | 1.22 | 1.30 | 0.87 | 1.23 |
| 21 | L021H | 1.37 | 0.96 | 0.83 | 1.01 | 1.64 |
| 21 | L021I | 1.53 | 0.94 | 0.81 | 0.96 | 1.82 |
| 21 | L021K | 1.52 | 0.91 | 0.78 | 0.97 | 1.88 |
| 21 | L021M | 1.17 | 0.91 | 0.96 | 0.93 | 1.42 |
| 21 | L021N | 1.47 | 0.94 | 0.80 | 0.97 | 1.72 |
| 21 | L021P | 1.41 | 0.89 | 0.82 | 0.89 | 1.59 |
| 21 | L021Q | 1.56 | 0.86 | 0.78 | 0.95 | 2.07 |
| 21 | L021R | 1.46 | 0.98 | 0.79 | 0.79 | 1.68 |
| 21 | L021S | 1.12 | 1.10 | 1.11 | 0.84 | 1.57 |
| 21 | L021T | 1.44 | 0.97 | 0.78 | 0.95 | 1.86 |
| 21 | L021V | 1.56 | 0.73 | 0.78 | 0.91 | 2.04 |
| 21 | L021W | 1.58 | 0.86 | 0.69 | 0.98 | 1.84 |
| 22 | T022A | 1.21 | 1.29 | 0.91 | 0.95 | 1.47 |
| 22 | T022C | 1.15 | 0.97 | 1.18 | 1.09 | 1.27 |
| 22 | T022G | 1.14 | 1.30 | 1.04 | 0.97 | 1.24 |
| 22 | T022I | 1.26 | 1.04 | 1.03 | 1.13 | 1.46 |
| 22 | T022K | 1.27 | 0.96 | 0.80 | 0.76 | 1.32 |
| 22 | T022L | 1.36 | 0.88 | 0.93 | 0.95 | 1.35 |
| 22 | T022M | 1.39 | 1.03 | 0.90 | 0.97 | 1.34 |
| 22 | T022N | 1.28 | 0.95 | 0.88 | 1.20 | 1.43 |
| 22 | T022P | 1.25 | 0.85 | 0.94 | 1.12 | 1.45 |
| 22 | T022Q | 1.31 | 0.95 | 0.95 | 1.02 | 1.48 |
| 22 | T022R | 1.16 | 0.94 | 0.83 | 0.57 | 1.34 |
| 22 | T022S | 0.49 | *0.05* | 1.11 | 1.01 | 0.54 |
| 22 | T022V | 1.33 | 1.04 | 1.05 | 1.15 | 1.31 |
| 22 | T022W | 1.46 | 1.02 | 0.88 | 1.28 | 1.48 |
| 22 | T022Y | 1.30 | 0.93 | 0.82 | 0.58 | 1.40 |
| 23 | G023A | 1.73 | 1.12 | 0.87 | 0.95 | 1.80 |
| 23 | G023C | *0.05* | *0.05* | *0.05* | *ND* | *0.05* |
| 23 | G023D | *0.05* | *0.05* | *0.05* | *ND* | *0.05* |
| 23 | G023E | *0.05* | *0.05* | *0.05* | *ND* | *0.05* |
| 23 | G023F | *0.05* | *0.05* | *0.05* | *ND* | *0.05* |
| 23 | G023I | *0.05* | *0.05* | *0.05* | *ND* | *0.05* |
| 23 | G023K | *0.05* | *0.05* | *0.05* | *ND* | *0.05* |
| 23 | G023L | *0.05* | *0.05* | *0.05* | *ND* | *0.05* |
| 23 | G023M | *0.05* | *0.05* | *0.05* | *ND* | *0.05* |
| 23 | G023Q | *0.05* | *0.05* | *0.05* | *ND* | *0.05* |
| 23 | G023R | *0.05* | *0.05* | *0.05* | *ND* | *0.05* |
| 23 | G023S | 1.32 | 0.88 | 0.92 | 0.82 | 1.38 |
| 23 | G023T | *0.05* | *0.05* | *0.05* | 1.04 | *0.05* |
| 24 | S024A | 1.26 | 1.17 | 0.99 | 0.98 | 1.51 |
| 24 | S024C | 1.00 | 1.04 | 1.24 | 1.11 | 1.14 |
| 24 | S024D | 1.38 | 0.83 | 1.03 | 1.13 | 1.31 |
| 24 | S024F | 1.18 | 1.24 | 1.01 | 1.02 | 1.47 |
| 24 | S024G | 1.27 | 1.10 | 0.91 | 1.06 | 1.51 |
| 24 | S024H | 1.21 | 1.13 | 0.94 | 1.08 | 1.32 |
| 24 | S024I | 0.42 | *0.05* | *0.05* | *ND* | *0.05* |
| 24 | S024L | 1.35 | 0.86 | 1.02 | 1.12 | 1.49 |
| 24 | S024M | 1.41 | 0.87 | 0.95 | 1.12 | 1.36 |
| 24 | S024N | 1.18 | 1.05 | 0.97 | 0.96 | 1.44 |
| 24 | S024P | 1.50 | 0.75 | 0.86 | 0.95 | 1.62 |
| 24 | S024Q | 1.34 | 0.94 | 0.95 | 1.05 | 1.52 |
| 24 | S024R | 1.21 | 1.03 | 0.87 | 1.00 | 1.29 |
| 24 | S024T | 1.40 | 0.95 | 0.98 | 1.01 | 1.40 |
| 24 | S024V | 1.25 | 1.12 | 1.05 | 1.10 | 1.29 |
| 24 | S024W | 1.01 | 1.05 | 0.98 | 1.11 | 1.08 |
| 25 | G025C | 0.87 | 1.85 | 1.16 | 0.99 | 1.04 |
| 25 | G025D | 1.16 | 1.03 | 1.10 | 1.13 | 1.32 |
| 25 | G025E | 1.01 | 1.39 | 1.15 | 1.15 | 1.21 |
| 25 | G025F | 0.90 | 1.80 | 1.18 | 1.02 | 1.15 |
| 25 | G025H | 0.56 | *0.05* | 1.28 | 1.06 | 0.75 |
| 25 | G025K | 1.17 | 1.05 | 0.88 | 0.99 | 1.36 |
| 25 | G025L | 1.24 | 0.80 | 0.91 | 1.12 | 1.34 |
| 25 | G025M | 0.98 | 1.39 | 1.12 | 0.98 | 1.15 |
| 25 | G025N | 0.74 | 4.69 | 1.24 | 1.04 | 0.86 |
| 25 | G025Q | 1.34 | 0.90 | 1.01 | 1.11 | 1.49 |
| 25 | G025R | 1.05 | 1.35 | 0.96 | 1.01 | 1.28 |
| 25 | G025S | 0.81 | 5.94 | 1.24 | 0.98 | 1.03 |
| 25 | G025T | 0.95 | 1.51 | 1.23 | 0.99 | 1.38 |
| 25 | G025V | 0.98 | 1.20 | 1.12 | 1.03 | 1.23 |
| 25 | G025W | 1.04 | 1.36 | 1.10 | 1.01 | 1.28 |
| 26 | V026C | 0.85 | 1.29 | 1.09 | 0.85 | 1.06 |
| 26 | V026F | 1.38 | 0.95 | 1.04 | 1.00 | 1.24 |
| 26 | V026G | 1.04 | 1.04 | 1.08 | 0.89 | 1.14 |
| 26 | V026I | 0.58 | 1.19 | 0.86 | 1.13 | 0.30 |
| 26 | V026L | 1.68 | 0.76 | 0.91 | 0.67 | 1.37 |
| 26 | V026M | 1.56 | 0.91 | 0.99 | 0.86 | 1.54 |
| 26 | V026N | 1.72 | 0.77 | 0.97 | 0.91 | 1.44 |
| 26 | V026P | 1.13 | 0.71 | 0.92 | 0.74 | 1.12 |
| 26 | V026R | 1.24 | 1.24 | 0.95 | 0.90 | 1.30 |
| 26 | V026S | 1.22 | 1.13 | 1.10 | 1.07 | 1.25 |
| 26 | V026T | 1.32 | 0.93 | 0.90 | 0.97 | 1.37 |
| 26 | V026Y | 0.29 | *0.05* | *0.05* | *ND* | *0.05* |
| 27 | K027A | 1.35 | 0.76 | 1.08 | 0.94 | 1.60 |
| 27 | K027C | 1.07 | 0.55 | 1.10 | 1.14 | 1.31 |
| 27 | K027D | 1.41 | 0.75 | 1.12 | 1.10 | 1.46 |
| 27 | K027F | 1.04 | 0.63 | 1.23 | 1.11 | 1.19 |
| 27 | K027G | 1.51 | 0.74 | 0.99 | 1.10 | 1.67 |
| 27 | K027H | *0.05* | *0.05* | *0.05* | *ND* | *0.05* |
| 27 | K027I | 0.38 | *0.05* | 1.73 | 0.91 | 0.53 |
| 27 | K027L | 0.97 | 0.57 | 1.18 | 1.08 | 1.21 |
| 27 | K027M | 0.82 | 1.01 | 1.39 | 0.96 | 1.03 |
| 27 | K027N | 1.85 | 0.81 | 0.90 | 1.14 | 1.86 |
| 27 | K027P | 1.92 | 0.75 | 0.92 | 1.10 | 1.56 |
| 27 | K027R | 1.79 | 1.11 | 0.78 | 1.02 | 1.85 |
| 27 | K027S | 1.52 | 1.35 | 0.96 | 0.95 | 1.66 |
| 27 | K027T | 1.18 | 0.86 | 1.10 | 0.96 | 1.22 |
| 27 | K027V | 0.58 | 4.24 | 1.45 | 0.91 | 0.74 |
| 27 | K027W | 1.06 | 0.65 | 1.02 | 0.94 | 1.12 |
| 27 | K027Y | 0.59 | 3.29 | 1.68 | 0.98 | 1.00 |
| 28 | V028A | 0.85 | 1.07 | 1.01 | 0.84 | 0.93 |
| 28 | V028D | 0.23 | *0.05* | *0.05* | *ND* | *0.05* |
| 28 | V028E | 0.37 | *0.05* | 1.10 | 1.07 | 0.33 |
| 28 | V028G | 0.18 | *0.05* | *0.05* | 0.97 | 0.07 |
| 28 | V028H | 0.51 | 8.94 | 1.17 | 0.83 | 0.54 |
| 28 | V028I | 1.39 | 0.89 | 1.05 | 1.07 | 1.48 |
| 28 | V028L | 1.49 | 0.83 | 0.94 | 0.93 | 1.28 |
| 28 | V028M | 1.28 | 0.97 | 0.99 | 0.98 | 1.20 |
| 28 | V028N | 0.41 | *0.05* | 1.13 | 1.01 | 0.44 |
| 28 | V028P | 0.22 | *0.05* | 0.92 | 0.98 | 0.18 |
| 28 | V028S | 0.80 | 0.79 | 1.08 | 1.04 | 0.70 |
| 28 | V028W | 0.31 | *0.05* | *0.05* | *ND* | *0.05* |
| 28 | V028Y | 0.41 | *0.05* | 1.07 | 0.65 | 0.41 |
| 29 | A029C | 1.00 | 1.28 | 1.04 | 1.04 | 1.24 |
| 29 | A029D | 0.39 | *0.05* | *0.05* | *ND* | *0.05* |
| 29 | A029E | 0.39 | *0.05* | *0.05* | *ND* | *0.05* |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 29 | A029F | 0.35 | *0.05* | *0.05* | *ND* | *0.05* |
| 29 | A029G | 0.98 | 1.11 | 1.09 | 1.00 | 0.93 |
| 29 | A029H | 0.39 | *0.05* | *0.05* | *ND* | *0.05* |
| 29 | A029I | 0.17 | *0.05* | *0.05* | *ND* | *0.05* |
| 29 | A029K | 0.37 | *0.05* | 1.29 | *ND* | *0.05* |
| 29 | A029L | 0.17 | *0.05* | *0.05* | *ND* | *0.05* |
| 29 | A029P | 0.26 | *0.05* | *0.05* | *ND* | *0.05* |
| 29 | A029Q | 0.25 | *0.05* | *0.05* | *ND* | *0.05* |
| 29 | A029R | 0.35 | *0.05* | *0.05* | *ND* | *0.05* |
| 29 | A029S | 0.98 | 1.28 | 1.20 | 0.96 | 1.04 |
| 29 | A029T | 0.34 | *0.05* | 1.27 | 0.79 | 0.44 |
| 29 | A029V | 0.95 | 1.13 | 1.07 | 0.81 | 0.96 |
| 29 | A029Y | 0.32 | *0.05* | *0.05* | *ND* | *0.05* |
| 30 | V030A | 0.98 | 0.88 | 0.96 | 0.95 | 0.79 |
| 30 | V030C | 1.17 | 1.00 | 1.01 | 1.14 | 0.94 |
| 30 | V030D | 0.21 | *0.05* | 1.10 | *ND* | *0.05* |
| 30 | V030E | 0.41 | *0.05* | 1.23 | 1.09 | 0.35 |
| 30 | V030F | 0.62 | 1.57 | 1.36 | 0.55 | 0.29 |
| 30 | V030G | 0.22 | *0.05* | *0.05* | *ND* | *0.05* |
| 30 | V030K | 0.34 | *0.05* | *0.05* | *ND* | *0.05* |
| 30 | V030L | 1.14 | 0.64 | 1.05 | 0.97 | 0.87 |
| 30 | V030M | 1.40 | 0.62 | 0.97 | 0.89 | 0.70 |
| 30 | V030Q | 0.31 | *0.05* | 0.98 | 1.10 | 0.08 |
| 30 | V030R | 0.40 | *0.05* | *0.05* | *ND* | *0.05* |
| 30 | V030S | 0.54 | 4.91 | 1.16 | 0.89 | 0.28 |
| 30 | V030T | 1.05 | 0.92 | 1.13 | 0.90 | 0.69 |
| 30 | V030W | 0.34 | *0.05* | *0.05* | *ND* | *0.05* |
| 31 | L031A | 0.90 | 1.27 | 1.04 | 1.04 | 1.04 |
| 31 | L031C | 0.43 | *0.05* | *0.05* | *ND* | *0.05* |
| 31 | L031E | *0.05* | *0.05* | *0.05* | *ND* | *0.05* |
| 31 | L031F | 1.54 | 1.42 | 0.70 | 0.94 | 2.86 |
| 31 | L031G | *0.05* | *0.05* | *0.05* | *ND* | *0.05* |
| 31 | L031I | 1.80 | 0.92 | 0.81 | 1.13 | 1.20 |
| 31 | L031M | 1.97 | 1.09 | 0.81 | 0.83 | 2.32 |
| 31 | L031P | 0.08 | *0.05* | *0.05* | *ND* | *0.05* |
| 31 | L031R | 0.30 | *0.05* | *0.05* | *ND* | *0.05* |
| 31 | L031S | 1.74 | 0.93 | 1.03 | 0.90 | 1.15 |
| 31 | L031T | 0.16 | *0.05* | 3.09 | 0.94 | 0.42 |
| 31 | L031V | 1.43 | 1.20 | 1.12 | 0.95 | 1.41 |
| 31 | L031Y | *0.05* | *0.05* | *0.05* | *ND* | *0.05* |
| 32 | D032A | 0.50 | *ND* | *0.05* | *ND* | *0.05* |
| 32 | D032C | 1.09 | *ND* | *ND* | *ND* | *0.05* |
| 32 | D032E | 0.44 | *0.05* | *ND* | *ND* | *0.05* |
| 32 | D032F | 0.49 | *0.05* | *0.05* | *ND* | *0.05* |
| 32 | D032G | 1.57 | *ND* | *ND* | *ND* | *0.05* |
| 32 | D032H | 0.46 | *0.05* | *0.05* | *ND* | *0.05* |
| 32 | D032I | 0.48 | *0.05* | *0.05* | *ND* | *0.05* |
| 32 | D032L | 0.39 | *0.05* | *0.05* | *ND* | *0.05* |
| 32 | D032M | 0.50 | *0.05* | *0.05* | *ND* | *0.05* |
| 32 | D032N | 0.46 | *0.05* | *0.05* | *ND* | *0.05* |
| 32 | D032P | 0.45 | *0.05* | *0.05* | *ND* | *0.05* |
| 32 | D032R | 0.42 | *0.05* | *0.05* | *ND* | *0.05* |
| 32 | D032S | 0.67 | *0.05* | *0.05* | *ND* | *0.05* |
| 32 | D032T | 0.58 | *0.05* | *0.05* | *ND* | *0.05* |
| 32 | D032V | 0.48 | *ND* | *0.05* | *ND* | *0.05* |
| 32 | D032W | 0.51 | *ND* | *0.05* | *ND* | *0.05* |
| 32 | D032Y | 0.48 | *0.05* | *0.05* | *ND* | *0.05* |
| 33 | T033A | 1.14 | 1.22 | 1.08 | 0.71 | 0.40 |
| 33 | T033C | 1.14 | 0.29 | 0.97 | 1.02 | 0.32 |
| 33 | T033D | 0.95 | 1.09 | 1.50 | 0.62 | 0.23 |
| 33 | T033E | 0.82 | 0.81 | 1.60 | 0.71 | 0.09 |
| 33 | T033F | 0.63 | *0.05* | 0.80 | 0.80 | 0.10 |
| 33 | T033G | 1.48 | 1.22 | 0.96 | 0.75 | 0.49 |
| 33 | T033H | 0.78 | 2.54 | 1.14 | 1.01 | 0.06 |
| 33 | T033I | 0.45 | *0.05* | 1.04 | 0.60 | 0.06 |
| 33 | T033L | 0.34 | *0.05* | 1.74 | 0.80 | 0.07 |
| 33 | T033M | 1.20 | 0.99 | 1.07 | 0.82 | 0.85 |
| 33 | T033N | 0.98 | 0.64 | 1.28 | 0.39 | 0.19 |
| 33 | T033P | 0.58 | *0.05* | *0.05* | *ND* | *0.05* |
| 33 | T033Q | 0.93 | 0.77 | 1.41 | 0.64 | 0.41 |
| 33 | T033R | 0.72 | 2.46 | 0.93 | *ND* | *0.05* |
| 33 | T033S | 2.07 | 0.89 | 0.72 | 0.92 | 1.65 |
| 33 | T033V | 0.43 | *0.05* | 2.28 | 0.17 | 0.06 |
| 33 | T033W | 0.59 | *0.05* | 0.34 | *ND* | *0.05* |
| 33 | T033Y | 0.75 | 0.75 | 1.17 | 0.82 | 0.07 |
| 34 | G034C | 0.33 | *0.05* | 0.38 | *ND* | *0.05* |
| 34 | G034D | 0.42 | *0.05* | *0.05* | *ND* | *0.05* |
| 34 | G034E | 0.40 | *0.05* | 1.36 | 0.16 | 0.06 |
| 34 | G034F | 0.31 | *0.05* | *0.05* | *ND* | *0.05* |
| 34 | G034H | 0.29 | *0.05* | 0.81 | *ND* | *0.05* |
| 34 | G034K | 0.43 | *0.05* | *0.05* | *ND* | *0.05* |
| 34 | G034L | 0.26 | *0.05* | *0.05* | *ND* | *0.05* |
| 34 | G034P | 0.33 | *0.05* | *0.05* | *ND* | *0.05* |
| 34 | G034Q | 0.30 | *0.05* | 0.98 | *ND* | *0.05* |
| 34 | G034R | 0.46 | *0.05* | *0.05* | *ND* | *0.05* |
| 34 | G034S | 0.28 | *0.05* | 1.18 | *ND* | *0.05* |
| 34 | G034T | 0.26 | *0.05* | 0.47 | *ND* | *0.05* |
| 34 | G034V | 0.27 | *0.05* | *0.05* | *ND* | *0.05* |
| 34 | G034W | 0.26 | *0.05* | *0.05* | *ND* | *0.05* |
| 34 | G034Y | 0.37 | *0.05* | 0.37 | *ND* | *0.05* |
| 35 | I035A | 1.13 | 1.09 | 1.00 | 0.64 | 1.07 |
| 35 | I035F | 0.97 | 0.19 | 1.15 | *ND* | *0.05* |
| 35 | I035H | 0.26 | *0.05* | 2.04 | *ND* | *0.05* |
| 35 | I035K | 0.36 | *0.05* | 1.08 | 0.71 | 0.19 |
| 35 | I035L | 1.14 | 0.92 | 1.05 | 0.95 | 1.00 |
| 35 | I035M | 1.16 | 1.03 | 1.17 | 0.82 | 1.12 |
| 35 | I035P | 0.94 | 0.69 | 1.21 | 1.11 | 0.50 |
| 35 | I035Q | 0.79 | 0.87 | 1.24 | 0.75 | 0.63 |
| 35 | I035R | 0.37 | *0.05* | 1.00 | 0.77 | 0.18 |
| 35 | I035S | 0.77 | 2.18 | 1.18 | 0.58 | 0.91 |
| 35 | I035Y | 0.61 | *0.05* | *0.05* | *ND* | *0.05* |
| 36 | S036A | 1.48 | 0.91 | 0.76 | 1.02 | 1.88 |
| 36 | S036C | 0.69 | *0.05* | 1.54 | 0.88 | 0.79 |
| 36 | S036E | 1.10 | 0.82 | 1.09 | 1.16 | 1.30 |
| 36 | S036F | 0.82 | 5.10 | 1.34 | 0.26 | 0.74 |
| 36 | S036G | 1.26 | 0.75 | 0.86 | 0.73 | 1.51 |
| 36 | S036H | 1.52 | 0.69 | 0.79 | 0.79 | 1.51 |
| 36 | S036I | 1.13 | 1.06 | 1.08 | 0.57 | 1.30 |
| 36 | S036L | 1.02 | 1.08 | 1.19 | *0.05* | 0.90 |
| 36 | S036M | 1.40 | 0.71 | 0.83 | 0.68 | 1.56 |
| 36 | S036N | 1.47 | 0.84 | 0.81 | 0.26 | 1.73 |
| 36 | S036P | 0.43 | *0.05* | 2.03 | 0.07 | 0.12 |
| 36 | S036Q | 1.27 | 0.94 | 0.68 | 0.42 | 1.69 |
| 36 | S036R | 1.12 | 1.00 | 0.75 | 0.46 | 1.32 |
| 36 | S036T | 1.35 | 0.87 | 0.78 | 0.83 | 1.63 |
| 36 | S036V | 1.31 | 0.82 | 1.03 | 0.80 | 1.56 |
| 36 | S036W | 0.78 | 17.10 | 1.29 | 0.21 | 0.68 |
| 36 | S036Y | 1.27 | 0.53 | 0.92 | 0.29 | 0.86 |
| 38 | T038C | 1.34 | 0.92 | 0.99 | 1.01 | 1.60 |
| 38 | T038F | 1.57 | 0.78 | 0.75 | 0.91 | 1.81 |
| 38 | T038G | 0.98 | 1.17 | 1.09 | 0.78 | 1.27 |
| 38 | T038H | 1.51 | 0.88 | 0.80 | 0.90 | 1.82 |
| 38 | T038I | 1.42 | 0.90 | 0.86 | 1.09 | 1.71 |
| 38 | T038K | 1.86 | 0.77 | 0.55 | 1.10 | 2.20 |
| 38 | T038L | 1.47 | 0.87 | 0.83 | 1.08 | 1.75 |
| 38 | T038M | 0.94 | 1.64 | 1.13 | 0.94 | 1.17 |
| 38 | T038N | 1.44 | 0.89 | 0.79 | 0.91 | 1.75 |
| 38 | T038Q | 1.69 | 0.75 | 0.68 | 0.92 | 1.87 |
| 38 | T038R | 1.80 | 0.70 | 0.51 | 1.22 | 2.04 |
| 38 | T038V | 1.04 | 1.37 | 1.04 | 1.02 | 1.31 |
| 38 | T038W | 0.72 | *0.05* | 1.41 | 0.99 | 0.91 |
| 38 | T038Y | 1.26 | 1.09 | 0.77 | 0.80 | 1.59 |
| 39 | H039A | 0.37 | *0.05* | 1.72 | *0.05* | 0.47 |
| 39 | H039D | 0.14 | *0.05* | *0.05* | *ND* | *0.05* |
| 39 | H039E | 0.63 | *0.05* | 1.58 | *0.05* | 0.95 |
| 39 | H039F | 0.19 | *0.05* | *0.05* | *ND* | *0.05* |
| 39 | H039G | 0.17 | *0.05* | 1.32 | *0.05* | 0.09 |
| 39 | H039K | 0.28 | *0.05* | *0.05* | *ND* | *0.05* |
| 39 | H039L | 0.14 | *0.05* | 0.98 | *0.05* | 0.07 |
| 39 | H039M | 0.15 | *0.05* | 0.86 | *0.05* | 0.07 |
| 39 | H039N | 0.36 | *0.05* | 1.66 | *0.05* | 0.34 |
| 39 | H039P | 0.17 | *0.05* | *0.05* | *ND* | *0.05* |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 39 | H039Q | 0.45 | *0.05* | 1.53 | *0.05* | 0.52 |
| 39 | H039R | 0.30 | *0.05* | *0.05* | *ND* | *0.05* |
| 39 | H039S | 0.40 | *0.05* | 1.58 | *0.05* | 0.46 |
| 39 | H039T | 0.13 | *0.05* | 2.04 | *0.05* | 0.10 |
| 39 | H039V | 0.91 | 1.70 | 1.08 | *0.05* | 1.17 |
| 39 | H039W | 0.21 | *0.05* | *0.05* | *ND* | *0.05* |
| 39 | H039Y | 0.33 | *0.05* | 2.16 | *0.05* | 0.42 |
| 40 | P040A | 1.67 | 1.03 | 0.83 | 0.83 | 2.20 |
| 40 | P040C | 0.89 | 2.43 | 1.68 | 0.79 | 1.49 |
| 40 | P040D | 1.03 | 1.34 | 1.35 | 1.12 | 1.51 |
| 40 | P040E | 0.92 | 1.93 | 1.44 | 1.67 | 1.40 |
| 40 | P040G | 1.21 | 1.61 | 1.10 | 0.06 | 1.96 |
| 40 | P040H | 1.51 | 1.14 | 0.95 | 0.22 | 2.04 |
| 40 | P040I | 1.32 | 1.25 | 0.99 | 1.01 | 1.81 |
| 40 | P040K | 1.51 | 1.24 | 0.75 | *0.05* | 2.02 |
| 40 | P040L | 1.26 | 1.21 | 1.11 | 1.04 | 1.85 |
| 40 | P040M | 1.34 | 1.20 | 1.09 | 0.62 | 1.65 |
| 40 | P040N | 1.71 | 1.02 | 0.86 | 0.59 | 2.21 |
| 40 | P040R | 1.48 | 1.15 | 0.74 | *0.05* | 2.20 |
| 40 | P040S | 1.34 | 1.32 | 1.00 | 0.27 | 2.08 |
| 40 | P040T | 1.42 | 1.23 | 0.90 | 0.18 | 2.02 |
| 40 | P040V | 1.29 | 1.23 | 1.02 | 1.06 | 1.70 |
| 40 | P040W | 1.14 | 1.41 | 0.96 | 0.55 | 1.65 |
| 40 | P040Y | 0.96 | 1.80 | 1.14 | 0.27 | 1.40 |
| 41 | D041A | 0.19 | *0.05* | *0.05* | *ND* | *0.05* |
| 41 | D041C | 0.17 | *0.05* | 1.65 | *0.05* | 0.17 |
| 41 | D041E | 1.11 | 1.19 | 0.99 | *0.05* | 1.29 |
| 41 | D041F | 0.18 | *0.05* | *0.05* | *ND* | *0.05* |
| 41 | D041G | 0.45 | *0.05* | *0.05* | *0.05* | *0.05* |
| 41 | D041I | 0.15 | *0.05* | *0.05* | *ND* | *0.05* |
| 41 | D041K | 0.13 | *0.05* | *0.05* | *ND* | *0.05* |
| 41 | D041L | 0.15 | *0.05* | *0.05* | *ND* | *0.05* |
| 41 | D041M | 0.19 | *0.05* | *0.05* | *ND* | *0.05* |
| 41 | D041N | 0.20 | *0.05* | 1.47 | *0.05* | 0.17 |
| 41 | D041P | 0.41 | *0.05* | 0.88 | *ND* | *0.05* |
| 41 | D041Q | 0.19 | *0.05* | 2.38 | *0.05* | 0.21 |
| 41 | D041R | 0.12 | *0.05* | *0.05* | *ND* | *0.05* |
| 41 | D041S | 0.16 | *0.05* | 0.90 | *0.05* | 0.10 |
| 41 | D041T | 0.14 | *0.05* | *0.05* | *0.05* | 0.08 |
| 41 | D041V | 0.14 | *0.05* | *0.05* | *ND* | *0.05* |
| 41 | D041W | 0.24 | *0.05* | *0.05* | *ND* | *0.05* |
| 41 | D041Y | 0.16 | *0.05* | *0.05* | *ND* | *0.05* |
| 42 | L042A | 0.63 | *0.05* | 1.60 | *0.05* | 0.61 |
| 42 | L042C | 0.82 | 1.99 | 1.29 | 0.11 | 1.08 |
| 42 | L042D | 0.33 | *0.05* | *0.05* | *ND* | *0.05* |
| 42 | L042E | 0.27 | *0.05* | *0.05* | *ND* | *0.05* |
| 42 | L042F | 0.79 | 2.39 | 1.48 | *0.05* | 0.91 |
| 42 | L042G | 0.30 | *0.05* | 1.64 | *0.05* | 0.24 |
| 42 | L042H | 1.31 | 0.79 | 0.94 | 0.10 | 1.35 |
| 42 | L042I | 1.56 | 0.96 | 0.76 | 0.63 | 2.08 |
| 42 | L042K | 0.19 | *0.05* | *0.05* | *0.05* | 0.07 |
| 42 | L042M | 1.77 | 0.89 | 0.66 | 0.78 | 2.27 |
| 42 | L042N | 1.20 | 0.92 | 1.15 | 0.14 | 1.50 |
| 42 | L042P | 0.57 | *0.05* | *0.05* | *ND* | *0.05* |
| 42 | L042Q | 0.39 | *0.05* | 2.03 | *0.05* | 0.38 |
| 42 | L042R | 0.38 | *0.05* | *0.05* | *ND* | *0.05* |
| 42 | L042S | 0.40 | *0.05* | 2.19 | 0.06 | 0.47 |
| 42 | L042T | 0.84 | 2.22 | 1.18 | 0.10 | 1.10 |
| 42 | L042V | 1.39 | 0.87 | 0.83 | 0.34 | 1.74 |
| 42 | L042Y | 0.39 | *0.05* | 2.41 | *0.05* | 0.45 |
| 43 | N043A | 1.28 | 1.01 | 0.97 | 1.12 | 1.71 |
| 43 | N043C | 0.92 | 1.43 | 1.38 | 1.29 | 1.21 |
| 43 | N043D | 0.98 | 0.85 | 1.27 | 1.29 | 1.25 |
| 43 | N043E | 1.05 | 0.94 | 1.43 | 1.39 | 1.34 |
| 43 | N043F | 0.97 | 1.26 | 1.23 | 1.00 | 1.45 |
| 43 | N043G | 1.64 | 0.56 | 0.75 | 1.12 | 2.06 |
| 43 | N043I | 1.69 | 0.82 | 0.87 | 0.91 | 1.92 |
| 43 | N043L | 1.39 | 0.81 | 0.97 | 0.94 | 1.77 |
| 43 | N043M | 1.70 | 0.83 | 0.80 | 1.16 | 1.96 |
| 43 | N043P | 1.46 | 0.82 | 0.74 | *0.05* | 1.78 |
| 43 | N043R | 1.47 | 0.78 | 0.64 | 1.84 | 1.67 |
| 43 | N043S | 1.79 | 0.86 | 0.79 | 1.07 | 2.36 |
| 43 | N043T | 1.52 | 1.03 | 0.87 | 1.09 | 1.90 |
| 43 | N043V | 1.52 | 0.79 | 0.90 | 0.77 | 1.75 |
| 43 | N043W | 1.25 | 0.85 | 1.06 | 0.98 | 1.62 |
| 43 | N043Y | 1.35 | 0.86 | 0.96 | 1.06 | 1.67 |
| 44 | I044A | 1.24 | 0.94 | 0.93 | 1.01 | 1.29 |
| 44 | I044C | 1.52 | 0.89 | 0.80 | 0.86 | 1.77 |
| 44 | I044D | 1.48 | 0.77 | 0.93 | 1.07 | 1.76 |
| 44 | I044F | 137 | 0.79 | 0.98 | 1.22 | 1.00 |
| 44 | I044G | 1.51 | 0.77 | 0.75 | 1.19 | 1.54 |
| 44 | I044K | 1.29 | 0.98 | 0.76 | 1.49 | 1.48 |
| 44 | I044L | 1.47 | 0.77 | 0.92 | 1.00 | 1.67 |
| 44 | I044M | 0.95 | 1.83 | 1.14 | 0.95 | 1.25 |
| 44 | I044N | 1.49 | 0.77 | 0.74 | 0.99 | 1.68 |
| 44 | I044P | 1.26 | 0.93 | 0.91 | 0.76 | 1.61 |
| 44 | I044Q | 1.23 | 0.91 | 0.93 | 0.91 | 1.41 |
| 44 | I044R | 1.05 | 1.08 | 0.76 | 1.57 | 1.04 |
| 44 | I044S | 1.56 | 0.79 | 0.80 | 1.08 | 1.56 |
| 44 | I044T | 1.07 | 1.06 | 1.13 | 0.93 | 1.38 |
| 44 | I044V | 1.28 | 1.22 | 0.88 | 0.90 | 1.71 |
| 44 | I044W | 1.01 | 0.52 | 1.24 | 0.74 | 0.12 |
| 44 | I044Y | 1.18 | 0.98 | 1.05 | 0.81 | 1.25 |
| 45 | R045A | 1.27 | 1.02 | 1.13 | 1.06 | 1.50 |
| 45 | R045D | 1.26 | 0.91 | 1.15 | 1.32 | 1.51 |
| 45 | R045E | 0.44 | *0.05* | *0.05* | *ND* | *0.05* |
| 45 | R045F | 1.35 | 0.87 | 1.11 | 1.21 | 1.39 |
| 45 | R045G | 1.23 | 1.00 | 1.04 | 1.04 | 1.36 |
| 45 | R045H | 1.28 | 1.01 | 1.06 | 1.19 | 1.35 |
| 45 | R045I | 1.40 | 0.79 | 0.93 | 1.22 | 1.37 |
| 45 | R045K | 1.27 | 0.91 | 1.03 | 1.02 | 1.49 |
| 45 | R045L | 1.37 | 0.85 | 1.02 | 1.12 | 1.40 |
| 45 | R045M | 1.44 | 0.90 | 0.99 | 1.19 | 1.39 |
| 45 | R045N | 1.32 | 0.95 | 1.09 | 1.16 | 1.44 |
| 45 | R045P | 0.88 | 0.88 | 1.11 | 1.15 | 0.99 |
| 45 | R045Q | 1.35 | 1.08 | 0.93 | 1.08 | 1.55 |
| 45 | R045S | 1.28 | 1.04 | 1.07 | 1.10 | 1.63 |
| 45 | R045T | 1.32 | 0.96 | 1.07 | 1.20 | 1.40 |
| 45 | R045V | 1.32 | 0.85 | 1.09 | 1.06 | 1.39 |
| 45 | R045W | 1.30 | 0.94 | 1.00 | 1.04 | 1.40 |
| 45 | R045Y | 1.22 | 0.86 | 1.11 | 0.97 | 1.24 |
| 46 | G046C | 0.99 | 0.75 | 1.33 | 1.23 | 0.84 |
| 46 | G046D | 1.20 | 0.90 | 1.15 | 1.05 | 1.48 |
| 46 | G046E | 1.24 | 0.89 | 1.22 | 1.11 | 1.33 |
| 46 | G046F | 0.59 | *0.05* | 1.45 | 1.05 | 0.54 |
| 46 | G046H | 1.10 | 0.72 | 1.17 | 1.13 | 1.18 |
| 46 | G046I | 1.03 | 0.97 | 1.00 | 1.29 | 0.98 |
| 46 | G046K | 1.57 | 0.79 | 0.70 | 1.19 | 1.53 |
| 46 | G046L | 0.83 | 1.97 | 1.27 | 1.17 | 0.78 |
| 46 | G046M | 0.95 | 1.29 | 1.34 | 1.09 | 0.96 |
| 46 | G046N | 1.10 | 0.85 | 1.11 | 1.03 | 1.30 |
| 46 | G046P | 1.24 | 0.72 | 0.82 | 1.22 | 1.20 |
| 46 | G046Q | 1.08 | 0.99 | 1.08 | 1.04 | 1.18 |
| 46 | G046R | 1.19 | 0.92 | 0.83 | 1.27 | 1.35 |
| 46 | G046S | 1.45 | 0.84 | 1.00 | 1.08 | 1.50 |
| 46 | G046T | 1.26 | 0.89 | 1.01 | 1.03 | 1.33 |
| 46 | G046V | 1.20 | 0.86 | 1.13 | 1.05 | 1.17 |
| 46 | G046W | 0.79 | 25.56 | 0.96 | 0.90 | 0.71 |
| 47 | G047A | 0.89 | 1.76 | 1.11 | 0.76 | 0.94 |
| 47 | G047C | 0.58 | 6.57 | 1.19 | 0.61 | 0.45 |
| 47 | G047E | 0.69 | 1.91 | 1.54 | 0.60 | 0.55 |
| 47 | G047F | 0.92 | 0.87 | 1.15 | 0.59 | 0.79 |
| 47 | G047H | 0.35 | *0.05* | 1.10 | 0.77 | 0.26 |
| 47 | G047K | 0.61 | 5.82 | 0.96 | 0.57 | 0.54 |
| 47 | G047L | 0.46 | *0.05* | 1.21 | 0.50 | 0.34 |
| 47 | G047M | 0.62 | 1.38 | 1.09 | 0.54 | 0.44 |
| 47 | G047N | 0.83 | 0.97 | 1.24 | 0.61 | 0.75 |
| 47 | G047P | 0.20 | *0.05* | *0.05* | *ND* | *0.05* |
| 47 | G047Q | 0.73 | 1.13 | 1.34 | 0.44 | 0.76 |
| 47 | G047R | 1.07 | 1.13 | 0.94 | 0.99 | 1.04 |
| 47 | G047S | 1.02 | 1.06 | 1.13 | 0.71 | 1.03 |
| 47 | G047T | 0.80 | 0.76 | 1.27 | 0.57 | 0.57 |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 47 | G047W | 1.07 | 0.80 | 1.16 | 0.48 | 0.85 |
| 48 | A048C | 1.16 | 0.93 | 1.19 | 1.01 | 1.45 |
| 48 | A048E | 1.25 | 0.86 | 1.17 | 1.01 | 1.45 |
| 48 | A048F | 1.07 | 1.15 | 1.34 | 1.06 | 1.23 |
| 48 | A048G | 0.27 | *0.05* | 1.01 | 1.12 | 0.11 |
| 48 | A048H | 1.41 | 0.94 | 1.01 | 0.97 | 1.63 |
| 48 | A048I | 1.28 | 0.93 | 1.07 | 1.16 | 1.25 |
| 48 | A048K | 1.51 | 1.00 | 0.88 | 1.14 | 1.59 |
| 48 | A048L | 1.29 | 0.89 | 1.02 | 1.09 | 1.37 |
| 48 | A048M | 1.31 | 1.11 | 1.05 | 1.03 | 1.52 |
| 48 | A048N | 1.24 | 0.99 | 1.09 | 1.08 | 1.40 |
| 48 | A048P | 1.11 | 0.77 | 1.22 | 0.96 | 0.98 |
| 48 | A048Q | 1.32 | 1.15 | 0.99 | 1.05 | 1.55 |
| 48 | A048R | 1.38 | 1.00 | 0.86 | 1.12 | 1.74 |
| 48 | A048S | 1.26 | 1.08 | 1.13 | 0.94 | 1.51 |
| 48 | A048T | 1.51 | 0.85 | 1.02 | 1.14 | 1.46 |
| 48 | A048V | 1.09 | 0.84 | 1.11 | 0.97 | 1.05 |
| 48 | A048Y | 1.33 | 0.96 | 0.84 | 1.05 | 1.47 |
| 49 | S049A | 0.96 | 1.28 | 1.19 | 1.02 | 0.99 |
| 49 | S049E | 0.70 | *0.05* | 2.15 | 0.16 | 0.35 |
| 49 | S049F | 0.74 | *0.05* | 1.26 | 1.05 | 0.59 |
| 49 | S049G | 0.90 | 1.12 | 1.35 | 0.81 | 0.78 |
| 49 | S049H | 1.09 | 0.42 | 0.91 | 0.92 | 0.94 |
| 49 | S049K | 0.74 | *0.05* | 1.39 | 0.57 | 0.49 |
| 49 | S049L | 0.59 | *0.05* | 1.38 | 1.12 | 0.35 |
| 49 | S049M | 0.51 | *0.05* | 1.52 | 0.99 | 0.26 |
| 49 | S049P | 0.39 | *0.05* | 2.01 | 0.86 | 0.32 |
| 49 | S049Q | 0.70 | *0.05* | 1.48 | 0.62 | 0.39 |
| 49 | S049R | 0.80 | 3.76 | 1.45 | 0.70 | 0.65 |
| 49 | S049T | 0.93 | 1.81 | 1.16 | 0.94 | 1.23 |
| 50 | F050C | 0.79 | 1.24 | 1.29 | 1.11 | 0.79 |
| 50 | F050D | 0.25 | *0.05* | *0.05* | ND | *0.05* |
| 50 | F050G | 0.23 | *0.05* | *0.05* | ND | *0.05* |
| 50 | F050H | 1.04 | 1.03 | 1.16 | 1.23 | 0.92 |
| 50 | F050I | 0.81 | 1.27 | 1.16 | 1.12 | 0.67 |
| 50 | F050L | 1.13 | 1.12 | 0.99 | 1.21 | 1.07 |
| 50 | F050N | 0.24 | *0.05* | 1.10 | 0.99 | 0.14 |
| 50 | F050P | 0.32 | *0.05* | *0.05* | ND | *0.05* |
| 50 | F050T | 1.24 | 1.01 | 1.04 | 1.13 | 1.07 |
| 50 | F050V | 1.33 | 0.96 | 1.02 | 1.13 | 1.01 |
| 50 | F050Y | 1.12 | 0.95 | 1.01 | 1.14 | 1.10 |
| 51 | V051F | 1.45 | 0.82 | 0.84 | 0.94 | 1.15 |
| 51 | V051G | 0.61 | *0.05* | 1.58 | 0.89 | 0.40 |
| 51 | V051H | 1.27 | 0.98 | 0.93 | 1.06 | 1.36 |
| 51 | V051K | 0.92 | 0.68 | 1.03 | 0.93 | 1.35 |
| 51 | V051L | 1.55 | 0.83 | 1.12 | 0.93 | 1.28 |
| 51 | V051N | 0.96 | 0.91 | 1.11 | 0.80 | 0.75 |
| 51 | V051P | 0.34 | *0.05* | 2.34 | 0.81 | 0.13 |
| 51 | V051R | 1.07 | 0.73 | 1.05 | 1.03 | 1.33 |
| 51 | V051S | 0.96 | 1.31 | 1.44 | 0.98 | 0.89 |
| 51 | V051T | 1.49 | 0.84 | 0.83 | 0.98 | 1.53 |
| 51 | V051W | 1.20 | 1.00 | 1.07 | 0.93 | 0.46 |
| 52 | P052A | 1.23 | 1.36 | 1.08 | 0.94 | 1.45 |
| 52 | P052C | 0.82 | 1.43 | 1.11 | 0.95 | 0.91 |
| 52 | P052E | 1.06 | 1.20 | 1.21 | 1.04 | 1.21 |
| 52 | P052F | 0.92 | 1.79 | 1.11 | 0.88 | 1.36 |
| 52 | P052G | 0.95 | 1.72 | 1.08 | 0.93 | 1.24 |
| 52 | P052H | 1.11 | 1.30 | 0.98 | 1.05 | 1.36 |
| 52 | P052I | 1.00 | 1.45 | 1.01 | 1.02 | 1.36 |
| 52 | P052L | 1.07 | 1.31 | 0.98 | 0.99 | 1.32 |
| 52 | P052M | 0.80 | 2.68 | 1.11 | 1.06 | 1.04 |
| 52 | P052N | 1.21 | 1.14 | 1.07 | 1.05 | 1.39 |
| 52 | P052Q | 1.15 | 1.36 | 1.08 | 1.00 | 1.55 |
| 52 | P052R | 1.12 | 1.28 | 0.85 | 0.96 | 1.61 |
| 52 | P052T | 1.07 | 1.51 | 1.18 | 0.99 | 1.34 |
| 52 | P052V | 1.00 | 1.66 | 1.10 | 1.03 | 1.25 |
| 52 | P052W | 1.00 | 1.74 | 0.89 | 0.94 | 1.31 |
| 52 | P052Y | 1.04 | 1.52 | 1.01 | 0.99 | 1.30 |
| 53 | G053A | 1.44 | 0.91 | 1.06 | 0.91 | 1.38 |
| 53 | G053C | 0.88 | 0.75 | 1.37 | 0.96 | 0.85 |
| 53 | G053D | 1.19 | 1.13 | 1.27 | 1.05 | 1.05 |
| 53 | G053E | 1.20 | 0.79 | 1.28 | 1.01 | 1.04 |
| 53 | G053H | 1.25 | 1.11 | 0.86 | 1.00 | 1.35 |
| 53 | G053I | 1.43 | 0.18 | 0.88 | 0.45 | 0.34 |
| 53 | G053K | 1.35 | 0.95 | 0.94 | 0.93 | 1.77 |
| 53 | G053L | 1.16 | 0.87 | 1.08 | 0.95 | 1.10 |
| 53 | G053M | 1.38 | 0.92 | 1.05 | 0.92 | 1.41 |
| 53 | G053P | 0.92 | 0.83 | 1.23 | 0.35 | 0.59 |
| 53 | G053Q | 1.34 | 0.96 | 1.06 | 0.89 | 1.54 |
| 53 | G053R | 1.37 | 0.82 | 0.86 | 1.00 | 1.69 |
| 53 | G053S | 1.55 | 0.88 | 0.89 | 0.99 | 1.52 |
| 53 | G053T | 1.36 | 0.84 | 0.97 | 0.98 | 1.36 |
| 53 | G053V | 0.99 | 0.81 | 1.18 | 0.46 | 0.74 |
| 53 | G053W | 1.28 | 0.97 | 0.88 | 0.92 | 1.10 |
| 53 | G053Y | 1.20 | 0.87 | 0.95 | 0.83 | 1.23 |
| 54 | E054A | 1.04 | 1.08 | 0.89 | 0.90 | 1.08 |
| 54 | E054C | 0.83 | 0.97 | 1.36 | 1.00 | 0.71 |
| 54 | E054D | 1.25 | 0.95 | 0.95 | 1.10 | 1.54 |
| 54 | E054F | 1.34 | 1.00 | 0.93 | 0.85 | 1.03 |
| 54 | E054G | 0.77 | 1.94 | 1.20 | 0.56 | 0.58 |
| 54 | E054H | 1.04 | 0.90 | 0.96 | 0.95 | 0.99 |
| 54 | E054I | 1.25 | 0.67 | 1.07 | 0.77 | 0.86 |
| 54 | E054K | 1.09 | 0.91 | 0.89 | 0.79 | 0.89 |
| 54 | E054L | 1.13 | 0.75 | 0.95 | 0.71 | 0.79 |
| 54 | E054M | 0.98 | 1.04 | 1.03 | 0.85 | 0.91 |
| 54 | E054N | 1.08 | 0.88 | 1.07 | 1.00 | 1.07 |
| 54 | E054P | 1.28 | 0.73 | 1.00 | 0.80 | 0.97 |
| 54 | E054Q | 1.41 | 0.75 | 0.87 | 1.02 | 1.74 |
| 54 | E054R | 1.09 | 0.65 | 0.79 | 0.44 | 0.81 |
| 54 | E054S | 1.41 | 0.92 | 0.85 | 0.91 | 1.33 |
| 54 | E054V | 1.10 | 0.73 | 0.91 | 0.80 | 1.16 |
| 54 | E054W | 0.91 | 0.72 | 0.99 | 0.50 | 0.63 |
| 54 | E054Y | 1.25 | 0.69 | 0.78 | 0.65 | 1.00 |
| 55 | P055A | 0.22 | *0.05* | 1.71 | 1.11 | 0.08 |
| 55 | P055C | 1.07 | 0.65 | 1.16 | 1.01 | 1.27 |
| 55 | P055E | 1.22 | 0.92 | 0.99 | 1.09 | 1.37 |
| 55 | P055F | 1.04 | 0.85 | 1.34 | 0.38 | 0.76 |
| 55 | P055G | 1.23 | 1.20 | 0.95 | 0.99 | 1.56 |
| 55 | P055H | 1.22 | 1.42 | 1.10 | 1.06 | 1.38 |
| 55 | P055I | 1.30 | 0.84 | 0.90 | 0.71 | 1.20 |
| 55 | P055K | 1.41 | 1.09 | 0.85 | 1.01 | 1.65 |
| 55 | P055L | 1.16 | 0.87 | 1.16 | 0.87 | 1.28 |
| 55 | P055M | 1.34 | 0.90 | 1.10 | 0.74 | 1.27 |
| 55 | P055N | 1.41 | 0.77 | 0.88 | *0.05* | 1.61 |
| 55 | P055Q | 1.31 | 0.82 | 0.85 | 0.85 | 1.24 |
| 55 | P055R | 2.15 | 0.49 | 0.59 | ND | *0.05* |
| 55 | P055S | 1.32 | 1.08 | 1.03 | 0.99 | 1.45 |
| 55 | P055T | 1.12 | 0.99 | 1.07 | 1.03 | 1.27 |
| 55 | P055V | 0.46 | *0.05* | *0.05* | ND | *0.05* |
| 55 | P055W | 1.20 | 0.84 | 1.07 | 0.80 | 1.22 |
| 55 | P055Y | 0.92 | 0.60 | 1.38 | 0.39 | 0.70 |
| 56 | S056A | 0.86 | 1.76 | 1.19 | 1.05 | 0.93 |
| 56 | S056C | 1.10 | 1.01 | 1.08 | 0.97 | 1.28 |
| 56 | S056D | 1.20 | 0.99 | 1.12 | 1.20 | 1.26 |
| 56 | S056E | 1.08 | 0.98 | 1.10 | 0.98 | 1.30 |
| 56 | S056F | 0.45 | *0.05* | *0.05* | ND | *0.05* |
| 56 | S056G | 0.43 | *0.05* | *0.05* | ND | *0.05* |
| 56 | S056H | 1.06 | 1.12 | 1.02 | 1.13 | 1.06 |
| 56 | S056I | 1.14 | 0.81 | 1.03 | 0.94 | 1.33 |
| 56 | S056M | 1.05 | 1.62 | 0.89 | 1.09 | 0.16 |
| 56 | S056N | 1.14 | 1.11 | 1.08 | 1.09 | 1.25 |
| 56 | S056P | 1.19 | 0.99 | 1.11 | 0.99 | 1.02 |
| 56 | S056Q | 1.18 | 0.81 | 1.03 | 0.85 | 1.38 |
| 56 | S056R | 1.99 | 0.48 | 0.57 | ND | *0.05* |
| 56 | S056T | 0.80 | 6.42 | 1.22 | 0.89 | 1.01 |
| 56 | S056V | 1.15 | 0.40 | 0.71 | ND | *0.05* |
| 57 | T057A | 1.08 | 1.18 | 1.11 | 0.59 | 1.38 |
| 57 | T057C | 0.84 | 1.28 | 1.35 | 1.00 | 1.00 |
| 57 | T057E | 1.35 | 1.14 | 1.04 | 0.97 | 1.65 |
| 57 | T057F | 0.92 | 1.13 | 1.26 | 0.95 | 1.21 |
| 57 | T057G | 1.10 | 1.17 | 1.08 | 0.85 | 1.12 |
| 57 | T057H | 1.38 | 0.99 | 1.05 | 1.07 | 1.65 |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 57 | T057I | 1.47 | 0.92 | 0.90 | 0.96 | 1.72 |
| 57 | T057K | 1.08 | 1.03 | 1.05 | 0.41 | 1.05 |
| 57 | T057L | 1.52 | 0.95 | 0.96 | 1.07 | 1.50 |
| 57 | T057M | 1.19 | 1.09 | 0.97 | 0.91 | 1.30 |
| 57 | T057N | 1.45 | 0.86 | 1.00 | 0.96 | 1.63 |
| 57 | T057P | 1.36 | 0.88 | 0.93 | 1.03 | 1.73 |
| 57 | T057Q | 1.31 | 0.92 | 0.95 | 0.90 | 1.38 |
| 57 | T057R | 1.34 | 0.90 | 0.96 | 1.18 | 1.44 |
| 57 | T057S | 0.99 | 1.36 | 1.17 | 1.07 | 1.20 |
| 57 | T057V | 1.39 | 0.90 | 0.91 | 0.91 | 1.60 |
| 57 | T057W | 1.65 | 0.85 | 0.85 | 1.11 | 1.91 |
| 57 | T057Y | 1.38 | 0.97 | 0.86 | 0.95 | 1.22 |
| 59 | Q059A | 1.02 | 1.03 | 1.11 | 0.86 | 1.30 |
| 59 | Q059C | 0.74 | 1.68 | 1.23 | 0.94 | 0.86 |
| 59 | Q059D | 0.82 | 1.66 | 1.32 | 0.96 | 0.92 |
| 59 | Q059E | 0.79 | 1.41 | 1.48 | 1.14 | 0.97 |
| 59 | Q059F | 1.13 | 0.97 | 1.08 | 0.77 | 1.25 |
| 59 | Q059G | 1.42 | 0.83 | 0.79 | 0.88 | 1.68 |
| 59 | Q059I | 1.50 | 0.92 | 0.85 | 0.88 | 1.66 |
| 59 | Q059K | 0.67 | 0.94 | *0.05* | ND | *0.05* |
| 59 | Q059L | 1.40 | 0.95 | 0.96 | 0.92 | 1.45 |
| 59 | Q059M | 1.45 | 0.96 | 1.05 | 0.82 | 1.62 |
| 59 | Q059N | 1.43 | 0.97 | 0.95 | 0.96 | 1.67 |
| 59 | Q059P | 1.49 | 0.89 | 1.04 | 0.80 | 1.47 |
| 59 | Q059R | 1.38 | 0.93 | 0.77 | 1.16 | 1.62 |
| 59 | Q059S | 1.39 | 0.96 | 0.97 | 0.96 | 1.66 |
| 59 | Q059T | 1.49 | 0.88 | 0.93 | 0.86 | 1.66 |
| 59 | Q059V | 1.65 | 0.81 | 0.92 | 0.86 | 1.61 |
| 59 | Q059W | 1.45 | 0.86 | 0.89 | 0.90 | 1.43 |
| 59 | Q059Y | 1.44 | 0.88 | 1.00 | 0.78 | 1.67 |
| 60 | D060A | 0.74 | 2.20 | 1.25 | *0.05* | 0.28 |
| 60 | D060C | 0.63 | 1.07 | 1.42 | 0.16 | 0.17 |
| 60 | D060E | 0.37 | *0.05* | *0.05* | ND | *0.05* |
| 60 | D060F | 0.68 | 1.06 | 1.07 | 0.06 | 0.20 |
| 60 | D060G | 0.65 | 3.32 | 1.34 | 0.08 | 0.23 |
| 60 | D060K | 0.47 | *0.05* | 1.15 | *0.05* | 0.14 |
| 60 | D060L | 0.64 | 2.31 | 1.23 | 0.07 | 0.21 |
| 60 | D060M | 0.68 | 3.41 | 1.32 | *0.05* | 0.22 |
| 60 | D060N | 0.58 | *0.05* | 1.51 | 0.09 | 0.27 |
| 60 | D060P | 0.75 | 1.46 | 1.12 | 0.08 | 0.25 |
| 60 | D060Q | 0.59 | *0.05* | 1.24 | *0.05* | 0.23 |
| 60 | D060R | 0.35 | *0.05* | 0.66 | 0.12 | 0.06 |
| 60 | D060S | 0.86 | 1.19 | 1.26 | *0.05* | 0.39 |
| 60 | D060T | 0.52 | *0.05* | 1.42 | *0.05* | 0.24 |
| 60 | D060V | 0.83 | 0.65 | 1.10 | 0.06 | 0.28 |
| 60 | D060W | 0.59 | *0.05* | 1.04 | *0.05* | 0.28 |
| 60 | D060Y | 0.66 | 1.77 | 1.33 | 0.07 | 0.21 |
| 61 | G061A | 1.42 | 0.99 | 0.98 | 1.02 | 1.69 |
| 61 | G061C | 1.14 | 0.88 | 1.07 | 0.97 | 1.52 |
| 61 | G061D | 1.48 | 0.90 | 1.00 | 1.13 | 1.74 |
| 61 | G061F | 1.45 | 0.98 | 0.91 | 1.01 | 1.87 |
| 61 | G061H | 1.39 | 0.89 | 0.77 | 1.08 | 1.74 |
| 61 | G061I | 1.42 | 0.97 | 0.91 | 1.08 | 2.06 |
| 61 | G061L | 1.33 | 0.97 | 0.99 | 1.07 | 1.43 |
| 61 | G061M | 1.44 | 0.87 | 1.01 | 1.08 | 1.79 |
| 61 | G061N | 1.48 | 0.91 | 0.86 | 1.03 | 1.79 |
| 61 | G061P | 1.23 | 0.80 | 0.89 | 1.02 | 1.67 |
| 61 | G061R | 1.58 | 0.84 | 0.69 | 1.00 | 1.81 |
| 61 | G061S | 0.97 | 1.42 | 1.06 | 1.05 | 1.31 |
| 61 | G061T | 0.88 | 1.51 | 1.14 | 1.09 | 1.45 |
| 61 | G061V | 0.90 | 1.35 | 1.07 | 1.02 | 1.48 |
| 61 | G061Y | 0.92 | 1.06 | 1.02 | 0.95 | 1.12 |
| 62 | N062C | 1.51 | 0.94 | 1.02 | 1.09 | 1.25 |
| 62 | N062E | 1.79 | 1.01 | 1.09 | 1.10 | 1.54 |
| 62 | N062F | 0.90 | 1.18 | 1.16 | 0.89 | 1.00 |
| 62 | N062G | 1.38 | 1.06 | 1.08 | 0.62 | 0.82 |
| 62 | N062H | 1.14 | 1.21 | 1.21 | 1.07 | 1.26 |
| 62 | N062I | 1.70 | 0.98 | 0.99 | 1.01 | 1.26 |
| 62 | N062K | 1.94 | 0.90 | 0.73 | 0.98 | 1.21 |
| 62 | N062L | 1.10 | 1.54 | 1.04 | 0.92 | 1.92 |
| 62 | N062M | 1.30 | 1.08 | 1.06 | 0.98 | 2.03 |
| 62 | N062P | 1.20 | 1.04 | 1.19 | 0.59 | 0.65 |
| 62 | N062Q | 1.46 | 1.22 | 1.10 | 0.93 | 1.68 |
| 62 | N062R | 1.90 | 1.05 | 0.73 | 0.95 | 0.94 |
| 62 | N062S | 1.17 | 1.46 | 1.17 | 0.90 | 1.64 |
| 62 | N062T | 2.21 | 0.84 | 0.89 | 0.94 | 3.23 |
| 62 | N062V | 1.73 | 1.03 | 1.03 | 1.05 | 1.30 |
| 62 | N062Y | 1.31 | 0.96 | 1.05 | 0.73 | 1.30 |
| 63 | G063A | 1.20 | 1.06 | 1.28 | 0.33 | 1.37 |
| 63 | G063C | 0.91 | 0.58 | 1.35 | 0.39 | 0.80 |
| 63 | G063D | 0.89 | 0.80 | 1.33 | 0.24 | 0.79 |
| 63 | G063E | 1.23 | 0.84 | 1.30 | 0.43 | 1.00 |
| 63 | G063F | 0.90 | 1.01 | 1.11 | *0.05* | 0.60 |
| 63 | G063H | 1.10 | 0.77 | 1.21 | 0.11 | 0.95 |
| 63 | G063I | 0.44 | *0.05* | 1.44 | *0.05* | 0.46 |
| 63 | G063K | 1.22 | 0.80 | 0.83 | *0.05* | 1.59 |
| 63 | G063M | 0.87 | 1.11 | 1.28 | *0.05* | 0.88 |
| 63 | G063P | 0.44 | *0.05* | 1.46 | *0.05* | 0.22 |
| 63 | G063Q | 1.07 | 1.06 | 1.14 | 0.07 | 0.99 |
| 63 | G063R | 1.07 | 0.98 | 0.87 | *0.05* | 1.28 |
| 63 | G063S | 1.19 | 0.90 | 1.21 | 0.31 | 1.31 |
| 63 | G063T | 0.66 | 3.06 | 1.49 | 0.09 | 0.62 |
| 63 | G063V | 0.50 | *0.05* | 1.46 | *0.05* | 0.53 |
| 63 | G063W | 1.37 | 0.81 | 0.87 | *0.05* | 2.28 |
| 64 | H064D | 0.51 | *0.05* | *0.05* | ND | *0.05* |
| 64 | H064E | 0.56 | *0.05* | *0.05* | ND | *0.05* |
| 64 | H064F | 0.51 | *0.05* | *0.05* | ND | *0.05* |
| 64 | H064G | 0.40 | *0.05* | *0.05* | ND | *0.05* |
| 64 | H064I | 0.55 | *0.05* | *0.05* | ND | *0.05* |
| 64 | H064K | 0.53 | *0.05* | *0.05* | ND | *0.05* |
| 64 | H064L | 0.40 | *0.05* | *0.05* | ND | *0.05* |
| 64 | H064M | 0.44 | *0.05* | *0.05* | ND | *0.05* |
| 64 | H064N | 0.61 | *0.05* | *0.05* | ND | *0.05* |
| 64 | H064Q | 0.77 | *0.05* | *0.05* | ND | *0.05* |
| 64 | H064R | 0.44 | *0.05* | *0.05* | ND | *0.05* |
| 64 | H064S | 0.55 | *0.05* | *0.05* | ND | *0.05* |
| 64 | H064T | 0.53 | *0.05* | *0.05* | ND | *0.05* |
| 64 | H064W | 0.40 | *0.05* | *0.05* | ND | *0.05* |
| 65 | G065C | 0.39 | *0.05* | *0.05* | ND | *0.05* |
| 65 | G065F | 0.46 | *0.05* | *0.05* | ND | *0.05* |
| 65 | G065H | 0.36 | *0.05* | *0.05* | ND | *0.05* |
| 65 | G065K | 0.38 | *0.05* | *0.05* | ND | *0.05* |
| 65 | G065L | 0.37 | *0.05* | *0.05* | ND | *0.05* |
| 65 | G065M | 0.42 | *0.05* | *0.05* | ND | *0.05* |
| 65 | G065N | 0.37 | *0.05* | *0.05* | ND | *0.05* |
| 65 | G065R | 0.39 | *0.05* | *0.05* | ND | *0.05* |
| 65 | G065T | 0.35 | *0.05* | *0.05* | ND | *0.05* |
| 65 | G065W | 0.37 | *0.05* | *0.05* | ND | *0.05* |
| 66 | T066A | 0.25 | *0.05* | 1.76 | 0.09 | 0.06 |
| 66 | T066C | 0.34 | *0.05* | 2.11 | 0.28 | 0.17 |
| 66 | T066D | 0.28 | *0.05* | 1.69 | 0.12 | 0.09 |
| 66 | T066E | 0.25 | *0.05* | 1.79 | ND | *0.05* |
| 66 | T066F | 0.21 | *0.05* | *0.05* | ND | *0.05* |
| 66 | T066I | 0.23 | *0.05* | 2.39 | 0.13 | 0.09 |
| 66 | T066K | 0.17 | *0.05* | 2.46 | 1.03 | 0.12 |
| 66 | T066L | 0.23 | *0.05* | 1.85 | *0.05* | 0.08 |
| 66 | T066N | 0.21 | *0.05* | 1.28 | *0.05* | 0.09 |
| 66 | T066Q | 0.22 | *0.05* | 2.31 | *0.05* | 0.13 |
| 66 | T066R | 0.36 | *0.05* | *0.05* | ND | *0.05* |
| 66 | T066S | 1.07 | 1.11 | 1.13 | 0.66 | 1.13 |
| 66 | T066W | 0.32 | *0.05* | *0.05* | ND | *0.05* |
| 66 | T066Y | 0.25 | *0.05* | *0.05* | ND | *0.05* |
| 67 | H067A | 1.47 | 0.56 | 0.49 | 0.59 | 0.30 |
| 67 | H067C | 1.24 | 0.73 | 0.59 | 0.07 | 0.22 |
| 67 | H067D | 0.26 | *0.05* | *0.05* | ND | *0.05* |
| 67 | H067E | 0.54 | *0.05* | 0.58 | ND | *0.05* |
| 67 | H067F | 0.38 | *0.05* | 1.73 | *0.05* | 0.15 |
| 67 | H067G | 0.65 | *0.05* | 0.79 | ND | *0.05* |
| 67 | H067I | 0.67 | *0.05* | 0.70 | ND | *0.05* |
| 67 | H067L | 1.71 | 0.40 | 0.32 | 0.37 | 0.08 |
| 67 | H067M | 1.82 | 0.39 | 0.40 | 0.77 | 0.12 |
| 67 | H067N | 0.40 | *0.05* | 1.12 | *0.05* | 0.10 |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 67 | H067P | 1.85 | 0.43 | 0.43 | 0.25 | 0.37 |
| 67 | H067Q | 1.83 | 0.43 | 0.34 | 0.28 | 0.11 |
| 67 | H067R | 1.59 | 0.34 | 0.21 | *ND* | *0.05* |
| 67 | H067S | 1.54 | 0.58 | 0.54 | 0.46 | 0.32 |
| 67 | H067T | 1.20 | 0.84 | 0.61 | *0.05* | 0.20 |
| 67 | H067V | 0.54 | *0.05* | 1.15 | *ND* | *0.05* |
| 67 | H067W | 0.18 | *0.05* | *0.05* | *ND* | *0.05* |
| 68 | V068A | 1.55 | 0.72 | 0.78 | 0.38 | 0.33 |
| 68 | V068C | 0.59 | *0.05* | 1.87 | 0.63 | 0.66 |
| 68 | V068D | 0.25 | *0.05* | 1.71 | *ND* | *0.05* |
| 68 | V068E | 1.22 | 0.34 | 0.87 | *ND* | *0.05* |
| 68 | V068F | 0.43 | *0.05* | *0.05* | *ND* | *0.05* |
| 68 | V068G | 0.64 | *0.05* | 1.55 | *ND* | *0.05* |
| 68 | V068H | 1.41 | *0.05* | *0.05* | *ND* | *0.05* |
| 68 | V068I | 1.23 | 0.91 | 1.07 | 0.96 | 0.75 |
| 68 | V068K | 0.46 | *0.05* | *0.05* | *ND* | *0.05* |
| 68 | V068L | 1.37 | 0.62 | 0.88 | 0.87 | 0.18 |
| 68 | V068M | 1.26 | 0.68 | 0.74 | 0.27 | 0.08 |
| 68 | V068N | 1.77 | 0.28 | 0.71 | *ND* | *0.05* |
| 68 | V068P | 0.33 | *0.05* | *0.05* | *ND* | *0.05* |
| 68 | V068Q | 2.13 | 0.16 | 0.38 | *ND* | *0.05* |
| 68 | V068R | 0.37 | *0.05* | *0.05* | *ND* | *0.05* |
| 68 | V068S | 1.80 | 0.57 | 0.71 | 0.27 | 0.11 |
| 68 | V068T | 1.10 | 1.05 | 1.06 | 0.30 | 0.56 |
| 68 | V068W | 0.46 | *0.05* | *0.05* | *ND* | *0.05* |
| 68 | V068Y | 0.40 | *0.05* | *0.05* | *ND* | *0.05* |
| 69 | A069C | 0.49 | *0.05* | 1.48 | 0.59 | 0.29 |
| 69 | A069D | 0.33 | *0.05* | *0.05* | *ND* | *0.05* |
| 69 | A069E | 0.28 | *0.05* | 1.24 | 0.87 | 0.32 |
| 69 | A069F | 0.29 | *0.05* | 1.25 | 0.22 | 0.16 |
| 69 | A069G | 0.99 | 1.22 | 1.09 | 0.86 | 1.12 |
| 69 | A069I | 0.23 | *0.05* | 1.48 | 0.25 | 0.07 |
| 69 | A069K | 0.20 | *0.05* | *0.05* | *ND* | *0.05* |
| 69 | A069L | 0.19 | *0.05* | 1.33 | *ND* | *0.05* |
| 69 | A069M | 0.54 | *0.05* | 1.49 | *ND* | *0.05* |
| 69 | A069N | 0.51 | *0.05* | 1.24 | 0.98 | 0.54 |
| 69 | A069P | 0.26 | *0.05* | *0.05* | *ND* | *0.05* |
| 69 | A069Q | 0.21 | *0.05* | *0.05* | *ND* | *0.05* |
| 69 | A069R | 0.19 | *0.05* | *0.05* | *ND* | *0.05* |
| 69 | A069S | 1.10 | 1.13 | 1.08 | 0.90 | 1.21 |
| 69 | A069T | 0.91 | 1.06 | 1.14 | 1.00 | 0.97 |
| 69 | A069V | 0.40 | *0.05* | 1.40 | 0.67 | 0.46 |
| 69 | A069W | 0.51 | *0.05* | 1.32 | 0.48 | 0.35 |
| 69 | A069Y | 0.19 | *0.05* | 0.76 | *0.05* | 0.08 |
| 70 | G070C | 0.40 | *0.05* | *0.05* | *ND* | *0.05* |
| 70 | G070D | 0.33 | *0.05* | *0.05* | *ND* | *0.05* |
| 70 | G070E | 0.42 | *0.05* | *0.05* | *ND* | *0.05* |
| 70 | G070I | 0.40 | *0.05* | *0.05* | *ND* | *0.05* |
| 70 | G070K | 0.46 | *0.05* | *0.05* | *ND* | *0.05* |
| 70 | G070N | 0.28 | *0.05* | *0.05* | *ND* | *0.05* |
| 70 | G070P | 0.50 | *0.05* | *0.05* | *ND* | *0.05* |
| 70 | G070Q | 0.30 | *0.05* | *0.05* | *ND* | *0.05* |
| 70 | G070R | 0.48 | *0.05* | *0.05* | *ND* | *0.05* |
| 70 | G070S | 0.35 | *0.05* | *0.05* | *ND* | *0.05* |
| 70 | G070V | 0.35 | *0.05* | *0.05* | *ND* | *0.05* |
| 70 | G070Y | 0.43 | *0.05* | *0.05* | *ND* | *0.05* |
| 71 | T071A | 1.03 | 1.43 | 1.21 | *0.05* | 0.91 |
| 71 | T071C | 0.66 | 2.03 | 1.65 | *0.05* | 0.64 |
| 71 | T071D | 0.18 | *0.05* | 1.17 | *ND* | *0.05* |
| 71 | T071E | 0.13 | *0.05* | 1.15 | *0.05* | 0.06 |
| 71 | T071F | 0.18 | *0.05* | *0.05* | *ND* | *0.05* |
| 71 | T071G | 0.63 | *0.05* | 1.58 | 0.06 | 0.59 |
| 71 | T071H | 0.21 | *0.05* | *0.05* | *ND* | *0.05* |
| 71 | T071I | 1.11 | 1.26 | 0.97 | 0.72 | 1.05 |
| 71 | T071K | 0.15 | *0.05* | *0.05* | *ND* | *0.05* |
| 71 | T071L | 0.67 | 1.13 | 1.04 | 0.12 | 0.52 |
| 71 | T071M | 0.30 | *0.05* | 2.00 | *0.05* | 0.20 |
| 71 | T071N | 0.95 | 1.75 | 1.20 | *0.05* | 1.44 |
| 71 | T071P | 0.57 | *0.05* | 1.59 | *0.05* | 0.67 |
| 71 | T071R | 0.19 | *0.05* | *0.05* | *ND* | *0.05* |
| 71 | T071S | 0.74 | 5.02 | 1.36 | 0.71 | 0.89 |
| 71 | T071V | 1.11 | 1.17 | 1.03 | 0.57 | 0.88 |
| 71 | T071W | 0.26 | *0.05* | 1.88 | 0.60 | 0.18 |
| 71 | T071Y | 0.31 | *0.05* | *0.05* | *ND* | *0.05* |
| 72 | I072C | 0.76 | 1.96 | 1.21 | 0.93 | 0.80 |
| 72 | I072D | 0.27 | *0.05* | *0.05* | *ND* | *0.05* |
| 72 | I072E | 0.25 | *0.05* | *0.05* | *ND* | *0.05* |
| 72 | I072F | 1.17 | 1.17 | 0.84 | 0.72 | 1.23 |
| 72 | I072G | 0.42 | *0.05* | *0.05* | *ND* | *0.05* |
| 72 | I072H | 0.34 | *0.05* | 1.26 | 0.74 | 0.28 |
| 72 | I072K | 0.22 | *0.05* | *0.05* | *ND* | *0.05* |
| 72 | I072L | 1.48 | 0.89 | 0.87 | 0.98 | 1.24 |
| 72 | I072M | 1.03 | 1.41 | 1.01 | 0.80 | 1.05 |
| 72 | I072N | 0.33 | *0.05* | 1.29 | 0.71 | 0.26 |
| 72 | I072Q | 0.38 | *0.05* | 1.23 | 0.77 | 0.32 |
| 72 | I072R | 0.48 | *0.05* | 0.27 | *ND* | *0.05* |
| 72 | I072S | 0.69 | 1.71 | 1.19 | 0.73 | 0.78 |
| 72 | I072T | 1.38 | 1.02 | 0.94 | 0.95 | 1.09 |
| 72 | I072V | 1.19 | 1.07 | 1.10 | 1.12 | 1.24 |
| 72 | I072W | 0.26 | *0.05* | 1.17 | 0.47 | 0.18 |
| 73 | A073C | 1.00 | 1.51 | 1.02 | 0.81 | 1.30 |
| 73 | A073D | 0.88 | 1.50 | 1.13 | 0.32 | 1.03 |
| 73 | A073E | 1.09 | 1.17 | 1.03 | 0.42 | 1.33 |
| 73 | A073H | 0.90 | 1.30 | 1.18 | 0.26 | 1.23 |
| 73 | A073I | 0.26 | *0.05* | *0.05* | *ND* | *0.05* |
| 73 | A073K | 0.97 | 1.11 | 0.85 | 0.24 | 1.09 |
| 73 | A073L | 1.02 | 1.04 | 1.12 | 0.48 | 1.10 |
| 73 | A073M | 0.55 | *0.05* | *0.05* | *ND* | *0.05* |
| 73 | A073N | 1.27 | 1.08 | 0.93 | 0.23 | 1.39 |
| 73 | A073R | 0.18 | *0.05* | 3.24 | 0.20 | 0.21 |
| 73 | A073S | 0.97 | 1.18 | 1.17 | 1.02 | 1.11 |
| 73 | A073T | 1.27 | 1.10 | 0.87 | 0.74 | 1.55 |
| 73 | A073V | 1.16 | 1.09 | 1.06 | 0.63 | 1.49 |
| 73 | A073W | 0.24 | *0.05* | *0.05* | *ND* | *0.05* |
| 74 | A074C | 1.12 | 1.08 | 0.98 | *0.05* | 1.44 |
| 74 | A074D | 0.34 | *0.05* | *0.05* | *ND* | *0.05* |
| 74 | A074E | 0.59 | *0.05* | *0.05* | *ND* | *0.05* |
| 74 | A074F | 0.34 | *0.05* | *0.05* | *ND* | *0.05* |
| 74 | A074I | 0.43 | *0.05* | *0.05* | *ND* | *0.05* |
| 74 | A074L | 0.33 | *0.05* | *0.05* | *ND* | *0.05* |
| 74 | A074M | 0.23 | *0.05* | *0.05* | *ND* | *0.05* |
| 74 | A074N | 0.23 | *0.05* | *0.05* | *ND* | *0.05* |
| 74 | A074P | 0.24 | *0.05* | *0.05* | *ND* | *0.05* |
| 74 | A074Q | 0.53 | *0.05* | *0.05* | *ND* | *0.05* |
| 74 | A074R | 0.36 | *0.05* | *0.05* | *ND* | *0.05* |
| 74 | A074S | 1.15 | 1.10 | 1.03 | 0.07 | 1.24 |
| 74 | A074T | 0.47 | *0.05* | 1.10 | *0.05* | 0.59 |
| 74 | A074V | 0.19 | *0.05* | *0.05* | *ND* | *0.05* |
| 74 | A074W | 0.26 | *0.05* | *0.05* | *ND* | *0.05* |
| 75 | L075A | 0.88 | 2.41 | 1.23 | *0.05* | 1.25 |
| 75 | L075C | 0.52 | *0.05* | 1.50 | 0.32 | 0.83 |
| 75 | L075D | 0.77 | 3.90 | 1.71 | *0.05* | 1.23 |
| 75 | L075E | 0.77 | 4.37 | 1.70 | *0.05* | 1.10 |
| 75 | L075F | 0.72 | 3.86 | 1.47 | *0.05* | 1.02 |
| 75 | L075G | 0.72 | 4.00 | 1.53 | *0.05* | 0.40 |
| 75 | L075H | 0.82 | 2.72 | 1.31 | *0.05* | 0.98 |
| 75 | L075I | 1.12 | 1.13 | 1.19 | 0.11 | 1.43 |
| 75 | L075M | 1.01 | 1.50 | 1.24 | 0.09 | 1.36 |
| 75 | L075N | 1.04 | 1.52 | 1.08 | *0.05* | 1.52 |
| 75 | L075P | 0.80 | 2.62 | 1.31 | *0.05* | 1.34 |
| 75 | L075Q | 1.03 | 1.65 | 1.22 | *0.05* | 1.40 |
| 75 | L075R | 0.94 | 1.94 | 1.15 | *0.05* | 1.32 |
| 75 | L075S | 0.89 | 2.48 | 1.35 | *0.05* | 1.29 |
| 75 | L075T | 0.68 | 1.17 | 1.43 | *0.05* | 1.11 |
| 75 | L075V | 0.99 | 1.56 | 1.28 | *0.05* | 1.34 |
| 75 | L075W | 0.55 | *0.05* | 1.73 | *0.05* | 0.84 |
| 76 | N076C | 0.60 | 1.56 | 1.15 | 0.07 | 0.74 |
| 76 | N076D | 1.43 | 1.03 | 0.99 | 1.19 | 1.64 |
| 76 | N076E | 1.41 | 1.05 | 1.09 | 0.22 | 1.66 |
| 76 | N076F | 0.81 | 1.45 | 0.94 | *0.05* | 1.05 |
| 76 | N076G | 1.10 | 1.28 | 0.93 | *0.05* | 1.41 |
| 76 | N076H | 1.40 | 0.97 | 0.97 | 0.49 | 1.47 |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 76 | N076I | 0.65 | 3.73 | 1.16 | *0.05* | 0.74 |
| 76 | N076K | 1.33 | 1.08 | 0.89 | *0.05* | 1.40 |
| 76 | N076L | 0.78 | 0.91 | 1.07 | *0.05* | 0.81 |
| 76 | N076M | 0.96 | 1.01 | 1.00 | *0.05* | 0.99 |
| 76 | N076Q | 1.62 | 0.87 | 0.96 | 0.12 | 1.70 |
| 76 | N076R | 1.30 | 0.97 | 0.72 | *0.05* | 1.27 |
| 76 | N076S | 1.29 | 0.97 | 0.87 | *0.05* | 1.36 |
| 76 | N076T | 1.07 | 0.92 | 1.04 | *0.05* | 1.08 |
| 76 | N076W | 1.09 | 1.15 | 0.91 | *0.05* | 1.22 |
| 76 | N076Y | 0.93 | 1.15 | 1.12 | *0.05* | 1.01 |
| 77 | N077A | 0.21 | *0.05* | 1.81 | *0.05* | 0.11 |
| 77 | N077C | 0.23 | *0.05* | 2.82 | 0.07 | 0.17 |
| 77 | N077D | 0.86 | 2.01 | 1.46 | *0.05* | 1.30 |
| 77 | N077E | 0.22 | *0.05* | 2.55 | *0.05* | 0.14 |
| 77 | N077F | 0.20 | *0.05* | 2.11 | *0.05* | 0.14 |
| 77 | N077G | 0.25 | *0.05* | 2.04 | *0.05* | 0.27 |
| 77 | N077H | 0.24 | *0.05* | 2.37 | *0.05* | 0.19 |
| 77 | N077K | 0.17 | *0.05* | 2.60 | *0.05* | 0.16 |
| 77 | N077L | 0.17 | *0.05* | 2.22 | *0.05* | 0.12 |
| 77 | N077M | 0.21 | *0.05* | 1.53 | *0.05* | 0.11 |
| 77 | N077P | 0.26 | *0.05* | *0.05* | ND | *0.05* |
| 77 | N077Q | 0.24 | *0.05* | 2.70 | *0.05* | 0.37 |
| 77 | N077R | 0.20 | *0.05* | 1.43 | *0.05* | 0.16 |
| 77 | N077S | 0.44 | *0.05* | 2.06 | 0.05 | 0.56 |
| 77 | N077T | *0.05* | *0.05* | *0.05* | ND | *0.05* |
| 77 | N077V | 0.15 | *0.05* | 2.33 | *0.05* | 0.12 |
| 77 | N077Y | 0.18 | *0.05* | 3.14 | *0.05* | 0.15 |
| 78 | S078A | 1.10 | 1.30 | 1.17 | 1.07 | 1.43 |
| 78 | S078C | 0.96 | 1.38 | 1.20 | 1.24 | 1.18 |
| 78 | S078E | 1.26 | 0.93 | 1.01 | 1.24 | 1.73 |
| 78 | S078F | 1.08 | 1.33 | 1.02 | 0.69 | 1.34 |
| 78 | S078G | 1.20 | 1.14 | 1.08 | *0.05* | 1.43 |
| 78 | S078H | 1.18 | 1.11 | 1.09 | 1.22 | 1.47 |
| 78 | S078I | 1.04 | 1.38 | 1.13 | 0.44 | 1.33 |
| 78 | S078K | 1.20 | 1.19 | 0.82 | 0.58 | 1.33 |
| 78 | S078L | 0.94 | 1.45 | 1.11 | 0.98 | 1.08 |
| 78 | S078M | 1.09 | 1.12 | 1.09 | 1.11 | 1.35 |
| 78 | S078N | 1.17 | 1.19 | 0.93 | 1.35 | 1.42 |
| 78 | S078P | 1.18 | 1.11 | 0.98 | 0.07 | 1.45 |
| 78 | S078Q | 1.18 | 1.05 | 0.91 | 1.14 | 1.46 |
| 78 | S078R | 1.21 | 1.10 | 0.75 | 0.74 | 1.53 |
| 78 | S078T | 0.87 | 1.81 | 1.64 | 1.31 | 1.09 |
| 78 | S078V | 0.89 | 1.68 | 1.26 | 0.63 | 1.10 |
| 78 | S078W | 0.70 | 8.50 | 1.31 | 0.33 | 0.91 |
| 78 | S078Y | 1.09 | 1.00 | 1.00 | 0.69 | 1.36 |
| 79 | I079C | 0.91 | 2.06 | 1.33 | *0.05* | 1.22 |
| 79 | I079D | 1.14 | 1.02 | 1.13 | *0.05* | 1.50 |
| 79 | I079E | 1.11 | 1.10 | 1.21 | *0.05* | 1.47 |
| 79 | I079F | 1.10 | 1.16 | 1.03 | 0.67 | 1.28 |
| 79 | I079G | 0.85 | 3.12 | 1.15 | *0.05* | 1.08 |
| 79 | I079K | 1.50 | 0.71 | 0.65 | *0.05* | 1.78 |
| 79 | I079L | 1.26 | 0.91 | 0.87 | 0.11 | 1.61 |
| 79 | I079M | 0.75 | 4.59 | 1.44 | *0.05* | 1.12 |
| 79 | I079N | 0.92 | 2.30 | 1.17 | *0.05* | 1.24 |
| 79 | I079P | 0.27 | *0.05* | 2.25 | *0.05* | 0.22 |
| 79 | I079Q | 1.46 | 0.73 | 0.75 | *0.05* | 1.81 |
| 79 | I079R | 1.19 | 0.96 | 0.83 | *0.05* | 1.48 |
| 79 | I079S | 0.82 | 6.60 | 1.28 | *0.05* | 1.15 |
| 79 | I079T | 0.85 | 3.62 | 1.42 | *0.05* | 1.28 |
| 79 | I079V | 1.02 | 1.34 | 0.93 | *0.05* | 1.38 |
| 79 | I079W | 1.05 | 1.20 | 1.07 | 0.12 | 1.32 |
| 79 | I079Y | 0.89 | 1.89 | 1.30 | 0.50 | 1.05 |
| 80 | G080A | 0.31 | *0.05* | 1.92 | *0.05* | 0.35 |
| 80 | G080D | 0.27 | *0.05* | 2.80 | *0.05* | 0.21 |
| 80 | G080E | 0.29 | *0.05* | 2.61 | *0.05* | 0.28 |
| 80 | G080K | 0.29 | *0.05* | 2.05 | *0.05* | 0.26 |
| 80 | G080L | 0.31 | *0.05* | 2.17 | 0.25 | 0.25 |
| 80 | G080M | 0.43 | *0.05* | 1.62 | *0.05* | 0.45 |
| 80 | G080P | 0.34 | *0.05* | *0.05* | ND | *0.05* |
| 80 | G080R | 0.23 | *0.05* | 1.51 | *0.05* | 0.20 |
| 80 | G080T | 0.24 | *0.05* | 2.33 | *0.05* | 0.22 |
| 80 | G080V | 0.50 | *0.05* | 1.24 | *0.05* | 0.22 |
| 80 | G080W | 0.23 | *0.05* | 1.45 | *0.05* | 0.15 |
| 80 | G080Y | 0.66 | *0.05* | 1.33 | *0.05* | 0.73 |
| 81 | V081A | 0.75 | 2.80 | 1.45 | *0.05* | 0.86 |
| 81 | V081C | 0.86 | 3.09 | 1.28 | *0.05* | 1.01 |
| 81 | V081D | 0.12 | *0.05* | 1.46 | 0.07 | 0.06 |
| 81 | V081E | 0.29 | *0.05* | 2.85 | *0.05* | 0.30 |
| 81 | V081F | 1.21 | 0.94 | 0.86 | *0.05* | 0.66 |
| 81 | V081G | 0.90 | 2.53 | 1.23 | *0.05* | 0.54 |
| 81 | V081H | 1.22 | 0.90 | 1.01 | *0.05* | 0.55 |
| 81 | V081I | 1.44 | 0.69 | 0.73 | *0.05* | 1.22 |
| 81 | V081K | 0.76 | 0.99 | 1.11 | *0.05* | 0.79 |
| 81 | V081L | 1.19 | 1.03 | 0.98 | *0.05* | 1.43 |
| 81 | V081M | 1.16 | 1.04 | 1.02 | *0.05* | 1.25 |
| 81 | V081P | 0.38 | *0.05* | 2.50 | *0.05* | 0.52 |
| 81 | V081Q | 0.82 | 2.73 | 1.11 | *0.05* | 0.84 |
| 81 | V081R | 0.73 | *0.05* | 1.12 | *0.05* | 0.67 |
| 81 | V081S | 0.90 | 3.07 | 1.11 | *0.05* | 0.65 |
| 81 | V081T | 1.13 | 1.06 | 0.95 | 0.18 | 0.73 |
| 81 | V081W | 0.38 | *0.05* | 1.98 | *0.05* | 0.24 |
| 81 | V081Y | 1.20 | 0.84 | 0.92 | 0.28 | 0.59 |
| 82 | L082A | 0.92 | 1.23 | 1.23 | *0.05* | 1.02 |
| 82 | L082E | 0.83 | 1.61 | 1.18 | *0.05* | 0.98 |
| 82 | L082F | 1.06 | 1.07 | 0.94 | *0.05* | 1.27 |
| 82 | L082G | 0.19 | *0.05* | 0.92 | ND | *0.05* |
| 82 | L082H | 0.37 | *0.05* | *0.05* | ND | *0.05* |
| 82 | L082K | 1.24 | 1.07 | 0.77 | *0.05* | 1.23 |
| 82 | L082M | 1.21 | 1.22 | 0.99 | *0.05* | 1.37 |
| 82 | L082N | 0.59 | *0.05* | 1.49 | *0.05* | 0.65 |
| 82 | L082P | 0.17 | *0.05* | *0.05* | ND | *0.05* |
| 82 | L082Q | 1.17 | 1.00 | 1.00 | *0.05* | 1.21 |
| 82 | L082R | 0.93 | 1.04 | 0.99 | *0.05* | 0.91 |
| 82 | L082S | 0.61 | 2.58 | 1.38 | *0.05* | 0.65 |
| 82 | L082T | 1.01 | 1.33 | 1.18 | *0.05* | 1.05 |
| 82 | L082V | 1.10 | 1.06 | 1.16 | 0.18 | 1.26 |
| 82 | L082W | 0.13 | *0.05* | 2.32 | 0.06 | 0.10 |
| 82 | L082Y | 0.92 | 1.45 | 1.32 | *0.05* | 0.94 |
| 83 | G083D | 0.49 | *0.05* | *0.05* | ND | *0.05* |
| 83 | G083F | 0.45 | *0.05* | *0.05* | ND | *0.05* |
| 83 | G083H | 0.36 | *0.05* | *0.05* | ND | *0.05* |
| 83 | G083I | 0.55 | *0.05* | *0.05* | ND | *0.05* |
| 83 | G083L | 0.49 | *0.05* | *0.05* | ND | *0.05* |
| 83 | G083N | 0.49 | *0.05* | *0.05* | ND | *0.05* |
| 83 | G083P | 0.31 | *0.05* | *0.05* | ND | *0.05* |
| 83 | G083R | 0.27 | *0.05* | *0.05* | ND | *0.05* |
| 83 | G083S | 1.20 | 0.99 | 1.00 | *0.05* | 1.37 |
| 83 | G083V | 0.44 | *0.05* | *0.05* | ND | *0.05* |
| 84 | V084C | 1.04 | 1.00 | 1.01 | 0.90 | 1.18 |
| 84 | V084E | 0.90 | 1.04 | 1.05 | 0.18 | 0.85 |
| 84 | V084F | 0.77 | 1.42 | 1.03 | *0.05* | 0.88 |
| 84 | V084G | 1.21 | 0.99 | 1.12 | 0.88 | 1.29 |
| 84 | V084H | 0.18 | *0.05* | 1.25 | 0.10 | 0.18 |
| 84 | V084I | 1.28 | 0.86 | 1.03 | 0.84 | 1.34 |
| 84 | V084L | 1.19 | 1.00 | 1.02 | 0.67 | 1.33 |
| 84 | V084M | 1.32 | 0.94 | 0.92 | 0.91 | 1.35 |
| 84 | V084N | 0.98 | 1.31 | 0.97 | 0.57 | 1.11 |
| 84 | V084P | 0.16 | *0.05* | 0.72 | 0.17 | 0.07 |
| 84 | V084Q | 0.45 | *0.05* | 1.35 | *0.05* | 0.52 |
| 84 | V084R | 0.28 | *0.05* | *0.05* | ND | *0.05* |
| 84 | V084S | 0.23 | *0.05* | 0.80 | 0.74 | 0.14 |
| 84 | V084T | 1.06 | 1.16 | 1.01 | 0.76 | 1.20 |
| 84 | V084W | 0.23 | *0.05* | *0.05* | ND | *0.05* |
| 84 | V084Y | 0.21 | *0.05* | *0.05* | ND | *0.05* |
| 85 | A085C | 0.66 | 3.56 | 1.30 | 0.86 | 0.77 |
| 85 | A085E | 0.28 | *0.05* | *0.05* | ND | *0.05* |
| 85 | A085F | 0.28 | *0.05* | *0.05* | ND | *0.05* |
| 85 | A085G | 0.26 | *0.05* | *0.05* | ND | *0.05* |
| 85 | A085I | 0.87 | 4.15 | 0.78 | ND | *0.05* |
| 85 | A085L | 0.22 | *0.05* | 1.08 | 0.08 | 0.16 |
| 85 | A085M | 0.20 | *0.05* | *0.05* | ND | *0.05* |
| 85 | A085N | 0.15 | *0.05* | 0.86 | 0.27 | 0.09 |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 85 | A085Q | 0.22 | *0.05* | *0.05* | *ND* | *0.05* |
| 85 | A085R | 0.38 | *0.05* | *0.05* | *ND* | *0.05* |
| 85 | A085W | 0.26 | *0.05* | *0.05* | *ND* | *0.05* |
| 86 | P086A | 1.02 | 0.91 | 1.09 | 0.74 | 1.14 |
| 86 | P086C | 1.01 | 0.96 | 1.01 | 1.00 | 1.03 |
| 86 | P086D | 0.62 | 3.78 | 1.39 | 1.23 | 0.74 |
| 86 | P086E | 0.68 | 1.77 | 1.27 | 0.84 | 0.86 |
| 86 | P086G | 0.89 | 1.22 | 1.13 | 0.07 | 1.06 |
| 86 | P086I | 0.68 | 1.55 | 1.07 | 0.15 | 0.71 |
| 86 | P086L | 0.50 | *0.05* | 1.23 | *0.05* | 0.63 |
| 86 | P086M | *0.05* | *0.05* | *0.05* | *ND* | *0.05* |
| 86 | P086R | 0.22 | *0.05* | 0.83 | *0.05* | 0.22 |
| 86 | P086S | 1.00 | 1.31 | 1.01 | 0.79 | 1.19 |
| 86 | P086V | 0.80 | 1.35 | 1.07 | 0.09 | 0.95 |
| 86 | P086W | 0.89 | 1.44 | 1.02 | 0.57 | 1.17 |
| 86 | P086Y | 0.96 | 1.38 | 0.93 | 0.77 | 1.20 |
| 87 | S087A | 1.20 | 1.19 | 1.03 | 0.82 | 1.36 |
| 87 | S087C | 1.21 | 1.04 | 1.05 | 0.93 | 1.32 |
| 87 | S087D | 1.26 | 1.15 | 1.14 | 1.17 | 1.46 |
| 87 | S087E | 1.38 | 1.01 | 1.02 | 1.14 | 1.57 |
| 87 | S087F | 0.95 | 1.17 | 1.19 | 0.62 | 1.06 |
| 87 | S087G | 1.35 | 1.01 | 0.99 | 0.92 | 1.33 |
| 87 | S087I | 1.37 | 0.89 | 0.97 | 0.57 | 1.37 |
| 87 | S087K | 1.35 | 0.99 | 0.92 | 0.84 | 1.18 |
| 87 | S087L | 1.37 | 0.93 | 0.99 | 0.97 | 1.34 |
| 87 | S087N | 1.37 | 0.97 | 0.98 | 0.95 | 1.50 |
| 87 | S087P | 0.22 | *0.05* | 1.01 | 0.60 | 0.17 |
| 87 | S087T | 1.33 | 1.01 | 1.00 | 0.79 | 1.39 |
| 87 | S087V | 1.40 | 0.96 | 1.00 | 0.96 | 1.44 |
| 87 | S087Y | 1.35 | 0.92 | 0.95 | 0.62 | 1.42 |
| 88 | A088C | 0.87 | 2.13 | 1.31 | 0.92 | 1.12 |
| 88 | A088D | 0.82 | 5.32 | 1.41 | 0.74 | 1.23 |
| 88 | A088E | 0.72 | 5.29 | 1.46 | 0.75 | 1.05 |
| 88 | A088F | 0.24 | *0.05* | *0.05* | *ND* | *0.05* |
| 88 | A088G | 1.68 | 0.57 | 0.82 | 0.96 | 1.93 |
| 88 | A088H | 0.22 | *0.05* | 1.88 | 0.69 | 0.23 |
| 88 | A088K | 0.24 | *0.05* | 2.99 | 0.69 | 0.33 |
| 88 | A088M | 0.48 | *0.05* | 1.97 | 0.78 | 0.59 |
| 88 | A088Q | 0.96 | 1.63 | 1.33 | 0.68 | 1.28 |
| 88 | A088R | 0.12 | *0.05* | 2.18 | 0.10 | 0.09 |
| 88 | A088S | 0.92 | 1.85 | 1.44 | 1.00 | 1.17 |
| 88 | A088V | 0.78 | 4.36 | *0.05* | *ND* | *0.05* |
| 88 | A088W | 0.23 | *0.05* | 2.85 | 0.93 | 0.26 |
| 88 | A088Y | 0.18 | *0.05* | *0.05* | *ND* | *0.05* |
| 89 | E089A | 0.91 | 1.97 | 1.09 | 0.85 | 1.15 |
| 89 | E089C | 0.79 | 3.65 | 1.19 | 1.00 | 0.96 |
| 89 | E089D | 1.06 | 1.19 | 1.07 | 1.00 | 1.37 |
| 89 | E089F | 0.63 | *0.05* | 1.27 | 0.92 | 0.89 |
| 89 | E089G | 1.01 | 1.64 | 1.04 | 0.90 | 1.41 |
| 89 | E089H | 1.02 | 1.50 | 1.00 | 0.97 | 1.31 |
| 89 | E089I | 0.92 | 1.36 | 1.09 | 0.97 | 1.13 |
| 89 | E089L | 0.66 | *0.05* | 1.10 | 1.03 | 0.78 |
| 89 | E089M | 0.27 | *0.05* | *0.05* | *ND* | *0.05* |
| 89 | E089N | 1.15 | 1.39 | 0.94 | 0.86 | 1.64 |
| 89 | E089P | 1.30 | 0.94 | 0.95 | 0.80 | 1.46 |
| 89 | E089Q | 1.30 | 1.11 | 0.89 | 0.96 | 1.47 |
| 89 | E089R | 0.92 | 1.81 | 0.87 | 1.13 | 1.21 |
| 89 | E089S | 1.12 | 1.33 | 1.06 | 0.86 | 1.51 |
| 89 | E089T | 0.90 | 1.82 | 1.02 | 0.89 | 1.08 |
| 89 | E089V | 0.78 | 3.34 | 1.14 | 0.93 | 0.86 |
| 89 | E089W | 0.93 | 1.35 | 1.07 | 0.99 | 1.03 |
| 90 | L090A | 0.97 | 1.08 | 0.98 | 0.75 | 1.25 |
| 90 | L090C | 0.81 | 0.98 | 1.06 | 0.97 | 0.90 |
| 90 | L090D | 0.26 | *0.05* | *0.05* | *ND* | *0.05* |
| 90 | L090E | 0.41 | *0.05* | 1.38 | 0.79 | 0.47 |
| 90 | L090F | 0.84 | 1.16 | 1.27 | 0.48 | 0.95 |
| 90 | L090G | 0.43 | *0.05* | 1.27 | 0.82 | 0.52 |
| 90 | L090I | 1.31 | 0.91 | 0.97 | 1.21 | 1.31 |
| 90 | L090K | 0.30 | *0.05* | 1.08 | 0.82 | 0.28 |
| 90 | L090M | 1.51 | 0.98 | 0.86 | 1.01 | 1.72 |
| 90 | L090P | 0.40 | *0.05* | 1.15 | 0.74 | 0.36 |
| 90 | L090Q | 1.09 | 0.93 | 0.91 | 0.97 | 1.25 |
| 90 | L090R | 0.25 | *0.05* | *0.05* | *ND* | *0.05* |
| 90 | L090T | 1.23 | 1.02 | 0.88 | 0.93 | 1.31 |
| 90 | L090V | 1.06 | 1.25 | 1.04 | 0.97 | 1.39 |
| 90 | L090W | 0.36 | *0.05* | 1.63 | 0.26 | 0.21 |
| 90 | L090Y | 0.72 | 1.79 | 1.22 | 0.49 | 0.89 |
| 91 | Y091C | 0.69 | 45.17 | 1.24 | 0.99 | 0.96 |
| 91 | Y091D | 1.09 | 1.12 | 1.07 | 0.94 | 1.39 |
| 91 | Y091F | 1.07 | 1.23 | 1.13 | 0.92 | 1.49 |
| 91 | Y091I | 1.00 | 1.26 | 1.22 | 1.03 | 1.19 |
| 91 | Y091K | 0.22 | *0.05* | 1.32 | 1.14 | 0.14 |
| 91 | Y091L | 0.55 | *0.05* | 1.49 | 1.11 | 0.66 |
| 91 | Y091M | 0.74 | 6.69 | 1.32 | 1.01 | 0.97 |
| 91 | Y091N | 1.05 | 1.12 | 1.06 | 0.96 | 1.26 |
| 91 | Y091P | 0.43 | *0.05* | *0.05* | *ND* | *0.05* |
| 91 | Y091Q | 0.32 | *0.05* | 1.84 | 0.96 | 0.39 |
| 91 | Y091R | 0.24 | *0.05* | 1.29 | 1.03 | 0.20 |
| 91 | Y091S | 0.90 | 1.40 | 1.23 | 0.90 | 1.02 |
| 91 | Y091T | 0.68 | 1.72 | 1.19 | 0.92 | 0.86 |
| 91 | Y091V | 1.07 | 1.11 | 1.19 | 1.09 | 1.15 |
| 91 | Y091W | 1.10 | 1.15 | 1.04 | 1.03 | 1.25 |
| 92 | A092C | 0.54 | *0.05* | 1.75 | 0.31 | 0.37 |
| 92 | A092D | 1.17 | 0.83 | 1.31 | 0.44 | 0.48 |
| 92 | A092E | 0.60 | *0.05* | 1.91 | 0.08 | 0.21 |
| 92 | A092F | 0.49 | *0.05* | 1.83 | *ND* | *0.05* |
| 92 | A092G | 1.07 | 1.23 | 1.28 | 0.94 | 1.27 |
| 92 | A092H | 0.21 | *0.05* | 2.34 | *ND* | *0.05* |
| 92 | A092I | 0.74 | 2.38 | 1.45 | 0.75 | 0.67 |
| 92 | A092K | 0.28 | *0.05* | 1.98 | 0.65 | 0.21 |
| 92 | A092L | 0.21 | *0.05* | 2.22 | *ND* | *0.05* |
| 92 | A092N | 1.02 | 1.05 | 1.12 | 0.62 | 0.89 |
| 92 | A092P | 1.52 | 0.70 | 1.10 | 1.12 | 1.46 |
| 92 | A092Q | 0.34 | *0.05* | 2.14 | 0.10 | 0.28 |
| 92 | A092R | 0.94 | 1.10 | 0.95 | 1.00 | 0.96 |
| 92 | A092T | 0.87 | 1.74 | 1.32 | 0.80 | 0.93 |
| 92 | A092V | 0.93 | 1.48 | 1.25 | 0.82 | 1.11 |
| 92 | A092W | 0.27 | *0.05* | 2.43 | 0.34 | 0.23 |
| 92 | A092Y | 0.35 | *0.05* | 2.14 | 0.46 | 0.25 |
| 93 | V093A | 0.97 | 1.22 | 1.06 | 0.89 | 0.87 |
| 93 | V093C | 1.03 | 1.17 | 1.08 | 1.02 | 1.02 |
| 93 | V093D | 0.26 | *0.05* | 0.87 | 1.00 | 0.11 |
| 93 | V093F | 0.20 | *0.05* | 0.60 | 1.09 | 0.10 |
| 93 | V093G | 0.95 | 1.00 | 1.15 | 0.92 | 0.87 |
| 93 | V093H | 0.28 | *0.05* | *0.05* | *ND* | *0.05* |
| 93 | V093K | 0.46 | *0.05* | *0.05* | *ND* | *0.05* |
| 93 | V093L | 1.26 | 0.89 | 1.00 | 1.11 | 1.38 |
| 93 | V093M | 0.91 | 0.74 | 1.06 | 1.00 | 0.85 |
| 93 | V093N | 0.22 | *0.05* | 0.57 | 1.09 | 0.09 |
| 93 | V093P | 0.25 | *0.05* | *0.05* | *ND* | *0.05* |
| 93 | V093R | 0.46 | *0.05* | *0.05* | *ND* | *0.05* |
| 93 | V093S | 0.34 | *0.05* | 1.42 | 0.99 | 0.24 |
| 93 | V093T | 1.45 | 0.82 | 0.91 | 1.05 | 1.22 |
| 93 | V093W | 0.31 | *0.05* | 0.83 | *ND* | *0.05* |
| 93 | V093Y | 0.33 | *0.05* | 1.41 | 1.11 | 0.29 |
| 94 | K094A | 0.30 | *0.05* | 1.53 | 0.25 | 0.07 |
| 94 | K094D | 0.36 | *0.05* | 1.33 | *ND* | *0.05* |
| 94 | K094E | 0.63 | *0.05* | 1.54 | 0.10 | 0.20 |
| 94 | K094F | 0.40 | *0.05* | *0.05* | *ND* | *0.05* |
| 94 | K094G | 0.27 | *0.05* | 1.83 | *ND* | *0.05* |
| 94 | K094H | 0.46 | *0.05* | 2.33 | 0.09 | 0.08 |
| 94 | K094I | 0.31 | *0.05* | 2.52 | *ND* | *0.05* |
| 94 | K094L | 0.24 | *0.05* | 1.48 | *ND* | *0.05* |
| 94 | K094M | 0.25 | *0.05* | 2.47 | 0.35 | 0.07 |
| 94 | K094N | 1.01 | 0.97 | 1.21 | 0.77 | 0.39 |
| 94 | K094P | 0.23 | *0.05* | *0.05* | *ND* | *0.05* |
| 94 | K094Q | 0.80 | 1.10 | 1.49 | 0.10 | 0.39 |
| 94 | K094R | 1.01 | 1.35 | 1.23 | 0.86 | 0.86 |
| 94 | K094S | 0.42 | *0.05* | *0.05* | *ND* | *0.05* |
| 94 | K094T | 0.53 | *0.05* | *0.05* | *ND* | *0.05* |
| 94 | K094V | 0.55 | *0.05* | 1.77 | 0.14 | 0.23 |
| 94 | K094W | 0.31 | *0.05* | *0.05* | *ND* | *0.05* |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 94 | K094Y | 0.28 | *0.05* | *0.05* | *ND* | *0.05* |
| 95 | V095A | 1.56 | 0.92 | 0.88 | 0.98 | 1.47 |
| 95 | V095C | 1.08 | 0.93 | 1.21 | 1.10 | 1.04 |
| 95 | V095D | 0.47 | *0.05* | *0.05* | *ND* | *0.05* |
| 95 | V095E | 0.25 | *0.05* | *0.05* | *ND* | *0.05* |
| 95 | V095F | 0.32 | *0.05* | *0.05* | *ND* | *0.05* |
| 95 | V095G | 0.44 | *0.05* | 1.23 | 1.07 | 0.40 |
| 95 | V095H | 0.48 | *0.05* | *0.05* | *ND* | *0.05* |
| 95 | V095I | 1.21 | 1.33 | 1.19 | 0.98 | 0.37 |
| 95 | V095K | 0.46 | *0.05* | 1.64 | 0.95 | 0.33 |
| 95 | V095L | 0.35 | *0.05* | 1.80 | *ND* | *0.05* |
| 95 | V095M | 0.34 | *0.05* | 1.28 | *ND* | *0.05* |
| 95 | V095P | 0.37 | *0.05* | *0.05* | *ND* | *0.05* |
| 95 | V095Q | 0.40 | *0.05* | *0.05* | *ND* | *0.05* |
| 95 | V095R | 0.55 | *0.05* | 1.49 | 0.98 | 0.38 |
| 95 | V095S | 1.07 | 1.00 | 1.04 | 0.99 | 0.70 |
| 95 | V095T | 0.97 | 1.50 | 1.06 | 0.79 | 0.77 |
| 95 | V095W | 0.19 | *0.05* | 1.87 | 0.98 | 0.10 |
| 95 | V095Y | 0.44 | *0.05* | *0.05* | *ND* | *0.05* |
| 96 | L096A | 1.93 | 0.78 | 0.72 | *ND* | *0.05* |
| 96 | L096C | 0.47 | *0.05* | *0.05* | *ND* | *0.05* |
| 96 | L096D | 0.60 | *0.05* | 0.56 | *ND* | *0.05* |
| 96 | L096E | 1.41 | 0.14 | 1.06 | *ND* | *0.05* |
| 96 | L096F | 2.15 | 0.76 | 0.85 | 0.92 | 0.32 |
| 96 | L096G | 2.30 | 0.36 | 0.58 | *ND* | *0.05* |
| 96 | L096H | 2.15 | 0.53 | 0.85 | *ND* | *0.05* |
| 96 | L096I | 1.47 | 1.20 | 0.98 | 1.11 | 1.47 |
| 96 | L096M | 1.12 | 1.36 | 1.17 | 1.09 | 1.14 |
| 96 | L096P | 0.41 | *0.05* | *0.05* | *ND* | *0.05* |
| 96 | L096Q | 2.16 | 0.58 | 0.76 | 1.03 | 0.32 |
| 96 | L096R | 1.62 | 0.10 | 0.50 | *ND* | *0.05* |
| 96 | L096S | 1.92 | 0.74 | 0.84 | *ND* | *0.05* |
| 96 | L096T | 1.65 | 1.01 | 0.98 | *ND* | *0.05* |
| 96 | L096W | 0.77 | 1.52 | 0.78 | *ND* | *0.05* |
| 96 | L096Y | 1.17 | 0.27 | 0.79 | *ND* | *0.05* |
| 97 | G097A | 1.06 | 1.29 | 1.23 | 0.93 | 1.32 |
| 97 | G097D | 1.00 | 1.76 | 1.38 | 1.12 | 0.45 |
| 97 | G097E | 1.29 | 1.13 | 1.15 | 1.10 | 0.89 |
| 97 | G097F | 1.31 | 0.86 | 0.91 | 1.05 | 0.71 |
| 97 | G097H | 1.17 | 1.20 | 1.10 | 1.07 | 1.13 |
| 97 | G097I | 0.76 | 1.49 | 1.50 | 1.12 | 0.34 |
| 97 | G097K | 1.24 | 0.92 | 0.88 | 1.15 | 2.02 |
| 97 | G097L | 1.71 | 0.70 | 0.83 | 1.13 | 1.13 |
| 97 | G097M | 1.48 | 0.71 | 0.93 | 0.90 | 1.26 |
| 97 | G097N | 1.41 | 0.96 | 0.93 | 0.99 | 1.18 |
| 97 | G097P | 2.33 | 0.78 | 0.60 | 1.23 | 5.70 |
| 97 | G097Q | 1.02 | 0.95 | 1.20 | 1.01 | 1.34 |
| 97 | G097R | 1.08 | 0.99 | 0.87 | 1.10 | 2.25 |
| 97 | G097S | 1.32 | 1.03 | 1.00 | 0.92 | 1.50 |
| 97 | G097T | 1.06 | 1.26 | 1.21 | 0.95 | 1.13 |
| 97 | G097V | 1.03 | 1.11 | 1.33 | 1.05 | 0.68 |
| 97 | G097W | 1.24 | 0.91 | 0.88 | 0.91 | 0.60 |
| 97 | G097Y | 1.33 | 1.10 | 0.98 | 1.12 | 0.74 |
| 98 | A098C | 0.82 | 8.98 | 1.36 | 1.05 | 0.92 |
| 98 | A098D | 0.98 | 1.11 | 1.49 | 1.13 | 1.14 |
| 98 | A098E | 0.91 | 2.10 | 1.60 | 1.12 | 1.33 |
| 98 | A098F | 0.84 | 4.17 | 1.40 | 0.96 | 1.30 |
| 98 | A098G | 1.10 | 1.08 | 1.19 | 1.03 | 1.00 |
| 98 | A098K | 1.62 | 0.78 | 0.73 | 1.13 | 1.97 |
| 98 | A098L | 1.17 | 1.02 | 1.12 | 1.19 | 1.61 |
| 98 | A098N | 1.29 | 0.91 | 0.98 | 0.99 | 1.92 |
| 98 | A098P | 1.25 | 0.68 | 1.09 | 0.95 | 1.23 |
| 98 | A098Q | 1.47 | 0.86 | 0.87 | 1.03 | 2.08 |
| 98 | A098R | 1.45 | 0.96 | 0.70 | 0.95 | 2.03 |
| 98 | A098S | 1.31 | 1.02 | 0.98 | 1.05 | 1.58 |
| 98 | A098T | 1.39 | 0.81 | 0.95 | 0.94 | 2.17 |
| 98 | A098V | 1.09 | 1.29 | 1.13 | 1.07 | 1.62 |
| 98 | A098Y | 1.13 | 0.99 | 1.06 | 0.99 | 1.41 |
| 99 | S099A | 1.26 | 1.17 | 1.04 | 0.98 | 1.42 |
| 99 | S099C | 0.84 | 1.38 | 1.19 | 0.91 | 0.69 |
| 99 | S099E | 0.40 | *0.05* | *0.05* | *ND* | *0.05* |
| 99 | S099F | 1.03 | 0.86 | 0.92 | 0.97 | 1.10 |
| 99 | S099G | 1.19 | 1.31 | 1.07 | 0.88 | 1.41 |
| 99 | S099K | 1.33 | 1.10 | 0.88 | 1.05 | 1.60 |
| 99 | S099L | *0.05* | *0.05* | *0.05* | *ND* | *0.05* |
| 99 | S099M | 1.34 | 0.90 | 1.09 | 1.01 | 1.34 |
| 99 | S099P | 1.17 | 0.89 | 1.12 | 1.11 | 0.61 |
| 99 | S099Q | 1.34 | 0.96 | 1.04 | 1.08 | 1.33 |
| 99 | S099R | 1.24 | 0.96 | 0.75 | 1.05 | 1.48 |
| 99 | S099T | 1.24 | 1.14 | 1.06 | 1.00 | 1.18 |
| 99 | S099V | 1.28 | 0.84 | 0.98 | 1.09 | 1.40 |
| 99 | S099Y | 1.24 | 0.76 | 0.97 | 1.00 | 1.26 |
| 100 | G100D | 1.63 | 0.69 | 1.05 | 1.06 | 0.31 |
| 100 | G100E | 2.32 | 0.74 | 0.84 | 1.01 | 1.02 |
| 100 | G100F | 1.12 | 0.50 | 0.73 | *ND* | *0.05* |
| 100 | G100I | 1.65 | 1.01 | 0.86 | 1.16 | 1.68 |
| 100 | G100K | 2.67 | 0.83 | 0.55 | 1.00 | 0.20 |
| 100 | G100L | 2.51 | 0.78 | 0.66 | 1.11 | 0.19 |
| 100 | G100M | 2.79 | 0.60 | 0.67 | 0.96 | 0.17 |
| 100 | G100N | 2.75 | 0.86 | 0.65 | 0.94 | 0.91 |
| 100 | G100P | 0.62 | *0.05* | 1.01 | 0.98 | 0.10 |
| 100 | G100Q | 3.36 | 0.55 | 0.60 | 1.01 | 0.50 |
| 100 | G100R | 2.68 | 0.86 | 0.63 | 1.07 | 0.15 |
| 100 | G100S | 2.34 | 0.84 | 0.84 | 1.04 | 1.17 |
| 100 | G100T | 1.91 | 0.92 | 0.81 | 0.93 | 0.67 |
| 100 | G100V | 1.07 | 1.17 | 0.81 | 1.03 | 0.15 |
| 100 | G100W | 0.69 | 9.51 | 0.84 | *ND* | *0.05* |
| 100 | G100Y | 0.94 | 1.31 | 1.10 | 1.00 | 0.13 |
| 101 | S101A | 1.11 | 1.35 | 0.95 | 1.04 | 1.25 |
| 101 | S101C | 0.96 | 0.44 | 0.85 | 0.87 | 0.19 |
| 101 | S101D | 1.29 | 1.36 | 1.22 | 1.05 | 0.62 |
| 101 | S101E | 1.46 | 1.31 | 1.10 | 1.08 | 0.66 |
| 101 | S101F | 1.39 | 1.23 | 0.87 | 1.16 | 2.18 |
| 101 | S101G | 1.32 | 0.96 | 1.06 | 1.06 | 1.45 |
| 101 | S101H | 1.34 | 1.24 | 1.06 | 1.21 | 1.65 |
| 101 | S101I | 1.45 | 1.11 | 0.79 | 1.11 | 1.29 |
| 101 | S101K | 1.39 | 1.32 | 0.91 | 1.23 | 1.77 |
| 101 | S101N | 1.34 | 1.18 | 1.11 | 1.07 | 1.42 |
| 101 | S101P | 1.51 | 0.89 | 1.15 | 1.33 | 2.74 |
| 101 | S101Q | 1.49 | 1.15 | 1.02 | 1.03 | 1.37 |
| 101 | S101R | 1.35 | 1.34 | 0.73 | 1.10 | 2.15 |
| 101 | S101T | 1.37 | 1.30 | 1.07 | 1.10 | 1.29 |
| 101 | S101V | 1.47 | 1.17 | 0.80 | 1.07 | 1.22 |
| 101 | S101W | 0.28 | *0.05* | *0.05* | *ND* | *0.05* |
| 101 | S101Y | 1.38 | 1.36 | 0.77 | 1.04 | 2.11 |
| 102 | G102A | 1.46 | 1.05 | 1.05 | 1.02 | 0.59 |
| 102 | G102C | 1.04 | 0.21 | 1.08 | *ND* | *0.05* |
| 102 | G102D | 0.61 | *0.05* | 1.42 | 0.99 | 0.06 |
| 102 | G102E | 0.57 | *0.05* | 1.65 | *ND* | *0.05* |
| 102 | G102F | 0.68 | 1.09 | 0.44 | *ND* | *0.05* |
| 102 | G102H | 0.58 | *0.05* | 1.34 | *ND* | *0.05* |
| 102 | G102I | 0.56 | *0.05* | *0.05* | *ND* | *0.05* |
| 102 | G102K | 0.48 | *0.05* | *0.05* | *ND* | *0.05* |
| 102 | G102L | 0.63 | *0.05* | 0.24 | *ND* | *0.05* |
| 102 | G102M | 0.58 | 0.62 | 1.22 | *ND* | *0.05* |
| 102 | G102N | 0.74 | 1.25 | 1.47 | 1.08 | 0.21 |
| 102 | G102P | 0.50 | *0.05* | *0.05* | *ND* | *0.05* |
| 102 | G102S | 0.52 | *0.05* | *0.05* | *ND* | *0.05* |
| 102 | G102T | 1.21 | 0.97 | 1.12 | 1.00 | 0.26 |
| 102 | G102V | 0.49 | *0.05* | 0.33 | *ND* | *0.05* |
| 102 | G102Y | 0.79 | 0.50 | 0.72 | *ND* | *0.05* |
| 103 | S103A | 1.08 | 1.18 | 1.17 | 1.10 | 1.29 |
| 103 | S103C | 0.96 | 0.63 | 0.88 | 1.07 | 0.52 |
| 103 | S103D | 0.93 | 0.81 | 1.32 | 1.09 | 0.47 |
| 103 | S103E | 0.73 | 0.80 | 1.13 | 1.12 | 0.27 |
| 103 | S103F | 1.22 | 0.83 | 0.83 | 0.98 | 1.24 |
| 103 | S103G | 0.84 | 1.22 | 1.09 | 0.91 | 0.71 |
| 103 | S103I | 0.85 | 1.20 | 0.95 | 0.98 | 0.72 |
| 103 | S103L | 1.28 | 0.93 | 0.98 | 1.06 | 1.52 |
| 103 | S103N | 1.25 | 1.08 | 1.06 | 1.08 | 0.84 |
| 103 | S103P | 1.05 | 1.10 | 1.00 | 1.09 | 1.20 |
| 103 | S103Q | 1.15 | 1.09 | 1.10 | 1.02 | 1.25 |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 103 | S103R | 1.37 | 0.88 | 0.82 | 1.03 | 1.93 |
| 103 | S103T | 1.28 | 1.20 | 1.08 | 0.95 | 1.16 |
| 103 | S103V | 0.93 | 1.15 | 0.98 | 0.89 | 1.01 |
| 103 | S103W | 1.03 | 0.96 | 0.88 | 0.93 | 0.97 |
| 103 | S103Y | 1.12 | 0.95 | 0.81 | 0.72 | 1.18 |
| 104 | V104A | 0.73 | 2.15 | 0.99 | 0.89 | 0.27 |
| 104 | V104C | 1.24 | 0.41 | 1.02 | 1.03 | 0.21 |
| 104 | V104D | 0.50 | *0.05* | 1.18 | 1.13 | 0.11 |
| 104 | V104E | 0.60 | 1.43 | 1.41 | 1.11 | 0.16 |
| 104 | V104F | 1.05 | 0.94 | 0.90 | 1.31 | 4.30 |
| 104 | V104G | 0.30 | *0.05* | 0.68 | 0.89 | 0.06 |
| 104 | V104H | 1.22 | 0.91 | 0.97 | 1.02 | 1.25 |
| 104 | V104I | 1.32 | 0.90 | 1.05 | 1.23 | 2.84 |
| 104 | V104L | 1.33 | 0.88 | 1.00 | 0.95 | 3.16 |
| 104 | V104P | 0.60 | 1.16 | 1.08 | 1.16 | 0.07 |
| 104 | V104R | 1.11 | 1.11 | 0.85 | 0.96 | 1.00 |
| 104 | V104S | 1.01 | 1.04 | 0.98 | 0.83 | 0.57 |
| 104 | V104T | 1.01 | 1.09 | 1.04 | 1.07 | 1.23 |
| 104 | V104W | 0.96 | 0.67 | 0.88 | 0.96 | 4.85 |
| 104 | V104Y | 0.98 | 1.07 | 0.77 | 1.03 | 3.89 |
| 105 | S105A | 1.29 | 0.88 | 0.97 | 1.00 | 1.62 |
| 105 | S105C | 1.13 | 0.44 | 1.00 | 1.04 | 0.89 |
| 105 | S105D | 1.02 | 0.56 | 1.26 | 1.02 | 1.04 |
| 105 | S105E | 1.13 | 0.62 | 1.25 | 1.00 | 1.11 |
| 105 | S105F | 0.90 | 1.10 | 0.97 | 1.00 | 1.08 |
| 105 | S105G | 0.87 | 1.23 | 1.33 | 0.96 | 1.12 |
| 105 | S105H | 0.79 | 1.40 | 1.08 | 1.10 | 0.74 |
| 105 | S105I | 0.45 | *0.05* | 1.58 | 0.99 | 0.63 |
| 105 | S105K | 1.60 | 1.03 | 0.70 | 0.93 | 2.20 |
| 105 | S105L | 1.00 | 0.83 | 0.97 | 1.05 | 1.21 |
| 105 | S105M | 0.80 | 0.76 | 0.67 | 1.12 | 0.36 |
| 105 | S105N | 1.10 | 0.73 | 1.01 | 1.06 | 1.14 |
| 105 | S105P | 0.31 | *0.05* | *0.05* | *ND* | *0.05* |
| 105 | S105Q | 1.41 | 0.72 | 0.98 | 0.92 | 1.51 |
| 105 | S105R | 1.43 | 0.78 | 0.72 | 0.94 | 1.57 |
| 105 | S105K | 1.62 | 0.88 | 0.83 | 0.92 | 1.77 |
| 105 | S105K | 0.85 | 1.28 | 1.11 | 0.89 | 1.26 |
| 105 | S105W | 0.28 | *0.05* | 1.15 | 0.94 | 0.36 |
| 105 | S105Y | 0.49 | *0.05* | 1.31 | 0.84 | 0.61 |
| 106 | S106A | 1.35 | 1.16 | 0.82 | 0.96 | 1.94 |
| 106 | S106D | 1.37 | 0.78 | 1.15 | 1.00 | 1.57 |
| 106 | S106E | 1.53 | 0.89 | 1.14 | 1.02 | 1.05 |
| 106 | S106F | 0.43 | *0.05* | 1.42 | 1.05 | 0.53 |
| 106 | S106G | 1.18 | 1.18 | 1.11 | 1.04 | 1.65 |
| 106 | S106I | 0.99 | 1.13 | 1.16 | 1.09 | 1.43 |
| 106 | S106L | 1.16 | 1.33 | 1.16 | 1.02 | 1.10 |
| 106 | S106M | 0.80 | 2.04 | 1.07 | 1.07 | 1.15 |
| 106 | S106N | 0.49 | *0.05* | *0.05* | *ND* | *0.05* |
| 106 | S106P | 0.29 | *0.05* | 1.12 | 1.06 | 0.24 |
| 106 | S106R | 1.11 | 1.16 | 0.78 | 0.98 | 1.15 |
| 106 | S106T | 1.40 | 0.98 | 0.99 | 1.09 | 0.74 |
| 106 | S106V | 0.89 | 1.19 | 1.08 | 1.19 | 1.36 |
| 106 | S106W | 1.00 | 1.07 | 0.94 | 1.20 | 1.42 |
| 107 | I107A | 2.12 | 1.08 | 0.57 | 0.82 | 0.50 |
| 107 | I107C | 1.72 | 0.96 | 0.45 | 0.93 | 0.89 |
| 107 | I107D | 0.57 | *0.05* | *0.05* | *ND* | *0.05* |
| 107 | I107E | 0.71 | 5.00 | 0.96 | *ND* | *0.05* |
| 107 | I107F | 2.25 | 1.15 | 0.72 | 0.87 | 0.22 |
| 107 | I107G | 0.39 | *0.05* | 0.77 | *ND* | *0.05* |
| 107 | I107H | 0.73 | 1.65 | 1.19 | *ND* | *0.05* |
| 107 | I107K | 0.50 | *0.05* | *0.05* | *ND* | *0.05* |
| 107 | I107L | 1.32 | 1.50 | 0.45 | 0.92 | 1.35 |
| 107 | I107M | 2.15 | 1.09 | 0.73 | 0.84 | 0.45 |
| 107 | I107P | 0.35 | *0.05* | *0.05* | *ND* | *0.05* |
| 107 | I107Q | 1.02 | 1.22 | 1.18 | 1.11 | 0.06 |
| 107 | I107R | 0.55 | *0.05* | *0.05* | *ND* | *0.05* |
| 107 | I107S | 1.47 | 1.53 | 0.49 | 0.91 | 0.38 |
| 107 | I107T | 2.29 | 1.01 | 0.43 | 0.85 | 0.59 |
| 107 | I107V | 1.05 | 1.29 | 0.51 | 0.93 | 2.10 |
| 107 | I107W | 0.73 | 2.83 | 0.70 | *ND* | *0.05* |
| 107 | I107Y | 2.08 | 0.58 | 0.65 | *ND* | *0.05* |
| 108 | A108C | 1.00 | 0.80 | 0.98 | 0.99 | 0.97 |
| 108 | A108D | 0.36 | *0.05* | *0.05* | *ND* | *0.05* |
| 108 | A108E | 0.56 | *0.05* | *0.05* | *ND* | *0.05* |
| 108 | A108F | 0.22 | *0.05* | *0.05* | *ND* | *0.05* |
| 108 | A108G | 0.61 | 2.14 | 1.20 | 0.96 | 0.62 |
| 108 | A108H | 0.26 | *0.05* | *0.05* | *ND* | *0.05* |
| 108 | A108I | 1.12 | 1.02 | 1.01 | 0.95 | 1.41 |
| 108 | A108L | 0.91 | 1.07 | 0.82 | 0.40 | 0.91 |
| 108 | A108M | 0.74 | 1.26 | 0.94 | 0.61 | 0.73 |
| 108 | A108P | 0.40 | *0.05* | *0.05* | *ND* | *0.05* |
| 108 | A108Q | 0.25 | *0.05* | *0.05* | *ND* | *0.05* |
| 108 | A108R | 0.40 | *0.05* | *0.05* | *ND* | *0.05* |
| 108 | A108S | 0.84 | 1.94 | 1.12 | 0.86 | 0.72 |
| 108 | A108T | 0.96 | 1.40 | 0.85 | 0.86 | 0.72 |
| 108 | A108V | 1.26 | 0.92 | 0.87 | 1.00 | 1.38 |
| 108 | A108W | 0.25 | *0.05* | *0.05* | *ND* | *0.05* |
| 109 | Q109A | 1.29 | 1.11 | 0.85 | 0.98 | 1.39 |
| 109 | Q109C | 0.70 | 31.03 | 1.35 | 0.97 | 0.84 |
| 109 | Q109E | 0.84 | 1.41 | 1.16 | 0.95 | 1.15 |
| 109 | Q109F | 0.93 | 1.78 | 0.98 | 1.06 | 1.28 |
| 109 | Q109G | 0.96 | 1.62 | 1.10 | 0.96 | 1.06 |
| 109 | Q109H | 1.01 | 1.10 | 0.86 | 1.01 | 1.19 |
| 109 | Q109I | 0.91 | 1.85 | 1.19 | 1.11 | 1.33 |
| 109 | Q109K | 1.65 | 0.81 | 0.74 | 0.93 | 1.93 |
| 109 | Q109L | 1.19 | 1.12 | 1.07 | 1.12 | 1.60 |
| 109 | Q109M | 1.28 | 1.19 | 1.03 | 1.04 | 1.73 |
| 109 | Q109N | 0.93 | 1.10 | 1.06 | 0.98 | 0.87 |
| 109 | Q109P | 0.23 | *0.05* | 0.82 | 1.00 | 0.17 |
| 109 | Q109R | 1.43 | 0.95 | 0.73 | 1.00 | 1.78 |
| 109 | Q109S | 1.08 | 1.19 | 1.12 | 0.98 | 1.16 |
| 109 | Q109T | 0.91 | 1.62 | 1.14 | 0.97 | 1.15 |
| 109 | Q109V | *0.05* | 0.05 | 0.05 | *ND* | *0.05* |
| 109 | Q109W | 0.92 | 1.21 | 0.95 | 0.91 | 1.22 |
| 109 | Q109Y | 0.93 | 1.47 | 0.99 | 1.00 | 1.18 |
| 110 | G110A | 1.25 | 1.29 | 0.81 | 0.95 | 1.36 |
| 110 | G110D | 0.62 | *0.05* | *0.05* | *ND* | *0.05* |
| 110 | G110E | 0.70 | *0.05* | *0.05* | *ND* | *0.05* |
| 110 | G110H | 0.58 | *0.05* | *0.05* | *ND* | *0.05* |
| 110 | G110I | 0.53 | *0.05* | *0.05* | *ND* | *0.05* |
| 110 | G110K | 0.54 | *0.05* | *0.05* | *ND* | *0.05* |
| 110 | G110L | 0.28 | *0.05* | *0.05* | *ND* | *0.05* |
| 110 | G110M | 0.44 | *0.05* | *0.05* | *ND* | *0.05* |
| 110 | G110N | 0.54 | *0.05* | *0.05* | *ND* | *0.05* |
| 110 | G110P | 0.54 | *0.05* | *0.05* | *ND* | *0.05* |
| 110 | G110Q | 0.46 | *0.05* | *0.05* | *ND* | *0.05* |
| 110 | G110R | 0.41 | *0.05* | *0.05* | *ND* | *0.05* |
| 110 | G110S | 0.39 | *0.05* | 1.26 | 0.89 | 0.28 |
| 110 | G110T | 0.52 | *0.05* | *0.05* | *ND* | *0.05* |
| 110 | G110V | 0.40 | *0.05* | *0.05* | *ND* | *0.05* |
| 110 | G110W | 0.37 | *0.05* | *0.05* | *ND* | *0.05* |
| 110 | G110Y | 0.39 | *0.05* | *0.05* | *ND* | *0.05* |
| 111 | L111A | 0.24 | *0.05* | 0.90 | 0.83 | 0.11 |
| 111 | L111C | 0.31 | *0.05* | 1.85 | 0.86 | 0.40 |
| 111 | L111E | 0.24 | *0.05* | 1.35 | 0.86 | 0.07 |
| 111 | L111F | 0.96 | 1.41 | 1.28 | 0.89 | 0.16 |
| 111 | L111G | 0.41 | *0.05* | *0.05* | *ND* | *0.05* |
| 111 | L111I | 1.02 | 1.60 | 1.41 | 0.80 | 0.69 |
| 111 | L111K | 0.39 | *0.05* | *0.05* | *ND* | *0.05* |
| 111 | L111M | 0.90 | 1.69 | 1.31 | 0.84 | 0.94 |
| 111 | L111P | 0.21 | *0.05* | 0.54 | *ND* | *0.05* |
| 111 | L111Q | 0.37 | *0.05* | *0.05* | *ND* | *0.05* |
| 111 | L111R | 0.28 | *0.05* | *0.05* | *ND* | *0.05* |
| 111 | L111S | 0.30 | *0.05* | *0.05* | *ND* | *0.05* |
| 111 | L111T | 0.20 | *0.05* | 0.98 | 0.92 | 0.07 |
| 111 | L111V | 1.05 | 1.37 | 1.13 | 0.80 | 0.76 |
| 111 | L111W | 0.29 | *0.05* | *0.05* | *ND* | *0.05* |
| 111 | L111Y | 0.30 | *0.05* | 1.36 | 1.05 | 0.07 |
| 112 | E112A | 0.69 | 5.15 | 1.16 | 0.93 | 0.86 |
| 112 | E112C | 0.59 | *0.05* | 1.40 | 0.98 | 0.57 |
| 112 | E112D | 1.25 | 0.93 | 1.01 | 1.00 | 1.48 |
| 112 | E112F | 0.26 | *0.05* | 1.08 | 0.98 | 0.20 |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 112 | E112G | 0.27 | *0.05* | 1.42 | 1.04 | 0.26 |
| 112 | E112I | 1.09 | 1.13 | 0.91 | 1.08 | 1.09 |
| 112 | E112K | 0.20 | *0.05* | *0.05* | *ND* | *0.05* |
| 112 | E112L | 0.78 | 2.81 | 1.29 | 1.05 | 0.87 |
| 112 | E112M | 0.37 | *0.05* | *0.05* | *ND* | *0.05* |
| 112 | E112N | 0.26 | *0.05* | 1.42 | 1.04 | 0.27 |
| 112 | E112Q | 0.82 | 3.22 | 1.15 | 0.93 | 1.03 |
| 112 | E112R | 0.16 | *0.05* | *0.05* | *ND* | *0.05* |
| 112 | E112S | 0.28 | *0.05* | 1.38 | 0.92 | 0.34 |
| 112 | E112T | 0.42 | *0.05* | 1.51 | 0.95 | 0.46 |
| 112 | E112V | 0.85 | 1.77 | 1.18 | 0.99 | 0.83 |
| 112 | E112W | 0.19 | *0.05* | 1.58 | 0.92 | 0.13 |
| 112 | E112Y | 0.21 | *0.05* | 1.23 | 0.94 | 0.16 |
| 113 | W113A | 0.20 | *0.05* | *0.05* | *ND* | *0.05* |
| 113 | W113C | 0.20 | *0.05* | 0.48 | *ND* | *0.05* |
| 113 | W113D | 0.31 | *0.05* | *0.05* | *ND* | *0.05* |
| 113 | W113E | 0.22 | *0.05* | *0.05* | *ND* | *0.05* |
| 113 | W113G | 0.38 | *0.05* | *0.05* | *ND* | *0.05* |
| 113 | W113I | 0.29 | *0.05* | *0.05* | *ND* | *0.05* |
| 113 | W113K | 0.32 | *0.05* | *0.05* | *ND* | *0.05* |
| 113 | W113L | 0.19 | *0.05* | 0.89 | 1.03 | 0.10 |
| 113 | W113M | 0.28 | *0.05* | 0.84 | 1.01 | 0.14 |
| 113 | W113N | 0.26 | *0.05* | *0.05* | *ND* | *0.05* |
| 113 | W113R | 0.29 | *0.05* | *0.05* | *ND* | *0.05* |
| 113 | W113S | 0.23 | *0.05* | *0.05* | *ND* | *0.05* |
| 113 | W113V | 0.22 | *0.05* | *0.05* | *ND* | *0.05* |
| 114 | A114C | 1.22 | 1.12 | 0.93 | 0.96 | 1.56 |
| 114 | A114F | 0.44 | *0.05* | *0.05* | *ND* | *0.05* |
| 114 | A114G | 0.50 | *0.05* | 1.34 | 1.05 | 0.60 |
| 114 | A114K | 0.41 | *0.05* | *0.05* | *ND* | *0.05* |
| 114 | A114M | 0.34 | *0.05* | *0.05* | *ND* | *0.05* |
| 114 | A114Q | 0.31 | *0.05* | *0.05* | *ND* | *0.05* |
| 114 | A114R | 0.30 | *0.05* | *0.05* | *ND* | *0.05* |
| 114 | A114S | *0.05* | *0.05* | *0.05* | *ND* | *0.05* |
| 114 | A114T | 0.76 | 2.09 | 1.10 | 0.85 | 0.85 |
| 114 | A114W | 0.40 | *0.05* | *0.05* | *ND* | *0.05* |
| 114 | A114Y | 0.40 | *0.05* | *0.05* | *ND* | *0.05* |
| 115 | G115C | 0.90 | 1.79 | 1.22 | 0.93 | 1.32 |
| 115 | G115E | 1.06 | 1.11 | 1.22 | 0.99 | 1.33 |
| 115 | G115F | 1.45 | 0.99 | 0.95 | 0.70 | 1.92 |
| 115 | G115H | 1.50 | 1.01 | 0.92 | 0.71 | 2.33 |
| 115 | G115I | 1.19 | 1.16 | 0.96 | 0.79 | 1.93 |
| 115 | G115K | 1.63 | 0.88 | 0.75 | 0.37 | 1.80 |
| 115 | G115L | 1.21 | 1.09 | 1.04 | 0.80 | 1.71 |
| 115 | G115M | 1.19 | 1.04 | 1.09 | 0.96 | 1.50 |
| 115 | G115N | 1.08 | 1.02 | 0.98 | 0.16 | 1.33 |
| 115 | G115P | 1.03 | 1.28 | 1.10 | 1.06 | 1.24 |
| 115 | G115Q | 1.13 | 1.22 | 1.06 | 0.89 | 1.66 |
| 115 | G115R | 1.28 | 1.24 | 0.86 | 0.12 | 1.50 |
| 115 | G115S | 0.97 | 1.63 | 1.15 | 1.00 | 1.45 |
| 115 | G115T | 1.06 | 1.10 | 1.15 | 0.93 | 1.51 |
| 115 | G115V | 0.19 | *0.05* | 2.21 | 0.86 | 0.43 |
| 115 | G115W | 1.46 | 0.86 | 0.82 | 1.01 | 1.98 |
| 115 | G115Y | 1.31 | 1.03 | 0.97 | 0.87 | 1.68 |
| 116 | N116A | 1.26 | 1.07 | 1.01 | 0.92 | 1.44 |
| 116 | N116C | 1.10 | 0.83 | 1.20 | 0.91 | 1.20 |
| 116 | N116D | 1.28 | 0.93 | 1.24 | 0.91 | 1.70 |
| 116 | N116F | 1.09 | 1.40 | 1.08 | 0.97 | 1.33 |
| 116 | N116G | 0.99 | 1.89 | 1.27 | 0.91 | 1.32 |
| 116 | N116I | 0.86 | 1.60 | 1.40 | 1.00 | 1.00 |
| 116 | N116K | 1.41 | 0.95 | 0.83 | 1.04 | 1.56 |
| 116 | N116L | 1.30 | 0.77 | 1.06 | 1.10 | 1.40 |
| 116 | N116M | 1.39 | 0.82 | 0.99 | 0.99 | 1.36 |
| 116 | N116Q | 1.27 | 0.89 | 1.08 | 1.01 | 1.49 |
| 116 | N116S | 1.22 | 1.07 | 1.01 | 0.92 | 1.45 |
| 116 | N116T | 1.33 | 0.89 | 1.09 | 0.96 | 1.56 |
| 116 | N116V | 1.21 | 1.00 | 1.13 | 0.85 | 1.59 |
| 116 | N116W | 0.88 | 2.02 | 1.24 | 0.99 | 1.08 |
| 117 | N117A | 1.21 | 1.43 | 1.00 | 0.96 | 1.29 |
| 117 | N117C | 0.91 | 1.30 | 1.19 | 0.93 | 1.15 |
| 117 | N117D | 0.74 | 1.58 | 1.08 | 1.02 | 1.01 |
| 117 | N117F | 0.79 | 1.47 | 1.01 | 1.03 | 0.95 |
| 117 | N117G | 0.65 | 4.40 | 1.20 | 1.01 | 0.84 |
| 117 | N117I | 0.78 | 1.42 | 1.25 | 1.05 | 1.01 |
| 117 | N117P | 0.22 | *0.05* | *0.05* | *ND* | *0.05* |
| 117 | N117Q | 1.22 | 0.92 | 0.84 | 1.08 | 1.38 |
| 117 | N117R | 1.03 | 1.34 | 0.84 | 1.01 | 1.40 |
| 117 | N117T | 1.05 | 1.15 | 0.93 | 1.04 | 1.24 |
| 117 | N117Y | 1.09 | 1.00 | 1.02 | 1.12 | 1.16 |
| 118 | G118A | 1.50 | 1.01 | 0.98 | 0.98 | 1.48 |
| 118 | G118C | 0.86 | 1.29 | 1.20 | 1.00 | 0.91 |
| 118 | G118D | 1.02 | 1.16 | 1.19 | 1.03 | 1.09 |
| 118 | G118E | 1.11 | 1.22 | 1.07 | 1.04 | 1.20 |
| 118 | G118F | 1.08 | 1.23 | 1.03 | 1.00 | 1.12 |
| 118 | G118I | 0.74 | 1.45 | 1.07 | 1.18 | 0.73 |
| 118 | G118K | 1.17 | 1.08 | 0.81 | 0.96 | 1.20 |
| 118 | G118L | 0.79 | 1.51 | 1.23 | 1.09 | 0.84 |
| 118 | G118M | 1.01 | 1.33 | 1.08 | 1.04 | 1.05 |
| 118 | G118N | 0.87 | 1.13 | 1.05 | 1.08 | 0.95 |
| 118 | G118P | 0.20 | *0.05* | 1.54 | 1.06 | 0.18 |
| 118 | G118Q | *0.05* | *0.05* | *0.05* | *ND* | *0.05* |
| 118 | G118R | 1.08 | 1.09 | 0.95 | 1.07 | 1.06 |
| 118 | G118S | 1.06 | 1.42 | 1.04 | 1.05 | 1.12 |
| 118 | G118T | 0.71 | 1.74 | 1.04 | 1.02 | 0.80 |
| 118 | G118V | 0.81 | 1.20 | 1.02 | 1.03 | 0.90 |
| 118 | G118W | 0.85 | 1.07 | 1.04 | 1.01 | 0.85 |
| 119 | M119A | 0.94 | 1.33 | 0.95 | 0.94 | 1.08 |
| 119 | M119C | 0.64 | 1.90 | 1.13 | 0.99 | 0.85 |
| 119 | M119E | 0.24 | *0.05* | *0.05* | *ND* | *0.05* |
| 119 | M119F | 1.07 | 1.08 | 1.13 | 1.08 | 1.14 |
| 119 | M119G | 0.22 | *0.05* | *0.05* | 1.00 | 0.07 |
| 119 | M119H | 0.49 | *0.05* | 1.36 | 1.08 | 0.60 |
| 119 | M119K | 0.22 | *0.05* | *0.05* | *ND* | *0.05* |
| 119 | M119N | 0.30 | *0.05* | 1.45 | 1.12 | 0.29 |
| 119 | M119P | 0.21 | *0.05* | *0.05* | *ND* | *0.05* |
| 119 | M119Q | 0.72 | 0.52 | 1.11 | 1.13 | 0.80 |
| 119 | M119R | 0.29 | *0.05* | *0.05* | *ND* | *0.05* |
| 119 | M119T | 1.07 | 0.95 | 0.81 | 0.97 | 1.19 |
| 119 | M119W | 0.16 | *0.05* | 1.88 | 1.03 | 0.15 |
| 120 | H120A | 1.14 | 1.12 | 0.97 | 0.93 | 1.81 |
| 120 | H120C | 0.92 | 1.36 | 1.12 | 1.04 | 1.21 |
| 120 | H120E | 1.12 | 1.17 | 1.12 | 1.11 | 1.30 |
| 120 | H120F | 1.05 | 1.16 | 1.01 | 1.09 | 1.31 |
| 120 | H120G | 1.08 | 1.56 | 1.07 | 0.99 | 1.33 |
| 120 | H120I | 1.06 | 0.93 | 0.92 | 1.17 | 1.24 |
| 120 | H120L | 1.04 | 1.17 | 1.20 | 1.13 | 1.32 |
| 120 | H120M | 1.19 | 1.12 | 1.08 | 0.97 | 1.50 |
| 120 | H120N | 1.21 | 1.04 | 1.04 | 1.08 | 1.43 |
| 120 | H120R | 1.05 | 1.13 | 0.98 | 0.91 | 1.49 |
| 120 | H120S | 1.19 | 1.16 | 1.07 | 1.11 | 1.61 |
| 120 | H120T | 1.19 | 1.05 | 0.98 | 1.12 | 1.53 |
| 120 | H120W | 0.95 | 1.07 | 1.07 | 1.01 | 1.08 |
| 121 | V121A | 1.09 | 0.96 | 1.07 | 0.91 | 1.52 |
| 121 | V121C | 0.85 | 1.67 | 1.41 | 0.97 | 1.08 |
| 121 | V121E | 0.82 | 2.12 | 1.37 | 0.79 | 0.99 |
| 121 | V121F | 1.01 | 1.42 | 1.29 | 0.95 | 1.12 |
| 121 | V121G | 0.46 | *0.05* | 2.16 | 0.96 | 0.59 |
| 121 | V121I | 1.40 | 0.90 | 1.11 | 0.95 | 1.58 |
| 121 | V121K | 0.30 | *0.05* | *0.05* | *ND* | *0.05* |
| 121 | V121L | 1.15 | 0.99 | 1.05 | 0.99 | 1.31 |
| 121 | V121M | 1.04 | 1.18 | 1.37 | 1.05 | 1.24 |
| 121 | V121P | 0.48 | *0.05* | *0.05* | *ND* | *0.05* |
| 121 | V121Q | 0.71 | 0.71 | 1.49 | 1.08 | 0.79 |
| 121 | V121R | 0.48 | *0.05* | *0.05* | *ND* | *0.05* |
| 121 | V121S | 1.18 | 1.00 | 1.09 | 0.95 | 1.52 |
| 121 | V121T | 0.91 | 1.64 | 1.40 | 1.04 | 1.12 |
| 121 | V121Y | 0.27 | *0.05* | 2.38 | 0.87 | 0.24 |
| 122 | A122C | 0.80 | 2.00 | 1.17 | 0.87 | 1.03 |
| 122 | A122G | 0.81 | 1.60 | 1.16 | 0.88 | 0.91 |
| 122 | A122H | 0.32 | *0.05* | *0.05* | *ND* | *0.05* |
| 122 | A122I | 0.95 | 1.04 | 1.14 | 0.58 | 0.79 |
| 122 | A122L | 1.12 | 0.71 | 1.05 | 0.69 | 0.72 |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 122 | A122N | 0.18 | *0.05* | *0.05* | *ND* | *0.05* |
| 122 | A122Q | 0.23 | *0.05* | *0.05* | *ND* | *0.05* |
| 122 | A122R | 0.32 | *0.05* | *0.05* | *ND* | *0.05* |
| 122 | A122S | 1.04 | 1.17 | 1.18 | 0.87 | 1.41 |
| 122 | A122T | 1.04 | 1.13 | 1.10 | 0.72 | 1.62 |
| 122 | A122V | 1.05 | 1.09 | 1.20 | 0.82 | 0.98 |
| 122 | A122Y | 0.26 | *0.05* | *0.05* | *ND* | *0.05* |
| 123 | N123E | 1.48 | 0.68 | 0.89 | 0.35 | 0.06 |
| 123 | N123F | 0.49 | *0.05* | *0.05* | *ND* | *0.05* |
| 123 | N123G | 1.71 | 0.82 | 1.15 | 0.53 | 0.43 |
| 123 | N123H | 0.47 | *0.05* | *0.05* | *ND* | *0.05* |
| 123 | N123I | 1.04 | 0.23 | 0.82 | *ND* | *0.05* |
| 123 | N123L | 1.17 | 0.27 | 0.81 | *ND* | *0.05* |
| 123 | N123M | 0.97 | 0.42 | 0.86 | *ND* | *0.05* |
| 123 | N123P | 0.91 | 0.52 | 0.93 | *ND* | *0.05* |
| 123 | N123R | 0.44 | *0.05* | *0.05* | *ND* | *0.05* |
| 123 | N123S | 1.15 | 1.13 | 1.12 | 0.48 | 0.45 |
| 123 | N123V | 0.93 | 0.25 | 0.94 | *ND* | *0.05* |
| 123 | N123W | 0.44 | *0.05* | *0.05* | *ND* | *0.05* |
| 124 | L124D | 0.50 | *0.05* | *0.05* | *ND* | *0.05* |
| 124 | L124E | 0.40 | *0.05* | 0.62 | *ND* | *0.05* |
| 124 | L124G | 1.31 | 1.26 | 1.05 | 0.98 | 1.72 |
| 124 | L124H | 0.43 | *0.05* | 1.28 | *ND* | *0.05* |
| 124 | L124K | 0.28 | *0.05* | *0.05* | *ND* | *0.05* |
| 124 | L124N | 0.44 | *0.05* | 1.97 | *ND* | *0.05* |
| 124 | L124P | 0.47 | *0.05* | *0.05* | *ND* | *0.05* |
| 124 | L124Q | 0.38 | *0.05* | 1.89 | *ND* | *0.05* |
| 124 | L124R | 0.44 | *0.05* | *0.05* | *ND* | *0.05* |
| 124 | L124S | 0.74 | 3.78 | 1.36 | 0.80 | 0.25 |
| 124 | L124T | 1.32 | 1.11 | 1.14 | 0.85 | 0.70 |
| 124 | L124Y | 0.78 | 0.87 | 0.86 | *ND* | *0.05* |
| 125 | S125A | 1.12 | 1.13 | 0.80 | 0.73 | 0.32 |
| 125 | S125C | 2.09 | 0.45 | 0.84 | *ND* | *0.05* |
| 125 | S125E | 0.54 | *0.05* | *0.05* | *ND* | *0.05* |
| 125 | S125G | 2.41 | 0.17 | 0.17 | *ND* | *0.05* |
| 125 | S125H | 0.47 | *0.05* | *0.05* | *ND* | *0.05* |
| 125 | S125I | 0.49 | *0.05* | *0.05* | *ND* | *0.05* |
| 125 | S125K | 0.35 | *0.05* | *0.05* | *ND* | *0.05* |
| 125 | S125L | 0.45 | *0.05* | *0.05* | *ND* | *0.05* |
| 125 | S125M | 0.46 | *0.05* | *0.05* | *ND* | *0.05* |
| 125 | S125N | 0.74 | *0.05* | *0.05* | *ND* | *0.05* |
| 125 | S125P | 0.93 | *0.05* | *0.05* | *ND* | *0.05* |
| 125 | S125R | 0.47 | *0.05* | *0.05* | *ND* | *0.05* |
| 125 | S125T | 1.75 | 0.07 | 0.14 | *ND* | *0.05* |
| 125 | S125W | 0.45 | *0.05* | *0.05* | *ND* | *0.05* |
| 125 | S125Y | 0.46 | *0.05* | *0.05* | *ND* | *0.05* |
| 126 | L126A | 1.08 | 1.68 | 0.81 | 0.82 | 0.26 |
| 126 | L126C | 1.09 | *0.05* | *0.05* | *ND* | *0.05* |
| 126 | L126E | 2.16 | *0.05* | 0.90 | *ND* | *0.05* |
| 126 | L126F | 1.30 | 1.15 | 0.93 | 1.07 | 0.47 |
| 126 | L126G | 2.16 | 0.49 | 0.42 | 0.88 | 0.07 |
| 126 | L126H | 2.49 | 0.43 | 0.73 | *ND* | *0.05* |
| 126 | L126I | 1.60 | 0.88 | 0.88 | 0.94 | 0.25 |
| 126 | L126K | 0.82 | 0.36 | 0.81 | *ND* | *0.05* |
| 126 | L126M | 1.55 | 0.92 | 0.93 | 1.03 | 0.13 |
| 126 | L126N | 2.30 | 0.56 | 0.92 | *ND* | *0.05* |
| 126 | L126P | 0.63 | *0.05* | *0.05* | *ND* | *0.05* |
| 126 | L126Q | 2.51 | 0.34 | 0.73 | *ND* | *0.05* |
| 126 | L126R | 0.24 | *0.05* | *0.05* | *ND* | *0.05* |
| 126 | L126S | 2.36 | 0.58 | 0.68 | 0.86 | 0.07 |
| 126 | L126T | 2.24 | 0.53 | 0.73 | *ND* | *0.05* |
| 126 | L126V | 1.54 | 0.84 | 0.94 | 0.85 | 0.16 |
| 126 | L126W | 2.63 | 0.32 | 0.59 | *ND* | *0.05* |
| 126 | L126Y | 2.76 | 0.10 | 0.30 | *ND* | *0.05* |
| 127 | G127A | 0.77 | *0.05* | *0.05* | *ND* | *0.05* |
| 127 | G127D | 1.85 | 0.93 | 0.87 | *ND* | *0.05* |
| 127 | G127F | 0.83 | 2.63 | 0.40 | *ND* | *0.05* |
| 127 | G127I | 1.88 | 1.02 | 0.69 | *ND* | *0.05* |
| 127 | G127L | 1.68 | 0.87 | 0.58 | *ND* | *0.05* |
| 127 | G127P | 0.44 | *0.05* | *0.05* | *ND* | *0.05* |
| 127 | G127Q | 2.00 | 0.96 | 0.78 | *ND* | *0.05* |
| 127 | G127R | 1.65 | 1.14 | 0.63 | *ND* | *0.05* |
| 127 | G127S | 1.41 | 1.37 | 1.03 | *ND* | *0.05* |
| 127 | G127T | 1.76 | 1.17 | 0.89 | *ND* | *0.05* |
| 127 | G127V | 2.00 | 0.93 | 0.70 | *ND* | *0.05* |
| 127 | G127W | 0.35 | *0.05* | 0.28 | *ND* | *0.05* |
| 128 | S128A | 1.30 | 0.87 | 0.97 | 1.02 | 1.46 |
| 128 | S128C | 1.69 | 0.14 | 0.66 | 1.10 | 0.06 |
| 128 | S128D | 2.83 | 0.72 | 0.64 | 1.03 | 0.33 |
| 128 | S128F | 2.91 | 0.62 | 0.58 | 0.96 | 1.59 |
| 128 | S128G | 0.95 | 1.33 | 1.11 | 1.01 | 1.32 |
| 128 | S128H | 2.62 | 0.73 | 0.63 | 1.06 | 0.54 |
| 128 | S128I | 2.96 | 0.72 | 0.58 | 1.12 | 3.27 |
| 128 | S128K | 2.21 | 0.96 | 0.48 | 1.01 | 1.44 |
| 128 | S128L | 3.03 | 0.69 | 0.62 | 1.08 | 2.47 |
| 128 | S128M | 2.62 | 0.77 | 0.63 | 1.10 | 5.64 |
| 128 | S128N | 1.38 | 1.16 | 1.09 | 0.95 | 0.51 |
| 128 | S128P | 1.28 | 0.14 | 0.48 | *ND* | *0.05* |
| 128 | S128Q | 2.70 | 0.80 | 0.56 | 1.10 | 1.17 |
| 128 | S128R | 1.39 | 1.10 | 0.66 | 1.11 | 1.55 |
| 128 | S128T | 1.48 | 1.02 | 0.82 | 1.13 | 2.85 |
| 128 | S128W | 1.47 | 0.69 | 1.03 | 1.09 | 0.18 |
| 128 | S128Y | 2.90 | 0.62 | 0.54 | 1.06 | 0.58 |
| 129 | P129A | 1.37 | 0.86 | 0.82 | 0.82 | 2.33 |
| 129 | P129E | 1.09 | 0.80 | 1.32 | 1.16 | 1.26 |
| 129 | P129F | 1.23 | 0.71 | 0.94 | 0.89 | 2.01 |
| 129 | P129G | 1.61 | 0.91 | 0.88 | 0.86 | 2.57 |
| 129 | P129I | 0.96 | 0.59 | 1.13 | 0.74 | 1.30 |
| 129 | P129L | 1.45 | 0.51 | 0.86 | 0.79 | 1.56 |
| 129 | P129M | 1.70 | 0.75 | 0.80 | 0.92 | 1.83 |
| 129 | P129N | 1.57 | 0.93 | 0.81 | 0.99 | 2.66 |
| 129 | P129R | 1.22 | 1.03 | 0.77 | 0.98 | 3.28 |
| 129 | P129S | 1.68 | 0.87 | 0.88 | 0.92 | 2.68 |
| 129 | P129T | 1.34 | 0.54 | 0.93 | 0.58 | 1.98 |
| 129 | P129V | 1.28 | 0.36 | 0.84 | 0.65 | 1.36 |
| 129 | P129W | 1.12 | 0.77 | 0.86 | 0.74 | 1.21 |
| 129 | P129Y | 1.08 | 0.77 | 1.16 | 0.91 | 1.90 |
| 130 | S130C | 1.18 | 0.44 | 1.12 | 0.98 | 0.74 |
| 130 | S130K | 1.62 | 0.86 | 0.82 | 1.11 | 2.07 |
| 130 | S130L | 1.25 | 1.12 | 0.83 | 1.07 | 1.29 |
| 130 | S130N | 1.33 | 1.03 | 1.02 | 1.14 | 1.53 |
| 130 | S130P | 1.00 | 0.16 | 0.91 | *ND* | *0.05* |
| 130 | S130Q | 1.31 | 1.00 | 1.05 | 1.10 | 1.17 |
| 130 | S130R | 1.43 | 0.87 | 0.70 | 0.93 | 2.06 |
| 130 | S130V | 1.08 | 1.21 | 0.95 | 0.93 | 1.29 |
| 130 | S130W | 1.33 | 0.92 | 0.83 | 0.91 | 1.18 |
| 130 | S130Y | 1.31 | 1.12 | 0.96 | 0.87 | 1.37 |
| 131 | P131A | 1.15 | 1.21 | 1.02 | 0.89 | 1.16 |
| 131 | P131D | 1.29 | 0.87 | 1.20 | 1.04 | 1.35 |
| 131 | P131E | 1.35 | 0.77 | 1.16 | 1.07 | 1.13 |
| 131 | P131F | 1.23 | 0.77 | 0.98 | 0.91 | 1.30 |
| 131 | P131G | 1.12 | 1.34 | 1.06 | 0.84 | 0.90 |
| 131 | P131I | 1.04 | 0.47 | 1.01 | 0.68 | 0.87 |
| 131 | P131K | 1.43 | 0.74 | 0.80 | 0.91 | 1.33 |
| 131 | P131L | 0.88 | 0.83 | 1.16 | 0.64 | 0.73 |
| 131 | P131M | 1.06 | 0.86 | 0.96 | 0.77 | 0.99 |
| 131 | P131Q | 1.33 | 0.76 | 0.93 | 0.94 | 1.18 |
| 131 | P131R | 1.30 | 0.87 | 0.79 | 0.78 | 1.54 |
| 131 | P131V | 0.96 | 0.94 | 1.07 | 0.55 | 0.99 |
| 132 | S132A | 1.04 | 1.07 | 1.08 | 0.98 | 1.00 |
| 132 | S132E | 0.72 | 3.77 | 1.51 | 0.92 | 0.57 |
| 132 | S132F | 0.72 | 8.36 | 1.05 | 1.05 | 1.08 |
| 132 | S132H | 0.89 | 1.54 | 1.04 | 0.97 | 1.01 |
| 132 | S132I | 0.83 | 1.39 | 1.09 | 0.89 | 0.86 |
| 132 | S132L | 0.75 | 3.33 | 1.21 | 0.83 | 1.35 |
| 132 | S132M | 0.73 | 4.11 | 1.32 | 0.91 | 1.20 |
| 132 | S132N | 0.82 | 2.12 | 1.19 | 0.99 | 1.06 |
| 132 | S132Q | 1.04 | 0.88 | 1.08 | 0.88 | 0.87 |
| 132 | S132R | 0.93 | 0.76 | 0.92 | 0.90 | 0.57 |
| 132 | S132T | 1.24 | 0.79 | 0.91 | 0.82 | 1.45 |
| 132 | S132W | 0.67 | 1.28 | 0.99 | 0.91 | 1.12 |
| 133 | A133F | 1.17 | 1.05 | 0.92 | 0.88 | 1.30 |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 133 | A133K | 1.44 | 0.96 | 0.86 | 1.11 | 1.56 |
| 133 | A133L | 0.39 | *0.05* | 1.38 | 1.14 | 0.23 |
| 133 | A133N | 1.13 | 0.97 | 1.11 | 1.15 | 1.20 |
| 133 | A133P | 1.42 | 0.95 | 1.04 | 1.17 | 1.26 |
| 133 | A133Q | 0.62 | *0.05* | 1.20 | 1.00 | 0.71 |
| 133 | A133S | 1.15 | 1.06 | 0.97 | 1.01 | 1.14 |
| 133 | A133T | 1.14 | 0.95 | 1.09 | 0.94 | 1.24 |
| 133 | A133V | 1.11 | 1.18 | 1.12 | 0.95 | 1.21 |
| 133 | A133Y | 1.37 | 0.97 | 0.89 | 0.90 | 1.45 |
| 134 | T134A | 0.85 | 2.30 | 1.32 | 1.00 | 1.07 |
| 134 | T134D | 0.34 | *0.05* | *0.05* | *ND* | *0.05* |
| 134 | T134F | 0.40 | *0.05* | 1.52 | 0.98 | 0.36 |
| 134 | T134H | 0.24 | *0.05* | *0.05* | *ND* | *0.05* |
| 134 | T134I | 0.44 | *0.05* | 1.40 | 1.11 | 0.47 |
| 134 | T134L | 0.26 | *0.05* | 1.59 | 1.02 | 0.26 |
| 134 | T134M | 0.31 | *0.05* | 1.73 | 0.94 | 0.32 |
| 134 | T134N | 0.26 | *0.05* | *0.05* | *ND* | *0.05* |
| 134 | T134P | 0.25 | *0.05* | 2.25 | 1.05 | 0.19 |
| 134 | T134S | 1.08 | 1.28 | 1.32 | 0.81 | 1.21 |
| 134 | T134V | 0.81 | 2.14 | 1.36 | 0.99 | 0.99 |
| 134 | T134Y | 0.21 | *0.05* | *0.05* | *ND* | *0.05* |
| 135 | L135A | 0.41 | *0.05* | 1.25 | 0.29 | 0.21 |
| 135 | L135C | 0.49 | *0.05* | 1.52 | 0.86 | 0.24 |
| 135 | L135D | 0.35 | *0.05* | *0.05* | *ND* | *0.05* |
| 135 | L135E | 0.42 | *0.05* | 1.35 | 1.02 | 0.20 |
| 135 | L135F | 0.57 | *0.05* | 1.03 | 0.19 | 0.91 |
| 135 | L135G | 0.27 | *0.05* | *0.05* | 0.13 | 0.09 |
| 135 | L135M | 1.02 | 1.40 | 0.98 | 0.84 | 1.91 |
| 135 | L135N | 0.26 | *0.05* | *0.05* | *ND* | *0.05* |
| 135 | L135Q | 0.33 | *0.05* | 1.66 | 0.41 | 0.32 |
| 135 | L135R | 0.39 | *0.05* | *0.05* | *ND* | *0.05* |
| 135 | L135S | 0.23 | *0.05* | 0.75 | 0.09 | 0.12 |
| 135 | L135T | 0.61 | *0.05* | 1.24 | 0.53 | 0.64 |
| 135 | L135W | 1.48 | 0.66 | 1.09 | 0.92 | 3.30 |
| 136 | E136A | 1.12 | 1.05 | 0.80 | 0.78 | 1.28 |
| 136 | E136D | 0.69 | 0.38 | 1.24 | 0.42 | 0.66 |
| 136 | E136F | 1.08 | 1.19 | 0.78 | 0.43 | 1.34 |
| 136 | E136G | 0.78 | 1.90 | 0.80 | 0.78 | 0.89 |
| 136 | E136I | 0.65 | *0.05* | 0.57 | 0.58 | 0.37 |
| 136 | E136K | 1.16 | 0.71 | 0.63 | 0.22 | 1.34 |
| 136 | E136L | 0.38 | *0.05* | *0.05* | *ND* | *0.05* |
| 136 | E136M | 0.45 | *0.05* | 0.83 | 0.69 | 0.46 |
| 136 | E136N | 0.62 | *0.05* | 1.05 | 0.49 | 0.47 |
| 136 | E136P | 0.36 | *0.05* | *0.05* | *ND* | *0.05* |
| 136 | E136Q | 1.13 | 1.07 | 0.92 | 0.84 | 1.46 |
| 136 | E136R | 1.01 | 0.71 | 0.37 | 0.15 | 1.41 |
| 136 | E136S | 0.96 | 1.05 | 0.74 | 0.78 | 0.92 |
| 136 | E136T | 0.46 | *0.05* | 0.45 | 0.55 | 0.20 |
| 136 | E136V | 0.82 | 1.04 | 0.68 | 0.57 | 0.76 |
| 136 | E136W | 0.84 | 1.47 | 0.49 | 0.18 | 1.03 |
| 136 | E136Y | 1.08 | 1.03 | 0.81 | 0.52 | 1.23 |
| 137 | Q137A | 1.28 | 1.38 | 1.15 | 1.00 | 1.42 |
| 137 | Q137C | 0.82 | 1.20 | 1.17 | 1.02 | 0.96 |
| 137 | Q137E | 1.16 | 0.84 | 1.19 | 1.07 | 1.22 |
| 137 | Q137G | 0.71 | 2.29 | 1.12 | 0.91 | 0.89 |
| 137 | Q137H | 1.25 | 1.00 | 1.01 | 0.99 | 1.33 |
| 137 | Q137K | 1.40 | 0.77 | 0.79 | 0.92 | 1.44 |
| 137 | Q137L | 1.22 | 1.12 | 1.04 | 1.01 | 1.31 |
| 137 | Q137M | 1.27 | 1.14 | 0.92 | 1.07 | 1.30 |
| 137 | Q137P | 0.19 | *0.05* | *0.05* | *ND* | *0.05* |
| 137 | Q137R | 1.19 | 0.99 | 0.80 | 0.88 | 1.28 |
| 137 | Q137S | 1.07 | 1.57 | 1.03 | 0.97 | 1.13 |
| 137 | Q137V | 0.82 | 1.70 | 1.12 | 0.79 | 1.15 |
| 137 | Q137W | 1.27 | 1.18 | 0.81 | 0.81 | 1.47 |
| 138 | A138C | 0.68 | 2.54 | 1.24 | 0.60 | 0.62 |
| 138 | A138D | 0.19 | *0.05* | *0.05* | *ND* | *0.05* |
| 138 | A138E | 0.18 | *0.05* | 1.52 | 0.80 | 0.11 |
| 138 | A138G | 0.48 | *0.05* | 1.35 | 0.88 | 0.86 |
| 138 | A138H | 0.14 | *0.05* | *0.05* | *ND* | *0.05* |
| 138 | A138K | 0.22 | *0.05* | *0.05* | *ND* | *0.05* |
| 138 | A138L | 0.61 | 1.35 | 1.01 | 0.07 | 0.43 |
| 138 | A138M | 1.07 | 1.02 | 0.98 | 0.53 | 0.79 |
| 138 | A138P | 0.16 | *0.05* | *0.05* | *ND* | *0.05* |
| 138 | A138Q | 0.23 | *0.05* | 1.45 | 0.63 | 0.21 |
| 138 | A138R | 0.23 | *0.05* | 1.65 | 1.02 | 0.35 |
| 138 | A138S | 0.31 | *0.05* | *0.05* | *ND* | *0.05* |
| 138 | A138V | 0.90 | 1.33 | 0.80 | 0.17 | 0.64 |
| 138 | A138W | 0.16 | *0.05* | *0.05* | *ND* | *0.05* |
| 139 | V139A | 1.06 | 1.01 | 1.22 | 0.26 | 0.88 |
| 139 | V139C | 0.92 | 1.91 | 1.34 | 0.84 | 1.09 |
| 139 | V139D | 0.37 | *0.05* | *0.05* | *ND* | *0.05* |
| 139 | V139E | 0.34 | *0.05* | 1.74 | 0.33 | 0.12 |
| 139 | V139F | 0.66 | *0.05* | 1.32 | *0.05* | 0.10 |
| 139 | V139G | 0.40 | *0.05* | 1.41 | 0.06 | 0.21 |
| 139 | V139I | 1.27 | 0.80 | 1.13 | 0.92 | 1.56 |
| 139 | V139L | 0.41 | *0.05* | *0.05* | *ND* | *0.05* |
| 139 | V139M | 0.85 | 1.99 | 1.38 | 0.22 | 0.86 |
| 139 | V139Q | 0.59 | *0.05* | 1.51 | *0.05* | 0.27 |
| 139 | V139R | 0.44 | *0.05* | *0.05* | *ND* | *0.05* |
| 139 | V139S | 0.74 | 0.22 | 1.34 | 0.12 | 0.46 |
| 139 | V139T | 0.95 | 2.01 | 1.32 | 0.72 | 0.95 |
| 139 | V139W | 0.40 | *0.05* | *0.05* | *ND* | *0.05* |
| 139 | V139Y | 0.35 | *0.05* | 1.74 | *ND* | *0.05* |
| 140 | N140A | 1.28 | 0.73 | 0.98 | 0.80 | 1.25 |
| 140 | N140C | 0.89 | 1.48 | 1.34 | 0.72 | 0.93 |
| 140 | N140D | 1.31 | 0.85 | 1.13 | 1.09 | 1.57 |
| 140 | N140E | 1.32 | 0.95 | 1.04 | 0.96 | 1.28 |
| 140 | N140F | 0.86 | 1.32 | 1.24 | 0.57 | 1.01 |
| 140 | N140G | 1.09 | 1.19 | 1.19 | 0.62 | 1.32 |
| 140 | N140I | 1.10 | 0.82 | 1.22 | 0.65 | 1.16 |
| 140 | N140K | 0.22 | *0.05* | 2.81 | *0.05* | 0.15 |
| 140 | N140L | 1.03 | 1.18 | 1.18 | 0.56 | 1.13 |
| 140 | N140M | 1.10 | 0.81 | 1.16 | 0.62 | 1.15 |
| 140 | N140P | 0.33 | *0.05* | *0.05* | *ND* | *0.05* |
| 140 | N140Q | 1.16 | 0.96 | 1.10 | 0.73 | 1.15 |
| 140 | N140R | 1.03 | 1.02 | 0.91 | 0.27 | 1.01 |
| 140 | N140S | 1.10 | 1.10 | 1.10 | 0.64 | 1.27 |
| 140 | N140T | 1.05 | 1.17 | 1.25 | 0.60 | 1.41 |
| 140 | N140V | 0.96 | 1.39 | 1.29 | 0.39 | 1.20 |
| 140 | N140Y | 0.91 | 1.54 | 1.20 | 0.39 | 0.98 |
| 141 | S141D | 1.17 | 0.71 | 1.06 | 1.12 | 1.19 |
| 141 | S141E | 0.87 | 0.75 | 1.10 | 0.95 | 0.99 |
| 141 | S141G | 1.06 | 1.29 | 1.12 | 0.99 | 1.21 |
| 141 | S141H | 1.11 | 1.08 | 1.07 | 1.03 | 1.17 |
| 141 | S141I | 1.19 | 1.02 | 0.95 | 0.97 | 1.29 |
| 141 | S141K | 1.29 | 1.12 | 0.87 | 0.99 | 1.36 |
| 141 | S141L | 0.80 | 0.83 | 1.12 | 1.01 | 0.90 |
| 141 | S141N | 1.05 | 1.07 | 1.10 | 1.09 | 1.15 |
| 141 | S141P | 0.36 | *0.05* | *0.05* | *ND* | *0.05* |
| 141 | S141Q | 1.04 | 0.92 | 0.93 | 0.97 | 1.16 |
| 141 | S141R | 1.19 | 1.01 | 0.84 | 1.01 | 1.40 |
| 141 | S141V | 1.33 | 0.90 | 0.86 | 0.86 | 1.42 |
| 141 | S141Y | 1.02 | 1.08 | 1.13 | 1.02 | 0.93 |
| 142 | A142C | 0.91 | 2.30 | 1.25 | 0.94 | 1.08 |
| 142 | A142D | 0.30 | *0.05* | *0.05* | *ND* | *0.05* |
| 142 | A142E | 0.34 | *0.05* | 1.71 | 0.49 | 0.33 |
| 142 | A142F | 0.27 | *0.05* | *0.05* | *ND* | *0.05* |
| 142 | A142G | 0.43 | *0.05* | 1.70 | 0.17 | 0.51 |
| 142 | A142H | 0.24 | *0.05* | *0.05* | *ND* | *0.05* |
| 142 | A142I | 0.72 | *0.05* | 1.08 | 0.42 | 0.50 |
| 142 | A142K | 0.36 | *0.05* | *0.05* | *ND* | *0.05* |
| 142 | A142L | 1.05 | 1.04 | 1.01 | 0.08 | 0.70 |
| 142 | A142M | 0.71 | 16.35 | 1.04 | *0.05* | 0.48 |
| 142 | A142N | 0.40 | *0.05* | 1.58 | 0.18 | 0.43 |
| 142 | A142P | 0.23 | *0.05* | *0.05* | *ND* | *0.05* |
| 142 | A142Q | 0.78 | 9.76 | 1.11 | 0.24 | 0.67 |
| 142 | A142R | 0.30 | *0.05* | *0.05* | *ND* | *0.05* |
| 142 | A142S | 0.77 | 6.91 | 1.35 | 0.72 | 1.19 |
| 142 | A142T | 0.87 | 2.44 | 1.18 | 0.70 | 1.12 |
| 142 | A142V | 1.15 | 1.20 | 0.99 | 0.94 | 1.36 |
| 142 | A142W | 0.18 | *0.05* | *0.05* | 0.07 | 0.06 |
| 142 | A142Y | 0.33 | *0.05* | 2.25 | 0.84 | 0.41 |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 143 | T143C | 1.24 | 0.85 | 1.15 | 0.87 | 1.46 |
| 143 | T143D | 1.10 | 1.05 | 1.11 | 0.96 | 1.19 |
| 143 | T143F | 1.20 | 0.80 | 1.10 | 0.98 | 1.20 |
| 143 | T143G | 0.94 | 1.12 | 1.04 | 0.31 | 0.95 |
| 143 | T143H | 1.26 | 0.93 | 0.96 | 1.08 | 1.18 |
| 143 | T143I | 0.95 | 0.92 | 1.04 | 0.46 | 0.98 |
| 143 | T143K | 1.25 | 0.95 | 0.84 | 0.08 | 1.45 |
| 143 | T143L | 1.10 | 0.74 | 1.09 | 0.18 | 1.19 |
| 143 | T143M | 0.90 | 1.12 | 1.10 | 0.52 | 1.05 |
| 143 | T143N | 1.25 | 0.91 | 1.09 | 0.94 | 1.39 |
| 143 | T143R | 0.55 | *0.05* | 1.00 | *0.05* | 0.61 |
| 143 | T143S | 0.94 | 1.31 | 1.22 | 0.75 | 1.09 |
| 143 | T143V | 1.27 | 0.86 | 0.96 | 0.77 | 1.63 |
| 143 | T143W | 1.37 | 0.79 | 1.03 | 0.79 | 1.38 |
| 143 | T143Y | 0.97 | 1.15 | 1.20 | 0.77 | 1.09 |
| 144 | S144A | 1.29 | 1.04 | 0.98 | 1.02 | 1.45 |
| 144 | S144C | 1.08 | 0.75 | 1.15 | 1.00 | 1.31 |
| 144 | S144D | 1.36 | 0.82 | 1.11 | 1.05 | 1.55 |
| 144 | S144E | 0.40 | *0.05* | *0.05* | *ND* | *0.05* |
| 144 | S144G | 1.19 | 1.13 | 0.98 | 1.03 | 1.41 |
| 144 | S144H | 1.21 | 0.94 | 0.85 | 1.04 | 1.43 |
| 144 | S144I | 1.15 | 1.01 | 1.05 | 0.97 | 1.41 |
| 144 | S144K | 0.37 | *0.05* | *0.05* | *ND* | *0.05* |
| 144 | S144L | 0.97 | 0.98 | 1.04 | 0.92 | 1.23 |
| 144 | S144M | 1.28 | 0.88 | 0.93 | 1.01 | 1.46 |
| 144 | S144N | 1.32 | 0.90 | 1.08 | 0.96 | 1.53 |
| 144 | S144P | 0.25 | *0.05* | 0.54 | *0.05* | 0.10 |
| 144 | S144Q | 0.62 | *0.05* | 1.29 | 0.94 | 0.74 |
| 144 | S144R | 1.30 | 0.86 | 0.91 | 0.92 | 1.46 |
| 144 | S144T | 1.21 | 1.01 | 1.00 | 0.86 | 1.63 |
| 144 | S144V | 1.25 | 1.06 | 1.09 | 0.92 | 1.44 |
| 144 | S144W | 0.98 | 1.31 | 1.04 | 0.55 | 1.22 |
| 144 | S144Y | 1.03 | 1.26 | 1.04 | 0.87 | 1.17 |
| 145 | R145A | 1.46 | 0.85 | 0.99 | 1.01 | 1.51 |
| 145 | R145C | 0.98 | 1.03 | 1.24 | 1.04 | 1.06 |
| 145 | R145D | 1.08 | 0.84 | 1.10 | 1.04 | 1.20 |
| 145 | R145E | 0.65 | 12.81 | 1.54 | 0.92 | 0.87 |
| 145 | R145F | 0.83 | 1.06 | 1.31 | 1.01 | 0.94 |
| 145 | R145G | 0.69 | 2.91 | 1.42 | 0.99 | 0.80 |
| 145 | R145I | 0.49 | *0.05* | *0.05* | *ND* | *0.05* |
| 145 | R145K | 1.30 | 1.03 | 1.06 | 1.08 | 1.37 |
| 145 | R145L | 1.01 | 1.06 | 1.20 | 1.06 | 1.20 |
| 145 | R145M | 0.73 | 1.73 | 1.50 | 1.02 | 0.87 |
| 145 | R145N | 1.12 | 1.09 | 1.13 | 0.98 | 1.32 |
| 145 | R145P | 0.26 | *0.05* | *0.05* | *ND* | *0.05* |
| 145 | R145Q | 1.51 | 0.87 | 1.06 | 1.00 | 1.68 |
| 145 | R145S | 0.57 | *0.05* | 1.56 | 0.95 | 0.79 |
| 145 | R145T | 0.77 | 1.06 | 1.21 | 1.04 | 0.93 |
| 145 | R145W | 0.64 | 2.55 | 1.28 | 0.95 | 0.85 |
| 145 | R145Y | 0.69 | 3.13 | 1.39 | 1.04 | 0.82 |
| 146 | G146A | 0.84 | 2.28 | 1.33 | 0.58 | 0.88 |
| 146 | G146C | 0.68 | *0.05* | 1.56 | 0.85 | 0.74 |
| 146 | G146D | 1.15 | 1.10 | 1.23 | 1.03 | 1.39 |
| 146 | G146E | 0.80 | 2.87 | 1.31 | 0.71 | 0.93 |
| 146 | G146F | 0.43 | *0.05* | 1.66 | 0.42 | 0.45 |
| 146 | G146I | 0.22 | *0.05* | 1.14 | 0.37 | 0.19 |
| 146 | G146K | 0.83 | 1.83 | 1.15 | 0.07 | 0.91 |
| 146 | G146L | 0.37 | *0.05* | 1.61 | 0.56 | 0.36 |
| 146 | G146M | 0.58 | *0.05* | 1.65 | 0.74 | 0.66 |
| 146 | G146P | 0.30 | *0.05* | *0.05* | *ND* | *0.05* |
| 146 | G146Q | 0.89 | 1.43 | 1.02 | 0.72 | 1.08 |
| 146 | G146R | 0.70 | *0.05* | 1.06 | *0.05* | 0.86 |
| 146 | G146S | 0.59 | *0.05* | 1.44 | 0.54 | 0.75 |
| 146 | G146T | 0.27 | *0.05* | 1.86 | 0.08 | 0.25 |
| 146 | G146V | 0.18 | *0.05* | 0.79 | 0.11 | 0.09 |
| 146 | G146W | 0.19 | *0.05* | 1.80 | 0.44 | 0.18 |
| 146 | G146Y | 0.30 | *0.05* | 2.16 | 0.45 | 0.31 |
| 147 | V147D | 0.31 | *0.05* | *0.05* | *ND* | *0.05* |
| 147 | V147F | 0.27 | *0.05* | 1.86 | 0.72 | 0.17 |
| 147 | V147G | 0.31 | *0.05* | 1.85 | 0.51 | 0.24 |
| 147 | V147H | 0.24 | *0.05* | *0.05* | *ND* | *0.05* |
| 147 | V147I | 1.07 | 1.28 | 0.93 | 1.09 | 1.66 |
| 147 | V147L | 1.19 | 0.85 | 0.92 | 0.90 | 1.54 |
| 147 | V147M | 1.18 | 0.93 | 1.03 | 0.73 | 1.43 |
| 147 | V147P | 0.27 | *0.05* | 1.25 | *0.05* | 0.13 |
| 147 | V147Q | 0.53 | *0.05* | 1.30 | 0.51 | 0.82 |
| 147 | V147R | 0.27 | *0.05* | *0.05* | *ND* | *0.05* |
| 147 | V147S | 0.35 | *0.05* | *0.05* | *ND* | *0.05* |
| 147 | V147T | 1.28 | 0.92 | 0.85 | 0.87 | 1.30 |
| 148 | L148A | 1.29 | 0.83 | 1.01 | 0.76 | 1.48 |
| 148 | L148C | 0.90 | 2.31 | 1.04 | 0.94 | 0.99 |
| 148 | L148D | 0.20 | *0.05* | *0.05* | *ND* | *0.05* |
| 148 | L148E | 0.24 | *0.05* | 1.80 | 0.89 | 0.19 |
| 148 | L148F | 1.06 | 1.25 | 1.07 | 0.69 | 1.08 |
| 148 | L148G | 0.71 | *0.05* | 1.25 | 0.73 | 0.82 |
| 148 | L148H | 0.91 | 1.65 | 1.18 | 0.77 | 1.30 |
| 148 | L148I | 0.98 | 1.54 | 1.05 | 0.95 | 1.21 |
| 148 | L148K | 0.17 | *0.05* | *0.05* | *ND* | *0.05* |
| 148 | L148M | 1.12 | 1.24 | 1.00 | 0.92 | 1.29 |
| 148 | L148N | 1.17 | 0.98 | 0.94 | 0.91 | 1.16 |
| 148 | L148P | 0.26 | *0.05* | *0.05* | *ND* | *0.05* |
| 148 | L148R | 0.25 | *0.05* | *0.05* | *ND* | *0.05* |
| 148 | L148S | 1.29 | 0.92 | 0.91 | 0.70 | 1.33 |
| 148 | L148T | 1.61 | 0.81 | 0.72 | 0.76 | 1.66 |
| 148 | L148V | 0.94 | 1.76 | 1.04 | 0.84 | 1.17 |
| 148 | L148W | 0.16 | *0.05* | 1.23 | 0.09 | 0.08 |
| 148 | L148Y | 1.25 | 1.02 | 0.86 | 0.13 | 1.05 |
| 149 | V149A | 0.50 | *0.05* | 1.94 | 0.89 | 0.72 |
| 149 | V149C | 0.81 | 1.23 | 1.66 | 1.04 | 1.22 |
| 149 | V149D | 0.22 | *0.05* | *0.05* | *ND* | *0.05* |
| 149 | V149E | 0.18 | *0.05* | *0.05* | *ND* | *0.05* |
| 149 | V149F | 0.29 | *0.05* | 2.43 | *ND* | *0.05* |
| 149 | V149G | 0.16 | *0.05* | 1.51 | 0.55 | 0.13 |
| 149 | V149H | 0.21 | *0.05* | 2.36 | 0.27 | 0.22 |
| 149 | V149I | 1.07 | 0.94 | 1.17 | 1.02 | 1.48 |
| 149 | V149K | 0.21 | *0.05* | *0.05* | *ND* | *0.05* |
| 149 | V149L | 0.98 | 1.18 | 1.27 | 1.04 | 1.19 |
| 149 | V149M | 0.81 | 1.06 | 1.18 | 0.76 | 0.99 |
| 149 | V149P | 0.46 | *0.05* | 1.91 | 1.21 | 0.59 |
| 149 | V149Q | 0.21 | *0.05* | 2.42 | 0.78 | 0.36 |
| 149 | V149R | 0.24 | *0.05* | *0.05* | *ND* | *0.05* |
| 149 | V149S | 0.39 | *0.05* | 2.27 | 0.89 | 0.59 |
| 149 | V149T | 0.83 | 0.84 | 1.48 | 0.77 | 1.04 |
| 149 | V149W | 0.15 | *0.05* | *0.05* | *ND* | *0.05* |
| 150 | V150A | 0.84 | 1.16 | 1.42 | 0.82 | 1.20 |
| 150 | V150D | 0.18 | *0.05* | *0.05* | *ND* | *0.05* |
| 150 | V150E | 0.21 | *0.05* | 1.09 | 0.14 | 0.08 |
| 150 | V150F | 0.99 | 1.22 | 1.14 | *0.05* | 1.01 |
| 150 | V150G | 0.23 | *0.05* | 2.66 | 0.49 | 0.27 |
| 150 | V150H | 0.20 | *0.05* | 2.79 | 0.20 | 0.27 |
| 150 | V150K | 0.17 | *0.05* | *0.05* | *ND* | *0.05* |
| 150 | V150L | 1.23 | 1.15 | 0.92 | 0.89 | 1.37 |
| 150 | V150P | 0.13 | *0.05* | 1.71 | 0.61 | 0.14 |
| 150 | V150Q | 0.16 | *0.05* | 3.34 | 0.39 | 0.19 |
| 150 | V150R | 0.26 | *0.05* | *0.05* | *ND* | *0.05* |
| 150 | V150S | 0.75 | 1.27 | 1.43 | 0.62 | 0.89 |
| 150 | V150T | 1.18 | 0.90 | 1.01 | 0.97 | 1.54 |
| 150 | V150W | 0.14 | *0.05* | *0.05* | *ND* | *0.05* |
| 151 | A151D | 0.42 | *0.05* | *0.05* | *ND* | *0.05* |
| 151 | A151E | 0.45 | *0.05* | *0.05* | *ND* | *0.05* |
| 151 | A151F | 0.47 | *0.05* | *0.05* | *ND* | *0.05* |
| 151 | A151G | 0.85 | 1.54 | 1.08 | 0.35 | 0.81 |
| 151 | A151H | 0.52 | *0.05* | *0.05* | *ND* | *0.05* |
| 151 | A151L | 0.70 | *0.05* | 0.42 | *ND* | *0.05* |
| 151 | A151M | 1.05 | 0.13 | 0.59 | *ND* | *0.05* |
| 151 | A151P | 0.19 | *0.05* | *0.05* | *ND* | *0.05* |
| 151 | A151R | 0.42 | *0.05* | *0.05* | *ND* | *0.05* |
| 151 | A151S | 1.26 | 0.93 | 1.01 | 0.87 | 1.13 |
| 151 | A151T | 1.27 | 0.38 | 0.93 | 0.64 | 0.44 |
| 151 | A151V | 1.19 | 0.59 | 0.92 | 0.36 | 0.82 |
| 151 | A151W | 0.42 | *0.05* | *0.05* | *ND* | *0.05* |
| 152 | A152C | 1.48 | 0.34 | 0.70 | *ND* | *0.05* |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 152 | A152D | 0.66 | *0.05* | *0.05* | *ND* | *0.05* |
| 152 | A152E | 0.60 | *0.05* | *0.05* | *ND* | *0.05* |
| 152 | A152K | 0.46 | *0.05* | *0.05* | *ND* | *0.05* |
| 152 | A152L | 0.46 | *0.05* | *0.05* | *ND* | *0.05* |
| 152 | A152M | 0.62 | *0.05* | *0.05* | *ND* | *0.05* |
| 152 | A152P | 2.74 | 0.23 | 0.56 | *ND* | *0.05* |
| 152 | A152R | 0.45 | *0.05* | 1.07 | *ND* | *0.05* |
| 152 | A152S | 0.88 | 2.71 | 0.70 | 0.84 | 0.37 |
| 152 | A152T | 1.08 | 0.07 | 0.68 | *ND* | *0.05* |
| 152 | A152V | 0.96 | 0.70 | 0.69 | *ND* | *0.05* |
| 152 | A152W | 0.44 | *0.05* | *0.05* | *ND* | *0.05* |
| 152 | A152Y | 0.44 | *0.05* | *0.05* | *ND* | *0.05* |
| 153 | S153A | 1.06 | 0.90 | 1.16 | 0.72 | 1.65 |
| 153 | S153E | 0.89 | *0.05* | *0.05* | *ND* | *0.05* |
| 153 | S153F | 0.94 | *0.05* | *0.05* | *ND* | *0.05* |
| 153 | S153G | 0.92 | 0.60 | 1.07 | 0.62 | 0.70 |
| 153 | S153I | 1.02 | 0.33 | 0.66 | 0.08 | 0.15 |
| 153 | S153K | 0.55 | *0.05* | *0.05* | *ND* | *0.05* |
| 153 | S153M | 1.03 | 0.35 | 0.42 | *ND* | *0.05* |
| 153 | S153N | 0.84 | 0.54 | 0.70 | *0.05* | 0.27 |
| 153 | S153P | 0.46 | *0.05* | *0.05* | *ND* | *0.05* |
| 153 | S153Q | 1.10 | *0.05* | *0.05* | *ND* | *0.05* |
| 153 | S153R | 0.59 | *0.05* | *0.05* | *ND* | *0.05* |
| 153 | S153V | 0.99 | 0.95 | 1.03 | 0.78 | 2.29 |
| 153 | S153Y | 0.85 | 0.48 | *0.05* | *ND* | *0.05* |
| 154 | G154A | 0.90 | *0.05* | *0.05* | *ND* | *0.05* |
| 154 | G154C | 0.97 | 0.53 | 0.20 | *ND* | *0.05* |
| 154 | G154D | 0.61 | *0.05* | 0.37 | *ND* | *0.05* |
| 154 | G154F | 0.38 | *0.05* | *0.05* | *ND* | *0.05* |
| 154 | G154H | 0.47 | *0.05* | *0.05* | *ND* | *0.05* |
| 154 | G154I | 0.31 | *0.05* | *0.05* | *ND* | *0.05* |
| 154 | G154M | 0.42 | *0.05* | *0.05* | *ND* | *0.05* |
| 154 | G154N | 0.99 | *0.05* | *0.05* | *ND* | *0.05* |
| 154 | G154P | 0.52 | *0.05* | *0.05* | *ND* | *0.05* |
| 154 | G154Q | 0.64 | 3.28 | *0.05* | *ND* | *0.05* |
| 154 | G154R | 0.43 | *0.05* | *0.05* | *ND* | *0.05* |
| 154 | G154S | 0.89 | 0.50 | *0.05* | *ND* | *0.05* |
| 154 | G154T | 0.29 | *0.05* | *0.05* | *ND* | *0.05* |
| 154 | G154V | 0.34 | *0.05* | *0.05* | *ND* | *0.05* |
| 154 | G154W | 0.34 | *0.05* | *0.05* | *ND* | *0.05* |
| 154 | G154Y | 0.42 | *0.05* | *0.05* | *ND* | *0.05* |
| 155 | N155A | 1.66 | *0.05* | 0.13 | *ND* | *0.05* |
| 155 | N155D | 1.55 | 0.10 | *0.05* | *ND* | *0.05* |
| 155 | N155E | 0.86 | *0.05* | *0.05* | *ND* | *0.05* |
| 155 | N155F | 1.25 | *0.05* | 0.18 | 0.81 | 0.06 |
| 155 | N155I | 1.01 | 0.14 | *0.05* | *ND* | *0.05* |
| 155 | N155L | 0.93 | *0.05* | *0.05* | *ND* | *0.05* |
| 155 | N155M | 0.70 | 0.55 | *0.05* | *ND* | *0.05* |
| 155 | N155P | 2.00 | *0.05* | 0.19 | *ND* | *0.05* |
| 155 | N155Q | 1.11 | 0.10 | 0.16 | *ND* | *0.05* |
| 155 | N155R | 1.65 | 0.07 | 0.12 | *ND* | *0.05* |
| 155 | N155S | 2.02 | 0.08 | *0.05* | *ND* | *0.05* |
| 155 | N155T | 1.59 | *0.05* | *0.05* | *ND* | *0.05* |
| 155 | N155V | 1.08 | 0.11 | *0.05* | *ND* | *0.05* |
| 155 | N155Y | 1.22 | 0.12 | *0.05* | *ND* | *0.05* |
| 156 | S156A | 1.01 | 0.79 | 1.05 | 0.62 | 0.83 |
| 156 | S156C | 0.26 | *0.05* | 1.28 | 0.94 | 0.10 |
| 156 | S156D | 1.06 | 0.38 | 1.12 | 0.84 | 0.62 |
| 156 | S156E | 0.91 | 0.49 | 1.32 | 0.83 | 0.44 |
| 156 | S156F | 0.80 | 1.37 | 1.16 | 0.82 | 0.38 |
| 156 | S156G | 1.26 | 0.71 | 0.98 | 0.52 | 0.83 |
| 156 | S156I | 0.90 | 0.30 | 0.84 | 0.50 | 0.31 |
| 156 | S156K | 1.45 | 0.60 | 0.74 | 0.67 | 0.93 |
| 156 | S156L | 1.12 | 1.01 | 0.95 | 0.99 | 0.69 |
| 156 | S156M | 1.05 | 0.55 | 1.02 | 0.74 | 0.56 |
| 156 | S156N | 1.35 | 0.84 | 0.98 | 0.94 | 1.40 |
| 156 | S156P | 1.21 | 0.06 | 0.21 | 0.70 | 0.11 |
| 156 | S156Q | 1.26 | 0.46 | 0.81 | 0.44 | 0.71 |
| 156 | S156R | 1.12 | 0.96 | 0.72 | 0.57 | 0.69 |
| 156 | S156T | 1.34 | 0.83 | 0.96 | 0.93 | 1.21 |
| 156 | S156V | 0.97 | 0.17 | 0.66 | 0.32 | 0.31 |
| 156 | S156W | 0.54 | *0.05* | 0.58 | 0.70 | 0.15 |
| 156 | S156Y | 0.68 | *0.05* | 0.99 | 0.55 | 0.22 |
| 157 | G157A | 0.93 | 0.35 | 0.96 | 0.16 | 0.77 |
| 157 | G157C | 0.80 | 0.42 | 1.00 | 0.34 | 0.35 |
| 157 | G157D | 0.97 | 0.13 | 0.69 | 0.09 | 0.13 |
| 157 | G157F | 0.76 | *0.05* | 0.34 | 0.15 | 0.18 |
| 157 | G157K | 0.99 | 0.22 | 0.33 | 0.14 | 0.14 |
| 157 | G157L | 1.00 | 0.12 | *0.05* | *ND* | *0.05* |
| 157 | G157M | 0.73 | *0.05* | 0.43 | 0.09 | 0.19 |
| 157 | G157N | 0.79 | 0.34 | 0.65 | 0.06 | 0.29 |
| 157 | G157Q | 0.90 | 0.20 | 0.52 | *0.05* | 0.19 |
| 157 | G157R | 0.89 | 0.21 | 0.16 | 0.13 | 0.11 |
| 157 | G157S | 0.85 | 0.69 | 0.94 | 0.19 | 0.75 |
| 157 | G157T | 0.74 | 0.33 | 0.52 | *0.05* | 0.18 |
| 157 | G157V | 1.07 | 0.11 | 0.16 | *ND* | *0.05* |
| 157 | G157Y | 0.62 | *0.05* | 0.42 | 0.17 | 0.18 |
| 158 | A158C | 1.14 | 0.83 | 1.15 | 1.00 | 1.13 |
| 158 | A158E | 1.22 | 0.98 | 1.10 | 1.17 | 1.11 |
| 158 | A158F | 1.11 | 0.88 | 0.86 | 0.87 | 1.24 |
| 158 | A158H | 1.31 | 1.03 | 0.92 | 1.21 | 1.34 |
| 158 | A158K | 1.44 | 0.86 | 0.72 | 1.02 | 1.61 |
| 158 | A158L | 1.34 | 0.86 | 0.91 | 0.93 | 1.58 |
| 158 | A158M | 1.35 | 0.89 | 1.00 | 1.02 | 1.36 |
| 158 | A158P | 1.67 | 0.07 | 0.21 | *ND* | *0.05* |
| 158 | A158Q | 1.46 | 0.88 | 0.85 | 0.96 | 1.58 |
| 158 | A158R | 1.24 | 1.06 | 0.74 | 0.90 | 1.47 |
| 158 | A158S | 0.85 | 1.04 | 1.07 | 0.88 | 0.95 |
| 158 | A158T | 1.07 | 0.99 | 1.01 | 0.94 | 1.21 |
| 158 | A158V | 1.16 | 0.92 | 0.98 | 0.89 | 1.32 |
| 158 | A158W | 1.10 | 0.97 | 0.86 | 0.75 | 1.00 |
| 159 | G159A | 1.15 | 1.04 | 1.12 | 0.96 | 1.34 |
| 159 | G159C | 1.01 | 0.85 | 1.02 | 1.06 | 1.01 |
| 159 | G159D | 0.26 | *0.05* | *0.05* | *ND* | *0.05* |
| 159 | G159E | 1.29 | 0.77 | 1.11 | 1.20 | 1.36 |
| 159 | G159F | 0.30 | *0.05* | *0.05* | *ND* | *0.05* |
| 159 | G159H | 1.19 | 0.81 | 0.93 | 0.86 | 1.15 |
| 159 | G159I | 0.71 | *0.05* | 0.76 | 0.78 | 0.21 |
| 159 | G159L | 0.85 | 0.36 | 0.58 | 0.85 | 0.19 |
| 159 | G159M | 0.89 | 0.71 | 1.06 | 0.97 | 0.77 |
| 159 | G159P | 1.50 | 0.74 | 0.89 | 1.07 | 1.66 |
| 159 | G159Q | 1.15 | 0.64 | 1.01 | 0.73 | 1.20 |
| 159 | G159R | 1.17 | 0.63 | 0.73 | 0.79 | 1.04 |
| 159 | G159S | 1.17 | 1.22 | 1.23 | 0.91 | 1.47 |
| 159 | G159T | 0.37 | *0.05* | *0.05* | *ND* | *0.05* |
| 159 | G159V | 0.74 | 5.22 | 0.78 | 0.62 | 0.23 |
| 159 | G159W | 0.82 | 1.05 | 0.81 | 0.72 | 0.65 |
| 159 | G159Y | 0.80 | 1.09 | 0.86 | 0.70 | 0.35 |
| 160 | S160A | 1.12 | 1.14 | 1.00 | 0.92 | 1.23 |
| 160 | S160C | 0.93 | 1.29 | 1.27 | 1.21 | 0.93 |
| 160 | S160D | 1.10 | 0.98 | 1.24 | 1.03 | 1.17 |
| 160 | S160F | 1.23 | 0.99 | 0.96 | 1.08 | 1.56 |
| 160 | S160G | 1.08 | 0.82 | 1.11 | 0.60 | 1.06 |
| 160 | S160I | 1.29 | 0.81 | 0.87 | 1.13 | 1.58 |
| 160 | S160L | 1.19 | 0.88 | 0.94 | 0.99 | 1.53 |
| 160 | S160M | 1.11 | 1.06 | 0.97 | 0.99 | 1.40 |
| 160 | S160N | 1.23 | 0.92 | 0.98 | 0.99 | 1.53 |
| 160 | S160Q | 1.24 | 0.91 | 0.91 | 1.05 | 1.60 |
| 160 | S160R | 1.03 | 1.29 | 0.76 | 0.76 | 1.72 |
| 160 | S160T | 1.19 | 0.98 | 1.01 | 1.11 | 1.60 |
| 160 | S160V | 1.26 | 0.86 | 0.93 | 1.08 | 1.68 |
| 160 | S160W | 0.24 | *0.05* | *0.05* | *ND* | *0.05* |
| 160 | S160Y | 1.23 | 0.91 | 1.00 | 1.10 | 1.58 |
| 165 | I165A | 0.92 | 0.12 | *0.05* | *ND* | *0.05* |
| 165 | I165C | 0.64 | *0.05* | 0.89 | 0.41 | 0.18 |
| 165 | I165D | 1.72 | *0.05* | 0.23 | *ND* | *0.05* |
| 165 | I165E | 1.38 | 0.10 | *0.05* | *ND* | *0.05* |
| 165 | I165F | 1.45 | *0.05* | 0.14 | *ND* | *0.05* |
| 165 | I165G | 1.53 | *0.05* | *0.05* | *ND* | *0.05* |
| 165 | I165H | 1.54 | *0.05* | *0.05* | *ND* | *0.05* |
| 165 | I165K | 1.53 | 0.06 | *0.05* | *ND* | *0.05* |
| 165 | I165L | 0.95 | 0.63 | 1.17 | 1.08 | 0.79 |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 165 | I165M | 0.92 | 0.31 | 0.53 | 0.76 | 0.14 |
| 165 | I165P | 0.92 | 0.29 | 0.94 | 0.09 | 0.72 |
| 165 | I165R | 1.54 | *0.05* | *0.05* | ND | *0.05* |
| 165 | I165S | 0.91 | 0.20 | 0.30 | ND | *0.05* |
| 165 | I165T | 0.80 | 1.12 | 0.81 | 0.15 | 0.32 |
| 165 | I165V | 1.20 | 1.07 | 0.95 | 0.99 | 1.41 |
| 165 | I165W | 1.53 | *0.05* | 0.12 | ND | *0.05* |
| 165 | I165Y | 1.28 | *0.05* | *0.05* | ND | *0.05* |
| 166 | S166A | 1.22 | 1.25 | 1.05 | 0.89 | 1.80 |
| 166 | S166C | 1.15 | 0.69 | 1.08 | 0.94 | 0.34 |
| 166 | S166D | 1.19 | 1.12 | 1.24 | 1.23 | 0.16 |
| 166 | S166E | 1.14 | 1.23 | 1.00 | 1.16 | 0.22 |
| 166 | S166F | 0.90 | 0.47 | 0.67 | 0.40 | 0.09 |
| 166 | S166H | 0.95 | 1.53 | 1.10 | 0.85 | 0.14 |
| 166 | S166I | 0.98 | 0.36 | 0.72 | 1.07 | 0.07 |
| 166 | S166L | 1.13 | 0.37 | 0.76 | ND | *0.05* |
| 166 | S166M | 1.02 | 1.13 | 0.90 | 0.95 | 0.23 |
| 166 | S166N | 1.23 | 1.08 | 1.01 | ND | *0.05* |
| 166 | S166P | 1.02 | *0.05* | 0.44 | *0.05* | 0.18 |
| 166 | S166R | 1.08 | 0.95 | 0.74 | 0.63 | 0.06 |
| 166 | S166T | 1.22 | 0.68 | 0.98 | 0.83 | 0.13 |
| 166 | S166V | 1.27 | 0.82 | 0.64 | ND | *0.05* |
| 166 | S166W | 1.27 | 0.86 | 0.71 | ND | *0.05* |
| 166 | S166Y | 0.95 | 0.49 | 1.00 | 0.55 | 0.13 |
| 167 | Y167A | 1.25 | 0.13 | 0.88 | 0.17 | 0.31 |
| 167 | Y167C | 0.88 | 0.24 | 1.01 | 0.29 | 0.07 |
| 167 | Y167D | 1.04 | 0.11 | 1.18 | *0.05* | 0.06 |
| 167 | Y167E | 1.54 | 0.14 | 1.01 | 0.10 | 0.17 |
| 167 | Y167F | 1.32 | 0.88 | 0.95 | 0.93 | 1.35 |
| 167 | Y167G | 1.18 | 0.06 | 0.46 | ND | *0.05* |
| 167 | Y167H | 0.92 | 0.29 | 0.94 | 0.13 | 0.60 |
| 167 | Y167I | 1.06 | 0.10 | 0.98 | 0.15 | 0.56 |
| 167 | Y167K | 0.91 | *0.05* | *0.05* | ND | *0.05* |
| 167 | Y167L | 0.98 | 0.16 | 0.73 | *0.05* | 0.23 |
| 167 | Y167M | 0.91 | 0.18 | 0.49 | 0.07 | 0.11 |
| 167 | Y167N | 0.97 | 0.13 | 0.57 | *0.05* | 0.10 |
| 167 | Y167P | 1.02 | 0.21 | 1.10 | 0.18 | 0.24 |
| 167 | Y167Q | 1.26 | *0.05* | 0.35 | ND | *0.05* |
| 167 | Y167R | 0.87 | *0.05* | *0.05* | ND | *0.05* |
| 167 | Y167S | 0.82 | 0.24 | 0.64 | 0.07 | 0.10 |
| 167 | Y167T | 0.91 | 0.21 | 0.74 | 0.07 | 0.11 |
| 167 | Y167V | 0.91 | 0.33 | 1.12 | 0.20 | 0.45 |
| 167 | Y167W | 1.19 | 0.88 | 1.05 | 0.73 | 1.49 |
| 168 | P168A | 0.84 | 0.36 | 0.32 | ND | *0.05* |
| 168 | P168C | 0.84 | *0.05* | *0.05* | ND | *0.05* |
| 168 | P168D | 0.44 | *0.05* | *0.05* | ND | *0.05* |
| 168 | P168E | 0.48 | *0.05* | *0.05* | ND | *0.05* |
| 168 | P168F | 1.07 | *0.05* | 0.35 | ND | *0.05* |
| 168 | P168G | 0.57 | *0.05* | 0.48 | ND | *0.05* |
| 168 | P168H | 0.47 | *0.05* | 0.49 | ND | *0.05* |
| 168 | P168I | 1.28 | 0.07 | 0.39 | ND | *0.05* |
| 168 | P168K | 0.49 | *0.05* | 0.49 | ND | *0.05* |
| 168 | P168L | 0.35 | *0.05* | *0.05* | ND | *0.05* |
| 168 | P168M | 1.01 | *0.05* | 0.26 | ND | *0.05* |
| 168 | P168N | 0.83 | 0.56 | *0.05* | ND | *0.05* |
| 168 | P168Q | 0.62 | *0.05* | *0.05* | ND | *0.05* |
| 168 | P168R | 0.49 | *0.05* | *0.05* | ND | *0.05* |
| 168 | P168S | 0.82 | *0.05* | 0.24 | ND | *0.05* |
| 168 | P168T | 0.91 | 0.23 | 0.20 | ND | *0.05* |
| 168 | P168V | 0.90 | *0.05* | 0.70 | ND | *0.05* |
| 168 | P168W | 0.76 | *0.05* | 0.29 | ND | *0.05* |
| 169 | A169C | 0.72 | 1.21 | 1.61 | *0.05* | *0.05* |
| 169 | A169D | 0.41 | *0.05* | *0.05* | ND | *0.05* |
| 169 | A169E | 0.30 | *0.05* | *0.05* | ND | *0.05* |
| 169 | A169F | 0.48 | *0.05* | *0.05* | ND | *0.05* |
| 169 | A169G | 1.08 | 1.21 | 1.08 | 0.80 | 0.56 |
| 169 | A169H | 0.51 | *0.05* | *0.05* | ND | *0.05* |
| 169 | A169I | 0.33 | *0.05* | *0.05* | ND | *0.05* |
| 169 | A169K | 0.50 | *0.05* | *0.05* | ND | *0.05* |
| 169 | A169L | 0.24 | *0.05* | *0.05* | ND | *0.05* |
| 169 | A169M | 0.39 | *0.05* | *0.05* | ND | *0.05* |
| 169 | A169N | 0.42 | *0.05* | *0.05* | ND | *0.05* |
| 169 | A169P | 0.37 | *0.05* | *0.05* | ND | *0.05* |
| 169 | A169Q | 0.55 | *0.05* | *0.05* | ND | *0.05* |
| 169 | A169R | 0.26 | *0.05* | *0.05* | ND | *0.05* |
| 169 | A169S | 1.03 | 1.12 | 1.00 | 0.57 | 0.97 |
| 169 | A169T | 0.40 | *0.05* | *0.05* | ND | *0.05* |
| 169 | A169V | 0.30 | *0.05* | *0.05* | ND | *0.05* |
| 169 | A169W | 0.50 | *0.05* | 0.45 | ND | *0.05* |
| 169 | A169Y | 0.25 | *0.05* | *0.05* | ND | *0.05* |
| 170 | R170A | 1.18 | 0.82 | 1.09 | 1.06 | 1.15 |
| 170 | R170D | 0.85 | 0.49 | 1.29 | 0.89 | 0.43 |
| 170 | R170E | 0.87 | 0.44 | 1.29 | 0.85 | 0.53 |
| 170 | R170G | 0.97 | 1.73 | 1.19 | 1.13 | 0.98 |
| 170 | R170H | 0.95 | 0.68 | 1.32 | 0.92 | 0.84 |
| 170 | R170K | 0.89 | 2.15 | 1.29 | 1.05 | 1.18 |
| 170 | R170L | 0.19 | *0.05* | 1.19 | 0.97 | 0.06 |
| 170 | R170N | 0.20 | *0.05* | 0.91 | 0.91 | 0.07 |
| 170 | R170P | 0.45 | *0.05* | 1.50 | 0.93 | 0.31 |
| 170 | R170Q | 1.09 | 0.67 | 1.14 | 1.01 | 1.03 |
| 170 | R170S | 0.98 | 0.68 | 1.19 | 0.85 | 0.85 |
| 170 | R170V | 0.88 | 1.07 | 1.39 | 0.88 | 0.93 |
| 170 | R170W | 0.90 | 0.56 | 1.23 | 0.80 | 0.68 |
| 170 | R170Y | 1.05 | 0.82 | 1.19 | 0.94 | 0.93 |
| 171 | Y171A | 0.70 | 1.25 | 1.26 | 0.12 | 0.38 |
| 171 | Y171C | 0.97 | 0.89 | 1.19 | 0.81 | 0.83 |
| 171 | Y171D | 0.65 | *0.05* | 1.24 | 0.09 | 0.41 |
| 171 | Y171E | 0.61 | *0.05* | 0.92 | 0.10 | 0.17 |
| 171 | Y171F | 1.24 | 0.86 | 1.07 | 0.60 | 1.40 |
| 171 | Y171G | 0.77 | 2.68 | 1.25 | *0.05* | 0.52 |
| 171 | Y171H | 0.77 | 1.78 | 1.27 | 0.33 | 0.82 |
| 171 | Y171I | 0.67 | *0.05* | 1.18 | *0.05* | 0.45 |
| 171 | Y171K | 0.30 | *0.05* | *0.05* | ND | *0.05* |
| 171 | Y171L | 1.03 | 0.66 | 0.94 | 0.23 | 1.08 |
| 171 | Y171M | 0.85 | *0.05* | 0.90 | *0.05* | 0.51 |
| 171 | Y171N | 0.86 | 1.24 | 1.14 | 0.28 | 1.00 |
| 171 | Y171P | 0.42 | *0.05* | *0.05* | ND | *0.05* |
| 171 | Y171Q | 0.67 | *0.05* | 1.20 | *0.05* | 0.40 |
| 171 | Y171R | 0.21 | *0.05* | *0.05* | ND | *0.05* |
| 171 | Y171S | 0.77 | 2.64 | 1.21 | 0.34 | 0.86 |
| 171 | Y171T | 0.59 | *0.05* | 1.23 | 0.08 | 0.39 |
| 171 | Y171V | 0.60 | *0.05* | 0.89 | 0.06 | 0.35 |
| 171 | Y171W | 0.69 | 1.22 | 1.30 | 0.14 | 0.46 |
| 172 | A172C | 1.15 | 0.88 | 1.11 | 1.13 | 1.18 |
| 172 | A172D | 1.17 | 1.09 | 1.10 | 1.12 | 1.24 |
| 172 | A172F | 1.16 | 0.99 | 0.93 | 0.77 | 1.34 |
| 172 | A172G | 1.12 | 1.23 | 1.07 | 0.92 | 1.32 |
| 172 | A172I | 1.21 | 0.95 | 0.98 | 1.00 | 1.30 |
| 172 | A172K | 0.91 | 1.12 | 0.82 | 0.92 | 1.16 |
| 172 | A172L | 1.22 | 0.85 | 1.04 | 0.93 | 1.26 |
| 172 | A172M | 1.08 | 1.04 | 0.97 | 1.02 | 1.14 |
| 172 | A172P | 1.37 | 1.02 | 1.10 | 1.03 | 1.60 |
| 172 | A172Q | 1.27 | 1.05 | 1.12 | 0.88 | 1.48 |
| 172 | A172R | 1.27 | 0.98 | 0.75 | 0.82 | 1.52 |
| 172 | A172S | 1.08 | 0.87 | 1.03 | 0.85 | 1.18 |
| 172 | A172T | 0.92 | 1.47 | 1.14 | 0.79 | 1.24 |
| 172 | A172V | 1.08 | 1.24 | 1.00 | 0.91 | 1.26 |
| 172 | A172W | 0.96 | 0.86 | 0.91 | 0.61 | 0.92 |
| 172 | A172Y | 1.29 | 1.07 | 0.89 | 0.84 | 1.33 |
| 173 | N173A | 1.23 | 1.03 | 0.92 | 0.96 | 1.37 |
| 173 | N173C | 0.89 | 0.87 | 1.13 | 1.01 | 0.94 |
| 173 | N173D | 0.93 | 0.78 | 1.07 | 1.01 | 0.94 |
| 173 | N173E | 0.79 | 1.09 | 1.14 | 1.01 | 0.79 |
| 173 | N173F | 1.38 | 0.90 | 0.95 | 0.59 | 1.19 |
| 173 | N173G | 1.02 | 1.23 | 1.09 | 0.78 | 1.01 |
| 173 | N173H | 1.11 | 0.95 | 1.04 | 0.96 | 1.17 |
| 173 | N173I | 1.06 | 0.37 | 0.87 | *0.05* | 0.43 |
| 173 | N173K | 1.26 | 1.08 | 0.89 | 0.49 | 1.36 |
| 173 | N173L | 1.80 | 0.73 | 0.92 | 0.78 | 1.48 |
| 173 | N173M | 1.02 | 0.96 | 1.01 | 0.81 | 1.21 |
| 173 | N173P | 1.04 | 0.67 | 0.94 | 0.64 | 0.86 |
| 173 | N173Q | 1.23 | 1.04 | 0.98 | 0.89 | 1.49 |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 173 | N173R | 1.14 | 1.01 | 0.78 | 0.51 | 1.28 |
| 173 | N173S | 0.36 | *0.05* | *0.05* | *ND* | *0.05* |
| 173 | N173T | 1.09 | 1.06 | 0.95 | 0.88 | 1.13 |
| 173 | N173V | 1.31 | 0.59 | 0.80 | 0.63 | 1.01 |
| 173 | N173W | 1.30 | 0.82 | 0.87 | 0.41 | 1.10 |
| 173 | N173Y | 1.01 | 0.99 | 0.88 | 0.42 | 0.99 |
| 174 | A174D | 0.28 | *0.05* | *0.05* | *ND* | *0.05* |
| 174 | A174E | 0.46 | *0.05* | *0.05* | *ND* | *0.05* |
| 174 | A174F | 0.52 | *0.05* | *0.05* | *ND* | *0.05* |
| 174 | A174G | 0.83 | 1.66 | 1.24 | 0.09 | 0.77 |
| 174 | A174H | 0.33 | *0.05* | *0.05* | *ND* | *0.05* |
| 174 | A174I | 1.17 | 0.11 | 0.85 | 0.27 | 0.39 |
| 174 | A174K | 0.39 | *0.05* | *0.05* | *ND* | *0.05* |
| 174 | A174L | 0.31 | *0.05* | *0.05* | *ND* | *0.05* |
| 174 | A174M | 0.58 | *0.05* | *0.05* | *ND* | *0.05* |
| 174 | A174N | 0.23 | *0.05* | 1.27 | *0.05* | 0.16 |
| 174 | A174P | 0.39 | *0.05* | 1.37 | *0.05* | 0.19 |
| 174 | A174Q | 0.39 | *0.05* | *0.05* | *ND* | *0.05* |
| 174 | A174R | 0.39 | *0.05* | *0.05* | *ND* | *0.05* |
| 174 | A174S | 1.32 | 0.99 | 0.98 | 0.92 | 1.70 |
| 174 | A174T | 1.22 | 1.29 | 0.87 | 0.99 | 1.40 |
| 174 | A174V | 1.10 | 1.15 | 0.94 | 1.01 | 1.46 |
| 174 | A174W | 0.47 | *0.05* | *0.05* | *ND* | *0.05* |
| 174 | A174Y | 0.42 | *0.05* | *0.05* | *ND* | *0.05* |
| 175 | M175A | 1.18 | 1.16 | 1.02 | 0.12 | 1.22 |
| 175 | M175C | 0.87 | 1.95 | 1.21 | 0.47 | 1.11 |
| 175 | M175E | 0.41 | *0.05* | 1.57 | *0.05* | 0.42 |
| 175 | M175G | 0.19 | *0.05* | 2.33 | *ND* | *0.05* |
| 175 | M175H | 0.35 | *0.05* | 1.08 | *0.05* | 0.32 |
| 175 | M175I | 1.16 | 1.12 | 0.70 | 0.70 | 1.09 |
| 175 | M175K | 0.18 | *0.05* | 1.04 | 0.08 | 0.11 |
| 175 | M175L | 1.28 | 1.22 | 1.05 | 0.92 | 1.18 |
| 175 | M175P | 0.41 | *0.05* | *0.05* | *ND* | *0.05* |
| 175 | M175Q | 0.98 | 1.06 | 0.99 | *0.05* | 1.14 |
| 175 | M175R | 0.40 | *0.05* | *0.05* | *ND* | *0.05* |
| 175 | M175S | 0.70 | 3.33 | 1.16 | *0.05* | 0.79 |
| 175 | M175T | 1.78 | 0.80 | 0.93 | 0.54 | 1.63 |
| 175 | M175V | 1.31 | 0.94 | 0.97 | 0.89 | 1.32 |
| 175 | M175W | 0.54 | *0.05* | 0.93 | *0.05* | 0.41 |
| 175 | M175Y | 1.38 | 0.97 | 0.97 | 0.08 | 1.03 |
| 176 | A176C | 0.77 | 3.85 | 1.32 | 0.58 | 0.84 |
| 176 | A176D | 0.68 | *0.05* | 0.23 | *ND* | *0.05* |
| 176 | A176E | 2.03 | *0.05* | 0.21 | *ND* | *0.05* |
| 176 | A176G | 1.29 | 0.85 | 0.94 | 0.55 | 1.59 |
| 176 | A176H | 0.61 | *0.05* | *0.05* | *ND* | *0.05* |
| 176 | A176I | 1.08 | 0.18 | 0.19 | *ND* | *0.05* |
| 176 | A176K | 0.98 | *0.05* | *0.05* | *ND* | *0.05* |
| 176 | A176L | 0.57 | *0.05* | *0.05* | *ND* | *0.05* |
| 176 | A176N | 0.61 | *0.05* | *0.05* | *ND* | *0.05* |
| 176 | A176P | 0.35 | *0.05* | 1.66 | *0.05* | 0.14 |
| 176 | A176R | 0.75 | *0.05* | *0.05* | *ND* | *0.05* |
| 176 | A176S | 1.25 | 1.07 | 1.10 | 0.92 | 1.50 |
| 176 | A176T | 1.63 | *0.05* | 0.34 | *ND* | *0.05* |
| 176 | A176V | 1.30 | 0.07 | 0.25 | *ND* | *0.05* |
| 176 | A176W | 0.64 | *0.05* | *0.05* | *ND* | *0.05* |
| 176 | A176Y | 0.61 | *0.05* | *0.05* | *ND* | *0.05* |
| 177 | V177A | 1.27 | 0.96 | 1.10 | 0.17 | 1.35 |
| 177 | V177C | 1.06 | 1.17 | 1.10 | 0.81 | 1.18 |
| 177 | V177D | 0.35 | *0.05* | *0.05* | *ND* | *0.05* |
| 177 | V177F | 0.31 | *0.05* | *0.05* | *ND* | *0.05* |
| 177 | V177G | 0.23 | *0.05* | *0.05* | *ND* | *0.05* |
| 177 | V177H | 0.45 | *0.05* | *0.05* | *ND* | *0.05* |
| 177 | V177I | 1.14 | 1.02 | 1.10 | 0.57 | 1.19 |
| 177 | V177K | 0.49 | *0.05* | *0.05* | *ND* | *0.05* |
| 177 | V177L | 0.25 | *0.05* | *0.05* | *ND* | *0.05* |
| 177 | V177M | 0.23 | *0.05* | *0.05* | *ND* | *0.05* |
| 177 | V177N | 0.25 | *0.05* | *0.05* | *0.05* | 0.06 |
| 177 | V177Q | 0.40 | *0.05* | *0.05* | *ND* | *0.05* |
| 177 | V177R | 0.47 | *0.05* | *0.05* | *ND* | *0.05* |
| 177 | V177S | 0.48 | *0.05* | *0.05* | *ND* | *0.05* |
| 177 | V177T | 1.67 | 0.78 | 0.93 | 0.33 | 1.59 |
| 177 | V177W | 0.38 | *0.05* | *0.05* | *ND* | *0.05* |
| 177 | V177Y | 0.36 | *0.05* | *0.05* | *ND* | *0.05* |
| 178 | G178A | 1.08 | 0.53 | 1.01 | *0.05* | 0.92 |
| 178 | G178C | 0.38 | *0.05* | 0.69 | *0.05* | 0.21 |
| 178 | G178D | 0.47 | *0.05* | *0.05* | *ND* | *0.05* |
| 178 | G178E | 0.53 | *0.05* | *0.05* | *ND* | *0.05* |
| 178 | G178F | 0.27 | *0.05* | *0.05* | *ND* | *0.05* |
| 178 | G178I | 0.40 | *0.05* | *0.05* | *ND* | *0.05* |
| 178 | G178L | 0.20 | *0.05* | *0.05* | *0.05* | 0.12 |
| 178 | G178M | 0.30 | *0.05* | *0.05* | *ND* | *0.05* |
| 178 | G178N | 0.30 | *0.05* | 0.42 | *0.05* | 0.16 |
| 178 | G178P | 0.42 | *0.05* | *0.05* | *ND* | *0.05* |
| 178 | G178R | 0.37 | *0.05* | *0.05* | *ND* | *0.05* |
| 178 | G178S | 0.72 | 1.66 | 0.89 | *0.05* | 1.02 |
| 178 | G178T | 0.55 | *0.05* | 0.93 | *0.05* | 0.80 |
| 178 | G178V | 0.22 | *0.05* | *0.05* | *ND* | *0.05* |
| 178 | G178W | 0.44 | *0.05* | *0.05* | *ND* | *0.05* |
| 178 | G178Y | 0.31 | *0.05* | *0.05* | *ND* | *0.05* |
| 179 | A179C | 0.41 | *0.05* | 1.20 | *0.05* | 0.47 |
| 179 | A179D | 0.47 | *0.05* | 0.46 | 0.60 | 0.08 |
| 179 | A179E | 0.40 | *ND* | *ND* | *ND* | *ND* |
| 179 | A179F | 0.25 | *ND* | *ND* | *ND* | *ND* |
| 179 | A179G | 0.87 | 1.38 | 1.08 | 0.20 | 0.95 |
| 179 | A179H | 0.41 | *0.05* | 0.74 | 0.91 | 0.18 |
| 179 | A179I | 0.30 | *0.05* | 0.85 | 0.92 | 0.12 |
| 179 | A179K | 0.36 | *ND* | *ND* | *ND* | *ND* |
| 179 | A179L | 0.31 | *ND* | *ND* | *ND* | *0.05* |
| 179 | A179M | 0.71 | 0.30 | 0.25 | *ND* | *0.05* |
| 179 | A179P | 0.44 | *ND* | *ND* | 0.07 | 0.07 |
| 179 | A179Q | 0.28 | *ND* | *ND* | *ND* | *ND* |
| 179 | A179R | 0.31 | *ND* | *ND* | *ND* | *ND* |
| 179 | A179T | 0.16 | *0.05* | 0.61 | *0.05* | 0.10 |
| 180 | T180C | 0.95 | 0.87 | 1.08 | 0.52 | 0.92 |
| 180 | T180D | 0.30 | *0.05* | *0.05* | *ND* | *0.05* |
| 180 | T180F | 0.19 | *0.05* | *0.05* | *ND* | *0.05* |
| 180 | T180G | 0.21 | *0.05* | 2.09 | *0.05* | 0.18 |
| 180 | T180H | 0.21 | *0.05* | 1.55 | *0.05* | 0.16 |
| 180 | T180I | 1.25 | 0.87 | 0.78 | 0.78 | 1.27 |
| 180 | T180K | 0.21 | *0.05* | *0.05* | *ND* | *0.05* |
| 180 | T180L | 0.96 | 0.81 | 1.04 | 0.18 | 0.92 |
| 180 | T180N | 0.27 | *0.05* | 1.75 | *0.05* | 0.29 |
| 180 | T180P | 0.35 | *0.05* | *0.05* | *ND* | *0.05* |
| 180 | T180Q | 0.13 | *0.05* | 1.32 | *0.05* | 0.09 |
| 180 | T180R | 0.27 | *0.05* | *0.05* | *ND* | *0.05* |
| 180 | T180S | 1.01 | 1.16 | 1.04 | 0.58 | 1.18 |
| 180 | T180V | 1.23 | 0.93 | 0.98 | 0.83 | 1.24 |
| 180 | T180W | 0.26 | *0.05* | *0.05* | *ND* | *0.05* |
| 181 | D181A | 0.66 | 1.70 | 0.93 | 0.18 | 0.70 |
| 181 | D181E | 0.57 | 6.09 | 0.27 | *0.05* | 0.14 |
| 181 | D181F | 0.11 | *ND* | *ND* | 0.21 | 0.07 |
| 181 | D181G | 0.55 | 20.14 | 0.89 | 0.15 | 0.65 |
| 181 | D181H | 0.21 | *0.05* | 0.99 | 0.26 | 0.21 |
| 181 | D181K | 0.56 | 0.64 | 0.43 | *0.05* | 0.58 |
| 181 | D181L | 0.61 | 5.03 | 0.64 | *0.05* | 0.50 |
| 181 | D181M | 0.80 | 0.96 | 0.69 | *0.05* | 0.84 |
| 181 | D181N | 1.20 | 0.74 | 0.71 | 0.15 | 1.15 |
| 181 | D181P | 0.34 | *ND* | *ND* | *ND* | *ND* |
| 181 | D181R | 0.31 | *0.05* | 0.39 | *0.05* | 0.34 |
| 181 | D181V | 0.27 | *0.05* | 0.56 | *0.05* | 0.28 |
| 182 | Q182A | 1.26 | 1.00 | 0.92 | 0.86 | 1.57 |
| 182 | Q182D | 1.15 | 0.95 | 1.21 | 1.11 | 1.47 |
| 182 | Q182E | 1.12 | 1.00 | 1.21 | 1.14 | 1.66 |
| 182 | Q182F | 1.21 | 1.14 | 0.94 | 0.43 | 1.48 |
| 182 | Q182G | 1.16 | 0.92 | 0.95 | 0.49 | 1.34 |
| 182 | Q182H | 1.15 | 0.94 | 0.95 | 0.73 | 1.36 |
| 182 | Q182I | 1.28 | 0.89 | 0.80 | 0.48 | 1.56 |
| 182 | Q182K | 1.25 | 0.99 | 0.77 | 0.08 | 1.54 |
| 182 | Q182L | 1.20 | 0.98 | 0.96 | 0.20 | 1.53 |
| 182 | Q182M | 1.55 | 0.87 | 0.65 | 0.75 | 1.83 |
| 182 | Q182N | 1.20 | 1.01 | 0.88 | 0.73 | 1.33 |
| 182 | Q182P | 1.12 | 0.93 | 0.95 | 0.51 | 1.27 |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 182 | Q182R | 1.08 | 1.06 | 0.75 | 0.06 | 1.24 |
| 182 | Q182S | 1.30 | 0.96 | 0.97 | 0.74 | 1.68 |
| 182 | Q182T | 1.23 | 1.09 | 1.03 | 0.66 | 1.61 |
| 182 | Q182V | 1.18 | 1.04 | 0.95 | 0.57 | 1.32 |
| 182 | Q182W | 1.57 | 0.80 | 0.63 | 0.09 | 1.61 |
| 182 | Q182Y | 1.31 | 0.91 | 0.83 | 0.78 | 1.30 |
| 183 | N183A | 1.30 | 1.01 | 0.98 | 0.82 | 1.21 |
| 183 | N183D | 0.97 | 1.08 | 1.22 | 1.15 | 1.10 |
| 183 | N183F | 1.12 | 1.00 | 0.93 | 0.27 | 1.27 |
| 183 | N183G | 1.16 | 1.26 | 0.99 | 0.69 | 1.28 |
| 183 | N183H | 1.43 | 0.88 | 0.90 | 0.75 | 1.36 |
| 183 | N183I | 1.28 | 0.81 | 0.89 | *0.05* | 1.31 |
| 183 | N183K | 1.52 | 0.98 | 0.75 | 0.06 | 1.40 |
| 183 | N183L | 1.48 | 0.84 | 0.91 | 0.28 | 1.34 |
| 183 | N183M | 1.30 | 0.76 | 0.89 | 0.57 | 1.35 |
| 183 | N183P | 0.16 | *0.05* | 1.75 | *0.05* | 0.15 |
| 183 | N183Q | 1.51 | 0.93 | 0.83 | 0.89 | 1.65 |
| 183 | N183R | 1.43 | 0.91 | 0.60 | *0.05* | 1.42 |
| 183 | N183S | 1.05 | 1.20 | 1.07 | 0.90 | 1.22 |
| 183 | N183T | 1.26 | 0.93 | 0.98 | 0.67 | 1.31 |
| 183 | N183V | 1.34 | 0.80 | 0.90 | 0.14 | 1.29 |
| 183 | N183W | 1.44 | 0.93 | 0.73 | 0.19 | 1.37 |
| 183 | N183Y | 1.32 | 0.83 | 0.89 | 0.65 | 1.32 |
| 184 | N184A | 0.22 | *0.05* | 1.48 | *0.05* | 0.15 |
| 184 | N184C | 0.60 | 5.16 | 1.27 | 0.25 | 0.53 |
| 184 | N184D | 1.31 | 0.99 | 1.09 | 1.18 | 1.51 |
| 184 | N184E | 0.50 | *0.05* | 1.44 | 0.58 | 0.43 |
| 184 | N184F | 0.23 | *0.05* | 0.91 | *0.05* | 0.11 |
| 184 | N184G | 0.78 | 1.45 | 1.26 | *0.05* | 0.77 |
| 184 | N184H | 0.31 | *0.05* | 1.31 | 0.14 | 0.19 |
| 184 | N184I | 0.15 | *0.05* | 0.70 | *ND* | *0.05* |
| 184 | N184K | 0.14 | *0.05* | *0.05* | *ND* | *0.05* |
| 184 | N184L | 0.50 | *0.05* | 1.18 | *0.05* | 0.35 |
| 184 | N184M | 0.40 | *0.05* | 1.36 | 0.07 | 0.25 |
| 184 | N184P | 0.23 | *0.05* | *0.05* | *ND* | *0.05* |
| 184 | N184R | 0.13 | *0.05* | *0.05* | 0.11 | 0.06 |
| 184 | N184S | 0.50 | *0.05* | 1.30 | *0.05* | 0.51 |
| 184 | N184T | 0.21 | *0.05* | 1.46 | *0.05* | 0.17 |
| 184 | N184V | 0.39 | *0.05* | *0.05* | *ND* | *0.05* |
| 184 | N184W | 0.15 | *0.05* | 0.94 | *0.05* | 0.09 |
| 184 | N184Y | 0.23 | *0.05* | 1.25 | *0.05* | 0.13 |
| 185 | N185A | 1.10 | 1.00 | 0.91 | 1.01 | 1.04 |
| 185 | N185C | 1.09 | 0.68 | 1.18 | 1.09 | 1.04 |
| 185 | N185E | 1.38 | 0.93 | 1.05 | 1.23 | 1.45 |
| 185 | N185F | 1.09 | 0.89 | 0.99 | 0.36 | 1.13 |
| 185 | N185G | 1.03 | 1.38 | 1.10 | 0.68 | 1.24 |
| 185 | N185H | 1.39 | 1.00 | 0.89 | 0.98 | 1.22 |
| 185 | N185I | 1.35 | 0.80 | 0.81 | 0.76 | 1.22 |
| 185 | N185K | 1.72 | 0.85 | 0.80 | 0.90 | 1.78 |
| 185 | N185L | 1.36 | 0.96 | 1.11 | 0.73 | 1.43 |
| 185 | N185M | 1.29 | 0.88 | 0.95 | 0.81 | 1.45 |
| 185 | N185Q | 1.47 | 1.00 | 0.96 | 1.19 | 1.41 |
| 185 | N185R | 1.36 | 0.92 | 0.74 | 0.59 | 1.51 |
| 185 | N185S | 0.95 | 1.26 | 1.10 | 0.73 | 1.19 |
| 185 | N185T | 1.19 | 0.80 | 1.06 | 0.95 | 1.12 |
| 185 | N185V | 1.01 | 0.99 | 1.01 | 0.89 | 1.03 |
| 185 | N185W | 0.28 | *ND* | *ND* | *ND* | *ND* |
| 185 | N185Y | 1.06 | 0.95 | 0.86 | 0.61 | 1.13 |
| 186 | R186A | 0.73 | 0.35 | 1.10 | 0.68 | 0.39 |
| 186 | R186C | 0.56 | *0.05* | 0.99 | 0.56 | 0.20 |
| 186 | R186F | 0.74 | 0.27 | 0.52 | *ND* | *0.05* |
| 186 | R186G | 0.38 | *0.05* | 1.02 | 0.38 | 0.14 |
| 186 | R186H | 0.80 | 0.99 | 1.11 | 1.05 | 0.74 |
| 186 | R186I | 0.85 | 0.46 | 1.12 | 1.19 | 0.62 |
| 186 | R186K | 1.29 | 1.05 | 1.01 | 1.10 | 1.55 |
| 186 | R186L | 0.99 | 0.57 | 1.09 | 1.17 | 1.00 |
| 186 | R186M | 0.62 | 1.33 | 0.97 | 0.80 | 0.29 |
| 186 | R186N | 0.52 | *0.05* | 0.85 | 0.22 | 0.12 |
| 186 | R186P | 0.78 | 0.22 | 0.81 | 0.69 | 0.17 |
| 186 | R186Q | 0.43 | *0.05* | 1.19 | 0.79 | 0.18 |
| 186 | R186S | 0.55 | *0.05* | 0.94 | 0.55 | 0.21 |
| 186 | R186T | 0.39 | *0.05* | 1.15 | 0.71 | 0.22 |
| 186 | R186V | 0.28 | *ND* | *ND* | *ND* | *ND* |
| 186 | R186W | 0.76 | 0.74 | 1.22 | 0.77 | 0.44 |
| 186 | R186Y | 0.54 | *0.05* | 0.71 | 0.63 | 0.06 |
| 187 | A187C | 1.13 | 0.72 | 0.91 | 0.87 | 0.65 |
| 187 | A187D | 0.75 | 0.76 | 0.99 | 0.06 | 0.06 |
| 187 | A187E | 0.45 | *0.05* | 1.13 | *0.05* | 0.12 |
| 187 | A187F | 1.58 | 0.42 | 0.68 | *0.05* | 0.21 |
| 187 | A187G | 0.76 | 1.54 | 0.97 | *0.05* | 0.63 |
| 187 | A187H | 1.30 | 0.18 | 0.64 | *0.05* | 0.11 |
| 187 | A187I | 1.04 | 0.14 | 0.41 | 0.13 | 0.13 |
| 187 | A187K | 0.52 | *0.05* | *0.05* | *ND* | *0.05* |
| 187 | A187L | 0.90 | 0.27 | 0.93 | 0.15 | 0.34 |
| 187 | A187M | 0.66 | 2.14 | 0.77 | 0.10 | 0.19 |
| 187 | A187N | 0.36 | *0.05* | 0.95 | *0.05* | 0.10 |
| 187 | A187P | 1.42 | 0.76 | 0.90 | 0.55 | 1.01 |
| 187 | A187Q | 0.57 | *0.05* | 0.92 | *0.05* | 0.11 |
| 187 | A187R | 0.55 | *0.05* | *0.05* | *ND* | *0.05* |
| 187 | A187S | 0.90 | 0.80 | 0.93 | 0.07 | 0.79 |
| 187 | A187T | 0.86 | 0.80 | 0.82 | 0.28 | 0.71 |
| 187 | A187V | 0.89 | 0.26 | 0.65 | 0.29 | 0.30 |
| 187 | A187W | 1.42 | 1.24 | 0.93 | 0.53 | 0.80 |
| 187 | A187Y | 2.08 | 0.69 | 0.87 | 0.32 | 0.40 |
| 188 | S188A | 1.39 | 0.80 | 0.87 | 0.96 | 1.38 |
| 188 | S188D | 1.25 | 0.86 | 1.11 | 1.11 | 1.36 |
| 188 | S188E | 1.24 | 0.84 | 0.98 | 1.12 | 1.27 |
| 188 | S188F | 1.10 | 0.59 | 0.78 | 0.87 | 1.03 |
| 188 | S188G | 1.29 | 0.90 | 0.92 | 0.80 | 1.40 |
| 188 | S188H | 1.28 | 0.74 | 0.92 | 0.98 | 1.23 |
| 188 | S188I | 1.39 | 0.86 | 0.78 | 0.89 | 1.64 |
| 188 | S188K | 1.53 | 0.81 | 0.72 | 0.95 | 1.40 |
| 188 | S188L | 1.41 | 0.73 | 0.91 | 0.86 | 1.51 |
| 188 | S188P | 1.55 | 0.71 | 0.97 | 1.16 | 1.29 |
| 188 | S188Q | 1.45 | 0.82 | 0.94 | 0.90 | 1.50 |
| 188 | S188R | 1.38 | 0.71 | 0.72 | 0.80 | 1.25 |
| 188 | S188T | 1.31 | 0.82 | 0.92 | 0.90 | 1.19 |
| 188 | S188V | 1.42 | 0.80 | 0.87 | 0.80 | 1.56 |
| 188 | S188W | 1.46 | 0.56 | 0.73 | 0.80 | 1.23 |
| 188 | S188Y | 1.40 | 0.59 | 0.81 | 0.74 | 1.31 |
| 189 | F189A | 0.50 | *0.05* | 1.04 | 0.07 | 0.07 |
| 189 | F189C | 2.04 | 0.43 | 0.86 | 0.77 | 0.20 |
| 189 | F189E | 2.15 | 0.54 | 0.92 | 0.24 | 0.28 |
| 189 | F189G | 2.00 | 0.50 | 0.90 | 0.16 | 0.45 |
| 189 | F189H | 1.28 | 0.29 | 0.81 | 0.08 | 0.21 |
| 189 | F189K | 1.82 | 0.34 | 0.64 | 0.07 | 0.32 |
| 189 | F189L | 1.79 | 0.58 | 0.99 | 0.11 | 0.49 |
| 189 | F189M | 2.27 | 0.63 | 0.92 | 0.49 | 0.47 |
| 189 | F189N | 2.35 | 0.51 | 0.89 | 0.07 | 0.67 |
| 189 | F189P | 1.12 | 0.19 | 0.69 | *0.05* | 0.10 |
| 189 | F189Q | 2.29 | 0.48 | 0.97 | 0.06 | 0.47 |
| 189 | F189R | 1.51 | 0.48 | 0.70 | 0.12 | 0.30 |
| 189 | F189S | 1.85 | 0.50 | 0.91 | 0.15 | 0.65 |
| 189 | F189T | 1.64 | 0.58 | 0.93 | 0.11 | 0.57 |
| 189 | F189V | 1.97 | 0.26 | 0.67 | *0.05* | 0.16 |
| 189 | F189Y | 0.97 | 0.29 | 0.91 | 0.19 | 0.85 |
| 190 | S190A | 0.86 | 0.30 | 0.89 | 0.11 | 0.44 |
| 190 | S190C | 0.77 | *0.05* | 0.22 | *ND* | *0.05* |
| 190 | S190D | 1.97 | *0.05* | *0.05* | *ND* | *0.05* |
| 190 | S190E | 1.51 | *0.05* | *0.05* | *ND* | *0.05* |
| 190 | S190F | 1.74 | *0.05* | 0.15 | *ND* | *0.05* |
| 190 | S190G | 1.01 | 0.10 | 0.55 | 0.10 | 0.19 |
| 190 | S190H | 1.84 | *0.05* | 0.19 | *ND* | *0.05* |
| 190 | S190I | 1.40 | *0.05* | *0.05* | *ND* | *0.05* |
| 190 | S190K | 1.15 | *0.05* | *0.05* | *ND* | *0.05* |
| 190 | S190L | 1.60 | *0.05* | 0.15 | *ND* | *0.05* |
| 190 | S190M | 1.56 | *0.05* | 0.18 | *ND* | *0.05* |
| 190 | S190N | 1.86 | *0.05* | 0.14 | *ND* | *0.05* |
| 190 | S190P | 1.58 | *0.05* | *0.05* | *ND* | *0.05* |
| 190 | S190Q | 1.92 | *0.05* | 0.23 | *ND* | *0.05* |
| 190 | S190R | 1.10 | 0.09 | *0.05* | *ND* | *0.05* |
| 190 | S190T | 0.80 | 0.33 | 0.61 | *0.05* | 0.24 |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 190 | S190V | 1.50 | *0.05* | 0.18 | *ND* | *0.05* |
| 190 | S190W | 1.45 | 0.06 | *0.05* | *ND* | *0.05* |
| 190 | S190Y | 1.33 | 0.07 | 0.20 | *ND* | *0.05* |
| 191 | Q191A | 1.08 | 0.54 | 0.91 | 0.96 | 0.60 |
| 191 | Q191D | 1.33 | 0.54 | 1.22 | 0.96 | 0.70 |
| 191 | Q191E | 0.95 | 0.15 | 0.93 | 0.24 | 0.58 |
| 191 | Q191F | 1.64 | *0.05* | 0.24 | *ND* | *0.05* |
| 191 | Q191G | 0.31 | *0.05* | *0.05* | *ND* | *0.05* |
| 191 | Q191H | 1.79 | 0.38 | 0.76 | 0.21 | 0.39 |
| 191 | Q191I | 1.94 | *0.05* | 0.34 | *ND* | *0.05* |
| 191 | Q191K | 1.72 | *0.05* | *0.05* | *ND* | *0.05* |
| 191 | Q191L | 1.63 | *0.05* | 0.27 | *ND* | *0.05* |
| 191 | Q191P | 2.08 | 0.19 | 0.47 | *ND* | *0.05* |
| 191 | Q191R | 0.94 | 0.35 | 0.48 | 0.53 | 0.38 |
| 191 | Q191S | 1.14 | 0.54 | 0.90 | 1.01 | 0.59 |
| 191 | Q191T | 0.81 | 0.20 | 0.63 | 0.51 | 0.11 |
| 191 | Q191V | 1.82 | 0.06 | 0.34 | *ND* | *0.05* |
| 191 | Q191W | 1.80 | *0.05* | 0.17 | *ND* | *0.05* |
| 191 | Q191Y | 1.39 | 0.09 | 0.35 | *ND* | *0.05* |
| 192 | Y192C | 0.96 | 0.14 | 0.71 | 0.29 | 0.13 |
| 192 | Y192D | 1.89 | *0.05* | 0.27 | *ND* | *0.05* |
| 192 | Y192E | 1.95 | *0.05* | 0.42 | *ND* | *0.05* |
| 192 | Y192G | 0.87 | *0.05* | 0.50 | 0.37 | 0.11 |
| 192 | Y192H | 1.07 | 0.78 | 0.97 | 0.56 | 1.00 |
| 192 | Y192I | 0.88 | 0.16 | 0.35 | *ND* | *0.05* |
| 192 | Y192K | 0.88 | 0.15 | 0.21 | *ND* | *0.05* |
| 192 | Y192L | 1.56 | *0.05* | 0.22 | *ND* | *0.05* |
| 192 | Y192M | 1.06 | 0.15 | 0.46 | 0.59 | 0.07 |
| 192 | Y192N | 0.89 | 0.36 | 0.54 | *0.05* | 0.14 |
| 192 | Y192P | 2.31 | *0.05* | *0.05* | *ND* | *0.05* |
| 192 | Y192Q | 1.39 | 0.06 | 0.35 | *ND* | *0.05* |
| 192 | Y192R | 1.01 | 0.10 | 0.18 | *ND* | *0.05* |
| 192 | Y192S | 0.82 | 0.35 | 0.72 | 0.08 | 0.20 |
| 192 | Y192T | 0.60 | 5.73 | 0.94 | 0.12 | 0.24 |
| 192 | Y192V | 1.09 | 0.11 | 0.43 | 0.82 | 0.08 |
| 192 | Y192W | 0.91 | 1.15 | 1.05 | 0.73 | 0.89 |
| 193 | G193A | 1.01 | *0.05* | 0.47 | 0.14 | 0.17 |
| 193 | G193D | 1.15 | *0.05* | 0.49 | 0.17 | 0.07 |
| 193 | G193E | 1.13 | *0.05* | 0.49 | *0.05* | 0.10 |
| 193 | G193F | 2.15 | *0.05* | *0.05* | *ND* | *0.05* |
| 193 | G193H | 1.66 | *0.05* | *0.05* | *ND* | *0.05* |
| 193 | G193I | 1.82 | *0.05* | 0.24 | *ND* | *0.05* |
| 193 | G193K | 1.95 | *0.05* | 0.14 | *ND* | *0.05* |
| 193 | G193L | 1.81 | *0.05* | *0.05* | *ND* | *0.05* |
| 193 | G193M | 0.39 | *0.05* | *0.05* | *ND* | *0.05* |
| 193 | G193R | 1.87 | *0.05* | *0.05* | *ND* | *0.05* |
| 193 | G193S | 1.00 | *0.05* | 0.31 | 0.12 | 0.08 |
| 193 | G193T | 2.32 | *0.05* | 0.10 | *ND* | *0.05* |
| 193 | G193V | 2.17 | *0.05* | 0.51 | *ND* | *0.05* |
| 193 | G193W | 1.65 | *0.05* | *0.05* | *ND* | *0.05* |
| 193 | G193Y | 1.94 | 0.06 | *0.05* | *ND* | *0.05* |
| 194 | A194C | 1.47 | 0.72 | 0.93 | 1.07 | 1.56 |
| 194 | A194D | 1.78 | 0.81 | 0.98 | 1.07 | 2.13 |
| 194 | A194E | 1.64 | 0.93 | 1.00 | 1.10 | 2.02 |
| 194 | A194F | 1.37 | 1.19 | 0.86 | 0.95 | 1.73 |
| 194 | A194G | 1.64 | 0.62 | 0.78 | 0.55 | 1.53 |
| 194 | A194H | 1.78 | 0.96 | 0.71 | 1.01 | 2.06 |
| 194 | A194I | 1.72 | 1.09 | 0.73 | 1.06 | 2.17 |
| 194 | A194L | 1.57 | 0.83 | 0.84 | 0.95 | 1.77 |
| 194 | A194M | 1.66 | 1.01 | 0.83 | 0.95 | 2.14 |
| 194 | A194P | 1.48 | 0.67 | 0.89 | 1.07 | 1.58 |
| 194 | A194Q | 1.29 | 0.89 | 1.00 | 0.97 | 1.62 |
| 194 | A194R | 1.48 | 0.87 | 0.68 | 0.83 | 2.03 |
| 194 | A194S | 1.62 | 0.90 | 0.77 | 0.84 | 1.98 |
| 194 | A194T | 1.03 | 1.04 | 1.09 | 0.90 | 1.32 |
| 194 | A194V | 0.52 | *0.05* | 1.84 | 0.92 | 0.73 |
| 194 | A194W | 1.06 | 1.17 | 0.99 | 0.81 | 1.31 |
| 194 | A194Y | 1.19 | 1.12 | 0.95 | 0.92 | 1.53 |
| 195 | G195A | 0.81 | 1.51 | 1.06 | 0.61 | 0.81 |
| 195 | G195C | 0.98 | 1.06 | 1.29 | 0.90 | 1.00 |
| 195 | G195D | 1.07 | 0.51 | 1.15 | 1.09 | 0.83 |
| 195 | G195E | 1.00 | 1.11 | 1.32 | 1.03 | 1.13 |
| 195 | G195F | 0.90 | 0.43 | 0.92 | 0.59 | 0.70 |
| 195 | G195I | 0.83 | *0.05* | 0.50 | 0.08 | 0.11 |
| 195 | G195K | 1.04 | 0.28 | 0.83 | 0.42 | 0.68 |
| 195 | G195L | 0.90 | 0.38 | 0.98 | 0.25 | 0.45 |
| 195 | G195P | 0.76 | 0.68 | 0.57 | 0.14 | 0.15 |
| 195 | G195Q | 0.92 | 1.07 | 1.08 | 0.80 | 0.91 |
| 195 | G195R | 0.77 | 1.49 | 0.87 | 0.59 | 0.52 |
| 195 | G195S | 0.78 | 2.14 | 1.11 | 0.57 | 0.87 |
| 195 | G195T | 0.73 | 2.97 | 1.22 | 0.54 | 0.56 |
| 195 | G195V | 0.15 | *0.05* | 2.20 | 0.22 | 0.17 |
| 195 | G195W | 0.80 | 0.67 | 0.93 | 0.36 | 0.55 |
| 195 | G195Y | 0.84 | 0.50 | 1.06 | 0.52 | 0.64 |
| 196 | L196A | 1.22 | *0.05* | *0.05* | *ND* | *0.05* |
| 196 | L196D | 1.61 | *0.05* | 0.17 | *ND* | *0.05* |
| 196 | L196E | 1.23 | 0.11 | 0.28 | *ND* | *0.05* |
| 196 | L196F | 0.75 | 1.57 | 0.24 | *ND* | *0.05* |
| 196 | L196G | 0.29 | *0.05* | *0.05* | *ND* | *0.05* |
| 196 | L196H | 0.52 | *0.05* | 0.41 | *ND* | *0.05* |
| 196 | L196I | 1.25 | 0.49 | 0.90 | 0.49 | 0.99 |
| 196 | L196M | 1.19 | 1.08 | 1.06 | 0.47 | 1.29 |
| 196 | L196P | 2.27 | *0.05* | *0.05* | *ND* | *0.05* |
| 196 | L196Q | 0.46 | *0.05* | 1.22 | *0.05* | 0.21 |
| 196 | L196R | 0.39 | *0.05* | *0.05* | *ND* | *0.05* |
| 196 | L196T | 0.68 | *0.05* | 1.03 | *0.05* | 0.29 |
| 196 | L196V | 0.98 | *0.05* | 0.62 | 0.23 | 0.18 |
| 196 | L196Y | 0.84 | *0.05* | *0.05* | *ND* | *0.05* |
| 197 | D197A | 1.36 | 1.15 | 1.03 | *0.05* | 1.59 |
| 197 | D197C | 1.25 | 0.84 | 1.27 | 0.48 | 1.26 |
| 197 | D197E | 0.78 | 1.16 | 1.36 | 0.87 | 1.02 |
| 197 | D197F | 0.49 | 1.32 | 1.52 | *0.05* | 0.58 |
| 197 | D197G | 1.16 | 0.93 | 1.04 | *0.05* | 1.29 |
| 197 | D197H | 0.58 | 1.45 | 1.60 | *0.05* | 0.48 |
| 197 | D197I | 0.41 | *0.05* | 1.39 | *0.05* | 0.48 |
| 197 | D197L | 0.31 | *0.05* | 1.72 | *0.05* | 0.32 |
| 197 | D197M | 0.61 | 1.06 | 1.60 | *0.05* | 0.63 |
| 197 | D197N | 1.67 | 0.93 | 1.00 | *0.05* | 1.95 |
| 197 | D197P | 0.43 | *0.05* | *0.05* | *ND* | *0.05* |
| 197 | D197Q | 1.30 | 0.97 | 1.13 | *0.05* | 1.34 |
| 197 | D197R | 0.16 | *0.05* | 0.90 | *0.05* | 0.11 |
| 197 | D197S | 1.86 | 1.00 | 0.94 | *0.05* | 2.10 |
| 197 | D197T | 1.41 | 1.16 | 1.01 | *0.05* | 1.71 |
| 197 | D197V | 0.73 | 1.17 | 1.50 | *0.05* | 0.93 |
| 197 | D197W | 0.60 | 1.20 | 1.47 | *0.05* | 0.66 |
| 197 | D197Y | 0.35 | *0.05* | 1.56 | *0.05* | 0.41 |
| 198 | I198A | 1.25 | 1.07 | 1.02 | 0.41 | 1.71 |
| 198 | I198D | 0.25 | *0.05* | 1.44 | 0.18 | 0.17 |
| 198 | I198E | 0.51 | *0.05* | 1.58 | 0.08 | 0.59 |
| 198 | I198F | 1.97 | 0.78 | 0.61 | *0.05* | 1.93 |
| 198 | I198G | 2.10 | 0.77 | 0.64 | *0.05* | 2.40 |
| 198 | I198H | 1.78 | 0.71 | 0.76 | *0.05* | 1.52 |
| 198 | I198L | 1.66 | 0.80 | 0.67 | 0.86 | 1.97 |
| 198 | I198M | 1.04 | 1.02 | 1.13 | 0.71 | 1.43 |
| 198 | I198N | 1.62 | 0.71 | 0.74 | *0.05* | 1.54 |
| 198 | I198P | 0.62 | *0.05* | *0.05* | *ND* | *0.05* |
| 198 | I198Q | 0.51 | *0.05* | 1.10 | 0.11 | 0.43 |
| 198 | I198R | 0.22 | *0.05* | 1.40 | 0.88 | 0.10 |
| 198 | I198S | 2.18 | 0.82 | 0.53 | *0.05* | 2.46 |
| 198 | I198T | 2.02 | 0.84 | 0.63 | 0.31 | 2.07 |
| 198 | I198V | 0.27 | *0.05* | *0.05* | 0.33 | 0.07 |
| 198 | I198W | 0.30 | *0.05* | 1.22 | *0.05* | 0.22 |
| 198 | I198Y | 1.31 | 0.62 | 0.82 | *0.05* | 1.12 |
| 199 | V199A | 1.01 | 1.52 | 0.93 | 0.41 | 1.05 |
| 199 | V199C | 1.21 | 1.02 | 0.99 | 0.94 | 1.19 |
| 199 | V199D | 0.30 | *0.05* | 1.40 | *0.05* | 0.24 |
| 199 | V199E | 0.18 | *0.05* | 1.60 | 0.06 | 0.12 |
| 199 | V199F | 0.52 | *0.05* | 1.05 | 0.31 | 0.20 |
| 199 | V199G | 0.76 | 1.38 | 1.09 | 0.14 | 0.83 |
| 199 | V199H | 0.40 | *0.05* | 0.96 | *0.05* | 0.31 |
| 199 | V199I | 0.86 | 1.13 | 1.32 | *0.05* | 0.87 |
| 199 | V199K | 0.44 | *0.05* | *0.05* | *ND* | *0.05* |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 199 | V199L | 0.57 | *0.05* | 1.15 | *0.05* | 0.51 |
| 199 | V199M | 1.46 | 0.93 | 0.98 | 1.03 | 1.36 |
| 199 | V199P | 0.37 | *0.05* | *0.05* | ND | *0.05* |
| 199 | V199Q | 0.32 | *0.05* | 1.35 | *0.05* | 0.30 |
| 199 | V199R | 0.21 | *0.05* | *0.05* | ND | *0.05* |
| 199 | V199S | 1.38 | 0.95 | 1.03 | 1.01 | 1.42 |
| 199 | V199T | 1.21 | 1.10 | 0.94 | 0.53 | 1.36 |
| 199 | V199W | 0.49 | *0.05* | 0.82 | 0.12 | 0.18 |
| 200 | A200C | 1.06 | 1.02 | 1.12 | *0.05* | 1.14 |
| 200 | A200E | 0.18 | *0.05* | *0.05* | *0.05* | 0.06 |
| 200 | A200G | 0.93 | 1.14 | 1.05 | 0.28 | 0.93 |
| 200 | A200H | 0.29 | *0.05* | 1.47 | ND | *0.05* |
| 200 | A200I | 0.51 | *0.05* | 1.30 | 0.37 | 0.53 |
| 200 | A200L | 0.43 | *0.05* | *0.05* | ND | *0.05* |
| 200 | A200P | 0.24 | *0.05* | *0.05* | ND | *0.05* |
| 200 | A200R | 0.51 | *0.05* | *0.05* | ND | *0.05* |
| 200 | A200S | 1.17 | 1.13 | 0.99 | 0.16 | 1.31 |
| 200 | A200W | 0.46 | *0.05* | *0.05* | ND | *0.05* |
| 200 | A200Y | 0.44 | *0.05* | *0.05* | ND | *0.05* |
| 201 | P201A | 0.44 | *0.05* | *0.05* | ND | *0.05* |
| 201 | P201C | 0.70 | 3.09 | 1.11 | *0.05* | 0.91 |
| 201 | P201D | 0.22 | *0.05* | *0.05* | ND | *0.05* |
| 201 | P201E | 0.26 | *0.05* | *0.05* | ND | *0.05* |
| 201 | P201F | 0.19 | *0.05* | *0.05* | ND | *0.05* |
| 201 | P201G | 0.48 | *0.05* | 1.43 | *0.05* | 0.65 |
| 201 | P201I | 0.19 | *0.05* | *0.05* | *0.05* | 0.06 |
| 201 | P201K | 0.33 | *0.05* | *0.05* | ND | *0.05* |
| 201 | P201L | 0.17 | *0.05* | *0.05* | ND | *0.05* |
| 201 | P201M | 0.18 | *0.05* | *0.05* | ND | *0.05* |
| 201 | P201N | 0.22 | *0.05* | *0.05* | ND | *0.05* |
| 201 | P201Q | 0.21 | *0.05* | *0.05* | ND | *0.05* |
| 201 | P201R | 0.32 | *0.05* | *0.05* | ND | *0.05* |
| 201 | P201S | 0.75 | 1.98 | 1.20 | *0.05* | 0.95 |
| 201 | P201T | 0.25 | *0.05* | 1.21 | *0.05* | 0.31 |
| 201 | P201V | 0.21 | *0.05* | 1.59 | *0.05* | 0.26 |
| 202 | G202A | 0.29 | *0.05* | 0.71 | *0.05* | 0.13 |
| 202 | G202C | 0.40 | *0.05* | *0.05* | ND | *0.05* |
| 202 | G202D | 0.42 | *0.05* | *0.05* | ND | *0.05* |
| 202 | G202E | 0.38 | *0.05* | *0.05* | ND | *0.05* |
| 202 | G202F | 1.11 | *0.05* | *0.05* | ND | *0.05* |
| 202 | G202H | 0.45 | *0.05* | *0.05* | ND | *0.05* |
| 202 | G202K | 0.48 | *0.05* | *0.05* | ND | *0.05* |
| 202 | G202L | 0.49 | *0.05* | *0.05* | ND | *0.05* |
| 202 | G202M | 0.47 | *0.05* | *0.05* | ND | *0.05* |
| 202 | G202N | 0.46 | *0.05* | *0.05* | ND | *0.05* |
| 202 | G202P | 0.48 | *0.05* | *0.05* | ND | *0.05* |
| 202 | G202Q | 0.47 | *0.05* | *0.05* | ND | *0.05* |
| 202 | G202R | 0.36 | *0.05* | *0.05* | ND | *0.05* |
| 202 | G202S | 0.17 | *0.05* | *0.05* | ND | *0.05* |
| 202 | G202T | 0.40 | *0.05* | *0.05* | ND | *0.05* |
| 202 | G202V | 0.40 | *0.05* | *0.05* | ND | *0.05* |
| 202 | G202W | 0.43 | *0.05* | *0.05* | ND | *0.05* |
| 202 | G202Y | 0.39 | *0.05* | *0.05* | ND | *0.05* |
| 203 | V203A | 0.86 | 1.14 | 1.10 | 0.38 | 0.94 |
| 203 | V203C | 0.84 | 0.94 | 1.19 | 0.97 | 0.75 |
| 203 | V203E | 0.82 | 1.06 | 1.25 | 1.07 | 0.88 |
| 203 | V203F | 0.71 | 0.58 | 1.25 | *0.05* | 0.54 |
| 203 | V203G | 0.17 | *0.05* | 1.58 | *0.05* | 0.16 |
| 203 | V203H | 0.45 | *0.05* | 1.27 | 0.09 | 0.31 |
| 203 | V203I | 1.43 | 0.93 | 1.04 | 0.65 | 1.27 |
| 203 | V203K | 1.09 | 0.79 | 0.81 | *0.05* | 0.89 |
| 203 | V203L | 1.09 | 0.91 | 1.01 | 0.25 | 1.00 |
| 203 | V203N | 0.50 | *0.05* | 1.42 | 0.10 | 0.52 |
| 203 | V203P | 0.16 | *0.05* | *0.05* | 0.08 | 0.06 |
| 203 | V203R | 0.76 | 0.60 | 0.88 | *0.05* | 0.60 |
| 203 | V203S | 0.82 | 0.90 | 1.04 | 0.43 | 0.72 |
| 203 | V203T | 1.29 | 1.10 | 0.87 | 1.02 | 1.42 |
| 203 | V203W | 0.70 | 0.76 | 1.18 | *0.05* | 0.47 |
| 203 | V203Y | 0.71 | 0.74 | 1.19 | 0.14 | 0.52 |
| 204 | N204A | 1.32 | 1.10 | 0.89 | 0.82 | 1.34 |
| 204 | N204C | 1.27 | 0.72 | 0.81 | 0.85 | 1.27 |
| 204 | N204E | 1.52 | 0.86 | 1.06 | 1.08 | 1.56 |
| 204 | N204F | 1.50 | 0.82 | 0.80 | 0.33 | 1.44 |
| 204 | N204G | 1.38 | 1.04 | 0.95 | 0.91 | 1.43 |
| 204 | N204I | 1.27 | 0.71 | 0.85 | 0.13 | 1.23 |
| 204 | N204K | 1.62 | 0.89 | 0.72 | 0.08 | 1.48 |
| 204 | N204L | 1.43 | 0.87 | 0.96 | 0.56 | 1.39 |
| 204 | N204P | 0.21 | *0.05* | 1.41 | *0.05* | 0.19 |
| 204 | N204R | 1.42 | 0.74 | 0.66 | *0.05* | 1.21 |
| 204 | N204S | 1.23 | 1.02 | 0.94 | 0.82 | 1.26 |
| 204 | N204T | 1.17 | 1.06 | 0.99 | 0.51 | 1.19 |
| 204 | N204W | 1.27 | 0.86 | 0.83 | 0.21 | 1.16 |
| 204 | N204Y | 1.34 | 0.78 | 0.87 | 0.38 | 1.31 |
| 205 | V205A | 0.61 | 3.19 | 0.98 | *0.05* | 0.64 |
| 205 | V205D | 0.08 | *0.05* | *0.05* | ND | *0.05* |
| 205 | V205E | 0.25 | *0.05* | *0.05* | ND | *0.05* |
| 205 | V205F | 0.27 | *0.05* | 0.43 | 1.07 | 0.07 |
| 205 | V205G | 0.23 | *0.05* | 1.16 | *0.05* | 0.12 |
| 205 | V205I | 0.31 | *0.05* | 1.52 | 1.08 | 0.25 |
| 205 | V205K | 0.22 | *0.05* | *0.05* | ND | *0.05* |
| 205 | V205L | 0.40 | *0.05* | 1.34 | *0.05* | 0.25 |
| 205 | V205M | 0.27 | *0.05* | 1.14 | *0.05* | 0.15 |
| 205 | V205P | 0.34 | *0.05* | *0.05* | ND | *0.05* |
| 205 | V205Q | 1.07 | 0.81 | 0.92 | *0.05* | 0.84 |
| 205 | V205R | 0.37 | *0.05* | *0.05* | ND | *0.05* |
| 205 | V205T | 1.03 | 1.22 | 1.05 | 0.73 | 1.41 |
| 205 | V205W | 0.35 | *0.05* | *0.05* | ND | *0.05* |
| 205 | V205Y | 0.29 | *0.05* | *0.05* | ND | *0.05* |
| 206 | Q206A | 0.91 | 0.87 | 1.16 | 0.77 | 1.15 |
| 206 | Q206C | 0.78 | 0.95 | 1.51 | 1.11 | 1.06 |
| 206 | Q206D | 0.92 | 1.06 | 1.40 | 1.14 | 1.31 |
| 206 | Q206E | 0.90 | 1.12 | 1.39 | 1.05 | 1.33 |
| 206 | Q206F | 0.51 | *0.05* | 1.68 | 0.37 | 0.65 |
| 206 | Q206G | 0.98 | 0.90 | 1.03 | 0.11 | 1.22 |
| 206 | Q206H | 1.40 | 0.82 | 0.97 | 0.99 | 1.50 |
| 206 | Q206I | 1.56 | 0.96 | 0.80 | 0.31 | 1.71 |
| 206 | Q206K | 1.69 | 0.87 | 0.71 | 0.14 | 2.04 |
| 206 | Q206L | 1.63 | 0.70 | 0.83 | 0.81 | 1.75 |
| 206 | Q206N | 1.11 | 0.91 | 1.10 | 0.93 | 1.52 |
| 206 | Q206P | 1.05 | 0.97 | 1.07 | 0.42 | 1.28 |
| 206 | Q206R | 1.62 | 0.94 | 0.71 | 0.39 | 1.85 |
| 206 | Q206S | 0.93 | 1.68 | 1.20 | 0.91 | 1.35 |
| 206 | Q206T | 0.95 | 1.03 | 1.25 | 0.79 | 1.25 |
| 206 | Q206V | 0.96 | 0.88 | 1.02 | 0.44 | 1.17 |
| 206 | Q206W | 1.13 | 0.96 | 0.82 | 0.08 | 1.26 |
| 206 | Q206Y | 0.95 | 1.05 | 1.18 | 0.65 | 1.16 |
| 207 | S207A | 0.95 | 1.71 | 1.09 | *0.05* | 1.05 |
| 207 | S207C | 0.19 | *0.05* | *0.05* | ND | *0.05* |
| 207 | S207D | 0.36 | *0.05* | *0.05* | ND | *0.05* |
| 207 | S207E | 0.36 | *0.05* | *0.05* | ND | *0.05* |
| 207 | S207F | 0.34 | *0.05* | *0.05* | ND | *0.05* |
| 207 | S207G | 0.74 | 12.54 | 1.05 | *0.05* | 0.42 |
| 207 | S207H | 0.37 | *0.05* | 0.98 | ND | *0.05* |
| 207 | S207I | 0.36 | *0.05* | *0.05* | ND | *0.05* |
| 207 | S207K | 0.38 | *0.05* | *0.05* | ND | *0.05* |
| 207 | S207L | 0.36 | *0.05* | *0.05* | ND | *0.05* |
| 207 | S207M | 0.29 | *0.05* | *0.05* | ND | *0.05* |
| 207 | S207N | 0.21 | *0.05* | *0.05* | ND | *0.05* |
| 207 | S207P | 0.24 | *0.05* | *0.05* | ND | *0.05* |
| 207 | S207R | 0.34 | *0.05* | *0.05* | ND | *0.05* |
| 207 | S207T | 0.34 | *0.05* | 0.78 | ND | *0.05* |
| 207 | S207V | 0.32 | *0.05* | *0.05* | ND | *0.05* |
| 207 | S207W | 0.44 | *0.05* | *0.05* | ND | *0.05* |
| 207 | S207Y | 0.35 | *0.05* | *0.05* | ND | *0.05* |
| 208 | T208A | 0.71 | 2.56 | 1.42 | *0.05* | 0.93 |
| 208 | T208C | 0.93 | 1.15 | 1.37 | 0.65 | 1.31 |
| 208 | T208D | 0.19 | *0.05* | *0.05* | ND | *0.05* |
| 208 | T208E | 0.35 | *0.05* | *0.05* | ND | *0.05* |
| 208 | T208F | 0.30 | *0.05* | 0.68 | *0.05* | 0.10 |
| 208 | T208G | 0.20 | *0.05* | *0.05* | ND | *0.05* |
| 208 | T208H | 0.22 | *0.05* | *0.05* | ND | *0.05* |
| 208 | T208K | 0.27 | *0.05* | *0.05* | ND | *0.05* |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 208 | T208L | 1.01 | 0.92 | 1.21 | *0.05* | 1.23 |
| 208 | T208M | 0.21 | *0.05* | *0.05* | ND | *0.05* |
| 208 | T208N | 0.22 | *0.05* | 1.51 | *0.05* | 0.12 |
| 208 | T208P | 0.28 | *0.05* | 2.26 | *0.05* | 0.39 |
| 208 | T208Q | 0.31 | *0.05* | *0.05* | ND | *0.05* |
| 208 | T208R | 0.43 | *0.05* | *0.05* | ND | *0.05* |
| 208 | T208S | 1.15 | 1.04 | 1.05 | *0.05* | 1.49 |
| 208 | T208V | 0.89 | 1.57 | 1.24 | *0.05* | 1.18 |
| 208 | T208W | 0.29 | *0.05* | *0.05* | ND | *0.05* |
| 208 | T208Y | 0.21 | *0.05* | *0.05* | ND | *0.05* |
| 209 | Y209A | 0.81 | 1.59 | 1.37 | 0.64 | 1.12 |
| 209 | Y209C | 1.19 | 0.80 | 1.21 | 0.78 | 1.72 |
| 209 | Y209D | 0.44 | *0.05* | 1.57 | *0.05* | 0.33 |
| 209 | Y209E | 0.72 | 1.68 | 1.58 | *0.05* | 1.09 |
| 209 | Y209F | 1.26 | 1.02 | 1.05 | 0.89 | 1.80 |
| 209 | Y209G | 0.93 | 1.29 | 1.29 | 0.11 | 1.15 |
| 209 | Y209H | 1.07 | 1.30 | 1.08 | 0.29 | 1.39 |
| 209 | Y209I | 1.25 | 0.86 | 1.04 | 0.63 | 2.04 |
| 209 | Y209K | 1.32 | 0.98 | 0.87 | *0.05* | 2.11 |
| 209 | Y209L | 1.03 | 0.83 | 1.14 | 0.23 | 1.79 |
| 209 | Y209M | 0.94 | 1.41 | 1.24 | 0.87 | 1.73 |
| 209 | Y209N | 1.02 | 1.11 | 1.14 | *0.05* | 1.33 |
| 209 | Y209P | 0.33 | *0.05* | *0.05* | ND | *0.05* |
| 209 | Y209R | 1.07 | 1.18 | 0.98 | *0.05* | 1.23 |
| 209 | Y209S | 0.96 | 1.05 | 1.38 | 0.54 | 1.56 |
| 209 | Y209T | 0.76 | 1.83 | 1.32 | 0.59 | 1.49 |
| 209 | Y209V | 0.83 | 1.30 | 1.35 | 0.77 | 1.61 |
| 209 | Y209W | 0.89 | 1.61 | 1.24 | 0.87 | 1.45 |
| 210 | P210A | 0.97 | 1.80 | 1.26 | 1.08 | 1.55 |
| 210 | P210C | 0.85 | 1.50 | 1.54 | 0.94 | 1.39 |
| 210 | P210D | 0.67 | 2.94 | 1.79 | 0.24 | 0.86 |
| 210 | P210E | 0.82 | 1.78 | 1.52 | 0.71 | 1.01 |
| 210 | P210F | 0.79 | 2.14 | 1.40 | 0.57 | 1.14 |
| 210 | P210G | 1.03 | 1.75 | 1.24 | 0.55 | 1.53 |
| 210 | P210H | 0.89 | 2.43 | 1.34 | 0.79 | 1.44 |
| 210 | P210I | 1.06 | 1.77 | 1.23 | 1.20 | 1.58 |
| 210 | P210L | 0.81 | 1.93 | 1.45 | 1.03 | 1.23 |
| 210 | P210M | 1.01 | 1.78 | 1.37 | 1.08 | 1.41 |
| 210 | P210N | 1.01 | 1.62 | 1.25 | 0.84 | 1.64 |
| 210 | P210Q | 0.69 | 4.64 | 1.58 | 0.76 | 1.17 |
| 210 | P210R | 0.85 | 2.12 | 1.17 | 0.29 | 1.39 |
| 210 | P210S | 0.67 | 5.84 | 1.68 | 0.95 | 1.21 |
| 210 | P210V | 0.64 | 9.61 | 1.78 | 1.05 | 1.05 |
| 210 | P210W | 0.61 | 14.30 | 1.57 | 0.14 | 1.07 |
| 210 | P210Y | 0.71 | 3.88 | 1.55 | 0.82 | 1.17 |
| 211 | G211A | 1.05 | 1.55 | 1.13 | 0.89 | 1.21 |
| 211 | G211C | 1.10 | 0.93 | 1.10 | 0.92 | 1.24 |
| 211 | G211E | 1.26 | 1.08 | 1.17 | 1.06 | 1.48 |
| 211 | G211F | 1.01 | 1.41 | 0.87 | 0.54 | 1.25 |
| 211 | G211H | 1.22 | 1.22 | 1.01 | 1.11 | 1.27 |
| 211 | G211I | 1.13 | 1.16 | 1.22 | 0.91 | 1.30 |
| 211 | G211L | 1.31 | 0.95 | 0.85 | 0.78 | 1.37 |
| 211 | G211M | 1.25 | 1.09 | 0.96 | 0.81 | 1.44 |
| 211 | G211P | 1.12 | 1.04 | 0.93 | 1.17 | 1.25 |
| 211 | G211Q | 1.34 | 0.83 | 1.14 | 0.99 | 1.50 |
| 211 | G211R | 1.30 | 0.90 | 0.85 | 0.57 | 1.37 |
| 211 | G211T | 1.29 | 0.99 | 1.10 | 0.81 | 1.53 |
| 211 | G211V | 1.13 | 1.08 | 0.97 | 0.95 | 1.32 |
| 211 | G211W | 1.18 | 1.05 | 0.80 | 0.39 | 1.28 |
| 211 | G211Y | 0.79 | 1.53 | 1.03 | 0.84 | 0.86 |
| 212 | S212C | 1.14 | 1.57 | 1.21 | 1.10 | 1.57 |
| 212 | S212F | 1.25 | 1.54 | 0.88 | 1.04 | 1.78 |
| 212 | S212G | 1.12 | 1.35 | 1.08 | 0.95 | 1.77 |
| 212 | S212H | 1.38 | 1.00 | 0.97 | 1.09 | 1.75 |
| 212 | S212I | 1.06 | 1.61 | 1.19 | 0.53 | 1.51 |
| 212 | S212M | 1.14 | 1.36 | 1.14 | 1.03 | 1.59 |
| 212 | S212N | 1.55 | 0.97 | 0.88 | 1.10 | 2.11 |
| 212 | S212P | 1.56 | 0.94 | 0.85 | 0.65 | 2.14 |
| 212 | S212R | 1.44 | 1.03 | 0.70 | 0.85 | 1.84 |
| 212 | S212T | 1.28 | 0.96 | 1.06 | 0.62 | 1.79 |
| 212 | S212V | 1.32 | 0.93 | 1.06 | 0.58 | 1.76 |
| 212 | S212W | 0.22 | *0.05* | *0.05* | ND | *0.05* |
| 212 | S212Y | 1.57 | 0.78 | 0.75 | 0.96 | 1.94 |
| 213 | T213A | 1.36 | 1.05 | 0.98 | 0.94 | 1.94 |
| 213 | T213C | 1.07 | 1.18 | 1.35 | 0.65 | 1.60 |
| 213 | T213D | 1.31 | 1.05 | 1.17 | 0.87 | 1.94 |
| 213 | T213E | 1.40 | 1.02 | 1.20 | 0.93 | 1.97 |
| 213 | T213F | 1.27 | 1.10 | 0.87 | *0.05* | 2.00 |
| 213 | T213G | 1.34 | 0.74 | 0.99 | 0.72 | 1.86 |
| 213 | T213I | 1.57 | 0.88 | 0.82 | 0.56 | 2.08 |
| 213 | T213K | 1.69 | 0.96 | 0.75 | 0.24 | 2.28 |
| 213 | T213L | 1.45 | 1.07 | 0.89 | 0.48 | 2.10 |
| 213 | T213M | 1.54 | 0.99 | 0.90 | 0.62 | 2.16 |
| 213 | T213N | 1.58 | 0.96 | 0.92 | 0.99 | 2.20 |
| 213 | T213P | 0.70 | *0.05* | 1.62 | *0.05* | 0.87 |
| 213 | T213Q | 1.57 | 0.82 | 0.90 | 0.95 | 2.32 |
| 213 | T213R | 1.59 | 0.86 | 0.66 | 0.12 | 2.08 |
| 213 | T213S | 1.53 | 0.93 | 0.92 | 1.05 | 2.14 |
| 213 | T213V | 1.60 | 0.92 | 0.94 | 0.56 | 2.23 |
| 213 | T213W | 1.52 | 0.81 | 0.74 | *0.05* | 2.07 |
| 213 | T213Y | 1.33 | 1.14 | 0.82 | *0.05* | 1.71 |
| 214 | Y214A | 0.23 | *0.05* | 1.09 | *0.05* | 0.10 |
| 214 | Y214C | 0.74 | 4.58 | 1.42 | 0.10 | 1.00 |
| 214 | Y214E | 0.67 | 2.33 | 1.49 | *0.05* | 0.87 |
| 214 | Y214F | 1.10 | 1.24 | 1.08 | *0.05* | 1.37 |
| 214 | Y214G | 0.19 | *0.05* | 2.32 | *0.05* | 0.17 |
| 214 | Y214H | 0.62 | *0.05* | 1.39 | 0.09 | 0.62 |
| 214 | Y214I | 0.77 | 6.29 | 1.24 | *0.05* | 0.79 |
| 214 | Y214K | 0.41 | *0.05* | 1.09 | *0.05* | 0.35 |
| 214 | Y214L | 1.15 | 1.12 | 1.09 | 0.08 | 1.27 |
| 214 | Y214M | 0.73 | 5.63 | 1.26 | *0.05* | 0.79 |
| 214 | Y214N | 0.35 | *0.05* | 1.71 | *0.05* | 0.34 |
| 214 | Y214P | 0.22 | *0.05* | 1.41 | *0.05* | 0.17 |
| 214 | Y214Q | 0.56 | *0.05* | 1.56 | *0.05* | 0.58 |
| 214 | Y214R | 0.23 | *0.05* | 1.10 | *0.05* | 0.16 |
| 214 | Y214S | 0.28 | *0.05* | 2.05 | *0.05* | 0.25 |
| 214 | Y214T | 0.60 | *0.05* | 1.48 | *0.05* | 0.79 |
| 214 | Y214V | 0.73 | 2.05 | 1.17 | *0.05* | 0.83 |
| 214 | Y214W | 1.14 | 0.98 | 1.05 | *0.05* | 1.40 |
| 215 | A215C | 0.96 | 1.27 | 1.30 | 1.04 | 1.30 |
| 215 | A215D | 1.22 | 0.93 | 1.26 | 1.00 | 1.32 |
| 215 | A215E | 1.09 | 0.78 | 1.35 | 1.30 | 1.14 |
| 215 | A215F | 1.40 | 1.28 | 1.06 | 0.71 | 1.70 |
| 215 | A215G | 1.50 | 0.93 | 0.99 | 0.49 | 1.89 |
| 215 | A215H | 1.24 | 1.43 | 1.14 | 1.12 | 1.46 |
| 215 | A215I | 1.53 | 1.07 | 1.01 | 1.31 | 2.23 |
| 215 | A215K | 1.47 | 1.51 | 0.95 | 0.85 | 1.80 |
| 215 | A215M | 1.54 | 0.89 | 0.95 | 1.08 | 1.81 |
| 215 | A215N | 1.25 | 0.96 | 1.14 | 0.90 | 1.50 |
| 215 | A215P | 1.13 | 0.66 | 1.18 | *0.05* | 1.88 |
| 215 | A215R | 1.17 | 1.08 | 0.90 | 0.60 | 1.45 |
| 215 | A215S | 1.13 | 1.22 | 1.27 | 0.88 | 1.47 |
| 215 | A215T | 1.12 | 0.70 | 1.14 | 1.18 | 1.40 |
| 215 | A215V | 1.02 | 1.18 | 1.13 | 1.27 | 1.46 |
| 215 | A215W | 1.27 | 1.02 | 0.97 | 0.58 | 1.40 |
| 215 | A215Y | 1.13 | 1.28 | 1.12 | 0.99 | 1.29 |
| 216 | S216A | 1.13 | 1.26 | 1.02 | 0.87 | 1.52 |
| 216 | S216C | 1.03 | 1.06 | 1.15 | 1.04 | 1.11 |
| 216 | S216D | 1.14 | 1.15 | 1.17 | 0.96 | 1.40 |
| 216 | S216E | 1.13 | 1.05 | 1.17 | 1.11 | 1.43 |
| 216 | S216F | 1.31 | 0.98 | 0.88 | 1.02 | 1.54 |
| 216 | S216G | 1.05 | 1.11 | 1.04 | 0.26 | 1.23 |
| 216 | S216H | 1.08 | 1.30 | 1.04 | 1.06 | 1.24 |
| 216 | S216I | 1.24 | 1.01 | 0.86 | 1.04 | 1.50 |
| 216 | S216K | 1.24 | 1.00 | 0.82 | 0.08 | 1.35 |
| 216 | S216L | 1.20 | 0.96 | 0.95 | 0.93 | 1.23 |
| 216 | S216M | 1.12 | 1.23 | 1.00 | 0.95 | 1.24 |
| 216 | S216N | 1.19 | 1.06 | 0.95 | 0.90 | 1.50 |
| 216 | S216P | 1.26 | 1.00 | 0.91 | 0.73 | 1.33 |
| 216 | S216Q | 1.10 | 1.34 | 1.04 | 0.91 | 1.23 |
| 216 | S216R | 1.15 | 1.07 | 0.93 | 0.28 | 1.43 |
| 216 | S216V | 1.18 | 0.80 | 1.03 | 0.84 | 1.29 |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 216 | S216W | 1.24 | 0.95 | 0.95 | 0.97 | 1.57 |
| 216 | S216Y | 1.06 | 1.25 | 1.12 | 1.08 | 1.18 |
| 217 | L217A | 0.85 | 3.15 | 0.95 | 0.84 | 0.42 |
| 217 | L217C | 0.95 | 1.63 | 1.08 | 1.05 | 0.34 |
| 217 | L217D | 1.78 | 0.93 | 0.89 | 0.95 | 0.09 |
| 217 | L217E | 0.84 | 4.61 | 1.44 | 0.98 | 0.10 |
| 217 | L217F | 1.22 | 1.09 | 0.79 | 0.87 | 1.06 |
| 217 | L217G | 0.90 | 2.21 | 0.78 | 0.66 | 0.58 |
| 217 | L217I | 0.98 | 1.92 | 0.93 | 0.06 | 0.50 |
| 217 | L217K | 1.31 | 1.06 | 0.79 | 1.08 | 0.59 |
| 217 | L217M | 0.81 | 4.01 | 1.10 | 1.09 | 0.56 |
| 217 | L217N | 0.79 | 5.86 | 1.31 | 0.60 | 0.26 |
| 217 | L217P | 0.19 | *0.05* | *0.05* | *ND* | *0.05* |
| 217 | L217Q | 0.91 | 2.34 | 1.18 | 1.05 | 0.44 |
| 217 | L217S | 0.60 | *0.05* | 1.55 | 0.75 | 0.27 |
| 217 | L217T | 0.74 | 13.21 | 1.19 | 0.13 | 0.27 |
| 217 | L217V | 0.77 | 7.00 | 1.13 | *0.05* | 0.25 |
| 217 | L217Y | 0.77 | 2.80 | 0.78 | 0.36 | 0.55 |
| 218 | N218C | 0.97 | 1.46 | 1.09 | 1.08 | 1.76 |
| 218 | N218D | 1.21 | 1.15 | 1.11 | 1.25 | 1.22 |
| 218 | N218E | 1.14 | 1.28 | 1.10 | 1.15 | 1.28 |
| 218 | N218F | 1.00 | 1.64 | 0.89 | *0.05* | 1.19 |
| 218 | N218G | 1.04 | 1.29 | 0.97 | 0.49 | 2.03 |
| 218 | N218H | 1.03 | 1.61 | 1.11 | 0.67 | 1.49 |
| 218 | N218I | 0.95 | 1.27 | 0.99 | *0.05* | 1.32 |
| 218 | N218L | 0.78 | 3.74 | 1.20 | *0.05* | 1.35 |
| 218 | N218M | 0.91 | 1.72 | 1.07 | 0.25 | 1.51 |
| 218 | N218P | 0.67 | *0.05* | 1.36 | *0.05* | 0.69 |
| 218 | N218Q | 1.11 | 1.09 | 1.11 | 0.82 | 1.58 |
| 218 | N218R | 1.17 | 0.97 | 0.80 | *0.05* | 1.80 |
| 218 | N218S | 0.65 | *0.05* | 1.55 | 0.97 | 1.24 |
| 218 | N218T | 0.63 | *0.05* | 1.45 | 1.03 | 1.34 |
| 218 | N218V | 1.00 | 1.26 | 1.08 | *0.05* | 1.76 |
| 218 | N218W | 0.77 | 4.67 | 1.01 | 0.18 | 0.55 |
| 218 | N218Y | 0.81 | 3.45 | 1.24 | 0.25 | 1.05 |
| 219 | G219A | 1.33 | 0.17 | *0.05* | *ND* | *0.05* |
| 219 | G219E | 0.56 | *0.05* | *0.05* | *ND* | *0.05* |
| 219 | G219F | 0.58 | *0.05* | *0.05* | *ND* | *0.05* |
| 219 | G219H | 0.67 | *0.05* | *0.05* | *ND* | *0.05* |
| 219 | G219I | 0.51 | *0.05* | *0.05* | *ND* | *0.05* |
| 219 | G219K | 0.61 | *0.05* | *0.05* | *ND* | *0.05* |
| 219 | G219L | 0.44 | *0.05* | *0.05* | *ND* | *0.05* |
| 219 | G219M | 0.64 | *0.05* | *0.05* | *ND* | *0.05* |
| 219 | G219P | 0.51 | *0.05* | *0.05* | *ND* | *0.05* |
| 219 | G219Q | 0.55 | *0.05* | *0.05* | *ND* | *0.05* |
| 219 | G219R | 0.51 | *0.05* | *0.05* | *ND* | *0.05* |
| 219 | G219S | 0.92 | *0.05* | *0.05* | *ND* | *0.05* |
| 219 | G219T | 0.52 | *0.05* | *0.05* | *ND* | *0.05* |
| 219 | G219V | 0.47 | *0.05* | *0.05* | *ND* | *0.05* |
| 219 | G219W | 0.47 | *0.05* | *0.05* | *ND* | *0.05* |
| 219 | G219Y | 0.52 | *0.05* | *0.05* | *ND* | *0.05* |
| 220 | T220A | 1.82 | 0.21 | 0.71 | 0.20 | 0.11 |
| 220 | T220C | 0.86 | 0.30 | 0.75 | *ND* | *0.05* |
| 220 | T220D | 0.44 | *0.05* | *0.05* | *ND* | *0.05* |
| 220 | T220E | 0.66 | 0.64 | *0.05* | *ND* | *0.05* |
| 220 | T220F | 0.54 | *0.05* | *0.05* | *ND* | *0.05* |
| 220 | T220G | 1.75 | 0.27 | 0.66 | *ND* | *0.05* |
| 220 | T220H | 0.65 | 3.46 | 0.68 | *ND* | *0.05* |
| 220 | T220M | 0.37 | *0.05* | *0.05* | *ND* | *0.05* |
| 220 | T220N | 1.83 | *0.05* | 0.19 | *ND* | *0.05* |
| 220 | T220P | 0.74 | 0.71 | *0.05* | *ND* | *0.05* |
| 220 | T220R | 0.48 | *0.05* | *0.05* | *ND* | *0.05* |
| 220 | T220S | 1.18 | 0.74 | 1.05 | 0.23 | 0.35 |
| 220 | T220V | 1.70 | 0.23 | 0.66 | 0.07 | 0.10 |
| 220 | T220W | 0.46 | *0.05* | *0.05* | *ND* | *0.05* |
| 220 | T220Y | 0.45 | *0.05* | *0.05* | *ND* | *0.05* |
| 221 | S221A | 0.62 | *0.05* | *0.05* | *ND* | *0.05* |
| 221 | S221C | 0.79 | *0.05* | *0.05* | *ND* | *0.05* |
| 221 | S221E | 0.65 | *0.05* | *0.05* | *ND* | *0.05* |
| 221 | S221F | 0.51 | *0.05* | *0.05* | *ND* | *0.05* |
| 221 | S221G | 1.23 | *0.05* | *0.05* | *ND* | *0.05* |
| 221 | S221H | 0.50 | *0.05* | *0.05* | *ND* | *0.05* |
| 221 | S221K | 0.51 | *0.05* | *0.05* | *ND* | *0.05* |
| 221 | S221L | 0.47 | *0.05* | *0.05* | *ND* | *0.05* |
| 221 | S221M | 0.51 | *0.05* | *0.05* | *ND* | *0.05* |
| 221 | S221N | 0.72 | *0.05* | *0.05* | *ND* | *0.05* |
| 221 | S221P | 0.48 | *0.05* | *0.05* | *ND* | *0.05* |
| 221 | S221R | 0.48 | *0.05* | *0.05* | *ND* | *0.05* |
| 221 | S221T | 0.98 | *0.05* | *0.05* | *ND* | *0.05* |
| 221 | S221V | 0.39 | *0.05* | *0.05* | *ND* | *0.05* |
| 221 | S221W | 0.53 | *0.05* | *0.05* | *ND* | *0.05* |
| 221 | S221Y | 0.65 | *0.05* | *0.05* | *ND* | *0.05* |
| 222 | M222A | 1.17 | 1.05 | 0.80 | 0.77 | 0.08 |
| 222 | M222C | 1.19 | 0.85 | 0.89 | 1.10 | 0.48 |
| 222 | M222E | 1.76 | 0.63 | 0.76 | *ND* | *0.05* |
| 222 | M222F | 1.23 | 0.80 | 0.91 | *ND* | *0.05* |
| 222 | M222G | 1.63 | 0.60 | 0.58 | 0.32 | 0.10 |
| 222 | M222I | 2.14 | 0.45 | 0.64 | *ND* | *0.05* |
| 222 | M222K | 2.31 | 0.37 | 0.20 | *ND* | *0.05* |
| 222 | M222L | 1.84 | 0.52 | 0.65 | *0.05* | 0.38 |
| 222 | M222N | 2.01 | 0.60 | 0.77 | 0.84 | 0.24 |
| 222 | M222P | 1.90 | 0.34 | 0.59 | 0.29 | 0.09 |
| 222 | M222Q | 1.32 | 1.13 | 1.01 | *ND* | *0.05* |
| 222 | M222R | 2.15 | 0.14 | 0.10 | *ND* | *0.05* |
| 222 | M222S | 1.53 | 0.86 | 0.74 | 0.91 | 0.11 |
| 222 | M222T | 1.85 | 0.50 | 0.53 | 0.89 | 0.18 |
| 222 | M222V | 1.75 | 0.51 | 0.68 | 0.56 | 0.09 |
| 222 | M222W | 2.41 | 0.33 | 0.36 | *ND* | *0.05* |
| 222 | M222Y | 0.26 | *0.05* | 0.64 | *ND* | *0.05* |
| 223 | A223C | 1.25 | 0.37 | 0.76 | *0.05* | 0.21 |
| 223 | A223D | 0.46 | *0.05* | *0.05* | *ND* | *0.05* |
| 223 | A223F | 0.43 | *0.05* | *0.05* | *ND* | *0.05* |
| 223 | A223G | 1.11 | 1.17 | 1.12 | 0.09 | 0.98 |
| 223 | A223H | 0.48 | *0.05* | *0.05* | *ND* | *0.05* |
| 223 | A223I | 0.49 | *0.05* | *0.05* | *ND* | *0.05* |
| 223 | A223K | 0.40 | *0.05* | *0.05* | *ND* | *0.05* |
| 223 | A223L | 0.42 | *0.05* | *0.05* | *ND* | *0.05* |
| 223 | A223M | 0.48 | *0.05* | 1.05 | *ND* | *0.05* |
| 223 | A223N | 0.42 | *0.05* | 0.31 | *ND* | *0.05* |
| 223 | A223P | 0.52 | *0.05* | *0.05* | *ND* | *0.05* |
| 223 | A223Q | 0.43 | *0.05* | *0.05* | *ND* | *0.05* |
| 223 | A223R | 0.48 | *0.05* | *0.05* | *ND* | *0.05* |
| 223 | A223S | 1.35 | 0.84 | 0.98 | 0.97 | 1.09 |
| 223 | A223T | 0.40 | *0.05* | 0.90 | *0.05* | 0.18 |
| 223 | A223V | 0.22 | *0.05* | *0.05* | *ND* | *0.05* |
| 223 | A223W | 0.44 | *0.05* | *0.05* | *ND* | *0.05* |
| 223 | A223Y | 0.35 | *0.05* | *0.05* | *ND* | *0.05* |
| 224 | T224A | 1.41 | 0.88 | 0.93 | 1.01 | 2.56 |
| 224 | T224D | 0.32 | *0.05* | 1.86 | *0.05* | 0.25 |
| 224 | T224E | 0.54 | *0.05* | 1.15 | *ND* | *0.05* |
| 224 | T224F | 0.51 | *0.05* | *0.05* | *ND* | *0.05* |
| 224 | T224G | 0.89 | 1.72 | 1.21 | 0.41 | 0.87 |
| 224 | T224H | 0.38 | *0.05* | *0.05* | *ND* | *0.05* |
| 224 | T224I | 1.23 | 0.09 | 0.67 | *0.05* | 0.09 |
| 224 | T224K | 0.39 | *0.05* | *0.05* | *ND* | *0.05* |
| 224 | T224L | 1.09 | 1.05 | 1.03 | 0.08 | 0.59 |
| 224 | T224M | 0.63 | *0.05* | 0.80 | *ND* | *0.05* |
| 224 | T224N | 1.52 | 0.87 | 0.90 | 0.84 | 1.56 |
| 224 | T224P | 2.00 | *0.05* | 0.41 | 0.37 | 0.08 |
| 224 | T224Q | 0.49 | *0.05* | *0.05* | *ND* | *0.05* |
| 224 | T224R | 0.36 | *0.05* | *0.05* | *ND* | *0.05* |
| 224 | T224S | 1.15 | 1.15 | 1.04 | 1.10 | 1.90 |
| 224 | T224W | 0.39 | *0.05* | *0.05* | *ND* | *0.05* |
| 224 | T224Y | 0.31 | *0.05* | *0.05* | *ND* | *0.05* |
| 225 | P225A | 1.92 | 0.49 | 0.64 | 1.26 | 0.09 |
| 225 | P225C | 0.81 | 2.26 | 0.79 | 0.57 | 0.12 |
| 225 | P225E | 0.37 | *0.05* | *0.05* | *ND* | *0.05* |
| 225 | P225F | 0.42 | *0.05* | *0.05* | *ND* | *0.05* |
| 225 | P225G | 1.81 | 0.56 | 0.73 | *ND* | *0.05* |
| 225 | P225H | 0.41 | *0.05* | *0.05* | *ND* | *0.05* |
| 225 | P225I | 0.68 | *0.05* | 0.84 | *ND* | *0.05* |
| 225 | P225K | 0.41 | *0.05* | *0.05* | *ND* | *0.05* |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 225 | P225L | 0.36 | *0.05* | *0.05* | *ND* | *0.05* |
| 225 | P225M | 0.45 | *0.05* | *0.05* | *ND* | *0.05* |
| 225 | P225N | 1.14 | 0.30 | 0.40 | *ND* | *0.05* |
| 225 | P225Q | 0.38 | *0.05* | *0.05* | *ND* | *0.05* |
| 225 | P225R | 0.37 | *0.05* | *0.05* | *ND* | *0.05* |
| 225 | P225S | 1.76 | 0.57 | 0.67 | 0.99 | 0.08 |
| 225 | P225T | 1.32 | 0.73 | 0.65 | 0.18 | 0.17 |
| 225 | P225V | 1.39 | 0.62 | 0.69 | *ND* | *0.05* |
| 225 | P225W | 0.31 | *0.05* | *0.05* | *ND* | *0.05* |
| 225 | P225Y | 0.39 | *0.05* | *0.05* | *ND* | *0.05* |
| 226 | H226C | 0.91 | 1.50 | 1.05 | *0.05* | 0.94 |
| 226 | H226D | 0.14 | *0.05* | 0.60 | *ND* | *0.05* |
| 226 | H226F | 1.16 | 0.89 | 1.10 | *0.05* | 0.54 |
| 226 | H226G | 0.49 | *0.05* | 1.33 | *0.05* | 0.49 |
| 226 | H226I | 0.70 | 2.09 | 1.17 | *0.05* | 0.64 |
| 226 | H226K | 0.23 | *0.05* | 0.68 | *0.05* | 0.15 |
| 226 | H226L | 0.57 | 1.68 | 1.18 | *0.05* | 0.61 |
| 226 | H226M | 0.87 | 1.69 | 1.17 | *0.05* | 0.83 |
| 226 | H226N | 0.51 | *0.05* | 1.46 | *0.05* | 0.54 |
| 226 | H226P | 0.20 | *0.05* | *0.05* | *ND* | *0.05* |
| 226 | H226R | 0.19 | *0.05* | 1.16 | *0.05* | 0.14 |
| 226 | H226S | 0.78 | 1.83 | 1.36 | *0.05* | 0.72 |
| 226 | H226T | 0.47 | *0.05* | 1.34 | *0.05* | 0.47 |
| 226 | H226V | 0.86 | 1.33 | 1.02 | *0.05* | 1.01 |
| 226 | H226W | 0.17 | *0.05* | *0.05* | *ND* | *0.05* |
| 226 | H226Y | 0.71 | 2.12 | 1.18 | *0.05* | 0.32 |
| 227 | V227A | 1.15 | 1.15 | 1.06 | 0.91 | 1.23 |
| 227 | V227C | 0.88 | 1.63 | 1.36 | 0.95 | 1.08 |
| 227 | V227E | 0.31 | *0.05* | *0.05* | *ND* | *0.05* |
| 227 | V227F | 0.56 | *0.05* | 1.39 | *0.05* | 0.48 |
| 227 | V227G | 1.08 | 0.67 | 1.03 | 0.79 | 0.97 |
| 227 | V227H | 0.25 | *0.05* | *0.05* | *ND* | *0.05* |
| 227 | V227I | 1.17 | 1.12 | 1.12 | 0.70 | 1.46 |
| 227 | V227L | 1.22 | 1.07 | 1.04 | 0.26 | 1.30 |
| 227 | V227M | 1.53 | 0.78 | 0.88 | *0.05* | 1.63 |
| 227 | V227P | 0.21 | *0.05* | *0.05* | *ND* | *0.05* |
| 227 | V227Q | 0.18 | *0.05* | 1.02 | *ND* | *0.05* |
| 227 | V227R | 0.40 | *0.05* | *0.05* | *ND* | *0.05* |
| 227 | V227S | 1.15 | 1.00 | 0.90 | 0.33 | 1.22 |
| 227 | V227T | 1.55 | 0.60 | 0.78 | 0.44 | 1.80 |
| 227 | V227W | 0.29 | *0.05* | *0.05* | *ND* | *0.05* |
| 227 | V227Y | 0.16 | *0.05* | 1.27 | 0.06 | 0.09 |
| 228 | A228C | 0.76 | 33.67 | 1.52 | 0.89 | 1.06 |
| 228 | A228D | 0.37 | *0.05* | *0.05* | *ND* | *0.05* |
| 228 | A228E | 0.46 | *0.05* | *0.05* | *ND* | *0.05* |
| 228 | A228F | 0.37 | *0.05* | *0.05* | *ND* | *0.05* |
| 228 | A228G | 1.51 | 0.79 | 0.89 | 1.03 | 1.72 |
| 228 | A228H | 0.46 | *0.05* | *0.05* | *ND* | *0.05* |
| 228 | A228I | 1.86 | 0.59 | 0.70 | 0.64 | 2.03 |
| 228 | A228K | 0.50 | *0.05* | *0.05* | *ND* | *0.05* |
| 228 | A228L | 0.45 | *0.05* | 1.92 | 0.41 | 0.55 |
| 228 | A228M | 0.34 | *0.05* | 2.16 | *ND* | *0.05* |
| 228 | A228N | 0.23 | *0.05* | *0.05* | *ND* | *0.05* |
| 228 | A228P | 0.29 | *0.05* | *0.05* | *ND* | *0.05* |
| 228 | A228Q | 0.37 | *0.05* | *0.05* | *ND* | *0.05* |
| 228 | A228R | 0.45 | *0.05* | *0.05* | *ND* | *0.05* |
| 228 | A228S | 1.42 | 0.93 | 0.90 | 1.01 | 1.81 |
| 228 | A228V | 1.47 | 0.71 | 0.82 | 0.90 | 1.98 |
| 228 | A228Y | 0.47 | *0.05* | *0.05* | *ND* | *0.05* |
| 229 | G229A | 0.88 | 1.72 | 1.27 | 0.65 | 1.09 |
| 229 | G229C | 0.22 | *0.05* | *0.05* | *ND* | *0.05* |
| 229 | G229D | 0.41 | *0.05* | *0.05* | *ND* | *0.05* |
| 229 | G229E | 0.41 | *0.05* | *0.05* | *ND* | *0.05* |
| 229 | G229F | 0.46 | *0.05* | *0.05* | *ND* | *0.05* |
| 229 | G229H | 0.45 | *0.05* | *0.05* | *ND* | *0.05* |
| 229 | G229K | 0.42 | *0.05* | *0.05* | *ND* | *0.05* |
| 229 | G229L | 0.40 | *0.05* | *0.05* | *ND* | *0.05* |
| 229 | G229P | 0.22 | *0.05* | 2.34 | 0.96 | 0.21 |
| 229 | G229R | 0.54 | *0.05* | *0.05* | *ND* | *0.05* |
| 229 | G229S | 1.06 | 1.36 | 1.02 | 0.28 | 1.38 |
| 229 | G229T | 0.18 | *0.05* | *0.05* | *ND* | *0.05* |
| 229 | G229V | 0.29 | *0.05* | *0.05* | *ND* | *0.05* |
| 229 | G229W | 0.51 | *0.05* | *0.05* | *ND* | *0.05* |
| 229 | G229Y | 0.43 | *0.05* | *0.05* | *ND* | *0.05* |
| 230 | A230D | 1.23 | 0.88 | 1.03 | 0.45 | 1.30 |
| 230 | A230E | 1.08 | 1.44 | 1.15 | 0.42 | 1.35 |
| 230 | A230F | 0.22 | *0.05* | 2.16 | *0.05* | 0.20 |
| 230 | A230G | 1.46 | 0.66 | 0.92 | 1.01 | 1.67 |
| 230 | A230H | 1.14 | 1.19 | 1.18 | 0.32 | 1.16 |
| 230 | A230I | 1.02 | 1.20 | 1.04 | 0.64 | 1.23 |
| 230 | A230L | 0.97 | 1.45 | 1.19 | 0.26 | 1.21 |
| 230 | A230N | 1.84 | 0.64 | 0.76 | 0.93 | 1.81 |
| 230 | A230P | 0.80 | 4.61 | 1.39 | 0.20 | 0.62 |
| 230 | A230Q | 1.29 | 0.86 | 1.01 | *0.05* | 1.46 |
| 230 | A230R | 0.27 | *0.05* | *0.05* | *ND* | *0.05* |
| 230 | A230S | 0.98 | 1.57 | 1.25 | 0.93 | 1.30 |
| 230 | A230T | 0.86 | 2.87 | 1.31 | 0.92 | 1.06 |
| 230 | A230V | 0.97 | 1.62 | 1.25 | 0.82 | 1.14 |
| 230 | A230W | 0.28 | *0.05* | 1.29 | *0.05* | 0.21 |
| 230 | A230Y | 0.19 | *0.05* | 2.62 | 0.16 | 0.19 |
| 231 | A231C | 1.01 | 1.48 | 1.21 | 0.82 | 1.19 |
| 231 | A231D | 0.45 | *0.05* | *0.05* | *ND* | *0.05* |
| 231 | A231E | 0.37 | *0.05* | *0.05* | *ND* | *0.05* |
| 231 | A231F | 1.90 | 1.07 | 0.84 | 0.80 | 1.88 |
| 231 | A231G | 1.43 | 0.85 | 0.96 | 1.02 | 1.67 |
| 231 | A231H | 0.21 | *0.05* | 1.13 | 0.91 | 0.12 |
| 231 | A231I | 1.76 | 1.01 | 0.86 | 0.71 | 1.40 |
| 231 | A231K | 0.50 | *0.05* | *0.05* | *ND* | *0.05* |
| 231 | A231L | 2.24 | 0.84 | 0.74 | 0.53 | 1.55 |
| 231 | A231P | 0.37 | *0.05* | *0.05* | *ND* | *0.05* |
| 231 | A231Q | 0.29 | *0.05* | *0.05* | *ND* | *0.05* |
| 231 | A231R | 0.42 | *0.05* | *0.05* | *ND* | *0.05* |
| 231 | A231S | 1.83 | 0.90 | 0.86 | 0.81 | 2.21 |
| 231 | A231T | 1.63 | 1.07 | 0.91 | 0.63 | 1.79 |
| 231 | A231W | 0.18 | *0.05* | 1.48 | 0.19 | 0.08 |
| 231 | A231Y | 1.71 | 0.86 | 0.85 | 0.62 | 1.80 |
| 232 | A232C | 0.41 | *0.05* | *0.05* | *ND* | *0.05* |
| 232 | A232G | 0.42 | *0.05* | 1.48 | 0.98 | 0.51 |
| 232 | A232H | 0.56 | *0.05* | 1.19 | 0.83 | 0.59 |
| 232 | A232K | 0.17 | *0.05* | 0.59 | *ND* | *0.05* |
| 232 | A232L | 0.98 | 1.33 | 1.17 | 0.97 | 1.22 |
| 232 | A232M | 1.24 | 1.15 | 1.05 | 1.01 | 1.36 |
| 232 | A232P | 0.23 | *0.05* | *0.05* | *ND* | *0.05* |
| 232 | A232S | 0.55 | *0.05* | 1.20 | 0.90 | 0.65 |
| 232 | A232V | 1.14 | 1.14 | 1.20 | 0.77 | 1.28 |
| 232 | A232Y | 0.19 | *0.05* | *0.05* | *ND* | *0.05* |
| 233 | L233A | 0.93 | 2.14 | 1.18 | 0.91 | 1.32 |
| 233 | L233C | 0.81 | 3.18 | 1.15 | 0.97 | 1.12 |
| 233 | L233E | 0.86 | 2.51 | 1.33 | 1.00 | 1.22 |
| 233 | L233F | 0.95 | 1.84 | 1.14 | 0.42 | 1.26 |
| 233 | L233G | 1.14 | 1.26 | 1.06 | 0.97 | 1.28 |
| 233 | L233I | 1.15 | 1.14 | 1.09 | 0.97 | 1.42 |
| 233 | L233M | 0.96 | 2.01 | 1.14 | 0.73 | 1.38 |
| 233 | L233N | 0.87 | 2.53 | 1.31 | 0.92 | 1.16 |
| 233 | L233P | 0.19 | *0.05* | 1.85 | 0.90 | 0.14 |
| 233 | L233Q | 1.07 | 1.37 | 1.14 | 0.97 | 1.36 |
| 233 | L233R | 0.17 | *0.05* | 2.14 | *ND* | *0.05* |
| 233 | L233S | 0.99 | 1.73 | 1.15 | 0.95 | 1.27 |
| 233 | L233T | 1.06 | 1.31 | 1.12 | 1.00 | 1.23 |
| 233 | L233V | 1.07 | 1.33 | 1.11 | 0.98 | 1.36 |
| 233 | L233W | 0.59 | *0.05* | *0.05* | *ND* | *0.05* |
| 233 | L233Y | 0.67 | 14.92 | 1.58 | 0.90 | 0.95 |
| 234 | V234D | 0.53 | *0.05* | 1.52 | 0.93 | 0.66 |
| 234 | V234F | 1.36 | 0.97 | 0.91 | 0.56 | 1.77 |
| 234 | V234G | 0.61 | *0.05* | 1.43 | 0.97 | 0.74 |
| 234 | V234H | 1.33 | 0.92 | 0.95 | 0.51 | 1.50 |
| 234 | V234L | 1.19 | 1.25 | 1.05 | 1.14 | 1.23 |
| 234 | V234M | 1.08 | 1.21 | 1.06 | 0.92 | 1.18 |
| 234 | V234N | 1.15 | 0.97 | 1.00 | 0.90 | 1.57 |
| 234 | V234P | 0.32 | *0.05* | 2.03 | 0.74 | 0.40 |
| 234 | V234Q | 1.76 | 0.71 | 0.74 | 0.92 | 1.88 |
| 234 | V234S | 1.20 | 1.10 | 1.07 | 0.91 | 1.43 |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 234 | V234T | 1.05 | 1.32 | 1.12 | 0.95 | 1.39 |
| 234 | V234Y | 1.67 | 0.86 | 0.82 | 0.47 | 1.73 |
| 235 | K235C | 1.24 | 1.11 | 1.04 | 0.97 | 1.63 |
| 235 | K235D | 0.26 | *0.05* | 1.32 | 1.12 | 0.15 |
| 235 | K235E | 0.69 | 7.13 | 1.34 | 1.07 | 0.80 |
| 235 | K235F | 1.50 | 1.05 | 1.11 | 1.05 | 1.76 |
| 235 | K235G | 1.65 | 0.95 | 0.98 | 0.85 | 2.12 |
| 235 | K235H | 1.22 | 1.25 | 1.09 | 1.06 | 1.44 |
| 235 | K235I | 1.05 | 1.62 | 1.23 | 1.01 | 1.37 |
| 235 | K235L | 1.21 | 1.00 | 1.13 | 1.10 | 1.39 |
| 235 | K235M | 1.47 | 1.01 | 1.02 | 0.91 | 1.58 |
| 235 | K235N | 1.69 | 0.76 | 1.05 | 1.02 | 2.05 |
| 235 | K235Q | 1.22 | 1.13 | 1.06 | 1.14 | 1.41 |
| 235 | K235R | 1.19 | 1.24 | 1.11 | 0.96 | 1.39 |
| 235 | K235S | 1.56 | 0.91 | 1.06 | 1.04 | 1.65 |
| 235 | K235V | 1.59 | 0.97 | 1.02 | 0.98 | 2.22 |
| 235 | K235W | 1.41 | 1.06 | 1.06 | 0.94 | 1.63 |
| 235 | K235Y | 1.77 | 0.74 | 1.00 | 0.97 | 1.94 |
| 236 | Q236A | 1.02 | 1.33 | 1.16 | 0.85 | 1.19 |
| 236 | Q236C | 0.87 | 2.36 | 1.37 | 0.89 | 1.14 |
| 236 | Q236E | 1.00 | 1.36 | 1.41 | 1.25 | 1.14 |
| 236 | Q236F | 0.98 | 1.58 | 1.22 | 0.95 | 1.12 |
| 236 | Q236G | 0.78 | 6.07 | 1.53 | 0.77 | 0.93 |
| 236 | Q236H | 1.01 | 1.31 | 1.17 | 1.02 | 1.39 |
| 236 | Q236K | 1.12 | 1.20 | 0.95 | 0.69 | 1.39 |
| 236 | Q236L | 0.72 | 1.99 | 1.56 | 0.71 | 0.57 |
| 236 | Q236N | 1.04 | 1.13 | 1.24 | 0.95 | 1.24 |
| 236 | Q236P | 0.17 | *0.05* | 2.71 | 0.81 | 0.17 |
| 236 | Q236R | 1.05 | 1.26 | 1.01 | 0.69 | 1.28 |
| 236 | Q236S | 0.89 | 2.14 | 1.28 | 0.86 | 1.03 |
| 236 | Q236T | 1.16 | 1.16 | 1.12 | 0.90 | 1.36 |
| 236 | Q236V | 0.45 | *0.05* | 2.14 | 0.92 | 0.62 |
| 236 | Q236W | 0.82 | 4.08 | 1.39 | 0.75 | 1.01 |
| 236 | Q236Y | 1.22 | 1.02 | 1.07 | 0.81 | 1.49 |
| 237 | K237A | 1.25 | 1.26 | 1.19 | 1.00 | 1.57 |
| 237 | K237C | 0.97 | 1.73 | 1.34 | 1.19 | 1.17 |
| 237 | K237D | 0.57 | *0.05* | *0.05* | ND | *0.05* |
| 237 | K237F | 1.19 | 1.25 | 1.13 | 0.92 | 1.58 |
| 237 | K237G | 1.25 | 0.83 | 1.03 | 1.11 | 1.45 |
| 237 | K237H | 1.28 | 1.02 | 1.09 | 1.18 | 1.45 |
| 237 | K237I | 1.23 | 1.05 | 1.13 | 1.11 | 1.53 |
| 237 | K237L | 1.27 | 1.14 | 1.17 | 1.12 | 1.46 |
| 237 | K237M | 1.11 | 1.04 | 1.07 | 1.03 | 1.42 |
| 237 | K237P | 0.36 | *0.05* | 1.60 | 0.93 | 0.42 |
| 237 | K237Q | 1.42 | 0.96 | 1.05 | 1.00 | 1.82 |
| 237 | K237R | 1.05 | 1.86 | 1.25 | 1.02 | 1.48 |
| 237 | K237S | 1.15 | 1.20 | 1.20 | 0.98 | 1.54 |
| 237 | K237T | 1.49 | 1.06 | 1.01 | 1.13 | 1.61 |
| 237 | K237V | 1.26 | 1.02 | 1.03 | 1.12 | 1.34 |
| 237 | K237W | 1.65 | 0.83 | 1.04 | 1.08 | 1.87 |
| 237 | K237Y | 1.17 | 1.05 | 1.19 | 0.99 | 1.43 |
| 238 | N238C | 1.24 | 1.08 | 1.13 | 1.12 | 1.45 |
| 238 | N238D | 1.23 | 1.03 | 1.04 | 1.02 | 1.51 |
| 238 | N238E | 1.14 | 1.31 | 1.02 | 1.09 | 1.35 |
| 238 | N238F | 1.26 | 1.16 | 1.10 | 1.02 | 1.56 |
| 238 | N238G | 1.05 | 1.36 | 1.21 | 0.94 | 1.33 |
| 238 | N238H | 1.17 | 1.08 | 0.99 | 1.01 | 1.37 |
| 238 | N238I | 1.47 | 1.01 | 0.95 | 1.10 | 1.75 |
| 238 | N238K | 1.47 | 0.95 | 0.89 | 0.99 | 1.60 |
| 238 | N238L | 1.59 | 0.89 | 0.98 | 1.11 | 1.68 |
| 238 | N238M | 1.03 | 1.17 | 1.11 | 0.92 | 1.28 |
| 238 | N238P | 0.28 | *0.05* | *0.05* | ND | *0.05* |
| 238 | N238Q | 1.29 | 0.94 | 1.03 | 0.94 | 1.50 |
| 238 | N238R | 1.10 | 1.14 | 1.06 | 0.90 | 1.34 |
| 238 | N238S | 1.15 | 1.34 | 1.02 | 0.91 | 1.33 |
| 238 | N238T | 1.32 | 1.04 | 1.06 | 1.03 | 1.33 |
| 238 | N238V | 0.94 | 1.62 | 1.02 | 0.96 | 1.15 |
| 238 | N238Y | 1.19 | 0.88 | 1.09 | 0.90 | 1.28 |
| 239 | P239C | 1.00 | 1.38 | 1.18 | 1.05 | 1.37 |
| 239 | P239D | 1.18 | 1.14 | 1.12 | 1.10 | 1.37 |
| 239 | P239F | 1.12 | 1.51 | 1.18 | 1.08 | 1.35 |
| 239 | P239G | 1.11 | 1.38 | 1.09 | 1.05 | 1.55 |
| 239 | P239H | 1.07 | 1.50 | 1.12 | 1.06 | 1.51 |
| 239 | P239I | 1.62 | 0.99 | 0.80 | *0.05* | 2.27 |
| 239 | P239K | 1.13 | 1.25 | 0.91 | 0.98 | 1.55 |
| 239 | P239L | 1.13 | 1.09 | 1.06 | 1.11 | 1.37 |
| 239 | P239M | 0.96 | 1.58 | 1.21 | 0.99 | 1.30 |
| 239 | P239N | 1.43 | 1.00 | 1.00 | 1.08 | 1.64 |
| 239 | P239Q | 1.53 | 0.93 | 0.99 | 1.04 | 1.61 |
| 239 | P239R | 0.99 | 1.78 | 0.96 | 1.03 | 1.13 |
| 239 | P239S | 1.06 | 1.34 | 1.18 | 1.00 | 1.28 |
| 239 | P239T | 1.11 | 1.29 | 1.10 | 1.00 | 1.32 |
| 239 | P239V | 1.04 | 1.45 | 1.09 | 1.05 | 1.21 |
| 239 | P239W | 0.94 | 1.48 | 1.25 | 0.97 | 1.15 |
| 239 | P239Y | 1.02 | 1.14 | 1.18 | 0.94 | 1.21 |
| 240 | S240A | 1.04 | 1.52 | 1.11 | 0.97 | 1.46 |
| 240 | S240C | 1.04 | 1.55 | 1.23 | 1.00 | 1.30 |
| 240 | S240E | 1.09 | 1.15 | 1.24 | 1.04 | 1.37 |
| 240 | S240F | 1.26 | 1.24 | 1.06 | 0.96 | 1.59 |
| 240 | S240I | 1.10 | 1.00 | 1.02 | 0.95 | 1.50 |
| 240 | S240K | 1.24 | 1.13 | 0.88 | 0.97 | 1.59 |
| 240 | S240L | 0.67 | 12.41 | 1.50 | 1.07 | 0.92 |
| 240 | S240M | 0.91 | 1.59 | 1.18 | 0.95 | 1.20 |
| 240 | S240N | 0.94 | 1.57 | 1.27 | 0.95 | 1.29 |
| 240 | S240Q | 1.03 | 1.06 | 1.17 | 1.00 | 1.32 |
| 240 | S240R | 1.02 | 1.23 | 0.97 | 0.87 | 1.31 |
| 240 | S240T | 1.06 | 1.29 | 0.91 | 0.93 | 1.35 |
| 240 | S240W | 1.18 | 1.02 | 1.01 | 0.97 | 1.41 |
| 240 | S240Y | 1.34 | 0.97 | 0.97 | 0.98 | 1.46 |
| 241 | W241A | 1.52 | 1.23 | 0.86 | 0.98 | 1.96 |
| 241 | W241C | 1.72 | 0.93 | 0.86 | 1.07 | 2.04 |
| 241 | W241D | 1.29 | 1.00 | 1.15 | 1.07 | 1.68 |
| 241 | W241E | 1.13 | 1.08 | 1.12 | 1.01 | 1.56 |
| 241 | W241F | 0.94 | 1.41 | 1.28 | 1.02 | 1.25 |
| 241 | W241G | 0.87 | 2.18 | 1.40 | 0.97 | 1.21 |
| 241 | W241H | 1.94 | 0.93 | 0.74 | 1.04 | 2.21 |
| 241 | W241I | 1.84 | 1.02 | 0.84 | 1.15 | 1.99 |
| 241 | W241K | 1.83 | 0.93 | 0.75 | 1.03 | 2.19 |
| 241 | W241L | 1.26 | 1.13 | 1.02 | 1.17 | 1.52 |
| 241 | W241M | 1.38 | 1.01 | 0.93 | 0.95 | 1.79 |
| 241 | W241N | 1.52 | 1.10 | 0.91 | 1.04 | 1.89 |
| 241 | W241P | 0.22 | *0.05* | 1.52 | 0.84 | 0.14 |
| 241 | W241Q | 1.59 | 0.96 | 0.87 | 1.03 | 2.06 |
| 241 | W241R | 1.55 | 1.05 | 0.78 | 0.96 | 1.80 |
| 241 | W241S | 1.55 | 1.13 | 0.87 | 0.91 | 2.00 |
| 241 | W241T | 1.14 | 1.24 | 1.14 | 1.05 | 1.47 |
| 241 | W241V | 1.95 | 0.79 | 0.75 | 1.06 | 2.07 |
| 241 | W241Y | 1.14 | 1.06 | 1.09 | 0.95 | 1.52 |
| 242 | S242A | 1.08 | 1.20 | 1.16 | 1.04 | 1.36 |
| 242 | S242C | 0.98 | 1.15 | 1.33 | 1.02 | 1.24 |
| 242 | S242D | 0.93 | 1.51 | 1.45 | 1.11 | 1.12 |
| 242 | S242F | 1.35 | 0.58 | 0.88 | 0.73 | 1.66 |
| 242 | S242G | 0.94 | 1.71 | 1.31 | 1.14 | 1.19 |
| 242 | S242H | 1.65 | 0.73 | 0.73 | 0.97 | 1.88 |
| 242 | S242I | 1.55 | 0.73 | 0.85 | 1.02 | 1.82 |
| 242 | S242L | 1.37 | 0.79 | 0.91 | 0.97 | 1.64 |
| 242 | S242M | 1.65 | 0.73 | 0.80 | 0.94 | 1.75 |
| 242 | S242P | 1.72 | 0.72 | 0.79 | 1.00 | 1.88 |
| 242 | S242Q | 1.32 | 0.90 | 0.98 | 1.04 | 1.45 |
| 242 | S242R | 1.29 | 0.90 | 0.86 | 0.63 | 1.42 |
| 242 | S242T | 0.93 | 1.70 | 1.30 | 0.88 | 1.28 |
| 242 | S242V | 1.49 | 0.80 | 0.88 | 0.98 | 1.62 |
| 242 | S242W | 1.14 | 0.91 | 0.99 | 0.65 | 1.22 |
| 243 | N243A | 0.60 | *0.05* | *0.05* | ND | *0.05* |
| 243 | N243C | 0.94 | 1.35 | 1.26 | 1.00 | 1.20 |
| 243 | N243D | 1.64 | 0.69 | 0.91 | 0.92 | 1.58 |
| 243 | N243E | 1.46 | 1.02 | 0.96 | 1.11 | 1.48 |
| 243 | N243F | 1.71 | 0.90 | 0.82 | 0.93 | 1.46 |
| 243 | N243G | 1.36 | 1.02 | 1.00 | 1.03 | 1.68 |
| 243 | N243H | 1.30 | 1.11 | 0.94 | 1.13 | 1.47 |
| 243 | N243I | 1.27 | 0.99 | 1.01 | 0.97 | 1.42 |
| 243 | N243K | 1.66 | 0.74 | 0.82 | 0.07 | 1.62 |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 243 | N243L | 1.21 | 1.42 | 1.06 | 0.90 | 1.51 |
| 243 | N243M | 1.14 | 1.28 | 1.06 | 0.99 | 1.48 |
| 243 | N243P | 1.63 | 0.90 | 0.78 | 0.96 | 2.05 |
| 243 | N243Q | 1.28 | 0.97 | 0.92 | 1.12 | 1.44 |
| 243 | N243R | 1.88 | 0.96 | 0.68 | 0.29 | 1.83 |
| 243 | N243S | 1.20 | 1.35 | 1.14 | 1.02 | 1.42 |
| 243 | N243T | 1.21 | 1.00 | 1.03 | 0.96 | 1.40 |
| 243 | N243V | 1.06 | 1.03 | 1.21 | 1.04 | 1.32 |
| 243 | N243W | 1.54 | 0.98 | 0.81 | 1.05 | 1.31 |
| 244 | V244A | 1.10 | 1.53 | 1.00 | 0.34 | 1.25 |
| 244 | V244D | 1.38 | 0.92 | 0.96 | 1.07 | 1.47 |
| 244 | V244E | 1.12 | 1.11 | 1.07 | 1.09 | 1.34 |
| 244 | V244F | 1.39 | 0.97 | 0.91 | 1.02 | 1.72 |
| 244 | V244H | 1.05 | 1.63 | 1.13 | 1.11 | 1.29 |
| 244 | V244I | 1.19 | 1.13 | 1.07 | 1.01 | 1.54 |
| 244 | V244L | 1.09 | 1.12 | 1.11 | 1.04 | 1.35 |
| 244 | V244M | 0.99 | 1.15 | 1.12 | 1.00 | 1.11 |
| 244 | V244N | 1.11 | 1.09 | 1.01 | 1.07 | 1.28 |
| 244 | V244P | 1.75 | 0.86 | 0.80 | 0.66 | 1.87 |
| 244 | V244Q | 0.99 | 1.05 | 1.15 | 1.01 | 1.28 |
| 244 | V244R | 1.08 | 1.14 | 0.88 | 0.63 | 1.31 |
| 244 | V244S | 1.34 | 1.13 | 0.87 | 0.89 | 1.71 |
| 244 | V244T | 1.16 | 1.11 | 1.05 | 1.09 | 1.24 |
| 244 | V244W | 1.13 | 0.80 | 0.97 | 0.97 | 1.29 |
| 244 | V244Y | 0.66 | 2.52 | 1.19 | 0.92 | 0.56 |
| 245 | Q245A | 1.26 | 1.15 | 1.04 | 0.95 | 1.81 |
| 245 | Q245C | 0.97 | 1.09 | 1.29 | 1.04 | 1.25 |
| 245 | Q245E | 1.25 | 1.02 | 1.01 | 1.03 | 1.61 |
| 245 | Q245G | 1.00 | 1.66 | 1.24 | 1.03 | 1.31 |
| 245 | Q245H | 1.23 | 1.02 | 0.99 | 1.10 | 1.58 |
| 245 | Q245K | 1.39 | 0.89 | 0.80 | 0.85 | 1.80 |
| 245 | Q245L | 1.11 | 1.05 | 1.08 | 1.14 | 1.28 |
| 245 | Q245P | 0.93 | 1.47 | 1.26 | 0.99 | 1.14 |
| 245 | Q245R | 1.24 | 1.08 | 0.84 | 0.76 | 1.62 |
| 245 | Q245S | 1.09 | 1.10 | 1.05 | 1.01 | 1.40 |
| 245 | Q245V | 1.15 | 0.98 | 0.99 | 0.92 | 1.59 |
| 245 | Q245W | 1.42 | 0.71 | 0.81 | 0.90 | 1.62 |
| 245 | Q245Y | 1.14 | 1.12 | 1.06 | 0.96 | 1.28 |
| 246 | I246A | 1.62 | 0.94 | 0.81 | 0.90 | 2.10 |
| 246 | I246C | 1.86 | 0.87 | 0.79 | 0.98 | 2.20 |
| 246 | I246E | 0.22 | *0.05* | 5.52 | 1.10 | 0.06 |
| 246 | I246F | 0.29 | *0.05* | 2.87 | 0.84 | 0.30 |
| 246 | I246G | 0.22 | *0.05* | 2.38 | 1.00 | 0.11 |
| 246 | I246H | 0.18 | *0.05* | 1.09 | 0.85 | 0.08 |
| 246 | I246L | 1.21 | 1.05 | 1.06 | 1.03 | 1.66 |
| 246 | I246M | 2.23 | 0.74 | 0.64 | 0.95 | 2.51 |
| 246 | I246N | 0.77 | 1.66 | 1.37 | 1.11 | 0.92 |
| 246 | I246P | 0.42 | *0.05* | 1.82 | *ND* | *0.05* |
| 246 | I246Q | 0.74 | 1.14 | 1.54 | 0.99 | 0.94 |
| 246 | I246R | 0.24 | *0.05* | 4.38 | *ND* | *0.05* |
| 246 | I246S | 0.74 | 3.01 | 1.38 | 0.96 | 0.92 |
| 246 | I246T | 2.16 | 0.72 | 0.74 | 0.99 | 2.45 |
| 246 | I246V | 1.33 | 0.94 | 1.04 | 0.90 | 1.97 |
| 246 | I246W | 0.35 | *0.05* | 2.29 | 1.02 | 0.47 |
| 246 | I246Y | 0.34 | *0.05* | 2.59 | 0.89 | 0.38 |
| 247 | R247A | 1.13 | 1.23 | 1.03 | 0.87 | 1.44 |
| 247 | R247C | 1.25 | 1.05 | 1.10 | 1.02 | 1.30 |
| 247 | R247D | 1.40 | 0.96 | 0.96 | 0.65 | 1.46 |
| 247 | R247E | 0.95 | 1.63 | 1.29 | 0.68 | 1.06 |
| 247 | R247F | 1.15 | 1.08 | 0.99 | 0.93 | 1.35 |
| 247 | R247G | 1.52 | 0.97 | 0.96 | 0.95 | 1.77 |
| 247 | R247H | 1.71 | 1.15 | 0.92 | 1.03 | 1.58 |
| 247 | R247I | 1.42 | 1.02 | 0.97 | 0.79 | 1.25 |
| 247 | R247K | 1.35 | 1.13 | 0.93 | 1.12 | 1.24 |
| 247 | R247L | 1.56 | 0.99 | 0.92 | 0.93 | 1.33 |
| 247 | R247M | 1.07 | 1.57 | 1.09 | 0.82 | 1.26 |
| 247 | R247N | 1.82 | 0.83 | 0.83 | 1.09 | 1.55 |
| 247 | R247P | 0.31 | *0.05* | 1.90 | 0.87 | 0.20 |
| 247 | R247Q | 1.65 | 0.88 | 0.81 | 0.78 | 1.65 |
| 247 | R247S | 1.20 | 1.58 | 1.07 | 0.91 | 1.28 |
| 247 | R247T | 0.97 | 1.78 | 1.26 | 0.88 | 0.93 |
| 247 | R247V | 1.01 | 1.15 | 1.13 | 0.90 | 0.95 |
| 247 | R247W | 0.96 | 1.02 | 1.27 | 0.87 | 1.04 |
| 247 | R247Y | 1.10 | 1.21 | 1.10 | 0.98 | 1.22 |
| 248 | N248C | 0.89 | 1.59 | 1.43 | 1.00 | 1.30 |
| 248 | N248D | 1.20 | 0.96 | 1.21 | 0.99 | 1.41 |
| 248 | N248E | 1.28 | 0.86 | 0.92 | 1.04 | 1.57 |
| 248 | N248G | 1.22 | 0.83 | 1.06 | 1.00 | 1.68 |
| 248 | N248H | 1.33 | 1.05 | 1.03 | 1.01 | 1.79 |
| 248 | N248I | 1.07 | 1.57 | 1.15 | 0.92 | 1.61 |
| 248 | N248K | 1.38 | 1.03 | 0.96 | 0.76 | 2.01 |
| 248 | N248L | 1.08 | 1.26 | 1.15 | 0.93 | 1.56 |
| 248 | N248M | 0.55 | *0.05* | 2.27 | *ND* | *0.05* |
| 248 | N248P | 1.21 | 0.72 | 1.04 | 0.95 | 1.57 |
| 248 | N248R | 1.39 | 0.98 | 0.79 | 0.87 | 1.79 |
| 248 | N248S | 1.50 | 0.99 | 0.94 | 0.98 | 2.10 |
| 248 | N248T | 1.28 | 1.02 | 1.03 | 1.03 | 1.76 |
| 248 | N248V | 1.11 | 1.46 | 1.02 | 0.95 | 1.68 |
| 248 | N248W | 1.22 | 1.06 | 1.06 | 0.77 | 1.74 |
| 248 | N248Y | 1.19 | 1.04 | 0.98 | 0.90 | 1.65 |
| 249 | H249A | 1.12 | 1.09 | 1.08 | 0.88 | 1.54 |
| 249 | H249D | 1.84 | 0.76 | 0.83 | 1.10 | 2.01 |
| 249 | H249E | 1.57 | 1.02 | 0.94 | 1.03 | 2.03 |
| 249 | H249F | 0.98 | 0.84 | 1.20 | 1.01 | 1.32 |
| 249 | H249G | 2.16 | 0.75 | 0.72 | 1.00 | 2.26 |
| 249 | H249I | 1.34 | 1.03 | 0.92 | 1.13 | 1.63 |
| 249 | H249K | 1.65 | 0.91 | 0.78 | 0.96 | 1.95 |
| 249 | H249L | 1.53 | 0.77 | 0.89 | 0.98 | 1.87 |
| 249 | H249M | 1.64 | 0.93 | 0.85 | 0.93 | 1.85 |
| 249 | H249N | 0.90 | 0.89 | 1.33 | 1.01 | 1.15 |
| 249 | H249P | 0.38 | *0.05* | *0.05* | *ND* | *0.05* |
| 249 | H249Q | 1.33 | 0.93 | 0.89 | 1.07 | 1.53 |
| 249 | H249R | 1.25 | 1.03 | 0.88 | 0.80 | 1.58 |
| 249 | H249S | 1.89 | 0.87 | 0.76 | 0.81 | 2.30 |
| 249 | H249T | 1.36 | 1.09 | 0.95 | 0.97 | 1.69 |
| 249 | H249V | 1.69 | 0.84 | 0.74 | 0.76 | 2.27 |
| 249 | H249W | 1.71 | 0.81 | 0.87 | 0.91 | 1.90 |
| 249 | H249Y | 1.44 | 0.97 | 0.91 | 0.90 | 1.82 |
| 250 | L250A | 0.45 | *0.05* | 2.21 | 0.87 | 0.67 |
| 250 | L250C | 1.57 | 0.99 | 0.78 | 0.95 | 2.04 |
| 250 | L250D | 0.50 | *0.05* | 0.62 | *ND* | *0.05* |
| 250 | L250E | 0.27 | *0.05* | 1.41 | *ND* | *0.05* |
| 250 | L250F | 1.17 | 0.89 | 1.09 | *0.05* | 1.30 |
| 250 | L250G | 0.32 | *0.05* | 3.73 | *ND* | *0.05* |
| 250 | L250H | 0.29 | *0.05* | 3.38 | *ND* | *0.05* |
| 250 | L250I | 1.33 | 1.05 | 1.03 | 0.93 | 1.86 |
| 250 | L250M | 1.47 | 0.92 | 0.94 | 0.98 | 1.76 |
| 250 | L250N | 0.32 | *0.05* | 3.47 | *ND* | *0.05* |
| 250 | L250P | 0.43 | *0.05* | *0.05* | *ND* | *0.05* |
| 250 | L250Q | 0.25 | *0.05* | 2.72 | 0.80 | 0.25 |
| 250 | L250R | 0.43 | *0.05* | *0.05* | *ND* | *0.05* |
| 250 | L250S | 0.23 | *0.05* | 1.96 | 0.89 | 0.10 |
| 250 | L250V | 0.81 | 1.45 | 1.42 | 0.82 | 1.06 |
| 250 | L250W | 0.24 | *0.05* | *0.05* | *ND* | *0.05* |
| 250 | L250Y | 0.19 | *0.05* | 4.27 | 0.10 | 0.07 |
| 251 | K251A | 1.16 | 1.15 | 1.08 | 0.86 | 1.41 |
| 251 | K251D | 1.10 | 1.13 | 0.96 | 1.05 | 1.41 |
| 251 | K251E | 1.18 | 1.01 | 1.01 | 1.06 | 1.29 |
| 251 | K251F | 1.55 | 0.84 | 0.89 | 0.98 | 1.58 |
| 251 | K251G | 1.74 | 1.03 | 0.99 | 0.94 | 2.15 |
| 251 | K251L | 1.16 | 0.91 | 1.07 | 1.17 | 1.24 |
| 251 | K251M | 0.96 | 1.03 | 1.35 | 1.14 | 1.04 |
| 251 | K251P | 0.37 | *0.05* | 1.80 | 0.48 | 0.30 |
| 251 | K251Q | 1.48 | 0.81 | 0.96 | 1.17 | 1.58 |
| 251 | K251R | 1.08 | 1.11 | 1.12 | 0.87 | 1.41 |
| 251 | K251S | 0.66 | *0.05* | 0.79 | 1.14 | 0.23 |
| 251 | K251T | 0.94 | 1.47 | 1.37 | 1.23 | 1.02 |
| 251 | K251V | 0.98 | 0.83 | 1.15 | 0.92 | 1.15 |
| 251 | K251Y | 1.31 | 0.94 | 1.08 | 0.96 | 1.37 |
| 252 | N252A | 1.23 | 1.15 | 1.02 | 1.01 | 1.61 |
| 252 | N252C | 0.91 | 1.34 | 1.29 | 1.12 | 1.16 |
| 252 | N252D | 1.12 | 0.85 | 1.09 | 1.19 | 1.34 |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 252 | N252F | 1.18 | 1.25 | 0.85 | 1.10 | 1.46 |
| 252 | N252G | 1.10 | 1.17 | 0.89 | 1.03 | 1.66 |
| 252 | N252H | 1.21 | 1.19 | 1.02 | 1.02 | 1.62 |
| 252 | N252I | 1.19 | 1.43 | 0.89 | 1.24 | 1.50 |
| 252 | N252K | 1.47 | 1.08 | 0.88 | 0.92 | 1.92 |
| 252 | N252L | 1.31 | 1.22 | 0.99 | 1.17 | 1.66 |
| 252 | N252M | 1.12 | 1.19 | 1.00 | 0.90 | 1.64 |
| 252 | N252P | 0.56 | *0.05* | 1.26 | *0.05* | 0.57 |
| 252 | N252R | 1.19 | 1.15 | 0.85 | 0.87 | 1.64 |
| 252 | N252S | 1.12 | 1.10 | 0.89 | 1.11 | 1.34 |
| 252 | N252V | 0.98 | 1.03 | 0.92 | 1.00 | 1.34 |
| 252 | N252W | 1.18 | 1.04 | 0.81 | 0.91 | 1.56 |
| 252 | N252Y | 0.49 | *0.05* | 1.65 | 1.05 | 0.63 |
| 253 | T253A | 1.13 | 1.28 | 1.20 | 0.84 | 1.50 |
| 253 | T253D | 1.13 | 0.67 | 0.93 | 0.39 | 1.17 |
| 253 | T253E | 1.33 | 0.61 | 1.04 | 1.00 | 1.64 |
| 253 | T253F | 0.91 | 1.45 | 1.25 | 0.74 | 1.27 |
| 253 | T253G | 1.78 | 0.88 | 0.78 | 0.61 | 1.86 |
| 253 | T253H | 1.55 | 0.85 | 0.84 | 0.91 | 1.79 |
| 253 | T253I | 1.05 | 0.92 | 1.01 | 0.21 | 1.16 |
| 253 | T253K | 1.51 | 0.76 | 0.84 | 0.74 | 1.93 |
| 253 | T253M | 0.99 | 1.33 | 0.97 | 0.91 | 1.28 |
| 253 | T253P | 0.15 | *0.05* | *0.05* | ND | *0.05* |
| 253 | T253R | 1.32 | 1.00 | 0.81 | 0.60 | 1.69 |
| 253 | T253S | 1.40 | 0.95 | 0.90 | 0.84 | 1.91 |
| 253 | T253V | 1.17 | 1.01 | 0.84 | 0.60 | 1.34 |
| 253 | T253W | 1.24 | 0.77 | 1.01 | 0.83 | 1.40 |
| 254 | A254C | 0.81 | 8.81 | 1.48 | 0.69 | 1.16 |
| 254 | A254D | 0.20 | *0.05* | 1.90 | 0.80 | 0.17 |
| 254 | A254E | 0.81 | 0.53 | *0.05* | ND | *0.05* |
| 254 | A254F | 0.14 | *0.05* | *0.05* | ND | *0.05* |
| 254 | A254G | 1.02 | 1.02 | 1.08 | 0.40 | 1.22 |
| 254 | A254H | 0.11 | *0.05* | *0.05* | ND | *0.05* |
| 254 | A254K | 0.15 | *0.05* | *0.05* | *0.05* | 0.13 |
| 254 | A254L | 0.11 | *0.05* | *0.05* | ND | *0.05* |
| 254 | A254M | 0.13 | *0.05* | *0.05* | ND | *0.05* |
| 254 | A254N | 0.29 | *0.05* | 1.84 | *0.05* | 0.29 |
| 254 | A254P | 0.28 | *0.05* | 2.02 | *0.05* | 0.24 |
| 254 | A254Q | 0.13 | *0.05* | *0.05* | *0.05* | 0.07 |
| 254 | A254R | 0.18 | *0.05* | *0.05* | *0.05* | 0.19 |
| 254 | A254S | 1.20 | 1.12 | 0.99 | 0.79 | 1.66 |
| 254 | A254T | 0.97 | 1.59 | 1.23 | 0.39 | 1.37 |
| 254 | A254V | 0.71 | *0.05* | 1.56 | *0.05* | 0.90 |
| 254 | A254W | 0.10 | *0.05* | *0.05* | ND | *0.05* |
| 254 | A254Y | 0.11 | *0.05* | *0.05* | ND | *0.05* |
| 255 | T255A | 1.44 | 0.88 | 0.98 | 0.81 | 1.85 |
| 255 | T255C | 1.37 | 0.89 | 1.01 | 1.04 | 1.84 |
| 255 | T255D | 1.58 | 0.88 | 0.99 | 1.31 | 2.04 |
| 255 | T255E | 1.59 | 0.84 | 0.95 | 1.29 | 1.87 |
| 255 | T255F | 1.28 | 1.13 | 1.05 | 0.78 | 1.75 |
| 255 | T255G | 0.20 | *0.05* | *0.05* | ND | *0.05* |
| 255 | T255H | 1.40 | 0.93 | 0.98 | *0.05* | 1.85 |
| 255 | T255I | 1.71 | 0.93 | 0.85 | 1.09 | 2.21 |
| 255 | T255L | 1.46 | 1.05 | 0.89 | 1.00 | 1.89 |
| 255 | T255N | 1.51 | 1.22 | 0.92 | 0.88 | 2.03 |
| 255 | T255P | 1.57 | 0.92 | 0.80 | 0.13 | 2.11 |
| 255 | T255Q | 1.67 | 0.85 | 0.81 | 0.99 | 2.11 |
| 255 | T255R | 1.58 | 1.02 | 0.63 | *0.05* | 2.13 |
| 255 | T255S | 1.24 | 1.08 | 1.03 | 0.75 | 1.81 |
| 255 | T255V | 1.54 | 0.94 | 0.92 | 1.02 | 1.96 |
| 255 | T255W | 1.65 | 0.90 | 0.77 | 0.52 | 2.13 |
| 255 | T255Y | 1.54 | 0.89 | 0.88 | 0.81 | 1.93 |
| 256 | S256A | 0.89 | 1.75 | 1.13 | 1.05 | 1.15 |
| 256 | S256C | 1.12 | 1.09 | 0.89 | 1.06 | 1.39 |
| 256 | S256D | 1.24 | 1.07 | 1.15 | 1.15 | 1.58 |
| 256 | S256E | 1.28 | 0.92 | 1.06 | 1.13 | 1.48 |
| 256 | S256G | 0.94 | 1.06 | 1.22 | 0.98 | 1.09 |
| 256 | S256H | 1.16 | 1.14 | 0.96 | 1.03 | 1.34 |
| 256 | S256I | 1.16 | 1.02 | 0.92 | 0.91 | 1.53 |
| 256 | S256K | 1.46 | 0.94 | 0.76 | 0.80 | 1.71 |
| 256 | S256L | 1.20 | 1.00 | 0.86 | 0.93 | 1.42 |
| 256 | S256M | 0.99 | 1.23 | 1.15 | 0.91 | 1.26 |
| 256 | S256N | 0.99 | 1.46 | 1.09 | 1.07 | 1.21 |
| 256 | S256P | 1.26 | 1.09 | 0.94 | 0.93 | 1.59 |
| 256 | S256R | 1.37 | 0.99 | 0.73 | 0.60 | 1.76 |
| 256 | S256T | 0.92 | 1.75 | 1.40 | 0.76 | 1.32 |
| 256 | S256V | 0.91 | 1.43 | 1.31 | 0.82 | 1.24 |
| 256 | S256W | 1.09 | 1.09 | 0.93 | 0.91 | 1.15 |
| 256 | S256Y | 1.02 | 1.22 | 0.88 | 0.90 | 1.19 |
| 257 | L257A | 0.80 | 2.90 | 1.28 | *0.05* | 1.06 |
| 257 | L257C | 0.89 | 1.29 | 1.32 | 0.57 | 0.96 |
| 257 | L257E | 0.26 | *0.05* | 2.35 | *0.05* | 0.33 |
| 257 | L257F | 0.92 | 1.42 | 1.17 | *0.05* | 1.04 |
| 257 | L257G | 0.55 | *0.05* | 1.48 | *0.05* | 0.73 |
| 257 | L257H | 0.61 | *0.05* | 1.56 | *0.05* | 0.79 |
| 257 | L257I | 1.38 | 0.96 | 0.82 | 0.77 | 1.59 |
| 257 | L257K | 0.92 | 2.29 | 0.98 | *0.05* | 1.33 |
| 257 | L257M | 1.02 | 1.11 | 1.03 | 0.64 | 1.29 |
| 257 | L257P | 0.42 | *0.05* | 1.82 | *0.05* | 0.50 |
| 257 | L257S | 0.50 | *0.05* | 1.76 | *0.05* | 0.69 |
| 257 | L257T | 0.60 | *0.05* | 1.65 | *0.05* | 0.83 |
| 257 | L257V | 0.95 | 1.32 | 1.29 | 0.43 | 1.28 |
| 257 | L257W | 0.46 | *0.05* | 1.58 | *0.05* | 0.57 |
| 257 | L257Y | 0.60 | *0.05* | 1.38 | *0.05* | 0.82 |
| 258 | G258A | 1.04 | 1.01 | 1.11 | 0.26 | 1.25 |
| 258 | G258C | 1.01 | 0.92 | 1.17 | 0.60 | 1.24 |
| 258 | G258D | 1.02 | 0.99 | 1.33 | 0.93 | 1.28 |
| 258 | G258E | 0.79 | 1.18 | 1.52 | 0.90 | 0.99 |
| 258 | G258F | 1.23 | 0.90 | 0.95 | *0.05* | 1.40 |
| 258 | G258H | 1.27 | 0.83 | 0.97 | 0.28 | 1.45 |
| 258 | G258I | 0.85 | 1.11 | 1.27 | 0.08 | 0.97 |
| 258 | G258L | 0.95 | 1.08 | 1.14 | 0.08 | 1.35 |
| 258 | G258M | 1.09 | 0.91 | 1.07 | 0.16 | 1.20 |
| 258 | G258P | 0.99 | 0.81 | 1.19 | *0.05* | 1.11 |
| 258 | G258Q | 1.12 | 0.77 | 1.10 | 0.34 | 1.40 |
| 258 | G258R | 1.15 | 1.07 | 0.86 | *0.05* | 1.31 |
| 258 | G258S | 1.25 | 1.21 | 1.00 | 0.28 | 1.49 |
| 258 | G258T | 0.90 | 1.07 | 1.16 | *0.05* | 1.14 |
| 258 | G258V | 0.85 | 1.03 | 1.32 | *0.05* | 0.96 |
| 258 | G258W | 0.88 | 1.31 | 1.02 | *0.05* | 1.02 |
| 258 | G258Y | 0.99 | 1.01 | 1.18 | 0.15 | 1.21 |
| 259 | S259A | 1.27 | 1.24 | 0.76 | 0.98 | 1.49 |
| 259 | S259C | 0.88 | 1.08 | 1.38 | 0.98 | 1.18 |
| 259 | S259E | 0.99 | 1.15 | 1.32 | 1.08 | 1.36 |
| 259 | S259G | 1.15 | 1.03 | 1.11 | 0.58 | 1.37 |
| 259 | S259I | 0.94 | 1.18 | 1.12 | 0.41 | 1.16 |
| 259 | S259L | 0.81 | 1.65 | 1.26 | 0.41 | 1.21 |
| 259 | S259M | 0.88 | 1.47 | 1.17 | 0.52 | 1.11 |
| 259 | S259P | 0.96 | 1.53 | 1.33 | 1.00 | 1.40 |
| 259 | S259Q | 0.92 | 1.76 | 1.22 | 0.87 | 1.15 |
| 259 | S259R | 0.97 | 1.64 | 0.83 | 0.26 | 1.29 |
| 259 | S259T | 0.98 | 1.25 | 1.19 | 0.75 | 1.25 |
| 259 | S259V | 1.05 | 1.07 | 1.18 | 0.45 | 1.30 |
| 260 | T260A | 1.52 | 1.06 | 0.98 | 0.88 | 1.66 |
| 260 | T260D | 0.89 | 1.30 | 1.45 | 1.01 | 1.11 |
| 260 | T260E | 0.93 | 1.15 | 1.26 | 1.11 | 1.11 |
| 260 | T260F | 1.03 | 1.22 | 1.05 | 0.47 | 1.29 |
| 260 | T260H | 1.37 | 1.19 | 0.90 | 0.81 | 1.79 |
| 260 | T260I | 1.23 | 1.27 | 1.09 | 0.95 | 1.42 |
| 260 | T260L | 1.36 | 1.09 | 1.09 | 0.54 | 1.59 |
| 260 | T260M | 1.30 | 1.17 | 1.14 | 0.77 | 1.59 |
| 260 | T260N | 1.29 | 0.99 | 1.00 | 0.94 | 1.73 |
| 260 | T260P | 1.32 | 1.01 | 1.11 | 1.15 | 1.53 |
| 260 | T260R | 1.19 | 1.25 | 0.89 | 0.60 | 1.65 |
| 260 | T260S | 1.07 | 1.34 | 1.19 | 0.94 | 1.38 |
| 260 | T260V | 0.97 | 1.32 | 1.06 | 0.93 | 1.24 |
| 260 | T260Y | 1.07 | 0.89 | 0.99 | 0.76 | 1.30 |
| 261 | N261A | 1.26 | 1.33 | 1.04 | 0.98 | 1.70 |
| 261 | N261C | 0.93 | 1.06 | 1.38 | 1.15 | 1.12 |
| 261 | N261E | 1.01 | 1.10 | 1.34 | 1.11 | 1.33 |
| 261 | N261F | 1.05 | 1.13 | 1.05 | 1.08 | 1.41 |
| 261 | N261G | 1.42 | 0.76 | 0.92 | 0.73 | 1.70 |

TABLE 4-1-continued

Performance Index (PI) Values for Variants of GCI-P036 for Various Tested Properties.

| POSITION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 261 | N261I | 1.37 | 1.10 | 0.99 | 1.14 | 1.72 |
| 261 | N261K | 1.59 | 1.05 | 0.80 | 0.88 | 1.91 |
| 261 | N261L | 1.34 | 1.01 | 1.00 | 1.27 | 1.44 |
| 261 | N261P | 1.40 | 0.96 | 1.04 | 0.97 | 1.70 |
| 261 | N261Q | 1.13 | 1.17 | 1.06 | 1.11 | 1.35 |
| 261 | N261R | 1.26 | 1.05 | 0.75 | 0.78 | 1.71 |
| 261 | N261S | 1.32 | 1.06 | 1.06 | 1.00 | 1.53 |
| 261 | N261T | 0.91 | 1.44 | 1.06 | 1.09 | 1.23 |
| 261 | N261V | 0.96 | 1.27 | 1.08 | 1.14 | 1.23 |
| 261 | N261W | 1.15 | 1.02 | 0.89 | 1.16 | 1.42 |
| 261 | N261Y | 0.97 | 1.19 | 0.95 | 1.18 | 1.13 |
| 262 | L262A | 1.24 | 1.31 | 1.02 | 0.85 | 1.66 |
| 262 | L262C | 1.22 | 0.90 | 1.16 | 1.04 | 1.60 |
| 262 | L262D | 1.07 | 1.09 | 1.33 | 1.20 | 1.38 |
| 262 | L262F | 1.21 | 1.12 | 1.05 | 1.03 | 1.60 |
| 262 | L262G | 0.99 | 0.89 | 1.06 | 0.39 | 1.31 |
| 262 | L262H | 1.34 | 0.98 | 0.96 | 1.21 | 1.60 |
| 262 | L262I | 1.40 | 1.00 | 0.97 | 1.06 | 1.78 |
| 262 | L262K | 1.32 | 0.99 | 0.72 | 0.62 | 1.67 |
| 262 | L262M | 1.42 | 1.05 | 0.96 | 0.99 | 1.80 |
| 262 | L262P | 0.62 | *0.05* | 1.53 | 0.06 | 0.86 |
| 262 | L262Q | 1.19 | 1.05 | 1.00 | 1.09 | 1.46 |
| 262 | L262R | 1.29 | 1.11 | 0.62 | 0.19 | 1.47 |
| 262 | L262S | 1.14 | 1.16 | 1.04 | 0.75 | 1.52 |
| 262 | L262T | 1.05 | 1.18 | 1.19 | 0.85 | 1.31 |
| 262 | L262V | 1.10 | 1.32 | 1.06 | 0.91 | 1.52 |
| 262 | L262W | 1.10 | 1.08 | 1.11 | 0.72 | 1.36 |
| 262 | L262Y | 1.16 | 1.13 | 1.04 | 0.90 | 1.63 |
| 263 | Y263A | 0.64 | 19.07 | 1.22 | *0.05* | 0.89 |
| 263 | Y263C | 0.84 | 0.62 | 1.19 | 0.38 | 0.85 |
| 263 | Y263D | 0.32 | *0.05* | 1.75 | *0.05* | 0.19 |
| 263 | Y263F | 1.35 | 1.10 | 1.13 | 0.69 | 1.84 |
| 263 | Y263G | 0.26 | *0.05* | 1.31 | *0.05* | 0.18 |
| 263 | Y263H | 0.71 | 4.21 | 1.15 | 0.48 | 0.98 |
| 263 | Y263I | 0.53 | *0.05* | 1.31 | *0.05* | 0.67 |
| 263 | Y263K | 0.54 | *0.05* | 0.84 | *0.05* | 0.60 |
| 263 | Y263L | 0.84 | 2.05 | 1.28 | 0.06 | 1.20 |
| 263 | Y263M | 0.53 | *0.05* | 1.44 | 0.13 | 0.63 |
| 263 | Y263N | 0.59 | 1.27 | 1.42 | 0.09 | 0.86 |
| 263 | Y263P | 0.33 | *0.05* | 1.27 | 0.07 | 0.09 |
| 263 | Y263Q | 0.36 | *0.05* | 1.68 | *0.05* | 0.43 |
| 263 | Y263R | 0.30 | *0.05* | 1.00 | *0.05* | 0.25 |
| 263 | Y263W | 0.45 | *0.05* | 1.36 | *0.05* | 0.44 |
| 264 | G264A | 0.92 | 1.99 | 1.10 | *0.05* | 1.18 |
| 264 | G264C | 0.27 | *0.05* | 2.39 | 0.06 | 0.22 |
| 264 | G264E | 0.28 | *0.05* | 1.97 | *0.05* | 0.07 |
| 264 | G264F | 0.21 | *0.05* | 1.36 | 0.06 | 0.08 |
| 264 | G264H | 0.15 | *0.05* | 1.36 | 0.13 | 0.06 |
| 264 | G264I | 0.21 | *0.05* | 1.07 | ND | *0.05* |
| 264 | G264L | 0.22 | *0.05* | 0.98 | 0.07 | 0.06 |
| 264 | G264P | 0.24 | *0.05* | 1.06 | *0.05* | 0.09 |
| 264 | G264Q | 0.22 | *0.05* | 1.38 | 0.08 | 0.07 |
| 264 | G264R | 0.15 | *0.05* | *0.05* | 0.10 | 0.06 |
| 264 | G264S | 0.62 | *0.05* | 1.47 | *0.05* | 0.74 |
| 264 | G264T | 0.22 | *0.05* | 0.96 | 0.18 | 0.07 |
| 264 | G264V | 0.22 | *0.05* | 1.10 | ND | *0.05* |
| 264 | G264Y | 0.24 | *0.05* | 1.16 | 0.09 | 0.06 |
| 265 | S265A | 1.21 | 1.49 | 1.05 | 0.86 | 1.65 |
| 265 | S265C | 0.79 | 1.85 | 1.22 | 0.99 | 1.06 |
| 265 | S265D | 1.02 | 1.07 | 1.17 | 1.04 | 1.16 |
| 265 | S265F | 1.02 | 1.32 | 1.09 | 0.26 | 1.25 |
| 265 | S265G | 0.94 | 1.76 | 1.05 | 0.31 | 1.22 |
| 265 | S265H | 1.11 | 1.17 | 1.07 | 0.73 | 1.59 |
| 265 | S265I | 0.34 | *0.05* | 1.45 | *0.05* | 0.33 |
| 265 | S265K | 1.46 | 1.12 | 0.83 | 0.16 | 2.00 |
| 265 | S265L | 0.77 | 3.33 | 1.18 | *0.05* | 0.90 |
| 265 | S265M | 1.02 | 1.45 | 1.16 | 0.55 | 1.42 |
| 265 | S265N | 0.37 | *0.05* | *0.05* | ND | *0.05* |
| 265 | S265P | 0.26 | *0.05* | 1.23 | *0.05* | 0.16 |
| 265 | S265Q | 1.06 | 1.00 | 1.20 | 0.79 | 1.26 |
| 265 | S265R | 1.03 | 1.99 | 0.86 | *0.05* | 1.56 |
| 265 | S265T | 0.87 | 2.15 | 1.20 | 0.39 | 1.26 |
| 265 | S265V | 0.75 | 4.75 | 1.34 | *0.05* | 0.97 |
| 265 | S265W | 0.93 | 1.08 | 1.29 | 0.31 | 1.17 |
| 265 | S265Y | 0.97 | 1.17 | 1.19 | 0.49 | 1.22 |
| 266 | G266A | 0.19 | *0.05* | 0.62 | ND | *0.05* |
| 266 | G266C | 0.25 | *0.05* | 0.72 | *0.05* | 0.09 |
| 266 | G266D | 0.24 | *0.05* | 0.78 | 0.08 | 0.07 |
| 266 | G266E | 0.22 | *0.05* | 0.55 | ND | *0.05* |
| 266 | G266H | 0.23 | *0.05* | 0.53 | 0.06 | 0.06 |
| 266 | G266I | 0.17 | *0.05* | *0.05* | *0.05* | 0.06 |
| 266 | G266K | 0.17 | *0.05* | 0.69 | 0.06 | 0.09 |
| 266 | G266L | 0.22 | *0.05* | 0.75 | *0.05* | 0.08 |
| 266 | G266M | 0.20 | *0.05* | *0.05* | ND | *0.05* |
| 266 | G266N | 0.21 | *0.05* | 0.59 | 0.12 | 0.06 |
| 266 | G266Q | 0.19 | *0.05* | 0.62 | ND | *0.05* |
| 266 | G266R | 0.18 | *0.05* | *0.05* | 0.06 | 0.09 |
| 266 | G266S | 0.20 | *0.05* | *0.05* | *0.05* | 0.06 |
| 266 | G266T | 0.11 | *0.05* | *0.05* | ND | *0.05* |
| 266 | G266V | 0.11 | *0.05* | *0.05* | *0.05* | 0.07 |
| 266 | G266W | 0.12 | *0.05* | 1.08 | *0.05* | 0.10 |
| 266 | G266Y | 0.13 | *0.05* | 0.95 | *0.05* | 0.10 |
| 267 | L267A | 0.77 | 3.80 | 1.43 | *0.05* | 1.03 |
| 267 | L267C | 0.55 | *0.05* | 1.63 | *0.05* | 0.75 |
| 267 | L267D | 0.20 | *0.05* | 1.41 | *0.05* | 0.12 |
| 267 | L267E | 0.15 | *0.05* | 2.22 | 0.16 | 0.16 |
| 267 | L267F | 0.70 | 0.89 | 1.47 | *0.05* | 0.87 |
| 267 | L267G | 0.85 | 2.17 | 1.08 | *0.05* | 1.18 |
| 267 | L267H | 0.65 | *0.05* | 1.29 | *0.05* | 0.88 |
| 267 | L267I | 1.32 | 1.05 | 0.96 | 0.90 | 1.54 |
| 267 | L267K | 0.76 | 1.17 | 1.21 | *0.05* | 1.24 |
| 267 | L267M | 0.87 | 2.12 | 1.22 | 0.58 | 1.12 |
| 267 | L267N | 0.92 | 1.55 | 1.08 | *0.05* | 1.37 |
| 267 | L267P | 0.19 | *0.05* | *0.05* | 0.09 | 0.06 |
| 267 | L267S | 0.58 | *0.05* | 1.74 | *0.05* | 0.85 |
| 267 | L267T | 0.46 | *0.05* | 1.81 | *0.05* | 0.63 |
| 267 | L267V | 0.94 | 1.50 | 0.93 | 0.08 | 1.26 |
| 267 | L267W | 0.17 | *0.05* | *0.05* | *0.05* | 0.24 |
| 267 | L267Y | 0.48 | *0.05* | 1.38 | *0.05* | 0.64 |
| 268 | V268A | 1.29 | 0.89 | 1.12 | 0.81 | 1.42 |
| 268 | V268D | 0.70 | *0.05* | 1.39 | 0.26 | 0.79 |
| 268 | V268E | 0.65 | *0.05* | 1.45 | 0.65 | 0.72 |
| 268 | V268G | 1.54 | 0.79 | 0.93 | 0.08 | 1.77 |
| 268 | V268H | 0.88 | 1.38 | 1.13 | *0.05* | 0.83 |
| 268 | V268K | 0.59 | *0.05* | 1.43 | 0.32 | 0.73 |
| 268 | V268L | 1.28 | 0.99 | 0.99 | 0.87 | 1.62 |
| 268 | V268M | 1.00 | 1.17 | 0.97 | 0.60 | 1.35 |
| 268 | V268N | 1.33 | 0.87 | 0.96 | 0.14 | 1.72 |
| 268 | V268P | 1.67 | 0.56 | 0.81 | 0.20 | 1.70 |
| 268 | V268Q | 1.39 | 0.89 | 0.93 | 0.35 | 1.69 |
| 268 | V268R | 0.33 | *0.05* | 2.81 | ND | *0.05* |
| 268 | V268S | 1.18 | 0.92 | 0.94 | 0.33 | 1.47 |
| 268 | V268W | 0.16 | *0.05* | 2.12 | 0.06 | 0.06 |
| 268 | V268Y | 0.15 | *0.05* | 2.50 | *0.05* | 0.12 |
| 269 | N269C | 0.67 | 3.47 | 1.37 | 0.99 | 1.06 |
| 269 | N269D | 0.95 | 1.22 | 1.39 | 1.12 | 1.39 |
| 269 | N269F | 1.33 | 1.35 | 1.10 | 0.07 | 1.96 |
| 269 | N269G | 1.29 | 1.00 | 1.08 | 0.43 | 1.61 |
| 269 | N269H | 1.04 | 1.72 | 1.17 | 0.94 | 1.41 |
| 269 | N269I | 1.59 | 1.14 | 1.04 | 0.44 | 2.15 |
| 269 | N269L | 1.68 | 0.99 | 1.03 | 0.19 | 2.17 |
| 269 | N269M | 1.18 | 1.31 | 1.18 | 0.75 | 1.61 |
| 269 | N269Q | 1.38 | 1.02 | 1.00 | 0.99 | 1.80 |
| 269 | N269R | 0.95 | 1.47 | 0.91 | *0.05* | 1.33 |
| 269 | N269S | 0.97 | 1.45 | 1.25 | 0.81 | 1.26 |
| 269 | N269T | 1.19 | 1.27 | 1.23 | 0.48 | 1.55 |
| 269 | N269V | 1.11 | 1.28 | 1.06 | 0.42 | 1.72 |
| 270 | A270C | 1.25 | 1.31 | 1.19 | 0.99 | 1.76 |
| 270 | A270D | 1.19 | 1.29 | 1.18 | 0.60 | 1.54 |
| 270 | A270E | 0.22 | *0.05* | 1.54 | *0.05* | 0.26 |
| 270 | A270F | 0.72 | 4.90 | 1.17 | *0.05* | 0.98 |
| 270 | A270G | 1.09 | 1.22 | 1.14 | 0.97 | 1.39 |

TABLE 4-1-continued

Performance Index (PI) Values for Variants of GCI-P036 for Various Tested Properties.

| POSI-TION (BPN' Numbering) | GG36 Variant (BPN' Numbering) | TCA Assay PI | CS-38 Microswatch Assay PI | PI BMI pH 8 32° C. | LAS-EDTA PI | AAPF Assay PI |
|---|---|---|---|---|---|---|
| 270 | A270H | 0.57 | *0.05* | 1.34 | *0.05* | 0.65 |
| 270 | A270I | 1.13 | 1.27 | 1.15 | 0.81 | 1.39 |
| 270 | A270K | 0.19 | *0.05* | *0.05* | ND | *0.05* |
| 270 | A270L | 0.97 | 1.66 | 1.19 | 0.86 | 1.30 |
| 270 | A270M | 1.19 | 1.20 | 1.18 | 0.54 | 1.52 |
| 270 | A270N | 0.92 | 1.84 | 1.20 | 0.82 | 1.33 |
| 270 | A270P | 0.80 | 1.50 | 1.25 | 0.25 | 1.05 |
| 270 | A270Q | 0.49 | *0.05* | 1.53 | 0.12 | 0.59 |
| 270 | A270S | 1.10 | 1.07 | 1.06 | 0.85 | 1.61 |
| 270 | A270T | 0.94 | 1.64 | 1.04 | 0.96 | 1.30 |
| 270 | A270V | 0.90 | 1.63 | 1.21 | 0.94 | 1.34 |
| 270 | A270W | 0.14 | *0.05* | *0.05* | ND | *0.05* |
| 271 | E271A | 1.52 | 1.14 | 0.79 | 0.42 | 1.81 |
| 271 | E271C | 1.20 | 1.09 | 1.21 | 0.88 | 1.61 |
| 271 | E271F | 1.13 | 1.44 | 0.91 | 0.22 | 1.56 |
| 271 | E271G | 1.22 | 1.40 | 0.89 | 0.36 | 1.73 |
| 271 | E271H | 1.18 | 1.73 | 1.00 | 0.52 | 1.63 |
| 271 | E271I | 1.23 | 1.04 | 0.98 | 0.06 | 1.60 |
| 271 | E271K | 1.21 | 1.28 | 0.70 | 0.06 | 1.62 |
| 271 | E271L | 0.98 | 1.53 | 0.93 | 0.29 | 1.24 |
| 271 | E271M | 1.21 | 1.35 | 0.92 | 0.39 | 1.65 |
| 271 | E271N | 1.01 | 1.35 | 0.93 | 0.33 | 1.32 |
| 271 | E271P | 0.95 | 1.43 | 0.94 | *0.05* | 1.21 |
| 271 | E271T | 0.94 | 1.64 | 1.05 | 0.30 | 1.32 |
| 271 | E271V | 0.95 | 1.25 | 1.00 | 0.13 | 1.57 |
| 271 | E271Y | 0.98 | 1.22 | 0.86 | 0.44 | 1.27 |
| 272 | A272C | 1.00 | 1.21 | 1.08 | 0.97 | 1.28 |
| 272 | A272D | 0.98 | 1.25 | 1.09 | 1.04 | 1.37 |
| 272 | A272E | 0.98 | 1.40 | 1.13 | 1.02 | 1.37 |
| 272 | A272F | 1.06 | 1.40 | 0.95 | 0.95 | 1.44 |
| 272 | A272G | 1.26 | 0.79 | 1.00 | 0.95 | 1.66 |
| 272 | A272H | 1.29 | 0.96 | 0.88 | 0.92 | 1.68 |
| 272 | A272K | 1.31 | 0.99 | 0.87 | 0.64 | 1.53 |
| 272 | A272L | 1.38 | 0.85 | 1.00 | 1.07 | 1.75 |
| 272 | A272M | 1.17 | 1.06 | 1.09 | 0.97 | 1.58 |
| 272 | A272N | 1.10 | 1.15 | 1.02 | 0.98 | 1.36 |
| 272 | A272P | 1.43 | 0.85 | 0.94 | 0.95 | 1.96 |
| 272 | A272R | 0.96 | 1.24 | 1.04 | 0.65 | 1.33 |
| 272 | A272S | 0.86 | 2.78 | 1.26 | 0.92 | 1.20 |
| 272 | A272T | 1.02 | 1.35 | 1.06 | 0.97 | 1.38 |
| 272 | A272W | 1.16 | 0.92 | 1.02 | 0.94 | 1.35 |
| 272 | A272Y | 1.03 | 1.08 | 1.17 | 1.02 | 1.28 |
| 273 | A273C | 1.01 | 1.38 | 1.14 | 0.99 | 1.23 |
| 273 | A273D | 0.95 | 1.36 | 1.11 | *0.05* | 1.23 |
| 273 | A273E | 0.99 | 1.31 | 1.15 | *0.05* | 1.31 |
| 273 | A273F | 1.14 | 1.09 | 1.08 | *0.05* | 1.28 |
| 273 | A273G | 0.99 | 1.43 | 1.01 | 1.03 | 1.24 |
| 273 | A273H | 0.99 | 1.19 | 1.10 | 0.08 | 1.19 |
| 273 | A273I | 0.97 | 1.61 | 1.04 | 0.17 | 1.12 |
| 273 | A273K | 0.65 | *0.05* | 1.18 | *0.05* | 0.85 |
| 273 | A273L | 1.12 | 1.08 | 1.01 | 0.40 | 1.41 |
| 273 | A273R | 0.68 | *0.05* | 1.12 | *0.05* | 0.76 |
| 273 | A273S | 0.89 | 2.21 | 1.06 | 0.82 | 1.29 |
| 273 | A273T | 0.81 | 4.52 | 1.09 | 0.53 | 1.06 |
| 273 | A273V | 1.07 | 1.22 | 1.03 | 0.62 | 1.36 |
| 273 | A273W | 0.38 | *0.05* | 1.70 | *0.05* | 0.48 |
| 273 | A273Y | 0.54 | *0.05* | 1.39 | *0.05* | 0.64 |
| 274 | T274A | 1.09 | 1.29 | 1.05 | 0.97 | 1.40 |
| 274 | T274C | 1.06 | 1.26 | 1.01 | 1.01 | 1.18 |
| 274 | T274D | 0.86 | 2.23 | 1.27 | 0.69 | 1.00 |
| 274 | T274E | 0.91 | 1.44 | 1.33 | 0.21 | 1.14 |
| 274 | T274G | 0.92 | 1.55 | 1.20 | 0.87 | 1.16 |
| 274 | T274H | 1.03 | 1.42 | 1.07 | 0.21 | 1.34 |
| 274 | T274K | 0.76 | 3.48 | 1.19 | 0.10 | 1.00 |
| 274 | T274L | 1.28 | 0.97 | 0.97 | 0.97 | 1.55 |
| 274 | T274M | 1.17 | 1.01 | 1.04 | 0.90 | 1.26 |
| 274 | T274N | 1.05 | 1.20 | 1.12 | 0.92 | 1.27 |
| 274 | T274P | 0.88 | 1.60 | 1.25 | *0.05* | 1.05 |
| 274 | T274Q | 1.23 | 0.97 | 1.03 | 0.49 | 1.38 |
| 274 | T274R | 0.89 | 1.52 | 1.06 | *0.05* | 1.09 |
| 274 | T274S | 1.33 | 0.98 | 0.97 | 1.02 | 1.44 |
| 274 | T274W | 1.09 | 1.27 | 1.14 | 0.13 | 1.27 |
| 275 | R275A | 0.51 | *0.05* | 1.62 | 1.06 | 0.67 |
| 275 | R275C | 0.46 | *0.05* | 1.37 | 1.06 | 0.62 |
| 275 | R275D | 1.12 | 1.25 | 0.94 | 1.07 | 1.70 |
| 275 | R275E | 1.26 | 0.92 | 1.19 | 1.12 | 1.65 |
| 275 | R275F | 1.12 | 1.02 | 1.03 | 1.16 | 1.42 |
| 275 | R275G | 0.64 | *0.05* | 1.42 | 1.10 | 0.90 |
| 275 | R275H | 1.15 | 1.06 | 1.05 | 1.13 | 1.46 |
| 275 | R275K | 1.30 | 0.95 | 1.02 | 1.07 | 1.59 |
| 275 | R275L | 0.82 | 2.73 | 1.25 | 1.08 | 1.13 |
| 275 | R275M | 0.81 | 5.83 | 1.31 | 1.16 | 1.03 |
| 275 | R275P | 1.05 | 0.94 | 1.09 | 0.90 | 1.38 |
| 275 | R275Q | 1.21 | 0.90 | 0.86 | 1.09 | 1.51 |
| 275 | R275V | 0.75 | 3.80 | 1.21 | 0.99 | 0.99 |
| 275 | R275W | 0.79 | 10.11 | 1.31 | 0.96 | 1.20 |

Example 5

Comparative Evaluation of GCI-P036 Variant Data

In this Example, results of experiments conducted to determine protein expression, stain removal activity, LAS/EDTA stability, and AAPF activity (tests of properties of interest) of GCI-P036 and GCI-P036 variants are compared. As described throughout, functionality of the GCI-P036 variants is quantified as a performance index (PI), which is the ratio of performance of a variant to a reference protease. PI classifications used herein include: Up mutations (PI>1.0); Neutral mutations (PI>0.5); Non-deleterious mutations (PI>0.05); and Deleterious mutations (PI≤0.05).

In initial screens of GCI-P036 variants, at least one mutation in the following positions was associated with a performance index greater than 1.0 (PI>1.0) for at least one property:

1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 38, 39, 40, 41, 42, 43, 44, 45, 46, 47, 48, 49, 50, 51, 52, 53, 54, 55, 56, 57, 59, 60, 61, 62, 63, 66, 67, 68, 69, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, and 275 (e.g., Up mutations). Mutations at these positions may be combined to improve activity or stability or expression.

In particular, the following substitutions in GCI-P036 were associated with a favorable outcome in at least one test of interest (e.g., better than the wild type enzyme). These mutations are especially useful to improve individual properties. As indicated elsewhere herein, in this list, the leading "0" is included to provide a three number designation for each site (e.g., "001" is the same as "1," so "A001C" is the same as "A1C"). In addition, as indicated elsewhere herein, "X" refers to any amino acid residue.

X001A, X001C, X001E, X001F, X001G, X001H, X001I, X001K, X001L, X001N, X001P, X001Q, X001R, X001S, X001T, X001V, X001Y, X002A, X002C, X002E, X002G, X002K, X002L, X002M, X002N, X002P, X002Q, X002R, X002S, X002T, X002V, X002W, X002Y, X003D, X003E, X003F, X003G, X003H, X003I, X003L, X003M, X003N, X003P, X003R, X003S, X003T, X003V, X003W, X003Y, X004A, X004C, X004D, X004E, X004F, X004G, X004H, X004K, X004L, X004N, X004P, X004R, X004S, X004T, X004V, X004W, X005A, X005C, X005D, X005E, X005G, X005I, X005M, X005P, X005Q, X005S, X005T, X005W, X005Y, X006A, X006D, X006E, X006M, X006W, X007A, X007C, X007D, X007G, X007H, X007N, X007P, X007Q, X007S, X007T, X008A, X008F, X008G, X008I, X008L, X008M, X008Q, X008T, X008V, X008W, X008Y, X009A, X009C, X009D, X009E, X009F, X009G, X009H, X009L, X009N, X009P, X009Q, X009R, X009S, X009T, X009V, X009W, X009Y, X010A, X010C, X010F, X010G, X010H, X010I, X010K, X010L, X010M, X010N, X010Q, X010R, X010S, X010T, X010V, X010W, X010Y, X011A, X011C, X011D, X011G, X011I, X011M, X011S, X011T, X011V, X012D, X012F, X012G, X012H, X012I, X012K, X012L, X012M, X012N, X012P, X012Q, X012R, X012S, X012T, X012V, X012W, X013A, X013G, X013I, X013M, X013Q, X013T, X013V, X014A, X014C, X014D, X014E, X014F, X014G, X014H, X014I, X014K, X014L, X014P, X014Q, X014S, X014T, X014V, X014Y, X015A, X015D, X015F, X015G, X015I, X015K, X015L, X015M, X015P, X015Q, X015R, X015S, X015V, X015W, X016A, X016D, X016E, X016G, X016L, X016N, X016P, X016Q, X016R, X016S, X016T, X016V, X017A, X017D, X017E, X017F, X017G, X017H, X017I, X017K, X017M, X017N, X017R, X017S, X017T, X017V, X017W, X017Y, X018A, X018C, X018D, X018E, X018F, X018G, X018H, X018K, X018L, X018M, X018N, X018P, X018Q, X018R, X018S, X018T, X018V, X018W, X018Y, X019A, X019C, X019D, X019E, X019F, X019G, X019H, X019K, X019L, X019M, X019N, X019P, X019R, X019S, X019T, X019V, X019W, X019Y, X020A, X020C, X020D, X020F, X020G, X020I, X020K, X020L, X020M, X020P, X020Q, X020R, X020S, X020T, X020V, X020W, X020Y, X021A, X021C, X021D, X021E, X021 G, X021H, X021I, X021K, X021L, X021M, X021N, X021P, X021Q, X021R, X021S, X021T, X021V, X021 W, X022A, X022C, X022G, X022I, X022K, X022L, X022M, X022N, X022P, X022Q, X022R, X022S, X022T, X022V, X022W, X022Y, X023A, X023G, X023S, X024A, X024C, X024D, X024F, X024G, X024H, X024L, X024M, X024N, X024P, X024Q, X024R, X024S, X024T, X024V, X024W, X025C, X025ID, X025E, X025F, X025G, X025H, X025K, X025L, X025M, X025N, X025Q, X025R, X025S, X025T, X025V, X025W, X026C, X026F, X026G, X026I, X026L, X026M, X026N, X026P, X026R, X026S, X026T, X026V, X027A, X027C, X027D, X027F, X027G, X027I, X027K, X027L, X027M, X027N, X027P, X027R, X027S, X027T, X027V, X027W, X027Y, X028A, X028E, X028H, X028I, X028L, X028M, X028N, X028S, X028V, X028Y, X029A, X029C, X029G, X029K, X029S, X029T, X029V, X030C, X030D, X030E, X030F, X030L, X030M, X030Q, X030S, X030T, X030V, X031A, X031F, X031I, X031L, X031M, X031S, X031T, X031V, X032C, X032D, X032G, X033A, X033C, X033D, X033E, X033G, X033H, X033I, X033L, X033M, X033N, X033Q, X033R, X033S, X033T, X033V, X033Y, X034E, X034G, X034S, X035A, X035F, X035H, X035I, X035K, X035L, X035M, X035P, X035Q, X035R, X035S, X036A, X036C, X036E, X036F, X036G, X036H, X036I, X036L, X036M, X036N, X036P, X036Q, X036R, X036S, X036T, X036V, X036W, X036Y, X038C, X038F, X038G, X038H, X038I, X038K, X038L, X038M, X038N, X038Q, X038R, X038T, X038V, X038W, X038Y, X039A, X039E, X039G, X039H, X039N, X039Q, X039S, X039T, X039V, X039Y, X040A, X040C, X040D, X040E, X040G, X040H, X040I, X040K, X040L, X040M, X040N, X040P, X040R, X040S, X040T, X040V, X040W, X040Y, X041C, X041D, X041E, X041N, X041Q, X042A, X042C, X042F, X042G, X042H, X042I, X042L, X042M, X042N, X042Q, X042S, X042T, X042V, X042Y, X043A, X043C, X043D, X043E, X043F, X043G, X043I, X043L, X043M, X043N, X043P, X043R, X043S, X043T, X043V, X043W, X043Y, X044A, X044C, X044D, X044F, X044G, X044I, X044K, X044L, X044M, X044N, X044P, X044Q, X044R, X044S, X044T, X044V, X044W, X044Y, X045A, X045D, X045F, X045G, X045H, X045I, X045K, X045L, X045M, X045N, X045P, X045Q, X045R, X045S, X045T, X045V, X045W, X045Y, X046C, X046D, X046E, X046F, X046G, X046H, X046I, X046K, X046L, X046M, X046N, X046P, X046Q, X046R, X046S, X046T, X046V, X046W, X047A, X047C, X047E, X047F, X047G, X047H, X047K, X047L, X047M, X047N, X047Q, X047R, X047S, X047T, X047W, X048A, X048C, X048E, X048F, X048G, X048H, X048I, X048K, X048L, X048M, X048N, X048P, X048Q, X048R, X048S, X048T, X048V, X048Y, X049A, X049E, X049F, X049G, X049H, X049K, X049L, X049M, X049P, X049Q, X049R, X049S, X049T, X050C, X050F, X050H, X050I, X050L, X050N, X050T, X050V, X050Y, X051F, X051G, X051H, X051K, X051L, X051N, X051P, X051R, X051S, X051T, X051V, X051W, X052A, X052C, X052E, X052F, X052G, X052H, X052I, X052L, X052M, X052N, X052P, X052Q, X052R, X052T, X052V, X052W, X052Y, X053A, X053C, X053D, X053E, X053G, X053H, X053I, X053K, X053L, X053M, X053P, X053Q, X053R, X053S, X053T, X053V, X053W, X053Y, X054A, X054C, X054D, X054E, X054F, X054G, X054H, X054I, X054K, X054L, X054M, X054N, X054P, X054Q, X054R, X054S, X054V, X054Y, X055A, X055C, X055F, X055F, X055G, X055H, X055I, X055K, X055L, X055M, X055N, X055P, X055Q, X055R, X055S, X055T, X055W, X055Y, X056A, X056C, X056D, X056E, X056H, X056L, X056M, X056N, X056P, X056Q, X056R, X056S, X056T, X056V, X057A, X057C, X057E, X057F, X057G, X057H, X057I, X057K, X057L, X057M, X057N, X057P, X057Q, X057R, X057S, X057T, X057V, X057W, X057Y, X059A, X059C, X059D, X059E, X059F, X059G, X059I, X059L, X059M, X059N, X059P, X059Q, X059R, X059S, X059T, X059V, X059W, X059Y, X060A, X060C, X060D, X060F, X060G, X060K, X060L, X060M, X060N, X060P, X060Q, X060S, X060T, X060V, X060W, X060Y, X061A, X061C, X061D, X061F, X061G, X061H, X061I, X061L, X061M, X061N, X061P, X061R, X061S, X061T, X061V, X061Y, X062C, X062E, X062F, X062G, X062H, X062I, X062K, X062L, X062M, X062N, X062P, X062Q, X062R, X062S, X062T, X062V, X062Y, X063A, X063C, X063D, X063E, X063F, X063G, X063H, X063I, X063K, X063M, X063P, X063Q, X063R, X063S, X063T, X063V, X063W, X066A, X066C, X066D, X066E, X066I, X066K, X066L, X066N, X066Q, X066S, X066T, X067A, X067C, X067F, X067H, X067L, X067M, X067N, X067P, X067Q, X067R, X067S, X067T, X067V, X068A, X068C, X068D, X068E, X068G, X068H, X068I, X068L, X068M, X068N, X068Q, X068S, X068T, X068V, X069A, X069C, X069E, X069F,

X069G, X069I, X069L, X069M, X069N, X069S, X069T, X069V, X069W, X071A, X071C, X071D, X071E, X071G, X071I, X071L, X071M, X071N, X071P, X071S, X071T, X071V, X071W, X072C, X072F, X072H, X072I, X072L, X072M, X072N, X072Q, X072S, X072T, X072V, X072W, X073A, X073C, X073D, X073E, X073H, X073K, X073L, X073N, X073R, X073S, X073T, X073V, X074A, X074C, X074S, X074T, X075A, X075C, X075D, X075E, X075F, X075G, X075H, X075I, X075L, X075M, X075N, X075P, X075Q, X075R, X075S, X075T, X075V, X075W, X076C, X076D, X076E, X076F, X076G, X076H, X076I, X076K, X076L, X076M, X076N, X076Q, X076R, X076S, X076T, X076W, X076Y, X077A, X077C, X077D, X077E, X077F, X077G, X077H, X077K, X077L, X077M, X077N, X077Q, X077R, X077S, X077V, X077Y, X078A, X078C, X078E, X078F, X078G, X078H, X078I, X078K, X078L, X078M, X078N, X078P, X078Q, X078R, X078S, X078T, X078V, X078W, X078Y, X079C, X079D, X079E, X079F, X079G, X079I, X079K, X079L, X079M, X079N, X079P, X079Q, X079R, X079S, X079T, X079V, X079W, X079Y, X080A, X080D, X080E, X080G, X080K, X080L, X080M, X080R, X080T, X080V, X080W, X080Y, X081A, X081C, X081D, X081E, X081F, X081G, X081H, X081I, X081K, X081L, X081M, X081P, X081Q, X081R, X081S, X081T, X081V, X081W, X081Y, X082A, X082E, X082F, X082K, X082L, X082M, X082N, X082Q, X082R, X082S, X082T, X082V, X082W, X082Y, X083G, X083S, X084C, X084E, X084F, X084G, X084H, X084I, X084L, X084M, X084N, X084Q, X084T, X084V, X085A, X085C, X085I, X085L, X086A, X086C, X086D, X086E, X086G, X086I, X086L, X086P, X086S, X086V, X086W, X086Y, X087A, X087C, X087D, X087E, X087F, X087G, X087I, X087K, X087L, X087N, X087P, X087S, X087T, X087V, X087Y, X088A, X088C, X088D, X088E, X088G, X088H, X088K, X088M, X088Q, X088R, X088S, X088V, X088W, X089A, X089C, X089D, X089E, X089F, X089G, X089H, X089I, X089L, X089N, X089P, X089Q, X089R, X089S, X089T, X089V, X089W, X090A, X090C, X090E, X090F, X090G, X090I, X090K, X090L, X090M, X090P, X090Q, X090T, X090V, X090W, X090Y, X091C, X091D, X091F, X091I, X091K, X091L, X091M, X091N, X091Q, X091R, X091S, X091T, X091V, X091W, X091Y, X092A, X092C, X092D, X092E, X092F, X092G, X092H, X092I, X092K, X092L, X092N, X092P, X092Q, X092R, X092T, X092V, X092W, X092Y, X093A, X093C, X093D, X093F, X093G, X093L, X093M, X093N, X093S, X093T, X093V, X093Y, X094A, X094D, X094E, X094G, X094H, X094I, X094K, X094L, X094M, X094N, X094Q, X094R, X094V, X095A, X095C, X095G, X095I, X095K, X095L, X095M, X095R, X095S, X095T, X095V, X095W, X096A, X096E, X096F, X096G, X096H, X096I, X096L, X096M, X096Q, X096R, X096S, X096T, X096W, X096Y, X097A, X097D, X097E, X097F, X097G, X097H, X097I, X097K, X097L, X097M, X097N, X097P, X097Q, X097R, X097S, X097T, X097V, X097W, X097Y, X098A, X098C, X098D, X098E, X098F, X098G, X098K, X098L, X098N, X098P, X098Q, X098R, X098S, X098T, X098V, X098Y, X099A, X099C, X099F, X099G, X099K, X099M, X099P, X099Q, X099R, X099S, X099T, X099V, X099Y, X100D, X100E, X100F, X100G, X100I, X100K, X100L, X100M, X100N, X100P, X100Q, X100R, X100S, X100T, X100V, X100W, X100Y, X101A, X101D, X101E, X101F, X101G, X101H, X101I, X101K, X101N, X101P, X101Q, X101R, X101S, X101T, X101V, X101Y, X102A, X102C, X102D, X102E, X102F, X102G, X102H, X102M, X102N, X102T, X103A, X103C, X103D, X103E, X103F, X103G, X103I, X103L, X103N, X103P, X103Q, X103R, X103S, X103T, X103V, X103W, X103Y, X104A, X104C, X104D, X104E, X104F, X104H, X104I, X104L, X104P, X104R, X104S, X104T, X104V, X104W, X104Y, X105A, X105C, X105D, X105E, X105F, X105G, X105H, X105I, X105K, X105L, X105M, X105N, X105Q, X105R, X105S, X105T, X105V, X105W, X105Y, X106A, X106D, X106E, X106F, X106G, X106I, X106L, X106M, X106P, X106R, X106S, X106T, X106V, X106W, X107A, X107C, X107E, X107F, X107H, X107I, X107L, X107M, X107Q, X107S, X107T, X107V, X107W, X107Y, X108A, X108C, X108G, X108I, X108L, X108M, X108S, X108T, X108V, X109A, X109C, X109E, X109F, X109G, X109H, X109I, X109K, X109L, X109M, X109N, X109P, X109Q, X109R, X109S, X109T, X109W, X109Y, X110A, X110G, X110S, X111C, X111E, X111F, X111I, X111L, X111M, X111V, X111Y, X112A, X112C, X112D, X112E, X112F, X112G, X112I, X112L, X112N, X112Q, X112S, X112T, X112V, X112W, X112Y, X113L, X113M, X113W, X114A, X114C, X114G, X114T, X115C, X115E, X115F, X115G, X115H, X115I, X115K, X115L, X115M, X115N, X115P, X115Q, X115R, X115S, X115T, X115V, X115W, X115Y, X116A, X116C, X116D, X116F, X116G, X116I, X116K, X116L, X116M, X116N, X116Q, X116S, X116T, X116V, X116W, X117A, X117C, X117D, X117F, X117G, X117I, X117N, X117Q, X117R, X117T, X117Y, X118A, X118C, X118D, X118E, X118F, X118G, X118I, X118K, X118L, X118M, X118N, X118P, X118R, X118S, X118T, X118V, X118W, X119A, X119C, X119F, X119G, X119H, X119M, X119N, X119Q, X119T, X119W, X120A, X120C, X120E, X120F, X120G, X120H, X120I, X120L, X120M, X120N, X120R, X120S, X120T, X120W, X121A, X121C, X121E, X121F, X121G, X121I, X121L, X121M, X121Q, X121S, X121T, X121V, X121Y, X122A, X122C, X122G, X122I, X122L, X122S, X122T, X122V, X123E, X123G, X123I, X123L, X123N, X123S, X124G, X124H, X124L, X124N, X124Q, X124S, X124T, X125A, X125C, X125G, X125S, X125T, X126A, X126C, X126E, X126F, X126G, X126H, X126I, X126L, X126M, X126N, X126Q, X126S, X126T, X126V, X126W, X126Y, X127D, X127F, X127G, X127I, X127L, X127Q, X127R, X127S, X127T, X127V, X128A, X128C, X128D, X128F, X128G, X128H, X128I, X128K, X128L, X128M, X128N, X128P, X128Q, X128R, X128S, X128T, X128W, X128Y, X129A, X129E, X129F, X129G, X129I, X129L, X129M, X129N, X129P, X129R, X129S, X129T, X129V, X129W, X129Y, X130C, X130K, X130L, X130N, X130Q, X130R, X130S, X130V, X130W, X130Y, X131A, X131D, X131E, X131F, X131G, X131I, X131K, X131L, X131M, X131P, X131Q, X131R, X131V, X132A, X132E, X132F, X132H, X132I, X132L, X132M, X132N, X132Q, X132S, X132T, X132W, X133A, X133F, X133K, X133L, X133N, X133P, X133Q, X133S, X133T, X133V, X133Y, X134A, X134F, X134I, X134L, X134M, X134P, X134S, X134T, X134V, X135A, X135C, X135E, X135F, X135L, X135M, X135Q, X135T, X135W, X136A, X136D, X136E, X136F, X136G, X136K, X136N, X136Q, X136R, X136S, X136V, X136W, X136Y, X137A, X137C, X137E, X137G, X137H, X137K, X137L, X137M, X137Q, X137R, X137S, X137V, X137W, X138A, X138C, X138E, X138G, X138L, X138M, X138Q, X138R, X138V, X139A, X139C, X139E, X139F, X139G, X139I, X139M, X139Q, X139S, X139T, X139V, X139Y, X140A, X140C, X140D, X140E, X140F, X140G, X140I, X140K, X140L, X140M, X140N, X140Q, X140R, X140S, X140T, X140V, X140Y, X141D, X141E, X141G, X141H, X141I, X141K, X141L, X141N, X141Q, X141R, X141S, X141V, X141Y, X142A, X142C, X142E, X142G, X142I, X142L, X142M, X142N, X142Q, X142S, X142T, X142V, X142Y, X143C, X143D, X143F, X143G, X143H, X143I, X143K, X143L, X143M, X143N, X143S, X143T, X143V,

X143W, X143Y, X144A, X144C, X144D, X144G, X144H, X144I, X144L, X144M, X144N, X144Q, X144R, X144S, X144T, X144V, X144W, X144Y, X145A, X145C, X145D, X145E, X145F, X145G, X145K, X145L, X145M, X145N, X145Q, X145R, X145S, X145T, X145W, X145Y, X146A, X146C, X146D, X146E, X146F, X146G, X146I, X146K, X146L, X146M, X146Q, X146R, X146S, X146T, X146W, X146Y, X147F, X147G, X147I, X147L, X147M, X147P, X147Q, X147T, X147V, X148A, X148C, X148E, X148F, X148G, X148H, X148I, X148L, X148M, X148N, X148S, X148T, X148V, X148W, X148Y, X149A, X149C, X149F, X149G, X149H, X149I, X149L, X149M, X149P, X149Q, X149S, X149T, X149V, X150A, X150E, X150F, X150G, X150H, X150L, X150P, X150Q, X150S, X150T, X150V, X151A, X151G, X151M, X151S, X151T, X151V, X152A, X152C, X152P, X152R, X152S, X152T, X153A, X153G, X153I, X153M, X153Q, X153S, X153V, X154G, X154Q, X155A, X155D, X155F, X155I, X155N, X155P, X155Q, X155R, X155S, X155T, X155V, X155Y, X156A, X156C, X156D, X156E, X156F, X156G, X156K, X156L, X156M, X156N, X156P, X156Q, X156R, X156S, X156T, X157G, X157L, X157V, X158A, X158C, X158E, X158F, X158H, X158K, X158L, X158M, X158P, X158Q, X158R, X158S, X158T, X158V, X158W, X159A, X159C, X159E, X159G, X159H, X159M, X159P, X159Q, X159R, X159S, X159V, X159W, X159Y, X160A, X160C, X160D, X160F, X160G, X160I, X160L, X160M, X160N, X160Q, X160R, X160S, X160T, X160V, X160Y, X165D, X165E, X165F, X165G, X165H, X165I, X165K, X165L, X165R, X165T, X165V, X165W, X165Y, X166A, X166C, X166D, X166E, X166H, X166I, X166L, X166M, X166N, X166P, X166R, X166S, X166T, X166V, X166W, X167A, X167C, X167D, X167E, X167F, X167G, X167I, X167P, X167Q, X167V, X167W, X167Y, X168F, X168I, X168M, X168P, X169A, X169C, X169G, X169S, X170A, X170D, X170E, X170G, X170H, X170K, X170L, X170P, X170Q, X170R, X170S, X170V, X170W, X170Y, X171A, X171C, X171D, X171F, X171G, X171H, X171I, X171L, X171N, X171Q, X171S, X171T, X171W, X171Y, X172A, X172C, X172D, X172F, X172G, X172I, X172K, X172L, X172M, X172P, X172Q, X172R, X172S, X172T, X172V, X172Y, X173A, X173C, X173D, X173E, X173F, X173G, X173H, X173I, X173K, X173L, X173M, X173N, X173P, X173Q, X173R, X173T, X173V, X173W, X173Y, X174A, X174G, X174I, X174N, X174P, X174S, X174T, X174V, X175A, X175C, X175E, X175G, X175H, X175I, X175K, X175L, X175M, X175Q, X175S, X175T, X175V, X175Y, X176A, X176C, X176E, X176G, X176I, X176P, X176S, X176T, X176V, X177A, X177C, X177I, X177T, X177V, X178A, X178G, X178S, X179A, X179C, X179G, X180C, X180G, X180H, X180I, X180L, X180N, X180Q, X180S, X180T, X180V, X181A, X181D, X181E, X181G, X181L, X181N, X182A, X182D, X182E, X182F, X182G, X182H, X182I, X182K, X182L, X182M, X182N, X182P, X182Q, X182R, X182S, X182T, X182V, X182W, X182Y, X183A, X183D, X183F, X183G, X183H, X183I, X183K, X183L, X183M, X183N, X183P, X183Q, X183R, X183S, X183T, X183V, X183W, X183Y, X184A, X184C, X184D, X184E, X184G, X184H, X184L, X184M, X184N, X184S, X184T, X184Y, X185A, X185C, X185E, X185F, X185G, X185H, X185I, X185K, X185L, X185M, X185N, X185Q, X185R, X185S, X185T, X185V, X185Y, X186A, X186G, X186H, X186I, X186K, X186L, X186M, X186Q, X186R, X186T, X186W, X187A, X187C, X187E, X187F, X187G, X187H, X187I, X187P, X187W, X187Y, X188A, X188D, X188E, X188F, X188G, X188H, X188I, X188K, X188L, X188P, X188Q, X188R, X188S, X188T, X188V, X188W, X188Y, X189A, X189C, X189E, X189F, X189G, X189H, X189K, X189L, X189M, X189N, X189P, X189Q, X189R, X189S, X189T, X189V, X190D, X190E, X190F, X190G, X190H, X190I, X190K, X190L, X190M, X190N, X190P, X190Q, X190R, X190S, X190V, X190W, X190Y, X191A, X191D, X191F, X191H, X191I, X191K, X191L, X191P, X191Q, X191S, X191V, X191W, X191Y, X192D, X192E, X192H, X192L, X192M, X192P, X192Q, X192R, X192T, X192V, X192W, X192Y, X193A, X193D, X193E, X193F, X193G, X193H, X193I, X193K, X193L, X193R, X193T, X193V, X193W, X193Y, X194A, X194C, X194D, X194E, X194F, X194G, X194H, X194I, X194L, X194M, X194P, X194Q, X194R, X194S, X194T, X194V, X194W, X194Y, X195A, X195C, X195D, X195E, X195G, X195K, X195Q, X195R, X195S, X195T, X195V, X195Y, X196A, X196D, X196E, X196F, X196I, X196L, X196M, X196P, X196Q, X196T, X197A, X197C, X197D, X197E, X197F, X197G, X197H, X197I, X197L, X197M, X197N, X197Q, X197S, X197T, X197V, X197W, X197Y, X198A, X198D, X198E, X198F, X198G, X198H, X198I, X198L, X198M, X198N, X198Q, X198R, X198S, X198T, X198W, X198Y, X199A, X199C, X199D, X199E, X199F, X199G, X199I, X199L, X199M, X199Q, X199S, X199T, X199V, X200A, X200C, X200G, X200H, X200I, X200S, X201C, X201G, X201P, X201S, X201T, X201V, X202F, X202A, X203C, X203E, X203F, X203G, X203H, X203I, X203K, X203L, X203N, X203S, X203T, X203V, X203W, X203Y, X204A, X204C, X204E, X204F, X204G, X204I, X204K, X204L, X204N, X204P, X204R, X204S, X204T, X204W, X204Y, X205A, X205F, X205G, X205I, X205L, X205M, X205Q, X205T, X205V, X206A, X206C, X206D, X206E, X206F, X206G, X206H, X206I, X206K, X206L, X206N, X206P, X206Q, X206R, X206S, X206T, X206V, X206W, X206Y, X207A, X207G, X207S, X208A, X208C, X208L, X208N, X208P, X208S, X208T, X208V, X209A, X209C, X209D, X209E, X209F, X209G, X209H, X209I, X209K, X209L, X209M, X209N, X209R, X209S, X209T, X209V, X209W, X209Y, X210A, X210C, X210D, X210E, X210F, X210G, X210H, X210I, X210L, X210M, X210N, X210P, X210Q, X210R, X210S, X210V, X210W, X210Y, X211A, X211C, X211E, X211F, X211G, X211H, X211I, X211L, X211M, X211P, X211Q, X211R, X211T, X211V, X211W, X211Y, X212C, X212F, X212G, X212H, X212I, X212M, X212N, X212P, X212R, X212S, X212T, X212V, X212Y, X213A, X213C, X213D, X213E, X213F, X213G, X213I, X213K, X213L, X213M, X213N, X213P, X213Q, X213R, X213S, X213T, X213V, X213W, X213Y, X214A, X214C, X214E, X214F, X214G, X214H, X214I, X214K, X214L, X214M, X214N, X214P, X214Q, X214R, X214S, X214T, X214V, X214W, X214Y, X215A, X215C, X215D, X215E, X215F, X215G, X215H, X215I, X215K, X215M, X215N, X215P, X215R, X215S, X215T, X215V, X215W, X215Y, X216A, X216C, X216D, X216E, X216F, X216G, X216H, X216I, X216K, X216L, X216M, X216N, X216P, X216Q, X216R, X216S, X216V, X216W, X216Y, X217A, X217C, X217D, X217E, X217F, X217G, X217I, X217K, X217L, X217M, X217N, X217Q, X217S, X217T, X217V, X217Y, X218C, X218D, X218E, X218F, X218G, X218H, X218I, X218L, X218M, X218N, X218P, X218Q, X218R, X218S, X218T, X218V, X218W, X218Y, X219A, X219G, X220A, X220G, X220H, X220N, X220S, X220T, X220V, X221G, X221S, X222A, X222C, X222E, X222F, X222G, X222I, X222K, X222L, X222M, X222N, X222P, X222Q, X222R, X222S, X222T, X222V, X222W, X223A, X223C, X223G, X223M, X223S, X224A, X224D, X224E, X224G, X224I, X224L, X224N, X224P, X224S, X224T, X225A, X225C, X225G, X225N, X225P, X225S, X225T, X225V, X226C, X226F, X226G, X226H, X226I, X226L,

X226M, X226N, X226R, X226S, X226T, X226V, X226Y, X227A, X227C, X227F, X227G, X227I, X227L, X227M, X227Q, X227S, X227T, X227V, X227Y, X228A, X228C, X228G, X228I, X228L, X228M, X228S, X228V, X229A, X229G, X229P, X229S, X230A, X230D, X230E, X230F, X230G, X230H, X230I, X230L, X230N, X230P, X230Q, X230S, X230T, X230V, X230W, X230Y, X231A, X231C, X231F, X231G, X231H, X231I, X231L, X231S, X231T, X231W, X231Y, X232A, X232G, X232H, X232L, X232M, X232S, X232V, X233A, X233C, X233E, X233F, X233G, X233I, X233L, X233M, X233N, X233P, X233Q, X233R, X233S, X233T, X233V, X233Y, X234D, X234F, X234G, X234H, X234L, X234M, X234N, X234P, X234Q, X234S, X234T, X234V, X234Y, X235C, X235D, X235E, X235F, X235G, X235H, X235I, X235K, X235L, X235M, X235N, X235Q, X235R, X235S, X235V, X235W, X235Y, X236A, X236C, X236E, X236F, X236G, X236H, X236K, X236L, X236N, X236P, X236Q, X236R, X236S, X236T, X236V, X236W, X236Y, X237A, X237C, X237F, X237G, X237H, X237I, X237K, X237L, X237M, X237P, X237Q, X237R, X237S, X237T, X237V, X237W, X237Y, X238C, X238D, X238E, X238F, X238G, X238H, X238I, X238K, X238L, X238M, X238N, X238Q, X238R, X238S, X238T, X238V, X238Y, X239C, X239D, X239F, X239G, X239H, X239I, X239K, X239L, X239M, X239N, X239P, X239Q, X239R, X239S, X239T, X239V, X239W, X239Y, X240A, X240C, X240E, X240F, X240I, X240K, X240L, X240M, X240N, X240Q, X240R, X240S, X240T, X240W, X240Y, X241A, X241C, X241D, X241E, X241F, X241G, X241H, X241I, X241K, X241L, X241M, X241N, X241P, X241Q, X241R, X241S, X241T, X241V, X241W, X241Y, X242A, X242C, X242D, X242F, X242G, X242H, X242I, X242L, X242M, X242P, X242Q, X242R, X242S, X242T, X242V, X242W, X243C, X243D, X243E, X243F, X243G, X243H, X243I, X243K, X243L, X243M, X243N, X243P, X243Q, X243R, X243S, X243T, X243V, X243W, X244A, X244D, X244E, X244F, X244H, X244I, X244L, X244M, X244N, X244P, X244Q, X244R, X244S, X244T, X244V, X244W, X244Y, X245A, X245C, X245E, X245G, X245H, X245K, X245L, X245P, X245Q, X245R, X245S, X245V, X245W, X245Y, X246A, X246C, X246E, X246F, X246G, X246H, X246I, X246L, X246M, X246N, X246P, X246Q, X246R, X246S, X246T, X246V, X246W, X246Y, X247A, X247C, X247D, X247E, X247F, X247G, X247H, X247I, X247K, X247L, X247M, X247N, X247P, X247Q, X247R, X247S, X247T, X247V, X247W, X247Y, X248C, X248D, X248E, X248G, X248H, X248I, X248K, X248L, X248M, X248N, X248P, X248R, X248S, X248T, X248V, X248W, X248Y, X249A, X249D, X249E, X249F, X249G, X249H, X249I, X249K, X249L, X249M, X249N, X249Q, X249R, X249S, X249T, X249V, X249W, X249Y, X250A, X250C, X250E, X250F, X250G, X250H, X250I, X250L, X250M, X250N, X250Q, X250S, X250V, X250Y, X251A, X251D, X251E, X251F, X251G, X251K, X251L, X251M, X251P, X251Q, X251R, X251S, X251T, X251V, X251Y, X252A, X252C, X252D, X252F, X252G, X252H, X252I, X252K, X252L, X252M, X252N, X252P, X252R, X252S, X252V, X252W, X252Y, X253A, X253D, X253E, X253F, X253G, X253H, X253I, X253K, X253M, X253R, X253S, X253T, X253V, X253W, X254A, X254C, X254D, X254G, X254N, X254P, X254S, X254T, X254V, X255A, X255C, X255D, X255E, X255F, X255H, X255I, X255L, X255N, X255P, X255Q, X255R, X255S, X255T, X255V, X255W, X255Y, X256A, X256C, X256D, X256E, X256G, X256H, X256I, X256K, X256L, X256M, X256N, X256P, X256R, X256S, X256T, X256V, X256W, X256Y, X257A, X257C, X257E, X257F, X257G, X257H, X257I, X257K, X257L, X257M, X257P, X257S, X257T, X257V, X257W, X257Y, X258A, X258C, X258D, X258E, X258F, X258G, X258H, X258I, X258L, X258M, X258P, X258Q, X258R, X258S, X258T, X258V, X258W, X258Y, X259A, X259C, X259E, X259G, X259I, X259L, X259M, X259P, X259Q, X259R, X259S, X259T, X259V, X260A, X260D, X260E, X260F, X260H, X260I, X260L, X260M, X260N, X260P, X260R, X260S, X260T, X260V, X260Y, X261A, X261C, X261E, X261F, X261G, X261I, X261K, X261L, X261N, X261P, X261Q, X261R, X261S, X261T, X261V, X261W, X261Y, X262A, X262C, X262D, X262F, X262G, X262H, X262I, X262K, X262L, X262M, X262P, X262Q, X262R, X262S, X262T, X262V, X262W, X262Y, X263A, X263C, X263D, X263F, X263G, X263H, X263I, X263L, X263M, X263N, X263P, X263Q, X263R, X263W, X263Y, X264A, X264C, X264E, X264F, X264G, X264H, X264I, X264P, X264Q, X264S, X264V, X264Y, X265A, X265C, X265D, X265F, X265G, X265H, X265I, X265K, X265L, X265M, X265P, X265Q, X265R, X265S, X265T, X265V, X265W, X265Y, X266G, X266W, X267A, X267C, X267D, X267E, X267F, X267G, X267H, X267I, X267K, X267L, X267M, X267N, X267S, X267T, X267V, X267Y, X268A, X268D, X268E, X268G, X268H, X268K, X268L, X268M, X268N, X268P, X268Q, X268R, X268S, X268V, X268W, X268Y, X269D, X269F, X269G, X269H, X269I, X269L, X269M, X269N, X269Q, X269R, X269S, X269T, X269V, X270A, X270C, X270D, X270E, X270F, X270G, X270H, X270I, X270L, X270M, X270N, X270P, X270Q, X270S, X270T, X270V, X271A, X271C, X271E, X271F, X271G, X271H, X271I, X271K, X271L, X271M, X271N, X271P, X271T, X271V, X271Y, X272A, X272C, X272D, X272E, X272F, X272G, X272H, X272K, X272L, X272M, X272N, X272P, X272R, X272S, X272T, X272W, X272Y, X273A, X273C, X273D, X273E, X273F, X273G, X273H, X273I, X273K, X273L, X273R, X273S, X273T, X273V, X273W, X273Y, X274A, X274C, X274D, X274E, X274G, X274H, X274K, X274L, X274M, X274N, X274P, X274Q, X274R, X274S, X274T, X274W, X275A, X275C, X275D, X275E, X275F, X275G, X275H, X275K, X275L, X275M, X275P, X275Q, X275R, X275V, X275W, X275W. In contrast, there were no mutations identified in initial screens of positions 64, 65 and 70 that were associated with a performance index greater than 1.0 (PI>1.0) for at least one property.

In screens of GCI-P036 variants, at least one mutation in the following 248 positions was associated with a performance index greater than 1 for either BMI, CS-38 microswatch assay or AAPF activity and had a performance index of greater than 0.8 for LAS stability or in a TCA assay: 1, 2, 3, 4, 5, 7, 8, 9, 10, 11, 12, 13, 14, 15, 16, 17, 18, 19, 20, 21, 22, 23, 24, 25, 26, 27, 28, 29, 30, 31, 33, 35, 36, 38, 39, 40, 41, 42, 43, 44, 45, 46, 47, 48, 49, 50, 51, 52, 53, 54, 55, 56, 57, 59, 60, 61, 62, 63, 66, 68, 69, 71, 72, 73, 74, 75, 76, 77, 78, 79, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 156, 158, 159, 160, 165, 166, 167, 169, 170, 171, 172, 173, 174, 175, 176, 177, 178, 179, 180, 181, 182, 183, 184, 185, 186, 187, 188, 191, 192, 194, 195, 196, 197, 198, 199, 200, 203, 204, 205, 206, 207, 208, 209, 210, 211, 212, 213, 214, 215, 216, 217, 218, 220, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 267, 268, 269, 270, 271, 272, 273, 274, and 275. Mutations at these positions can be combined to improve activity while maintaining either stability or expression. Mutations at these positions can also be combined to produce variants with improved stability or expression, while retaining or enhancing activity.

The following list provides the substitutions with a performance index greater than 1 for either BMI, CS-38 microswatch assay, or AAPF activity and that had a performance index of greater than 0.8 for LAS stability or in a TCA assay (as used herein, "X" refers to any amino acid). These variants can be combined to improve activity while maintaining or enhancing stability or expression, or to improve stability or expression, while maintaining or enhancing activity: X001A, X001C, X001E, X001F, X001G, X001H, X001I, X001K, X001L, X001N, X001Q, X001R, X001S, X001T, X001V, X001Y, X002A, X002C, X002E, X002G, X002K, X002L, X002M, X002N, X002P, X002Q, X002R, X002S, X002T, X002V, X002W, X002Y, X003D, X003E, X003F, X003G, X003H, X003I, X003L, X003M, X003N, X003P, X003R, X003S, X003T, X003V, X003W, X003Y, X004A, X004C, X004D, X004E, X004F, X004H, X004K, X004L, X004N, X004P, X004R, X004S, X004T, X004V, X004W, X005A, X005C, X005D, X005E, X005G, X005P, X005Q, X005S, X005T, X007A, X007C, X007D, X007G, X007H, X007N, X007S, X007T, X008A, X008F, X008I, X008L, X008M, X008T, X008V, X009D, X009E, X009F, X009G, X009H, X009L, X009N, X009P, X009Q, X009R, X009S, X009T, X009V, X009W, X009Y, X010A, X010C, X010G, X010H, X010K, X010M, X010N, X010Q, X010R, X010S, X010T, X010W, X011A, X011I, X011M, X011S, X011V, X012D, X012F, X012G, X012H, X012I, X012K, X012L, X012M, X012N, X012Q, X012R, X012S, X012T, X012V, X012W, X013A, X013G, X013I, X013T, X013V, X014A, X014D, X014E, X014F, X014H, X014I, X014K, X014L, X014P, X014Q, X014S, X014T, X014V, X014Y, X015A, X015D, X015F, X015G, X015I, X015K, X015L, X015M, X015P, X015Q, X015R, X015S, X015V, X015W, X016A, X016G, X016L, X016N, X016P, X016Q, X016S, X016T, X016V, X017A, X017F, X017H, X017I, X017K, X017M, X017N, X017R, X017S, X017V, X017W, X017Y, X018A, X018C, X018D, X018E, X018F, X018G, X018H, X018K, X018L, X018M, X018N, X018P, X018Q, X018R, X018S, X018T, X018V, X018W, X018Y, X019A, X019C, X019D, X019E, X019F, X019G, X019H, X019K, X019L, X019M, X019N, X019R, X019S, X019T, X019V, X019W, X019Y, X020A, X020C, X020D, X020F, X020G, X020I, X020K, X020L, X020M, X020P, X020Q, X020R, X020S, X020T, X020V, X020W, X020Y, X021A, X021C, X021D, X021E, X021G, X021H, X021I, X021K, X021L, X021M, X021N, X021P, X021Q, X021R, X021S, X021T, X021V, X021W, X022A, X022C, X022G, X022I, X022K, X022L, X022M, X022N, X022P, X022Q, X022R, X022S, X022T, X022V, X022W, X022Y, X023A, X023G, X023S, X024A, X024C, X024D, X024F, X024G, X024H, X024L, X024M, X024N, X024P, X024Q, X024R, X024S, X024T, X024V, X024W, X025C, X025D, X025E, X025F, X025G, X025H, X025K, X025L, X025M, X025N, X025Q, X025R, X025S, X025T, X025V, X025W, X026C, X026F, X026G, X026I, X026L, X026M, X026N, X026P, X026R, X026S, X026T, X026V, X027A, X027C, X027D, X027F, X027G, X027I, X027K, X027L, X027M, X027N, X027P, X027R, X027S, X027T, X027V, X027W, X027Y, X028A, X028E, X028H, X028I, X028L, X028M, X028N, X028S, X028V, X029A, X029C, X029G, X029S, X029V, X030C, X030E, X030L, X030S, X030T, X030V, X031A, X031F, X031I, X031L, X031M, X031S, X031T, X031V, X033A, X033D, X033E, X033G, X033H, X033M, X033N, X033Q, X033S, X033T, X033Y, X035A, X035F, X035I, X035L, X035M, X035P, X036A, X036C, X036E, X036F, X036G, X036H, X036I, X036L, X036M, X036N, X036Q, X036R, X036S, X036T, X036V, X038C, X038F, X038G, X038H, X038I, X038K, X038L, X038M, X038N, X038Q, X038R, X038T, X038V, X038W, X038Y, X039H, X039V, X040A, X040C, X040D, X040E, X040G, X040H, X040I, X040K, X040L, X040M, X040N, X040P, X040R, X040S, X040T, X040V, X040W, X040Y, X041D, X041E, X042C, X042H, X042I, X042L, X042M, X042N, X042T, X042V, X043A, X043C, X043D, X043E, X043F, X043G, X043I, X043L, X043M, X043N, X043P, X043R, X043S, X043T, X043V, X043W, X043Y, X044A, X044C, X044D, X044G, X044I, X044K, X044L, X044M, X044N, X044P, X044Q, X044R, X044S, X044T, X044V, X044W, X044Y, X045A, X045D, X045F, X045G, X045H, X045I, X045K, X045L, X045M, X045N, X045P, X045Q, X045R, X045S, X045T, X045V, X045W, X045Y, X046C, X046D, X046E, X046F, X046G, X046H, X046I, X046K, X046L, X046M, X046N, X046P, X046Q, X046R, X046S, X046T, X046V, X046W, X047A, X047F, X047G, X047N, X047R, X047S, X047T, X047W, X048A, X048C, X048E, X048F, X048G, X048H, X048I, X048K, X048L, X048M, X048N, X048P, X048Q, X048R, X048S, X048T, X048V, X048Y, X049A, X049F, X049G, X049L, X049M, X049P, X049S, X049T, X050C, X050F, X050H, X050I, X050L, X050N, X050T, X050V, X050Y, X051F, X051G, X051H, X051K, X051L, X051N, X051P, X051R, X051S, X051T, X051V, X051W, X052A, X052C, X052E, X052F, X052G, X052H, X052I, X052L, X052M, X052N, X052P, X052Q, X052R, X052T, X052V, X052W, X052Y, X053A, X053C, X053D, X053E, X053G, X053H, X053K, X053L, X053M, X053P, X053Q, X053R, X053S, X053T, X053V, X053W, X053Y, X054A, X054C, X054D, X054E, X054F, X054I, X054M, X054N, X054Q, X054S, X054V, X055A, X055C, X055E, X055F, X055G, X055H, X055I, X055K, X055L, X055M, X055N, X055P, X055Q, X055S, X055T, X055W, X055Y, X056A, X056C, X056D, X056E, X056H, X056L, X056M, X056N, X056P, X056Q, X056S, X056T, X057A, X057C, X057E, X057F, X057G, X057H, X057I, X057K, X057L, X057M, X057N, X057P, X057Q, X057R, X057S, X057T, X057V, X057W, X057Y, X059A, X059C, X059D, X059E, X059F, X059G, X059I, X059L, X059M, X059N, X059P, X059Q, X059R, X059S, X059T, X059V, X059W, X059Y, X060D, X060S, X060V, X061A, X061C, X061D, X061F, X061G, X061H, X061I, X061L, X061M, X061N, X061P, X061R, X061S, X061T, X061V, X061Y, X062C, X062E, X062F, X062G, X062H, X062I, X062K, X062L, X062M, X062N, X062P, X062Q, X062R, X062S, X062T, X062V, X062Y, X063A, X063C, X063D, X063E, X063F, X063G, X063H, X063K, X063M, X063Q, X063R, X063S, X063W, X066K, X066S, X066T, X068I, X068T, X068V, X069A, X069E, X069G, X069N, X069S, X069T, X071A, X071I, X071N, X071T, X071V, X072C, X072F, X072I, X072L, X072M, X072T, X072V, X073A, X073C, X073D, X073E, X073H, X073K, X073L, X073N, X073S, X073T, X073V, X074A, X074C, X074S, X075A, X075H, X075I, X075L, X075M, X075N, X075P, X075Q, X075R, X075S, X075V, X076D, X076E, X076F, X076G, X076H, X076K, X076M, X076N, X076Q, X076R, X076S, X076T, X076W, X076Y, X077D, X077N, X078A, X078C, X078E, X078F, X078G, X078H, X078I, X078K, X078L, X078M, X078N, X078P, X078Q, X078R, X078S, X078T, X078V, X078Y, X079C, X079D, X079E, X079F, X079G, X079I, X079K, X079L, X079N, X079Q, X079R, X079S, X079T, X079V, X079W, X079Y, X081C, X081G, X081H, X081I, X081L, X081M, X081Q, X081S, X081T, X081V, X082A, X082E, X082F, X082K, X082L, X082M, X082Q, X082R, X082T, X082V, X082Y, X083G, X083S, X084C, X084E, X084G, X084I, X084L, X084M, X084N, X084T, X084V, X085A, X085C, X085I, X086A, X086C, X086D, X086E, X086G, X086P, X086S, X086W, X086Y, X087A, X087C, X087D, X087E, X087F, X087G, X087I, X087K, X087L, X087N, X087S, X087T, X087V, X087Y, X088A, X088C, X088D, X088G, X088Q, X088S, X088W, X089A, X089C, X089D, X089E, X089F, X089G, X089H, X089I, X089L, X089N, X089P, X089Q, X089R, X089S, X089T, X089V, X089W, X090A, X090C, X090F, X090G, X090I, X090K, X090L, X090M, X090Q, X090T, X090V, X091C, X091D, X091F, X091I, X091K, X091L, X091M, X091N, X091Q, X091R, X091S, X091T, X091V, X091W, X091Y, X092A, X092D, X092G, X092N, X092P, X092R, X092T, X092V, X093A, X093C, X093G, X093L, X093M, X093S, X093T, X093V, X093Y, X094K, X094N, X094Q, X094R, X095A, X095C, X095G, X095I, X095K, X095R, X095S, X095T, X095V, X095W, X096E, X096I, X096L. X096M, X096T, X097A, X097D, X097E, X097G, X097H, X097I, X097K, X097L, X097M, X097N, X097P, X097Q, X097R, X097S, X097T, X097V, X097Y, X098A, X098C, X098D, X098E, X098F, X098G, X098K, X098L, X098N, X098P, X098Q, X098R, X098S, X098T, X098V, X098Y, X099A, X099C, X099F, X099G, X099K, X099M, X099P, X099Q, X099R, X099S, X099T, X099V, X099Y, X100D, X100E, X100G, X100I, X100P, X100S, X100V, X100Y, X101A, X101D, X101E, X101F, X101G, X101H, X101I, X101K, X101N, X101P, X101Q, X101R, X101S, X101T, X101V, X101Y, X102A, X102C, X102D, X102G, X102N, X102T, X103A, X103D, X103E, X103F, X103G, X103I, X103L, X103N, X103P, X103Q, X103R, X103S, X103T, X103V, X103Y, X104A, X104C, X104D, X104E, X104F, X104H, X104I, X104L, X104P, X104R, X104S, X104T, X104V, X104W, X104Y, X105A, X105C, X105D, X105E, X105F, X105G, X105H, X105I, X105K, X105L, X105N, X105Q, X105R, X105S, X105T, X105V, X105W, X105Y, X106A, X106D, X106E, X106F, X106G, X106I, X106L, X106M, X106P, X106R, X106S, X106V, X106W, X107A, X107F, X107I, X107L, X107M, X107Q, X107S, X107T, X107V, X108A, X108G, X108I, X108L, X108S, X108T, X108V, X109A, X109C, X109E, X109F, X109G, X109H, X109I, X109K, X109L, X109M, X109N, X109Q, X109R, X109S, X109T, X109W, X109Y, X110A, X110G, X110S, X111C, X111E, X111F, X111I, X111L, X111M, X111V, X111Y, X112A, X112C, X112D, X112E, X112F, X112G, X112I, X112L, X112N, X112Q, X112S, X112T, X112V, X112W, X112Y, X114A, X114C, X114G, X114T, X115C, X115E, X115F, X115G, X115H, X115I, X115K, X115L, X115M, X105N, X105P, X105Q, X105R, X105S, X115T, X115V, X115W, X115Y, X116A, X116C, X116D, X116F, X116, X116I, X116K, X116L, X116M, X116N, X116Q, X116S, X116T, X116V, X116W, X117A, X117C, X117D, X117F, X117G, X117I, X117N, X117Q, X117R, X117T, X117Y, X118A, X118C, X118D, X118E, X118F, X118G, X118I, X118K, X118L, X118M, X118N, X118P, X118R, X118S, X118T, X118V, X118W, X119A, X119C, X119F, X119H, X119M, X119N, X119Q, X119T, X119W, X120A, X120C, X120E, X120F, X120G, X120H, X120L X120L, X120M, X120N, X120R, X120S, X120T, X120 W, X121A, X121C, X121E, X121F, X121G, X121I, X121L, X121M, X121Q, X121S, X121T, X121V, X121Y, X122A, X122C, X122G, X122I, X122L, X122S, X122T, X122V, X123G, X123N, X123S, X124G, X124L, X124S, X124T, X125A, X125S, X126A, X126F, X126L, X127F, X127G, X127I, X127R, X127S, X127T, X128A, X128G, X128I, X128K, X128L, X128M, X128N, X128Q, X128R, X128S, X128T, X128W, X129A, X129E, X129F, X129G, X129I, X129L, X129M, X129N, X129P, X129R, X129S, X129T, X129V, X129W, X129Y, X130C, X130K, X130L, X130N, X130Q, X130R, X130S, X130V, X130W, X130Y, X131A, X131D, X131E, X131F, X131G, X131I, X131K, X131L, X131P, X131Q, X131R, X131V, X132A, X132E, X132F, X132H, X132I, X132L, X132M, X132N, X132Q, X132S, X132T, X132W, X133A, X133F, X133K, X133L, X133N, X133P, X133Q, X133S, X133T, X133V, X133Y, X134A, X134F, X134I, X134L, X134M, X134P, X134S, X134T, X134V, X135C, X135E, X135L, X135M, X135W, X136A, X136E, X136F, X136K, X136Q, X136R, X136S, X136V, X136W, X136Y, X137A, X137C, X137E, X137G, X137H, X137K, X137L, X137M, X137Q, X137R, X137S, X137V, X137W, X138A, X138G, X138M, X138R, X138V, X139A, X139C, X139I, X139M, X139T, X139V, X140A, X140C, X140D, X140E, X140F, X140G, X140I, X140L, X140M, X140N, X140Q, X140R, X140S, X140T, X140V, X140Y, X141D, X141E, X141G, X141H, X141I, X141K, X141L, X141N, X141Q, X141R, X141S, X141V, X141Y, X142A, X142C, X142L, X142T, X142V, X142Y, X143C, X143D, X143F, X143G, X143H, X143I, X143K, X143L, X143M, X143N, X143S, X143T, X143V, X143W, X143Y, X144A, X144C, X144D, X144G, X144H, X144I, X144L, X144M, X144N, X144Q, X144R, X144S, X144T, X144V, X144W, X144Y, X145A, X145C, X145D, X145E, X145F, X145G, X145K, X145L, X145M, X145N, X145Q, X145R, X145S, X145T, X145W, X145Y, X146A, X146C, X146D, X146E, X146G, X146K, X146Q, X147I, X147L, X147M, X147T, X147V, X148A, X148C, X148E, X148F, X148H, X148I, X148L, X148M, X148N, X148S, X148T, X148V, X148Y, X149A, X149C, X149I, X149L, X149M, X149P, X149S, X149T, X149V, X150A, X150F, X150L, X150T, X150V, X151A, X151G, X151S, X152A, X152S, X153A, X153G, X153S, X153V, X156A, X156C, X156D, X156E, X156F, X156L, X156M, X156N, X156S, X156T, X158A, X158C, X158E, X158F, X158H, X158K, X158L, X158M, X158Q, X158R, X158S, X158T, X158V, X158W, X159A, X159C, X159E, X159G, X159H, X159M, X159P, X159Q, X159R, X159S, X159W, X160A, X160C, X160D, X160F, X160G, X160I, X160L, X160M, X160N, X160Q, X160R, X160S, X160T, X160V, X160Y, X165I, X165L, X165T, X165V, X166A, X166C, X166D, X166E, X166H, X166M, X166N, X166S, X167C, X167D, X167E, X167F, X167P, X167V, X167W, X167Y, X169A, X169G, X169S, X170A, X170D, X170E, X170G, X170H, X170K, X170L, X170P, X170Q, X170R, X170S, X170V, X170W, X170Y, X171C, X171F, X171L, X171N, X171Y, X172A, X172C, X172D, X172F, X172G, X172I, X172K, X172L, X172M, X172P, X172Q, X172R, X172S, X172T, X172V, X172Y, X173A, X173C, X173D, X173E, X173F, X173G, X173H, X173K, X173L, X173M, X173N, X173Q, X173R, X173T, X173V, X173W, X174A, X174G, X174S, X174T, X174V, X175A, X175C, X175I, X175L, X175M, X175Q, X175T, X175V, X175Y, X176A, X176G, X176S, X177A, X177C, X177I, X177T, X177V, X178A, X178G, X179A, X179G, X180C, X180I, X180L, X180S, X180T, X180V, X181D, X181N, X182A, X182D, X182E, X182F, X182G, X182H, X182I, X182K, X182L, X182M, X182N, X182P, X182Q, X182R, X182S, X182T, X182V, X182W, X182Y, X183A, X183D, X183F, X183G, X183H, X183I, X183K, X183L, X183M, X183N, X183Q, X183R, X183S, X183T, X183V, X183W, X183Y, X184D, X184N, X185A, X185C, X185E, X185F, X185G, X185H, X185I, X185K, X185L, X185M, X185N, X185Q, X185R, X185S, X185T, X185V, X185Y, X186H, X186I, X186K, X186L, X186R, X187A, X187P, X187W, X188A, X188D, X188E, X188F, X188G, X188H, X188I, X188K, X188L, X188P, X188Q, X188R, X188S, X188T, X188V, X188W, X188Y,

X191D, X191Q, X192W, X192Y, X194A, X194C, X194D, X194E, X194F, X194G, X194H, X194I, X194L, X194M, X194P, X194Q, X194R, X194S, X194T, X194V, X194W, X194Y, X195A, X195C, X195D, X195E, X195G, X195Q, X195Y, X196L, X196M, X197A, X197C, X197D, X197E, X197G, X197N, X197Q, X197S, X197T, X198A, X198F, X198G, X198H, X198I, X198L, X198M, X198N, X198R, X198S, X198T, X198Y, X199A, X199C, X199I, X199M, X199S, X199T, X199V, X200A, X200C, X200G, X200S, X203A, X203C, X203E, X203I, X203L, X203S, X203T, X203V, X204A, X204C, X204E, X204F, X204G, X204I, X204K, X204L, X204N, X204R, X204S, X204T, X204W, X204Y, X205I, X205T, X205V, X206A, X206C, X206D, X206E, X206G, X206H, X206I, X206K, X206L, X206N, X206P, X206Q, X206R, X206S, X206T, X206V, X206W, X206Y, X207A, X207S, X208C, X208L, X208S, X208T, X208V, X209A, X209C, X209F, X209G, X209H, X209I, X209K, X209L, X209M, X209N, X209R, X209S, X209V, X209W, X209Y, X210A, X210C, X210E, X210G, X210H, X210I, X210L, X210M, X210N, X210P, X210R, X210S, X210V, X210Y, X211A, X211C, X211E, X211F, X211G, X211H, X211I, X211L, X211M, X211P, X211Q, X211R, X211T, X211V, X211W, X211Y, X212C, X212F, X212G, X212H, X212I, X212M, X212N, X212P, X212R, X212S, X212T, X212V, X212Y, X213A, X213C, X213D, X213E, X213F, X213G, X213I, X213K, X213L, X213M, X213N, X213Q, X213R, X213S, X213T, X213V, X213W, X213Y, X214F, X214L, X214W, X214Y, X215A, X215C, X215D, X215E, X215F, X215G, X215H, X215I, X215K, X215M, X215N, X215P, X215R, X215S, X215T, X215V, X215W, X215Y, X216A, X216C, X216D, X216E, X216F, X216G, X216H, X216I, X216K, X216L, X216M, X216N, X216P, X216Q, X216R, X216S, X216V, X216W, X216Y, X217A, X217C, X217E, X217F, X217G, X217I, X217K, X217L, X217M, X217Q, X218C, X218D, X218E, X218F, X218G, X218H, X218I, X218M, X218N, X218Q, X218R, X218S, X218T, X218V, X218Y, X220S, X220T, X222A, X222M, X222Q, X223A, X223G, X223S, X224A, X224G, X224L, X224N, X224S, X224T, X225C, X225P, X226C, X226F, X226H, X226M, X226V, X227A, X227C, X227G, X227I, X227L, X227M, X227S, X227T, X227V, X228A, X228C, X228G, X228I, X228S, X228V, X229A, X229G, X229P, X229S, X230A, X230D, X230E, X230G, X230H, X230I, X230L, X230N, X230Q, X230S, X230T, X230V, X231A, X231C, X231F, X231G, X231H, X231I, X231L, X231S, X231T, X231Y, X232A, X232G, X232H, X232L, X232M, X232S, X232V, X233A, X233C, X233E, X233F, X233G, X233I, X233L, X233M, X233N, X233P, X233Q, X233S, X233T, X233V, X233Y, X234D, X234F, X234G, X234H, X234L, X234M, X234N, X234Q, X234S, X234T, X234V, X234Y, X235C, X235D, X235E, X235F, X235G, X235H, X235I, X235K, X235L, X235M, X235N, X235Q, X235R, X235S, X235V, X235W, X235Y, X236A, X236C, X236E, X236F, X236H, X236K, X236N, X236P, X236Q, X236R, X236S, X236T, X236V, X236W, X236Y, X237A, X237C, X237F, X237G, X237H, X237I, X237K, X237L, X237M, X237P, X237Q, X237R, X237S, X237T, X237V, X237W, X237Y, X238C, X238D, X238E, X238F, X238G, X238H, X238I, X238K, X238L, X238M, X238N, X238Q, X238R, X238S, X238T, X238V, X238Y, X239C, X239D, X239F, X239G, X239H, X239I, X239K, X239L, X239M, X239N, X239P, X239Q, X239R, X239S, X239T, X239V, X239W, X239Y, X240A, X240C, X240E, X240F, X240I, X240K, X240L, X240M, X240N, X240Q, X240R, X240S, X240T, X240W, X240Y, X241A, X241C, X241D, X241E, X241F, X241G, X241H, X241I, X241K, X241L, X241M, X241N, X241P, X241Q, X241R, X241S, X241T, X241V, X241W, X241Y, X242A, X242C, X242D, X242F, X242G, X242H, X242I, X242L, X242M, X242P, X242Q, X242R, X242S, X242T, X242V, X242W, X243C, X243D, X243E, X243F, X243G, X243H, X243I, X243K, X243L, X243M, X243N, X243P, X243Q, X243R, X243S, X243T, X243V, X243W, X244A, X244D, X244E, X244F, X244H, X244I, X244L, X244M, X244N, X244P, X244Q, X244R, X244S, X244T, X244V, X244W, X244Y, X245A, X245C, X245E, X245G, X245H, X245K, X245L, X245P, X245Q, X245R, X245S, X245V, X245W, X245Y, X246A, X246C, X246E, X246F, X246G, X246H, X246I, X246L, X246M, X246N, X246Q, X246S, X246T, X246V, X246W, X246Y, X247A, X247C, X247D, X247E, X247F, X247G, X247H, X247I, X247K, X247L, X247M, X247N, X247P, X247Q, X247R, X247S, X247T, X247V, X247W, X247Y, X248C, X248D, X248E, X248G, X248H, X248I, X248K, X248L, X248N, X248P, X248R, X248S, X248T, X248V, X248W, X248Y, X249A, X249D, X249E, X249F, X249G, X249H, X249I, X249K, X249L, X249M, X249N, X249Q, X249R, X249S, X249T, X249V, X249W, X249Y, X250A, X250C, X250F, X250I, X250L, X250M, X250Q, X250S, X250V, X251A, X251D, X251E, X251F, X251G, X251K, X251L, X251M, X251Q, X251R, X251T, X251V, X251Y, X252A, X252C, X252D, X252F, X252G, X252I, X252K, X252L, X252M, X252N, X252R, X252S, X252V, X252W, X252Y, X253A, X253D, X253E, X253F, X253G, X253H, X253I, X253K, X253M, X253R, X253S, X253T, X253V, X253W, X254A, X254C, X254G, X254S, X254T, X255A, X255C, X255D, X255E, X255F, X255H, X255I, X255L, X255N, X255P, X255Q, X255R, X255S, X255T, X255V, X255W, X255Y, X256A, X256C, X256D, X256E, X256G, X256H, X256I, X256K, X256L, X256M, X256N, X256P, X256R, X256S, X256T, X256V, X256W, X256Y, X257C, X257F, X257I, X257K, X257L, X257M, X257V, X258A, X258C, X258D, X258E, X258F, X258G, X258H, X258I, X258L, X258M, X258P, X258Q, X258R, X258S, X258T, X258V, X258W, X258Y, X259A, X259C, X259E, X259G, X259I, X259L, X259M, X259P, X259Q, X259R, X259S, X259T, X259V, X260A, X260D, X260E, X260F, X260H, X260I, X260L, X260M, X260N, X260P, X260R, X260S, X260T, X260V, X260Y, X261A, X261C, X261E, X261F, X261G, X261I, X261K, X261L, X261N, X261P, X261Q, X261R, X261S, X261T, X261V, X261W, X261Y, X262A, X262C, X262D, X262F, X262G, X262H, X262I, X262K, X262L, X262M, X262Q, X262R, X262S, X262T, X262V, X262W, X262Y, X263C, X263F, X263L, X263Y, X264A, X264G, X265A, X265C, X265D, X265F, X265G, X265H, X265K, X265M, X265Q, X265R, X265S, X265T, X265W, X265Y, X267G, X267I, X267L, X267M, X267N, X267V, X268A, X268G, X268H, X268L, X268M, X268N, X268P, X268Q, X268S, X268V, X269C, X269D, X269F, X269G, X269H, X269I, X269L, X269M, X269N, X269Q, X269R, X269S, X269T, X269V, X270A, X270C, X270D, X270G, X270I, X270L, X270M, X270N, X270S, X270T, X270V, X271A, X271C, X271E, X271F, X271G, X271H, X271I, X271K, X271L, X271M, X271N, X271P, X271T, X271V, X271Y, X272A, X272C, X272D, X272E, X272F, X272G, X272H, X272K, X272L, X272M, X272N, X272P, X272R, X272S, X272T, X272W, X272Y, X273A, X273C, X273D, X273E, X273F, X273G, X273H, X273I, X273L, X273S, X273T, X273V, X274A, X274C, X274D, X274E, X274G, X274H, X274L, X274M, X274N, X274P, X274Q, X274R, X274S, X274T, X274W, X275A, X275C, X275D, X275E, X275F, X275G, X275H, X275K, X275L, X275M, X275P, X275Q, X275R, X275V, and X275W.

In screens of GCI-P036 variants, at least one mutation in the following 204 positions was associated with a performance index greater than 0.8 for either BMI, EGG or AAPF activity and had a performance index of greater than 0.8 both LAS stability and in a TCA assay: 1, 3, 4, 8, 9, 10, 11, 12, 13, 15, 16, 17, 18, 19, 20, 21, 22, 23, 24, 25, 26, 27, 28, 29, 30, 31, 33, 35, 36, 38, 40, 43, 44, 45, 46, 47, 48, 49, 50, 51, 52, 53, 54, 55, 56, 57, 59, 61, 62, 68, 69, 72, 73, 76, 78, 84, 86, 87, 88, 89, 90, 91, 92, 93, 94, 95, 96, 97, 98, 99, 100, 101, 102, 103, 104, 105, 106, 107, 108, 109, 110, 111, 112, 114, 115, 116, 117, 118, 119, 120, 121, 122, 124, 126, 128, 129, 130, 131, 132, 133, 134, 135, 136, 137, 139, 140, 141, 142, 143, 144, 145, 146, 147, 148, 149, 150, 151, 152, 156, 158, 159, 160, 165, 166, 167, 170, 171, 172, 173, 174, 175, 176, 177, 180, 182, 183, 184, 185, 186, 187, 188, 191, 194, 195, 198, 199, 203, 204, 206, 209, 210, 211, 212, 213, 215, 216, 217, 218, 222, 223, 224, 227, 228, 230, 231, 232, 233, 234, 235, 236, 237, 238, 239, 240, 241, 242, 243, 244, 245, 246, 247, 248, 249, 250, 251, 252, 253, 255, 256, 258, 259, 260, 261, 262, 265, 267, 268, 269, 270, 271, 272, 273, 274, and 275.

Mutations at these positions can be combined to improve activity while maintaining either stability and/or expression. Mutations at these positions can also be combined to produce variants with improved stability and/or expression, while retaining or enhancing activity.

The following list provides the substitutions with a performance index greater than 0.8 for either BMI, CS-38 microswatch assay or AAPF activity assay, and that had a performance index of greater than 0.8 for LAS stability and in a TCA assay (as used herein, "X" refers to any amino acid). These variants can be combined to improve activity while maintaining or enhancing stability and/or expression, or to improve stability and/or expression, while maintaining or enhancing activity: X001A, X001E, X001G, X001H, X001Q, X001V, X003E, X003H, X003I, X003M, X003S, X003T, X003V, X004T, X004V, X008I, X008V, X009E, X009H, X009N, X009Q, X009S, X009T, X010A, X010C, X010G, X010H, X010K, X010M, X010N, X010R, X010S, X010T, X011I, X011V, X012G, X012I, X012N, X012Q, X012S, X012T, X012V, X013A, X013G, X015A, X015D, X015F, X015G, X015I, X015L, X015M, X015P, X015Q, X015S, X015V, X015W, X016A, X016G, X016N, X016P, X016S, X016T, X016V, X017H, X017I, X017M, X017N, X018A, X018C, X018D, X018E, X018G, X018H, X018L, X018M, X018N, X018P, X018Q, X018S, X018T, X018V, X018Y, X019A, X019C, X019D, X019E, X019F, X019G, X019H, X019K, X019L, X019M, X019N, X019R, X019S, X019V, X019W, X019Y, X020A, X020C, X020D, X020F, X020G, X020I, X020K, X020L, X020M, X020P, X020Q, X020R, X020S, X020T, X020V, X020W, X020Y, X021A, X021C, X021E, X021G, X021H, X021I, X021K, X021L, X021M, X021N, X021P, X021Q, X021S, X021T, X021V, X021W, X022A, X022C, X022G, X022I, X022L, X022M, X022N, X022P, X022Q, X022T, X022V, X022W, X023A, X023G, X023S, X024A, X024C, X024D, X024F, X024G, X024H, X024L, X024M, X024N, X024P, X024Q, X024R, X024S, X024T, X024V, X024W, X025C, X025D, X025E, X025F, X025G, X025K, X025L, X025M, X025Q, X025R, X025S, X025T, X025V, X025W, X026C, X026F, X026G, X026M, X026N, X026R, X026S, X026T, X026V, X027A, X027C, X027D, X027F, X027G, X027K, X027L, X027M, X027N, X027P, X027R, X027S, X027T, X027W, X028A, X028I, X028L, X028M, X028V, X029A, X029C, X029G, X029S, X029V, X030A, X030C, X030L, X030M, X030T, X030V, X031A, X031F, X031I, X031L, X031M, X031S, X031V, X033C, X033M, X033S, X033T, X035I, X035L, X035M, X035P, X036A, X036E, X036S, X036T, X036V, X038C, X038F, X038H, X038I, X038K, X038L, X038M, X038N, X038Q, X038R, X038T, X038V, X038Y, X040A, X040D, X040E, X040I, X040L, X040P, X040V, X043A, X043C, X043D, X043E, X043F, X043G, X043I, X043L, X043M, X043N, X043R, X043S, X043T, X043W, X043Y, X044A, X044C, X044D, X044F, X044G, X044I, X044K, X044L, X044M, X044N, X044Q, X044R, X044S, X044T, X044V, X044Y, X045A, X045D, X045F, X045G, X045H, X045I, X045K, X045L, X045M, X045N, X045P, X045Q, X045R, X045S, X045T, X045V, X045W, X045Y, X046C, X046D, X046E, X046G, X046H, X046I, X046K, X046L, X046M, X046N, X046P, X046Q, X046R, X046S, X046T, X046V, X047G, X047R, X048A, X048C, X048E, X048F, X048H, X048I, X048K, X048L, X048M, X048N, X048P, X048Q, X048R, X048S, X048T, X048V, X048Y, X049A, X049G, X049H, X049S, X049T, X050F, X050H, X050I, X050L, X050T, X050V, X050Y, X051F, X051H, X051K, X051L, X051R, X051S, X051T, X051V, X051W, X052A, X052C, X052E, X052F, X052G, X052H, X052I, X052L, X052M, X052N, X052P, X052Q, X052R, X052T, X052V, X052W, X052Y, X053A, X053C, X053D, X053E, X053G, X053H, X053K, X053L, X053M, X053Q, X053R, X053S, X053T, X053W, X053Y, X054A, X054C, X054D, X054E, X054F, X054H, X054M, X054N, X054Q, X054S, X055C, X055E, X055G, X055H, X055K, X055L, X055P, X055Q, X055S, X055T, X055W, X056A, X056C, X056D, X056E, X056H, X056L, X056M, X056N, X056P, X056Q, X056S, X056T, X057C, X057E, X057F, X057G, X057H, X057I, X057L, X057M, X057N, X057P, X057Q, X057R, X057S, X057T, X057V, X057W, X057Y, X059A, X059D, X059G, X059I, X059L, X059M, X059N, X059Q, X059R, X059S, X059T, X059V, X059W, X061A, X061C, X061D, X061F, X061G, X061H, X061I, X061L, X061M, X061N, X061P, X061R, X061S, X061T, X061V, X061Y, X062C, X062E, X062F, X062H, X062I, X062K, X062L, X062M, X062N, X062Q, X062R, X062S, X062T, X062V, X068I, X068L, X068V, X069A, X069G, X069S, X069T, X072I, X072L, X072T, X072V, X073A, X073C, X073S, X076D, X076N, X078A, X078C, X078E, X078H, X078L, X078M, X078N, X078Q, X078S, X078T, X084C, X084G, X084I, X084M, X084V, X086C, X086P, X087A, X087C, X087D, X087E, X087G, X087K, X087L, X087N, X087S, X087V, X088A, X088C, X088G, X088S, X089A, X089D, X089E, X089G, X089H, X089I, X089N, X089Q, X089R, X089S, X089T, X089W, X090C, X090I, X090L, X090M, X090Q, X090T, X090V, X091D, X091F, X091I, X091N, X091S, X091V, X091W, X091Y, X092A, X092G, X092P, X092R, X092V, X093A, X093C, X093G, X093L, X093M, X093T, X093V, X094K, X094R, X095A, X095C, X095I, X095S, X095V, X096F, X096I, X096L, X096M, X097A, X097D, X097E, X097F, X097G, X097H, X097K, X097L, X097M, X097N, X097P, X097Q, X097R, X097S, X097T, X097V, X097W, X097Y, X098A, X098C, X098D, X098E, X098F, X098G, X098K, X098L, X098N, X098P, X098Q, X098R, X098S, X098T, X098V, X098Y, X099A, X099C, X099F, X099G, X099K, X099M, X099P, X099Q, X099R, X099S, X099T, X099V, X099Y, X100D, X100E, X100G, X100I, X100K, X100N, X100R, X100S, X100T, X100V, X100Y, X101A, X101C, X101D, X101E, X101F, X101G, X101H, X101I, X101K, X101N, X101P, X101Q, X101R, X101S, X101T, X101V, X101Y, X102A, X102G, X102T, X103A, X103C, X103D, X103F, X103G, X103I, X103L, X103N, X103P, X103Q, X103R, X103S, X103T, X103V, X103W, X104C, X104F, X104H, X104I, X104L, X104R, X104S, X104T, X104V, X104W, X104Y, X105A, X105C, X105D, X105E, X105F, X105G, X105K, X105L, X105N, X105Q, X105R, X105S, X105T, X105V, X106A, X106D, X106E, X106G, X106I, X106L, X106R, X106S, X106T, X106V, X106W, X107A, X107C, X107F, X107I, X107L, X107M, X107Q, X107S, X107T, X107V, X108A, X108C, X108I, X108S, X108T, X108V, X109A, X109E, X109F, X109G, X109H, X109I, X109K, X109L, X109M, X109N, X109Q, X109R, X109S, X109T, X109W, X109Y, X110A, X110G, X111F, X111I, X111L, X111M, X112D, X112E, X112I, X112Q, X112V, X114A, X114C, X115C, X115E, X115G, X115L, X115M, X115P, X115Q, X115S, X115T, X115W, X115Y, X116A, X116C, X116D, X116F, X116G, X116I, X116K, X116L, X116M, X116N, X116Q, X116S, X116T, X116V, X116W, X117A, X117C, X117N, X117Q, X117R, X117T, X117Y, X118A, X118C, X118D, X118E, X118F, X118G, X118K, X118M, X118N, X118R, X118S, X118V, X118W, X119A, X119F, X119M, X119T, X120A, X120C, X120E, X120F, X120G, X120H, X120I, X120L, X120M, X120N, X120R, X120S, X120T, X120W, X121A, X121C, X121F, X121I, X121L, X121M, X121S, X121T, X121V, X122A, X122G, X122S, X122V, X124G, X124L, X124T, X126A, X126F, X126I, X126L, X126M, X126V, X128A, X128F, X128G, X128I, X128K, X128L, X128M, X128N, X128Q, X128R, X128S, X128T, X128W, X129A, X129E, X129F, X129G, X129M, X129N, X129P, X129R, X129S, X129Y, X130C, X130K, X130L, X130N, X130Q, X130R, X130S, X130V, X130W, X130Y, X131A, X131D, X131E, X131F, X131G, X131K, X131P, X131Q, X132A, X132H, X132I, X132N, X132Q, X132R, X132S, X132T, X133A, X133F, X133K, X133N, X133P, X133S, X133T, X133V, X133Y, X134A, X134S, X134T, X134V, X135L, X135M, X135W, X136E, X136Q, X137A, X137C, X137E, X137H, X137K, X137L, X137M, X137Q, X137R, X137S, X137W, X139C, X139I, X139V, X140D, X140E, X140N, X141D, X141E, X141G, X141H, X141I, X141K, X141L, X141N, X141Q, X141R, X141S, X141V, X141Y, X142A, X142C, X142V, X143C, X143D, X143F, X143H, X143N, X143T, X144A, X144C, X144D, X144G, X144H, X144I, X144L, X144M, X144N, X144R, X144S, X144T, X144V, X144Y, X145A, X145C, X145D, X145F, X145K, X145L, X145N, X145Q, X145R, X146D, X146G, X147I, X147L, X147T, X147V, X148C, X148I, X148L, X148M, X148N, X148V, X149C, X149I, X149L, X149V, X150A, X150L, X150T, X150V, X151A, X151S, X152A, X152S, X156D, X156E, X156L, X156N, X156S, X156T, X158A, X158C, X158E, X158F, X158H, X158K, X158L, X158M, X158Q, X158R, X158S, X158T, X158V, X159A, X159C, X159E, X159G, X159H, X159M, X159P, X159S, X160A, X160C, X160D, X160F, X160I, X160L, X160M, X160N, X160Q, X160S, X160T, X160V, X160Y, X165I, X165L, X165V, X166A, X166C, X166D, X166E, X166H, X166M, X166S, X166T, X167F, X167Y, X170A, X170D, X170E, X170G, X170H, X170K, X170Q, X170R, X170S, X170V, X170Y, X171C, X171Y, X172A, X172C, X172D, X172G, X172I, X172K, X172L, X172M, X172P, X172Q, X172R, X172S, X172V, X172Y, X173A, X173C, X173D, X173H, X173M, X173N, X173Q, X173T, X174A, X174S, X174T, X174V, X175L, X175M, X175V, X176A, X176S, X177C, X177V, X180T, X180V, X182A, X182D, X182E, X182Q, X183A, X183D, X183N, X183Q, X183S, X184D, X184N, X185A, X185C, X185E, X185H, X185K, X185M, X185N, X185Q, X185T, X185V, X186I, X186K, X186L, X186R, X187A, X187C, X188A, X188D, X188E, X188F, X188H, X188I, X188K, X188L, X188P, X188Q, X188S, X188T, X191A, X191D, X191Q, X191S, X194A, X194C, X194D, X194E, X194F, X194H, X194I, X194L, X194M, X194P, X194Q, X194R, X194S, X194T, X194W, X194Y, X195C, X195D, X195E, X195G, X195Q, X198I, X198L, X199C, X199M, X199S, X199V, X203C, X203E, X203T, X203V, X204A, X204C, X204E, X204G, X204N, X204S, X206D, X206E, X206H, X206L, X206N, X206Q, X206S, X209F, X209M, X209W, X209Y, X210A, X210C, X210I, X210L, X210M, X210N, X210P, X211A, X211C, X211E, X211G, X211H, X211I, X211M, X211P, X211Q, X211T, X211V, X212C, X212F, X212G, X212H, X212M, X212N, X212R, X212S, X212Y, X213A, X213D, X213E, X213N, X213Q, X213S, X213T, X215A, X215C, X215D, X215E, X215H, X215I, X215K, X215M, X215N, X215S, X215T, X215V, X215Y, X216A, X216C, X216D, X216E, X216F, X216H, X216I, X216L, X216M, X216N, X216Q, X216S, X216V, X216W, X216Y, X217A, X217C, X217D, X217E, X217F, X217K, X217L, X217M, X217Q, X218C, X218D, X218E, X218N, X218Q, X222C, X222M, X222S, X223A, X223S, X224A, X224N, X224S, X224T, X227A, X227C, X227V, X228A, X228G, X228S, X228V, X230A, X230G, X230N, X230S, X230T, X230V, X231A, X231C, X231F, X231G, X231S, X232A, X232L, X232M, X233A, X233C, X233E, X233G, X233I, X233L, X233N, X233Q, X233S, X233T, X233V, X234L, X234M, X234N, X234Q, X234S, X234T, X234V, X235C, X235F, X235G, X235H, X235I, X235K, X235L, X235M, X235N, X235Q, X235R, X235S, X235V, X235W, X235Y, X236A, X236C, X236E, X236F, X236H, X236N, X236Q, X236S, X236T, X236Y, X237A, X237C, X237F, X237G, X237H, X237I, X237K, X237L, X237M, X237Q, X237R, X237S, X237T, X237V, X237W, X237Y, X238C, X238D, X238E, X238F, X238G, X238H, X238I, X238K, X238L, X238M, X238N, X238Q, X238R, X238S, X238T, X238V, X238Y, X239C, X239D, X239F, X239G, X239H, X239K, X239L, X239M, X239N, X239P, X239Q, X239R, X239S, X239T, X239V, X239W, X239Y, X240A, X240C, X240E, X240F, X240I, X240K, X240M, X240N, X240Q, X240R, X240S, X240T, X240W, X240Y, X241A, X241C, X241D, X241E, X241F, X241G, X241H, X241I, X241K, X241L, X241M, X241N, X241Q, X241R, X241S, X241T, X241V, X241W, X241Y, X242A, X242C, X242D, X242G, X242H, X242I, X242L, X242M, X242P, X242Q, X242S, X242T, X242V, X243C, X243D, X243E, X243F, X243G, X243H, X243I, X243L, X243M, X243N, X243P, X243Q, X243S, X243T, X243V, X243W, X244D, X244E, X244F, X244H, X244I, X244L, X244M, X244N, X244Q, X244S, X244T, X244V, X244W, X245A, X245C, X245E, X245G, X245H, X245K, X245L, X245P, X245Q, X245S, X245V, X245W, X245Y, X246A, X246C, X246I, X246L, X246M, X246T, X246V, X247A, X247C, X247F, X247G, X247H, X247K, X247L, X247M, X247N, X247R, X247S, X247T, X247V, X247W, X247Y, X248C, X248D, X248E, X248G, X248H, X248I, X248L, X248N, X248P, X248R, X248S, X248T, X248V, X248Y, X249A, X249D, X249E, X249F, X249G, X249H, X249I, X249K, X249L, X249M, X249N, X249Q, X249S, X249T, X249W, X249Y, X250C, X250I, X250L, X250M, X250V, X251A, X251D, X251E, X251F, X251G, X251K, X251L, X251M, X251Q, X251R, X251T, X251V, X251Y, X252A, X252C, X252D, X252F, X252G, X252H, X252I, X252K, X252L, X252M, X252N, X252R, X252S, X252V, X252W, X253A, X253E, X253H, X253M, X253S, X253T, X253W, X255A, X255C, X255D, X255E, X255I, X255L, X255N, X255Q, X255T, X255V, X255Y, X256A, X256C, X256D, X256E, X256G, X256H, X256I, X256K, X256L, X256M, X256N, X256P, X256S, X256V, X256W, X256Y, X258D, X258G, X259A, X259C, X259E, X259P, X259Q, X259S, X260A, X260D, X260E, X260H, X260I, X260N, X260P, X260S, X260T, X260V, X261A, X261C, X261E, X261F, X261I, X261K, X261L, X261N, X261P, X261Q, X261S, X261T, X261V, X261W, X261Y, X262A, X262C, X262D, X262F, X262H, X262I, X262L, X262M, X262Q, X262T, X262V, X262Y, X265A, X265D, X265S, X267I, X267L, X268A, X268L, X268V, X269D, X269H, X269N, X269Q, X269S, X270A, X270C, X270G, X270I, X270L, X270N, X270S, X270T, X270V, X271C, X271E, X272A, X272C, X272D, X272E, X272F, X272G, X272H, X272L, X272M, X272N, X272P, X272S, X272T, X272W, X272Y, X273A, X273C, X273G, X273S, X274A, X274C, X274G, X274L, X274M, X274N, X274S, X274T, X275D, X275E, X275F, X275H, X275K, X275L, X275M, X275P, X275Q, X275R.

Example 6

Comparative Evaluation of Variant Protease Data

In this Example, results of experiments conducted to determine cleaning performance, LAS/EDTA stability, AAPF activity and protein content (tests of properties of interest) of BPN', GCI-P036 and variant proteases are compared. The detergents used and conditions used are provided in Example 1. In the following Tables, the "EGG" results refer to CS-38 microswatch assay results in CALGONIT® (WE ADW) as described in Table 1-1. As described throughout functionality of the variant proteases is quantified as a performance index (PI), which is the ratio of performance of a variant to a referencet protease. PI classifications used herein include: Up mutations (PI>1.0); Neutral mutations (PI>0.5); Non-deleterious mutations (PI>0.05); and Deleterious mutations (PI≤0.05). BPN' variants were produced and assayed as described in PCT/09/046,066 and PCT/US09/046,156, incorporated herein by reference in their entirety.

"Productive sites" are those having at least one Up mutation for any property. "Productive, non-restrictive" sites are those having ≥20% neutral mutations (PI>0.5) and at least one Up mutation (PI>1.0) for any property tested (besides protein expression). In Table 6-1 below, the results for variants that contain sites that meet the definition of a productive, non-restrictive site are shown as a percentage (%) of variants tested that meet the definition of an Up mutation (PI>1).

TABLE 6-1

Productive, Non-Restrictive Sites for BPN' and GG36

| Position (BPN #) | BPN' WT Residue | # BPN' Variants | BPN' TCA Assay | BPN' BMI pH 7/16° C. | BPN' BMI pH 8/16° C. | BPN' BMI pH 8/32° C. | BPN' LAS/ETDA Assay | BPN' AAPF Assay | GG36 WT Residue | # GG36 Variants | GG36 BMI pH 8/32° C. | GG36 EGG | GG36 LAS/EDTA Assay | GG36 AAPF Assay | GG36 TCA Assay |
|---|---|---|---|---|---|---|---|---|---|---|---|---|---|---|---|
| 1 | A | 19 | 63 | 21 | 47 | 32 | 26 | 32 | A | 16 | 44 | 38 | 6 | 94 | 88 |
| 2 | Q | 19 | 11 | 32 | 26 | 58 | 0 | 0 | Q | 15 | 20 | 73 | 0 | 100 | 100 |
| 3 | S | 19 | 84 | 21 | 32 | 32 | 21 | 26 | S | 15 | 13 | 20 | 20 | 100 | 100 |
| 4 | V | 19 | 26 | 26 | 74 | 26 | 5 | 42 | V | 15 | 33 | 53 | 0 | 93 | 93 |
| 5 | P | 19 | 0 | 42 | 37 | 42 | 0 | 11 | P | 16 | 56 | 56 | 0 | 38 | 44 |
| 6 | Y | 19 | 58 | 63 | 37 | 11 | 11 | 11 | W | 13 | 31 | 0 | 0 | 0 | 0 |
| 7 | G | 15 | 0 | 7 | 7 | 27 | 0 | 0 | G | 18 | 22 | 28 | 0 | 39 | 39 |
| 8 | V | 16 | 0 | 38 | 13 | 75 | 0 | 42 | I | 14 | 29 | 36 | 7 | 43 | 43 |
| 9 | S | 19 | 74 | 11 | 11 | 5 | 16 | 26 | S | 16 | 75 | 63 | 19 | 88 | 63 |
| 10 | Q | 19 | 74 | 11 | 21 | 11 | 5 | 16 | R | 17 | 88 | 47 | 29 | 41 | 35 |
| 11 | I | 19 | 16 | 37 | 26 | 21 | 5 | 16 | V | 15 | 53 | 33 | 0 | 27 | 27 |
| 12 | K | 19 | 79 | 11 | 16 | 16 | 79 | 11 | Q | 16 | 69 | 63 | 25 | 69 | 69 |
| 13 | A | 19 | 11 | 37 | 21 | 16 | 11 | 11 | A | 13 | 31 | 31 | 0 | 31 | 23 |
| 14 | P | 19 | 68 | 0 | 63 | 16 | 0 | 79 | P | 15 | 73 | 100 | 7 | 73 | 53 |
| 15 | A | 19 | 79 | 0 | 0 | 26 | 42 | 21 | A | 13 | 23 | 31 | 54 | 100 | 100 |
| 16 | L | 19 | 32 | 5 | 79 | 58 | 11 | 11 | A | 15 | 60 | 33 | 7 | 47 | 47 |
| 17 | H | 19 | 26 | 11 | 42 | 47 | 0 | 5 | H | 16 | 56 | 56 | 13 | 63 | 31 |
| 18 | S | 19 | 89 | 0 | 84 | 37 | 32 | 5 | N | 19 | 47 | 58 | 32 | 95 | 89 |
| 19 | Q | 19 | 21 | 42 | 26 | 11 | 21 | 42 | R | 18 | 89 | 44 | 89 | 83 | 67 |
| 20 | G | 19 | 16 | 0 | 84 | 58 | 21 | 26 | G | 16 | 19 | 13 | 50 | 100 | 94 |
| 21 | Y | 17 | 41 | 0 | 6 | 35 | 35 | 12 | L | 17 | 29 | 18 | 12 | 94 | 82 |
| 22 | T | 18 | 78 | 44 | 0 | 78 | 83 | 39 | T | 15 | 33 | 40 | 53 | 93 | 93 |
| 24 | S | 16 | 56 | 75 | 13 | 81 | 88 | 50 | S | 16 | 31 | 56 | 75 | 94 | 94 |
| 25 | N | 19 | 47 | 0 | 84 | 63 | 37 | 37 | G | 15 | 80 | 80 | 67 | 87 | 47 |
| 26 | V | 17 | 6 | 35 | 12 | 76 | 59 | 18 | V | 12 | 33 | 42 | 17 | 83 | 75 |
| 27 | K | 19 | 21 | 11 | 84 | 42 | 58 | 42 | K | 17 | 65 | 29 | 47 | 82 | 65 |
| 28 | V | 16 | 13 | 38 | 25 | 56 | 44 | 6 | V | 13 | 54 | 15 | 31 | 23 | 23 |
| 29 | A | 17 | 0 | 35 | 29 | 35 | 18 | 12 | A | 16 | 38 | 25 | 6 | 13 | 0 |
| 30 | V | 18 | 11 | 50 | 50 | 50 | 17 | 53 | V | 14 | 50 | 21 | 29 | 0 | 29 |
| 31 | I | 19 | 11 | 68 | 58 | 58 | 79 | 53 | L | 13 | 31 | 31 | 15 | 46 | 38 |
| 33 | S | 15 | 0 | 60 | 0 | 20 | 7 | 7 | T | 18 | 61 | 28 | 11 | 6 | 28 |
| 34 | G | 19 | 81 | 5 | 11 | 5 | 0 | 0 | T | 15 | 13 | 0 | 0 | 0 | 0 |
| 35 | I | 19 | 0 | 5 | 53 | 47 | 0 | 11 | G | 11 | 82 | 27 | 9 | 27 | 27 |
| 36 | D | 18 | 0 | 17 | 11 | 22 | 16 | 0 | I | 17 | 47 | 24 | 12 | 65 | 76 |
| 37 | S | 19 | 47 | 58 | 26 | 5 | 16 | 37 | S | — | — | — | — | — | — |
| 38 | S | 19 | 74 | 42 | 53 | 74 | 68 | 16 | T | 14 | 29 | 29 | 43 | 93 | 79 |
| 39 | H | 19 | 5 | 11 | 53 | 47 | 0 | 26 | H | 17 | 53 | 6 | 0 | 6 | 0 |
| 40 | P | 19 | 47 | 74 | 74 | 84 | 16 | 89 | H | 17 | 53 | 100 | 29 | 100 | 82 |
| 41 | D | 19 | 0 | 37 | 16 | 26 | 0 | 0 | P | 18 | 17 | 6 | 6 | 6 | 6 |
| 42 | L | 19 | 5 | 16 | 16 | 26 | 16 | 5 | D | 18 | 50 | 17 | 29 | 39 | 28 |
| 43 | K | 19 | 16 | 0 | 74 | 0 | 74 | 79 | L | 16 | 31 | 25 | 63 | 100 | 81 |
| 44 | V | 19 | 0 | 21 | 6 | 68 | 0 | 16 | N | 17 | 24 | 24 | 47 | 88 | 94 |
| 45 | A | 16 | 81 | 31 | 18 | 31 | 81 | 94 | I | 18 | 78 | 22 | 89 | 89 | 89 |
| 46 | G | 17 | 0 | 59 | 59 | 59 | 18 | 41 | R | 17 | 71 | 18 | 94 | 65 | 71 |
| 47 | G | 19 | 0 | 26 | 42 | 68 | 5 | 0 | G | 15 | 80 | 53 | 0 | 13 | 20 |

TABLE 6-1-continued

Productive, Non-Restrictive Sites for BPN' and GG36

| Position (BPN' #) | BPN' WT Residue | # BPN' Variants | BPN' TCA Assay | BPN' BMI pH 7/16° C. | BPN' BMI pH 8/16° C. | BPN' BMI pH 8/32° | BPN' LAS/ETDA Assay | BPN' AAPF Assay | GG36 WT Residue | # GG36 Variants | GG36 BMI pH 8/32° C. | GG36 EGG | GG36 LAS/EDTA Assay | GG36 AAPF Assay | GG36 TCA Assay |
|---|---|---|---|---|---|---|---|---|---|---|---|---|---|---|---|
| 48 | A | 17 | 65 | 35 | 12 | 29 | 65 | 24 | A | 17 | 76 | 35 | 76 | 88 | 94 |
| 49 | S | 18 | 0 | 22 | 22 | 39 | 6 | 0 | S | 12 | 92 | 33 | 25 | 8 | 8 |
| 50 | M | 17 | 6 | 82 | 6 | 41 | 65 | 65 | F | 11 | 64 | 45 | 73 | 36 | 45 |
| 51 | V | 19 | 0 | 42 | 68 | 63 | 26 | 0 | V | 11 | 73 | 9 | 18 | 55 | 55 |
| 52 | P | 19 | 0 | 74 | 95 | 89 | 5 | 0 | P | 16 | 75 | 100 | 38 | 94 | 69 |
| 53 | S | 19 | 74 | 37 | 63 | 26 | 53 | 16 | G | 17 | 53 | 12 | 12 | 76 | 82 |
| 54 | E | 19 | 0 | 53 | 53 | 47 | 0 | 0 | E | 18 | 28 | 17 | 22 | 39 | 78 |
| 55 | T | 19 | 53 | 21 | 42 | 0 | 79 | 47 | P | 18 | 56 | 22 | 33 | 72 | 83 |
| 56 | N | 19 | 5 | 68 | 74 | 63 | 5 | 0 | S | 15 | 67 | 40 | 33 | 60 | 73 |
| 57 | P | 19 | 5 | 68 | 84 | 63 | 0 | 0 | T | 18 | 44 | 44 | 39 | 100 | 83 |
| 58 | F | 19 | 11 | 63 | 89 | 32 | 11 | 16 | — | — | — | — | — | — | — |
| 59 | Q | 19 | 68 | 68 | 84 | 53 | 47 | 16 | Q | 18 | 44 | 22 | 11 | 78 | 78 |
| 60 | D | 19 | 5 | 68 | 58 | 32 | 0 | 0 | D | 17 | 88 | 53 | 0 | 0 | 0 |
| 61 | N | 19 | 100 | 5 | 53 | 21 | 68 | 68 | D | 15 | 47 | 27 | 87 | 100 | 73 |
| 62 | N | 19 | 74 | 53 | 42 | 26 | 74 | 16 | G | 16 | 75 | 69 | 31 | 75 | 94 |
| 63 | S | 19 | 89 | 58 | 21 | 21 | 32 | 32 | N | 16 | 81 | 31 | 0 | 31 | 50 |
| 66 | T | 14 | 5 | 47 | 0 | 0 | 0 | 0 | G | 14 | 71 | 7 | 7 | 0 | 7 |
| 67 | H | 19 | 79 | 0 | 0 | 0 | 0 | 0 | T | 17 | 18 | 0 | 0 | 0 | 53 |
| 68 | V | 19 | 26 | 42 | 26 | 26 | 11 | 5 | H | 19 | 26 | 5 | 5 | 11 | 53 |
| 69 | A | 19 | 0 | 58 | 11 | 26 | 5 | 5 | V | 18 | 67 | 17 | 0 | 11 | 6 |
| 71 | T | 19 | 5 | 32 | 47 | 47 | 0 | 5 | A | 18 | 67 | 39 | 0 | 11 | 17 |
| 72 | V | 17 | 6 | 65 | 71 | 53 | 6 | 0 | T | 16 | 50 | 38 | 13 | 31 | 31 |
| 73 | A | 17 | 6 | 59 | 59 | 65 | 0 | 18 | I | 14 | 57 | 71 | 7 | 71 | 36 |
| 74 | L | 19 | 11 | 68 | 5 | 11 | 0 | 0 | A | 15 | 13 | 13 | 0 | 13 | 13 |
| 75 | N | 19 | 32 | 11 | 11 | 63 | 0 | 68 | L | 17 | 100 | 88 | 0 | 76 | 24 |
| 76 | N | 19 | 32 | 11 | 5 | 42 | 0 | 58 | N | 16 | 38 | 63 | 6 | 75 | 63 |
| 77 | S | 19 | 0 | 63 | 11 | 21 | 5 | 0 | N | 16 | 88 | 6 | 0 | 6 | 0 |
| 78 | I | 19 | 84 | 74 | 16 | 26 | 42 | 32 | S | 18 | 67 | 89 | 44 | 94 | 72 |
| 79 | G | 19 | 74 | 0 | 74 | 42 | 5 | 21 | I | 17 | 71 | 71 | 0 | 94 | 53 |
| 80 | V | 19 | 0 | 0 | 21 | 32 | 0 | 0 | G | 12 | 92 | 0 | 0 | 0 | 0 |
| 81 | L | 19 | 21 | 11 | 5 | 74 | 0 | 0 | V | 18 | 72 | 44 | 15 | 22 | 39 |
| 82 | G | 19 | 0 | 79 | 72 | 83 | 0 | 17 | L | 16 | 56 | 69 | 14 | 44 | 38 |
| 84 | V | 18 | 16 | 78 | 0 | 5 | 0 | 26 | V | 16 | 56 | 31 | 0 | 44 | 38 |
| 85 | L | 19 | 0 | 0 | 13 | 7 | 25 | 0 | A | 11 | 18 | 18 | 0 | 0 | 0 |
| 86 | V | 15 | 21 | 11 | 71 | 93 | 6 | 17 | P | 13 | 77 | 62 | 15 | 46 | 15 |
| 87 | A | 15 | 0 | 20 | 38 | 69 | 16 | 57 | S | 14 | 50 | 50 | 14 | 93 | 86 |
| 88 | P | 14 | 69 | 79 | 88 | 50 | 7 | 25 | A | 14 | 71 | 43 | 0 | 43 | 7 |
| 89 | S | 16 | 5 | 94 | 74 | 53 | 58 | 44 | A | 17 | 71 | 76 | 12 | 71 | 41 |
| 90 | A | 19 | 0 | 69 | 71 | 71 | 16 | 32 | E | 16 | 56 | 31 | 13 | 38 | 31 |
| 91 | S | 19 | 5 | 58 | 74 | 63 | 7 | 14 | L | 15 | 93 | 67 | 47 | 47 | 33 |
| 92 | L | 14 | 0 | 79 | 74 | 60 | 58 | 5 | Y | 17 | 94 | 35 | 12 | 18 | 24 |
| 93 | Y | 19 | 7 | 26 | 53 | 40 | 20 | 0 | A | 15 | 38 | 19 | 56 | 19 | 19 |
| 94 | A | 15 | 0 | 53 | 40 | 40 | 13 | 7 | V | 16 | 67 | 11 | 0 | 0 | 11 |
| 95 | V | 15 | 0 | 40 | 44 | 19 | 17 | 11 | K | 18 | 38 | 11 | 22 | 11 | 22 |
| 96 | K | 16 | 6 | 25 | 6 | 11 | 12 | 0 | V | 18 | 56 | 25 | 31 | 13 | 75 |
| 97 | V | 18 | 6 | 17 | 29 | 53 | 59 | 11 | L | 16 | 13 | 11 | 67 | 0 | 89 |
| 98 | L | 17 | 35 | 71 | 53 | 94 | 12 | 6 | G | 18 | 50 | 50 | 60 | 61 | 73 |
|    | G | 17 | 42 | 94 | 63 | 63 | 32 | 47 | A | 15 | 60 | 53 |   | 93 |   |

TABLE 6-1-continued

Productive, Non-Restrictive Sites for BPN' and GG36

| Position (BPN' #) | BPN' WT Residue | # BPN' Variants | BPN' TCA Assay | BPN' BMI pH 7/16° C. | BPN' BMI pH 8/16° C. | BPN' BMI pH 8/32° | BPN' LAS/ETDA Assay | BPN' AAPF Assay | GG36 WT Residue | # GG36 Variants | GG36 BMI pH 8/32° C. | GG36 EGG | GG36 LAS/EDTA Assay | GG36 AAPF Assay | GG36 TCA Assay |
|---|---|---|---|---|---|---|---|---|---|---|---|---|---|---|---|
| 99 | D | 18 | 11 | 83 | 0 | 61 | 50 | 0 | S | 14 | 50 | 36 | 50 | 71 | 79 |
| 100 | G | 19 | 16 | 79 | 68 | 79 | 21 | 0 | G | 16 | 19 | 25 | 56 | 19 | 81 |
| 101 | S | 16 | 56 | 100 | 19 | 50 | 75 | 56 | S | 17 | 47 | 76 | 88 | 76 | 88 |
| 102 | G | 14 | 7 | 29 | 14 | 14 | 14 | 0 | G | 16 | 50 | 19 | 19 | 0 | 19 |
| 103 | Q | 16 | 50 | 63 | 38 | 19 | 69 | 19 | S | 16 | 50 | 50 | 56 | 56 | 63 |
| 104 | Y | 17 | 0 | 47 | 59 | 65 | 47 | 6 | V | 15 | 40 | 47 | 60 | 53 | 53 |
| 105 | S | 19 | 0 | 47 | 42 | 32 | 53 | 11 | S | 19 | 53 | 26 | 37 | 63 | 53 |
| 106 | W | 19 | 0 | 74 | 63 | 74 | 26 | 0 | S | 14 | 64 | 57 | 71 | 71 | 57 |
| 107 | I | 15 | 5 | 40 | 33 | 27 | 13 | 7 | I | 18 | 11 | 61 | 6 | 11 | 56 |
| 108 | I | 19 | 0 | 37 | 42 | 32 | 5 | 0 | A | 16 | 19 | 38 | 0 | 6 | 19 |
| 109 | N | 19 | 11 | 32 | 11 | 68 | 58 | 42 | Q | 18 | 50 | 78 | 39 | 13 | 39 |
| 110 | G | 16 | 0 | 19 | 25 | 19 | 0 | 0 | G | 17 | 6 | 6 | 0 | 78 | 6 |
| 111 | I | 19 | 5 | 37 | 21 | 42 | 11 | 0 | L | 16 | 44 | 25 | 6 | 6 | 13 |
| 112 | E | 19 | 0 | 42 | 21 | 53 | 63 | 0 | E | 17 | 76 | 29 | 24 | 18 | 12 |
| 113 | W | 19 | 0 | 5 | 42 | 21 | 26 | 17 | W | 13 | 0 | 0 | 46 | 0 | 0 |
| 114 | A | 18 | 0 | 33 | 33 | 33 | 11 | 16 | A | 11 | 18 | 18 | 9 | 9 | 9 |
| 115 | I | 19 | 0 | 79 | 42 | 79 | 26 | 74 | G | 17 | 53 | 76 | 18 | 94 | 82 |
| 116 | A | 19 | 53 | 47 | 47 | 47 | 58 | 47 | N | 14 | 86 | 43 | 29 | 100 | 79 |
| 117 | N | 19 | 5 | 53 | 42 | 68 | 58 | 68 | N | 11 | 64 | 73 | 73 | 73 | 45 |
| 118 | N | 19 | 32 | 26 | 58 | 32 | 26 | 17 | G | 13 | 76 | 88 | 76 | 47 | 47 |
| 119 | M | 18 | 0 | 50 | 44 | 28 | 33 | 5 | M | 17 | 46 | 23 | 69 | 23 | 15 |
| 120 | D | 19 | 17 | 47 | 56 | 37 | 68 | 0 | H | 13 | 69 | 92 | 69 | 100 | 85 |
| 121 | V | 19 | 47 | 57 | 68 | 5 | 21 | 5 | V | 15 | 80 | 33 | 27 | 53 | 40 |
| 122 | I | 19 | 5 | 24 | 16 | 47 | 32 | 0 | A | 12 | 58 | 50 | 0 | 25 | 33 |
| 123 | N | 19 | 0 | 41 | 42 | 47 | 6 | 5 | N | 12 | 17 | 8 | 0 | 0 | 42 |
| 124 | M | 18 | 17 | 63 | 58 | 39 | 0 | 0 | L | 12 | 50 | 25 | 0 | 8 | 17 |
| 126 | L | 14 | 21 | 11 | 44 | 43 | 11 | 0 | L | 18 | 0 | 11 | 22 | 0 | 83 |
| 127 | G | 17 | 53 | 0 | 36 | 0 | 14 | 0 | G | 12 | 8 | 42 | 8 | 0 | 67 |
| 128 | G | 17 | 12 | 29 | 0 | 29 | 0 | 0 | G | 12 | 18 | 24 | 82 | 59 | 94 |
| 129 | P | 19 | 58 | 41 | 35 | 53 | 6 | 32 | P | 14 | 21 | 7 | 7 | 100 | 93 |
| 130 | S | 19 | 74 | 63 | 37 | 11 | 16 | 42 | S | 10 | 30 | 40 | 40 | 80 | 90 |
| 131 | G | 19 | 5 | 11 | 16 | 11 | 53 | 32 | P | 12 | 58 | 17 | 17 | 58 | 83 |
| 132 | S | 19 | 5 | 0 | 32 | 11 | 16 | 0 | S | 12 | 75 | 75 | 8 | 58 | 25 |
| 133 | A | 19 | 21 | 53 | 53 | 47 | 16 | 58 | A | 10 | 60 | 30 | 50 | 80 | 80 |
| 134 | A | 19 | 0 | 21 | 5 | 0 | 63 | 21 | T | 12 | 67 | 25 | 25 | 17 | 8 |
| 135 | L | 13 | 8 | 42 | 26 | 26 | 58 | 0 | L | 13 | 54 | 8 | 8 | 15 | 15 |
| 136 | K | 19 | 5 | 62 | 46 | 46 | 15 | 26 | L | 15 | 12 | 47 | 0 | 41 | 35 |
| 137 | A | 19 | 21 | 68 | 42 | 26 | 21 | 89 | E | 17 | 62 | 69 | 38 | 77 | 69 |
| 138 | A | 19 | 0 | 47 | 16 | 16 | 53 | 32 | Q | 13 | 43 | 29 | 14 | 0 | 7 |
| 139 | V | 19 | 5 | 63 | 53 | 74 | 0 | 11 | A | 14 | 73 | 27 | 0 | 13 | 13 |
| 140 | D | 19 | 0 | 16 | 16 | 32 | 11 | 21 | V | 15 | 82 | 53 | 6 | 76 | 65 |
| 141 | K | 19 | 5 | 5 | 11 | 0 | 0 | 79 | N | 13 | 54 | 54 | 46 | 69 | 77 |
| 142 | A | 19 | 21 | 21 | 89 | 79 | 74 | 26 | S | 13 | 58 | 37 | 6 | 21 | 11 |
| 143 | V | 19 | 0 | 42 | 32 | 32 | 5 | 47 | A | 19 | 73 | 33 | 7 | 80 | 60 |
| 144 | A | 19 | 16 | 11 | 47 | 37 | 26 | 58 | T | 15 | 50 | 39 | 33 | 78 | 67 |
| 145 | S | 19 | 53 | 68 | 84 | 26 | 42 | 74 | S | 18 | 82 | 65 | 53 | 41 | 35 |
| 146 | G | 19 | 5 | 32 | 74 | 47 | 53 | 58 | G | 17 | 88 | 29 | 6 | 12 | 6 |

TABLE 6-1-continued

Productive, Non-Restrictive Sites for BPN' and GG36

| Position (BPN' #) | BPN' WT Residue | # BPN' Variants | BPN' TCA Assay | BPN' BMI pH 7/16° C. | BPN' BMI pH 8/16° C. | BPN' BMI pH 8/32° | BPN' LAS/ETDA Assay | BPN' AAPF Assay | GG36 WT Residue | # GG36 Variants | GG36 BMI pH 8/32° C. | GG36 EGG | GG36 LAS/EDTA Assay | GG36 AAPF Assay | GG36 TCA Assay |
|---|---|---|---|---|---|---|---|---|---|---|---|---|---|---|---|
| 147 | V | 16 | 6 | 88 | 94 | 50 | 56 | 38 | V | 12 | 42 | 8 | 8 | 33 | 33 |
| 148 | V | 17 | 0 | 47 | 65 | 65 | 18 | 6 | L | 18 | 56 | 39 | 0 | 56 | 39 |
| 149 | V | 16 | 0 | 44 | 69 | 63 | 88 | 19 | V | 17 | 71 | 18 | 24 | 24 | 6 |
| 150 | V | 18 | 0 | 17 | 44 | 50 | 28 | 11 | V | 14 | 64 | 29 | 0 | 29 | 14 |
| 151 | A | 17 | 40 | 18 | 35 | 35 | 6 | 0 | A | 13 | 15 | 8 | 0 | 8 | 31 |
| 152 | A | 15 | 0 | 7 | 7 | 13 | 0 | 0 | A | 13 | 8 | 8 | 0 | 0 | 23 |
| 153 | A | 19 | 0 | 26 | 26 | 21 | 0 | 0 | S | 13 | 23 | 0 | 0 | 15 | 31 |
| 154 | G | 19 | 0 | 0 | 0 | 0 | 0 | 0 | G | 16 | 0 | 6 | 0 | 0 | 0 |
| 155 | N | 17 | 35 | 0 | 0 | 0 | 13 | 56 | N | 14 | 0 | 0 | 0 | 0 | 79 |
| 156 | E | 16 | 44 | 0 | 0 | 6 | 0 | 11 | S | 18 | 33 | 6 | 0 | 11 | 61 |
| 157 | G | 19 | 0 | 5 | 0 | 0 | 0 | 21 | G | 14 | 0 | 11 | 0 | 0 | 14 |
| 158 | T | 19 | 16 | 74 | 16 | 16 | 16 | 11 | A | 14 | 29 | 21 | 36 | 86 | 93 |
| 159 | S | 19 | 37 | 74 | 63 | 63 | 32 | 21 | — | — | — | — | — | — | — |
| 160 | G | 19 | 11 | 11 | 11 | 11 | 5 | 5 | — | — | — | — | — | — | — |
| 161 | S | 19 | 53 | 58 | 53 | 32 | 37 | 47 | G | 17 | 35 | 29 | 18 | 47 | 47 |
| 162 | S | 19 | 32 | 63 | 74 | 16 | 37 | 37 | S | 15 | 27 | 27 | 53 | 87 | 87 |
| 163 | S | 19 | 5 | 21 | 11 | 5 | 0 | 0 | I | 17 | 6 | 12 | 6 | 6 | 59 |
| 164 | T | 17 | 0 | 12 | 5 | 29 | 0 | 0 | S | 16 | 38 | 38 | 19 | 6 | 75 |
| 165 | V | 15 | 0 | 7 | 13 | 33 | 7 | 0 | S | 17 | 32 | 16 | 0 | 11 | 47 |
| 166 | G | 16 | 63 | 0 | 6 | 6 | 69 | 0 | Y | 16 | 11 | 21 | 29 | 21 | 11 |
| 167 | Y | 18 | 5 | 58 | 84 | 74 | 6 | 0 | A | 19 | 93 | 32 | 0 | 16 | 21 |
| 168 | G | 19 | 6 | 11 | 6 | 11 | 11 | 6 | R | 14 | 63 | 56 | 25 | 94 | 81 |
| 169 | K | 18 | 11 | 100 | 83 | 50 | 0 | 11 | Y | 19 | 56 | 37 | 16 | 63 | 79 |
| 170 | Y | 18 | 0 | 33 | 22 | 33 | 11 | 0 | A | 16 | 32 | 17 | 6 | 17 | 22 |
| 171 | P | 17 | 0 | 88 | 71 | 76 | 0 | 76 | N | 19 | 50 | 38 | 0 | 50 | 38 |
| 172 | S | 19 | 0 | 68 | 37 | 74 | 24 | 26 | A | 18 | 19 | 13 | 0 | 13 | 38 |
| 173 | V | 19 | 0 | 32 | 21 | 42 | 5 | 16 | M | 16 | 41 | 12 | 0 | 24 | 24 |
| 174 | I | 19 | 5 | 42 | 26 | 37 | 0 | 11 | A | 16 | 53 | 24 | 24 | 5 | 6 |
| 175 | A | 19 | 0 | 11 | 5 | 21 | 5 | 5 | Y | 17 | 5 | 12 | 0 | 0 | 37 |
| 176 | V | 19 | 5 | 5 | 11 | 26 | 11 | 0 | V | 19 | 6 | 6 | 0 | 0 | 0 |
| 177 | G | 17 | 0 | 0 | 6 | 12 | 0 | 0 | G | 16 | 14 | 7 | 0 | 6 | 6 |
| 178 | A | 19 | 11 | 11 | 5 | 16 | 0 | 0 | A | 14 | 47 | 7 | 0 | 0 | 0 |
| 179 | V | 19 | 5 | 32 | 16 | 53 | 0 | 16 | T | 15 | 0 | 33 | 0 | 20 | 20 |
| 180 | D | 19 | 0 | 5 | 5 | 32 | 16 | 16 | D | 12 | 17 | 33 | 11 | 8 | 8 |
| 181 | S | 19 | 32 | 53 | 79 | 42 | 32 | 53 | Q | 18 | 18 | 29 | 6 | 100 | 100 |
| 182 | S | 19 | 53 | 42 | 58 | 42 | 11 | 42 | N | 15 | 61 | 11 | 6 | 94 | 88 |
| 183 | N | 19 | 5 | 53 | 74 | 47 | 16 | 53 | N | 18 | 41 | 24 | 24 | 6 | 6 |
| 184 | Q | 19 | 11 | 47 | 63 | 53 | 5 | 84 | R | 17 | 53 | 12 | 24 | 94 | 88 |
| 185 | R | 19 | 0 | 89 | 95 | 79 | 16 | 0 | A | 19 | 5 | 16 | 0 | 12 | 6 |
| 186 | A | 19 | 11 | 68 | 74 | 26 | 5 | 11 | S | 16 | 6 | 0 | 19 | 5 | 37 |
| 187 | S | 19 | 47 | 32 | 84 | 26 | 0 | 32 | F | 16 | 6 | 0 | 0 | 100 | 100 |
| 188 | F | 17 | 29 | 24 | 12 | 29 | 11 | 0 | S | 19 | 6 | 12 | 0 | 0 | 88 |
| 189 | S | 19 | 0 | 21 | 26 | 16 | 0 | 5 | Q | 16 | 6 | 0 | 13 | 0 | 84 |
| 190 | Q | 19 | 5 | 5 | 11 | 11 | 0 | 0 | Y | 17 | 6 | 12 | 6 | 0 | 75 |
| 191 | Y | 19 | 0 | 32 | 53 | 26 | 0 | 5 | G | 15 | 0 | 0 | 0 | 0 | 53 |
| 192 | G | 19 | 0 | 21 | 11 | 0 | 0 | 0 | A | 17 | 18 | 35 | 35 | 94 | 94 |
| 193 | P | 19 | 0 | 74 | 47 | 68 | 0 | 68 | A | 17 | 18 | 35 | 35 | 94 | 94 |

TABLE 6-1-continued

Productive, Non-Restrictive Sites for BPN' and GG36

| Position (BPN' #) | BPN' WT Residue | # BPN' Variants | BPN' TCA Assay | BPN' BMI pH 7/16° C. | BPN' BMI pH 8/16° C. | BPN' BMI pH 8/32° | BPN' LAS/ETDA Assay | BPN' AAPF Assay | GG36 WT Residue | # GG36 Variants | GG36 BMI pH 8/32° C. | GG36 EGG | GG36 LAS/EDTA Assay | GG36 AAPF Assay | GG36 TCA Assay |
|---|---|---|---|---|---|---|---|---|---|---|---|---|---|---|---|
| 195 | E | 19 | 0 | 32 | 11 | 21 | 0 | 0 | G | 16 | 56 | 44 | 13 | 13 | 19 |
| 196 | L | 19 | 0 | 21 | 21 | 26 | 5 | 5 | L | 14 | 21 | 14 | 0 | 7 | 43 |
| 197 | D | 15 | 0 | 27 | 40 | 47 | 11 | 0 | D | 18 | 83 | 50 | 0 | 44 | 39 |
| 198 | V | 18 | 0 | 6 | 33 | 33 | 0 | 17 | I | 17 | 41 | 12 | 0 | 59 | 59 |
| 199 | M | 18 | 0 | 50 | 28 | 33 | 0 | 6 | V | 17 | 47 | 29 | 12 | 29 | 29 |
| 200 | A | 19 | 0 | 42 | 16 | 32 | 0 | 16 | A | 11 | 36 | 27 | 0 | 18 | 18 |
| 201 | P | 18 | 0 | 44 | 44 | 78 | 0 | 22 | P | 16 | 31 | 13 | 0 | 0 | 0 |
| 202 | V | 18 | 0 | 33 | 38 | 67 | 17 | 50 | V | 16 | 75 | 19 | 13 | 19 | 25 |
| 203 | S | 16 | 0 | 13 | 0 | 0 | 31 | 44 | N | 14 | 14 | 29 | 7 | 93 | 93 |
| 204 | I | 19 | 0 | 16 | 11 | 32 | 5 | 11 | V | 15 | 33 | 13 | 13 | 7 | 13 |
| 205 | Q | 19 | 68 | 53 | 32 | 84 | 26 | 16 | Q | 18 | 67 | 28 | 17 | 94 | 44 |
| 206 | S | 19 | 0 | 5 | 5 | 0 | 0 | 0 | S | 18 | 11 | 11 | 0 | 6 | 0 |
| 207 | T | 19 | 0 | 37 | 37 | 37 | 0 | 21 | T | 18 | 39 | 22 | 0 | 22 | 11 |
| 208 | L | 19 | 0 | 32 | 21 | 37 | 0 | 32 | T | 18 | 83 | 67 | 29 | 89 | 44 |
| 209 | P | 19 | 5 | 74 | 42 | 68 | 0 | 11 | Y | 17 | 100 | 100 | 20 | 94 | 24 |
| 210 | G | 19 | 0 | 79 | 79 | 53 | 21 | 37 | P | 15 | 53 | 67 | 38 | 93 | 93 |
| 211 | N | 19 | 26 | 42 | 42 | 32 | 5 | 16 | G | 13 | 46 | 46 | 6 | 92 | 92 |
| 212 | K | 17 | 47 | 94 | 100 | 18 | 94 | 29 | S | 18 | 22 | 39 | 0 | 94 | 94 |
| 213 | Y | 18 | 0 | 72 | 50 | 44 | 0 | 0 | T | 18 | 100 | 39 | 41 | 22 | 17 |
| 214 | G | 19 | 11 | 68 | 26 | 32 | 11 | 21 | Y | 17 | 71 | 59 | 33 | 100 | 94 |
| 215 | A | 19 | 42 | 32 | 42 | 37 | 53 | 58 | A | 18 | 56 | 72 | 25 | 100 | 100 |
| 216 | Y | 19 | 32 | 47 | 26 | 58 | 53 | 32 | S | 18 | 50 | 81 | 24 | 6 | 19 |
| 217 | N | 19 | 0 | 26 | 11 | 16 | 16 | 0 | L | 16 | 76 | 76 | 0 | 88 | 35 |
| 218 | G | 19 | 5 | 0 | 0 | 0 | 0 | 0 | N | 17 | 0 | 0 | 0 | 0 | 6 |
| 219 | T | 19 | 5 | 5 | 5 | 5 | 5 | 5 | G | 15 | 7 | 7 | 0 | 0 | 33 |
| 220 | S | 18 | 67 | 0 | 0 | 17 | 28 | 0 | T | 17 | 6 | 12 | 12 | 6 | 94 |
| 222 | M | 18 | 5 | 11 | 26 | 42 | 0 | 6 | M | 18 | 11 | 6 | 0 | 18 | 17 |
| 223 | A | 19 | 11 | 37 | 0 | 0 | 5 | 5 | A | 17 | 29 | 18 | 12 | 0 | 35 |
| 224 | S | 19 | 42 | 0 | 26 | 42 | 11 | 0 | T | 16 | 0 | 6 | 11 | 0 | 33 |
| 225 | P | 19 | 16 | 58 | 0 | 0 | 38 | 15 | P | 18 | 75 | 44 | 0 | 6 | 6 |
| 226 | H | 19 | 0 | 18 | 53 | 63 | 27 | 0 | H | 16 | 50 | 25 | 0 | 44 | 44 |
| 227 | V | 19 | 0 | 37 | 47 | 26 | 21 | 16 | V | 16 | 18 | 6 | 12 | 29 | 24 |
| 228 | A | 16 | 32 | 32 | 32 | 38 | 21 | 0 | A | 17 | 20 | 13 | 0 | 13 | 7 |
| 229 | G | 19 | 47 | 32 | 21 | 5 | 68 | 32 | G | 15 | 19 | 50 | 6 | 69 | 44 |
| 230 | A | 19 | 42 | 26 | 5 | 58 | 26 | 32 | A | 16 | 81 | 25 | 6 | 50 | 50 |
| 231 | A | 19 | 79 | 37 | 47 | 58 | 37 | 42 | A | 16 | 19 | 30 | 20 | 30 | 20 |
| 232 | A | 19 | 0 | 58 | 58 | 23 | 58 | 58 | A | 10 | 60 | 81 | 6 | 75 | 31 |
| 233 | L | 13 | 0 | 38 | 54 | 18 | 84 | 26 | L | 16 | 94 | 33 | 8 | 75 | 75 |
| 234 | I | 11 | 0 | 18 | 36 | 26 | 27 | 53 | V | 12 | 58 | 63 | 56 | 88 | 88 |
| 235 | L | 19 | 32 | 37 | 32 | 47 | 21 | 42 | V | 16 | 88 | 88 | 13 | 88 | 50 |
| 236 | S | 19 | 47 | 32 | 21 | 32 | 68 | 32 | K | 16 | 94 | 71 | 65 | 88 | 82 |
| 237 | K | 19 | 42 | 26 | 37 | 26 | 26 | 42 | Q | 17 | 94 | 71 | 47 | 94 | 88 |
| 238 | H | 19 | 79 | 37 | 47 | 42 | 37 | 58 | K | 17 | 71 | 82 | 65 | 100 | 82 |
| 239 | P | 19 | 0 | 58 | 16 | 47 | 58 | 26 | N | 17 | 71 | 71 | 14 | 93 | 79 |
| 240 | N | 19 | 42 | 58 | 11 | 47 | 84 | 53 | P | 17 | 71 | 82 | 47 | 95 | 84 |
| 241 | W | 19 | 0 | 68 | 21 | 79 | 79 | 42 | W | 19 | 42 | 93 | 63 | 100 | 73 |
| 242 | T | 19 | 32 | 16 | 74 | 32 | 63 | 58 | S | 15 | 33 | 63 | 14 | 93 | 73 |
| 243 | N | 19 | 11 | 11 | 63 | 37 | 89 | 21 | N | 18 | 39 | 50 | 39 | 94 | 89 |

TABLE 6-1-continued

Productive, Non-Restrictive Sites for BPN' and GG36

| Position (BPN' #) | BPN' WT Residue | # BPN' Variants | BPN' TCA Assay | BPN' BMI pH 7/16° C. | BPN' BMI pH 8/16° C. | BPN' BMI pH 8/32° | BPN' LAS/ETDA Assay | BPN' AAPF Assay | GG36 WT Residue | # GG36 Variants | GG36 BMI pH 8/32° C. | GG36 EGG | GG36 LAS/EDTA Assay | GG36 AAPF Assay | GG36 TCA Assay |
|---|---|---|---|---|---|---|---|---|---|---|---|---|---|---|---|
| 244 | T | 19 | 47 | 16 | 74 | 53 | 68 | 37 | V | 16 | 56 | 75 | 63 | 94 | 81 |
| 245 | Q | 19 | 16 | 11 | 79 | 26 | 84 | 32 | Q | 13 | 62 | 77 | 46 | 100 | 77 |
| 246 | V | 17 | 6 | 18 | 35 | 18 | 18 | 12 | I | 17 | 76 | 24 | 29 | 35 | 35 |
| 247 | R | 19 | 0 | 53 | 74 | 42 | 0 | 0 | R | 19 | 53 | 68 | 21 | 84 | 79 |
| 248 | S | 19 | 47 | 37 | 79 | 42 | 32 | 58 | N | 16 | 69 | 56 | 31 | 94 | 88 |
| 249 | S | 19 | 42 | 5 | 68 | 37 | 5 | 42 | H | 18 | 17 | 28 | 39 | 29 | 83 |
| 250 | L | 19 | 0 | 26 | 32 | 26 | 0 | 16 | L | 17 | 65 | 12 | 0 | 86 | 24 |
| 251 | E | 19 | 0 | 37 | 11 | 63 | 0 | 0 | K | 16 | 64 | 50 | 50 | 88 | 64 |
| 252 | N | 19 | 21 | 58 | 37 | 74 | 53 | 42 | N | 16 | 38 | 81 | 63 | 93 | 75 |
| 253 | T | 19 | 16 | 53 | 58 | 68 | 11 | 16 | T | 14 | 36 | 29 | 7 | 22 | 79 |
| 254 | T | 19 | 16 | 53 | 47 | 63 | 11 | 5 | A | 18 | 39 | 22 | 0 | 94 | 11 |
| 255 | T | 19 | 26 | 58 | 53 | 37 | 0 | 42 | T | 17 | 18 | 29 | 35 | 40 | 94 |
| 256 | K | 19 | 11 | 89 | 95 | 58 | 0 | 68 | S | 17 | 47 | 82 | 35 | 100 | 65 |
| 257 | L | 19 | 0 | 47 | 53 | 32 | 0 | 16 | L | 15 | 87 | 40 | 0 | 40 | 13 |
| 258 | G | 17 | 0 | 47 | 82 | 94 | 0 | 0 | G | 17 | 82 | 59 | 0 | 82 | 53 |
| 259 | D | 19 | 21 | 5 | 0 | 11 | 0 | 89 | S | 12 | 83 | 100 | 8 | 100 | 25 |
| 260 | S | 19 | 26 | 21 | 63 | 37 | 0 | 47 | T | 14 | 64 | 86 | 21 | 100 | 79 |
| 261 | F | 19 | 0 | 63 | 32 | 11 | 5 | 0 | N | 16 | 56 | 88 | 63 | 100 | 75 |
| 262 | Y | 19 | 11 | 0 | 26 | 37 | 0 | 0 | L | 17 | 71 | 71 | 35 | 94 | 88 |
| 263 | Y | 19 | 5 | 26 | 32 | 26 | 0 | 5 | Y | 15 | 93 | 33 | 0 | 13 | 7 |
| 264 | G | 19 | 0 | 37 | 5 | 16 | 0 | 0 | G | 14 | 79 | 7 | 0 | 7 | 0 |
| 265 | K | 19 | 21 | 84 | 84 | 58 | 47 | 11 | S | 18 | 83 | 83 | 6 | 72 | 44 |
| 266 | G | 19 | 0 | 0 | 5 | 5 | 0 | 0 | G | 17 | 6 | 0 | 0 | 0 | 0 |
| 267 | L | 18 | 0 | 61 | 83 | 89 | 11 | 56 | L | 17 | 76 | 41 | 6 | 41 | 6 |
| 268 | I | 19 | 0 | 26 | 37 | 37 | 5 | 5 | V | 15 | 53 | 13 | 0 | 53 | 47 |
| 269 | N | 19 | 5 | 32 | 26 | 63 | 11 | 5 | N | 13 | 85 | 85 | 8 | 100 | 69 |
| 270 | V | 18 | 17 | 11 | 50 | 33 | 17 | 6 | A | 17 | 88 | 71 | 0 | 65 | 35 |
| 271 | Q | 19 | 53 | 32 | 32 | 79 | 47 | 26 | E | 14 | 29 | 100 | 0 | 100 | 64 |
| 272 | A | 19 | 26 | 16 | 68 | 32 | 37 | 16 | A | 16 | 69 | 63 | 25 | 100 | 69 |
| 273 | A | 13 | 0 | 69 | 85 | 100 | 0 | 0 | A | 15 | 100 | 73 | 7 | 73 | 27 |
| 274 | A | 19 | 5 | 42 | 0 | 53 | 16 | 26 | T | 15 | 87 | 80 | 13 | 87 | 60 |
| 275 | Q | 19 | 26 | 47 | 53 | 47 | 58 | 26 | R | 14 | 86 | 50 | 79 | 71 | 50 |

"Highly productive" sites are those having ≥20% Up mutations (PI>1) for at least one property other than protein expression (e.g., as indicated in a TCA assay). In Table 6-2 below, the results for variants that contain sites that meet the definition of a highly productive site are shown as a percentage (%) of variants tested that meet the definition of an Up mutation (PI>1).

TABLE 6-2

Highly Productive Sites for BPN' and GG36

| Position (BPN #) | BPN' WT Residue | # BPN' Variants | BPN' TCA Assay | BPN' BMI pH 7/16° C. | BPN' BMI pH 8/16° C. | BPN' BMI pH 8/32° C. | BPN' LAS/EDTA Assay | BPN' AAPF Assay | GG36 WT Residue | # GG36 Variants | GG36 BMI pH 8/32° C. | GG36 Egg | GG36 LAS/EDTA Assay | GG36 AAPF Assay | GG36 TCA Assay |
|---|---|---|---|---|---|---|---|---|---|---|---|---|---|---|---|
| 1 | A | 19 | 63 | 21 | 47 | 32 | 26 | 32 | A | 16 | 44 | 38 | 6 | 94 | 88 |
| 2 | Q | 19 | 11 | 32 | 26 | 58 | 0 | 0 | Q | 15 | 20 | 73 | 0 | 100 | 100 |
| 3 | S | 19 | 84 | 21 | 32 | 32 | 21 | 26 | S | 15 | 13 | 20 | 20 | 100 | 100 |
| 4 | V | 19 | 26 | 26 | 74 | 26 | 5 | 42 | V | 16 | 33 | 53 | 0 | 93 | 93 |
| 5 | P | 19 | 0 | 42 | 37 | 42 | 0 | 11 | P | 16 | 56 | 56 | 0 | 38 | 44 |
| 6 | Y | 19 | 58 | 63 | 37 | 11 | 11 | 11 | W | 13 | 31 | 0 | 0 | 0 | 0 |
| 7 | G | 15 | 0 | 7 | 7 | 27 | 0 | 0 | G | 18 | 22 | 28 | 0 | 39 | 39 |
| 8 | V | 19 | 74 | 38 | 13 | 75 | 16 | 42 | I | 14 | 29 | 36 | 7 | 43 | 43 |
| 9 | S | 19 | 74 | 11 | 11 | 5 | 5 | 26 | S | 16 | 75 | 63 | 19 | 88 | 63 |
| 10 | Q | 19 | 16 | 37 | 21 | 11 | 5 | 16 | R | 17 | 88 | 47 | 29 | 41 | 35 |
| 11 | I | 19 | 16 | 11 | 16 | 21 | 11 | 16 | V | 15 | 53 | 33 | 0 | 27 | 27 |
| 12 | K | 19 | 79 | 37 | 21 | 16 | 79 | 11 | Q | 16 | 69 | 63 | 25 | 69 | 69 |
| 13 | A | 19 | 11 | 11 | 21 | 16 | 11 | 11 | A | 13 | 31 | 31 | 0 | 31 | 23 |
| 14 | P | 19 | 68 | 37 | 63 | 16 | 0 | 79 | P | 15 | 73 | 100 | 7 | 73 | 53 |
| 15 | A | 19 | 79 | 0 | 0 | 26 | 42 | 21 | A | 13 | 23 | 31 | 54 | 100 | 100 |
| 16 | L | 19 | 32 | 0 | 79 | 58 | 11 | 11 | A | 15 | 60 | 33 | 7 | 47 | 47 |
| 17 | H | 19 | 26 | 5 | 42 | 47 | 0 | 5 | H | 16 | 56 | 56 | 13 | 63 | 31 |
| 18 | S | 19 | 89 | 11 | 84 | 37 | 32 | 5 | N | 19 | 47 | 58 | 32 | 95 | 89 |
| 19 | Q | 19 | 21 | 42 | 26 | 11 | 21 | 42 | R | 18 | 89 | 44 | 89 | 83 | 67 |
| 20 | G | 19 | 16 | 0 | 84 | 58 | 21 | 26 | G | 16 | 19 | 13 | 50 | 100 | 94 |
| 21 | Y | 17 | 41 | 0 | 6 | 35 | 35 | 12 | L | 17 | 29 | 18 | 12 | 94 | 82 |
| 22 | T | 18 | 78 | 44 | 0 | 78 | 83 | 39 | T | 15 | 40 | 40 | 53 | 93 | 93 |
| 24 | N | 16 | 56 | 75 | 13 | 81 | 88 | 50 | S | 16 | 31 | 56 | 75 | 94 | 94 |
| 25 | S | 17 | 47 | 0 | 84 | 63 | 37 | 37 | G | 15 | 80 | 80 | 67 | 87 | 47 |
| 26 | V | 17 | 6 | 35 | 12 | 76 | 59 | 18 | V | 12 | 33 | 42 | 17 | 83 | 75 |
| 27 | K | 19 | 21 | 11 | 84 | 42 | 58 | 42 | V | 17 | 65 | 29 | 47 | 82 | 65 |
| 28 | V | 19 | 13 | 38 | 25 | 56 | 44 | 6 | K | 13 | 54 | 15 | 31 | 23 | 23 |
| 29 | A | 16 | 0 | 35 | 29 | 35 | 18 | 12 | V | 16 | 38 | 25 | 6 | 13 | 0 |
| 30 | V | 17 | 11 | 50 | 50 | 50 | 17 | 0 | A | 14 | 50 | 21 | 29 | 0 | 29 |
| 31 | I | 18 | 11 | 50 | 58 | 58 | 79 | 53 | V | 13 | 31 | 31 | 15 | 46 | 38 |
| 33 | S | 15 | 0 | 68 | 6 | 20 | 7 | 7 | L | 18 | 61 | 28 | 11 | 6 | 28 |
| 35 | I | 19 | 11 | 60 | 53 | 47 | 0 | 11 | T | 11 | 82 | 27 | 9 | 27 | 27 |
| 36 | D | 18 | 0 | 5 | 11 | 22 | 0 | 0 | I | 17 | 47 | 24 | 12 | 65 | 76 |
| 37 | S | 19 | 47 | 17 | 26 | 5 | 16 | 37 | S | — | — | — | — | — | — |
| 38 | S | 19 | 74 | 58 | 53 | 74 | 68 | 16 | T | 14 | 29 | 29 | 43 | 93 | 79 |
| 39 | H | 19 | 5 | 42 | 53 | 47 | 0 | 26 | H | 17 | 53 | 6 | 0 | 6 | 0 |
| 40 | P | 19 | 47 | 11 | 74 | 84 | 16 | 89 | P | 17 | 53 | 100 | 29 | 100 | 82 |
| 41 | D | 19 | 0 | 74 | 16 | 26 | 0 | 0 | D | 18 | 17 | 6 | 0 | 6 | 6 |
| 42 | L | 19 | 5 | 37 | 16 | 26 | 5 | 5 | L | 18 | 50 | 17 | 0 | 39 | 28 |
| 43 | K | 19 | 16 | 16 | 74 | 0 | 74 | 79 | N | 16 | 31 | 25 | 63 | 100 | 81 |
| 44 | V | 19 | 0 | 0 | 74 | 68 | 0 | 16 | I | 18 | 24 | 24 | 47 | 88 | 94 |
| 45 | A | 16 | 81 | 21 | 6 | 31 | 81 | 94 | R | 18 | 78 | 22 | 89 | 89 | 89 |
| 46 | G | 17 | 0 | 31 | 18 | 59 | 18 | 41 | G | 17 | 71 | 18 | 94 | 65 | 71 |
| 47 | G | 19 | 0 | 59 | 42 | 68 | 5 | 0 | G | 15 | 80 | 53 | 0 | 13 | 20 |
| 48 | A | 17 | 65 | 35 | 12 | 29 | 65 | 24 | A | 17 | 76 | 35 | 76 | 88 | 94 |

TABLE 6-2-continued

Highly Productive Sites for BPN' and GG36

| Position (BPN' #) | BPN' WT Residue | # BPN' Variants | BPN' TCA Assay | BPN' BMI pH 7/16° C. | BPN' BMI pH 8/16° C. | BPN' BMI pH 8/32° | BPN' LAS/EDTA Assay | BPN' AAPF Assay | GG36 WT Residue | # GG36 Variants | GG36 BMI pH 8/32° C. | GG36 Egg | GG36 LAS/EDTA Assay | GG36 AAPF Assay | GG36 TCA Assay |
|---|---|---|---|---|---|---|---|---|---|---|---|---|---|---|---|
| 49 | S | 18 | 0 | 22 | 22 | 39 | 6 | 0 | S | 12 | 92 | 33 | 25 | 8 | 8 |
| 50 | M | 17 | 6 | 82 | 6 | 41 | 65 | 65 | F | 11 | 64 | 45 | 73 | 36 | 45 |
| 51 | V | 19 | 0 | 42 | 68 | 63 | 26 | 0 | V | 11 | 73 | 9 | 18 | 55 | 55 |
| 52 | P | 19 | 0 | 74 | 95 | 89 | 5 | 16 | P | 16 | 75 | 100 | 38 | 94 | 69 |
| 53 | S | 19 | 74 | 37 | 63 | 26 | 53 | 0 | G | 17 | 53 | 12 | 12 | 76 | 82 |
| 54 | E | 19 | 0 | 53 | 53 | 47 | 0 | 47 | E | 18 | 28 | 17 | 22 | 39 | 78 |
| 55 | T | 19 | 53 | 21 | 42 | 0 | 79 | 0 | P | 18 | 56 | 22 | 33 | 72 | 83 |
| 56 | N | 19 | 5 | 68 | 74 | 63 | 5 | 0 | S | 15 | 67 | 40 | 33 | 60 | 73 |
| 57 | P | 19 | 5 | 68 | 84 | 63 | 0 | 0 | T | 18 | 44 | 44 | 39 | 100 | 83 |
| 58 | F | 19 | 11 | 63 | 89 | 32 | 11 | 16 | — | — | — | — | — | — | — |
| 59 | Q | 19 | 68 | 68 | 84 | 53 | 47 | 16 | Q | 18 | 44 | 22 | 11 | 78 | 78 |
| 60 | D | 19 | 5 | 5 | 58 | 32 | 0 | 0 | D | 17 | 88 | 53 | 0 | 0 | 0 |
| 61 | N | 19 | 100 | 53 | 53 | 21 | 68 | 68 | G | 15 | 47 | 27 | 87 | 100 | 73 |
| 62 | N | 19 | 74 | 58 | 42 | 26 | 74 | 16 | N | 16 | 75 | 69 | 31 | 75 | 94 |
| 63 | S | 19 | 89 | 47 | 21 | 21 | 32 | 32 | G | 16 | 81 | 31 | 0 | 31 | 50 |
| 66 | T | 17 | 5 | 0 | 0 | 0 | 0 | 0 | T | 14 | 71 | 7 | 7 | 7 | 7 |
| 67 | H | 14 | 79 | 0 | 0 | 0 | 0 | 0 | H | 17 | 18 | 0 | 0 | 0 | 53 |
| 68 | V | 19 | 26 | 42 | 26 | 26 | 11 | 0 | V | 19 | 26 | 5 | 0 | 11 | 53 |
| 69 | A | 19 | 0 | 58 | 11 | 26 | 5 | 5 | A | 18 | 67 | 17 | 6 | 11 | 6 |
| 71 | T | 19 | 5 | 32 | 47 | 47 | 6 | 5 | T | 18 | 67 | 39 | 0 | 11 | 17 |
| 72 | V | 17 | 6 | 65 | 71 | 53 | 0 | 0 | I | 18 | 50 | 38 | 13 | 31 | 31 |
| 73 | A | 17 | 6 | 59 | 59 | 65 | 0 | 18 | A | 16 | 57 | 71 | 0 | 31 | 36 |
| 74 | A | 19 | 11 | 68 | 5 | 11 | 0 | 0 | A | 15 | 13 | 13 | 7 | 13 | 13 |
| 75 | L | 19 | 32 | 11 | 11 | 63 | 0 | 68 | L | 17 | 100 | 88 | 0 | 76 | 24 |
| 76 | N | 19 | 32 | 11 | 5 | 42 | 0 | 58 | N | 18 | 38 | 63 | 6 | 75 | 63 |
| 77 | N | 19 | 0 | 63 | 11 | 21 | 0 | 0 | N | 17 | 88 | 6 | 0 | 6 | 0 |
| 78 | S | 19 | 84 | 74 | 16 | 26 | 42 | 32 | S | 18 | 67 | 89 | 44 | 94 | 72 |
| 79 | I | 19 | 74 | 0 | 74 | 42 | 5 | 21 | I | 17 | 71 | 71 | 0 | 94 | 53 |
| 80 | G | 19 | 0 | 11 | 21 | 32 | 0 | 0 | G | 12 | 92 | 0 | 0 | 0 | 0 |
| 81 | V | 19 | 16 | 79 | 5 | 74 | 0 | 0 | V | 18 | 72 | 44 | 13 | 22 | 39 |
| 82 | L | 18 | 0 | 78 | 72 | 83 | 0 | 17 | L | 16 | 56 | 69 | 0 | 44 | 38 |
| 84 | V | 19 | 21 | 0 | 0 | 5 | 0 | 26 | V | 16 | 56 | 31 | 0 | 44 | 38 |
| 85 | A | 15 | 0 | 20 | 13 | 7 | 0 | 0 | P | 11 | 18 | 18 | 0 | 0 | 0 |
| 86 | P | 14 | 0 | 79 | 71 | 93 | 25 | 57 | S | 13 | 77 | 62 | 15 | 46 | 15 |
| 87 | S | 16 | 69 | 94 | 38 | 69 | 6 | 25 | A | 14 | 50 | 50 | 14 | 93 | 86 |
| 88 | A | 19 | 0 | 69 | 88 | 50 | 16 | 44 | E | 17 | 71 | 43 | 0 | 43 | 7 |
| 89 | S | 19 | 5 | 58 | 74 | 53 | 7 | 32 | L | 17 | 71 | 76 | 12 | 71 | 41 |
| 90 | L | 14 | 0 | 79 | 71 | 71 | 58 | 14 | L | 16 | 56 | 31 | 13 | 38 | 31 |
| 91 | Y | 19 | 5 | 26 | 74 | 63 | 7 | 5 | Y | 15 | 93 | 67 | 47 | 47 | 33 |
| 92 | A | 15 | 7 | 53 | 53 | 60 | 20 | 7 | A | 17 | 94 | 35 | 12 | 18 | 24 |
| 93 | V | 15 | 0 | 40 | 40 | 40 | 13 | 0 | V | 16 | 38 | 19 | 56 | 19 | 19 |
| 94 | K | 16 | 25 | 25 | 44 | 19 | 17 | 11 | K | 18 | 67 | 11 | 0 | 0 | 11 |
| 95 | V | 18 | 0 | 17 | 6 | 0 | 12 | 0 | V | 18 | 56 | 11 | 12 | 11 | 22 |
| 96 | L | 17 | 6 | 71 | 29 | 11 | 59 | 6 | L | 16 | 13 | 25 | 22 | 13 | 75 |
| 97 | G | 17 | 35 | 94 | 53 | 53 | 32 | 47 | G | 18 | 50 | 50 | 31 | 61 | 89 |
| 98 | A | 19 | 42 | 0 | 63 | 94 | 59 | 0 | A | 15 | 60 | 53 | 67 | 93 | 73 |
| 99 | D | 18 | 11 | 83 | 0 | 61 | 50 | 0 | S | 14 | 50 | 36 | 50 | 71 | 79 |

TABLE 6-2-continued

Highly Productive Sites for BPN' and GG36

| Position (BPN' #) | BPN' WT Residue | # BPN' Variants | BPN' TCA Assay | BPN' BMI pH 7/16° C. | BPN' BMI pH 8/16° C. | BPN' BMI pH 8/32° | BPN' LAS/EDTA Assay | BPN' AAPF Assay | GG36 WT Residue | # GG36 Variants | GG36 BMI pH 8/32° C. | GG36 Egg | GG36 LAS/EDTA Assay | GG36 AAPF Assay | GG36 TCA Assay |
|---|---|---|---|---|---|---|---|---|---|---|---|---|---|---|---|
| 100 | G | 19 | 16 | 79 | 68 | 79 | 21 | 0 | G | 16 | 19 | 25 | 56 | 19 | 81 |
| 101 | S | 16 | 56 | 100 | 19 | 50 | 75 | 56 | S | 17 | 47 | 76 | 88 | 76 | 88 |
| 102 | G | 14 | 7 | 29 | 14 | 14 | 14 | 0 | G | 16 | 50 | 19 | 19 | 0 | 19 |
| 103 | Q | 16 | 50 | 63 | 38 | 19 | 69 | 19 | S | 16 | 50 | 50 | 56 | 56 | 63 |
| 104 | Y | 17 | 0 | 47 | 59 | 65 | 47 | 6 | V | 15 | 40 | 47 | 60 | 53 | 53 |
| 105 | S | 19 | 0 | 47 | 42 | 32 | 53 | 11 | S | 19 | 53 | 26 | 37 | 63 | 53 |
| 106 | W | 19 | 0 | 74 | 63 | 74 | 26 | 0 | S | 14 | 64 | 57 | 71 | 71 | 57 |
| 107 | I | 15 | 5 | 40 | 33 | 27 | 13 | 7 | I | 18 | 11 | 61 | 6 | 11 | 56 |
| 108 | I | 19 | 0 | 37 | 42 | 32 | 5 | 0 | A | 16 | 19 | 38 | 0 | 13 | 19 |
| 109 | N | 19 | 11 | 32 | 11 | 68 | 58 | 42 | Q | 18 | 50 | 78 | 39 | 78 | 39 |
| 110 | G | 16 | 0 | 19 | 25 | 19 | 0 | 0 | G | 17 | 6 | 6 | 0 | 6 | 6 |
| 111 | I | 19 | 0 | 37 | 21 | 42 | 11 | 0 | L | 16 | 44 | 25 | 6 | 0 | 13 |
| 112 | E | 19 | 5 | 42 | 21 | 53 | 63 | 0 | E | 17 | 76 | 29 | 24 | 18 | 12 |
| 113 | W | 19 | 0 | 5 | 42 | 21 | 26 | 0 | W | 13 | 0 | 0 | 46 | 0 | 0 |
| 114 | A | 18 | 0 | 33 | 33 | 33 | 11 | 17 | A | 11 | 18 | 18 | 9 | 9 | 9 |
| 115 | I | 19 | 0 | 79 | 42 | 79 | 26 | 16 | G | 17 | 53 | 76 | 18 | 94 | 82 |
| 116 | A | 19 | 53 | 47 | 42 | 47 | 26 | 74 | N | 14 | 86 | 43 | 29 | 100 | 79 |
| 117 | N | 19 | 5 | 53 | 47 | 68 | 58 | 47 | N | 11 | 64 | 73 | 73 | 73 | 45 |
| 118 | N | 19 | 32 | 26 | 42 | 32 | 58 | 68 | G | 17 | 76 | 88 | 76 | 47 | 47 |
| 119 | M | 18 | 0 | 50 | 56 | 28 | 33 | 17 | M | 13 | 46 | 23 | 69 | 23 | 15 |
| 120 | D | 19 | 47 | 47 | 68 | 37 | 68 | 5 | H | 13 | 69 | 92 | 69 | 100 | 85 |
| 121 | V | 19 | 5 | 5 | 16 | 5 | 21 | 0 | V | 15 | 80 | 33 | 27 | 53 | 40 |
| 122 | I | 19 | 0 | 42 | 42 | 47 | 32 | 5 | A | 12 | 58 | 50 | 0 | 25 | 33 |
| 123 | N | 19 | 17 | 58 | 58 | 53 | 0 | 0 | N | 12 | 17 | 8 | 0 | 0 | 42 |
| 124 | M | 18 | 0 | 50 | 44 | 11 | 11 | 0 | L | 12 | 50 | 25 | 0 | 8 | 17 |
| 126 | L | 14 | 21 | 57 | 36 | 43 | 14 | 0 | L | 18 | 0 | 11 | 22 | 0 | 83 |
| 127 | G | 17 | 53 | 24 | 0 | 0 | 0 | 0 | G | 12 | 8 | 42 | 8 | 0 | 67 |
| 128 | G | 17 | 12 | 41 | 35 | 29 | 6 | 32 | S | 17 | 18 | 24 | 82 | 59 | 94 |
| 129 | P | 19 | 58 | 63 | 37 | 53 | 16 | 42 | P | 14 | 21 | 7 | 7 | 100 | 93 |
| 130 | S | 19 | 74 | 11 | 16 | 11 | 53 | 32 | P | 10 | 30 | 40 | 40 | 80 | 90 |
| 131 | G | 19 | 5 | 0 | 32 | 11 | 16 | 0 | S | 12 | 58 | 17 | 17 | 58 | 83 |
| 132 | S | 19 | 5 | 53 | 53 | 47 | 63 | 58 | S | 12 | 75 | 75 | 8 | 58 | 25 |
| 133 | A | 19 | 21 | 21 | 5 | 0 | 58 | 21 | A | 10 | 60 | 30 | 50 | 80 | 80 |
| 134 | A | 13 | 0 | 42 | 26 | 26 | 58 | 0 | T | 12 | 67 | 25 | 25 | 17 | 8 |
| 135 | L | 19 | 8 | 62 | 46 | 46 | 15 | 26 | T | 12 | 54 | 8 | 8 | 15 | 35 |
| 136 | K | 19 | 5 | 68 | 42 | 26 | 21 | 89 | L | 13 | 12 | 47 | 0 | 41 | 69 |
| 137 | A | 19 | 21 | 47 | 16 | 16 | 53 | 32 | E | 17 | 62 | 69 | 38 | 77 | 0 |
| 138 | A | 13 | 0 | 63 | 53 | 74 | 0 | 11 | Q | 13 | 43 | 29 | 14 | 0 | 7 |
| 139 | V | 19 | 5 | 16 | 16 | 32 | 11 | 21 | A | 14 | 73 | 27 | 0 | 13 | 13 |
| 140 | D | 19 | 5 | 5 | 11 | 0 | 0 | 79 | V | 15 | 82 | 53 | 6 | 76 | 65 |
| 141 | K | 19 | 21 | 21 | 89 | 79 | 74 | 47 | N | 17 | 54 | 54 | 46 | 69 | 77 |
| 142 | A | 19 | 0 | 42 | 32 | 32 | 5 | 26 | S | 13 | 58 | 37 | 0 | 21 | 11 |
| 143 | V | 19 | 16 | 11 | 47 | 37 | 26 | 47 | A | 19 | 73 | 33 | 7 | 80 | 60 |
| 144 | A | 19 | 53 | 68 | 16 | 26 | 42 | 58 | T | 15 | 50 | 39 | 33 | 78 | 67 |
| 145 | S | 19 | 47 | 16 | 84 | 74 | 53 | 74 | S | 18 | 82 | 65 | 53 | 41 | 35 |
| 146 | G | 19 | 5 | 32 | 74 | 47 | 21 | 58 | R | 17 | 88 | 29 | 6 | 12 | 6 |
| 147 | V | 16 | 6 | 88 | 94 | 50 | 56 | 38 | V | 12 | 42 | 8 | 8 | 33 | 33 |

TABLE 6-2-continued

Highly Productive Sites for BPN' and GG36

| Position (BPN' #) | BPN' WT Residue | # BPN' Variants | BPN' TCA Assay | BPN' BMI pH 7/16° C. | BPN' BMI pH 8/16° C. | BPN' BMI pH 8/32° | BPN' LAS/EDTA Assay | BPN' AAPF Assay | GG36 WT Residue | # GG36 Variants | GG36 BMI pH 8/32° C. | GG36 Egg | GG36 LAS/EDTA Assay | GG36 AAPF Assay | GG36 TCA Assay |
|---|---|---|---|---|---|---|---|---|---|---|---|---|---|---|---|
| 148 | V | 17 | 0 | 47 | 65 | 65 | 18 | 6 | L | 18 | 56 | 39 | 0 | 56 | 39 |
| 149 | V | 16 | 0 | 44 | 69 | 63 | 88 | 19 | V | 17 | 71 | 18 | 24 | 24 | 6 |
| 150 | V | 18 | 0 | 17 | 44 | 50 | 28 | 11 | V | 14 | 64 | 29 | 0 | 29 | 14 |
| 151 | A | 17 | 0 | 18 | 35 | 35 | 6 | 0 | A | 13 | 15 | 8 | 0 | 8 | 31 |
| 152 | A | 15 | 40 | 7 | 7 | 13 | 0 | 0 | A | 13 | 8 | 8 | 0 | 0 | 23 |
| 153 | A | 19 | 0 | 26 | 26 | 21 | 0 | 0 | S | 13 | 23 | 0 | 0 | 15 | 31 |
| 155 | N | 17 | 35 | 0 | 0 | 0 | 13 | 56 | N | 14 | 0 | 11 | 0 | 0 | 79 |
| 156 | E | 16 | 44 | 74 | 16 | 6 | 16 | 11 | S | 18 | 33 | 11 | 36 | 11 | 61 |
| 158 | T | 19 | 16 | 74 | 63 | 16 | 32 | 21 | A | 14 | 29 | 21 | 36 | 86 | 93 |
| 159 | S | 19 | 37 | 11 | 53 | 63 | 5 | 5 | — | — | — | — | — | — | — |
| 160 | G | 19 | 11 | 58 | 74 | 11 | 37 | 47 | — | — | — | — | — | — | — |
| 161 | S | 19 | 53 | 63 | 11 | 32 | 37 | 37 | — | — | — | — | — | — | — |
| 162 | S | 19 | 32 | 21 | 5 | 16 | 0 | 0 | G | 17 | 35 | 29 | 18 | 47 | 47 |
| 163 | S | 19 | 5 | 12 | 29 | 29 | 0 | 0 | S | 15 | 27 | 27 | 53 | 87 | 87 |
| 164 | T | 17 | 0 | 7 | 13 | 33 | 7 | 0 | I | 17 | 6 | 12 | 6 | 6 | 59 |
| 165 | V | 15 | 63 | 0 | 6 | 6 | 69 | 0 | S | 16 | 38 | 38 | 19 | 6 | 75 |
| 166 | G | 16 | 5 | 58 | 84 | 74 | 0 | 0 | S | 19 | 32 | 0 | 0 | 11 | 47 |
| 167 | Y | 19 | 11 | 100 | 83 | 50 | 11 | 11 | Y | 14 | 93 | 21 | 29 | 21 | 21 |
| 170 | K | 18 | 0 | 33 | 22 | 33 | 0 | 0 | R | 19 | 63 | 32 | 0 | 16 | 11 |
| 171 | Y | 18 | 0 | 88 | 71 | 76 | 24 | 76 | Y | 19 | 56 | 56 | 25 | 94 | 81 |
| 172 | P | 17 | 0 | 68 | 37 | 74 | 5 | 26 | A | 19 | 32 | 37 | 16 | 63 | 79 |
| 173 | S | 19 | 0 | 32 | 21 | 42 | 0 | 16 | N | 18 | 17 | 17 | 6 | 17 | 22 |
| 174 | V | 19 | 0 | 42 | 26 | 37 | 5 | 11 | A | 16 | 50 | 38 | 0 | 50 | 38 |
| 175 | I | 19 | 0 | 11 | 5 | 21 | 11 | 5 | M | 19 | 19 | 13 | 0 | 13 | 38 |
| 176 | A | 19 | 5 | 5 | 11 | 26 | 0 | 0 | A | 16 | 18 | 12 | 0 | 24 | 24 |
| 177 | V | 19 | 11 | 32 | 16 | 53 | 0 | 16 | V | 17 | 47 | 7 | 0 | 20 | 20 |
| 180 | V | 19 | 0 | 5 | 5 | 32 | 0 | 16 | T | 15 | 0 | 33 | 11 | 8 | 8 |
| 181 | D | 19 | 5 | 53 | 79 | 42 | 16 | 16 | D | 12 | 17 | 33 | 11 | 100 | 100 |
| 182 | S | 19 | 32 | 53 | 58 | 42 | 32 | 53 | Q | 18 | 18 | 29 | 6 | 94 | 88 |
| 183 | S | 19 | 53 | 42 | 42 | 42 | 11 | 42 | N | 17 | 61 | 11 | 6 | 17 | 88 |
| 184 | N | 19 | 5 | 53 | 21 | 47 | 16 | 53 | N | 18 | 41 | 24 | 24 | 50 | 84 |
| 185 | Q | 19 | 11 | 47 | 26 | 53 | 5 | 84 | R | 17 | 53 | 12 | 24 | 13 | 6 |
| 186 | R | 19 | 0 | 89 | 63 | 79 | 0 | 0 | A | 19 | 5 | 16 | 0 | 5 | 88 |
| 187 | A | 19 | 47 | 68 | 95 | 26 | 11 | 11 | A | 16 | 6 | 0 | 19 | 100 | 6 |
| 188 | S | 19 | 11 | 32 | 74 | 74 | 5 | 32 | S | 17 | 6 | 0 | 0 | 0 | 37 |
| 189 | F | 17 | 47 | 24 | 12 | 26 | 0 | 0 | F | 16 | 0 | 0 | 0 | 100 | 100 |
| 190 | S | 19 | 29 | 21 | 26 | 29 | 5 | 5 | S | 19 | 6 | 0 | 13 | 0 | 88 |
| 191 | Q | 19 | 0 | 5 | 11 | 16 | 0 | 0 | Q | 16 | 6 | 12 | 6 | 0 | 84 |
| 192 | Y | 19 | 5 | 32 | 53 | 11 | 0 | 5 | Q | 15 | 6 | 0 | 13 | 0 | 75 |
| 193 | G | 19 | 0 | 21 | 11 | 53 | 5 | 0 | Y | 17 | 0 | 12 | 6 | 0 | 53 |
| 194 | P | 19 | 0 | 74 | 47 | 26 | 0 | 68 | G | 16 | 18 | 35 | 35 | 94 | 87 |
| 195 | E | 19 | 0 | 32 | 11 | 21 | 16 | 16 | A | 14 | 56 | 44 | 13 | 13 | 94 |
| 196 | L | 19 | 0 | 21 | 21 | 26 | 32 | 53 | G | 18 | 21 | 14 | 0 | 7 | 19 |
| 197 | D | 15 | 0 | 27 | 40 | 47 | 11 | 42 | L | 17 | 83 | 50 | 0 | 44 | 43 |
| 198 | V | 18 | 0 | 6 | 33 | 33 | 0 | 0 | D | 18 | 41 | 12 | 0 | 59 | 39 |
| 199 | M | 18 | 0 | 50 | 28 | 33 | 0 | 17 | I | 17 | 47 | 29 | 12 | 29 | 59 |
| 200 | A | 19 | 0 | 42 | 16 | 32 | 0 | 6 | V | 17 | 36 | 27 | 0 | 18 | 29 |
|     |   |    |   |    |    |    |   | 16 | A | 11 |    |    |    |    | 18 |

TABLE 6-2-continued

Highly Productive Sites for BPN' and GG36

| Position (BPN' #) | BPN' WT Residue | # BPN' Variants | BPN' TCA Assay | BPN' BMI pH 7/16° C. | BPN' BMI pH 8/16° C. | BPN' BMI pH 8/32° | BPN' LAS/EDTA Assay | BPN' AAPF Assay | GG36 WT Residue | # GG36 Variants | GG36 BMI pH 8/32° C. | GG36 Egg | GG36 LAS/EDTA Assay | GG36 AAPF Assay | GG36 TCA Assay |
|---|---|---|---|---|---|---|---|---|---|---|---|---|---|---|---|
| 201 | P | 18 | 0 | 44 | 44 | 78 | 0 | 22 | P | 16 | 31 | 13 | 0 | 0 | 0 |
| 203 | V | 18 | 0 | 33 | 78 | 67 | 17 | 50 | V | 16 | 75 | 19 | 13 | 19 | 25 |
| 204 | S | 16 | 0 | 13 | 38 | 0 | 31 | 44 | N | 14 | 14 | 29 | 7 | 93 | 93 |
| 205 | I | 19 | 0 | 16 | 11 | 32 | 5 | 11 | V | 15 | 33 | 13 | 13 | 7 | 13 |
| 206 | Q | 19 | 68 | 53 | 32 | 84 | 26 | 16 | Q | 18 | 67 | 28 | 17 | 94 | 44 |
| 208 | T | 19 | 0 | 37 | 37 | 37 | 0 | 21 | T | 18 | 39 | 22 | 0 | 22 | 11 |
| 209 | L | 19 | 5 | 32 | 21 | 37 | 0 | 32 | Y | 17 | 83 | 67 | 0 | 89 | 44 |
| 210 | P | 19 | 0 | 74 | 42 | 68 | 21 | 11 | P | 17 | 100 | 100 | 29 | 94 | 24 |
| 211 | G | 19 | 5 | 79 | 79 | 53 | 5 | 37 | G | 15 | 53 | 67 | 20 | 93 | 93 |
| 212 | N | 19 | 26 | 42 | 42 | 32 | 21 | 11 | S | 13 | 46 | 46 | 38 | 92 | 92 |
| 213 | K | 17 | 47 | 72 | 100 | 18 | 94 | 37 | T | 18 | 22 | 39 | 6 | 94 | 94 |
| 214 | Y | 18 | 0 | 94 | 50 | 44 | 0 | 16 | Y | 17 | 100 | 39 | 0 | 22 | 17 |
| 215 | G | 19 | 11 | 68 | 26 | 32 | 11 | 29 | A | 18 | 71 | 59 | 41 | 100 | 94 |
| 216 | A | 19 | 42 | 32 | 42 | 37 | 53 | 0 | S | 17 | 56 | 72 | 33 | 100 | 100 |
| 217 | Y | 19 | 32 | 47 | 26 | 58 | 53 | 0 | L | 18 | 50 | 81 | 25 | 6 | 19 |
| 218 | N | 19 | 5 | 26 | 11 | 16 | 16 | 21 | N | 16 | 76 | 76 | 24 | 88 | 35 |
| 220 | T | 19 | 0 | 5 | 5 | 5 | 0 | 58 | T | 15 | 7 | 7 | 0 | 0 | 33 |
| 222 | M | 18 | 67 | 0 | 0 | 17 | 28 | 32 | M | 17 | 6 | 12 | 12 | 0 | 94 |
| 224 | S | 19 | 11 | 37 | 26 | 42 | 5 | 6 | T | 18 | 29 | 18 | 12 | 18 | 35 |
| 225 | P | 19 | 16 | 0 | 0 | 0 | 0 | 5 | P | 18 | 0 | 6 | 11 | 0 | 33 |
| 226 | H | 19 | 0 | 58 | 53 | 63 | 0 | 16 | H | 16 | 75 | 44 | 0 | 6 | 6 |
| 227 | V | 19 | 5 | 32 | 47 | 26 | 5 | 0 | V | 16 | 50 | 25 | 0 | 44 | 44 |
| 228 | A | 16 | 0 | 25 | 25 | 38 | 6 | 0 | A | 17 | 18 | 6 | 12 | 29 | 24 |
| 229 | G | 19 | 5 | 0 | 0 | 5 | 0 | 5 | G | 15 | 20 | 13 | 0 | 13 | 7 |
| 230 | A | 19 | 11 | 21 | 47 | 47 | 11 | 21 | A | 16 | 81 | 50 | 6 | 69 | 44 |
| 231 | A | 19 | 0 | 47 | 58 | 58 | 5 | 5 | A | 16 | 19 | 25 | 6 | 50 | 50 |
| 232 | A | 13 | 0 | 38 | 54 | 23 | 38 | 15 | A | 10 | 60 | 30 | 20 | 30 | 20 |
| 233 | L | 11 | 0 | 18 | 36 | 18 | 27 | 0 | L | 16 | 94 | 81 | 6 | 75 | 31 |
| 234 | I | 19 | 32 | 37 | 32 | 26 | 21 | 32 | V | 12 | 58 | 33 | 8 | 75 | 75 |
| 235 | L | 19 | 47 | 32 | 37 | 47 | 68 | 32 | K | 16 | 88 | 63 | 56 | 88 | 88 |
| 236 | S | 19 | 42 | 32 | 21 | 32 | 26 | 16 | Q | 16 | 88 | 88 | 13 | 75 | 50 |
| 237 | K | 19 | 79 | 26 | 37 | 37 | 37 | 42 | K | 17 | 94 | 71 | 65 | 88 | 82 |
| 238 | H | 17 | 0 | 37 | 47 | 26 | 58 | 58 | N | 17 | 94 | 71 | 47 | 94 | 88 |
| 239 | P | 19 | 0 | 58 | 16 | 42 | 84 | 26 | P | 17 | 71 | 82 | 65 | 100 | 88 |
| 240 | N | 19 | 42 | 68 | 11 | 47 | 79 | 53 | S | 14 | 71 | 93 | 14 | 93 | 82 |
| 241 | W | 19 | 0 | 68 | 21 | 79 | 63 | 42 | W | 19 | 42 | 63 | 63 | 95 | 84 |
| 242 | T | 19 | 32 | 16 | 74 | 32 | 89 | 58 | S | 15 | 33 | 33 | 47 | 100 | 73 |
| 243 | N | 19 | 11 | 16 | 63 | 37 | 21 | 21 | N | 18 | 39 | 50 | 39 | 94 | 89 |
| 244 | T | 19 | 47 | 16 | 74 | 53 | 68 | 16 | V | 16 | 56 | 75 | 63 | 94 | 81 |
| 245 | Q | 19 | 16 | 11 | 79 | 26 | 84 | 37 | Q | 13 | 62 | 77 | 46 | 100 | 77 |
| 246 | V | 17 | 6 | 18 | 35 | 18 | 18 | 32 | I | 17 | 76 | 24 | 29 | 35 | 35 |
| 247 | R | 19 | 0 | 53 | 74 | 42 | 0 | 12 | R | 19 | 53 | 68 | 21 | 84 | 79 |
| 248 | S | 19 | 47 | 37 | 79 | 47 | 32 | 0 | N | 16 | 69 | 56 | 31 | 94 | 88 |
| 249 | S | 19 | 42 | 5 | 68 | 26 | 5 | 58 | H | 18 | 17 | 28 | 39 | 94 | 83 |
| 250 | L | 19 | 0 | 26 | 32 | 63 | 0 | 42 | L | 17 | 65 | 12 | 0 | 29 | 24 |
| 251 | E | 19 | 0 | 37 | 11 | 63 | 0 | 16 | K | 14 | 64 | 50 | 50 | 86 | 64 |
| 252 | N | 19 | 21 | 58 | 37 | 74 | 53 | 42 | N | 16 | 38 | 81 | 63 | 88 | 75 |

TABLE 6-2-continued

Highly Productive Sites for BPN' and GG36

| Position (BPN' #) | BPN' WT Residue | # BPN' Variants | BPN' TCA Assay | BPN' BMI pH 7/16° C. | BPN' BMI pH 8/16° C. | BPN' BMI pH 8/32° | BPN' LAS/EDTA Assay | BPN' AAPF Assay | GG36 WT Residue | # GG36 Variants | GG36 BMI pH 8/32° C. | GG36 Egg | GG36 LAS/EDTA Assay | GG36 AAPF Assay | GG36 TCA Assay |
|---|---|---|---|---|---|---|---|---|---|---|---|---|---|---|---|
| 253 | T | 19 | 16 | 53 | 58 | 68 | 11 | 16 | T | 14 | 36 | 29 | 7 | 93 | 79 |
| 254 | T | 19 | 16 | 53 | 47 | 63 | 11 | 5 | A | 18 | 39 | 22 | 0 | 22 | 11 |
| 255 | T | 19 | 26 | 58 | 53 | 37 | 0 | 42 | T | 17 | 18 | 29 | 35 | 94 | 94 |
| 256 | K | 19 | 11 | 89 | 95 | 58 | 0 | 68 | S | 17 | 47 | 82 | 35 | 100 | 65 |
| 257 | L | 19 | 0 | 47 | 53 | 32 | 0 | 16 | L | 15 | 87 | 40 | 0 | 40 | 13 |
| 258 | G | 17 | 0 | 47 | 82 | 94 | 0 | 0 | G | 17 | 82 | 59 | 0 | 82 | 53 |
| 259 | D | 19 | 21 | 5 | 0 | 11 | 0 | 89 | S | 12 | 83 | 100 | 8 | 100 | 25 |
| 260 | S | 19 | 26 | 63 | 63 | 37 | 5 | 47 | T | 14 | 64 | 86 | 21 | 100 | 79 |
| 261 | F | 19 | 0 | 0 | 32 | 11 | 0 | 0 | N | 16 | 56 | 88 | 63 | 100 | 75 |
| 262 | Y | 19 | 11 | 26 | 26 | 37 | 0 | 0 | L | 17 | 71 | 71 | 35 | 94 | 88 |
| 263 | Y | 19 | 5 | 37 | 32 | 26 | 0 | 5 | Y | 15 | 93 | 33 | 0 | 13 | 7 |
| 264 | G | 19 | 0 | 5 | 5 | 16 | 0 | 0 | G | 14 | 79 | 7 | 0 | 7 | 0 |
| 265 | K | 19 | 21 | 84 | 84 | 58 | 47 | 11 | S | 18 | 83 | 83 | 6 | 72 | 44 |
| 267 | L | 19 | 0 | 61 | 83 | 89 | 11 | 56 | L | 17 | 76 | 41 | 0 | 41 | 6 |
| 268 | I | 18 | 0 | 26 | 37 | 37 | 0 | 5 | V | 15 | 53 | 13 | 6 | 53 | 47 |
| 269 | N | 19 | 5 | 26 | 26 | 63 | 11 | 5 | N | 13 | 85 | 85 | 0 | 100 | 69 |
| 270 | V | 18 | 17 | 32 | 50 | 33 | 17 | 6 | A | 17 | 88 | 71 | 8 | 65 | 35 |
| 271 | Q | 19 | 53 | 11 | 32 | 79 | 47 | 26 | E | 14 | 29 | 100 | 0 | 100 | 64 |
| 272 | A | 19 | 26 | 32 | 68 | 32 | 37 | 16 | A | 16 | 69 | 63 | 25 | 100 | 69 |
| 273 | A | 13 | 0 | 16 | 85 | 100 | 0 | 0 | A | 15 | 100 | 73 | 7 | 73 | 27 |
| 274 | A | 19 | 5 | 69 | 0 | 53 | 16 | 26 | T | 15 | 87 | 80 | 13 | 87 | 60 |
| 275 | Q | 19 | 26 | 47 | 53 | 47 | 58 | 26 | R | 14 | 86 | 50 | 79 | 71 | 50 |

"Restrictive" sites are those sites that have less than 20% neutral mutations for activity and stability. In Table 6-3 below, the results for variants that contain sites that meet the definition of a restrictive site are shown as a percentage (%) of variants evaluated that meet definition of a neutral mutation (PI>0.5).

TABLE 6-3

Restrictive Sites for BPN' and GG36

| Position (BPN' #) | BPN' WT Residue | # BPN' Variants | BPN' BMI pH 7/ 16° C. | BPN' BMI pH 8/16° C. | BPN' BMI pH 8/32° | BPN' LAS | BPN' AAPF | GG36 WT Residue | # GG36 Variants | GG36 BMI pH 8/32° C. | GG36 Egg | GG36 LAS/ EDTA | GG36 AAPF |
|---|---|---|---|---|---|---|---|---|---|---|---|---|---|
| 23 | G | 18 | 11 | 17 | 11 | 11 | 6 | G | 13 | 15 | 15 | 15 | 15 |
| 32 | D | 16 | 0 | 0 | 0 | 0 | 0 | D | 17 | 12 | 18 | 0 | 0 |
| 64 | H | 13 | 0 | 0 | 0 | 0 | 0 | H | 14 | 0 | 0 | 7 | 0 |
| 65 | G | 17 | 6 | 12 | 12 | 6 | 6 | G | 10 | 0 | 0 | 0 | 0 |
| 70 | G | 16 | 0 | 0 | 0 | 0 | 0 | G | 12 | 0 | 0 | 0 | 0 |
| 83 | G | 19 | 5 | 5 | 5 | 5 | 5 | G | 10 | 10 | 10 | 0 | 10 |
| 125 | S | 19 | 16 | 5 | 5 | 5 | 0 | S | 15 | 13 | 7 | 13 | 0 |
| 168 | P | 19 | 16 | 11 | 0 | 0 | 0 | P | 18 | 6 | 6 | 0 | 0 |
| 202 | G | 19 | 0 | 0 | 11 | 0 | 0 | G | 18 | 6 | 0 | 0 | 0 |
| 221 | S | 16 | 0 | 0 | 0 | 0 | 0 | S | 16 | 0 | 0 | 0 | 0 |

In short, as determined during development of the present invention, 10 positions in the mature region of two reference subtilisins are restrictive positions for activity and stability. Thus the remaining 265 positions in the mature region of two reference subtilisins are nonrestrictive positions (≥20% neutral mutations) for activity and stability Example 7

Evaluation of Stain Removal by GCI P036 Combinatorial Library Variants

In this Example, results for variants of GCI-P036 were tested for their stain removal performance in automatic dishwashing and liquid laundry detergent applications are provided. Cloning of the combinatorial library was performed by Sloning BioTechnology using the Slonomax Technology. Preparation of variant protease samples was performed as described above. Briefly, combinatorial library variants were tested in blood, milk, ink (BMI) microswatch and CS-38 microswatch assays in detergents representing various market geographies (e.g., differing pH, temperature, and/or water hardness), in both laundry and automatic dishwashing (ADW) applications. As described throughout, functionality of protease variants was quantified as a performance index (PI), which is the ratio of performance of a variant to that of a reference protease. The substitutions are listed relative to the GCI-P036 reference protease using BPN' numbering and the PI is determined in relationship to the GCI-P036 reference. Data is shown in Tables 7-1 to 7-5.

TABLE 7-1

Protease Variants with PI ≥0.8 on Baked Egg Assay in CASCADE ® Detergent (NA ADW)

| Variant | S87 | Q109 | G118 | S128 | P129 | S130 | S188 | T213 | S248 | PI |
|---|---|---|---|---|---|---|---|---|---|---|
| 75 | S87N | Q109Q | G118D | S128L | P129Q | S130A | S188S | T213E | N248R | 2.23 |
| 46 | S87N | Q109R | G118V | S128L | P129Q | S130A | S188D | T213R | N248D | 1.72 |
| 1 | S87N | Q109Q | G118V | S128L | P129Q | S130A | S188S | T213T | N248N | 1.68 |
| 47 | S87N | Q109R | G118V | S128L | P129Q | S130A | S188D | T213E | N248N | 1.64 |
| 48 | S87N | Q109R | G118V | S128L | P129Q | S130A | S188D | T213E | N248R | 1.63 |
| 42 | S87N | Q109R | G118V | S128L | P129Q | S130A | S188D | T213T | N248R | 1.62 |
| 26 | S87N | Q109R | G118V | S128L | P129Q | S130A | S188S | T213T | N248R | 1.52 |
| 63 | S87R | Q109R | G118V | S128L | P129Q | S130A | S188D | T213E | N248R | 1.51 |
| 80 | S87R | Q109Q | G118R | S128L | P129Q | S130A | S188D | T213T | N248R | 1.51 |
| 79 | S87R | Q109R | G118R | S128L | P129Q | S130A | S188D | T213T | N248R | 1.42 |
| 45 | S87N | Q109V | G118V | S128L | P129Q | S130A | S188D | T213R | N248R | 1.41 |
| 67 | S87R | Q109Q | G118R | S128L | P129Q | S130A | S188S | T213E | N248R | 1.40 |

TABLE 7-1-continued

Protease Variants with PI ≥0.8 on Baked Egg Assay in CASCADE ® Detergent (NA ADW)

| Variant | S87 | Q109 | G118 | S128 | P129 | S130 | S188 | T213 | S248 | PI |
|---|---|---|---|---|---|---|---|---|---|---|
| 64 | S87R | Q109Q | G118R | S128L | P129Q | S130A | S188D | T213E | N248R | 1.37 |
| 32 | S87N | Q109R | G118V | S128L | P129Q | S130A | S188S | T213E | N248R | 1.32 |
| 34 | S87N | Q109R | G118V | S128L | P129Q | S130A | S188R | T213T | N248R | 1.28 |
| 62 | S87R | Q109R | G118R | S128L | P129Q | S130A | S188D | T213E | N248R | 1.26 |
| 66 | S87R | Q109Q | G118R | S128L | P129Q | S130A | S188D | T213E | N248N | 1.25 |
| 73 | S87N | Q109R | G118R | S128L | P129Q | S130A | S188D | T213E | N248R | 1.24 |
| 39 | S87N | Q109R | G118V | S128L | P129Q | S130A | S188R | T213E | N248N | 1.20 |
| 40 | S87N | Q109R | G118V | S128L | P129Q | S130A | S188R | T213E | N248N | 1.19 |
| 17 | S87N | Q109Q | G118V | S128L | P129Q | S130A | S188D | T213T | N248N | 1.17 |
| 38 | S87N | Q109R | G118V | S128L | P129Q | S130A | S188R | T213R | N248D | 1.16 |
| 2 | S87N | Q109Q | G118V | S128L | P129Q | S130A | S188S | T213T | N248R | 1.16 |
| 37 | S87N | Q109R | G118V | S128L | P129Q | S130A | S188R | T213R | N248R | 1.15 |
| 25 | S87N | Q109R | G118V | S128L | P129Q | S130A | S188S | T213T | N248N | 1.15 |
| 43 | S87N | Q109R | G118V | S128L | P129Q | S130A | S188D | T213T | N248D | 1.14 |
| 44 | S87N | Q109R | G118V | S128L | P129Q | S130A | S188D | T213R | N248N | 1.14 |
| 31 | S87N | Q109R | G118V | S128L | P129Q | S130A | S188S | T213E | N248N | 1.14 |
| 35 | S87N | Q109R | G118V | S128L | P129Q | S130A | S188R | T213T | N248D | 1.13 |
| 21 | S87N | Q109Q | G118V | S128L | P129Q | S130A | S188D | T213R | N248N | 1.09 |
| 36 | S87N | Q109R | G118V | S128L | P129Q | S130A | S188R | T213R | N248N | 1.04 |
| 15 | S87N | Q109Q | G118V | S128L | P129Q | S130A | S188R | T213E | N248N | 1.03 |
| 23 | S87N | Q109Q | G118V | S128L | P129Q | S130A | S188D | T213E | N248N | 1.03 |
| 13 | S87N | Q109Q | G118V | S128L | P129Q | S130A | S188R | T213R | N248R | 1.02 |
| 18 | S87N | Q109Q | G118V | S128L | P129Q | S130A | S188D | T213T | N248R | 1.00 |
| 28 | S87N | Q109Q | G118V | S128L | P129Q | S130A | S188S | T213E | N248N | 0.98 |
| 33 | S87N | Q109R | G118V | S128L | P129Q | S130A | S188R | T213T | N248N | 0.97 |
| 65 | S87R | Q109Q | G118V | S128L | P129Q | S130A | S188D | T213E | N248R | 0.96 |
| 24 | S87N | Q109Q | G118V | S128L | P129Q | S130A | S188D | T213E | N248R | 0.94 |
| 55 | S87N | Q109D | G118V | S128L | P129Q | S130A | S188R | T213R | N248N | 0.94 |
| 27 | S87N | Q109Q | G118V | S128L | P129Q | S130A | S188S | T213T | N248D | 0.91 |
| 53 | S87N | Q109R | G118V | S128L | P129Q | S130A | S188R | T213E | N248D | 0.91 |
| 22 | S87N | Q109Q | G118V | S128L | P129Q | S130A | S188D | T213R | N248D | 0.90 |
| 7 | S87N | Q109Q | G118V | S128L | P129Q | S130A | S188S | T213E | N248R | 0.88 |
| 54 | S87N | Q109Q | G118V | S128L | P129Q | S130A | S188D | T213E | N248D | 0.87 |
| 71 | S87R | Q109D | G118R | S128L | P129Q | S130A | S188D | T213E | N248N | 0.87 |
| 81 | S87N | Q109R | G118V | S128L | P129Q | S130A | S188R | T213E | N248R | 0.86 |
| 12 | S87N | Q109Q | G118V | S128L | P129Q | S130A | S188R | T213R | N248N | 0.86 |
| 10 | S87N | Q109Q | G118V | S128L | P129Q | S130A | S188R | T213T | N248R | 0.85 |
| 8 | S87N | Q109Q | G118V | S128L | P129Q | S130A | S188S | T213E | N248R | 0.85 |
| 30 | S87N | Q109R | G118V | S128L | P129Q | S130A | S188S | T213R | N248D | 0.83 |
| 16 | S87N | Q109Q | G118V | S128L | P129Q | S130A | S188R | T213E | N248R | 0.82 |

TABLE 7-2

Protease Variants with PI ≥0.8 on Baked Egg Assay in CALGONIT ® Detergent (WE ADW)

| Variant | S87 | Q109 | G118 | S128 | P129 | S130 | S188 | T213 | S248 | PI |
|---|---|---|---|---|---|---|---|---|---|---|
| 75 | S87N | Q109Q | G118D | S128L | P129Q | S130A | S188S | T213E | N248R | 3.23 |
| 32 | S87N | Q109R | G118V | S128L | P129Q | S130A | S188S | T213E | N248R | 1.87 |
| 48 | S87N | Q109R | G118V | S128L | P129Q | S130A | S188D | T213E | N248R | 1.68 |
| 47 | S87N | Q109R | G118V | S128L | P129Q | S130A | S188D | T213E | N248N | 1.67 |
| 42 | S87N | Q109R | G118V | S128L | P129Q | S130A | S188D | T213T | N248R | 1.63 |
| 80 | S87N | Q109Q | G118R | S128L | P129Q | S130A | S188D | T213T | N248R | 1.59 |
| 46 | S87N | Q109R | G118V | S128L | P129Q | S130A | S188D | T213R | N248D | 1.56 |
| 63 | S87R | Q109R | G118V | S128L | P129Q | S130A | S188D | T213E | N248R | 1.41 |
| 66 | S87R | Q109Q | G118R | S128L | P129Q | S130A | S188D | T213E | N248N | 1.38 |
| 64 | S87R | Q109Q | G118R | S128L | P129Q | S130A | S188D | T213E | N248R | 1.36 |
| 39 | S87N | Q109R | G118V | S128L | P129Q | S130A | S188R | T213E | N248N | 1.36 |
| 67 | S87R | Q109Q | G118R | S128L | P129Q | S130A | S188S | T213E | N248R | 1.26 |
| 31 | S87N | Q109R | G118V | S128L | P129Q | S130A | S188S | T213E | N248N | 1.26 |
| 15 | S87N | Q109Q | G118V | S128L | P129Q | S130A | S188R | T213E | N248N | 1.22 |
| 40 | S87N | Q109R | G118V | S128L | P129Q | S130A | S188R | T213E | N248N | 1.20 |
| 34 | S87N | Q109R | G118V | S128L | P129Q | S130A | S188R | T213T | N248R | 1.20 |
| 26 | S87N | Q109R | G118V | S128L | P129Q | S130A | S188S | T213T | N248R | 1.18 |
| 27 | S87N | Q109Q | G118V | S128L | P129Q | S130A | S188S | T213T | N248D | 1.14 |
| 16 | S87N | Q109Q | G118V | S128L | P129Q | S130A | S188R | T213E | N248R | 1.14 |
| 7 | S87N | Q109Q | G118V | S128L | P129Q | S130A | S188S | T213E | N248N | 1.11 |
| 8 | S87N | Q109Q | G118V | S128L | P129Q | S130A | S188S | T213E | N248R | 1.09 |
| 23 | S87N | Q109Q | G118V | S128L | P129Q | S130A | S188D | T213E | N248N | 1.09 |
| 65 | S87R | Q109Q | G118V | S128L | P129Q | S130A | S188D | T213E | N248R | 1.09 |

TABLE 7-2-continued

Protease Variants with PI ≥0.8 on Baked Egg Assay in CALGONIT ® Detergent (WE ADW)

| Variant | S87 | Q109 | G118 | S128 | P129 | S130 | S188 | T213 | S248 | PI |
|---|---|---|---|---|---|---|---|---|---|---|
| 35 | S87N | Q109R | G118V | S128L | P129Q | S130A | S188R | T213T | N248R | 1.07 |
| 2 | S87N | Q109Q | G118V | S128L | P129Q | S130A | S188S | T213T | N248R | 1.06 |
| 10 | S87N | Q109Q | G118V | S128L | P129Q | S130A | S188R | T213T | N248R | 1.06 |
| 21 | S87N | Q109Q | G118V | S128L | P129Q | S130A | S188D | T213R | N248R | 1.06 |
| 45 | S87N | Q109R | G118V | S128L | P129Q | S130A | S188D | T213R | N248R | 1.04 |
| 73 | S87N | Q109R | G118R | S128L | P129Q | S130A | S188D | T213E | N248R | 1.02 |
| 24 | S87N | Q109Q | G118V | S128L | P129Q | S130A | S188D | T213E | N248R | 1.02 |
| 28 | S87N | Q109R | G118V | S128L | P129Q | S130A | S188S | T213R | N248N | 0.98 |
| 25 | S87N | Q109R | G118V | S128L | P129Q | S130A | S188S | T213T | N248N | 0.98 |
| 43 | S87N | Q109R | G118V | S128L | P129Q | S130A | S188D | T213T | N248D | 0.97 |
| 38 | S87N | Q109R | G118V | S128L | P129Q | S130A | S188R | T213R | N248D | 0.94 |
| 44 | S87N | Q109R | G118V | S128L | P129Q | S130A | S188D | T213R | N248N | 0.91 |
| 22 | S87N | Q109Q | G118V | S128L | P129Q | S130A | S188D | T213R | N248D | 0.88 |
| 71 | S87R | Q109D | G118R | S128L | P129Q | S130A | S188D | T213E | N248R | 0.87 |
| 33 | S87N | Q109R | G118V | S128L | P129Q | S130A | S188R | T213T | N248N | 0.85 |
| 13 | S87N | Q109Q | G118V | S128L | P129Q | S130A | S188R | T213R | N248R | 0.83 |
| 1 | S87N | Q109Q | G118V | S128L | P129Q | S130A | S188S | T213T | N248N | 0.83 |
| 18 | S87N | Q109Q | G118V | S128L | P129Q | S130A | S188D | T213T | N248N | 0.83 |
| 17 | S87N | Q109Q | G118V | S128L | P129Q | S130A | S188D | T213T | N248N | 0.82 |

TABLE 7-3

Protease Variants with PI ≥0.8 on CS-38 Microswatch Assay in CASCADE ® Detergent (NA ADW)

| Variant | S87 | Q109 | G118 | S128 | P129 | S130 | S188 | T213 | S248 | PI |
|---|---|---|---|---|---|---|---|---|---|---|
| 38 | S87N | Q109R | G118V | S128L | P129Q | S130A | S188R | T213R | N248D | 4.02 |
| 1 | S87N | Q109Q | G118V | S128L | P129Q | S130A | S188S | T213T | N248N | 4.00 |
| 74 | S87N | Q109Q | G118R | S128L | P129Q | S130A | S188D | T213E | N248R | 3.87 |
| 33 | S87N | Q109R | G118V | S128L | P129Q | S130A | S188R | T213T | N248N | 3.78 |
| 40 | S87N | Q109R | G118V | S128L | P129Q | S130A | S188R | T213E | N248R | 3.47 |
| 75 | S87N | Q109Q | G118D | S128L | P129Q | S130A | S188S | T213E | N248R | 3.01 |
| 42 | S87N | Q109R | G118V | S128L | P129Q | S130A | S188D | T213T | N248R | 2.74 |
| 32 | S87N | Q109R | G118V | S128L | P129Q | S130A | S188S | T213E | N248R | 2.52 |
| 12 | S87N | Q109Q | G118V | S128L | P129Q | S130A | S188R | T213E | N248N | 2.48 |
| 73 | S87N | Q109R | G118R | S128L | P129Q | S130A | S188D | T213E | N248R | 2.46 |
| 21 | S87N | Q109Q | G118V | S128L | P129Q | S130A | S188D | T213R | N248R | 2.43 |
| 66 | S87R | Q109Q | G118R | S128L | P129Q | S130A | S188D | T213E | N248N | 2.41 |
| 63 | S87R | Q109R | G118V | S128L | P129Q | S130A | S188D | T213E | N248R | 2.41 |
| 10 | S87N | Q109Q | G118V | S128L | P129Q | S130A | S188R | T213T | N248R | 2.38 |
| 39 | S87N | Q109R | G118V | S128L | P129Q | S130A | S188R | T213E | N248N | 2.31 |
| 45 | S87N | Q109R | G118V | S128L | P129Q | S130A | S188D | T213R | N248R | 2.30 |
| 35 | S87N | Q109R | G118V | S128L | P129Q | S130A | S188R | T213T | N248D | 2.25 |
| 37 | S87N | Q109R | G118V | S128L | P129Q | S130A | S188R | T213R | N248R | 2.19 |
| 17 | S87N | Q109Q | G118V | S128L | P129Q | S130A | S188D | T213T | N248N | 2.16 |
| 7 | S87N | Q109Q | G118V | S128L | P129Q | S130A | S188S | T213E | N248N | 2.14 |
| 31 | S87N | Q109R | G118V | S128L | P129Q | S130A | S188S | T213E | N248N | 2.02 |
| 15 | S87N | Q109Q | G118V | S128L | P129Q | S130A | S188R | T213E | N248N | 2.02 |
| 79 | S87R | Q109R | G118R | S128L | P129Q | S130A | S188D | T213E | N248N | 1.95 |
| 27 | S87N | Q109R | G118V | S128L | P129Q | S130A | S188S | T213T | N248D | 1.93 |
| 30 | S87N | Q109R | G118V | S128L | P129Q | S130A | S188S | T213R | N248D | 1.83 |
| 34 | S87N | Q109R | G118V | S128L | P129Q | S130A | S188R | T213T | N248R | 1.81 |
| 62 | S87R | Q109R | G118R | S128L | P129Q | S130A | S188D | T213E | N248R | 1.69 |
| 16 | S87N | Q109Q | G118V | S128L | P129Q | S130A | S188R | T213E | N248R | 1.63 |
| 46 | S87N | Q109R | G118V | S128L | P129Q | S130A | S188D | T213R | N248D | 1.61 |
| 67 | S87R | Q109Q | G118R | S128L | P129Q | S130A | S188S | T213E | N248R | 1.56 |
| 13 | S87N | Q109Q | G118V | S128L | P129Q | S130A | S188R | T213R | N248R | 1.55 |
| 47 | S87N | Q109R | G118V | S128L | P129Q | S130A | S188D | T213E | N248N | 1.52 |
| 64 | S87R | Q109Q | G118R | S128L | P129Q | S130A | S188D | T213E | N248R | 1.49 |
| 4 | S87N | Q109Q | G118V | S128L | P129Q | S130A | S188S | T213R | N248N | 1.48 |
| 8 | S87N | Q109Q | G118V | S128L | P129Q | S130A | S188S | T213E | N248R | 1.46 |
| 25 | S87N | Q109R | G118V | S128L | P129Q | S130A | S188S | T213T | N248N | 1.39 |
| 3 | S87N | Q109Q | G118V | S128L | P129Q | S130A | S188S | T213T | N248D | 1.13 |
| 49 | S87N | Q109Q | G118V | S128L | P129Q | S130A | S188S | T213E | N248D | 1.13 |
| 69 | S87R | Q109D | G118R | S128L | P129Q | S130A | S188D | T213E | N248R | 1.08 |
| 14 | S87N | Q109Q | G118V | S128L | P129Q | S130A | S188R | T213R | N248D | 0.96 |
| 28 | S87N | Q109R | G118V | S128L | P129Q | S130A | S188S | T213R | N248N | 0.88 |
| 61 | S87R | Q109D | G118R | S128L | P129Q | S130A | S188S | T213E | N248R | 0.82 |

TABLE 7-4

Protease Variants with PI ≥0.8 on C-S38 Microswatch Assay in CALGONIT ® Detergent (WE ADW)

| Variant | S87 | Q109 | G118 | S128 | P129 | S130 | S188 | T213 | S248 | PI |
|---|---|---|---|---|---|---|---|---|---|---|
| 38 | S87N | Q109R | G118V | S128L | P129Q | S130A | S188R | T213R | N248D | 1.36 |
| 1 | S87N | Q109Q | G118V | S128L | P129Q | S130A | S188S | T213T | N248N | 1.30 |
| 74 | S87N | Q109Q | G118R | S128L | P129Q | S130A | S188D | T213E | N248N | 1.47 |
| 33 | S87N | Q109R | G118V | S128L | P129Q | S130A | S188R | T213T | N248N | 1.75 |
| 40 | S87N | Q109R | G118V | S128L | P129Q | S130A | S188R | T213E | N248N | 1.10 |
| 75 | S87N | Q109Q | G118D | S128L | P129Q | S130A | S188S | T213E | N248R | 1.47 |
| 42 | S87N | Q109R | G118V | S128L | P129Q | S130A | S188D | T213T | N248R | 1.06 |
| 12 | S87N | Q109Q | G118V | S128L | P129Q | S130A | S188R | T213R | N248N | 1.18 |
| 73 | S87N | Q109R | G118R | S128L | P129Q | S130A | S188D | T213E | N248N | 1.13 |
| 21 | S87N | Q109Q | G118V | S128L | P129Q | S130A | S188D | T213R | N248R | 1.20 |
| 66 | S87R | Q109Q | G118R | S128L | P129Q | S130A | S188D | T213E | N248N | 1.78 |
| 63 | S87N | Q109Q | G118V | S128L | P129Q | S130A | S188D | T213E | N248R | 1.34 |
| 10 | S87N | Q109Q | G118V | S128L | P129Q | S130A | S188R | T213T | N248R | 1.21 |
| 80 | S87R | Q109Q | G118R | S128L | P129Q | S130A | S188D | T213T | N248N | 1.37 |
| 39 | S87N | Q109R | G118V | S128L | P129Q | S130A | S188R | T213E | N248N | 1.38 |
| 45 | S87N | Q109R | G118V | S128L | P129Q | S130A | S188D | T213E | N248R | 0.97 |
| 35 | S87N | Q109R | G118V | S128L | P129Q | S130A | S188R | T213T | N248D | 1.19 |
| 37 | S87N | Q109R | G118V | S128L | P129Q | S130A | S188R | T213R | N248D | 0.91 |
| 81 | S87N | Q109R | G118V | S128L | P129Q | S130A | S188R | T213R | N248R | 1.22 |
| 36 | S87N | Q109R | G118V | S128L | P129Q | S130A | S188R | T213E | N248N | 1.03 |
| 17 | S87N | Q109Q | G118V | S128L | P129Q | S130A | S188D | T213T | N248N | 1.43 |
| 7 | S87N | Q109Q | G118V | S128L | P129Q | S130A | S188S | T213E | N248N | 1.20 |
| 44 | S87N | Q109R | G118V | S128L | P129Q | S130A | S188D | T213R | N248N | 1.13 |
| 31 | S87N | Q109R | G118V | S128L | P129Q | S130A | S188S | T213E | N248N | 0.81 |
| 15 | S87N | Q109Q | G118V | S128L | P129Q | S130A | S188R | T213E | N248N | 1.40 |
| 79 | S87R | Q109R | G118R | S128L | P129Q | S130A | S188D | T213T | N248R | 1.17 |
| 26 | S87N | Q109R | G118V | S128L | P129Q | S130A | S188S | T213T | N248R | 0.80 |
| 27 | S87N | Q109R | G118V | S128L | P129Q | S130A | S188S | T213T | N248D | 1.12 |
| 48 | S87N | Q109R | G118V | S128L | P129Q | S130A | S188D | T213E | N248N | 0.99 |
| 30 | S87N | Q109R | G118V | S128L | P129Q | S130A | S188S | T213R | N248D | 1.20 |
| 34 | S87N | Q109R | G118V | S128L | P129Q | S130A | S188R | T213T | N248R | 1.13 |
| 62 | S87R | Q109Q | G118R | S128L | P129Q | S130A | S188D | T213E | N248R | 0.86 |
| 16 | S87N | Q109Q | G118V | S128L | P129Q | S130A | S188R | T213E | N248R | 1.22 |
| 24 | S87N | Q109Q | G118V | S128L | P129Q | S130A | S188D | T213E | N248R | 0.82 |
| 46 | S87N | Q109R | G118V | S128L | P129Q | S130A | S188D | T213R | N248D | 1.41 |
| 43 | S87N | Q109R | G118V | S128L | P129Q | S130A | S188D | T213T | N248D | 0.81 |
| 67 | S87R | Q109Q | G118V | S128L | P129Q | S130A | S188S | T213E | N248R | 1.26 |
| 13 | S87N | Q109Q | G118V | S128L | P129Q | S130A | S188R | T213R | N248R | 1.12 |
| 47 | S87N | Q109R | G118V | S128L | P129Q | S130A | S188D | T213E | N248N | 1.13 |
| 64 | S87R | Q109Q | G118R | S128L | P129Q | S130A | S188D | T213E | N248R | 1.09 |
| 71 | S87R | Q109D | G118R | S128L | P129Q | S130A | S188D | T213E | N248R | 0.86 |
| 2 | S87N | Q109Q | G118V | S128L | P129Q | S130A | S188S | T213T | N248R | 0.99 |
| 4 | S87N | Q109Q | G118V | S128L | P129Q | S130A | S188S | T213R | N248N | 0.83 |
| 8 | S87N | Q109Q | G118V | S128L | P129Q | S130A | S188S | T213E | N248R | 1.16 |
| 25 | S87N | Q109R | G118V | S128L | P129Q | S130A | S188S | T213T | N248N | 1.43 |
| 53 | S87N | Q109R | G118V | S128L | P129Q | S130A | S188R | T213E | N248D | 0.92 |
| 65 | S87R | Q109Q | G118V | S128L | P129Q | S130A | S188D | T213E | N248N | 0.83 |
| 49 | S87N | Q109Q | G118V | S128L | P129Q | S130A | S188S | T213E | N248D | 1.05 |
| 69 | S87R | Q109D | G118R | S128L | P129Q | S130A | S188D | T213E | N248R | 0.83 |
| 22 | S87N | Q109Q | G118V | S128L | P129Q | S130A | S188D | T213R | N248D | 1.17 |
| 18 | S87N | Q109Q | G118V | S128L | P129Q | S130A | S188D | T213T | N248R | 1.18 |
| 14 | S87N | Q109Q | G118V | S128L | P129Q | S130A | S188R | T213R | N248D | 0.85 |
| 50 | S87N | Q109Q | G118V | S128L | P129Q | S130A | S188R | T213E | N248D | 0.91 |

TABLE 7-5

Protease Variants with PI ≥0.8 on BMI Assay in TIDE ® 2X Coldwater (NA Liquid Laundry)

| Variant | S87 | Q109 | G118 | S128 | P129 | S130 | S188 | T213 | S248 | PI GCI-P036 | PI FNA |
|---|---|---|---|---|---|---|---|---|---|---|---|
| 75 | S87N | Q109Q | G118D | S128L | P129Q | S130A | S188S | T213E | N248R | 1.74 | 1.16 |
| 17 | S87N | Q109Q | G118V | S128L | P129Q | S130A | S188D | T213T | N248N | 1.72 | 1.15 |
| 60 | S87D | Q109D | G118R | S128L | P129Q | S130A | S188R | T213E | N248D | 1.70 | 1.13 |
| 7 | S87N | Q109Q | G118V | S128L | P129Q | S130A | S188S | T213E | N248N | 1.69 | 1.13 |
| 50 | S87N | Q109Q | G118V | S128L | P129Q | S130A | S188R | T213E | N248D | 1.69 | 1.13 |
| 23 | S87N | Q109Q | G118V | S128L | P129Q | S130A | S188D | T213E | N248N | 1.59 | 1.06 |
| 43 | S87N | Q109R | G118V | S128L | P129Q | S130A | S188D | T213T | N248D | 1.58 | 1.06 |
| 3 | S87N | Q109Q | G118V | S128L | P129Q | S130A | S188S | T213T | N248D | 1.57 | 1.05 |
| 49 | S87N | Q109Q | G118V | S128L | P129Q | S130A | S188S | T213E | N248D | 1.54 | 1.03 |

TABLE 7-5-continued

Protease Variants with PI ≥0.8 on BMI Assay in TIDE ® 2X Coldwater (NA Liquid Laundry)

| Variant | S87 | Q109 | G118 | S128 | P129 | S130 | S188 | T213 | S248 | PI GCI-P036 | PI FNA |
|---|---|---|---|---|---|---|---|---|---|---|---|
| 22 | S87N | Q109Q | G118V | S128L | P129Q | S130A | S188D | T213R | N248D | 1.54 | 1.03 |
| 19 | S87N | Q109Q | G118V | S128L | P129Q | S130A | S188D | T213T | N248D | 1.53 | 1.02 |
| 71 | S87R | Q109D | G118R | S128L | P129Q | S130A | S188D | T213E | N248N | 1.52 | 1.02 |
| 1 | S87N | Q109Q | G118V | S128L | P129Q | S130A | S188S | T213T | N248N | 1.46 | 0.98 |
| 59 | S87D | Q109Q | G118D | S128L | P129Q | S130A | S188S | T213E | N248D | 1.45 | 0.97 |
| 52 | S87N | Q109V | G118V | S128L | P129Q | S130A | S188S | T213E | N248D | 1.41 | 0.94 |
| 51 | S87N | Q109Q | G118V | S128L | P129Q | S130A | S188D | T213E | N248D | 1.38 | 0.92 |
| 69 | S87R | Q109D | G118R | S128L | P129Q | S130A | S188D | T213E | N248R | 1.34 | 0.90 |
| 18 | S87N | Q109Q | G118V | S128L | P129Q | S130A | S188D | T213T | N248R | 1.34 | 0.89 |
| 15 | S87N | Q109Q | G118V | S128L | P129Q | S130A | S188R | T213E | N248N | 1.33 | 0.89 |
| 47 | S87N | Q109R | G118V | S128L | P129Q | S130A | S188D | T213E | N248N | 1.32 | 0.88 |
| 8 | S87N | Q109Q | G118V | S128L | P129Q | S130A | S188S | T213E | N248R | 1.31 | 0.88 |
| 27 | S87N | Q109R | G118V | S128L | P129Q | S130A | S188S | T213T | N248D | 1.30 | 0.87 |
| 24 | S87N | Q109Q | G118V | S128L | P129Q | S130A | S188D | T213E | N248R | 1.29 | 0.86 |
| 66 | S87R | Q109Q | G118R | S128L | P129Q | S130A | S188D | T213E | N248N | 1.26 | 0.84 |
| 54 | S87N | Q109R | G118V | S128L | P129Q | S130A | S188D | T213E | N248D | 1.25 | 0.84 |
| 31 | S87N | Q109R | G118V | S128L | P129Q | S130A | S188S | T213E | N248N | 1.22 | 0.82 |
| 46 | S87N | Q109Q | G118V | S128L | P129Q | S130A | S188D | T213R | N248D | 1.21 | 0.81 |
| 25 | S87N | Q109R | G118V | S128L | P129Q | S130A | S188S | T213T | N248N | 1.19 | 0.80 |
| 65 | S87N | Q109Q | G118V | S128L | P129Q | S130A | S188D | T213E | N248R | 1.18 | 0.79 |
| 61 | S87R | Q109D | G118R | S128L | P129Q | S130A | S188S | T213E | N248R | 1.15 | 0.77 |
| 11 | S87N | Q109Q | G118V | S128L | P129Q | S130A | S188R | T213R | N248D | 1.13 | 0.75 |
| 2 | S87N | Q109Q | G118V | S128L | P129Q | S130A | S188S | T213T | N248R | 1.08 | 0.72 |
| 6 | S87N | Q109Q | G118V | S128L | P129Q | S130A | S188S | T213R | N248D | 1.08 | 0.72 |
| 21 | S87N | Q109Q | G118V | S128L | P129Q | S130A | S188D | T213R | N248R | 1.08 | 0.72 |
| 4 | S87N | Q109Q | G118V | S128L | P129Q | S130A | S188S | T213R | N248N | 1.05 | 0.70 |
| 48 | S87N | Q109R | G118V | S128L | P129Q | S130A | S188D | T213E | N248R | 1.05 | 0.70 |
| 42 | S87N | Q109R | G118V | S128L | P129Q | S130A | S188D | T213T | N248R | 1.04 | 0.70 |
| 35 | S87N | Q109R | G118V | S128L | P129Q | S130A | S188R | T213T | N248D | 1.02 | 0.68 |
| 32 | S87N | Q109R | G118V | S128L | P129Q | S130A | S188S | T213E | N248R | 1.02 | 0.68 |
| 78 | S87R | Q109D | G118R | S128L | P129Q | S130A | S188D | T213T | N248R | 1.01 | 0.68 |
| 44 | S87N | Q109R | G118V | S128L | P129Q | S130A | S188D | T213R | N248N | 1.00 | 0.67 |
| 53 | S87N | Q109R | G118V | S128L | P129Q | S130A | S188R | T213E | N248D | 0.97 | 0.65 |
| 12 | S87N | Q109Q | G118V | S128L | P129Q | S130A | S188R | T213R | N248N | 0.93 | 0.62 |
| 16 | S87N | Q109Q | G118V | S128L | P129Q | S130A | S188R | T213E | N248R | 0.85 | 0.57 |
| 67 | S87R | Q109Q | G118R | S128L | P129Q | S130A | S188S | T213E | N248R | 0.85 | 0.57 |
| 39 | S87N | Q109R | G118V | S128L | P129Q | S130A | S188R | T213E | N248N | 0.83 | 0.55 |
| 14 | S87N | Q109Q | G118V | S128L | P129Q | S130A | S188R | T213R | N248D | 0.82 | 0.55 |
| 10 | S87N | Q109Q | G118V | S128L | P129Q | S130A | S188R | T213T | N248R | 0.81 | 0.54 |
| 64 | S87R | Q109Q | G118R | S128L | P129Q | S130A | S188D | T213E | N248R | 0.81 | 0.54 |
| 26 | S87N | Q109R | G118V | S128L | P129Q | S130A | S188S | T213T | N248R | 0.80 | 0.53 |

Evaluation of Stain Removal by Multiple Mutation Library (MML) Variants of GCI-P036

Variants of GCI-P036 were tested for their stain removal performance in cleaning applications. Cloning of the combinatorial library was performed by Sloning BioTechnology using the Slonomax Technology. Preparation of variant protease samples was performed as previously described. Briefly, MML variants were tested in blood, milk, ink (BMI) microswatch CS-38 microswatch assays, using the methods of Example 1. As described throughout, functionality of protease variants was quantified as a performance index (PI), which is the ratio of performance of a variant to that of a reference protease. The substitutions are listed relative to the GCI-P036 reference protease using BPN' numbering and the PI is determined in relationship to the GCI-P036 reference. Results are shown in Tables 7-6 and 7-7.

TABLE 7-6

Multiple Mutation Variants of GCI-P036 Having a PI ≥0.5 in BMI Assay (pH 8; 32° C.)

| | PI |
|---|---|
| G097P/N185Q/A215I | 0.76 |
| N018R/N185R/S256W | 0.62 |
| N018Q/N185R/A215R | 0.75 |
| N018Q/N185Q/Y209W/S256W | 0.91 |
| N018K/G097P/N185K/S256W | 0.51 |
| N185K/Y209W/S256W | 1.15 |
| N018Q/N185K/Y209W/A215V/S256W | 0.84 |
| N018R/N185Q/A215V/S256W | 0.80 |
| N018R/G097P/Y209W/S256W | 0.62 |
| N018R/N185R/Y209W/S256W | 0.55 |
| N185Q/A215R/S256W | 0.80 |

TABLE 7-6-continued

Multiple Mutation Variants of GCI-P036 Having a PI ≥0.5 in BMI Assay (pH 8; 32° C.)

| | PI |
|---|---|
| N018K/A215R | 0.86 |
| N018K/G097P/Y209W/A215V/S256W | 0.59 |
| N018K/N185R/A215V | 0.68 |
| N018K/N185K/Y209W/A215R | 0.53 |
| N185K/A215V | 1.00 |
| N018K/N185K | 0.83 |
| N018R/N185R/A215R | 0.58 |
| N018K/G097P/N185K/Y209W/A215I/S256W | 0.53 |
| G097P/Y209W/A215V/S256W | 0.67 |
| N018K/N185K/S256W | 0.86 |
| N018R/Y209W/S256W | 0.74 |
| N018Q/N185K/S256W | 0.83 |
| N018K/N185Q/A215V/S256W | 1.10 |
| N018K/S256W | 0.75 |
| N018R/Y209W/A215V/S256W | 0.66 |
| N018Q/G097P/N185K/Y209W | 0.92 |
| N018R/G097P/Y209W/A215V | 0.66 |
| N185R/S256W | 0.85 |
| N018K/G097P/N185Q/Y209W/A215V/S256W | 0.62 |
| N018K/N185R/A215I/S256W | 0.60 |
| N185R/Y209W/A215I | 0.83 |
| N018R/N185K/S256W | 0.54 |
| N018K/N185Q/A215R/S256W | 0.63 |
| N018K/N185K/A215V/S256W | 0.64 |
| N018Q/N185R/S256W | 0.89 |
| N018K/A215I | 1.94 |
| N018Q/N185Q/A215V | 1.19 |
| N018R/N185Q/Y209W/S256W | 0.83 |
| N185R/Y209W/S256W | 0.85 |
| N018K/N185Q/Y209W/S256W | 0.63 |
| N018Q/N185K/Y209W/A215V | 0.79 |
| N018K/A215V | 1.07 |
| N018Q/N185Q/S256W | 1.01 |
| N018K/N185Q/S256W | 1.17 |
| N018R/N185K/A215V/S256W | 0.66 |
| N018Q/N185K | 0.71 |
| N018K/G097P/N185R/Y209W | 0.76 |
| N018K/N185R/Y209W/A215V/S256W | 0.51 |
| N018Q/N185K/Y209W/A215I/S256W | 0.76 |
| N018R/G097P/N185Q/A215I | 0.60 |
| N018Q/G097P/N185K/A215V | 0.82 |
| N185Q/S256W | 0.90 |
| N018K/G097P/N185R/Y209W/S256W | 0.52 |
| N043V/S101T/N248K | 1.08 |
| N043S/N117Y/N248K | 1.29 |
| N043E/S101E | 1.59 |
| N043S/S101E/N117Y/N248K | 1.31 |
| S101R/N248K | 0.83 |
| N043E/S101V | 2.16 |
| N043S/S101Y/N117I | 1.32 |
| N043I/N117Y | 1.29 |
| N043S/S101F | 1.07 |
| S101E/N117Y/N248K | 1.37 |
| S101Y/N117Y | 1.19 |
| N043V/S101V/N248K | 1.08 |
| N043I/S101R/N248K | 1.14 |
| N043F/N117I | 1.21 |
| S101F/N248K | 1.05 |
| N043S/S101Y/N248K | 1.10 |
| N043S/N248I | 1.78 |
| N043I/S101E/N248I | 1.79 |
| N043V/S101R/N117I/N248K | 0.76 |
| N043V/S101F/N248K | 0.99 |
| S101T/N248I | 1.53 |
| N043E/S101Y/N117Y/N248K | 1.23 |
| N043V/S101Y/N117I | 1.27 |
| N043V/S101V/N117I | 1.56 |
| S101Y/N248K | 1.06 |
| N043S/S101R/N117I/N248K | 0.85 |
| N043V/N248I | 2.00 |
| N043V/S101F/N117Y | 1.29 |
| N043E/S101F | 1.36 |
| N043S/S101N/N117I | 1.41 |
| S101V/N248K | 1.33 |
| N043I/S101N/N117Y/N248K | 1.19 |

TABLE 7-6-continued

Multiple Mutation Variants of GCI-P036 Having a PI ≥0.5 in BMI Assay (pH 8; 32° C.)

| | PI |
|---|---|
| S101F/N117I/N248I | 2.01 |
| S101F/N117Y/N248K | 0.82 |
| N043I/S101F/N117Y/N248K | 1.25 |
| N043S/S101F/N248K | 1.16 |
| N043E/S101N/N117Y | 1.53 |
| S101T/N117Y/N248K | 0.97 |
| N043S/S101E/N248K | 1.46 |
| S101R/N117I/N248K | 0.65 |
| N043E/S101Y/N117I/N248K | 1.21 |
| N043S/S101Y | 1.97 |
| N043E/S101E/N248K | 1.39 |
| N043V/S101Y | 1.26 |
| S101F/N117Y/N248I | 1.21 |
| N043S/S101E/N117I/N248I | 2.68 |
| N043F/S101R | 1.14 |
| N043V/S101E/N248I | 1.54 |
| N043V/N248K | 1.23 |
| S101E/N117I | 1.84 |
| N043V/S101Y/N117I/N248K | 1.01 |
| N043S/S101E | 1.50 |
| S101R/N117Y | 1.62 |
| N043I/S101Y/N117Y/N248K | 0.89 |
| N043V/S101F | 1.09 |
| N043S/S101Y/N117Y | 1.27 |
| S101Y/N117I/N248K | 0.82 |
| P052I/S144Y/N185R/Y209W | 1.01 |
| P052V/S144T | 1.56 |
| P052V/M119F/S144T/N185R/S256T | 1.62 |
| S144Y/Y209W/S256I | 1.15 |
| P052I/S144Y/Y209W/S256I | 1.36 |
| S144T/N185V | 1.33 |
| S144V/N185R/Y209W/S256T | 0.93 |
| M119F/Y209W | 0.78 |
| M119F/N185V/Y209W | 1.19 |
| M119F/N185R | 0.79 |
| S144V/Y209W | 1.21 |
| P052I/S144T/N185R/Y209W/S256T | 1.20 |
| P052I/N185V/Y209W | 1.34 |
| P052V/S144V/N185R/Y209W/S256T | 1.13 |
| S144W/S256I | 1.30 |
| S144V/N185R/Y209W | 0.98 |
| P052V/S144W/Y209W | 1.50 |
| P052V/M119F/S144T/Y209W | 1.73 |
| P052V/S144T/Y209W/S256I | 1.58 |
| P052V/S144Y/Y209W | 1.36 |
| P052I/S144T/Y209W/S256T | 1.60 |
| P052I/N185R/Y209W/S256I | 1.07 |
| P052V/S144W/N185R | 1.47 |
| P052V/M119F/S144T/N185R/Y209W | 1.05 |
| P052V/N185V/Y209W/S256I | 1.54 |
| P052I/S144Y/N185V/S256T | 1.63 |
| S144V/N185R/S256I | 0.75 |
| S144T/N185R | 1.02 |
| P052I/S144Y/N185V | 1.75 |
| P052V/M119F/S144T | 2.01 |
| M119F/N185R/Y209W/S256T | 0.84 |
| P052I/S144T/N185V/Y209W/S256T | 1.47 |
| M119F/Y209W/S256I | 1.26 |
| S144W/N185R/Y209W/S256T | 0.81 |
| P052V/S144V/N185V/Y209W | 1.37 |
| P052I/M119F | 1.52 |
| M119F/S144W/N185R/S256L | 0.94 |
| P052V/S144W/N185V/Y209W | 1.47 |
| N185V/Y209W | 0.99 |
| P052I/M119F/S144V/Y209W | 1.91 |
| P052I/S144V/Y209W | 1.25 |
| P052I/M119F/S144T/N185R/Y209W | 1.52 |
| S144W/N185V/Y209W/S256I | 1.22 |
| M119F/S144T/N185V/S256I | 1.18 |
| P052I/M119F/Y209W/S256I | 2.11 |
| P052I/N185V/Y209W/S256I | 1.60 |
| S144T/N185R/Y209W/S256I | 0.82 |
| P052V/M119F/N185V/Y209W/S256I | 1.93 |
| P052I/S144T | 1.44 |
| S144T/N185R/Y209W/S256T | 0.83 |

TABLE 7-6-continued

| Multiple Mutation Variants of GCI-P036 Having a PI ≥0.5 in BMI Assay (pH 8; 32° C.) | PI |
|---|---|
| S144V/S256I | 1.27 |
| P052I/S144T/S256I | 1.46 |
| P052V/S144T/N185V/Y209W/S256T | 1.47 |
| P052V/S144Y/S256T | 1.68 |
| P052I/S144T/Y209W/S256I | 1.01 |
| P052V/S256T | 1.48 |
| P052V/S144V/Y209W/S256I | 1.63 |
| P052V/S144T/N185V/Y209W/S256I | 1.62 |
| A001K/R045K/I072V/L126F/S164Q | 0.81 |
| A001K/L126F/S164Q | 1.11 |
| A001K/R045F/V104I/L126F/S164Q | 0.86 |
| A001K/I072V/V104I | 0.92 |
| A001K/R045K/I072V/S164F | 0.95 |
| A001K/L126F | 0.93 |
| A001K/R045F/I072V/V104G/S164T | 1.06 |
| R045L/I072S/S164I | 1.15 |
| L126A/S164N | 0.96 |
| A001K/L126F/S164F | 0.82 |
| R045K/L126F/S164F | 0.73 |
| A001K/R045K/I072V/V104I/L126F/S164F | 0.66 |
| A001K/I072C/V104I/L126F/S164Q | 0.73 |
| A001K/I072V/V104I/S164F | 0.83 |
| A001K/V104I/L126F/S164I | 0.85 |
| A001K/R045K/L126F | 1.17 |
| A001K/R045F/L126F/S164I | 0.70 |
| A001K/R045K/L126F/S164I | 0.77 |
| A001L/I072C | 0.80 |
| A001K/R045K/I072V/S164Q | 0.92 |
| A001K/I072C/L126F/S164Q | 0.78 |
| A001K/V104E | 0.91 |
| A001K/I072C/L126F | 0.95 |
| L126F/S164V | 0.98 |
| R045F/I072V/L126F/S164Q | 1.22 |
| A001K/R045S/V104C/L126Y/S164F | 0.72 |
| A001K/R045F/I072V/L126F/S164I | 0.76 |
| A001K/V104I/L126F/S164Q | 0.76 |
| A001K/R045K/V104I/S164Q | 0.81 |
| A001K/R045K/I072V/L126F | 0.73 |
| A001K/R045K/I072V/V104I/L126F/S164I | 1.48 |
| A001K/R045K/V104L/S164A | 1.02 |
| A001K/R045F/L126F/S164F | 0.82 |
| A001K/I072V/V104I/S164Q | 0.87 |
| A001K/I072V/L126F | 1.08 |
| A001K/I072V/L126F/S164F | 0.87 |
| V104E/L126I/S164L | 1.13 |
| A001K/R045K/L126F/S164Q | 0.73 |
| A001K/I072V | 0.91 |
| A001K/I072V/V104I/L126F/S164I | 1.00 |
| A001K/V104I/L126F | 0.78 |
| A001K/R045K/I072V/V104I/L126F/S164Q | 0.86 |
| A001K/R045K/I072V/L126F/S164F | 0.84 |
| A001K/R045F/I072V/L126F/S164Q | 0.73 |
| A001K/R045K/I072C/L126F/S164Q | 0.79 |
| A001K/R045K/S164F | 1.55 |
| A001K/R045F/I072C/V104I/S164F | 1.42 |
| A001K/R045F/I072C | 1.22 |
| A001K/S164Q | 1.01 |
| A001K/R045K/L126F/S164P | 0.80 |
| A001K/I072C/V104I/L126F | 0.71 |
| A001K/L126F/S164I | 0.71 |
| S024W/Q109V/G118S/S132Y | 0.59 |
| S024W/Q109K/G118R | 0.80 |
| S024H/Q109L | 0.60 |
| S024V/Q109R/G118F | 0.90 |
| S024R/Q109V | 0.69 |
| Q109T/G118N | 1.08 |
| S024W/Q109I | 0.94 |
| S024V/Q109C/G118L | 1.10 |
| S024R/Q109T/S132Y | 0.58 |
| S024H/Q109T/G118R | 0.67 |
| S024R/G118R/S132N | 1.03 |
| Q109I/S132N | 0.71 |
| Q109I/G118S | 1.07 |
| S024C/Q109K/G118I | 0.65 |
| S024W/Q109L | 0.95 |

TABLE 7-6-continued

Multiple Mutation Variants of GCI-P036 Having a PI ≥0.5 in BMI Assay (p

TABLE 7-6-continued

| Multiple Mutation Variants of GCI-P036 Having a PI ≥0.5 in BMI Assay (pH 8; 32° C.) | PI |
|---|---|
| S024R/Q109V/G118C/S132A | 1.23 |
| A001K/S024R/R045N/A172C | 0.71 |
| A001R/S024H/R045N/I107T/A172Q | 0.67 |
| R045F/I107T | 0.64 |
| R045V/I107R/A172D | 1.10 |
| A001R/A172Q | 1.10 |
| S024T/R045K/I107V | 0.68 |
| S024T/I107T | 0.56 |
| A001T/S024H/I107L/A172Y | 0.72 |
| A001R/S024W/R045K/I107T/A172Q | 0.55 |
| S024N/R045K/A172L | 0.93 |
| A001R/R045N/I107T | 0.64 |
| A001K/R045F/I107T | 0.72 |
| S024N/I107T | 0.56 |
| A001R/R045K/A172Q | 0.92 |
| R045K/I107T | 0.53 |
| A001K/S024L/R045A | 0.68 |
| A001R/R045F | 0.91 |
| I107Q/A172D | 0.70 |
| A001R/S024R/A172Q | 0.75 |
| A001K/A172L | 0.62 |
| A001S/A172V | 0.55 |
| A001I/R045T/I107R/A172T | 0.61 |
| A001R/S024H/R045K/I107T | 0.51 |
| S024W/A172Q | 0.94 |
| S024W/R045N/A172Q | 1.00 |
| R045N/I107T/A172Q | 0.61 |
| A001R/S024R | 0.59 |
| A001K/A172W | 0.78 |
| A001R/S024N | 0.74 |
| A001R/S024R/A172H | 0.74 |
| R045S/I107L | 0.66 |
| A001R/S024T/R045N/I107T/A172Q | 0.52 |
| A001Q/R045K/I107T | 0.60 |
| S024N/R045K/I107V/A172N | 0.63 |
| A001R/S024T/I107T/A172Q | 0.63 |
| A001K/S024N/R045K/A172Y | 0.80 |
| S024R/R045F/I107T/A172Q | 0.62 |
| R045N/I107V/A172Q | 0.50 |
| A001R/I107V/A172Q | 1.13 |
| A001K/R045F/I107L/A172N | 0.71 |
| A001P/A172V | 0.68 |
| S024I/I107R/G127I/A172R | 0.64 |
| A001K/S024T/I107T/G127Q/A172Q | 0.53 |
| A001C/S024V/I107L | 0.50 |
| A001R/S024T/R045K/A172Q | 0.84 |
| A001R/A172G | 0.62 |
| A001R/R045N/A172K | 0.54 |
| A001K/R045F/I107T | 0.51 |
| A001K/S024T/R045N/G127Q/A172Q | 0.60 |
| A001K/R045K/I107A/A172T | 0.62 |
| A001K/R045K/I107R/G127A/A172N | 0.79 |
| R045N/I107A/A172R | 0.62 |
| A001R/S024W/I107V/A172S | 0.56 |
| A001R/R045N/A172Q | 0.84 |
| S024T/R045K/I107T/G127R/A172Q | 0.52 |
| A001K/R045N/I107T/G127Q | 0.53 |
| A001K/S024H/I107V | 0.58 |
| I107A/G127K/A172G | 0.55 |
| A001R/S024W/R045K | 0.87 |
| A001R/R045N/I107V/A172V | 0.60 |
| A001K/S024H/R045N/I107T/G127Q/A172Q | 0.56 |
| S024Y/G127R/A172E | 0.67 |
| S024W/S099Q | 0.93 |
| S024W/S099T/S103P/G118T/S132N | 0.76 |
| S099Q/S103N/S132H | 1.04 |
| S099K/G118R | 0.57 |
| S024W/S099T/S103P | 1.14 |
| S024W/S103K/S132R | 0.97 |
| S024W/S103P | 0.83 |
| S099T/G118T/S132N | 1.61 |
| S024W/S099T/S103P/G118R | 0.82 |
| S024H/S099Q/S103P | 1.08 |
| S024H/S099K/S103R/G118A/S132P | 1.29 |
| S024H/S099T/S103P/G118R/S132H | 1.44 |

TABLE 7-6-continued

Multiple Mutation Variants of GCI-P036 Having a PI ≥0.5 in BMI Assay (pH 8; 32° C.)

| | PI |
|---|---|
| S024W/G118K | 0.74 |
| S024H/S099T/S103N/S132N | 1.11 |
| S099K/S103P/S132H | 0.81 |
| S099Q/S103N/G118R/S132N | 0.87 |
| S024W/S099T/S103N | 1.03 |
| S024P/S099Q/S103P/G118R | 1.18 |
| S099T/G118T/S132H | 1.86 |
| S024W/S099Q/S103N/G118T | 1.01 |
| S024W/S132H | 1.34 |
| S103L/S132E | 1.14 |
| S103R/S132P | 0.92 |
| S099Q/S103P/G118R | 0.83 |
| S099Q/S103N/G118T | 1.21 |
| S024H/S099Q/S132N | 1.09 |
| S024W/S099T/G118T/S132H | 1.39 |
| S099K/S103N/G118T | 0.95 |
| S024H/S099Q/S103P/S132H | 1.23 |
| S024H/S132R | 0.88 |
| S024W/S099T/S103N/S132N | 1.12 |
| S024T/G118D | 0.89 |
| S099N/S132R | 0.88 |
| S099H/S103I/G118N | 1.03 |
| S024W/S099Q/S103N/G118R/S132N | 0.97 |
| S024W/S099T/S103P/G118R/S132H | 1.20 |
| S024W/S099Q/G118T | 0.94 |
| S024W/S099T/G118R/S132R | 0.78 |
| S024H/S099Q/S132H | 0.88 |
| S099Q/S132R | 0.81 |
| S099Q/S103P/G118R/S132N | 1.26 |
| S024M/G118V | 0.72 |
| S024W/S132N | 0.88 |
| S099K/S103R/G118A/S132P | 0.85 |
| S024W/S099T/S103P/S132H | 1.41 |
| S024W/S099T/S103N/S132H | 0.91 |
| S087N/G118V/S128L/P129Q/S130A/S024R/Q109K | 0.86 |
| S087N/G118V/S128L/P129Q/S130A/S024W/Q109V | 1.02 |
| S087N/G118V/S128L/P129Q/S130A/S024W/Q109T | 1.04 |
| S087N/G118V/S128L/P129Q/S130A/S024W/Q109L | 0.58 |
| S087N/G118V/S128L/P129Q/S130A/S024H/Q109V | 1.04 |
| S087N/G118V/S128L/P129Q/S130A/S024W/Q109R/G127Q | 0.81 |
| S087N/G118V/S128L/P129Q/S130A/S024R | 0.70 |
| S087N/G118V/S128L/P129Q/S130A/S024H | 0.99 |
| S087N/G118V/S128L/P129Q/S130A/S024R/Q109L | 0.97 |
| S087N/G118V/S128L/P129Q/S130A/Q109T | 1.06 |
| S087N/G118V/S128L/P129Q/S130A/S024R/Q109V | 0.75 |
| S087N/G118V/S128L/P129Q/S130A/S024W/Q109I | 0.86 |
| S087N/G118V/S128L/P129Q/S130A/Q109V | 1.09 |
| S087N/G118V/S128L/P129Q/S130A/S024R/G127R | 0.56 |
| S087N/G118V/S128L/P129Q/S130A/S024W | 1.07 |
| S087N/G118V/S128L/P129Q/S130A/Q109T/G127Q | 0.80 |
| S087N/G118V/S128L/P129Q/S130A/S024T/G127T | 0.84 |
| S087N/G118V/S128L/P129Q/S130A/G127T | 0.84 |
| S087N/G118V/S128L/P129Q/S130A/Q109I | 1.10 |
| S087N/G118V/S128L/P129Q/S130A/S024T | 0.87 |
| S087N/G118V/S128L/P129Q/S130A/S024T/Q109V/G127T | 0.90 |
| S087N/G118V/S128L/P129Q/S130A/S024H/Q109V/G127Q | 0.67 |
| S087N/G118V/S128L/P129Q/S130A/S024N/Q109K | 0.83 |
| S087N/G118V/S128L/P129Q/S130A/G127Q | 0.85 |
| S087N/G118V/S128L/P129Q/S130A/S024N/Q109T/G127T | 0.93 |
| S087N/G118V/S128L/P129Q/S130A/S024R/Q109L/G127Q | 0.73 |
| S087N/G118V/S128L/P129Q/S130A/Q109L/G127Q | 0.99 |
| S087N/G118V/S128L/P129Q/S130A/R045S | 0.67 |
| S087N/G118V/S128L/P129Q/S130A/S024R/I107T/A172Q | 0.70 |
| S087N/G118V/S128L/P129Q/S130A/A001K/S024W/R045N/I107T | 0.64 |
| S087N/G118V/S128L/P129Q/S130A/S024N/I107V | 0.78 |
| S087N/G118V/S128L/P129Q/S130A/A001R/R045K/I107T | 0.65 |
| S087N/G118V/S128L/P129Q/S130A/S024H/I107V/A172S | 0.81 |
| S087N/G118V/S128L/P129Q/S130A/A001K/I107W/A172P | 0.69 |
| S087N/G118V/S128L/P129Q/S130A/A001R | 0.82 |
| S087N/G118V/S128L/P129Q/S130A/A001K/I107T/A172Q | 0.63 |
| S087N/G118V/S128L/P129Q/S130A/A001K/R045N/I107V | 0.80 |
| S087N/G118V/S128L/P129Q/S130A/A001K/S024H/A172Q | 0.93 |
| S087N/G118V/S128L/P129Q/S130A/A001R/S024W/A172W | 0.68 |
| S087N/G118V/S128L/P129Q/S130A/A172N | 0.69 |
| S087N/G118V/S128L/P129Q/S130A/A001R/I107V/A172Q | 0.68 |

TABLE 7-6-continued

Multiple Mutation Variants of GCI-P036 Having a PI ≥0.5 in BMI Assay (pH 8; 32° C.)

|  | PI |
| --- | --- |
| S087N/G118V/S128L/P129Q/S130A/S024T/I107T/A172Q | 0.78 |
| S087N/G118V/S128L/P129Q/S130A/A001K/S024H/I107V | 0.77 |
| S087N/G118V/S128L/P129Q/S130A/S024W/I107T | 0.85 |
| S087N/G118V/S128L/P129Q/S130A/A001R/R045K | 1.02 |
| S087N/G118V/S128L/P129Q/S130A/A001R/I107V/A172W | 0.67 |
| S087N/G118V/S128L/P129Q/S130A/A001K/R045K/I107S | 0.75 |
| S087N/G118V/S128L/P129Q/S130A/S024T/R045N/I107V/A172S | 0.82 |
| S087N/G118V/S128L/P129Q/S130A/S024N/I107N | 0.67 |
| S087N/G118V/S128L/P129Q/S130A/S024H/R045N/I107T | 0.95 |
| S087N/G118V/S128L/P129Q/S130A/A001K/S024T/I107V/A172W | 0.69 |
| S087N/G118V/S128L/P129Q/S130A/R045N/I107V/A172P | 0.78 |
| S087N/G118V/S128L/P129Q/S130A/R045F/I107T/A172Q | 0.91 |
| S087N/G118V/S128L/P129Q/S130A/A001K/R045F | 0.73 |
| S087N/G118V/S128L/P129Q/S130A/A001R/S024H/R045F/I107T | 0.65 |
| S087N/G118V/S128L/P129Q/S130A/A001K/R045N/I107T/A172Q | 0.88 |
| S087N/G118V/S128L/P129Q/S130A/A001R/S024R/R045K/I107G/A172L | 0.63 |
| S087N/G118V/S128L/P129Q/S130A/S024R/I107V/A172S | 0.78 |
| S087N/G118V/S128L/P129Q/S130A/A001R/S024N/I107T | 0.63 |
| S087N/G118V/S128L/P129Q/S130A/A001R/S024T/R045N/I107T | 0.74 |
| S087N/G118V/S128L/P129Q/S130A/A001R/A172I | 0.61 |
| S087N/G118V/S128L/P129Q/S130A/A001R/S024H/R045K/A172N | 0.72 |
| S087N/G118V/S128L/P129Q/S130A/S024R/R045F/I107T | 0.82 |
| S087N/G118V/S128L/P129Q/S130A/A001R/I107V/A172P | 0.72 |
| S087N/G118V/S128L/P129Q/S130A/S024T | 1.03 |
| S087N/G118V/S128L/P129Q/S130A/A001R/R045N/I107T/A172Q | 0.70 |
| S087N/G118V/S128L/P129Q/S130A/R045N/A172Q | 1.06 |
| S087N/G118V/S128L/P129Q/S130A/S024W/R045F/I107V/A172Q | 0.83 |
| S087N/G118V/S128L/P129Q/S130A/A001R/A172Q | 0.79 |
| S087N/G118V/S128L/P129Q/S130A/S024N/I107T | 0.57 |
| S087N/G118V/S128L/P129Q/S130A/A001R/S024H/R045K/I107T/A172Q | 0.54 |
| S087N/G118V/S128L/P129Q/S130A/S024W/S099K | 1.07 |
| S087N/G118V/S128L/P129Q/S130A/S024W/S099T/S103N/G127R/S132N | 0.51 |
| S087N/G118V/S128L/P129Q/S130A/S024W/S099K/S103P | 1.32 |
| S087N/G118V/S128L/P129Q/S130A/S099T/S103N/S132H | 0.70 |
| S087N/G118V/S128L/P129Q/S130A/S099Q/S103N | 1.06 |
| S087N/G118V/S128L/P129Q/S130A/S099Q | 0.96 |
| S087N/G118V/S128L/P129Q/S130A/S024W | 1.20 |
| S087N/G118V/S128L/P129Q/S130A/S024W/S099T/S103N/S132N | 1.77 |
| S087N/G118V/S128L/P129Q/S130A/S024W/S099T/S132N | 1.28 |
| S087N/G118V/S128L/P129Q/S130A/S024W/S099T | 0.99 |
| S087N/G118V/S128L/P129Q/S130A/S024W/S099T/S103N | 0.96 |
| S087N/G118V/S128L/P129Q/S130A/S103N/S132H | 1.52 |
| S087N/G118V/S128L/P129Q/S130A/S024W/S099T/G127R/S132H | 0.65 |
| S087N/G118V/S128L/P129Q/S130A/S099K/S103N | 0.95 |
| S087N/G118V/S128L/P129Q/S130A/S024H/S099Q/S132N | 1.70 |
| S087N/G118V/S128L/P129Q/S130A/S024W/S099Q/S103P | 1.36 |
| S087N/G118V/S128L/P129Q/S130A/S024H/S099Q | 0.98 |
| S087N/G118V/S128L/P129Q/S130A/S103P | 1.25 |
| S087N/G118V/S128L/P129Q/S130A/S099K/S132H | 1.17 |
| S087N/G118V/S128L/P129Q/S130A/S024H/S099Q/S103P | 1.36 |
| S087N/G118V/S128L/P129Q/S130A/S024W/S103P/S132N | 0.98 |
| S087N/G118V/S128L/P129Q/S130A/S024H/S099T/S103P/S132N | 0.87 |
| S087N/G118V/S128L/P129Q/S130A/S099T/S132H | 1.09 |
| S087N/G118V/S128L/P129Q/S130A/S024L/S099K/S103P/S132N | 0.98 |
| S087N/G118V/S128L/P129Q/S130A/S099T/S103N | 1.49 |
| S087N/G118V/S128L/P129Q/S130A/S099K/S103P | 1.25 |
| S087N/G118V/S128L/P129Q/S130A/S024W/G127T | 0.93 |
| S087N/G118V/S128L/P129Q/S130A/S024H/S099T/S132N | 1.73 |
| S087N/G118V/S128L/P129Q/S130A/S024H/S099T/S103P | 1.41 |
| S087N/G118V/S128L/P129Q/S130A/S099Q/S132H | 1.43 |
| S087N/G118V/S128L/P129Q/S130A/S024W/S099Q/S132H | 1.29 |
| S087N/G118V/S128L/P129Q/S130A/S099K | 0.92 |
| S087N/G118V/S128L/P129Q/S130A/S024W/S099Q | 0.97 |
| S087N/G118V/S128L/P129Q/S130A/S099T/S103P | 1.20 |
| S087N/G118V/S128L/P129Q/S130A/S024H/S099K/S103N | 0.99 |
| S087N/G118V/S128L/P129Q/S130A/S024W/S099Q/S132N | 1.41 |
| S087N/G118V/S128L/P129Q/S130A/S099Q/S103P | 0.85 |
| S087N/G118V/S128L/P129Q/S130A/S024H/S099K/S103N/S132N | 1.32 |
| S087N/G118V/S128L/P129Q/S130A/S024W/S099Q/S103N/S132N | 1.53 |
| S087N/G118V/S128L/P129Q/S130A/S024W/S099K/S132H | 0.99 |
| S087N/G118V/S128L/P129Q/S130A/N018K/N185K | 0.82 |
| S087N/G118V/S128L/P129Q/S130A/N018R/G097P/N185K/A215R | 0.75 |
| S087N/G118V/S128L/P129Q/S130A/N185R/Y209W | 0.83 |
| S087N/G118V/S128L/P129Q/S130A/N018R/N185K | 0.68 |
| S087N/G118V/S128L/P129Q/S130A/N018K | 1.03 |

TABLE 7-6-continued

Multiple Mutation Variants of GCI-P036 Having a PI ≥0.5 in BMI Assay (pH 8; 32° C.)

| | PI |
|---|---|
| S087N/G118V/S128L/P129Q/S130A/N018K/G097P/N185Q/A215I/S256W | 0.83 |
| S087N/G118V/S128L/P129Q/S130A/N018Q/N185Q/S256W | 0.91 |
| S087N/G118V/S128L/P129Q/S130A/N018Q/N185Q/Y209W/S256W | 0.85 |
| S087N/G118V/S128L/P129Q/S130A/N018Q/N185R/A215R/S256P | 1.03 |
| S087N/G118V/S128L/P129Q/S130A/N018R/N185K/Y209W/A215I/S256W | 0.71 |
| S087N/G118V/S128L/P129Q/S130A/Y209W/S256W | 0.86 |
| S087N/G118V/S128L/P129Q/S130A/N018R/S256W | 0.89 |
| S087N/G118V/S128L/P129Q/S130A/N018R/Y209W/A215I/S256W | 0.73 |
| S087N/G118V/S128L/P129Q/S130A/N018K/N185R | 0.82 |
| S087N/G118V/S128L/P129Q/S130A/N018K/N185K/S256W | 0.76 |
| S087N/G118V/S128L/P129Q/S130A/N018Q/Y209W/S256W | 0.87 |
| S087N/G118V/S128L/P129Q/S130A/N185R/Y209W/A215V/S256R | 0.81 |
| S087N/G118V/S128L/P129Q/S130A/N185K/A215V/S256W | 0.97 |
| S087N/G118V/S128L/P129Q/S130A/N018K/Y209W | 0.82 |
| S087N/G118V/S128L/P129Q/S130A/N018K/N185Q/S256W | 0.80 |
| S087N/G118V/S128L/P129Q/S130A/N018R/Y209W/S256W | 0.73 |
| S087N/G118V/S128L/P129Q/S130A/N018K/A215R/S256W | 0.57 |
| S087N/G118V/S128L/P129Q/S130A/N018K/G097P/N185R/A215R | 0.68 |
| S087N/G118V/S128L/P129Q/S130A/N018R/N185R/Y209W/S256W | 0.68 |
| S087N/G118V/S128L/P129Q/S130A/N018Q/A215R/S256W | 0.76 |
| S087N/G118V/S128L/P129Q/S130A/N018K/G097P/N185R/Y209W | 0.70 |
| S087N/G118V/S128L/P129Q/S130A/A215V/S256W | 1.00 |
| S087N/G118V/S128L/P129Q/S130A/N185K/Y209W/A215V/S256W | 0.85 |
| S087N/G118V/S128L/P129Q/S130A/N018R/N185R/A215R | 0.82 |
| S087N/G118V/S128L/P129Q/S130A/N185K/Y209W/A215V | 0.89 |
| S087N/G118V/S128L/P129Q/S130A/N018K/N185R/A215V/S256W | 0.63 |
| S087N/G118V/S128L/P129Q/S130A/N018R/N185K/A215V/S256W | 0.74 |
| S087N/G118V/S128L/P129Q/S130A/G097P/N185R/A215I/S256W | 0.83 |
| S087N/G118V/S128L/P129Q/S130A/N018R | 0.92 |
| S087N/G118V/S128L/P129Q/S130A/N018K/N185K/Y209W/A215I | 0.91 |
| S087N/G118V/S128L/P129Q/S130A/N018Q/A215I/S256W | 0.90 |
| S087N/G118V/S128L/P129Q/S130A/N018K/N185Q | 0.77 |
| S087N/G118V/S128L/P129Q/S130A/N018K/N185R/A215I/S256W | 0.71 |
| S087N/G118V/S128L/P129Q/S130A/G097P/N185Q/Y209W/A215V/S256W | 0.82 |
| S087N/G118V/S128L/P129Q/S130A/N018K/N185Q/A215R | 0.62 |
| S087N/G118V/S128L/P129Q/S130A/Y209W/A215I/S256W | 0.98 |
| S087N/G118V/S128L/P129Q/S130A/N018K/N185Q/A215V/S256W | 0.72 |
| S087N/G118V/S128L/P129Q/S130A/N185Q/Y209W/A215R | 0.88 |
| S087N/G118V/S128L/P129Q/S130A/N018Q/G097P/N185R | 1.01 |
| S087N/G118V/S128L/P129Q/S130A/N185R/A215V/S256W | 0.83 |
| S087N/G118V/S128L/P129Q/S130A/N018R/N185K/Y209W | 0.63 |
| S087N/G118V/S128L/P129Q/S130A/A215V | 1.20 |
| S087N/G118V/S128L/P129Q/S130A/N018R/N185Q/A215I/S256W | 0.88 |
| S087N/G118V/S128L/P129Q/S130A/G097P/N185K/A215I | 0.87 |
| S087N/G118V/S128L/P129Q/S130A/N018Q/N185K/A215R | 0.84 |
| S087N/G118V/S128L/P129Q/S130A/N018K/Y209W/A215V | 0.84 |
| S087N/G118V/S128L/P129Q/S130A/N018K/N185K/Y209W | 0.76 |
| S087N/G118V/S128L/P129Q/S130A/N018R/G097P/N185K/Y209W/A215I/S256W | 0.67 |
| S087N/G118V/S128L/P129Q/S130A/N018Q/N185K/A215V | 0.88 |
| S087N/G118V/S128L/P129Q/S130A/N185R/Y209W/S256L | 0.80 |
| S087N/G118V/S128L/P129Q/S130A/N018K/S256W | 0.72 |
| S087N/G118V/S128L/P129Q/S130A/N018Q/N185K/S256W | 0.84 |
| S087N/G118V/S128L/P129Q/S130A/N185Q/Y209W/A215V/S256W | 0.77 |
| S087N/G118V/S128L/P129Q/S130A/P052I/N248K | 1.07 |
| S087N/G118V/S128L/P129Q/S130A/N043W/S101F/N248K | 0.97 |
| S087N/G118V/S128L/P129Q/S130A/N043V/P052I/S101Y | 1.33 |
| S087N/G118V/S128L/P129Q/S130A/N043V/S101T | 1.08 |
| S087N/G118V/S128L/P129Q/S130A/N043V/P052V/S101F/N248K | 1.53 |
| S087N/G118V/S128L/P129Q/S130A/P052V | 1.20 |
| S087N/G118V/S128L/P129Q/S130A/N043S | 1.37 |
| S087N/G118V/S128L/P129Q/S130A/N043V/S101Y | 1.04 |
| S087N/G118V/S128L/P129Q/S130A/N043S/P052V/S101R | 1.18 |
| S087N/G118V/S128L/P129Q/S130A/N043S/P052V/S101F | 1.30 |
| S087N/G118V/S128L/P129Q/S130A/N043F/P052V/S101T/N248K | 1.12 |
| S087N/G118V/S128L/P129Q/S130A/N043I/S101E/N248K | 1.13 |
| S087N/G118V/S128L/P129Q/S130A/S101E/N248K | 1.08 |
| S087N/G118V/S128L/P129Q/S130A/N248K | 0.97 |
| S087N/G118V/S128L/P129Q/S130A/N043W/S101E | 1.09 |
| S087N/G118V/S128L/P129Q/S130A/N043S/S101E/N248K | 1.29 |
| S087N/G118V/S128L/P129Q/S130A/P052I/S101V/N248K | 0.99 |
| S087N/G118V/S128L/P129Q/S130A/S101F/N248K | 0.72 |
| S087N/G118V/S128L/P129Q/S130A/N043V/S101T/N248K | 1.00 |
| S087N/G118V/S128L/P129Q/S130A/N043V/P052V/N248K | 1.52 |
| S087N/G118V/S128L/P129Q/S130A/N043S/S101N/N248I | 1.64 |
| S087N/G118V/S128L/P129Q/S130A/S101Y | 0.86 |

TABLE 7-6-continued

Multiple Mutation Variants of GCI-P036 Having a PI ≥0.5 in BMI Assay (

TABLE 7-6-continued

Multiple Mutation Variants of GCI-P036 Having a PI ≥0.5 in BMI Assay (pH 8; 32° C.)

| | PI |
|---|---|
| S087N/G118V/S128L/P129Q/S130A/S144V/Y209W/S256I | 1.15 |
| S087N/G118V/S128L/P129Q/S130A/N043V/S144W/Y209W/S256I | 1.12 |
| S087N/G118V/S128L/P129Q/S130A/N185V/Y209W | 0.86 |
| S087N/G118V/S128L/P129Q/S130A/P052V/S144T/N185R/S256T | 0.97 |
| S087N/G118V/S128L/P129Q/S130A/S144T/N185V/S256I | 1.17 |
| S087N/G118V/S128L/P129Q/S130A/N043S/N185R/Y209W/S256T | 0.86 |
| S087N/G118V/S128L/P129Q/S130A/S144T/N185V/Y209W | 1.01 |
| S087N/G118V/S128L/P129Q/S130A/S144V | 0.99 |
| S087N/G118V/S128L/P129Q/S130A/N043T/S144V/Y209W/S256T | 1.17 |
| S087N/G118V/S128L/P129Q/S130A/P052V/S144Y/N185R/Y209W/S256T | 1.30 |
| S087N/G118V/S128L/P129Q/S130A/S144Y/N185V/Y209W | 1.25 |
| S087N/G118V/S128L/P129Q/S130A/G097T/Y209W/S256I | 1.08 |
| S087N/G118V/S128L/P129Q/S130A/N185R/S256T | 0.87 |
| S087N/G118V/S128L/P129Q/S130A/P052V/S144V/N185V/Y209W/S256I | 1.29 |
| S087N/G118V/S128L/P129Q/S130A/P052V/S144T/Y209W/S256T | 1.12 |
| S087N/G118V/S128L/P129Q/S130A/S144T/S256I | 1.11 |
| S087N/G118V/S128L/P129Q/S130A/S144T/N185R/S256I | 0.80 |
| S087N/G118V/S128L/P129Q/S130A/N043S/S256I | 0.94 |
| S087N/G118V/S128L/P129Q/S130A/S144Y/N185R/Y209W/S256T | 1.06 |
| S087N/G118V/S128L/P129Q/S130A/N043V/N185V/Y209W/S256I | 1.00 |
| S087N/G118V/S128L/P129Q/S130A/P052V/S144Y/N185V/Y209W/S256I | 1.23 |
| S087N/G118V/S128L/P129Q/S130A/G097T/S144T/S256I | 1.11 |
| S087N/G118V/S128L/P129Q/S130A/P052V/S144V/Y209W | 1.27 |
| S087N/G118V/S128L/P129Q/S130A/N043V/P052V/S144V/N185R/Y209W/S256I | 0.90 |
| S087N/G118V/S128L/P129Q/S130A/G097T/S144T/N185R/Y209W/S256I | 0.90 |
| S087N/G118V/S128L/P129Q/S130A/N043S/S144W | 1.23 |
| S087N/G118V/S128L/P129Q/S130A/N043V/S144T/N185V/S256I | 1.19 |
| S087N/G118V/S128L/P129Q/S130A/P052V/S144Y/N185V | 1.37 |
| S087N/G118V/S128L/P129Q/S130A/P052V/Y209W/S256T | 1.02 |
| S087N/G118V/S128L/P129Q/S130A/A001K/I072C/V104I/S164I | 0.67 |
| S087N/G118V/S128L/P129Q/S130A/S164I | 1.03 |
| S087N/G118V/S128L/P129Q/S130A/A001K/V104I/S164I | 0.87 |
| S087N/G118V/S128L/P129Q/S130A/A001K/I072C | 1.24 |
| S087N/G118V/S128L/P129Q/S130A/R045K/I072C/L126F | 1.05 |
| S087N/G118V/S128L/P129Q/S130A/A001K/V104I/S164F | 0.93 |
| S087N/G118V/S128L/P129Q/S130A/I072C/S164I | 1.46 |
| S087N/G118V/S128L/P129Q/S130A/A001K/I072C/S164Q | 1.16 |
| S087N/G118V/S128L/P129Q/S130A/A001K/S164F | 0.99 |
| S087N/G118V/S128L/P129Q/S130A/S164Q | 0.94 |
| S087N/G118V/S128L/P129Q/S130A/I072C/L126F | 1.08 |
| S087N/G118V/S128L/P129Q/S130A/A001K/I072V/S164Q | 0.57 |
| S087N/G118V/S128L/P129Q/S130A/A001K/S164I | 0.99 |
| S087N/G118V/S128L/P129Q/S130A/I072C/S164Q | 1.48 |
| S087N/G118V/S128L/P129Q/S130A/A001K/L126F/S164F | 1.32 |
| S087N/G118V/S128L/P129Q/S130A/A001K/I072C/S164I | 0.68 |
| S087N/G118V/S128L/P129Q/S130A/L126F/S164I | 0.85 |
| S087N/G118V/S128L/P129Q/S130A/A001K/I072V/S164I | 1.07 |
| S087N/G118V/S128L/P129Q/S130A/I072V/S164F | 1.13 |
| S087N/G118V/S128L/P129Q/S130A/I072C/L126F/S164F | 1.01 |
| S087N/G118V/S128L/P129Q/S130A/V104I/L126F/S164F | 0.89 |
| S087N/G118V/S128L/P129Q/S130A/V104I/S164Q | 0.88 |
| S087N/G118V/S128L/P129Q/S130A/A001K/V104I/L126F/S164Q | 0.77 |
| S087N/G118V/S128L/P129Q/S130A/V104I/L126F/S164I | 0.90 |
| S087N/G118V/S128L/P129Q/S130A/I072C | 1.51 |
| S087N/G118V/S128L/P129Q/S130A/A001K/I072C/V104I/L126F | 0.91 |
| S087N/G118V/S128L/P129Q/S130A/V104I/S164I | 1.00 |
| S087N/G118V/S128L/P129Q/S130A/A001K/I072V/V104I/L126F/S164F | 0.75 |
| S087N/G118V/S128L/P129Q/S130A/A001K/I072V/S164F | 1.07 |
| S087N/G118V/S128L/P129Q/S130A/I072P | 1.27 |
| S087N/G118V/S128L/P129Q/S130A/A001K/I072C/L126F/S164I | 0.92 |
| S087N/G118V/S128L/P129Q/S130A/L126F | 0.93 |
| S087N/G118V/S128L/P129Q/S130A/I072C/V104I/L126F/S164I | 1.06 |
| S087N/G118V/S128L/P129Q/S130A/V104I | 0.99 |
| S087N/G118V/S128L/P129Q/S130A/A001K/V104I/L126F/S164F | 0.71 |
| S087N/G118V/S128L/P129Q/S130A/A001K/I072C/L126F | 0.99 |
| S087N/G118V/S128L/P129Q/S130A/A001K/I072C/L126F/S164F | 0.78 |

TABLE 7-7

Multiple Mutation Variants of GCI-P036 Having a
PI ≥0.5 in CS-38 Microswatch Assay (pH 10; 32° C.)

| | PI |
|---|---|
| G097P/N185Q/A215I | 0.97 |
| N018R/N185R/S256W | 0.96 |
| N018Q/N185R/A215R | 0.72 |
| N018Q/N185Q/Y209W/S256W | 0.90 |
| N018K/G097P/N185K/S256W | 0.93 |
| N018Q/N185K/Y209W/A215V/S256W | 0.97 |
| N018R/N185Q/A215V/S256W | 0.81 |
| N018R/G097P/Y209W/S256W | 0.92 |
| N018R/N185R/Y209W/S256W | 0.98 |
| N185Q/A215R/S256W | 0.83 |
| N018K/A215R | 1.12 |
| N018K/G097P/Y209W/A215V/S256W | 1.02 |
| N018K/N185R/A215V | 0.81 |
| N018K/N185K/Y209W/A215R | 0.68 |
| N185K/A215V | 1.19 |
| N018K/N185K | 1.22 |
| N018R/N185R/A215R | 1.48 |
| N018K/G097P/N185K/Y209W/A215I/S256W | 1.12 |
| G097P/Y209W/A215V/S256W | 1.01 |
| N018R/Y209W/S256W | 0.93 |
| N018Q/N185K/S256W | 0.88 |
| N018K/N185Q/A215V/S256W | 1.46 |
| N018K/S256W | 0.94 |
| N018R/Y209W/A215V/S256W | 0.80 |
| N018Q/G097P/N185K/Y209W | 1.33 |
| N018R/G097P/Y209W/A215V | 1.21 |
| N185R/S256W | 0.99 |
| N018K/G097P/N185Q/Y209W/A215V/S256W | 1.09 |
| N018K/G097P/N185R/A215R/S256W | 0.64 |
| N018K/N185R/A215I/S256W | 0.67 |
| N185R/Y209W/A215I | 1.10 |
| N018R/N185K/S256W | 0.76 |
| N018K/G097P/N185R/S256W | 0.97 |
| N018K/N185Q/A215R/S256W | 0.91 |
| N018K/N185K/A215V/S256W | 0.95 |
| N018Q/N185R/S256W | 0.79 |
| N018Q/N185Q/A215V | 1.03 |
| N018R/N185Q/Y209W/S256W | 0.60 |
| N185R/Y209W/S256W | 1.42 |
| N018K/N185Q/Y209W/S256W | 0.97 |
| N018Q/N185K/Y209W/A215V | 0.80 |
| N018K/A215V | 1.58 |
| N018Q/N185Q/S256W | 0.77 |
| N018R/N185K/A215V/S256W | 0.76 |
| N018Q/N185K | 0.77 |
| N018K/G097P/N185R/Y209W | 1.25 |
| N018K/N185R/Y209W/A215V/S256W | 0.82 |
| N018Q/N185K/Y209W/A215I/S256W | 0.78 |
| N018K/G097P/N185R/A215V/S256W | 0.72 |
| N018K/G097P/A215I/S256W | 0.61 |
| N018R/G097P/N185Q/A215I | 0.85 |
| N018Q/G097P/N185K/A215V | 1.31 |
| N185Q/S256W | 0.92 |
| N018K/G097P/N185R/Y209W/S256W | 1.34 |
| N043V/S101T/N248K | >4.0 |
| N043S/N117Y/N248K | >4.0 |
| N043E/S101E | >4.0 |
| N043S/S101E/N117Y/N248K | >4.0 |
| S101R/N248K | 3.40 |
| N043S/S101Y/N117I | >4.0 |
| N043I/N117Y | 1.32 |
| N043S/S101F | 3.07 |
| S101E/N117Y/N248K | >4.0 |
| S101Y/N117Y | >4.0 |
| N043V/S101V/N248K | 3.55 |
| N043F/N117I | 0.76 |
| S101F/N248K | >4.0 |
| N043S/S101Y/N248K | >4.0 |
| N043S/N248I | 0.75 |
| N043V/S101R/N117I/N248K | 3.18 |
| N043V/S101F/N248K | >4.0 |
| S101T/N248I | >4.0 |
| N043V/S101Y/N117I | 1.11 |
| S101Y/N248K | >4.0 |
| N043S/S101R/N117I/N248K | 3.54 |

TABLE 7-7-continued

Multiple Mutation Variants of GCI-P036 Having a PI ≥0.5 in CS-38 Microswatch Assay (pH 10; 32° C.)

| | PI |
|---|---|
| N043E/S101F | >4.0 |
| N043S/S101N/N117I | >4.0 |
| N043I/S101N/N117Y/N248K | 3.56 |
| S101F/N117Y/N248K | 2.15 |
| N043S/S101F/N248K | 3.24 |
| N043E/S101N/N117Y | 2.29 |
| S101T/N117Y/N248K | 3.14 |
| N043S/S101E/N248K | >4.0 |
| S101R/N117I/N248K | 3.80 |
| N043E/S101E/N248K | 3.98 |
| N043V/S101Y | >4.0 |
| S101F/N117Y/N248I | >4.0 |
| N043F/S101R | >4.0 |
| N043V/S101E/N248I | >4.0 |
| N043V/N248K | 1.93 |
| N043V/S101Y/N117I/N248K | >4.0 |
| N043S/S101E | >4.0 |
| N043I/S101Y/N117Y/N248K | 2.50 |
| N043V/S101F | 3.24 |
| N043S/S101Y/N117Y | >4.0 |
| S101Y/N117I/N248K | 2.65 |
| P052I/S144Y/N185R/Y209W | 3.93 |
| P052V/S144T | 1.41 |
| S144Y/Y209W/S256I | 2.38 |
| S144T/N185V | 1.83 |
| S144V/N185R/Y209W/S256T | 2.22 |
| M119F/Y209W | 0.98 |
| M119F/N185V/Y209W | 1.46 |
| M119F/N185R | 0.73 |
| S144V/Y209W | 2.25 |
| P052I/N185V/Y209W | >4.0 |
| S144V/N185R/Y209W | 1.89 |
| P052V/S144Y/Y209W | 2.15 |
| P052I/N185R/Y209W/S256I | 3.36 |
| S144V/N185R/S256I | 0.98 |
| S144T/N185R | 1.23 |
| M119F/N185R/Y209W/S256T | 1.17 |
| M119F/Y209W/S256I | 1.52 |
| S144W/N185R/Y209W/S256T | >4.0 |
| P052V/S144V/N185V/Y209W | >4.0 |
| N185V/Y209W | 1.09 |
| P052I/S144V/Y209W | >4.0 |
| S144W/N185V/Y209W/S256I | >4.0 |
| M119F/S144T/N185V/S256I | 1.10 |
| S144T/N185R/Y209W/S256I | 2.35 |
| S144T/N185R/Y209W/S256T | 1.12 |
| S144V/S256I | 1.73 |
| P052I/S144T/Y209W/S256I | 1.01 |
| A001K/R045K/I072V/L126F/S164Q | 1.14 |
| A001K/L126F/S164Q | 0.92 |
| A001K/R045F/V104I/L126F/S164Q | 0.83 |
| A001K/I072V/V104I | 1.16 |
| A001K/R045K/I072V/S164F | 1.09 |
| A001K/L126F | 1.46 |
| A001K/R045F/I072V/V104G/S164T | 0.93 |
| R045L/I072S/S164I | 1.35 |
| A001K/L126F/S164F | 0.92 |
| R045K/L126F/S164F | 0.72 |
| A001K/R045K/I072V/V104I/L126F/S164F | 0.76 |
| A001K/I072C/V104I/L126F/S164Q | 0.81 |
| A001K/I072V/V104I/S164F | 1.00 |
| A001K/V104I/L126F/S164I | 0.81 |
| A001K/R045F/L126F/S164I | 0.65 |
| A001K/R045K/L126F/S164I | 0.95 |
| A001L/I072C | 0.76 |
| A001K/R045K/I072V/S164Q | 1.00 |
| A001K/I072C/L126F/S164Q | 1.04 |
| A001K/V104E | 1.07 |
| A001K/I072C/L126F | 0.55 |
| L126F/S164V | 0.94 |
| A001K/R045S/V104C/L126Y/S164F | 0.86 |
| A001K/R045F/I072V/L126F/S164I | 0.66 |
| A001K/V104I/L126F/S164Q | 0.85 |
| A001K/R045K/V104I/S164Q | 0.75 |
| A001K/R045K/I072V/L126F | 0.93 |

TABLE 7-7-continued

Multiple Mutation Variants of GCI-P036 Having a
PI ≥0.5 in CS-38 Microswatch Assay (pH 10; 32° C.)

| Variant | PI |
|---|---|
| A001K/R045K/V104L/S164A | 0.85 |
| A001K/R045F/L126F/S164F | 0.80 |
| A001K/I072V/V104I/S164Q | 0.92 |
| A001K/I072V/L126F | >4.0 |
| A001K/I072V/L126F/S164F | 1.20 |
| V104E/L126I/S164L | 1.20 |
| A001K/I072V | 1.44 |
| A001K/V104I/L126F | 0.91 |
| A001K/R045K/I072V/V104I/L126F/S164Q | 1.03 |
| A001K/R045K/I072V/L126F/S164F | 1.21 |
| A001K/R045F/I072V/L126F/S164Q | 0.64 |
| A001K/R045K/I072C/L126F/S164Q | 0.86 |
| A001K/R045K/S164F | 0.66 |
| A001K/R045F/I072C | 2.48 |
| A001K/S164Q | 1.66 |
| A001K/R045K/L126F/S164P | 1.08 |
| A001K/I072C/V104I/L126F | 0.72 |
| A001K/L126F/S164I | 0.83 |
| S024W/Q109V/G118S/S132Y | >4.0 |
| S024W/Q109K/G118R | 0.84 |
| S024H/Q109L | 0.57 |
| S024V/Q109R/G118F | 0.75 |
| S024R/Q109V | 2.54 |
| S024W/Q109I | 1.32 |
| S024V/Q109C/G118L | 1.94 |
| S024R/Q109T/S132Y | 1.47 |
| S024H/Q109T/G118R | 0.96 |
| S024R/G118R/S132N | 0.83 |
| Q109I/G118S | 1.34 |
| S024C/Q109K/G118I | 1.11 |
| S024W/Q109L | 1.24 |
| Q109A/G118S | 0.80 |
| S024R/S132Y | 0.99 |
| Q109P/G118Q | 1.00 |
| S024V/Q109R/G118F | 1.29 |
| S024R/Q109V | 3.28 |
| Q109T/G118N | 0.99 |
| S024V/Q109C/G118L | 1.36 |
| S024H/Q109T/G118R | 1.61 |
| Q109I/G118S | 1.15 |
| S024C/Q109K/G118I | 0.72 |
| S024W/Q109L | 2.74 |
| Q109I/G118R | 3.89 |
|

TABLE 7-7-continued

Multiple Mutation Variants of GCI-P036 Having a
PI ≥0.5 in CS-38 Microswatch Assay (pH 10; 32° C.)

| Variant | PI |
|---|---|
| A001R/S024W/R045F/I107V/G127Q | 2.33 |
| R045N/I107A/A172R | 1.27 |
| A001R/R045N/I107T/G127Q | 1.09 |
| I107P/A172S | 1.47 |
| A001R/S024W/I107V/A172S | 1.54 |
| A001K/S024H/I107T/G127Q | 1.46 |
| A001R/S024H/R045K/I107T/A172Q | 1.01 |
| A001R/R045N/A172Q | 0.83 |
| A001K/R045F/I107V/G127

TABLE 7-7-continued

Multiple Mutation Variants of GCI-P036 Having a PI ≥0.5 in CS-38 Microswatch Assay (pH 10; 32° C.)

| | PI |
|---|---|
| S87N/G118V/S128L/P129Q/S130A/S024W | 0.90 |
| S87N/G118V/S128L/P129Q/S130A/S024W/S099T | 1.33 |
| S87N/G118V/S128L/P129Q/S130A/S024W/S099T/S103N | 1.61 |
| S87N/G118V/S128L/P129Q/S130A/S099K/S103N | 1.69 |
| S87N/G118V/S128L/P129Q/S130A/S024H/S099Q | 1.39 |
| S87N/G118V/S128L/P129Q/S130A/S024W/G127T | >4.0 |
| S87N/G118V/S128L/P129Q/S130A/S099K | 1.33 |
| S87N/G118V/S128L/P129Q/S130A/S024W/S099Q | 1.56 |
| S87N/G118V/S128L/P129Q/S130A/S024H/S099K/S103N | 1.52 |
| S87N/G118V/S128L/P129Q/S130A/N018K/N185K | 0.94 |
| S87N/G118V/S128L/P129Q/S130A/N185R/Y209W | 0.97 |
| S87N/G118V/S128L/P129Q/S130A/N018K | 1.35 |
| S87N/G118V/S128L/P129Q/S130A/N018Q/N185Q/S256W | 1.02 |
| S87N/G118V/S128L/P129Q/S130A/N018Q/N185Q/Y209W/S256W | 1.24 |
| S87N/G118V/S128L/P129Q/S130A/N018R/N185K/Y209W/A215I/S256W | 1.65 |
| S87N/G118V/S128L/P129Q/S130A/Y209W/S256W | 0.79 |
| S87N/G118V/S128L/P129Q/S130A/N018R/Y209W/A215I/S256W | 1.61 |
| S87N/G118V/S128L/P129Q/S130A/N018K/N185R | 1.00 |
| S87N/G118V/S128L/P129Q/S130A/N018K/N185K/S256W | 1.22 |
| S87N/G118V/S128L/P129Q/S130A/N018Q/Y209W/S256W | 1.26 |
| S87N/G118V/S128L/P129Q/S130A/N185R/Y209W/A215V/S256R | 0.81 |
| S87N/G118V/S128L/P129Q/S130A/N185K/A215V/S256W | 1.15 |
| S87N/G118V/S128L/P129Q/S130A/N018K/Y209W | 0.99 |
| S87N/G118V/S128L/P129Q/S130A/N018K/N185Q/S256W | 1.07 |
| S87N/G118V/S128L/P129Q/S130A/N018R/Y209W/S256W | 1.28 |
| S87N/G118V/S128L/P129Q/S130A/N018K/A215R/S256W | 1.23 |
| S87N/G118V/S128L/P129Q/S130A/N018Q/A215R/S256W | 1.16 |
| S87N/G118V/S128L/P129Q/S130A/N018K/G097P/N185R/Y209W | 2.83 |
| S87N/G118V/S128L/P129Q/S130A/A215V/S256W | 1.54 |
| S87N/G118V/S128L/P129Q/S130A/N185K/Y209W/A215V/S256W | 0.85 |
| S87N/G118V/S128L/P129Q/S130A/N018R/N185R/A215R | 1.27 |
| S87N/G118V/S128L/P129Q/S130A/N185K/Y209W/A215V | 0.88 |
| S87N/G118V/S128L/P129Q/S130A/N018K/N185R/A215V/S256W | 1.03 |
| S87N/G118V/S128L/P129Q/S130A/N018R | 0.98 |
| S87N/G118V/S128L/P129Q/S130A/N018K/N185K/Y209W/A215I | >4.0 |
| S87N/G118V/S128L/P129Q/S130A/N018Q/A215I/S256W | 2.09 |
| S87N/G118V/S128L/P129Q/S130A/N018K/N185Q | 1.09 |
| S87N/G118V/S128L/P129Q/S130A/N018K/N185R/A215I/S256W | 1.12 |
| S87N/G118V/S128L/P129Q/S130A/G097P/N185Q/Y209W/A215V/S256W | 0.68 |
| S87N/G118V/S128L/P129Q/S130A/N018K/N185Q/A215R | 0.98 |
| S87N/G118V/S128L/P129Q/S130A/Y209W/A215I/S256W | 1.96 |
| S87N/G118V/S128L/P129Q/S130A/N018K/N185Q/A215V/S256W | 1.04 |
| S87N/G118V/S128L/P129Q/S130A/N185Q/Y209W/A215R | 0.82 |
| S87N/G118V/S128L/P129Q/S130A/N185R/A215V/S256W | 1.11 |
| S87N/G118V/S128L/P129Q/S130A/N018R/N185K/Y209W | 0.85 |
| S87N/G118V/S128L/P129Q/S130A/A215V | >4.0 |
| S87N/G118V/S128L/P129Q/S130A/N018R/N185Q/A215I/S256W | >4.0 |
| S87N/G118V/S128L/P129Q/S130A/G097P/N185K/A215I | >4.0 |
| S87N/G118V/S128L/P129Q/S130A/N018Q/N185K/A215R | 1.14 |
| S87N/G118V/S128L/P129Q/S130A/N018K/Y209W/A215V | 1.21 |
| S87N/G118V/S128L/P129Q/S130A/N018K/N185K/Y209W | 0.89 |
| S87N/G118V/S128L/P129Q/S130A/N018Q/N185K/A215V | 0.68 |
| S87N/G118V/S128L/P129Q/S130A/N185R/Y209W/S256L | 0.87 |
| S87N/G118V/S128L/P129Q/S130A/N018K/S256W | 1.10 |
| S87N/G118V/S128L/P129Q/S130A/N018Q/N185K/S256W | 0.71 |
| S87N/G118V/S128L/P129Q/S130A/N185Q/Y209W/A215V/S256W | 0.79 |
| S87N/G118V/S128L/P129Q/S130A/P052I/N248K | 1.24 |
| S87N/G118V/S128L/P129Q/S130A/N043V/S101T | 1.84 |
| S87N/G118V/S128L/P129Q/S130A/P052V | >4.0 |
| S87N/G118V/S128L/P129Q/S130A/N043V/S101Y | >4.0 |
| S87N/G118V/S128L/P129Q/S130A/S101E/N248K | 3.92 |
| S87N/G118V/S128L/P129Q/S130A/N248K | 1.40 |
| S87N/G118V/S128L/P129Q/S130A/N043W/S101E | 3.08 |
| S87N/G118V/S128L/P129Q/S130A/P052I/S101V/N248K | >4.0 |
| S87N/G118V/S128L/P129Q/S130A/S101F/N248K | >4.0 |
| S87N/G118V/S128L/P129Q/S130A/N043V/S101T/N248K | 3.71 |
| S87N/G118V/S128L/P129Q/S130A/S101Y | >4.0 |
| S87N/G118V/S128L/P129Q/S130A/N043E | 1.36 |
| S87N/G118V/S128L/P129Q/S130A/N043S/S101T | 2.49 |
| S87N/G118V/S128L/P129Q/S130A/N043V/S101F | >4.0 |
| S87N/G118V/S128L/P129Q/S130A/N043E/S101R | 1.17 |
| S87N/G118V/S128L/P129Q/S130A/N043E/S101Y | >4.0 |
| S87N/G118V/S128L/P129Q/S130A/N043E/S101E | 3.61 |
| S87N/G118V/S128L/P129Q/S130A/N043T/N248K | >4.0 |
| S87N/G118V/S128L/P129Q/S130A/P052V/S101R | >4.0 |
| S87N/G118V/S128L/P129Q/S130A/S101N/N248K | >4.0 |
| S87N/G118V/S128L/P129Q/S130A/N043V/S101R | 1.63 |
| S87N/G118V/S128L/P129Q/S130A/N043F/S101Y/N248K | >4.0 |
| S87N/G118V/S128L/P129Q/S130A/S101R/N248K | 0.94 |
| S87N/G118V/S128L/P129Q/S130A/N043I/S101Y | >4.0 |
| S87N/G118V/S128L/P129Q/S130A/N043T | >4.0 |
| S87N/G118V/S128L/P129Q/S130A/Y209W | 0.54 |
| S87N/G118V/S128L/P129Q/S130A/P052V/Y209W | 2.14 |
| S87N/G118V/S128L/P129Q/S130A/S144V/N185R/Y209W | >4.0 |
| S87N/G118V/S128L/P129Q/S130A/G097S/N185R/S256I | >4.0 |
| S87N/G118V/S128L/P129Q/S130A/S144V/N185V/Y209W | >4.0 |
| S87N/G118V/S128L/P129Q/S130A/S144V/N185V | 0.63 |
| S87N/G118V/S128L/P129Q/S130A/P052V/S144T/N185R/Y209W | >4.0 |
| S87N/G118V/S128L/P129Q/S130A/S144T/N185R/Y209W | 1.63 |
| S87N/G118V/S128L/P129Q/S130A/S144T/N185R | 1.79 |
| S87N/G118V/S128L/P129Q/S130A/S144T/Y209W/S256I | 3.43 |
| S87N/G118V/S128L/P129Q/S130A/N043S/N185R/Y209W/S256T | 1.35 |
| S87N/G118V/S128L/P129Q/S130A/S144T/N185V/Y209W | 1.11 |
| S87N/G118V/S128L/P129Q/S130A/G097T/Y209W/S256I | >4.0 |
| S87N/G118V/S128L/P129Q/S130A/N185R/S256T | 0.99 |
| S87N/G118V/S128L/P129Q/S130A/S144T/S256I | >4.0 |
| S87N/G118V/S128L/P129Q/S130A/S144T/N185R/S256I | >4.0 |
| S87N/G118V/S128L/P129Q/S130A/N043S/S256I | >4.0 |
| S87N/G118V/S128L/P129Q/S130A/N043V/N185V/Y209W/S256I | >4.0 |
| S87N/G118V/S128L/P129Q/S130A/P052V/Y209W/S256T | >4.0 |
| S87N/G118V/S128L/P129Q/S130A/S164I | 0.97 |
| S87N/G118V/S128L/P129Q/S130A/A001K/V104I/S164I | 0.99 |
| S87N/G118V/S128L/P129Q/S130A/A001K/V104I/S164F | 1.12 |
| S87N/G118V/S128L/P129Q/S130A/A001K/S164F | 1.67 |
| S87N/G118V/S128L/P129Q/S130A/S164Q | 0.95 |
| S87N/G118V/S128L/P129Q/S130A/A001K/S164I | 1.74 |
| S87N/G118V/S128L/P129Q/S130A/L126F/S164I | 1.01 |
| S87N/G118V/S128L/P129Q/S130A/I072V/S164F | 3.75 |
| S87N/G118V/S128L/P129Q/S130A/V104I/L126F/S164F | 0.76 |
| S87N/G118V/S128L/P129Q/S130A/V104I/S164Q | 0.87 |
| S87N/G118V/S128L/P129Q/S130A/A001K/V104I/L126F/S164Q | 1.91 |
| S87N/G118V/S128L/P129Q/S130A/V104I/L126F/S164I | 0.65 |
| S87N/G118V/S128L/P129Q/S130A/V104I/S164I | 0.75 |
| S87N/G118V/S128L/P129Q/S130A/A001K/I072V/V104I/L126F/S164F | 1.25 |
| S87N/G118V/S128L/P129Q/S130A/L126F | 0.76 |
| S87N/G118V/S128L/P129Q/S130A/V104I | 0.87 |
| S87N/G118V/S128L/P129Q/S130A/A001K/V104I/L126F/S164F | 0.83 |

Evaluation of LAS/EDTA Stability by Multiple Mutation Library (MML)

Variants of GCI-P036

Variants of GCI-P036 were tested for their stability after incubation in a composition containing LAS and EDTA stability. Cloning of the combinatorial library was performed by Sloning BioTechnology using the Slonomax Technology. Preparation of variant protease samples was performed as described above. Briefly, MML variants were in an LAS/EDTA stability assay using the methods of Example 1. As described throughout, functionality of protease variants was quantified as a performance index (PI), which is the ratio of performance of a variant to that of a reference protease. The substitutions are listed relative to the GCI-P036 reference protease using BPN' numbering and the PI is determined in relationship to the GCI-P036 reference. Results are shown in Table 7-8.

TABLE 7-8

| Multiple Mutation Variants of GCI-P036 Having a PI ≥0.5 for LAS/EDTA Stability | PI |
|---|---|
| G097P/N185Q/A215I | 1.51 |
| N018Q/N185Q/Y209W/S256W | 1.08 |
| N018K/G097P/N185K/S256W | 0.54 |
| N185K/Y209W/S256W | 0.93 |
| N018Q/N185K/Y209W/A215V/S256W | 1.23 |
| N185Q/A215R/S256W | 0.72 |
| N018K/G097P/Y209W/A215V/S256W | 0.87 |
| N185K/A215V | 1.15 |
| N018K/G097P/N185K/Y209W/A215I/S256W | 0.85 |
| G097P/Y209W/A215V/S256W | 1.55 |
| N018Q/N185K/S256W | 0.52 |
| N018K/N185Q/A215V/S256W | 1.34 |
| N018Q/G097P/N185K/Y209W | 1.06 |
| N185R/S256W | 0.78 |
| N018K/G097P/N185Q/Y209W/A215V/S256W | 0.95 |
| N185R/Y209W/A215I | 0.96 |
| N018K/N185K/A215V/S256W | 0.68 |
| N018Q/N185R/S256W | 0.64 |
| N018K/A215I | 1.39 |
| N018Q/N185Q/A215V | 1.37 |
| N185R/Y209W/S256W | 0.83 |
| N018K/N185Q/Y209W/S256W | 0.53 |
| N018Q/N185K/Y209W/A215V | 1.12 |
| N018K/A215V | 0.77 |
| N018Q/N185Q/S256W | 1.14 |
| N018K/N185Q/S256W | 0.56 |
| N018Q/N185K | 1.22 |
| N018K/N185R/Y209W/A215V/S256W | 0.63 |
| N018Q/N185K/Y209W/A215I/S256W | 1.09 |
| N018K/G097P/N185R/A215V/S256W | 0.79 |
| N018K/G097P/A215I/S256W | 0.85 |
| N018Q/G097P/N185K/A215V | 1.33 |
| N185Q/S256W | 1.02 |
| N018K/G097P/N185R/Y209W/S256W | 0.52 |
| N043V/S101T/N248K | 0.62 |
| N043S/N117Y/N248K | 0.92 |
| N043E/S101E | 1.35 |
| N043S/S101E/N117Y/N248K | 1.20 |
| S101R/N248K | 1.06 |
| N043V/S101E/N117I/N248K | 0.91 |
| N043E/S101V | 1.25 |
| N043S/S101Y/N117I | 1.29 |
| N043I/N117Y | 0.82 |
| N043S/S101F | 1.27 |
| S101E/N117Y/N248K | 1.03 |
| S101Y/N117Y | 1.01 |
| N043V/S101V/N248K | 0.67 |
| N043I/S101R/N248K | 0.86 |
| N043F/N117I | 1.07 |
| S101F/N248K | 0.92 |
| N043S/S101Y/N248K | 1.01 |
| N043S/N248I | 1.01 |
| N043I/S101E/N248I | 0.85 |
| N043V/S101R/N117I/N248K | 0.86 |
| N043V/S101F/N248K | 0.78 |
| N043V/N117Y/N248I | 1.24 |
| S101T/N248I | 0.90 |
| N043E/S101Y/N117Y/N248K | 1.15 |
| N043V/S101Y/N117I | 0.81 |
| N043V/S101V/N117I | 0.83 |
| S101Y/N248K | 0.89 |
| N043S/S101R/N117I/N248K | 1.12 |
| N043V/N248I | 0.64 |
| N043V/S101F/N117Y | 0.81 |
| N043S/S101V/N117I/N248I | 1.12 |
| N043E/S101F | 1.33 |
| N043S/S101N/N117I | 1.25 |
| N043I/S101N/N117Y/N248K | 0.79 |
| S101F/N117I/N248I | 0.90 |
| S101F/N117Y/N248K | 1.06 |
| N043I/S101F/N117Y/N248K | 0.76 |
| N043S/S101F/N248K | 1.10 |
| N043E/S101N/N117Y | 1.17 |
| S101T/N117Y/N248K | 0.84 |
| N043S/S101E/N248K | 1.18 |

TABLE 7-8-continued

Multiple Mutation Variants of GCI-P036 Having a PI ≥0.5 for LAS/EDTA Stability

| | PI |
|---|---|
| N043I/S101Y/N117I/N248I | 0.85 |
| N043V/S101F/N117I | 0.68 |
| N043E/S101Y/N117I/N248K | 1.09 |
| N043S/S101Y | 0.58 |
| N043E/S101E/N248K | 1.24 |
| N043V/S101Y | 0.86 |
| S101F/N117Y/N248I | 1.03 |
| N043S/S101E/N117I/N248I | 1.24 |
| N043F/S101R | 0.95 |
| N043V/S101E/N248I | 0.80 |
| N043V/N248K | 0.61 |
| S101E/N117I | 0.96 |
| N043V/S101Y/N117I/N248K | 0.66 |
| N043S/S101E | 1.30 |
| S101R/N117Y | 1.06 |
| N043I/S101Y/N117Y/N248K | 0.73 |
| N043V/S101F | 0.72 |
| N043S/S101Y/N117Y | 1.15 |
| S101Y/N117I/N248K | 0.81 |
| P052V/S144T | 0.98 |
| P052V/M119F/S144T/N185R/S256T | 0.61 |
| S144Y/Y209W/S256I | 0.89 |
| P052I/S144Y/Y209W/S256I | 0.83 |
| S144T/N185V | 0.94 |
| S144V/N185R/Y209W/S256T | 0.60 |
| M119F/Y209W | 0.94 |
| M119F/N185V/Y209W | 0.96 |
| M119F/N185R | 0.71 |
| S144V/Y209W | 0.90 |
| P052I/N185V/Y209W | 0.95 |
| P052I/M119F/S144Y/N185R/Y209W/S256I | 0.52 |
| S144V/N185R/Y209W | 0.51 |
| P052V/S144W/Y209W | 0.62 |
| P052V/M119F/S144T/Y209W | 0.99 |
| P052V/S144T/Y209W/S256I | 0.83 |
| P052V/S144Y/Y209W | 0.94 |
| P052I/N185R/Y209W/S256I | 0.51 |
| P052V/M119F/S144T/N185R/Y209W | 0.76 |
| P052V/N185V/Y209W/S256I | 0.91 |
| P052I/S144Y/N185V/S256T | 0.78 |
| P052I/M119F/S144Y/N185R | 0.53 |
| S144T/N185R | 0.58 |
| P052I/S144Y/N185V | 0.96 |
| P052V/M119F/S144T | 1.12 |
| P052I/S144T/N185V/Y209W/S256T | 0.89 |
| M119F/Y209W/S256I | 0.99 |
| P052V/S144V/N185V/Y209W | 0.84 |
| P052I/M119F | 0.99 |
| P052V/S144W/N185V/Y209W | 0.66 |
| N185V/Y209W | 0.92 |
| P052I/M119F/S144V/Y209W | 0.88 |
| P052I/S144V/Y209W | 0.84 |
| P052I/M119F/S144T/N185R/Y209W | 0.65 |
| S144W/N185V/Y209W/S256I | 0.61 |
| M119F/S144T/N185V/S256I | 0.85 |
| P052I/M119F/Y209W/S256I | 0.89 |
| P052I/N185V/Y209W/S256I | 0.81 |
| P052V/M119F/S144T/S256T | 0.94 |
| P052V/M119F/N185V/Y209W/S256I | 0.87 |
| P052I/S144T | 0.93 |
| S144T/N185R/Y209W/S256T | 0.56 |
| S144V/S256I | 0.66 |
| P052I/S144T/S256I | 0.80 |
| P052V/S144T/N185V/Y209W/S256T | 0.90 |
| P052V/M119F/S144V/N185V/S256I | 0.87 |
| P052V/S144Y/S256T | 0.78 |
| P052I/S144T/Y209W/S256I | 0.83 |
| P052V/S256T | 0.83 |
| P052V/S144V/Y209W/S256I | 0.74 |
| P052V/S144T/N185V/Y209W/S256I | 0.78 |
| A001K/R045K/I072V/L126F/S164Q | 0.74 |
| A001K/L126F/S164Q | 0.78 |
| A001K/R045F/V104I/L126F/S164Q | 0.96 |
| A001K/I072V/V104I | 0.66 |
| A001K/R045K/I072V/S164F | 0.99 |

TABLE 7-8-continued

Multiple Mutation Variants of GCI-P036 Having a PI ≥0.5 for LA

TABLE 7-8-continued

Multiple Mutation Variants of GCI-P036 Having a PI ≥0.5 for LAS/EDTA Stability

| | PI |
|---|---|
| S024R/G118L/G127R/S132R | 1.02 |
| S024A/G118I | 0.87 |
| G118L/G127R/S132L | 0.88 |
| S024R/Q109V/G118C/S132A | 0.74 |
| R045F/I107T | 1.03 |
| R045V/I107R/A172D | 1.01 |
| S024T/R045K/I107V | 0.99 |
| S024T/I107T | 0.85 |
| A001T/S024H/I107L/A172Y | 0.81 |
| S024N/R045K/A172L | 0.91 |
| S024N/I107T | 1.00 |
| R045K/I107T | 0.98 |
| I107Q/A172D | 1.04 |
| S024W/A172Q | 0.94 |
| S024W/R045N/A172Q | 1.12 |
| A001Q/R045K/I107T | 0.85 |
| S024N/R045K/I107V/A172N | 1.03 |
| S024R/R045F/I107T/A172Q | 0.84 |
| A001K/R045F/I107L/A172N | 0.55 |
| S024I/I107R/G127I/A172R | 0.52 |
| A001K/S024H/R045N/I107T | 0.69 |
| A001K/R045F/I107T | 0.62 |
| A001K/R045K/I107A/A172T | 0.50 |
| R045N/I107A/A172R | 0.56 |
| A001R/R045N/I107T/G127Q | 0.53 |
| A001K/S024R/R045N/I107T | 0.51 |
| S024W/S099Q | 1.17 |
| S024W/S099T/S103P/G118T/S132N | 1.14 |
| S099Q/S103N/S132H | 1.06 |
| S024W/S099T/S103P | 1.16 |
| S024W/S103K/S132R | 1.26 |
| S024W/S103P | 1.09 |
| S099T/G118T/S132N | 1.10 |
| S024W/S099T/S103P/G118R | 1.11 |
| S024H/S099Q/S103P | 1.26 |
| S024H/S099K/S103R/G118A/S132P | 1.41 |
| S024H/S099T/S103P/G118R/S132H | 1.15 |
| S024W/G118K | 0.68 |
| S024H/S099T/S103N/S132N | 1.18 |
| S099K/S103P/S132H | 0.59 |
| S099Q/S103N/G118R/S132N | 1.09 |
| S024W/S099T/S103N | 1.16 |
| S099T/S103P/G118L/S132H | 1.13 |
| S024P/S099Q/S103P/G118R | 1.07 |
| S099T/G118T/S132H | 1.06 |
| S024W/S099Q/S103N/G118T | 1.27 |
| S024W/S132H | 1.12 |
| S103L/S132E | 0.95 |
| S103R/S132P | 0.94 |
| S099Q/S103P/G118R | 1.02 |
| S099Q/S103N/G118T | 1.04 |
| S024H/S099Q/S132N | 1.01 |
| S099Q/S103N/G118T/S132H | 1.08 |
| S024W/S099T/G118T/S132H | 1.08 |
| S099K/S103N/G118T | 1.14 |
| S024H/S099Q/S103P/S132H | 1.11 |
| S024H/S132R | 1.07 |
| S024W/S099T/S103N/S132N | 0.85 |
| S024T/G118D | 1.00 |
| S099N/S132R | 0.82 |
| S099K/S103P/G118L/S132N | 0.97 |
| S099H/S103I/G118N | 1.28 |
| S024W/S099Q/S103N/G118R/S132N | 1.00 |
| S024W/S099T/S103P/G118R/S132H | 1.00 |
| S024W/S099Q/G118T | 0.91 |
| S024H/S099Q/S132H | 1.11 |
| S099Q/S132R | 1.14 |
| S099Q/S103P/G118R/S132N | 0.96 |
| S024M/G118V | 0.55 |
| S024W/S132N | 0.66 |
| S099K/S103R/G118A/S132P | 0.79 |
| S024W/S099T/S103P/S132H | 0.84 |
| S024W/S099T/S103N/S132H | 0.87 |
| S024W/S099T/S103N/G118R | 1.13 |
| S099T/G118F | 0.90 |

TABLE 7-8-continued

| Multiple Mutation Variants of GCI-P036 Having a PI ≥0.5 for LAS/EDTA Stability | PI |
|---|---|
| S024W/S103P/G118F/S132H | 1.13 |
| S103G/G118I/G127E/S132E | 1.03 |
| S024H/S099T/S103N | 1.16 |
| S024H/S099Q/S132H | 1.02 |
| S024W/S099K/S103P/S132H | 1.03 |
| S024H/S099Q/G118R/S132H | 1.03 |
| S024H/S099K/S103P/G118F | 1.08 |
| S099T/G118R/S132H | 1.10 |
| S024W/S099Q/S103P/G118R/S132H | 1.07 |
| S024L/G127R | 1.06 |
| S024W/S099T/S103P/G118T/S132N | 0.71 |
| S024W/S099T | 0.91 |
| S024H/S099T/S103P/S132N | 0.95 |
| S099T/S103P | 1.03 |
| S024W/S132H | 1.14 |
| S024W/S099T/S103P | 1.16 |
| S024H/S099Q/S103P/G118R/S132H | 0.87 |
| S024H/S099K/S103P | 1.11 |
| S024W/S103P | 1.04 |
| S024H/S103N/S132H | 0.98 |
| S024W/S099Q/S103P/S132N | 1.02 |
| S024W/S099Q/S103P | 1.12 |
| S024H/S132N | 0.96 |
| S024W/S099T/G118R | 0.96 |
| S024H/S099Q/S103N/G118T/S132H | 1.21 |
| S099Q/S103P/S132H | 1.01 |
| S024W/S099T/S103P/G118T | 0.87 |
| S024H/S099T/G118R | 0.86 |
| S024W/S099Q/S103P/G118T/S132N | 0.88 |
| S024H/S099T/S103P/G118R | 0.97 |
| S087N/G118V/S128L/P129Q/S130A/S024R/Q109K | 0.80 |
| S087N/G118V/S128L/P129Q/S130A/S024W/Q109V | 1.06 |
| S087N/G118V/S128L/P129Q/S130A/S024W/Q109T | 0.95 |
| S087N/G118V/S128L/P129Q/S130A/S024W/Q109L | 0.61 |
| S087N/G118V/S128L/P129Q/S130A/S024H/Q109V | 0.97 |
| S087N/G118V/S128L/P129Q/S130A/S024R | 0.84 |
| S087N/G118V/S128L/P129Q/S130A/S024H | 1.04 |
| S087N/G118V/S128L/P129Q/S130A/S024R/Q109L | 0.86 |
| S087N/G118V/S128L/P129Q/S130A/Q109T | 1.05 |
| S087N/G118V/S128L/P129Q/S130A/S024R/Q109V | 0.91 |
| S087N/G118V/S128L/P129Q/S130A/S024W/Q109I | 1.04 |
| S087N/G118V/S128L/P129Q/S130A/Q109V | 1.03 |
| S087N/G118V/S128L/P129Q/S130A/S024W | 1.01 |
| S087N/G118V/S128L/P129Q/S130A/G127T | 0.90 |
| S087N/G118V/S128L/P129Q/S130A/Q109I | 1.10 |
| S087N/G118V/S128L/P129Q/S130A/S024T | 0.98 |
| S087N/G118V/S128L/P129Q/S130A/S024N/Q109K | 1.11 |
| S087N/G118V/S128L/P129Q/S130A/R045S | 0.50 |
| S087N/G118V/S128L/P129Q/S130A/A001N/R045N/I107T | 0.72 |
| S087N/G118V/S128L/P129Q/S130A/A001S/S024L/R045L/I107W/A172F | 0.60 |
| S087N/G118V/S128L/P129Q/S130A/S024R/I107T/A172Q | 0.67 |
| S087N/G118V/S128L/P129Q/S130A/A001K/S024W/R045N/I107T | 0.60 |
| S087N/G118V/S128L/P129Q/S130A/S024N/I107V | 0.92 |
| S087N/G118V/S128L/P129Q/S130A/S024H/I107V/A172S | 0.99 |
| S087N/G118V/S128L/P129Q/S130A/A001K/S024H/A172Q | 0.58 |
| S087N/G118V/S128L/P129Q/S130A/S024T/I107T/A172Q | 0.82 |
| S087N/G118V/S128L/P129Q/S130A/A001K/I107T | 0.57 |
| S087N/G118V/S128L/P129Q/S130A/S024W/I107T | 0.92 |
| S087N/G118V/S128L/P129Q/S130A/S024T/R045N/I107V/A172S | 0.98 |
| S087N/G118V/S128L/P129Q/S130A/A001C/S024E/I107G | 0.95 |
| S087N/G118V/S128L/P129Q/S130A/S024N/I107N | 0.89 |
| S087N/G118V/S128L/P129Q/S130A/S024H/R045N/I107T | 0.94 |
| S087N/G118V/S128L/P129Q/S130A/R045N/I107V/A172P | 1.08 |
| S087N/G118V/S128L/P129Q/S130A/R045F/I107T/A172Q | 0.89 |
| S087N/G118V/S128L/P129Q/S130A/A001K/R045F | 0.56 |
| S087N/G118V/S128L/P129Q/S130A/S024R/I107V/A172S | 0.85 |
| S087N/G118V/S128L/P129Q/S130A/S024R/R045F/I107T | 0.77 |
| S087N/G118V/S128L/P129Q/S130A/S024T | 0.99 |
| S087N/G118V/S128L/P129Q/S130A/R045N/A172Q | 1.02 |
| S087N/G118V/S128L/P129Q/S130A/S024W/R045F/I107V/A172Q | 0.95 |
| S087N/G118V/S128L/P129Q/S130A/S024W/S099K | 0.74 |
| S087N/G118V/S128L/P129Q/S130A/S024W/S099K/S103P | 0.68 |
| S087N/G118V/S128L/P129Q/S130A/S099T/S103N/S132H | 0.62 |
| S087N/G118V/S128L/P129Q/S130A/S099Q/S103N | 0.93 |
| S087N/G118V/S128L/P129Q/S130A/S099Q | 0.98 |

TABLE 7-8-continued

Multiple Mutation Variants of GCI-P036 Having a PI ≥0.5 for LAS/EDTA Stability

| | PI |
|---|---|
| S087N/G118V/S128L/P129Q/S130A/S024W | 1.01 |
| S087N/G118V/S128L/P129Q/S130A/S024W/S099T/S103N/S132N | 0.89 |
| S087N/G118V/S128L/P129Q/S130A/S024W/S099T/S132N | 1.01 |
| S087N/G118V/S128L/P129Q/S130A/S024W/S099T | 0.97 |
| S087N/G118V/S128L/P129Q/S130A/S024H/S099T/S103P/S132H | 1.14 |
| S087N/G118V/S128L/P129Q/S130A/S024W/S099T/S103N | 0.91 |
| S087N/G118V/S128L/P129Q/S130A/S103N/S132H | 1.02 |
| S087N/G118V/S128L/P129Q/S130A/S024W/S099T/G127R/S132H | 1.14 |
| S087N/G118V/S128L/P129Q/S130A/S099K/S103N | 0.72 |
| S087N/G118V/S128L/P129Q/S130A/S024H/S099Q/S132N | 1.00 |
| S087N/G118V/S128L/P129Q/S130A/S024W/S099Q/S103P | 0.87 |
| S087N/G118V/S128L/P129Q/S130A/S024H/S099Q | 1.04 |
| S087N/G118V/S128L/P129Q/S130A/S103P | 1.01 |
| S087N/G118V/S128L/P129Q/S130A/S099K/S132H | 0.97 |
| S087N/G118V/S128L/P129Q/S130A/S024H/S099Q/S103P | 0.52 |
| S087N/G118V/S128L/P129Q/S130A/S024H/S103P/S132N | 1.07 |
| S087N/G118V/S128L/P129Q/S130A/S024H/S099T/S103P/S132N | 1.15 |
| S087N/G118V/S128L/P129Q/S130A/S099T/S132H | 1.14 |
| S087N/G118V/S128L/P129Q/S130A/S024L/S099K/S103P/S132N | 0.84 |
| S087N/G118V/S128L/P129Q/S130A/S099T/S103N | 0.91 |
| S087N/G118V/S128L/P129Q/S130A/S099K/S103P | 0.82 |
| S087N/G118V/S128L/P129Q/S130A/S024H/S099T/S132N | 1.00 |
| S087N/G118V/S128L/P129Q/S130A/S024H/S099T/S103P | 0.94 |
| S087N/G118V/S128L/P129Q/S130A/S099Q/S132H | 0.86 |
| S087N/G118V/S128L/P129Q/S130A/S099T/G127Q | 0.66 |
| S087N/G118V/S128L/P129Q/S130A/S024W/S099Q/S132H | 1.10 |
| S087N/G118V/S128L/P129Q/S130A/S024W/S099T/S103P/S132H | 1.34 |
| S087N/G118V/S128L/P129Q/S130A/S099K | 0.82 |
| S087N/G118V/S128L/P129Q/S130A/S099Q/S103P/S132H | 1.11 |
| S087N/G118V/S128L/P129Q/S130A/S024W/S099Q | 0.93 |
| S087N/G118V/S128L/P129Q/S130A/S099T/S103P | 0.61 |
| S087N/G118V/S128L/P129Q/S130A/S024H/S099K/S103N | 0.73 |
| S087N/G118V/S128L/P129Q/S130A/S024W/S099Q/S132N | 0.95 |
| S087N/G118V/S128L/P129Q/S130A/S099Q/S103P | 0.83 |
| S087N/G118V/S128L/P129Q/S130A/S099T/S103P/S132H | 1.09 |
| S087N/G118V/S128L/P129Q/S130A/S024W/S099Q/S103N/G127R/S132N | 0.92 |
| S087N/G118V/S128L/P129Q/S130A/S024H/S099K/S103N/S132N | 0.74 |
| S087N/G118V/S128L/P129Q/S130A/S024W/S099K/S132H | 0.93 |
| S087N/G118V/S128L/P129Q/S130A/N185R/Y209W | 1.23 |
| S087N/G118V/S128L/P129Q/S130A/N018K/G097P/N185Q/A215I/S256W | 0.86 |
| S087N/G118V/S128L/P129Q/S130A/N018Q/N185Q/S256W | 1.09 |
| S087N/G118V/S128L/P129Q/S130A/N018Q/N185Q/Y209W/S256W | 1.11 |
| S087N/G118V/S128L/P129Q/S130A/Y209W/S256W | 1.08 |
| S087N/G118V/S128L/P129Q/S130A/N018Q/Y209W/S256W | 0.98 |
| S087N/G118V/S128L/P129Q/S130A/N185R/Y209W/A215V/S256R | 0.97 |
| S087N/G118V/S128L/P129Q/S130A/N185K/A215V/S256W | 1.31 |
| S087N/G118V/S128L/P129Q/S130A/N018Q/A215R/S256W | 0.55 |
| S087N/G118V/S128L/P129Q/S130A/A215V/S256W | 1.37 |
| S087N/G118V/S128L/P129Q/S130A/N185K/Y209W/A215V/S256W | 1.26 |
| S087N/G118V/S128L/P129Q/S130A/N185K/Y209W/A215V | 1.26 |
| S087N/G118V/S128L/P129Q/S130A/N018K/N185R/A215V/S256W | 0.59 |
| S087N/G118V/S128L/P129Q/S130A/G097P/N185R/A215I/S256W | 1.13 |
| S087N/G118V/S128L/P129Q/S130A/N018K/N185K/Y209W/A215I | 0.57 |
| S087N/G118V/S128L/P129Q/S130A/N018Q/A215I/S256W | 1.20 |
| S087N/G118V/S128L/P129Q/S130A/G097P/N185Q/Y209W/A215V/S256W | 1.16 |
| S087N/G118V/S128L/P129Q/S130A/Y209W/A215I/S256W | 1.50 |
| S087N/G118V/S128L/P129Q/S130A/N018K/N185Q/A215V/S256W | 0.82 |
| S087N/G118V/S128L/P129Q/S130A/N185Q/Y209W/A215R | 0.66 |
| S087N/G118V/S128L/P129Q/S130A/N018Q/G097P/N185R | 0.71 |
| S087N/G118V/S128L/P129Q/S130A/N185R/A215V/S256W | 1.06 |
| S087N/G118V/S128L/P129Q/S130A/A215V | 1.19 |
| S087N/G118V/S128L/P129Q/S130A/G097P/N185K/A215I | 1.28 |
| S087N/G118V/S128L/P129Q/S130A/N018K/Y209W/A215V | 0.75 |
| S087N/G118V/S128L/P129Q/S130A/N018Q/N185K/A215V | 1.17 |
| S087N/G118V/S128L/P129Q/S130A/N185R/Y209W/S256L | 0.93 |
| S087N/G118V/S128L/P129Q/S130A/N018Q/N185K/S256W | 0.82 |
| S087N/G118V/S128L/P129Q/S130A/N185Q/Y209W/A215V/S256W | 1.31 |
| S087N/G118V/S128L/P129Q/S130A/P052I/N248K | 0.83 |
| S087N/G118V/S128L/P129Q/S130A/N043W/S101F/N248K | 0.93 |
| S087N/G118V/S128L/P129Q/S130A/N043V/P052I/S101Y | 0.76 |
| S087N/G118V/S128L/P129Q/S130A/N043V/S101T | 0.72 |
| S087N/G118V/S128L/P129Q/S130A/N043V/P052V/S101F/N248K | 0.63 |
| S087N/G118V/S128L/P129Q/S130A/P052V | 0.96 |
| S087N/G118V/S128L/P129Q/S130A/N043S | 1.19 |
| S087N/G118V/S128L/P129Q/S130A/N043V/S101Y | 0.79 |

TABLE 7-8-continued

Multiple Mutation Variants of GCI-P036 Having a PI ≥0.5 for LAS/EDTA Stability

| | PI |
|---|---|
| S087N/G118V/S128L/P129Q/S130A/N043S/P052V/S101R | 1.08 |
| S087N/G118V/S128L/P129Q/S130A/N043S/P052V/S101F | 1.10 |
| S087N/G118V/S128L/P129Q/S130A/N043F/P052V/S101T/N248K | 0.85 |
| S087N/G118V/S128L/P129Q/S130A/N043I/S101E/N248K | 0.81 |
| S087N/G118V/S128L/P129Q/S130A/S101E/N248K | 1.02 |
| S087N/G118V/S128L/P129Q/S130A/N248K | 0.69 |
| S087N/G118V/S128L/P129Q/S130A/N043W/S101E | 1.10 |
| S087N/G118V/S128L/P129Q/S130A/N043S/S101E/N248K | 1.00 |
| S087N/G118V/S128L/P129Q/S130A/P052I/S101V/N248K | 0.84 |
| S087N/G118V/S128L/P129Q/S130A/S101F/N248K | 0.97 |
| S087N/G118V/S128L/P129Q/S130A/N043V/S101T/N248K | 0.73 |
| S087N/G118V/S128L/P129Q/S130A/N043V/P052V/N248K | 0.70 |
| S087N/G118V/S128L/P129Q/S130A/N043S/S101N/N248I | 1.03 |
| S087N/G118V/S128L/P129Q/S130A/S101Y | 1.02 |
| S087N/G118V/S128L/P129Q/S130A/N043S/P052V/S101Y/N248K | 1.00 |
| S087N/G118V/S128L/P129Q/S130A/N043I/S101N | 0.74 |
| S087N/G118V/S128L/P129Q/S130A/N043E/P052V/S101E/N248K | 1.23 |
| S087N/G118V/S128L/P129Q/S130A/N043V/P052I | 0.73 |
| S087N/G118V/S128L/P129Q/S130A/P052I/S101F/N248K | 0.97 |
| S087N/G118V/S128L/P129Q/S130A/P052V/S101E/N248I | 0.83 |
| S087N/G118V/S128L/P129Q/S130A/N043W/P052V/S101E/N248K | 1.05 |
| S087N/G118V/S128L/P129Q/S130A/N043E | 1.14 |
| S087N/G118V/S128L/P129Q/S130A/N043S/S101T | 1.20 |
| S087N/G118V/S128L/P129Q/S130A/N043V/S101F | 0.75 |
| S087N/G118V/S128L/P129Q/S130A/N043V/P052I/S101T/N248K | 0.66 |
| S087N/G118V/S128L/P129Q/S130A/N043V/S101Y/N248I | 0.78 |
| S087N/G118V/S128L/P129Q/S130A/N043E/S101R | 1.26 |
| S087N/G118V/S128L/P129Q/S130A/N043S/P052I/N248K | 1.11 |
| S087N/G118V/S128L/P129Q/S130A/N043E/S101Y | 1.41 |
| S087N/G118V/S128L/P129Q/S130A/N043E/S101E | 1.25 |
| S087N/G118V/S128L/P129Q/S130A/N043I/P052I/S101F/N248K | 0.63 |
| S087N/G118V/S128L/P129Q/S130A/N043T/N248K | 0.98 |
| S087N/G118V/S128L/P129Q/S130A/N043T/P052I/S101Y | 1.11 |
| S087N/G118V/S128L/P129Q/S130A/P052V/S101R | 0.82 |
| S087N/G118V/S128L/P129Q/S130A/N043I/P052V/S101F/N248K | 0.71 |
| S087N/G118V/S128L/P129Q/S130A/N043W/P052V/S101Y/N248K | 0.91 |
| S087N/G118V/S128L/P129Q/S130A/P052I/S101E/N248K | 1.08 |
| S087N/G118V/S128L/P129Q/S130A/S101N/N248K | 0.89 |
| S087N/G118V/S128L/P129Q/S130A/N043V/S101E/N248K | 0.61 |
| S087N/G118V/S128L/P129Q/S130A/N043V/S101R | 0.70 |
| S087N/G118V/S128L/P129Q/S130A/N043V/P052V/S101F | 0.69 |
| S087N/G118V/S128L/P129Q/S130A/S101E | 1.03 |
| S087N/G118V/S128L/P129Q/S130A/N043F/S101Y/N248K | 0.96 |
| S087N/G118V/S128L/P129Q/S130A/N043S/P052V | 1.07 |
| S087N/G118V/S128L/P129Q/S130A/N043W/P052V/S101Y | 1.05 |
| S087N/G118V/S128L/P129Q/S130A/N043S/P052I | 1.13 |
| S087N/G118V/S128L/P129Q/S130A/N043T/S101E/N248I | 1.14 |
| S087N/G118V/S128L/P129Q/S130A/N043V/S101E/N248I | 0.74 |
| S087N/G118V/S128L/P129Q/S130A/N043V/S101R/N248I | 0.57 |
| S087N/G118V/S128L/P129Q/S130A/N248I | 1.00 |
| S087N/G118V/S128L/P129Q/S130A/N043E/P052I/S101Y/N248K | 0.97 |
| S087N/G118V/S128L/P129Q/S130A/S101R/N248K | 0.86 |
| S087N/G118V/S128L/P129Q/S130A/N043S/P052V/N248K | 0.96 |
| S087N/G118V/S128L/P129Q/S130A/N043I/S101Y | 0.79 |
| S087N/G118V/S128L/P129Q/S130A/N043I/S101Y/N248K | 0.72 |
| S087N/G118V/S128L/P129Q/S130A/N043S/P052V/S101V/N248K | 0.93 |
| S087N/G118V/S128L/P129Q/S130A/N043T | 0.89 |
| S087N/G118V/S128L/P129Q/S130A/N043T/P052V/S101Y/N248K | 0.88 |
| S087N/G118V/S128L/P129Q/S130A/P052V/S144T | 0.93 |
| S087N/G118V/S128L/P129Q/S130A/Y209W | 1.01 |
| S087N/G118V/S128L/P129Q/S130A/G097S/S144Y/S256I | 0.96 |
| S087N/G118V/S128L/P129Q/S130A/N043S/N185V/S256T | 1.10 |
| S087N/G118V/S128L/P129Q/S130A/P052V/Y209W | 0.99 |
| S087N/G118V/S128L/P129Q/S130A/G097S/S144V/Y209W/S256I | 0.85 |
| S087N/G118V/S128L/P129Q/S130A/S144V/N185V/S256I | 0.91 |
| S087N/G118V/S128L/P129Q/S130A/G097T/S144W/Y209W/S256I | 0.77 |
| S087N/G118V/S128L/P129Q/S130A/S144T/N185R/Y209W/S256I | 0.55 |
| S087N/G118V/S128L/P129Q/S130A/G097T/Y209W | 0.66 |
| S087N/G118V/S128L/P129Q/S130A/N043S/S144W/N185R/S256P | 0.78 |
| S087N/G118V/S128L/P129Q/S130A/S144V/N185R/Y209W | 0.71 |
| S087N/G118V/S128L/P129Q/S130A/P052V/S144Y/N185R/Y209W/S256I | 0.62 |
| S087N/G118V/S128L/P129Q/S130A/S144V/Y209W/S256T | 0.96 |
| S087N/G118V/S128L/P129Q/S130A/P052V/G097T/N185R/Y209W/S256T | 0.70 |
| S087N/G118V/S128L/P129Q/S130A/N043S/S144W/N185V/S256T | 0.93 |
| S087N/G118V/S128L/P129Q/S130A/S144W/Y209W | 0.94 |

TABLE 7-8-continued

| Multiple Mutation Variants of GCI-P036 Having a PI ≥0.5 for LAS/EDTA Stability | |
|---|---|
| | PI |
| S087N/G118V/S128L/P129Q/S130A/S144V/N185V/Y209W | 1.03 |
| S087N/G118V/S128L/P129Q/S130A/S144V/N185V | 1.01 |
| S087N/G118V/S128L/P129Q/S130A/P052V/S144T/N185R/Y209W | 0.76 |
| S087N/G118V/S128L/P129Q/S130A/S144Y/N185R | 0.68 |
| S087N/G118V/S128L/P129Q/S130A/N043V/S144W/N185V | 0.70 |
| S087N/G118V/S128L/P129Q/S130A/S144T/N185R/Y209W | 0.73 |
| S087N/G118V/S128L/P129Q/S130A/S144T/N185R | 0.68 |
| S087N/G118V/S128L/P129Q/S130A/S144T/Y209W/S256I | 0.99 |
| S087N/G118V/S128L/P129Q/S130A/N043V/S144Y/N185V/Y209W/S256I | 0.68 |
| S087N/G118V/S128L/P129Q/S130A/P052V/S144V/N185R/S256I | 0.52 |
| S087N/G118V/S128L/P129Q/S130A/P052V/S144V/N185R/Y209W/S256T | 0.66 |
| S087N/G118V/S128L/P129Q/S130A/S144V/Y209W/S256I | 0.86 |
| S087N/G118V/S128L/P129Q/S130A/N043V/S144W/Y209W/S256I | 0.59 |
| S087N/G118V/S128L/P129Q/S130A/N185V/Y209W | 0.90 |
| S087N/G118V/S128L/P129Q/S130A/P052V/S144T/N185R/S256T | 0.56 |
| S087N/G118V/S128L/P129Q/S130A/S144T/N185V/S256I | 1.06 |
| S087N/G118V/S128L/P129Q/S130A/N043S/N185R/Y209W/S256T | 0.93 |
| S087N/G118V/S128L/P129Q/S130A/S144T/N185V/Y209W | 1.01 |
| S087N/G118V/S128L/P129Q/S130A/P052V/S144V/N185R/Y209W | 0.66 |
| S087N/G118V/S128L/P129Q/S130A/S144V | 1.04 |
| S087N/G118V/S128L/P129Q/S130A/N043T/S144V/Y209W/S256T | 0.98 |
| S087N/G118V/S128L/P129Q/S130A/S144Y/N185V/Y209W | 1.02 |
| S087N/G118V/S128L/P129Q/S130A/G097T/Y209W/S256I | 1.06 |
| S087N/G118V/S128L/P129Q/S130A/N185R/S256T | 0.66 |
| S087N/G118V/S128L/P129Q/S130A/P052V/S144V/N185V/Y209W/S256I | 0.86 |
| S087N/G118V/S128L/P129Q/S130A/P052V/S144T/Y209W/S256T | 0.93 |
| S087N/G118V/S128L/P129Q/S130A/S144T/S256I | 0.99 |
| S087N/G118V/S128L/P129Q/S130A/S144T/N185R/S256I | 0.52 |
| S087N/G118V/S128L/P129Q/S130A/N043S/S256I | 1.11 |
| S087N/G118V/S128L/P129Q/S130A/S144Y/N185R/Y209W/S256T | 0.65 |
| S087N/G118V/S128L/P129Q/S130A/N043V/P052V/S144W/S256T | 0.70 |
| S087N/G118V/S128L/P129Q/S130A/N043V/N185V/Y209W/S256I | 0.77 |
| S087N/G118V/S128L/P129Q/S130A/P052V/S144Y/N185V/Y209W/S256I | 0.91 |
| S087N/G118V/S128L/P129Q/S130A/G097T/S144T/S256I | 0.91 |
| S087N/G118V/S128L/P129Q/S130A/P052V/S144V/Y209W | 0.85 |
| S087N/G118V/S128L/P129Q/S130A/G097T/S144T/N185R/Y209W/S256I | 0.65 |
| S087N/G118V/S128L/P129Q/S130A/N043S/S144W | 1.09 |
| S087N/G118V/S128L/P129Q/S130A/N043V/S144T/N185V/S256I | 0.63 |
| S087N/G118V/S128L/P129Q/S130A/P052V/S144Y/N185V | 0.94 |
| S087N/G118V/S128L/P129Q/S130A/P052V/Y209W/S256T | 0.88 |
| S087N/G118V/S128L/P129Q/S130A/A001K/I072C/V104I/S164I | 0.60 |
| S087N/G118V/S128L/P129Q/S130A/S164I | 1.04 |
| S087N/G118V/S128L/P129Q/S130A/A001K/V104I/S164I | 0.64 |
| S087N/G118V/S128L/P129Q/S130A/R045K/I072C/L126F | 0.84 |
| S087N/G118V/S128L/P129Q/S130A/A001K/V104I/S164F | 0.75 |
| S087N/G118V/S128L/P129Q/S130A/I072C/S164I | 0.83 |
| S087N/G118V/S128L/P129Q/S130A/A001K/S164F | 0.72 |
| S087N/G118V/S128L/P129Q/S130A/S164Q | 0.92 |
| S087N/G118V/S128L/P129Q/S130A/I072C/L126F | 0.83 |
| S087N/G118V/S128L/P129Q/S130A/A001K/I072V/S164Q | 0.65 |
| S087N/G118V/S128L/P129Q/S130A/A001K/S164I | 0.74 |
| S087N/G118V/S128L/P129Q/S130A/I072C/S164Q | 0.89 |
| S087N/G118V/S128L/P129Q/S130A/A001K/L126F/S164F | 0.92 |
| S087N/G118V/S128L/P129Q/S130A/A001K/I072C/S164I | 0.52 |
| S087N/G118V/S128L/P129Q/S130A/L126F/S164I | 0.91 |
| S087N/G118V/S128L/P129Q/S130A/A001K/I072V/S164I | 0.76 |
| S087N/G118V/S128L/P129Q/S130A/I072V/S164F | 1.08 |
| S087N/G118V/S128L/P129Q/S130A/I072C/L126F/S164F | 0.84 |
| S087N/G118V/S128L/P129Q/S130A/V104I/L126F/S164F | 1.03 |
| S087N/G118V/S128L/P129Q/S130A/V104I/S164Q | 1.06 |
| S087N/G118V/S128L/P129Q/S130A/A001K/V104I/L126F/S164Q | 0.74 |
| S087N/G118V/S128L/P129Q/S130A/V104I/L126F/S164I | 0.98 |
| S087N/G118V/S128L/P129Q/S130A/I072C | 0.85 |
| S087N/G118V/S128L/P129Q/S130A/V104I/S164I | 0.97 |
| S087N/G118V/S128L/P129Q/S130A/A001K/I072V/V104I/L126F/S164F | 0.71 |
| S087N/G118V/S128L/P129Q/S130A/A001K/I072V/S164F | 0.74 |
| S087N/G118V/S128L/P129Q/S130A/I072P | 0.96 |
| S087N/G118V/S128L/P129Q/S130A/L126F | 1.00 |
| S087N/G118V/S128L/P129Q/S130A/I072C/V104I/L126F/S164I | 0.80 |
| S087N/G118V/S128L/P129Q/S130A/V104I | 0.92 |
| S087N/G118V/S128L/P129Q/S130A/A001K/V104I/L126F/S164F | 0.66 |

Evaluation of Protein Content of Multiple Mutation Library (MML) Variant Cultures Expressing GCI-P036

Recombinant expression of variants of GCI-P036 was measured by assessing protein content of cultures in the TCA assay of Example 1. Cloning of the combinatorial library was performed by Sloning BioTechnology using Slonomax Technology. Preparation of variant protease samples was performed as described above. Briefly, MML variants were tested in a TCA assay using the methods of Example 1. As described throughout, functionality of protease variants was quantified as a performance index (PI), which is the ratio of performance of a variant to that of a reference protease. The substitutions are listed relative to the GCI-P036 reference protease using BPN' numbering and the PI is determined in relationship to the GCI—P036 reference. Results are shown in Table 7-9.

TABLE 7-9

Multiple Mutation Variants of GCI-P036 Having a PI ≥0.5 in a TCA Assay

| | PI |
|---|---|
| G097P/N185Q/A215I | 1.59 |
| N018R/N185R/S256W | 1.08 |
| N018Q/N185R/A215R | 1.16 |
| N018Q/N185Q/Y209W/S256W | 1.17 |
| N018K/G097P/N185K/S256W | 1.72 |
| N185K/Y209W/S256W | 0.66 |
| N018Q/N185K/Y209W/A215V/S256W | 1.10 |
| N018R/N185Q/A215V/S256W | 1.15 |
| N018R/G097P/Y209W/S256W | 1.48 |
| N018R/N185R/Y209W/S256W | 1.14 |
| N018K/N185R/A215R/S256W | 1.01 |
| N185Q/A215R/S256W | 1.06 |
| N018K/A215R | 0.98 |
| N018K/G097P/Y209W/A215V/S256W | 1.52 |
| N018K/N185R/A215V | 1.18 |
| N018K/N185K/Y209W/A215R | 1.29 |
| N185K/A215V | 0.98 |
| N018K/N185K | 1.01 |
| N018R/N185R/A215R | 1.09 |
| N018K/G097P/N185K/Y209W/A215I/S256W | 1.44 |
| G097P/Y209W/A215V/S256W | 1.63 |
| N018K/N185K/S256W | 0.91 |
| N018R/Y209W/S256W | 1.19 |
| N018Q/N185K/S256W | 1.12 |
| N018K/N185Q/A215V/S256W | 1.00 |
| N018K/S256W | 1.19 |
| N018R/Y209W/A215V/S256W | 1.04 |
| N018Q/G097P/N185K/Y209W | 1.08 |
| N018R/G097P/Y209W/A215V | 1.52 |
| N185R/S256W | 1.03 |
| N018K/G097P/N185Q/Y209W/A215V/S256W | 1.44 |
| N018K/G097P/N185R/A215R/S256W | 2.30 |
| N018K/N185R/A215I/S256W | 1.13 |
| N185R/Y209W/A215I | 1.18 |
| N018R/N185K/S256W | 1.06 |
| N018K/G097P/N185R/S256W | 1.70 |
| N018K/N185Q/A215R/S256W | 1.15 |
| N018K/N185K/A215V/S256W | 1.16 |
| N018Q/N185R/S256W | 1.06 |
| N018K/A215I | 0.57 |
| N018Q/N185Q/A215V | 1.07 |
| N018R/N185Q/Y209W/S256W | 1.13 |
| N185R/Y209W/S256W | 0.95 |
| N018K/N185Q/Y209W/S256W | 1.19 |
| N018Q/N185K/Y209W/A215V | 1.10 |
| N018K/A215V | 0.91 |
| N018Q/N185Q/S256W | 1.16 |
| N018K/N185Q/S256W | 0.68 |
| N018R/N185K/A215V/S256W | 1.14 |
| N018Q/N185K | 1.31 |
| N018K/G097P/N185R/Y209W | 1.38 |
| N018K/N185R/Y209W/A215V/S256W | 1.20 |
| N018Q/N185K/Y209W/A215I/S256W | 1.13 |
| N018K/G097P/N185R/A215V/S256W | 2.14 |
| N018K/G097P/A215I/S256W | 2.49 |
| N018R/G097P/N185Q/A215I | 1.83 |
| N018Q/G097P/N185K/A215V | 1.30 |
| N185Q/S256W | 1.06 |
| N018K/G097P/N185R/Y209W/S256W | 1.31 |
| N043V/S101T/N248K | 0.89 |
| N043S/N117Y/N248K | 0.79 |
| N043E/S101E | 0.87 |
| N043S/S101E/N117Y/N248K | 0.94 |
| S101R/N248K | 1.13 |

TABLE 7-9-continued

| Multiple Mutation Variants of GCI-P036 Having a PI ≥0.5 in a TCA Assay | PI |
|---|---|
| N043E/S101V | 0.57 |
| N043S/S101Y/N117I | 0.74 |
| N043I/N117Y | 0.94 |
| N043S/S101F | 0.89 |
| S101E/N117Y/N248K | 0.78 |
| S101Y/N117Y | 0.86 |
| N043V/S101V/N248K | 0.90 |
| N043I/S101R/N248K | 0.64 |
| N043F/N117I | 1.07 |
| S101F/N248K | 0.80 |
| N043S/S101Y/N248K | 0.75 |
| N043S/N248I | 0.62 |
| N043I/S101E/N248I | 0.67 |
| N043V/S101R/N117I/N248K | 1.03 |
| N043V/S101F/N248K | 0.96 |
| S101T/N248I | 0.75 |
| N043E/S101Y/N117Y/N248K | 0.67 |
| N043V/S101Y/N117I | 0.75 |
| N043V/S101V/N117I | 0.68 |
| S101Y/N248K | 0.81 |
| N043S/S101R/N117I/N248K | 0.99 |
| N043V/N248I | 0.51 |
| N043F/S101E/N117I/N248K | 0.53 |
| N043V/S101F/N117Y | 0.70 |
| N043E/S101F | 0.80 |
| N043S/S101N/N117I | 0.77 |
| N043I/S101N/N117Y/N248K | 0.90 |
| S101F/N117I/N248I | 0.58 |
| S101F/N117Y/N248K | 1.07 |
| N043I/S101F/N117Y/N248K | 0.54 |
| N043S/S101F/N248K | 0.72 |
| N043E/S101N/N117Y | 0.99 |
| S101T/N117Y/N248K | 0.96 |
| N043S/S101E/N248K | 0.87 |
| S101R/N117I/N248K | 0.83 |
| N043E/S101Y/N117I/N248K | 0.66 |
| N043E/S101E/N248K | 0.90 |
| N043V/S101Y | 0.83 |
| S101F/N117Y/N248I | 0.77 |
| N043F/S101R | 0.79 |
| N043V/S101E/N248I | 0.92 |
| N043V/N248K | 0.89 |
| S101E/N117I | 0.64 |
| N043V/S101Y/N117I/N248K | 0.77 |
| N043S/S101E | 0.89 |
| S101R/N117Y | 0.50 |
| N043I/S101Y/N117Y/N248K | 0.99 |
| N043V/S101F | 0.85 |
| N043S/S101Y/N117Y | 0.76 |
| S101Y/N117I/N248K | 0.96 |
| P052I/S144Y/N185R/Y209W | 0.91 |
| P052V/S144T | 0.70 |
| S144Y/Y209W/S256I | 0.82 |
| P052I/S144Y/Y209W/S256I | 0.71 |
| S144T/N185V | 0.96 |
| S144V/N185R/Y209W/S256T | 0.90 |
| M119F/Y209W | 1.39 |
| M119F/N185V/Y209W | 0.95 |
| M119F/N185R | 1.33 |
| S144V/Y209W | 0.87 |
| P052I/S144T/N185R/Y209W/S256T | 0.65 |
| P052I/N185V/Y209W | 0.78 |
| P052V/S144V/N185R/Y209W/S256T | 0.74 |
| S144W/S256I | 0.73 |
| S144V/N185R/Y209W | 0.97 |
| P052V/S144W/Y209W | 0.64 |
| P052V/M119F/S144T/Y209W | 0.64 |
| P052V/S144T/Y209W/S256I | 0.71 |
| P052V/S144Y/Y209W | 0.75 |
| P052I/S144T/Y209W/S256T | 0.57 |
| P052I/N185R/Y209W/S256I | 0.79 |
| P052V/M119F/S144T/N185R/Y209W | 0.64 |
| P052V/N185V/Y209W/S256I | 0.67 |
| P052I/S144Y/N185V/S256T | 0.60 |
| S144V/N185R/S256I | 0.93 |

TABLE 7-9-continued

| Multiple Mutation Variants of GCI-P036 Having a PI ≥0.5 in a TCA Assay | PI |
|---|---|
| S144T/N185R | 0.98 |
| P052I/S144Y/N185V | 0.62 |
| P052I/S144Y/S256T | 0.51 |
| P052V/M119F/S144T | 0.54 |
| M119F/N185R/Y209W/S256T | 1.09 |
| P052I/S144T/N185V/Y209W/S256T | 0.70 |
| M119F/Y209W/S256I | 0.90 |
| S144W/N185R/Y209W/S256T | 0.83 |
| P052V/S144V/N185V/Y209W | 0.81 |
| P052I/M119F | 0.74 |
| M119F/S144W/N185R/S256L | 0.75 |
| P052V/S144W/N185V/Y209W | 0.75 |
| N185V/Y209W | 1.03 |
| P052I/S144V/Y209W | 0.81 |
| S144W/N185V/Y209W/S256I | 0.80 |
| M119F/S144T/N185V/S256I | 0.93 |
| P052I/N185V/Y209W/S256I | 0.69 |
| S144T/N185R/Y209W/S256I | 0.89 |
| P052V/M119F/N185V/Y209W/S256I | 0.56 |
| P052I/S144T | 0.70 |
| S144T/N185R/Y209W/S256T | 1.06 |
| S144V/S256I | 0.74 |
| P052I/S144T/S256I | 0.69 |
| P052V/S144T/N185V/Y209W/S256T | 0.73 |
| P052V/S144Y/S256T | 0.62 |
| P052I/S144T/Y209W/S256I | 1.19 |
| P052V/S256T | 0.68 |
| P052V/S144V/Y209W/S256I | 0.66 |
| P052V/S144T/N185V/Y209W/S256I | 0.62 |
| A001K/R045K/I072V/L126F/S164Q | 1.38 |
| A001K/L126F/S164Q | 1.03 |
| A001K/R045F/V104I/L126F/S164Q | 1.58 |
| A001K/I072V/V104I | 1.13 |
| A001K/R045K/I072V/S164F | 1.18 |
| A001K/L126F | 0.76 |
| A001K/R045F/I072V/V104G/S164T | 1.25 |
| R045L/I072S/S164I | 1.03 |
| L126A/S164N | 0.99 |
| A001K/L126F/S164F | 1.42 |
| R045K/L126F/S164F | 1.66 |
| A001K/R045K/I072V/V104I/L126F/S164F | 1.71 |
| A001K/I072C/V104I/L126F/S164Q | 1.53 |
| A001K/I072V/V104I/S164F | 1.25 |
| A001K/V104I/L126F/S164I | 1.56 |
| A001K/R045K/L126F | 0.73 |
| A001K/R045F/L126F/S164I | 1.84 |
| A001K/R045K/L126F/S164I | 1.10 |
| A001L/I072C | 1.55 |
| A001K/R045K/I072V/S164Q | 1.39 |
| A001K/I072C/L126F/S164Q | 1.53 |
| A001K/R045F/S164F | 0.60 |
| A001K/V104E | 1.25 |
| A001K/I072C/L126F | 1.05 |
| L126F/S164V | 1.32 |
| R045F/I072V/L126F/S164Q | 0.59 |
| A001K/R045S/V104C/L126Y/S164F | 1.25 |
| A001K/R045F/I072V/L126F/S164I | 1.87 |
| A001K/V104I/L126F/S164Q | 1.52 |
| A001K/R045K/V104I/S164Q | 1.60 |
| A001K/R045K/I072V/L126F | 1.21 |
| A001K/R045K/V104L/S164A | 1.20 |
| A001K/R045F/L126F/S164F | 1.61 |
| A001K/I072V/V104I/S164Q | 1.27 |
| A001K/I072V/L126F | 0.88 |
| A001K/I072V/L126F/S164F | 1.19 |
| V104E/L126I/S164L | 1.14 |
| A001K/R045K/L126F/S164Q | 0.70 |
| A001K/R045F/I072V/S164F | 0.54 |
| A001K/I072V | 1.26 |
| A001K/R045F/I072C/L126F | 0.52 |
| A001K/V104I/L126F | 1.43 |
| A001K/R045K/I072V/V104I/L126F/S164Q | 1.37 |
| A001K/R045K/I072V/L126F/S164F | 1.26 |
| A001K/R045F/I072V/L126F/S164Q | 1.98 |
| A001K/R045K/I072C/L126F/S164Q | 1.69 |

TABLE 7-9-continued

Multiple Mutation Variants of GCI-P036 Having a PI ≥0.5 in a TCA Assay

| | PI |
|---|---|
| A001K/R045K/S164F | 0.86 |
| A001K/R045F/I072C/V104I/S164F | 0.68 |
| A001K/R045F/I072C | 0.76 |
| A001K/S164Q | 0.91 |
| A001K/R045K/L126F/S164P | 1.33 |
| A001K/I072C/V104I/L126F | 1.79 |
| A001K/L126F/S164I | 1.56 |
| S024W/Q109V/G118S/S132Y | 0.85 |
| S024W/Q109K/G118R | 1.58 |
| S024H/Q109L | 2.53 |
| S024V/Q109R/G118F | 1.64 |
| S024R/Q109V | 1.18 |
| S024W/Q109I | 1.17 |
| S024V/Q109C/G118L | 0.90 |
| S024R/Q109T/S132Y | 1.41 |
| S024H/Q109T/G118R | 1.72 |
| S024R/G118R/S132N | 1.30 |
| Q109I/S132N | 0.62 |
| Q109I/G118S | 1.07 |
| S024C/Q109K/G118I | 1.58 |
| S024W/Q109L | 1.20 |
| S024W/Q109T/G118L | 0.81 |
| Q109A/G118S | 1.49 |
| S024R/S132Y | 1.71 |
| Q109P/G118Q | 1.75 |
| S024V/Q109R/G118F | 1.14 |
| S024R/Q109V | 0.89 |
| Q109T/G118N | 1.49 |
| S024V/Q109C/G118L | 0.81 |
| S024H/Q109T/G118R | 0.93 |
| S024R/Q109V/S132N | 0.56 |
| Q109I/G118S | 1.13 |
| S024C/Q109K/G118I | 1.80 |
| S024W/Q109L | 0.93 |
| Q109I/G118R | 0.73 |
| Q109A/G118S | 1.25 |
| Q109V/G118F | 1.34 |
| Q109P/G118Q | 1.42 |
| S024W/Q109T/G118R/G127Q/S132N | 0.73 |
| S024W/Q109V/G127T/S132Y | 1.13 |
| S024R/Q109L/G127Q | 0.52 |
| S024H/G127R | 1.58 |
| S024R/Q109C/G127H | 1.57 |
| S024R/Q109R/G118T/G127R | 1.12 |
| S024V/Q109L/G118V | 0.83 |
| S024W/G127R | 1.01 |
| Q109S/G118R | 0.96 |
| S024N/Q109T/G127R/S132N | 0.93 |
| S024H/G118L/G127T/S132Y | 1.94 |
| S024R/Q109V/G127S | 1.22 |
| Q109H/G127R | 0.85 |
| S024N/Q109T/G127T/S132R | 2.06 |
| Q109I/G127T/S132Y | 1.31 |
| S024R/G118H/S132V | 1.16 |
| S024R/Q109T/G127R/S132N | 0.95 |
| S024N/G127R | 1.93 |
| Q109D/G118V/G127H | 1.03 |
| S024W/G118L/G127T/S132Y | 1.96 |
| S024R/Q109I/G127T | 0.57 |
| S024R/Q109T/G127T/S132Y | 1.61 |
| S024R/Q109K/G118T/G127Q/S132N | 1.57 |
| S024W/Q109L/G127R/S132N | 1.11 |
| S024W/Q109T/G127R/S132R | 0.73 |
| S024L/Q109K/G127R/S132Y | 1.07 |
| Q109H/G118S/S132P | 0.68 |
| S024W/Q109V/G127T | 0.88 |
| S024N/Q109V/G127R/S132N | 0.69 |
| S024N/G118R/G127L/S132Y | 0.87 |
| S024N/S132R | 2.10 |
| Q109K/G118F/G127Q/S132N | 1.85 |
| S024R/Q109T/G127R/S132Y | 0.68 |
| Q109V/G127R | 0.76 |
| S024H/Q109V/G127T | 1.28 |
| S024A/Q109Y/G118C | 1.23 |
| S024H/Q109V/G127R/S132N | 0.63 |

TABLE 7-9-continued

Multiple Mutation Variants of GCI-P036 Having a PI ≥0.5 in a TCA Assay

| | PI |
|---|---|
| S024T/Q109I/G127T | 1.61 |
| S024N/Q109T/G127T/S132Y | 1.93 |
| S024A/G118I | 1.15 |
| G118L/G127R/S132L | 0.91 |
| Q109V/G127R/S132N | 0.79 |
| S024N/Q109V/G118R/G127T/S132Y | 1.15 |
| S024W/Q109I/G127T | 1.24 |
| S024R/Q109V/G118R/G127T | 0.80 |
| Q109R/G118V | 1.31 |
| Q109I/G127C | 2.19 |
| S024W/Q109R/G127T/S132N | 2.42 |
| S024L/Q109V/G118R/G127Q | 0.52 |
| Q109V/G127Q | 1.18 |
| S024Q/Q109R/S132R | 1.64 |
| S024H/G118K/G127I | 1.10 |
| A001K/S024R/R045N/A172C | 1.20 |
| A001S/S024L/I107Y/A172S | 1.18 |
| I107C/A172S | 1.24 |
| A001R/S024H/I107T | 1.43 |
| A001R/S024H/R045N/I107T/A172Q | 1.37 |
| R045F/I107T | 1.70 |
| R045V/I107R/A172D | 0.80 |
| A001R/A172Q | 1.11 |
| S024T/R045K/I107V | 1.08 |
| A001V/I107L/A172I | 1.02 |
| S024T/I107T | 1.75 |
| A001T/S024H/I107L/A172Y | 1.01 |
| A001R/S024W/R045K/I107T/A172Q | 1.40 |
| A001R/S024R/I107V/A172L | 0.87 |
| S024N/R045K/A172L | 1.43 |
| A001R/R045N/I107T | 1.33 |
| A001K/S024R/I107T | 0.51 |
| A001R/I107T | 1.47 |
| S024N/I107T | 1.81 |
| A001R/R045K/A172Q | 1.32 |
| R045K/I107T | 2.13 |
| A001K/S024L/R045A | 1.07 |
| A001R/R045F | 1.16 |
| A001R/S024W/R045N/I107T | 1.45 |
| I107Q/A172D | 0.94 |
| A001R/S024R/A172Q | 1.19 |
| A001K/A172L | 1.10 |
| A001S/A172V | 0.96 |
| A001I/R045T/I107R/A172T | 0.98 |
| A001R/S024H/R045K/I107T | 1.50 |
| S024W/A172Q | 1.28 |
| S024W/R045N/A172Q | 1.08 |
| S024V/R045I/A172V | 1.11 |
| R045N/I107T/A172Q | 1.44 |
| A001R/S024R | 1.30 |
| A001K/A172W | 1.49 |
| A001R/S024N | 1.11 |
| A001R/S024R/A172H | 1.36 |
| R045S/I107L | 1.22 |
| A001R/S024T/R045N/I107T/A172Q | 1.60 |
| A001Q/R045K/I107T | 1.73 |
| S024N/R045K/I107V/A172N | 1.42 |
| A001R/S024T/I107T/A172Q | 1.40 |
| A001K/S024N/R045K/A172Y | 1.44 |
| S024R/R045F/I107T/A172Q | 1.84 |
| A001R/I107T/A172Q | 1.53 |
| R045N/I107V/A172Q | 0.89 |
| A001R/I107V/A172Q | 0.76 |
| A001K/R045F/I107L/A172N | 1.21 |
| A001P/A172V | 1.18 |
| S024H/I107K | 1.54 |
| A001L/S024D/R045Y/I107Y | 1.01 |
| A001M/R045S/I107E/A172D | 1.33 |
| S024I/I107R/G127I/A172R | 1.06 |
| A001K/S024T/I107T/G127Q/A172Q | 1.34 |
| A001R/S024R/R045F/I107T/G127R | 1.15 |
| A001C/S024V/I107L | 0.96 |
| A001K/S024H/R045N/I107T | 1.47 |
| A001K/I107V/G127Q | 1.80 |
| A001K/S024R/R045N/I107T/G127R | 1.12 |

TABLE 7-9-continued

Multiple Mutation Variants of GCI-P036 Having a PI ≥0.5 in a TCA Assay

| | PI |
|---|---|
| A001R/S024T/R045K/A172Q | 1.46 |
| A001R/A172G | 1.72 |
| A001R/R045N/A172K | 1.32 |
| A001L/R045Q/G127H/A172R | 1.23 |
| A001K/I107V/G127R/A172Q | 1.01 |
| A001K/R045F/I107T | 1.51 |
| A001K/S024T/R045N/G127Q/A172Q | 1.69 |
| A001K/R045K/I107A/A172T | 1.03 |
| A001R/I107T/G127Q/A172Q | 1.75 |
| A001K/R045K/I107R/G127A/A172N | 1.56 |
| A001R/S024W/R045F/I107V/G127Q | 1.11 |
| R045N/I107A/A172R | 1.07 |
| A001R/R045N/I107T/G127Q | 1.69 |
| I107P/A172S | 1.08 |
| A001R/S024W/I107V/A172S | 1.03 |
| A001K/S024H/I107T/G127Q | 1.45 |
| A001R/S024H/R045K/I107T/A172Q | 1.60 |
| A001R/R045N/A172Q | 1.42 |
| A001K/R045F/I107V/G127Q | 1.94 |
| A001K/S024N/I107V/G127T | 2.01 |
| A001R/S024W/R045F/I107V/G127R | 0.73 |
| S024T/R045K/I107T/G127R/A172Q | 0.75 |
| A001K/R045N/I107T/G127Q | 1.65 |
| A001K/S024W/I107V/G127T/A172Q | 1.45 |
| A001K/I107V/G127Q/A172Q | 1.68 |
| A001R/R045N/I107V/G127R | 1.53 |
| A001K/S024H/I107T/G127R | 1.35 |
| A001R/I107T | 1.65 |
| A001K/S024H/I107V | 0.88 |
| I107A/G127K/A172G | 1.35 |
| A001R/R045K/G127R | 1.26 |
| A001R/R045K/I107T/G127Q | 1.61 |
| A001R/S024W/R045K | 1.16 |
| A001R/R045N/I107T | 1.71 |
| A001K/S024R/R045N/I107T | 1.19 |
| A001K/R045K/I107T/G127R/A172Q | 1.21 |
| A001K/I107T/A172Q | 1.80 |
| A001R/R045N/I107V/A172V | 1.31 |
| A001R/S024R/R045K/I107T/G127Q | 1.68 |
| A001R/R045N/I107V/G127Q/A172Q | 1.70 |
| A001R/S024R/I107V/G127R | 1.52 |
| A001R/S024R/R045F/I107T/G127Q | 1.62 |
| A001K/S024H/R045N/I107T/G127Q/A172Q | 1.51 |
| S024Y/G127R/A172E | 1.06 |
| A001K/S024W/I107T/G127R | 0.94 |
| A001R/R045K/I107V/G127R | 1.36 |
| A001K/R045K/I107T/G127R | 1.35 |
| A001R/S024T/R045K/I107L/G127P/A172P | 1.17 |
| S024W/S099Q | 1.36 |
| S024W/S099K/S103P/G118R/S132H | 0.50 |
| S099Q/S103N/S132H | 1.03 |
| S099K/G118R | 1.97 |
| S024W/S099T/S103P | 0.72 |
| S024W/S103K/S132R | 1.08 |
| S024W/S103P | 1.61 |
| S024W/S099T/S103P/G118R | 1.12 |
| S024H/S099Q/S103P | 1.03 |
| S024H/S099K/S103R/G118A/S132P | 0.68 |
| S024W/G118K | 0.84 |
| S024H/S099T/S103N/S132N | 0.91 |
| S099Q/S103N/G118R/S132N | 1.13 |
| S024W/S099T/S103N | 1.09 |
| S024W/S099Q/S103N/G118T | 1.32 |
| S024W/S132H | 0.52 |
| S103L/S132E | 1.08 |
| S103R/S132P | 0.82 |
| S099Q/S103P/G118R | 1.13 |
| S099Q/S103N/G118T | 0.75 |
| S024H/S099Q/S132N | 1.03 |
| S099K/S103N/G118T | 1.13 |
| S024H/S099Q/S103P/S132H | 0.63 |
| S024H/S132R | 1.42 |
| S024W/S099T/S103N/S132N | 1.09 |
| S024T/G118D | 1.36 |
| S099N/S132R | 0.84 |

TABLE 7-9-continued

Multiple Mutation Variants of GCI-P036 Having a PI ≥0.5 in a TCA Assay

| | PI |
|---|---|
| S099H/S103I/G118N | 1.19 |
| S024W/S099Q/S103N/G118R/S132N | 1.05 |
| S024W/S099Q/G118T | 0.70 |
| S024W/S099T/G118R/S132R | 0.63 |
| S024H/S099Q/S132H | 1.56 |
| S099Q/S132R | 1.87 |
| S024M/G118V | 0.98 |
| S024W/S132N | 1.49 |
| S099K/S103R/G118A/S132P | 0.79 |
| S024W/S099T/S103P/S132H | 0.55 |
| S024W/S099T/S103N/S132H | 1.44 |
| S099Q/G118T/G127Q | 1.76 |
| S024W/S099T/S103N/G118R | 0.92 |
| S099T/G118F | 0.72 |
| S024H/S099Q/G118R/G127Q/S132H | 1.01 |
| S103G/G118I/G127E/S132E | 0.90 |
| S024H/S099T/S103N | 1.00 |
| S024H/S099Q/S132H | 0.83 |
| S024W/S099Q/S103N/G118R/G127Q/S132N | 0.95 |
| S024W/S099K/S103P/S132H | 0.72 |
| S024H/S099Q/G118R/S132H | 0.90 |
| S024G/G118F/G127R/S132N | 0.53 |
| S024H/S099K/S103P/G118F | 0.74 |
| G118T/G127Q | 1.62 |
| S099T/G118R/S132H | 1.12 |
| S024H/S099K/G118F/G127R | 0.92 |
| S024H/S103P/G127R/S132R | 1.07 |
| S024N/S099T/G127T/S132H | 2.06 |
| S024H/S099T/S103N/G127R/S132N | 0.98 |
| S024H/S099K/G118R/G127R/S132H | 0.60 |
| S024L/G127R | 1.00 |
| S024W/G127R/S132N | 0.77 |
| S024W/S099T | 0.85 |
| S024H/S099T/S103P/S132N | 1.15 |
| S024W/S099T/S103N/G127R/S132H | 0.69 |
| S099T/S103P | 1.31 |
| S024W/S099T/G118R/G127Q | 1.81 |
| S024W/S132H | 0.84 |
| S024W/S099T/S103P | 0.97 |
| S024H/S099Q/S103N/G118R/G127T/S132N | 1.54 |
| S024H/S099K/S103P | 1.67 |
| S024W/S103P | 1.77 |
| S024H/S103N/S132H | 1.41 |
| S024W/S099Q/S103P/S132N | 0.71 |
| S024W/S099Q/S103P | 1.20 |
| S024H/S132N | 0.81 |
| S024W/S099T/G118R | 0.52 |
| S099K/S103P/G127Q | 2.82 |
| S099Q/G118F/G127R | 1.58 |
| S099Q/S103P/S132H | 0.82 |
| S024W/S099T/S103P/G118T | 0.62 |
| S024H/S099T/G118R | 1.78 |
| S024H/S099T/S103P/G118R | 1.42 |
| S087N/G118V/S128L/P129Q/S130A/S024R/Q109K | 0.87 |
| S087N/G118V/S128L/P129Q/S130A/S024R | 0.72 |
| S087N/G118V/S128L/P129Q/S130A/S024H | 1.30 |
| S087N/G118V/S128L/P129Q/S130A/S024R/Q109L | 0.82 |
| S087N/G118V/S128L/P129Q/S130A/S024R/Q109V | 1.09 |
| S087N/G118V/S128L/P129Q/S130A/Q109V | 0.57 |
| S087N/G118V/S128L/P129Q/S130A/S024R/G127R | 0.57 |
| S087N/G118V/S128L/P129Q/S130A/S024W | 0.71 |
| S087N/G118V/S128L/P129Q/S130A/S024T/G127T | 1.42 |
| S087N/G118V/S128L/P129Q/S130A/G127T | 1.22 |
| S087N/G118V/S128L/P129Q/S130A/Q109I | 0.58 |
| S087N/G118V/S128L/P129Q/S130A/S024T | 1.85 |
| S087N/G118V/S128L/P129Q/S130A/S024N/Q109K | 1.58 |
| S087N/G118V/S128L/P129Q/S130A/G127Q | 0.86 |
| S087N/G118V/S128L/P129Q/S130A/S024R/Q109L/G127Q | 0.59 |
| S087N/G118V/S128L/P129Q/S130A/Q109L/G127Q | 0.59 |
| S087N/G118V/S128L/P129Q/S130A/R045S | 1.31 |
| S087N/G118V/S128L/P129Q/S130A/S024H/I107V/A172S | 1.10 |
| S087N/G118V/S128L/P129Q/S130A/A001K/I107W/A172P | 1.06 |
| S087N/G118V/S128L/P129Q/S130A/A001R | 1.22 |
| S087N/G118V/S128L/P129Q/S130A/A001K/R045N/I107V | 1.05 |
| S087N/G118V/S128L/P129Q/S130A/A001K/S024H/A172Q | 1.13 |

TABLE 7-9-continued

Multiple Mutation Variants of GCI-P036 Having a PI ≥0.5 in a TCA Assay

| | PI |
|---|---|
| S087N/G118V/S128L/P129Q/S130A/A001R/S024W/A172W | 0.90 |
| S087N/G118V/S128L/P129Q/S130A/A172N | 1.01 |
| S087N/G118V/S128L/P129Q/S130A/A001R/I107V/A172Q | 1.03 |
| S087N/G118V/S128L/P129Q/S130A/A001K/S024H/I107V | 0.66 |
| S087N/G118V/S128L/P129Q/

TABLE 7-9-continued

| Multiple Mutation Variants of GCI-P036 Having a PI ≥0.5 in a TCA Assay | PI |
|---|---|
| S087N/G118V/S128L/P129Q/S130A/N185Q/Y209W/A215R | 1.32 |
| S087N/G118V/S128L/P129Q/S130A/N018Q/G097P/N185R | 0.72 |
| S087N/G118V/S128L/P129Q/S130A/N185R/A215V/S256W | 1.16 |
| S087N/G118V/S128L/P129Q/S130A/N018R/N185K/Y209W | 1.27 |
| S087N/G118V/S128L/P129Q/S130A/A215V | 0.79 |
| S087N/G118V/S128L/P129Q/S130A/N018R/N185Q/A215I/S256W | 0.74 |
| S087N/G118V/S128L/P129Q/S130A/G097P/N185K/A215I | 0.81 |
| S087N/G118V/S128L/P129Q/S130A/N018Q/N185K/A215R | 1.07 |
| S087N/G118V/S128L/P129Q/S130A/N018K/Y209W/A215V | 1.09 |
| S087N/G118V/S128L/P129Q/S130A/N018K/N185K/Y209W | 1.36 |
| S087N/G118V/S128L/P129Q/S130A/N018R/G097P/N185K/Y209W/A215I/S256W | 0.73 |
| S087N/G118V/S128L/P129Q/S130A/N018Q/N185K/A215V | 1.44 |
| S087N/G118V/S128L/P129Q/S130A/N185R/Y209W/S256L | 1.31 |
| S087N/G118V/S128L/P129Q/S130A/N018K/S256W | 1.13 |
| S087N/G118V/S128L/P129Q/S130A/N018Q/N185K/S256W | 1.37 |
| S087N/G118V/S128L/P129Q/S130A/N185Q/Y209W/A215V/S256W | 1.28 |
| S087N/G118V/S128L/P129Q/S130A/P052I/N248K | 0.63 |
| S087N/G118V/S128L/P129Q/S130A/N043W/S101F/N248K | 0.51 |
| S087N/G118V/S128L/P129Q/S130A/N043V/S101T | 1.05 |
| S087N/G118V/S128L/P129Q/S130A/P052V | 0.84 |
| S087N/G118V/S128L/P129Q/S130A/N043S | 0.52 |
| S087N/G118V/S128L/P129Q/S130A/N043V/S101Y | 0.87 |
| S087N/G118V/S128L/P129Q/S130A/N043S/P052V/S101R | 0.70 |
| S087N/G118V/S128L/P129Q/S130A/N043F/P052V/S101T/N248K | 0.51 |
| S087N/G118V/S128L/P129Q/S130A/N043I/S101E/N248K | 0.68 |
| S087N/G118V/S128L/P129Q/S130A/S101E/N248K | 0.90 |
| S087N/G118V/S128L/P129Q/S130A/N248K | 0.93 |
| S087N/G118V/S128L/P129Q/S130A/N043W/S101E | 0.88 |
| S087N/G118V/S128L/P129Q/S130A/N043S/S101E/N248K | 0.66 |
| S087N/G118V/S128L/P129Q/S130A/P052I/S101V/N248K | 0.75 |
| S087N/G118V/S128L/P129Q/S130A/S101F/N248K | 0.80 |
| S087N/G118V/S128L/P129Q/S130A/N043V/S101T/N248K | 0.89 |
| S087N/G118V/S128L/P129Q/S130A/S101Y | 0.89 |
| S087N/G118V/S128L/P129Q/S130A/N043V/P052I | 0.65 |
| S087N/G118V/S128L/P129Q/S130A/N043E | 0.98 |
| S087N/G118V/S128L/P129Q/S130A/N043S/S101T | 0.97 |
| S087N/G118V/S128L/P129Q/S130A/N043V/S101F | 0.79 |
| S087N/G118V/S128L/P129Q/S130A/N043E/S101R | 1.31 |
| S087N/G118V/S128L/P129Q/S130A/N043E/S101Y | 0.73 |
| S087N/G118V/S128L/P129Q/S130A/N043E/S101E | 0.87 |
| S087N/G118V/S128L/P129Q/S130A/N043T/N248K | 0.79 |
| S087N/G118V/S128L/P129Q/S130A/P052V/S101R | 0.89 |
| S087N/G118V/S128L/P129Q/S130A/P052I/S101E/N248K | 0.52 |
| S087N/G118V/S128L/P129Q/S130A/S101N/N248K | 0.86 |
| S087N/G118V/S128L/P129Q/S130A/N043V/S101E/N248K | 0.59 |
| S087N/G118V/S128L/P129Q/S130A/N043V/S101R | 1.17 |
| S087N/G118V/S128L/P129Q/S130A/N043F/S101Y/N248K | 0.70 |
| S087N/G118V/S128L/P129Q/S130A/N043S/P052V | 0.57 |
| S087N/G118V/S128L/P129Q/S130A/S101R/N248K | 1.45 |
| S087N/G118V/S128L/P129Q/S130A/N043I/S101Y | 0.80 |
| S087N/G118V/S128L/P129Q/S130A/N043I/S101Y/N248K | 0.54 |
| S087N/G118V/S128L/P129Q/S130A/N043S/P052V/S101V/N248K | 0.53 |
| S087N/G118V/S128L/P129Q/S130A/N043T | 0.83 |
| S087N/G118V/S128L/P129Q/S130A/Y209W | 1.11 |
| S087N/G118V/S128L/P129Q/S130A/N043S/N185V/S256T | 0.52 |
| S087N/G118V/S128L/P129Q/S130A/P052V/Y209W | 0.92 |
| S087N/G118V/S128L/P129Q/S130A/S144V/N185R/Y209W | 0.74 |
| S087N/G118V/S128L/P129Q/S130A/S144V/Y209W/S256T | 0.59 |
| S087N/G118V/S128L/P129Q/S130A/P052V/G097T/N185R/Y209W/S256T | 0.51 |
| S087N/G118V/S128L/P129Q/S130A/G097S/N185R/S256I | 0.75 |
| S087N/G118V/S128L/P129Q/S130A/S144V/N185V/Y209W | 0.71 |
| S087N/G118V/S128L/P129Q/S130A/S144V/N185V | 0.72 |
| S087N/G118V/S128L/P129Q/S130A/P052V/S144T/N185R/Y209W | 0.70 |
| S087N/G118V/S128L/P129Q/S130A/S144T/N185R/Y209W | 0.93 |
| S087N/G118V/S128L/P129Q/S130A/S144T/N185R | 0.91 |
| S087N/G118V/S128L/P129Q/S130A/S144T/Y209W/S256I | 0.77 |
| S087N/G118V/S128L/P129Q/S130A/P052V/S144T/N185R/S256T | 0.54 |
| S087N/G118V/S128L/P129Q/S130A/S144T/N185V/S256I | 0.64 |
| S087N/G118V/S128L/P129Q/S130A/N043S/N185R/Y209W/S256T | 1.05 |
| S087N/G118V/S128L/P129Q/S130A/S144T/N185V/Y209W | 1.04 |
| S087N/G118V/S128L/P129Q/S130A/S144V | 0.66 |
| S087N/G118V/S128L/P129Q/S130A/N043T/S144V/Y209W/S256T | 0.51 |
| S087N/G118V/S128L/P129Q/S130A/S144Y/N185V/Y209W | 0.50 |
| S087N/G118V/S128L/P129Q/S130A/G097T/Y209W/S256I | 0.68 |
| S087N/G118V/S128L/P129Q/S130A/N185R/S256T | 1.26 |

TABLE 7-9-continued

Multiple Mutation Variants of GCI-P036 Having a PI ≥0.5 in a TCA Assay

| | PI |
|---|---|
| S087N/G118V/S128L/P129Q/S130A/P052V/S144T/Y209W/S256T | 0.55 |
| S087N/G118V/S128L/P129Q/S130A/S144T/S256I | 0.65 |
| S087N/G118V/S128L/P129Q/S130A/S144T/N185R/S256I | 0.74 |
| S087N/G118V/S128L/P129Q/S130A/N043S/S256I | 0.75 |
| S087N/G118V/S128L/P129Q/S130A/N043V/N185V/Y209W/S256I | 0.76 |
| S087N/G118V/S128L/P129Q/S130A/G097T/S144T/N185R/Y209W/S256I | 0.53 |

TABLE 8-1-continued $P_i$ Values of GCI-PO36 Variants Tested for Stain Removal Performance on CS-38 Swatches, LAS/EDTA Stability, Thermostability and Protein Determination

| Clone | Variants based on GCI-P036 | Calgonit 5 in 1 40° C. | Calgonit 5 in 1 50° C. | Cascade Complete 50° C. | LAS-EDTA Stability | TCA Assay | Thermo-stability |
|---|---|---|---|---|---|---|---|
| 11 | S87R/G118R/S128L/P129Q/S130A/I72V/S164I/S188D/N248R | 0.76 | 0.9 | 1.09 | 0.72 | 1.14 | 0.37 |
| 12 | S87N/G118V/S128L/P129Q/S130A/N76D | 0.48 | 0.71 | 0.97 | 1.4 | 0.97 | 1.04 |
| 13 | S87N/G118V/S128L/P129Q/S130A/S24W/S101Y/Q109K | 1.68 | 1.69 | 1.39 | 1.01 | 1.06 | 1.03 |
| 14 | S87N/G118V/S128L/P129Q/S130A/N43S/P52V/S101R/Q109R | 3.76 | 4.86 | 2.13 | 1.09 | 0.72 | 0.85 |
| 15 | S87N/G118V/S128L/P129Q/S130A/I72V/S101Y/Q109R/S164I | 5.94 | 4.01 | 1.95 | 1.03 | 0.63 | 1.2 |
| 16 | S87N/G118V/S128L/P129Q/S130A/S101L/Q109L/S188D/N248R | ND | ND | 1.66 | 1.08 | 0.37 | 0.62 |
| 17 | S87N/G118V/S128L/P129Q/S130A/I72V/Q109R/S164I/S188D/N248R | 0.67 | 0.98 | 0.56 | 1.1 | 0.59 | 0.88 |
| 18 | S87N/G118V/S128L/P129Q/S130A/N76D/S101L | 1.72 | 2.52 | 1.97 | 1.41 | 0.87 | 1.07 |
| 19 | S87N/G118V/S128L/P129Q/S130A/S24W/S101Y/Q109L | 3.89 | 4.14 | 1.65 | 1 | 0.5 | 1.04 |
| 20 | S87N/G118V/S128L/P129Q/S130A/N76D/S164I | 0.56 | 1.03 | 0.82 | 1.46 | 0.94 | 1.17 |
| 21 | S87R/G118R/S128L/P129Q/S130A/N76D/S188D/N248R | 0.93 | 1.20 | 1.24 | 1.54 | 1.39 | 0.7 |
| 22 | S87N/G118V/S128L/P129Q/S130A/S101Y/Q109L/S188D/N248R | 3.8 | 4.24 | 1.83 | 1.11 | 0.46 | 0.72 |
| 23 | S87R/G118R/S128L/P129Q/S130A/V118R/S188D/N248R | 0.89 | 0.99 | 1.2 | 0.87 | 1.13 | 0.17 |
| 24 | S87N/G118V/S128L/P129Q/S130A/N76D/S101M | 1.05 | 1.63 | 1.35 | 1.48 | 0.94 | 1.09 |
| 25 | S87N/G118V/S128L/P129Q/S130A/N18K/N76D/G97P/N185R/A215R | 1.64 | 2.35 | 0.9 | 0.46 | 0.52 | 1.22 |
| 26 | S87N/G118V/S128L/P129Q/S130A/I72V/S101L/S164I | 2.01 | 2.72 | 1.85 | 1.01 | 0.59 | 1.23 |
| 27 | S87R/G118R/S128L/P129Q/S130A/S101L/S188D/N248R | 1.9 | 2.15 | 1.88 | 0.76 | 1.21 | 0.18 |
| 28 | S87N/G118V/S128L/P129Q/S130A/S101Y/Q109L/S188D/T213E/N248R | 2.7 | 2.98 | 1.72 | 1.07 | 0.52 | 0.2 |
| 29 | S87R/G118R/S128L/P129Q/S130A/Q109L/S188D/N248R | 0.94 | 1.24 | 1.27 | 0.78 | 1.02 | 0.22 |
| 30 | S87N/G118V/S128L/P129Q/S130A/N18K/G97P/S101L/N185R/A215R | 3.94 | 4.66 | 1.32 | 0.02 | 0.48 | 1.3 |
| 31 | S87N/G118V/S128L/P129Q/S130A/I72V/S101Y/S164I | 1.95 | 2.74 | 1.68 | 1.05 | 0.58 | 1.26 |
| 32 | S87N/G118V/S128L/P129Q/S130A/S101Y/T213E/N248R | 4.32 | 4 | 1.87 | 0.96 | 0.71 | 0.36 |
| 33 | S87N/G118V/S128L/P129Q/S130A/I72V/S101L/Q109L/S164I | ND | ND | 1.16 | 1.03 | 0.3 | 1.22 |
| 34 | S87R/G118R/S128L/P129Q/S130A/S101V/S188D/N248R | 2.62 | 2.65 | 1.74 | 0.77 | 1.35 | 0.19 |
| 35 | S87N/G118V/S128L/P129Q/S130A/N18K/G97P/S101Y/N185R/A215R | 7.52 | 7.71 | 1.75 | 0.02 | 0.43 | 1.22 |
| 36 | S87N/G118V/S128L/P129Q/S130A/I72V/S101V/S164I | 1.92 | 2.51 | 1.72 | 1.01 | 0.84 | 1.2 |
| 37 | S87N/G118V/S128L/P129Q/S130A/S101L/T213E/N248R | 2.94 | 3.06 | 1.83 | 1 | 0.79 | 0.41 |
| 38 | S87N/G118V/S128L/P129Q/S130A/I72V/S101Y/Q109L/S164I | ND | ND | 0.98 | 1.04 | 0.29 | 1.21 |
| 39 | S87R/G118R/S128L/P129Q/S130A/S101H/S188D/N248R | 2.13 | 2.56 | 1.58 | 0.8 | 1.33 | 0.19 |
| 40 | S87N/G118V/S128L/P129Q/S130A/N18K/G97P/Q109R/N185R/A215R | 2.31 | 3.33 | 1.2 | 0.02 | 0.52 | 1.03 |
| 41 | S87N/G118V/S128L/P129Q/S130A/I72V/S101H/S164I | 1.23 | 4 | 1.59 | 0.99 | 0.65 | 1.22 |
| 42 | S87N/G118V/S128L/P129Q/S130A/S101L/Q109R/S188D/N248R | 2.78 | 2.71 | 1.8 | 0.98 | 0.88 | 0.56 |
| 43 | S87N/G118V/S128L/P129Q/S130A/N18K/G97P/S101L/Q109L/N185R/A215R | ND | ND | 1.11 | 0.02 | 0.25 | 1.18 |
| 44 | S87R/G118R/S128L/P129Q/S130A/S101M/S188D/N248R | 1.53 | 1.69 | 1.75 | 0.73 | 1.26 | 0.17 |
| 47 | N76D/S87R/G118R/S128L/P129Q/S130A/S188D | 1.02 | 1.11 | 1.23 | ND | ND | ND |
| 49 | N76D/S87R/G118R/S128L/P129Q/S130A/S188D/N248K | 0.86 | 1.12 | 1.08 | ND | ND | ND |
| 100 | S87N/G118V/G127S/S128L/P129Q/S130A | ND | 1.38 | 1.10 | ND | ND | ND |
| 101 | S87N/S101H/G118V/S128L/P129Q/S130A | ND | 1.52 | 1.31 | 1.28 | ND | 1.06 |
| 102 | S87N/S101K/G118V/S128L/P129Q/S130A | ND | 1.74 | 1.60 | 1.18 | ND | 0.99 |
| 103 | S87N/S101V/G118V/S128L/P129Q/S130A | ND | 1.72 | 1.56 | 1.19 | ND | 1.05 |
| 104 | S87N/S101Y/G118V/S128L/P129Q/S130A | ND | 1.31 | 1.23 | 1.18 | ND | 1.09 |
| 105 | S87N/S101L/G118V/S128L/P129Q/S130A | ND | 1.65 | 1.48 | 1.06 | ND | 1.03 |
| 106 | I72V/S87N/G118V/S128L/P129Q/S130A//S164I | ND | 1.04 | 1.01 | ND | ND | ND |

Example 9

Evaluation of Stain Removal by Multiple Mutation Library (MML) Variants in Laundry Application Studies Results of experiments conducted to determine stain removal activity (microswatch assay to determine cleaning performance in laundry applications) of variants of GCI-P036 (clones 8, 47, 49 as described in Example 8) are shown in Table 9-1. The results were obtained using the methods described in Example 1. The test detergents used were heat inactivated P&G TIDE® 2× (NA HDL) and P&G TIDE® (NA HDG). Cleaning performance of BMI stained microswatches was tested using 0.2 ppm of the variants at 25° C. for 30 minutes with 1400 rpm shaking in a volume of 200 uL. As described throughout, functionality of GCI-P036 variants were quantified as a performance index (Pi), which is the ratio of performance of a variant to a parent GCI-P036 protein. Subtilisin FNA (BPN'-Y217L) and GCI-P036-S87N-G118V-S128L-P129Q-S130A proteins were also tested.

TABLE 9-1

$P_i$ Values of GCI-PO36 Variants Tested for Stain Removal Performance on BMI Microswatches in NA HDL and NA HDG Detergents

| Clone # | Variants based on GCI-P036 | NA HDL pH 8 | NA HDG pH 10 |
|---|---|---|---|
| GCI-P036 | — | 1.00 | 1.00 |
| 8 | N18K/S87N/ G97P/Q109R/ G118V/S128L/ P129Q/S130A/ N185R/A215R | 0.46 | 0.38 |
| 47 | S87R/N76D/ G118R/S128L/ P129Q/S130A/ S188D | 1.12 | 1.19 |
| 49 | N76D/S87R/ G118R/S128L/ P129Q/S130A/ S188D/N248K | 0.92 | 1.06 |

TABLE 9-1-continued

P$_i$ Values of GCI-PO36 Variants Tested for
Stain Removal Performance on BMI Microswatches
in NA HDL and NA HDG Detergents

| Clone # | Variants based on GCI-P036 | NA HDL pH 8 | NA HDG pH 10 |
|---|---|---|---|
| GCI-P036-variant | S87N-G118V-S128L-P129Q-S130A | 1.22 | 1.14 |
| FNA | BPN' Y217L | 1.29 | 0.66 |

Example 10

Protease Variants with Increased Production Titers

Figure 3:
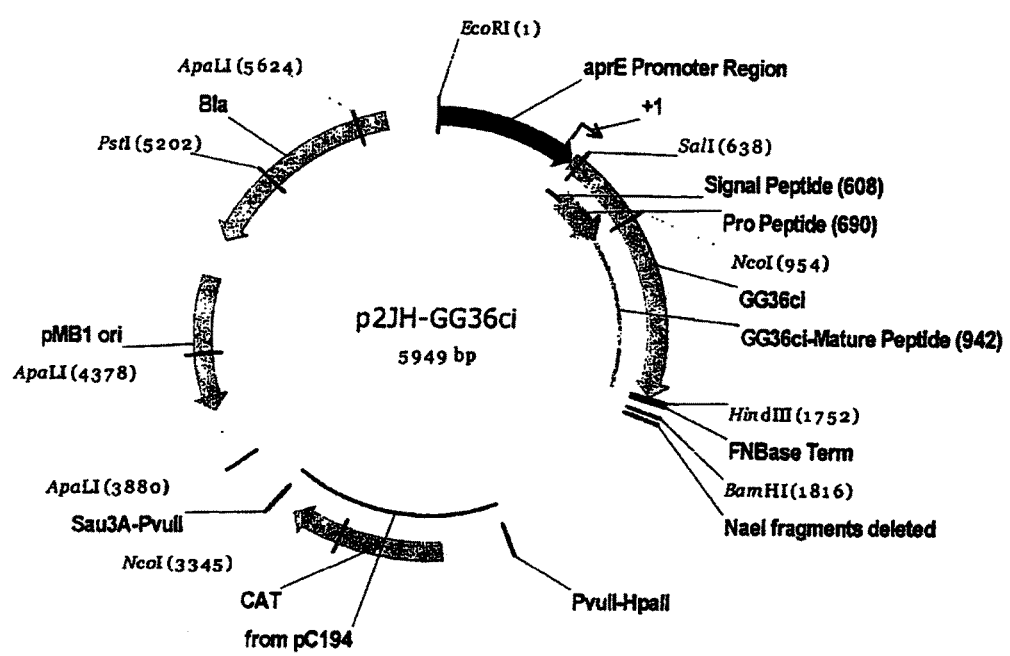
FIG. 3 provides a map of p2JH-GG36ci.
Figure 4:
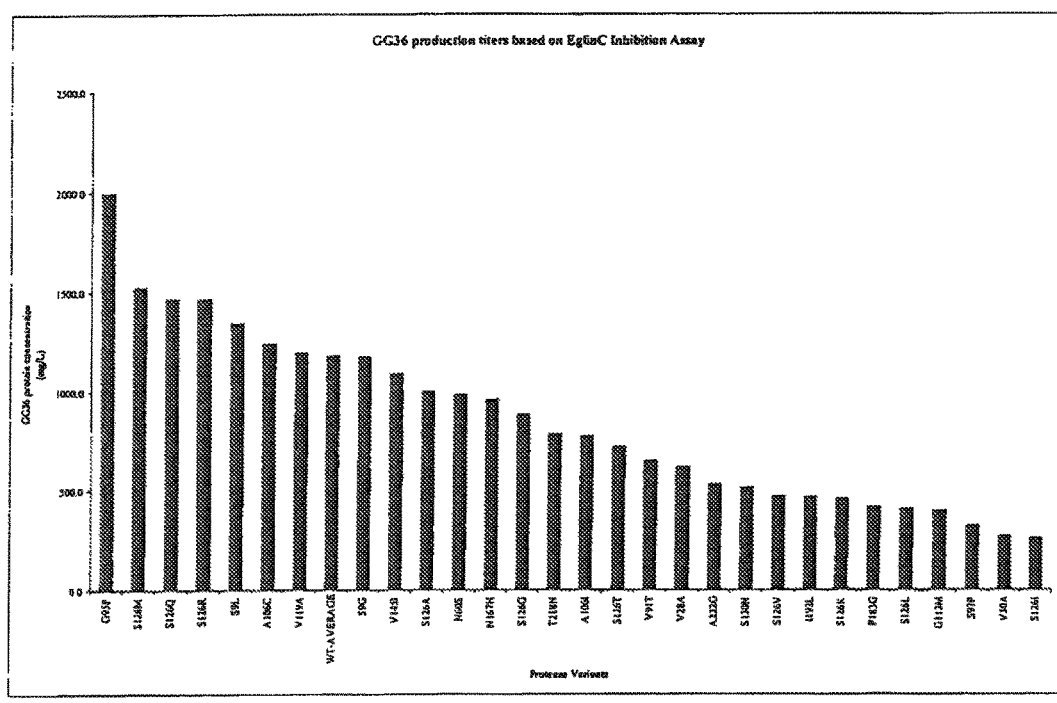
FIG. 4 depicts protease concentration as determined using an eglin c inhibition assay for variant proteases.
Figure 5:
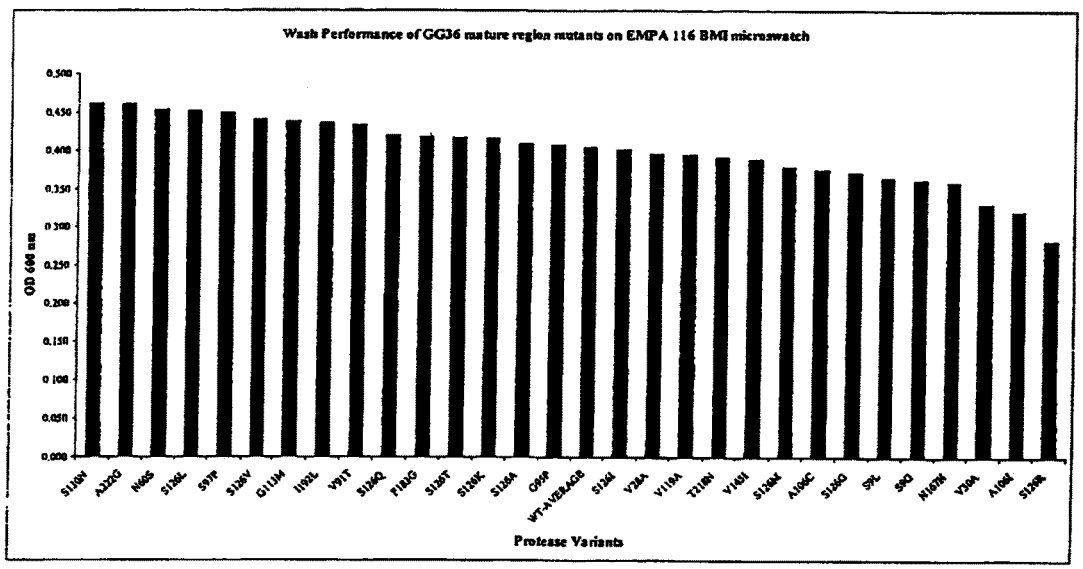
FIG. 5 depicts wash performance (BMI microswatch) of variant proteases.

Mutations within the mature region of GCI-P036 were selected based on beneficial gains in protein titer or microswatch wash performance observed during the superscreen carried out in microtiter plates. The protease samples tested in the prior examples were obtained using a replicating plasmid expression system. For the expression of the 45 variants described in this example, a gene labeled GCI-P036ci, encoding the wildtype GCI-P036 protein, was used. This "ci" synthetic gene consists of a codon improved version based on FNA codon usage (a protein expressed to very high levels). Nucleic acids encoding these variants were introduced into the GCI-P036ci gene template as described below, to generate a series of plasmids in the p2JH backbone (p2JH-GCI-P036ci, FIG. 3), an integrating vector system amenable to protein production at large scale. This integrating *Bacillus* expression system was used to evaluate the variants listed in Table 9-1 using culture broth from shake flask cultures. Protein expression and microswatch performance was again evaluated. Since certain variants displayed diminished protease activity versus the suc-AAPF-pNA substrate when compared to wild type, an eglin c titration assay was used for determining protease concentration. Results obtained for eglin c and BMI assays are shown in FIG. 4 and FIG. 5, respectively.

TABLE 10-1

| Protease Variants | | |
|---|---|---|
| GCI-P036 WT Position | BPN' Position | Variants Evaluated |
| S9 | S9 | L, G |
| V28 | V28 | A |
| V30 | V30 | A |
| N60 | N62 | S |
| V91 | V93 | T |
| L94 | L96 | A |
| G95 | G97 | P |
| S97 | D99 | P |
| I105 | I107 | F |
| A106 | I108 | I, C, M |
| G113 | I115 | M |
| V119 | V121 | A |
| L124 | M126 | F, N |
| G125 | G127 | S |
| S126 | G128 | I, L, W, K, V, Y, N, F, T, G, E, A, C, D, H, P, R, Q, M |
| S130 | S132 | N |
| V145 | V147 | I |
| N167 | S173 | H |
| F183 | F189 | G |
| I192 | V198 | L |
| T218 | S224 | N |
| A222 | A228 | G |

Integrating Plasmid

Integrating plasmid p2JH-GCI-P036ci was assembled using a GCI-P036 codon-improved synthetic gene (GCI-P036ci), fused at the eighth codon of the AprE signal sequence, under the control of the AprE promoter and FNBase terminator (Wells et al., Nucleic Acids Res, 11:7911-25, 1983). In the GCI-P036ci sequence of p2JH-GCI-P036ci provided below, bold and italicized font indicates AprE promoter, standard font indicates the signal sequence region, underlined font indicates the GCI-P036 pro sequence region, boldfaced font indicates DNA that encodes GCI-P036 mature protease region, and underlined italicized font indicates FNBase terminator.

(SEQ ID NO: 8)

AATTCTCCATTTTCTTCTGCTATCAAAATAACAGACTCGTGATTTTCCAAACGAGCTTTCAAAA

AAGCCTCTGCCCCTTGCAAATCGGATGCCTGTCTATAAAATTCCCGATATTGGTTAAACAGCG

GCGCAATGGCGGCCGCATCTGATGTCTTTGCTTGGCGAATGTTCATCTTATTTCTTCCTCCCTC

TCAATAATTTTTTCATTCTATCCCTTTTCTGTAAAGTTTATTTTTCAGAATACTTTTATCATCATG

CTTTGAAAAAATATCACGATAATATCCATTGTTCTCACGGAAGCACACGCAGGTCATTTGAACG

AATTTTTTCGACAGGAATTTGCCGGGACTCAGGAGCATTTAACCTAAAAAAGCATGACATTTCA

GCATAATGAACATTTACTCATGTCTATTTTCGTTCTTTTCTGTATGAAAATAGTTATTTCGAGTC

TCTACGGAAATAGCGAGAGATGATATACCTAAATAGAGATAAAATCATCTCAAAAAAATGGGT

CTACTAAAATATTATTCCATCTATTACAATAAATTCACAGAATAGTCTTTTAAGTAAGTCTACTC

TGAATTTTTTAAAAGGAGAGGGTAAAGAGTGAGAAGCAAAAAATTGTGGATCGTCGCGTCG

ACCGCATTGCTGATTTCTGTTGCTTTTAGCTCATCCATCGCATCCGCTGCTGAAGAAGCAAA

AGAAAAATATTTAATTGGCTTTAATGAGCAGGAAGCTGTCAGTGAGTTTGTAGAACAAGTT

GAGGCAAATGACGAGGTAGCCATTCTCTCTGAGGAAGAGGAAGTCGAAATTGAATTGCTTC

ATGAATTTGAAACGATTCCTGTTCTGTCCGTTGAGTTAAGCCCAGAAGATGTGGACGCGTTA

-continued

GAGCTCGATCCAGCTATTTCTTATATTGAAGAGGATGCAGAAGTAACTACAATGGCGCAAT

CGGTACCATGGGGAATTAGCAGAGTACAAGCCCCAGCTGCACATAACCGTGGATTGAC

AGGTTCTGGTGTAAAAGTTGCTGTCCTTGATACCGGTATTTCCACTCATCCAGACTTAA

ATATTCGTGGTGGAGCTAGCTTTGTACCAGGGGAACCATCCACTCAAGATGGCAATGG

ACATGGCACTCATGTTGCCGGCACAATCGCGGCTCTTAACAATTCAATTGGTGTTCTTG

GCGTAGCGCCAAGCGCAGAACTATACGCTGTTAAAGTATTAGGAGCAAGCGGTTCAGG

CTCTGTCAGCTCTATTGCCCAAGGATTGGAATGGGCAGGGAACAATGGCATGCACGTT

GCTAATCTTAGTTTAGGATCTCCTTCGCCAAGTGCCACACTTGAGCAAGCTGTTAATAG

CGCGACTTCTAGAGGCGTTCTTGTTGTAGCGGCCTCTGGAAATTCAGGTGCAGGCTCA

ATCAGCTATCCGGCCCGTTATGCGAACGCTATGGCAGTCGGAGCTACTGACCAAAACA

ACAACCGCGCCAGCTTTTCACAGTATGGCGCAGGGCTTGACATTGTCGCACCAGGTGT

AAACGTGCAGAGCACTTACCCAGGTTCAACATATGCCAGCTTAAACGGTACATCAATG

GCTACTCCTCATGTTGCAGGTGCGGCTGCACTTGTTAAACAAAAGAACCCATCTTGGT

CCAATGTACAAATCCGCAATCATCTTAAGAATACGGCAACTAGCTTAGGAAGCACAAA

CTTGTATGGAAGCGGACTTGTCAATGCAGAAGCTGCAACTCGTTAAAAGCTTAACTCGA

GATAAAAAACCGGCCTTGGCCCCGCCGGTTTTT.

Features of p2JH-GCI-P036ci include: CAT=chloramphenicol resistance gene from pC194, pMB1 origin=origin of replication from pBR322, bla=beta-lactamase from pBR322, aprE promoter=transcriptional promoter, Signal Peptide=signal peptide, Pro Peptide=GCI-P036 pro region, GCI-P036ci Mature Peptide=mature GCI-P036, FNBase Term=FNBase Terminator. The amino acid sequence of the GCI-P036 precursor and GCI-P036 mature protease is provided above as SEQ ID NOS: 6 and SEQ ID NO: 2, respectively.

Generation of Further GCI-P036 Variants

Site-directed mutagenesis using Multi-site QuickChange Kit (Stratagene) was carried out using the p2JH-GCI-P036ci plasmid as a template and site-specific primer sets, forward (F) and reverse (R) with the sequences shown in Table 9-2. Five microliters of the mutated product was used to transform chemically competent Top10 E. coli cells (Invitrogen) and plated on LA+50 ppm carbenicillin for growth under selection. Plates were incubated overnight at 37° C.

TABLE 10-2

Site specific Primer Sets Used for Creating Mature Region Mutants in p2JH-GCI-P036ci.

| Primer Name | SEQ ID NO: | Primer Sequence (5'-3') |
|---|---|---|
| S126A-F | 9 | ctaatcttagtttaggagctccttcgccaagtgcc |
| S126A-R | 10 | ggcacttggcgaaggagctcctaaactaagattag |
| S126C-F | 11 | cacgttgctaatcttagtttaggatgcccttcgccaagtgc |
| S126C-R | 12 | gcacttggcgaagggcatcctaaactaagattagcaacgtg |
| S126D-F | 13 | gcacgttgctaatcttagtttaggagatccttcgccaagtg |
| S126D-R | 14 | cacttggcgaaggatctcctaaactaagattagcaacgtgc |
| S126E-F | 15 | catgcacgttgctaatcttagtttaggagaaccttcgccaagtgcc |
| S126E-R | 16 | ggcacttggcgaaggttctcctaaactaagattagcaacgtgcatg |
| S126F-F | 17 | cacgttgctaatcttagtttaggattcccttcgccaagtgc |
| S126F-R | 18 | gcacttggcgaagggaatcctaaactaagattagcaacgtg |
| S126G-F | 19 | catgcacgttgctaatcttagtttaggaggcccttcgccaagtgcc |
| S126G-R | 20 | ggcacttggcgaagggcctcctaaactaagattagcaacgtgcatg |
| S126H-F | 21 | catgcacgttgctaatcttagtttaggacaccttcgccaagtgcc |
| S126H-R | 22 | ggcacttggcgaagggtgtcctaaactaagattagcaacgtgcatg |

TABLE 10-2-continued

Site specific Primer Sets Used for Creating Mature Region Mutants in p2JH-GCI-P036ci.

| Primer Name | SEQ ID NO: | Primer Sequence (5'-3') |
|---|---|---|
| S126I-F | 23 | catgcacgttgctaatcttagtttaggaatcccttcgccaagtgcc |
| S126I-R | 24 | ggcacttggcgaagggattcctaaactaagattagcaacgtgcatg |
| S126K-F | 25 | Catgcacgttgctaatcttagtttaggaaaaccttcgccaagtgcc |
| S126K-R | 26 | Ggcacttggcgaaggttttcctaaactaagattagcaacgtgcatg |
| S126L-F | 27 | Gcacgttgctaatcttagtttaggacttccttcgccaagtg |
| S126L-R | 28 | Cacttggcgaaggaagtcctaaactaagattagcaacgtgc |
| S126M-F | 29 | Catgcacgttgctaatcttagtttaggaatgccttcgccaagtgcc |
| S126M-R | 30 | Ggcacttggcgaaggcattcctaaactaagattagcaacgtgcatg |
| S126N-F | 31 | Catgcacgttgctaatcttagtttaggaaacccttcgccaagtgcc |
| S126N-R | 32 | Ggcacttggcgaagggtttcctaaactaagattagcaacgtgcatg |
| S126P-F | 33 | Ctaatcttagtttaggacctccttcgccaagtgcc |
| S126P-R | 34 | Ggcacttggcgaaggaggtcctaaactaagattag |
| S126Q-F | 35 | Catgcacgttgctaatcttagtttaggacaaccttcgccaagtgcc |
| S126Q-R | 36 | Ggcacttggcgaaggttgtcctaaactaagattagcaacgtgcatg |
| S126R-F | 37 | Catgcacgttgctaatcttagtttaggaagaccttcgccaagtgcc |
| S126R-R | 38 | Ggcacttggcgaaggtcttcctaaactaagattagcaacgtgcatg |
| S126T-F | 39 | Cacgttgctaatcttagtttaggaacaccttcgccaagtg |
| S126T-R | 40 | Cacttggcgaaggtgttcctaaactaagattagcaacgtg |
| S126V-F | 41 | Gcacgttgctaatcttagtttaggagttccttcgccaagtg |
| S126V-R | 42 | Cacttggcgaaggaactcctaaactaagattagcaacgtgc |
| S126W-F | 43 | Cacgttgctaatcttagtttaggatggccttcgccaagtgc |
| S126W-R | 44 | Gcacttggcgaaggccatcctaaactaagattagcaacgtg |
| S126Y-F | 45 | Cacgttgctaatcttagtttaggataccccttcgccaagtgc |
| S126Y-R | 46 | Gcacttggcgaagggtatcctaaactaagattagcaacgtg |
| S9L-F | 47 | Gcaatcggtaccatggggaattcttagagtacaagccccagc |
| S9L-R | 48 | Gctggggcttgtactctaagaattccccatggtaccgattgc |
| S9G-F | 49 | Aatcggtaccatggggaattggcagagtacaagc |
| S9G-R | 50 | Gcttgtactctgccaattccccatggtaccgatt |
| A106C-F | 51 | Caggctctgtcagctctatttgccaaggattggaatggg |
| A106C-R | 52 | Cccattccaatccttggcaaatagagctgacagagcctg |
| A106I-F | 53 | Ggaacaatggcatgcacgctgctaatcttagtttagg |
| A106I-R | 54 | Cctaaactaagattagcagcgtgcatgccattgttcc |
| A106M-F | 55 | Tcaggctctgtcagctctattatgcaaggattggaatgggcag |
| A106M-R | 56 | Ctgcccattccaatccttgcataatagagctgacagagcctga |
| V119A-F | 57 | Caggctctgtcagctctattatccaaggattggaatggg |
| V119A-R | 58 | Cccattccaatccttggataatagagctgacagagcctg |
| L124F-F | 59 | gcatgcacgttgctaatcttagtttcggatctccttcgc |

TABLE 10-2-continued

Site specific Primer Sets Used for Creating Mature Region Mutants in p2JH-GCI-P036ci.

| Primer Name | SEQ ID NO: | Primer Sequence (5'-3') |
|---|---|---|
| L124F-R | 60 | Gcgaaggagatccgaaactaagattagcaacgtgcatgc |
| L124N-F | 61 | Acaatggcatgcacgttgctaatcttagtaacggatctccttcgcca |
| L124N-R | 62 | Tggcgaaggagatccgttactaagattagcaacgtgcatgccattgt |
| G125S-F | 63 | Atggcatgcacgttgctaatcttagtttatcttctccttcgccaagt |
| G125S-R | 64 | Acttggcgaaggagaagataaactaagattagcaacgtgcatgccat |
| N167H-F | 65 | Cggcccgttatgcgcacgctatggcagtc |
| N167H-R | 66 | Gactgccatagcgtgcgcataacgggccg |
| V28A-F | 67 | Gttctggtgtaaaagctgctgtccttgataccggtatttccact |
| V28A-R | 68 | Caagaccacattttcgacgacaggaactatggccataaaggtga |
| V30A-F | 69 | Gttctggtgtaaaagttgctgctcttgataccggtatttccact |
| V30A-R | 70 | Agtggaaataccggtatcaagagcagcaacttttacaccagaac |
| N60S-F | 71 | Ccatccactcaagatggctctggacatggcactcatgt |
| N60S-R | 72 | Acatgagtgccatgtccagagccatcttgagtggatgg |
| V91T-F | 73 | Ccaagcgcagaactatacgctacaaaagtattaggagcaagcggt |
| V91T-R | 74 | Accgcttgctcctaatacttttgtagcgtatagttctgcgcttgg |
| L94A-F | 75 | Aagcgcagaactatacgctgttaaagtagctggagcaagcggttca |
| L94A-R | 76 | Tgaaccgcttgctccagctactttaacagcgtatagttctgcgctt |
| G95P-F | 77 | Gcgcagaactatacgctgttaaagtattacctgcaagcggttcaggc |
| G95P-R | 78 | Gcctgaaccgcttgcaggtaatactttaacagcgtatagttctgcgc |
| I105F-F | 79 | Gttcaggctctgtcagctctttcgcccaaggattggaa |
| I105F-R | 80 | Ttccaatccttgggcgaaagagctgacagagcctgaac |
| G113M-F | 81 | Tcaggctctgtcagctctattatgcaaggattggaatgggcag |
| G113M-R | 82 | Ctgcccattccaatccttgcataatagagctgacagagcctga |
| S123A-F | 83 | Catgcacgttgctaatcttgctttaggatctccttcgcca |
| S123A-R | 84 | Tggcgaaggagatcctaaagcaag |
| S130N-F | 85 | Tttaggatctccttcgccaaacgccacacttgagcaagc |
| S130N-R | 86 | Gcttgctcaagtgtggcgtttggcgaaggagatcctaaa |
| V145I-F | 87 | Cgcgacttctagaggcatccttgttgtagcggcct |
| V145I-R | 88 | Aggccgctacaacaaggatgcctctagaagtcgcg |
| F183G-F | 89 | Acaacaaccgcgccagcggctcacagtatggcgcagg |
| F183G-R | 90 | Cctgcgccatactgtgagccgctggcgcggttgttgt |
| I192L-F | 91 | Cgcagggcttgaccttgtcgcaccagg |
| I192L-R | 92 | Cctggtgcgacaaggtcaagccctgcg |
| T218N-F | 93 | Aaacggtacatcaatggctaaccctcatgttgcaggtgcg |

TABLE 10-2-continued

Site specific Primer Sets Used for Creating Mature
Region Mutants in p2JH-GCI-P036ci.

| Primer Name | SEQ ID NO: | Primer Sequence (5'-3') |
|---|---|---|
| T218N-R | 94 | Cgcacctgcaacatgagggttagccattgatgtaccgttt |
| A222G-F | 95 | Gctactcctcatgttggcggtgcggctgcactt |
| A222G-R | 96 | Aagtgcagccgcaccgccaacatgaggagtagc |

Five transformants per mutation were selected and screened for the presence of insert using PCR beads (GE/Amersham) as per manufacturer's instructions. Sequences of insertion PCR primers were as follows: forward primer=ISH-PCR-GCI-P036-5832F 5'-acaaataggg gttc-cgcgca-3' (SEQ ID NO: 97); and reverse primer=ISH-PCR-GCI-P036-1902R 5'-cgcaagaattg attggctcc-3' (SEQ ID NO: 98). Cycling conditions were as follows: hot start at 95° C. for 2 min, 40 cycles of denaturation at 95° C. for 1 min, primer annealing at 53° C. for 1 min, elongation at 72° C. for 1 min, then hold at 4° C. Five microliters of PCR product was analyzed by agarose gel electrophoresis. PCR products of the expected fragment size of ~2 Kb were purified and sequenced. Clones with verified mutations were expanded for plasmid preps using QiaPrep Spin Miniprep Kit (Qiagen).

Purified plasmids were sequenced and 5 μl of plasmid was transformed into competent B. subtilis cells (phenotype: ΔaprE, ΔnprE, oppA, ΔspoIIE, degUHy32, ΔamyE::[xylR, pxylA-comK]), incubated for one hour in 37° C. shaker (250 rpm), then plated on LA+1.6 Skim Milk+5 ppm chloramphenicol and incubated overnight at 37° C. Two transformants (per mutation) that showed halos were picked and subcultured on LA+1.6 Skim Milk+25 ppm chloramphenicol to select for additional gene amplification.

Single colonies, from fresh plates (post-amplification), were picked and transferred into 5 ml of LB broth+25 ppm chloramphenicol and incubated in 37° C. shaker (250 rpm) for 6-7 hours to generate a pre-culture. Frozen stocks were made by mixing 8000 of pre-culture aliquots with 4000 of 50% (v/v) sterile glycerol. Shake flasks containing 25 mL of semi-defined medium (phosphate-buffered soymeal and urea based medium, containing salts) were inoculated with 1 mL of pre-culture, and incubated in 37° C. shaker (250 rpm) for 48 hours. Samples were taken at 18, 24, 42 and 48 hours for analysis by SDS-PAGE, AAPF, EglinC inhibition assay, and BMI wash performance assay as described in Example 1 above.

Protein Analysis

Analysis of protein expression in shake flasks was performed by SDS-PAGE, with titers based on a standard curve of purified GCI-P036 of known protein concentration. For SDS-PAGE, 10 μL of 2M HCl was added to 450 of culture supernatant and incubated on ice for 10 min. Then, 50 μL of 2× glycine sample buffer was added to each sample and 10 μL of each sample mixture was loaded on a 10 Bis-Tris gel and run in MES buffer at 200V for 30 min. The gel was washed three times in deionized water, then stained with SimplyBlue Safe stain (Invitrogen) for one hour and destained with deionized water overnight.

Protein expression was also monitored by an eglin c inhibition assay. In the case of certain mutations, it was inferred that the mutation led to a reduction of protease activity against the synthetic substrate suc-AAPF-pNA, when an estimation of the quantity of the variant by SDS PAGE was not comparable to activity of the variant on the suc-AAPF-pNA substrate. For this reason, eglin c binding was also measured to eliminate potential bias of the AAPF assay.

Relative specific activities of variants were calculated by dividing the specific activity of the variants by the specific activity of the wildtype control. Corrected (normalized) protease titers were obtained by dividing titers from AAPF activity assay by relative specific activity of the variant obtained by the eglin C inhibition assay. Normalized protein titers for multiple variant proteases are shown in FIG. 4.

Analysis of variant performance by BMI wash assay was conducted as described in Example 1, except one microswatch was used per well and the variant proteases were dosed at 0.5 ppm and incubated at room temperature. The EMPA 116 BMI microswatches were used as a stain source, and ECE non-phosphate reference detergent powder was used for testing cleaning performance under alkaline conditions. The buffer solution was made in 2 mM sodium carbonate ($Na_2CO_3$, MW=105.99 g/mol, anhydrous) at pH 10.5. The final concentrations of buffer components were as follows: 6 gpg water hardness, 6.16 g/L ECE-2 non-phosphate powder detergent, 1.6 g/L sodium perborate tetrahydrate (PB4), and 0.24 g/L tetraacetyl ethylene diamine (TAED). Enzyme dilutions based on corrected titers from EglinC inhibition analysis were performed in 10 mM NaCl+ 0.005 TWEEN®80 buffer. The results for the BMI assay are shown in FIG. 5. Several variant proteases (G95P, S126M, Q, and R, S9L and A106C with GCI-P036 numbering=G97P, S128M, Q, and R, S9L and A108C with BPN' numbering) showed increased production in liquid cultures while maintaining wash performance comparable to the GCI-P036 reference protease.

Example 11

Generation of Charge Ladder Variants of GCI-P036

This Example describes the production of GCI-P036 charge ladder and combinatorial charge libraries. Testing the variant proteases of the present invention was done in comparison with a reference protease(s) to determine a performance index (PI) for the variant proteases.

Charge Ladders

Multiple protein variants spanning a range of physical properties of interest are selected from existing libraries or are generated by site-directed mutagenesis techniques as known in the art (See e.g., U.S. application Ser. Nos. 10/576,331, 11/581,102, and 11/583,334). This defined set of probe proteins is then assayed in a test of interest. Exemplary protease charge ladder variants are shown in the following Tables and assayed as described herein. In these tables, the charge change is relative to the reference protease, which in this example is the wild-type protease.

TABLE 11-1

GCI-P036 Charge Ladder Variants

| GCI-P036 Variant (GG36 numbering) | GCI-P036 Variant (BPN' numbering) | Δ Charge |
|---|---|---|
| S85D-Q107D-S182D-N242D | S87D-Q109D-S188D-N248D | −4 |
| S85D-Q107D-S182D | S87D-Q109D-S188D | −3 |
| S85D-Q107D | S87D-Q109D | −2 |
| Q107D | Q109D | −1 |
| (GG36) | (GG36) | 0 |
| Q107R | Q109R | +1 |
| S85R-Q107R | S87R-Q109R | +2 |
| S85R-Q107R-S182R | S87R-Q109R-S188R | +3 |
| S85R-Q107R-S182R-N242R | S87R-Q109R-S188R-N248R | +4 |

Generation of GCI-P036 Combinatorial Charge Libraries (CCL)

The pAC-GG36ci plasmid containing the codon-improved gene was used to generate CCL by DNA 2.0. *Bacillus subtilis* strain (genotype: ΔaprE, ΔnprE, ΔspoIIE, amyE::xylRPxylAcomK-phleo) was used for transformations. In addition, positional libraries at each of the four sites in GCI-P036 protease that are shown in Table 10-2 were produced. Variants were supplied as glycerol stocks in 96-well plates.

The GCI-P036 CCL was designed by identifying four well-distributed, surface-exposed, uncharged polar amino-acid residues outside the active site. These residues are Ser-85, Gln-107, Ser-182, and Asn-242 (residues 87, 109, 188, and 248 in BPN' numbering). An 81-member combinatorial library (G-1 to G-81) was created by making all combinations of three possibilities at each site: wild-type, arginine, or aspartic acid.

TABLE 11-2

GCI-P036 CCL Variants

| Variant # | S 85 | Q 107 | S 182 | N 242 | Δ Charge |
|---|---|---|---|---|---|
| G-01 | — | — | — | — | 0 |
| G-02 | — | — | — | D | −1 |
| G-03 | — | — | — | R | +1 |
| G-04 | — | — | D | — | −1 |
| G-05 | — | — | D | D | −2 |
| G-06 | — | — | D | R | 0 |
| G-07 | — | — | R | — | +1 |
| G-08 | — | — | R | D | 0 |
| G-09 | — | — | R | R | +2 |
| G-10 | — | D | — | — | −1 |
| G-11 | — | D | — | D | −2 |
| G-12 | — | D | — | R | 0 |
| G-13 | — | D | D | — | −2 |
| G-14 | — | D | D | D | −3 |
| G-15 | — | D | D | R | −1 |
| G-16 | — | D | R | — | 0 |
| G-17 | — | D | R | D | −1 |
| G-18 | — | D | R | R | +1 |
| G-19 | — | R | — | — | +1 |
| G-20 | — | R | — | D | 0 |
| G-21 | — | R | — | R | +2 |
| G-22 | — | R | D | — | 0 |
| G-23 | — | R | D | D | −1 |
| G-24 | — | R | D | R | +1 |
| G-25 | — | R | R | — | +2 |
| G-26 | — | R | R | D | +1 |
| G-27 | — | R | R | R | +3 |
| G-28 | D | — | — | — | −1 |
| G-29 | D | — | — | D | −2 |
| G-30 | D | — | — | R | 0 |
| G-31 | D | — | D | — | −2 |
| G-32 | D | — | D | D | −3 |
| G-33 | D | — | D | R | −1 |
| G-34 | D | — | R | — | 0 |
| G-35 | D | — | R | D | −1 |
| G-36 | D | — | R | R | +1 |
| G-37 | D | D | — | — | −2 |
| G-38 | D | D | — | D | −3 |
| G-39 | D | D | — | R | −1 |
| G-40 | D | D | D | — | −3 |
| G-41 | D | D | D | D | −4 |
| G-42 | D | D | D | R | −2 |
| G-43 | D | D | R | — | −1 |
| G-44 | D | D | R | D | −2 |
| G-45 | D | D | R | R | 0 |
| G-46 | D | R | — | — | 0 |
| G-47 | D | R | — | D | −1 |
| G-48 | D | R | — | R | +1 |
| G-49 | D | R | D | — | −1 |
| G-50 | D | R | D | D | −2 |
| G-51 | D | R | D | R | 0 |
| G-52 | D | R | R | — | +1 |
| G-53 | D | R | R | D | 0 |
| G-54 | D | R | R | R | +2 |
| G-55 | R | — | — | — | +1 |
| G-56 | R | — | — | D | 0 |
| G-57 | R | — | — | R | +2 |
| G-58 | R | — | D | — | 0 |
| G-59 | R | — | D | D | −1 |
| G-60 | R | — | D | R | +1 |
| G-61 | R | — | R | — | +2 |
| G-62 | R | — | R | D | +1 |
| G-63 | R | — | R | R | +3 |
| G-64 | R | D | — | — | 0 |
| G-65 | R | D | — | D | −1 |
| G-66 | R | D | — | R | +1 |
| G-67 | R | D | D | — | −1 |
| G-68 | R | D | D | D | −2 |
| G-69 | R | D | D | R | 0 |
| G-70 | R | D | R | — | +1 |
| G-71 | R | D | R | D | 0 |
| G-72 | R | D | R | R | +2 |
| G-73 | R | R | — | — | +2 |
| G-74 | R | R | — | D | +1 |
| G-75 | R | R | — | R | +3 |
| G-76 | R | R | D | — | +1 |
| G-77 | R | R | D | D | 0 |
| G-78 | R | R | D | R | +2 |
| G-79 | R | R | R | — | +3 |
| G-80 | R | R | R | D | +2 |
| G-81 | R | R | R | R | +4 |

Example 12

Stain Removal Performance of GCI-P036 Charge Variants

In this Example, results for variants of GCI-P036 tested in blood, milk, ink (BMI) microswatch and baked egg yolk microswatch assays in detergents representing various market geographies (e.g., differing pH, temperature, and/or water hardness), in both laundry and automatic dishwashing (ADW) applications are provided. Market geographies represented in the Tables of this example include NA (North America), WE (Western Europe), and WE (ADW), as described in Table 1-1. In Table 12-1, results for dish (i.e., "PI Dish") are for assays conducted using the baked egg microtiter assay in CALGONIT® (Reckitt-Benckiser), at 40° C. 12 gpg, pH 10, as described in Example 1.

TABLE 12-1

Evaluation of Stain Removal Performance of GCI-P036 Charge Variants

| GCI-P036 Variants | Net Charge | PI NA Laundry | PI WE Laundry | PI Dish |
|---|---|---|---|---|
| GCI-P036 | 0 | 1.000 | 1.000 | 1.000 |
| G-2 | −1 | 0.950 | 0.939 | 1.450 |
| G-3 | 1 | 0.578 | 0.759 | 1.231 |
| G-4 | −1 | 1.219 | 1.539 | 1.467 |
| G-5 | −2 | 1.261 | 1.194 | 1.508 |
| G-6 | 0 | 0.936 | 0.999 | 1.563 |
| G-7 | 1 | 0.568 | 0.834 | 0.712 |
| G-8 | 0 | 0.043 | 0.151 | −0.033 |
| G-9 | 2 | 0.350 | 0.601 | 0.708 |
| G-10 | −1 | 1.266 | 1.089 | 1.022 |
| G-11 | −2 | 1.280 | 1.209 | 0.788 |
| G-12 | 0 | 0.810 | 1.074 | 0.977 |
| G-13 | −2 | 1.317 | 1.411 | 1.300 |
| G-14 | −3 | 0.080 | 0.144 | −0.007 |
| G-15 | −1 | 0.917 | 1.254 | 1.393 |
| G-16 | 0 | 0.750 | 1.081 | 0.742 |
| G-17 | −1 | 0.815 | 0.894 | 0.909 |
| G-18 | 1 | 0.675 | 0.931 | 0.867 |
| G-19 | 1 | 0.713 | 0.856 | 1.310 |
| G-20 | 0 | 0.071 | 0.129 | −0.015 |
| G-21 | 2 | 0.434 | 0.834 | 1.098 |
| G-22 | 0 | 0.782 | 1.014 | 1.447 |
| G-23 | −1 | 0.964 | 0.939 | 1.396 |
| G-24 | 1 | 0.466 | 0.729 | 1.368 |
| G-25 | 2 | 0.322 | 0.744 | 0.638 |
| G-26 | 1 | 0.517 | 0.984 | 0.694 |
| G-27 | 3 | 0.303 | 1.074 | 0.971 |
| G-28 | −1 | 1.126 | 1.141 | 1.023 |
| G-29 | −2 | 1.126 | 0.991 | 1.037 |
| G-30 | 0 | 0.945 | 1.149 | 1.006 |
| G-31 | −2 | 1.331 | 1.149 | 1.412 |
| G-32 | −3 | 1.345 | 0.999 | 1.303 |
| G-33 | −1 | 0.950 | 1.036 | 1.420 |
| G-34 | 0 | 0.671 | 0.999 | 0.673 |
| G-35 | −1 | 0.694 | 1.021 | 1.026 |
| G-36 | 1 | 0.415 | 0.774 | 0.704 |
| G-37 | −2 | 1.410 | 1.554 | −0.011 |
| G-38 | −3 | 0.457 | 0.759 | 1.081 |
| G-39 | −1 | 0.936 | 1.186 | 0.940 |
| G-40 | −3 | 0.043 | 0.106 | −0.006 |
| G-41 | −4 | 1.163 | 0.496 | 0.988 |
| G-42 | −2 | 1.359 | 1.276 | 1.165 |
| G-43 | −1 | 0.782 | 1.119 | 0.740 |
| G-44 | −2 | 0.926 | 1.051 | 0.748 |
| G-45 | 0 | 0.503 | 0.961 | 0.619 |
| G-46 | 0 | 0.759 | 0.916 | 1.035 |
| G-47 | −1 | 0.871 | 1.051 | 1.057 |
| G-48 | 1 | 0.452 | 0.864 | 1.060 |
| G-49 | −1 | 0.885 | 0.909 | 1.239 |
| G-50 | −2 | 0.912 | 0.909 | 1.613 |
| G-51 | 0 | 0.638 | 1.006 | 1.723 |
| G-52 | 1 | 0.396 | 0.909 | 0.820 |
| G-53 | 0 | 0.568 | 0.909 | 0.806 |
| G-54 | 2 | 0.345 | 0.766 | 0.641 |
| G-55 | 1 | 0.689 | 1.036 | 1.230 |
| G-56 | 0 | 0.675 | 1.134 | 0.818 |
| G-57 | 2 | 0.452 | 0.766 | 0.922 |
| G-58 | 0 | 1.024 | 1.216 | 1.444 |
| G-59 | −1 | 1.131 | 1.306 | 1.473 |
| G-60 | 1 | 0.699 | 0.946 | 1.520 |
| G-61 | 2 | 0.457 | 0.886 | 0.680 |
| G-62 | 1 | 0.759 | 1.059 | 1.169 |
| G-63 | 3 | 0.327 | 0.669 | 0.687 |
| G-64 | 0 | 0.847 | 1.119 | 1.001 |
| G-65 | −1 | 0.601 | 0.879 | 1.014 |
| G-66 | 1 | 1.001 | 1.261 | 1.042 |
| G-67 | −1 | 1.196 | 1.411 | 1.489 |
| G-68 | −2 | 1.131 | 1.179 | 1.163 |
| G-69 | 0 | 0.768 | 0.999 | 1.488 |
| G-70 | 1 | 0.647 | 1.809 | 0.229 |
| G-71 | 0 | 0.620 | 1.081 | 0.631 |
| G-72 | 2 | 0.364 | 0.819 | 0.634 |
| G-73 | 2 | 0.387 | 0.729 | 0.997 |
| G-74 | 1 | 0.638 | 0.939 | 1.105 |
| G-75 | 3 | 0.657 | 0.856 | 1.081 |
| G-76 | 1 | 0.071 | 0.136 | −0.018 |
| G-77 | 0 | 0.866 | 0.969 | 1.400 |
| G-78 | 2 | 0.434 | 0.789 | 1.175 |
| G-79 | 3 | 0.327 | 0.789 | 0.874 |
| G-80 | 2 | 0.355 | 0.781 | 0.833 |
| G-81 | 4 | 0.229 | 0.466 | 0.653 |

Example 13

Liquid Laundry Detergent Compositions

In this Example, various formulations for liquid laundry detergent compositions are provided. The following liquid laundry detergent compositions of the present invention are prepared as shown below. In each of these formulations, at least one protease variant provided herein is included at a concentration of from about 0.0001 to about 10 weight percent. In some alternative embodiments, other concentrations will find use, as determined by the formulator, based on their needs.

TABLE 13-1

Liquid Laundry Detergent Compositions

| Compound | I | II | III | IV | V |
|---|---|---|---|---|---|
| LAS | 24.0 | 32.0 | 6.0 | 3.0 | 6.0 |
| NaC$_{16}$-C$_{17}$ HSAS | — | — | — | 5.0 | — |
| C$_{12}$-C$_{15}$ AE$_{1.8}$S | — | — | 8.0 | 7.0 | 5.0 |
| C$_8$-C$_{10}$ propyl dimethyl amine | 2.0 | 2.0 | 2.0 | 2.0 | 1.0 |
| C$_{12}$-C$_{14}$ alkyl dimethyl amine oxide | — | — | — | — | 2.0 |
| C$_{12}$-C$_{15}$ AS | — | — | 17.0 | — | 8.0 |
| CFAA | — | 5.0 | 4.0 | 4.0 | 3.0 |
| C$_{12}$-C$_{14}$ Fatty alcohol ethoxylate | 12.0 | 6.0 | 1.0 | 1.0 | 1.0 |
| C$_{12}$-C$_{18}$ Fatty acid | 3.0 | — | 4.0 | 2.0 | 3.0 |
| Citric acid (anhydrous) | 4.5 | 5.0 | 3.0 | 2.0 | 1.0 |
| DETPMP | — | — | 1.0 | 1.0 | 0.5 |
| Monoethanolamine | 5.0 | 5.0 | 5.0 | 5.0 | 2.0 |
| Sodium hydroxide | — | — | 2.5 | 1.0 | 1.5 |
| 1N HCl aqueous solution | #1 | #1 | — | — | — |

TABLE 13-1-continued

Liquid Laundry Detergent Compositions

| Compound | I | II | III | IV | V |
|---|---|---|---|---|---|
| Propanediol | 12.7 | 14.5 | 13.1 | 10. | 8.0 |
| Ethanol | 1.8 | 2.4 | 4.7 | 5.4 | 1.0 |
| DTPA | 0.5 | 0.4 | 0.3 | 0.4 | 0.5 |
| Pectin Lyase | — | — | — | 0.005 | — |
| Amylase | 0.001 | 0.002 | — | — | — |
| Cellulase | — | — | 0.0002 | — | 0.0001 |
| Lipase | 0.1 | — | 0.1 | — | 0.1 |
| NprE (optional) | 0.05 | 0.3 | — | 0.5 | 0.2 |
| PMN | — | — | 0.08 | — | — |
| Protease A (optional) | — | — | — | — | 0.1 |
| Aldose Oxidase | — | — | 0.3 | — | 0.003 |
| ZnCl2 | 0.1 | 0.05 | 0.05 | 0.05 | 0.02 |
| Ca formate | 0.05 | 0.07 | 0.05 | 0.06 | 0.07 |
| DETBCHD | — | — | 0.02 | 0.01 | — |
| SRP1 | 0.5 | 0.5 | — | 0.3 | 0.3 |
| Boric acid | — | — | — | — | 2.4 |
| Sodium xylene sulfonate | — | — | 3.0 | — | — |
| Sodium cumene sulfonate | — | — | — | 0.3 | 0.5 |
| DC 3225C | 1.0 | 1.0 | 1.0 | 1.0 | 1.0 |
| 2-butyl-octanol | 0.03 | 0.04 | 0.04 | 0.03 | 0.03 |
| Brightener 1 | 0.12 | 0.10 | 0.18 | 0.08 | 0.10 |
| Balance to 100% perfume/dye and/or water | | | | | |

1: Add 1N HCl aq. soln to adjust the neat pH of the formula in the range from about 3 to about 5.

The pH of Examples above 13(I)-(II) is about 5 to about 7, and of 13(III)-(V) is about 7.5 to about 8.5.

Example 14

Hand Dish Liquid Detergent Compositions

In this Example, various hand dish liquid detergent formulations are provided. The following hand dish liquid detergent compositions of the present invention are provided below. In each of these formulations, at least one protease variant provided herein is included at a concentration of from about 0.0001 to about 10 weight percent. In some alternative embodiments, other concentrations will find use, as determined by the formulator, based on their needs.

TABLE 14-1

Hand Dish Liquid Detergent Compositions

| Compound | I | II | III | IV | V | VI |
|---|---|---|---|---|---|---|
| $C_{12}$-$C_{15}$ $AE_{1.8}S$ | 30.0 | 28.0 | 25.0 | — | 15.0 | 10.0 |
| LAS | — | — | — | 5.0 | 15.0 | 12.0 |
| Paraffin Sulfonate | — | — | — | 20.0 | — | — |
| $C_{10}$-$C_{18}$ Alkyl Dimethyl Amine Oxide | 5.0 | 3.0 | 7.0 | — | — | — |
| Betaine | 3.0 | — | 1.0 | 3.0 | 1.0 | — |
| $C_{12}$ poly-OH fatty acid amide | — | — | — | 3.0 | — | 1.0 |
| $C_{14}$ poly-OH fatty acid amide | — | 1.5 | — | — | — | — |
| $C_{11}E_9$ | 2.0 | — | 4.0 | — | — | 20.0 |
| DTPA | — | — | — | — | 0.2 | — |
| Tri-sodium Citrate dihydrate | 0.25 | — | — | 0.7 | — | — |
| Diamine | 1.0 | 5.0 | 7.0 | 1.0 | 5.0 | 7.0 |
| MgCl$_2$ | 0.25 | — | — | 1.0 | — | — |
| nprE (optional) | 0.02 | 0.01 | — | 0.01 | — | 0.05 |
| PMN | — | — | 0.03 | — | 0.02 | — |
| Protease A (optional) | — | 0.01 | — | — | — | — |
| Amylase | 0.001 | — | — | 0.002 | — | 0.001 |
| Aldose Oxidase | 0.03 | — | 0.02 | — | 0.05 | — |
| Sodium Cumene Sulphonate | — | — | — | 2.0 | 1.5 | 3.0 |
| PAAC | 0.01 | 0.01 | 0.02 | — | — | — |
| DETBCHD | — | — | — | 0.01 | 0.02 | 0.01 |
| Balance to 100% perfume/dye and/or water | | | | | | |

The pH of Examples 14(I)-(VI) is about 8 to about 11

Example 15

Liquid Automatic Dishwashing Detergent Compositions

In this Example, various liquid automatic dishwashing detergent formulations are provided. The following hand dish liquid detergent compositions of the present invention are provided below. In each of these formulations, at least one protease variant provided herein is included at a concentration of from about 0.0001 to about 10 weight percent. In some alternative embodiments, other concentrations will find use, as determined by the formulator, based on their needs.

TABLE 15-1

Liquid Automatic Dishwashing Detergent Compositions

| Compound | I | II | III | IV | V |
|---|---|---|---|---|---|
| STPP | 16 | 16 | 18 | 16 | 16 |
| Potassium Sulfate | — | 10 | 8 | — | 10 |

TABLE 15-1-continued

Liquid Automatic Dishwashing Detergent Compositions

| Compound | I | II | III | IV | V |
|---|---|---|---|---|---|
| 1,2 propanediol | 6.0 | 0.5 | 2.0 | 6.0 | 0.5 |
| Boric Acid | — | — | — | 4.0 | 3.0 |
| CaCl$_2$ dihydrate | 0.04 | 0.04 | 0.04 | 0.04 | 0.04 |
| Nonionic | 0.5 | 0.5 | 0.5 | 0.5 | 0.5 |
| nprE (optional) | 0.1 | 0.03 | — | 0.03 | — |
| PMN | — | — | 0.05 | — | 0.06 |
| Protease B (optional) | — | — | — | 0.01 | — |
| Amylase | 0.02 | — | 0.02 | 0.02 | — |
| Aldose Oxidase | — | 0.15 | 0.02 | — | 0.01 |
| Galactose Oxidase | — | — | 0.01 | — | 0.01 |
| PAAC | 0.01 | — | — | 0.01 | — |
| DETBCHD | — | 0.01 | — | — | 0.0132 |
| Balance to 100% perfume/dye and/or water | | | | | |

Example 16

Granular and/or Tablet Laundry Compositions

This Example provides various formulations for granular and/or tablet laundry detergents. The following laundry compositions of present invention, which may be in the form of granules or tablet, are provided below. In each of these formulations, at least one protease variant provided herein is included at a concentration of from about 0.0001 to about 10 weight percent. In some alternative embodiments, other concentrations will find use, as determined by the formulator, based on their needs.

TABLE 16-1

Granular and/or Tablet Laundry Compositions

| Compound | I | II | III | IV | V |
|---|---|---|---|---|---|
| Base Product | | | | | |
| C$_{14}$-C$_{15}$AS or TAS | 8.0 | 5.0 | 3.0 | 3.0 | 3.0 |
| LAS | 8.0 | — | 8.0 | — | 7.0 |
| C$_{12}$-C$_{15}$AE$_3$S | 0.5 | 2.0 | 1.0 | — | — |
| C$_{12}$-C$_{15}$E$_5$ or E$_3$ | 2.0 | — | 5.0 | 2.0 | 2.0 |
| QAS | — | — | — | 1.0 | 1.0 |
| Zeolite A | 20.0 | 18.0 | 11.0 | — | 10.0 |
| SKS-6 (dry add) | — | — | 9.0 | — | — |
| MA/AA | 2.0 | 2.0 | 2.0 | — | — |
| AA | — | — | — | — | 4.0 |
| 3Na Citrate 2H$_2$O | — | 2.0 | — | — | — |
| Citric Acid (Anhydrous) | 2.0 | — | 1.5 | 2.0 | — |
| DTPA | 0.2 | 0.2 | — | — | — |
| EDDS | — | — | 0.5 | 0.1 | — |
| HEDP | — | — | 0.2 | 0.1 | — |
| PB1 | 3.0 | 4.8 | — | — | 4.0 |
| Percarbonate | — | — | 3.8 | 5.2 | — |
| NOBS | 1.9 | — | — | — | — |
| NACA OBS | — | — | 2.0 | — | — |
| TAED | 0.5 | 2.0 | 2.0 | 5.0 | 1.00 |
| BB1 | 0.06 | — | 0.34 | — | 0.14 |
| BB2 | — | 0.14 | — | 0.20 | — |
| Anhydrous Na Carbonate | 15.0 | 18.0 | — | 15.0 | 15.0 |
| Sulfate | 5.0 | 12.0 | 5.0 | 17.0 | 3.0 |
| Silicate | — | 1.0 | — | — | 8.0 |
| nprE (optional) | 0.03 | — | 0.1 | 0.06 | — |
| PMN | — | 0.05 | — | — | 0.1 |
| Protease B (optional) | — | 0.01 | — | — | — |
| Protease C (optional) | — | — | — | 0.01 | — |

TABLE 16-1-continued

Granular and/or Tablet Laundry Compositions

| Compound | I | II | III | IV | V |
|---|---|---|---|---|---|
| Lipase | — | 0.008 | — | — | — |
| Amylase | 0.001 | — | — | — | 0.001 |
| Cellulase | — | 0.0014 | — | — | — |
| Pectin Lyase | 0.001 | 0.001 | 0.001 | 0.001 | 0.001 |
| Aldose Oxidase | 0.03 | — | 0.05 | — | — |
| PAAC | — | 0.01 | — | — | 0.05 |
| Balance to 100% Moisture and/or Minors* | | | | | |

*Perfume, dye, brightener/SRP1/Na carboxymethylcellulose/photobleach/MgSO$_4$/PVPVI/suds suppressor/high molecular PEG/clay.

Example 17

Liquid Laundry Detergents

This Example provides various formulations for liquid laundry detergents. The following liquid laundry detergent formulations of the present invention are provided below. In each of these formulations, at least one protease variant provided herein is included at a concentration of from about 0.0001 to about 10 weight percent. In some alternative embodiments, other concentrations will find use, as determined by the formulator, based on their needs.

TABLE 17-1

Liquid Laundry Detergents

| Compound | I | I | II | III | IV | V |
|---|---|---|---|---|---|---|
| LAS | 11.5 | 11.5 | 9.0 | — | 4.0 | — |
| C$_{12}$-C$_{15}$AE$_{2.85}$S | — | — | 3.0 | 18.0 | — | 16.0 |
| C$_{14}$-C$_{15}$E$_{2.5}$ S | 11.5 | 11.5 | 3.0 | — | 16.0 | — |
| C$_{12}$-C$_{13}$E$_9$ | — | — | 3.0 | 2.0 | 2.0 | 1.0 |
| C$_{12}$-C$_{13}$E$_7$ | 3.2 | 3.2 | — | — | — | — |
| CFAA | — | — | — | 5.0 | — | 3.0 |
| TPKFA | 2.0 | 2.0 | — | 2.0 | 0.5 | 2.0 |
| Citric Acid (Anhydrous) | 3.2 | 3.2 | 0.5 | 1.2 | 2.0 | 1.2 |
| Ca formate | 0.1 | 0.1 | 0.06 | 0.1 | — | — |
| Na formate | 0.5 | 0.5 | 0.06 | 0.1 | 0.05 | 0.05 |
| ZnCl2 | 0.1 | 0.05 | 0.06 | 0.03 | 0.05 | 0.05 |
| Na Culmene Sulfonate | 4.0 | 4.0 | 1.0 | 3.0 | 1.2 | — |
| Borate | 0.6 | 0.6 | 1.5 | — | — | — |
| Na Hydroxide | 6.0 | 6.0 | 2.0 | 3.5 | 4.0 | 3.0 |
| Ethanol | 2.0 | 2.0 | 1.0 | 4.0 | 4.0 | 3.0 |
| 1,2 Propanediol | 3.0 | 3.0 | 2.0 | 8.0 | 8.0 | 5.0 |
| Monoethanolamine | 3.0 | 3.0 | 1.5 | 1.0 | 2.5 | 1.0 |
| TEPAE | 2.0 | 2.0 | — | 1.0 | 1.0 | 1.0 |
| nprE (optional) | 0.03 | 0.05 | — | 0.03 | — | 0.02 |
| PMN | — | — | 0.01 | — | 0.08 | — |
| Protease A (optional) | — | — | 0.01 | — | — | — |
| Lipase | — | — | — | 0.002 | — | — |
| Amylase | — | — | — | — | 0.002 | — |
| Cellulase | — | — | — | — | — | 0.0001 |
| Pectin Lyase | 0.005 | 0.005 | — | — | — | — |
| Aldose Oxidase | 0.05 | — | — | 0.05 | — | 0.02 |
| Galactose oxidase | — | 0.04 | — | — | — | — |
| PAAC | 0.03 | 0.03 | 0.02 | — | — | — |
| DETBCHD | — | — | — | 0.02 | 0.01 | — |
| SRP 1 | 0.2 | 0.2 | — | 0.1 | — | — |
| DTPA | — | — | — | 0.3 | — | — |

TABLE 17-1-continued

Liquid Laundry Detergents

| Compound | I | I | II | III | IV | V |
|---|---|---|---|---|---|---|
| PVNO | — | — | — | 0.3 | — | 0.2 |
| Brightener 1 | 0.2 | 0.2 | 0.07 | 0.1 | — | — |
| Silicone antifoam | 0.04 | 0.04 | 0.02 | 0.1 | 0.1 | 0.1 |
| Balance to 100% perfume/dye and/or water | | | | | | |

Example 18

High Density Dishwashing Detergents

This Example provides various formulations for high density dishwashing detergents. The following compact high density dishwashing detergents of the present invention are provided below. In each of these formulations, at least one protease variant provided herein is included at a concentration of from about 0.0001 to about 10 weight percent. In some alternative embodiments, other concentrations will find use, as determined by the formulator, based on their needs.

TABLE 18-1

High Density Dishwashing Detergents

| Compound | I | II | III | IV | V | VI |
|---|---|---|---|---|---|---|
| STPP | — | 45.0 | 45.0 | — | — | 40.0 |
| 3Na Citrate 2H$_2$O | 17.0 | — | — | 50.0 | 40.2 | — |
| Na Carbonate | 17.5 | 14.0 | 20.0 | — | 8.0 | 33.6 |
| Bicarbonate | — | — | — | 26.0 | — | — |
| Silicate | 15.0 | 15.0 | 8.0 | — | 25.0 | 3.6 |
| Metasilicate | 2.5 | 4.5 | 4.5 | — | — | — |
| PB1 | — | — | 4.5 | — | — | — |
| PB4 | — | — | — | 5.0 | — | — |
| Percarbonate | — | — | — | — | — | 4.8 |

TABLE 18-1-continued

High Density Dishwashing Detergents

| Compound | I | II | III | IV | V | VI |
|---|---|---|---|---|---|---|
| BB1 | — | 0.1 | 0.1 | — | 0.5 | — |
| BB2 | 0.2 | 0.05 | — | 0.1 | — | 0.6 |
| Nonionic | 2.0 | 1.5 | 1.5 | 3.0 | 1.9 | 5.9 |
| HEDP | 1.0 | — | — | — | — | — |
| DETPMP | 0.6 | — | — | — | — | — |
| PAAC | 0.03 | 0.05 | 0.02 | — | — | — |
| Paraffin | 0.5 | 0.4 | 0.4 | 0.6 | — | — |
| nprE (optional) | 0.072 | 0.053 | — | 0.026 | — | 0.01 |
| PMN | — | — | 0.053 | — | 0.059 | — |
| Protease B (optional) | — | — | — | — | — | 0.01 |
| Amylase | 0.012 | — | 0.012 | — | 0.021 | 0.006 |
| Lipase | — | 0.001 | — | 0.005 | — | — |
| Pectin Lyase | 0.001 | 0.001 | 0.001 | — | — | — |
| Aldose Oxidase | 0.05 | 0.05 | 0.03 | 0.01 | 0.02 | 0.01 |
| BTA | 0.3 | 0.2 | 0.2 | 0.3 | 0.3 | 0.3 |
| Poly-carboxylate | 6.0 | — | — | — | 4.0 | 0.9 |
| Perfume | 0.2 | 0.1 | 0.1 | 0.2 | 0.2 | 0.2 |
| Balance to 100% Moisture and/or Minors* | | | | | | |

*Brightener/dye/SRP1/Na carboxymethylcellulose/photobleach/MgSO$_4$/PVPVI/suds suppressor/high molecular PEG/clay.

The pH of Examples 18(I) through (VI) is from about 9.6 to about 11.3.

Example 19

Tablet Detergent Compositions

This Example provides various tablet detergent formulations. The following tablet detergent compositions of the present invention are prepared by compression of a granular dishwashing detergent composition at a pressure of 13 KN/cm$^2$ using a standard 12 head rotary press. In each of these formulations, at least one protease variant provided herein is included at a concentration of from about 0.0001 to about 10 weight percent. In some alternative embodiments, other concentrations will find use, as determined by the formulator, based on their needs.

TABLE 19-1

Tablet Detergent Compositions

| Compound | I | II | III | IV | V | VI | VII | VIII |
|---|---|---|---|---|---|---|---|---|
| STPP | — | 48.8 | 44.7 | 38.2 | — | 42.4 | 46.1 | 46.0 |
| 3Na Citrate 2H$_2$O | 20.0 | — | — | — | 35.9 | — | — | — |
| Na Carbonate | 20.0 | 5.0 | 14.0 | 15.4 | 8.0 | 23.0 | 20.0 | — |
| Silicate | 15.0 | 14.8 | 15.0 | 12.6 | 23.4 | 2.9 | 4.3 | 4.2 |
| Lipase | 0.001 | — | 0.01 | — | 0.02 | — | — | — |
| Protease B (optional) | 0.01 | — | — | — | — | — | — | — |
| Protease C (optional) | — | — | — | — | — | 0.01 | — | — |
| nprE (optional) | 0.01 | 0.08 | — | 0.04 | — | 0.023 | — | 0.05 |
| PMN | — | — | 0.05 | — | 0.052 | — | 0.023 | — |
| Amylase | 0.012 | 0.012 | 0.012 | — | 0.015 | — | 0.017 | 0.002 |
| Pectin Lyase | 0.005 | — | — | 0.002 | — | — | — | — |
| Aldose Oxidase | — | 0.03 | — | 0.02 | 0.02 | — | 0.03 | — |
| PB1 | — | — | 3.8 | — | 7.8 | — | — | 4.5 |
| Percarbonate | 6.0 | — | — | 6.0 | — | 5.0 | — | — |
| BB1 | 0.2 | — | 0.5 | — | 0.3 | 0.2 | — | — |
| BB2 | — | 0.2 | — | 0.5 | — | — | 0.1 | 0.2 |
| Nonionic | 1.5 | 2.0 | 2.0 | 2.2 | 1.0 | 4.2 | 4.0 | 6.5 |
| PAAC | 0.01 | 0.01 | 0.02 | — | — | — | — | — |
| DETBCHD | — | — | — | 0.02 | 0.02 | — | — | — |

TABLE 19-1-continued

Tablet Detergent Compositions

| Compound | I | II | III | IV | V | VI | VII | VIII |
|---|---|---|---|---|---|---|---|---|
| TAED | — | — | — | — | — | 2.1 | — | 1.6 |
| HEDP | 1.0 | — | — | 0.9 | — | 0.4 | 0.2 | — |
| DETPMP | 0.7 | — | — | — | — | — | — | — |
| Paraffin | 0.4 | 0.5 | 0.5 | 0.5 | — | — | 0.5 | — |
| BTA | 0.2 | 0.3 | 0.3 | 0.3 | 0.3 | 0.3 | 0.3 | — |
| Polycarboxylate | 4.0 | — | — | — | 4.9 | 0.6 | 0.8 | — |
| PEG 400-30,000 | — | — | — | — | — | 2.0 | — | 2.0 |
| Glycerol | — | — | — | — | — | 0.4 | — | 0.5 |
| Perfume | — | — | — | 0.05 | 0.2 | 0.2 | 0.2 | 0.2 |
| Balance to 100% Moisture and/or Minors* | | | | | | | | |

*Brightener/SRP1/Na carboxymethylcellulose/photobleach/MgSO$_4$/PVPVI/suds suppressor/high molecular PEG/clay.

The pH of Examples 19(I) through 19(VII) is from about 10 to about 11.5; pH of 19(VIII) is from 8-10. The tablet weight of Examples 19(I) through 19(VIII) is from about 20 grams to about 30 grams.

Example 20

Liquid Hard Surface Cleaning Detergents

This Example provides various formulations for liquid hard surface cleaning detergents. The following liquid hard surface cleaning detergent compositions of the present invention are provided below. In each of these formulations, at least one protease variant provided herein is included at a concentration of from about 0.0001 to about 10 weight percent. In some alternative embodiments, other concentrations will find use, as determined by the formulator, based on their needs.

TABLE 20-1

Liquid Hard Surface Cleaning Detergents

| Compound | I | II | III | IV | V | VI | VII |
|---|---|---|---|---|---|---|---|
| C$_9$-C$_{11}$E$_5$ | 2.4 | 1.9 | 2.5 | 2.5 | 2.5 | 2.4 | 2.5 |
| C$_{12}$-C$_{14}$E$_5$ | 3.6 | 2.9 | 2.5 | 2.5 | 2.5 | 3.6 | 2.5 |
| C$_7$-C$_9$E$_6$ | — | — | — | — | 8.0 | — | — |
| C$_{12}$-C$_{14}$E$_{21}$ | 1.0 | 0.8 | 4.0 | 2.0 | 2.0 | 1.0 | 2.0 |
| LAS | — | — | — | 0.8 | 0.8 | — | 0.8 |
| Sodium culmene sulfonate | 1.5 | 2.6 | — | 1.5 | 1.5 | 1.5 | 1.5 |
| Isachem ® AS | 0.6 | 0.6 | — | — | — | 0.6 | — |
| Na$_2$CO$_3$ | 0.6 | 0.13 | 0.6 | 0.1 | 0.2 | 0.6 | 0.2 |
| 3Na Citrate 2H$_2$O | 0.5 | 0.56 | 0.5 | 0.6 | 0.75 | 0.5 | 0.75 |
| NaOH | 0.3 | 0.33 | 0.3 | 0.3 | 0.5 | 0.3 | 0.5 |
| Fatty Acid | 0.6 | 0.13 | 0.6 | 0.1 | 0.4 | 0.6 | 0.4 |
| 2-butyl octanol | 0.3 | 0.3 | — | 0.3 | 0.3 | 0.3 | 0.3 |
| PEG DME-2000 ® | 0.4 | — | 0.3 | 0.35 | 0.5 | — | — |
| PVP | 0.3 | 0.4 | 0.6 | 0.3 | 0.5 | — | — |
| MME PEG (2000) ® | — | — | — | — | — | 0.5 | 0.5 |
| Jeffamine ® ED-2001 | — | 0.4 | — | — | 0.5 | — | — |
| PAAC | — | — | — | 0.03 | 0.03 | 0.03 | — |
| DETBCHD | 0.03 | 0.05 | 0.05 | — | — | — | — |
| nprE (optional) | 0.07 | — | 0.08 | 0.03 | — | 0.01 | 0.04 |
| PMN | — | 0.05 | — | — | 0.06 | — | — |
| Protease B (optional) | — | — | — | — | — | 0.01 | — |
| Amylase | 0.12 | 0.01 | 0.01 | — | 0.02 | — | 0.01 |
| Lipase | — | 0.001 | — | 0.005 | — | 0.005 | — |
| Pectin Lyase | 0.001 | — | 0.001 | — | — | — | 0.002 |
| ZnCl2 | 0.02 | 0.01 | 0.03 | 0.05 | 0.1 | 0.05 | 0.02 |
| Calcium Formate | 0.03 | 0.03 | 0.01 | — | — | — | — |
| PB1 | — | 4.6 | — | 3.8 | — | — | — |
| Aldose Oxidase | 0.05 | — | 0.03 | — | 0.02 | 0.02 | 0.05 |
| Balance to 100% perfume/dye and/or water | | | | | | | |

The pH of Examples 20(I) through (VII) is from about 7.4 to about 9.5.

We claim:

1. An isolated subtilisin variant of a *Bacillus* subtilisin, wherein said subtilisin variant is a mature form having proteolytic activity and at least 70% sequence identity to SEQ ID NO:2, and, wherein said variant comprises a combination of substitutions selected from: S87N/G118V/S128L/P129Q/S130A/S24W/S101L/Q109K, S87N/G118V/S128L/P129Q/S130A/N18K/G97P/S101L/Q109R/N185R/A215R, S87N/G118V/S128L/P129Q/S130A/I72V/Q109R/S164I, S87N/G118V/S128L/P129Q/S130A/S101Y/Q109R/S188D/N248R, S87N/G118V/S128L/P129Q/S130A/N18K/G97P/S101Y/Q109L/N185R/A215R, S87R/G118R/S128L/P129Q/S130A/S101K/S188D/N248R, S87N/G118V/S128L/P129Q/S130A/S24W/S101L/Q109L, S87N/G118V/S128L/P129Q/S130A/N18K/G97P/S101Y/Q109R/N185R/A215R, S87N/G118V/S128L/P129Q/S130A/I72V/S101L/Q109R/S164I, S87N/G118V/S128L/P129Q/S130A/S101Y/Q109R/S188D/T213E/N248R, S87R/G118R/S128L/P129Q/S130A/I72V/S164I/S188D/N248R, S 87N/G118V/S 128L/P129Q/S130A/S24W/S101Y/Q109K, S87N/G118V/S128L/P129Q/S130A/N43S/P52V/S 101R/Q109R, S 87N/G118 V/S128L/P129Q/S130A/I72V/S101Y/Q109R/S164I, S87N/G118V/S128L/P129Q/S130A/S101L/Q109L/S188D/N248R, S87N/G118V/S128L/P129Q/S130A/I72V/Q109R/S164I/S188D/N248R, S87N/G118V/S128L/P129Q/S130A/N76D/S101L, S 87N/G118V/S128L/P129Q/S130A/S24W/S101Y/Q109L, S87N/G118V/S128L/P129Q/S130A/N76D/S164I, S87R/G118R/S128L/P129Q/S130A/N76D/S188D/N248R, S87N/G118V/S128L/P129Q/S130A/S101Y/Q109L/S188D/N248R, S87N/G118V/S128L/P129Q/S130A/N76D/S101M, S87N/G118V/S128L/P129Q/S130A/N18K/N76D/G97P/N185R/A215R, S87N/G118V/S128L/P129Q/S130A/I72V/S101L/S164I, S87R/G118R/S128L/P129Q/S130A/S101L/S188D/N248R, S87N/G118 V/S128L/P129Q/S130A/S101Y/Q109L/S188D/T213E/N248R, S87R/G118R/S128L/P129Q/S130A/Q109L/S188D/N248R, S87N/G118V/S128L/P129Q/S130A/N18K/G97P/S101L/N185R/A215R, S 87N/G118V/S128L/P129Q/S130A/I72V/S101Y/S164I, S87N/G118V/S128L/P129Q/S130A/S101Y/T213E/N248R, S 87N/G118V/S128L/P129Q/S130A/I72V/S101L/Q109L/S164I, S87R/G118R/S128L/P129Q/S130A/S101V/S188D/N248R, S87N/G118V/S128L/P129Q/S130A/N18K/G97P/S101Y/N185R/A215R, S87N/G118V/S128L/P129Q/S130A/I72V/S101V/S164I, S87N/G118V/S128L/P129Q/S130A/S101L/T213E/N248R, S87N/G118V/S128L/P129Q/S130A/I72V/S101Y/Q109L/S164I, S87R/G118R/S128L/P129Q/S130A/S101H/S188D/N248R, S87N/G118V/S128L/P129Q/S130A/N18K/G97P/Q109R/N185R/A215R, S87N/G118V/S128L/P129Q/S130A/I72V/S101H/S164I, S87N/G118V/S128L/P129Q/S130A/S101L/Q109R/S188D/N248R, S87N/G118V/S128L/P129Q/S130A/N18K/G97P/S101L/Q109L/N185R/A215R, S87R/G118R/S128L/P129Q/S130A/S101M/S188D/N248R, N76D/S87R/G118R/S128L/P129Q/S130A/S188D, N76D/S87R/G118R/S128L/P129Q/S130A/S188D/N248K, S87N/G118V/G127S/S128L/P129Q/S130A, S87N/S101H/G118V/S128L/P129Q/S130A, S87N/S101K/G118V/S128L/P129Q/S130A, S87N/S101V/G118V/S128L/P129Q/S130A, S87N/S101Y/G118V/S128L/P129Q/S130A, S87N/S101L/G118V/S128L/P129Q/S130A, and I72V/S87N/G118V/S128L/P1290/S130A/S164I, wherein the positions are numbered by correspondence with the amino acid sequence of *B. amyloliquefaciens* subtilisin BPN' set forth as SEQ ID NO:1.

2. A cleaning composition comprising the subtilisin variant set forth in claim 1.

3. The cleaning composition of claim 2, wherein said composition comprises a liquid, gel, tablet, powder and/or granule detergent.

4. The cleaning composition of claim 2, further comprising at least one additional enzyme.

5. The cleaning composition of claim 4, wherein said at least one additional enzyme is selected from hemicellulases, cellulases, peroxidases, proteases, metalloproteases, xylanases, lipases, phospholipases, esterases, perhydrolasess, cutinases, pectinases, pectate lyases, mannanases, keratinases, reductases, oxidases, phenoloxidases, lipoxygenases, ligninases, pullulanases, tannases, pentosanases, malanases, ß-glucanases, arabinosidases, hyaluronidase, chondroitinase, laccase, and amylases, or mixtures thereof.

6. The cleaning composition of claim 2, wherein said cleaning composition is selected from laundry detergents and dish detergents.

7. The cleaning composition of claim 2, comprising a laundry detergent.

8. The cleaning composition of claim 7, wherein said laundry detergent is a heavy duty detergent.

9. The cleaning composition of claim 2, further comprising at least one bleaching agent.

10. The cleaning composition of claim 2, wherein said cleaning composition is a phosphate-free detergent.

11. The cleaning composition of claim 2, wherein said cleaning composition is a cold water detergent.

* * * * *